United States Patent
Chang et al.

(10) Patent No.: US 8,461,163 B2
(45) Date of Patent: Jun. 11, 2013

(54) SUBSTITUTED N-(PYRAZOLO[1,5-A]PYRIMIDIN-5-YL) AMIDES AS INHIBITORS OF APOPTOSIS SIGNAL-REGULATING KINASE 1

(75) Inventors: Edcon Chang, San Diego, CA (US); Tracy Duong, San Diego, CA (US); Takehiro Hirano, Osaka (JP); Matthew H. McNiell, San Diego, CA (US); Yoshito Terao, Osaka (JP); Angie Vassar, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 20 days.

(21) Appl. No.: 12/935,542

(22) PCT Filed: Mar. 30, 2009

(86) PCT No.: PCT/US2009/038840
§ 371 (c)(1),
(2), (4) Date: Dec. 1, 2010

(87) PCT Pub. No.: WO2009/123986
PCT Pub. Date: Oct. 8, 2009

(65) Prior Publication Data
US 2011/0077235 A1    Mar. 31, 2011

Related U.S. Application Data

(60) Provisional application No. 61/041,166, filed on Mar. 31, 2008.

(51) Int. Cl.
*A01N 43/90* (2006.01)
*A61K 31/519* (2006.01)

(52) U.S. Cl.
USPC ...................................... 514/259.3; 544/281

(58) Field of Classification Search
USPC ...................................... 514/259.3; 544/281
See application file for complete search history.

(56) References Cited

FOREIGN PATENT DOCUMENTS

| | | |
|---|---|---|
| EP | 1666468 | 6/2006 |
| EP | 1671962 | 6/2006 |
| WO | 2004/076458 | 9/2004 |
| WO | 2004/081013 | 9/2004 |
| WO | 2004/087707 | 10/2004 |
| WO | 2007/013673 | 2/2007 |
| WO | 2007/044449 | 4/2007 |
| WO | 2008/016131 | 2/2008 |
| WO | 2008/063671 | 5/2008 |
| WO | 2008/109177 | 9/2008 |

OTHER PUBLICATIONS

Reimlinger, Hans et al: "Syntheses with heterocyclic amines. V. Further reactions with 5-oxopyrazolopyrimidines" Chemische Berichte, vol. 104, No. 7, 1971, pp. 2237-2240, ISSN: 0009-2940.
Troschuetz, Reinhard et al: "Synthesis of 5,7-diaminopyrazolo[1,5-a]pyrimidines" Archiv Der Pharmazie, vol. 318, No. 1, 1985, pp. 87-88, ISSN: 0365-6233.
Ayman Wahba Erian et al: "The reactivity of .beta.-enaminonitriles towards amino heterocycles: a novel synthesis of fused pyrazole systems" Journal of Chemical Research. Synopses, vol. 9, 1993, pp. 352-353, ISSN: 0308-2342.
Delettre, Jean et al: "Molecular structure and molecular properties of four derivatives of the formula C8H10N4" Journal of Heterocyclic Chemistry, vol. 15, No. 2, 1978, pp. 185-192, ISSN: 0022-152X.

*Primary Examiner* — Yong Chu
*Assistant Examiner* — Valerie Rodriguez-Garcia
(74) *Attorney, Agent, or Firm* — Matthew J. Russo; C. Amy Smith

(57) ABSTRACT

The present invention relates to apoptosis signal-regulating kinase 1 ("ASK1"). inhibiting compounds of the formula

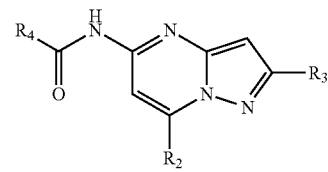

wherein the variables are as defined herein. The invention also relates to pharmaceutical compositions, kits and articles of manufacture comprising such compounds, to methods and intermediates useful for making the compounds, and to methods of using the compounds.

36 Claims, 1 Drawing Sheet

DNA Sequence Encoding First PCR Primer [SEQ ID NO: 1]

aaaagtcgac atggactaca aggacgacga tgacaaggtg aacaccatta ccgaagagaa    60
gggga                                                                65

DNA Sequence Encoding Second PCR Primer [SEQ ID NO: 2]

aaagcggccg ctcaagtctg tttgtttcga aagtcaatg                           39

SUBSTITUTED N-(PYRAZOLO[1,5-A]PYRIMIDIN-5-YL)AMIDES AS INHIBITORS OF APOPTOSIS SIGNAL-REGULATING KINASE 1

FIELD OF THE INVENTION

The present invention relates to compounds that may be used to inhibit apoptosis signal-regulating kinase 1 (ASK1) as well as compositions of matter, kits and articles of manufacture comprising these compounds. The invention also relates to methods for inhibiting ASK1 and treatment methods using compounds according to the present invention. In addition, the invention relates to methods of making the compounds of the present invention, as well as intermediates useful in such methods. In particular, the present invention relates to ASK1 inhibitors, compositions of matter, kits and articles of manufacture comprising these compounds, methods for inhibiting ASK1, and methods and intermediates useful for making the inhibitors.

BACKGROUND OF THE INVENTION

Apoptosis signal-regulating kinase 1 (ASK1), is a member of the mitogen-activated protein kinases (MAPKs) family, which are members of the serine/threonine kinase family. Wang et al. *J. Biol. Chem.* 1996, 271, 31607-31611, Ichijo et al. *Science* 1997, 275, 90-94. ASK1 is also known as mitogen-activated protein kinase kinase kinase 5 (MAPKKK5, MAP3K5), MAP/ERK kinase kinase 5 (MEKK5), MEK kinase 5, MEKK5, MAP/ERK kinase kinase 5. The protein kinase composes of 1375 amino acids encompassing 11 kinase subdomains; particularly a serine/threonine kinase domain in the middle part of the molecule with long NH- amd COOH-terminal flanking regions. Wang et al. *J. Biol. Chem.* 1996, 271, 31607-31611, Ichijo et al. *Science* 1997, 275, 90-94; Tobiume et al. *Biochem. Biophys. Res. Commun.* 1997, 239, 905-910; U.S. Pat. Nos. 6,080,546 and 6,194,187. The nucleotide sequence of ASK1 is accessible in the protein databases by the accession number NM_005923. ASK1 is ubiquitously expressed with the highest expression in the heart, pancreas, testis, and ovaries.

The MAP kinases mediate signal transduction from the cell surface to the nucleus via phosphorylation cascades. Egan and Weinbery *Nature* 1993, 365, 781-783.

The MAPK cascades are multifunctional intracellular signaling pathways that are evolutionarily conserved in all eukaryotic cells. Widmann et al. *Physiol Rev* 1999, 79, 143-180; Kyriakis and Avruch, J. *Physiol Rev* 2001, 81, 807-869; Ichijo *Oncogene* 1999, 18:6087-6093. All eukaryotic cells possess multiple MAPK pathways. In mammalian cells, three MAPK cascades that converge on ERKs, c-Jun N-terminal kinases (JNKs), and p38 MAP kinases have been extensively characterized. Egan and Weinbery *Nature* 1993, 365, 781-783; Boulton et al. *Cell* 1994, 65, 663-675; and Zhou et al. *J. Biol. Chem.* 1995, 270, 12665-12669 (the MAPK/ERK pathway); Derujard et al. *Cell* 1994, 76, 1025-1037; Galcheva-Gargova et al. *Science* 1994, 265, 806-808; Minden et al. *Mol. Cell. Biol.* 1994, 14, 6683-6688 (the c-Jun N-terminal kinase (JNK) pathway; and Lee et al. *Science* 1994, 265, 808-811, (the p38 MAPK pathways). ERK pathway is activated by various growth factors and closely linked to the regulation of cell cycle. The JNK and p38 pathways are preferentially activated by various cytotoxic stress such as UV radiation, X-ray, heat shock, osmotic shock, oxidative stress and pro-inflammatory cytokines such as tumor necrosis factor (TNF) and interleukin-1 Tibbles and Woodgett, *Cell Mol*, Life Sci. 1999, 55:1230-1254. JNK and p38 are thus also called stress-activated protein kinases (SAPKs).

Each MAPK cascade involves three classes of serine/threonine kinases, MAPK, MAPK kinanse (MAP2K) and MAP2K kinase (MAP3K). In the MAPK signaling cascades, MAP3K phosphorylates and thereby activates MAP2K in turn phosphorylates and activates MAPK. Activated MAPK may translocate to the cell nucleus and regulate the activities of transcription factors and thereby control gene expression. Sturgill and Wu, *Biochim. Biophys. Acta* 1993, 1092, 350; Nishida and Gotoh, *Trends Biochem. Sci.* 1993, 18, 128; Errede and Levin *Curr. Opin. Cell Biol.* 1993, 5, 254; Marshall *Curr. Opin. Genet. Dev.* 1994, 82.

MAP3Ks play pivotal roles in sensing and signaling of cellular and environmental stress. The MAP3Ks in the JNK and p38 pathways are highly divergent in number and structure. At least eleven MAP3Ks have been identified upstream of JNK, each of which activates single or multiple downstream MAPK cascades. This diversity and complexity are consistent with the variety of stimuli that activate MAPK pathways. Kyriakis and Avruch *Physiol. Rev.* 2001, 81, 807-869.

One of the important biological responses mediated through these stress-activated MAP kinase pathways appears to be the decision of cell fate by regulating apoptosis. The possible roles of the JNK pathway in pro-apoptosis signaling have been demonstrated by knockout mouse studies. Yang et al. *Nature* 1997, 389:865-870; Sabapathy et al. *Curr. Biol.* 1999, 9:116-125; Kuan et al. *Neuron* 1999, 22:667-676. Several lines of evidence have also suggested the pro-apoptotic roles of the p38 pathway. Xia et al. *Science* 1995, 270:1326-1331; Kawaski et al. *J. Biol. Chem.* 1997, 272:18518-18521; Harper and LoGrasso et al. *Cell Signal.* 2001, 13:299-310.

ASK1 was originally identified as an apoptosis-inducing MAP3K. ASK1 regulates the p38 and JNK pathways by directly phosphorylating and thereby activating their respective MAPKKs, MKK4(SEK1)/MKK7 and MKK3/MKK6. Wang et al. *J. Biol. Chem.* 1996, 271, 31607-31611; Ichijo et al. *Science* 1997, 275, 90-94. The activity of ASK1 is tightly regulated; a ubiquitously expressed reduction/oxidation protein thioredoxin (Trx) binds to the N-terminal and inhibits its activity. ASK1 is activated by various cytotoxic stresses including oxidative stress, endoplasmic reticulum (ER) stress, and calcium overload, and by receptor-mediated inflammatory signals such as tumor necrosis factor (TNF) and endotoxic lipopolysaccharide (LPS). Hayakaw et al. *Microbes and Infection* 2006, 8, 1098-1107; Saitoh et al *EMBO J.* 1998, 17:2596-2606; Nishitoh et al. *Genes Dev.* 2002, 16:1345-1355; Takeda et al. *EMBO Rep.* 2004, 5, 161-166; Nishitoh et al. *Mol Cell* 1998, 2, 389-395; Matsukawa et al. *Nat Immunol* 2005, 6, 587-592. It has been shown that ASK1 is required for apoptosis induced by oxidative stress, TNF and ER stresses. Nishitoh et al. *Genes Dev.* 2002, 16:1345-1355; Matsukawa et al. *Nat Immunol* 2005, 6, 587-592; Tobiume et al. *EMBO Rep.* 2001, 2:222-228. Overexpression of wild-type or constitutively active ASK1 induces apoptosis in various cells through mitochondria-dependent caspase activation. Saitoh et al *EMBO J.* 1998, 17:2596-2606; Kanamoto et al. *Mol. Cell. Biol.* 2000, 20, 196-204; Hatai et al. *J. Biol. Chem.* 2000, 275, 26576-26588.

Recent studies revealed that ASK1 contributes not only to regulation of cell death but also has diverse functions in the decision of cell fate such as cytokine responses, cell differentiation, and innate immune responses. Matsukawa et al. *J Biochem.* (Toyko) 2004, 136, 261-265. Sayama et al. *J. Biol. Chem.* 2000, 276:999-1004; Takeda et al. *J. Biol. Chem.* 2000, 275:9805-9813; Sagasti et al. *Cell* 2001, 105:221-232; Kim et al. *Science* 2002, 297:623-626; Nishitoh et al. *Genes Dev.* 2002, 16:1345-1355; Matsukawa et al. *Nat Immunol* 2005, 6, 587-592; Tobiume et al. *EMBO Rep.* 2001, 2:222-228; Imoto, et al. *Diabetes* 2006, 55:1197-1204. Constitutively active ASK1 induces neurite outgrowth in PC12 cells. ASK1 is activated by CaMKII, which activates ASK1-p38 pathway in neurons, suggesting that ASK1 might play critical roles in synaptic plasticity. Moreover, TRAF6-ASK1-p38 pathway plays an essential role in inflammatory and innate immune responses. Hayakawa et al. *Microbes and Infection* 2006, 8, 1098-1107. It has also been demonstrated that ASK1 has a role in the pathogenesis of TNF-α-induced insulin resistance. Overexpression of wild-type ASK1 increases serine phosphorylation of insulin receptor substrate (IRS)-1, and decreases insulin-stimulated tyrosine phosphorylation of IIRS-1, leading to impair insulin signaling. Imoto, et al. *Diabetes* 2006, 55:1197-1204.

ASK1 is thus a pivotal component not only in stress-induced cell death but also in a broad range of biological activities in order for cells to adapt to or oppose various stresses. Modulating the activity of ASK1 potertially have beneficial effect in treating or preventing a wide range of diseases and conditions including, but not limited to, cardiovascular diseases, inflammatory diseases, autoimmune diseases, destructive bone disorders, neurodegenerative disorders, and metabolic diseases such as diabetes. Thompson, *Science* 1995, 267, 1456-1462; Yuan and Yanker *Nature* 2000, 407, 802-809; Los et al. *Immunity* 1999, 10, 629-639.

Currently, there are no known therapeutical agents that effectively inhibit the expression and/or activation of ASK1, and to date, strategies aimed at modulating ASK1 function have involved the use of antibodies, dominant negative and dominant active mutants of the protein.

U.S. Pat. No. 5,981,265 and No. 6,074,861 claim methods for regulating MAP3K protein activity in a cell by transforming or transfecting the cell with a nucleic acid that is capable of hybridizing under stringent conditions to a nucleic acid molecule encoding MAP3K1, MAP3K2, MAP3K3, MAP3K4, MAP3K5, and MAP3K6. Oligonucleotides for use in antisense, and triplex formation, as ribozymes, probes or primers and in other applications are generally disclosed. WO 01/07461 discloses antisense compositions and methods for using the antisense compositions to modulate the expression of MAP3K5 and treat diseases associated with expression of MAP3K5.

Consequently, there remains a long felt need for agents capable of effectively modulating the activity of ASK1. A small molecule inhibitor may be proof to be an effective means for regulating ASK1 activities.

SUMMARY OF THE INVENTION

The present invention relates to compounds that have activity for inhibiting ASK1. The present invention also provides compositions, articles of manufacture and kits comprising these compounds. In addition, the invention relates to methods of making the compounds of the present invention, as well as intermediates useful in such methods.

In one aspect, the invention is directed to compounds having the formula:

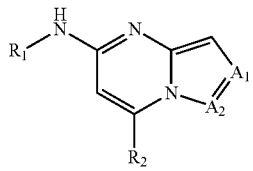

or a hydrate, solvate, tautomer, stereoisomer, or pharmaceutically acceptable salt thereof,
wherein
$A_1$ and $A_2$ are each selected from the group consisting of $CR_3$ and N, provided that only one of $A_1$ and $A_2$ is N;

$R_1$ is selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_2$ is selected from the group consisting of nitro, cyano, thio, oxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{2-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, provided that $R_2$ is not an unsubstituted n-$(C_{1-3})$alkyl; and $R_3$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;
provided that
when $R_2$ is an amino group, $R_1$ is not unsubstituted or substituted alkyl or unsubstituted or substituted cyclyl; and
when $R_1$ is hydrogen, $R_2$ is an unsubstituted or substituted cyclyl.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula," "compound having the formula" and "compound of the formula" is intended to encompass the compound and all pharmaceutically acceptable ionized forms and solvates, all possible stereoisomers, and all possible resonance forms and tautomers unless otherwise specifically specified in the particular claim.

In another aspect, the invention is directed to pharmaceutical compositions that comprise an ASK1 inhibitor according to the present invention as an active ingredient. Pharmaceutical compositions according to the invention may optionally comprise 0.001%-100% of one or more inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stert), subcutaneously, intraadiposally, intraarticularly, or intrathecally. The compositions may also be administered or coadministered in slow release dosage forms.

In another aspect, the invention is directed to kits and articles of manufacture for treating disease states associated with ASK1.

In one embodiment, the kit comprises a composition comprising at least one ASK1 inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another aspect, the invention is directed to articles of manufacture that comprise a composition comprising at least one ASK1 inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The article of manufacture may also optionally comprise additional components, such as syringes for administration of the composition. The article of manufacture may comprise the composition in single or multiple dose forms.

In yet another aspect of the invention is directed to methods for preparing compounds, compositions, kits, and articles of manufacture according to the present invention. For example, several synthetic schemes are provided herein for synthesizing compounds according to the present invention.

In yet other aspect, the invention is directed to methods of using compounds, compositions, kits and articles of manufacture according to the present invention.

In one embodiment, the compounds, compositions, kits and articles of manufacture are used to inhibit ASK1.

In another embodiment, the compounds, compositions, kits and articles of manufacture are used to treat a disease state for which ASK1 possess activity that contributes to the pathology and/or symptomology of the disease state.

In another embodiment, a compound is administered to a subject wherein ASK1 activity within the subject is altered, preferably reduced.

In another embodiment, a prodrug of a compound is administered to a subject that is converted to the compound in vivo where it inhibits ASK1.

In another embodiment, a method of inhibiting ASK1 is provided that comprises contacting an ASK1 with a compound according to the present invention.

In another embodiment, a method of inhibiting ASK1 is provided that comprises causing a compound according to the present invention to be present in a subject in order to inhibit ASK1 in vivo.

In another embodiment, a method is provided for using a compound according to the present invention in order to manufacture a medicament for use in the treatment of a disease state that is known to be mediated by ASK1, or that is known to be treated by ASK1 inhibitors.

It is noted that in the various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting ASK1 and thus may themselves be prodrugs for another compound. Such prodrugs of another compound may or may not themselves independently have ASK1 inhibitory activity.

BRIEF DESCRIPTION OF THE FIGURES

FIG. 1 illustrates SEQ ID NO:1 and SEQ ID NO: 2 referred to in this application.

DEFINITION

Unless otherwise stated, the following terms used in the specification and claims shall have the following meanings for the purposes of this Application.

It is noted that, as used in the specification and the appended claims, the singular forms "a," "an" and "the" include plural referents unless the context clearly dictates otherwise. Further, definitions of standard chemistry terms may be found in reference works, including Carey and Sundberg "ADVANCED ORGANIC CHEMISTRY 5$^{TH}$ ED." Vols. A (2007) and B (2007), Springer Science and Business Media, New York. Also, unless otherwise indicated, conventional methods of mass spectroscopy, NMR, HPLC, protein chemistry, biochemistry, recombinant DNA techniques and pharmacology, within the skill of the art are employed.

"Acetyl" means the radical —C(O)CH$_3$.

"Acetylamino" means the radical —NR—C(O)CH$_3$ where R is hydrogen or a further substituent.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with (C$_{3-8}$) rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR=CR'— or —CR=CR'R", wherein R, R' and R" are each independently hydrogen or further substituents). Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl," either alone or represented along with another radical, can be a $(C_{2-20})$alkenyl, a $(C_{2-15})$alkenyl, a $(C_{2-10})$alkenyl, a $(C_{2-5})$alkenyl or a $(C_{2-3})$alkenyl. Alternatively, "alkenyl," either alone or represented along with another radical, can be a $(C_2)$alkenyl, a $(C_3)$alkenyl or a $(C_4)$alkenyl.

"Alkenylene" means a straight or branched, divalent carbon chain having one or more carbon-carbon double bonds (—CR=CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another radical, can be a $(C_{2-20})$ alkenylene, a $(C_{2-15})$ alkenylene, a $(C_{2-10})$ alkenylene, a $(C_{2-5})$ alkenylene or a $(C_{2-3})$ alkenylene. Alternatively, "alkenylene," either alone or represented along with another radical, can be a $(C_2)$ alkenylene, a $(C_3)$ alkenylene or a $(C_4)$ alkenylene.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with one or more of the carbon atoms being replaced with oxygen (See "oxaalkyl"), a carbonyl group (See "oxoalkyl"), sulfur (See "thioalkyl"), and/or nitrogen (See "azaalkyl"). $(C_X)$alkyl and $(C_{X-Y})$alkyl are typically used where X and Y indicate the number of carbon atoms in the chain. For example, $(C_{1-6})$alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., $(C_{6-10})$aryl$(C_{1-3})$alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a $(C_{1-20})$alkyl, a $(C_{1-15})$alkyl, a $(C_{1-10})$alkyl, a $(C_{1-5})$alkyl or a $(C_{1-3})$alkyl. Alternatively, "alkyl," either alone or represented along with another radical, can be a $(C_1)$alkyl, a $(C_2)$alkyl or a $(C_3)$alkyl.

"Alkylene", unless indicated otherwise, means a straight or branched, saturated or unsaturated, aliphatic, divalent radical. $(C_X)$alkylene and $(C_{X-Y})$alkylene are typically used where X and Y indicate the number of carbon atoms in the chain. For example, $(C_{1-6})$alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—), 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—), and the like. In particular embodiments, "alkylene," either alone or represented along with another radical, can be a $(C_{1-20})$alkylene, a $(C_{1-15})$alkylene, a $(C_{1-10})$alkylene, a $(C_{1-5})$alkylene or a $(C_{1-3})$alkylene. Alternatively, "alkylene," either alone or represented along with another radical, can be a $(C_1)$alkylene, a $(C_2)$alkylene or a $(C_3)$alkylene.

"Alkylidene" means a straight or branched, saturated or unsaturated, aliphatic radical connected to the parent molecule by a double bond. $(C_X)$alkylidene and $(C_{X-Y})$alkylidene are typically used where X and Y indicate the number of carbon atoms in the chain. For example, $(C_{1-6})$alkylidene includes methylene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like. In particular embodiments, "alkylidene," either alone or represented along with another radical, can be a $(C_{1-20})$alkylidene, a $(C_{1-15})$alkylidene, a $(C_{1-10})$alkylidene, a $(C_{1-5})$alkylidene or a $(C_{1-3})$alkylidene. Alternatively, "alkylidene," either alone or represented along with another radical, can be a $(C_1)$alkylidene, a $(C_2)$alkylidene or a $(C_3)$alkylidene.

"Alkynyl" means a straight or branched, carbon chain that contains at least one carbon-carbon triple bond (—C≡C— or —C≡CR, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a $(C_{2-20})$alkynyl, a $(C_{2-15})$alkynyl, a $(C_{2-10})$alkynyl, a $(C_{2-5})$alkynyl or a $(C_{2-3})$alkynyl. Alternatively, "alkynyl," either alone or represented along with another radical, can be a $(C_2)$alkynyl, a $(C_3)$alkynyl or a $(C_4)$alkynyl.

"Alkynylene" means a straight or branched, divalent carbon chain having one or more carbon-carbon triple bonds (—CR≡CR', wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a $(C_{2-20})$ alkynylene, a $(C_{2-15})$ alkynylene, a $(C_{2-10})$ alkynylene, a $(C_{2-5})$ alkynylene or a $(C_{2-3})$ alkynylene. Alternatively, "alkynylene," either alone or represented along with another radical, can be a $(C_2)$ alkynylene, a $(C_3)$ alkynylene or a $(C_4)$ alkynylene.

"Amido" means the radical —NR—C(=O)R', wherein R and R' are each hydrogen.

"Amino" —NH$_2$. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (See "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $(C_X)$aryl and $(C_{X-Y})$aryl are typically used where X and Y indicate the number of carbon atoms in the ring. In particular embodiments, "aryl," either alone or represented along with another radical, can be a $(C_{3-14})$aryl, a $(C_{3-10})$aryl, a $(C_{3-7})$aryl, a $(C_{8-10})$aryl or a $(C_{5-7})$aryl. Alternatively, "aryl," either alone or represented along with another radical, can be a $(C_5)$aryl, a $(C_6)$aryl, a $(C_7)$aryl, a $(C_8)$aryl, a $(C_9)$aryl or a $(C_{10})$aryl.

"Azaalkyl" means an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a $(C_{1-10})$azaalkyl refers to a chain comprising between 1 and 10 carbons and one or more nitrogen atoms.

"Aza-cyclyl" means a heterocyclyl moiety containing at least one nitrogen atom and the point of attachment of the cyclyl is through the nitrogen atom.

"Bicycloalkyl" means a saturated or partially unsaturated fused, spiro or bridged bicyclic ring assembly. In particular embodiments, "bicycloalkyl," either alone or represented along with another radical, can be a $(C_{4-15})$bicycloalkyl, a $(C_{4-10})$bicycloalkyl, a $(C_{6-10})$bicycloalkyl or a $(C_{8-10})$bicycloalkyl. Alternatively, "bicycloalkyl," either alone or represented along with another radical, can be a $(C_8)$bicycloalkyl, a $(C_9)$bicycloalkyl or a $(C_{10})$bicycloalkyl.

"Bicycloaryl" means a fused, spiro or bridged bicyclic ring assembly wherein at least one of the rings comprising the assembly is aromatic. $(C_X)$bicycloaryl and $(C_{X-Y})$bicycloaryl are typically used where X and Y indicate the number of carbon atoms in the bicyclic ring assembly and directly attached to the ring. In particular embodiments, "bicycloaryl," either alone or represented along with another radical, can be a (a $(C_{4-15})$bicycloaryl, a $(C_{4-10})$bicycloaryl, a $(C_{6-10})$bicycloaryl or a $(C_{8-10})$bicycloaryl. Alternatively, "bicycloalkyl," either alone or represented along with another radical, can be a $(C_8)$bicycloaryl, a $(C_9)$bicycloaryl or a $(C_{10})$bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" or "aminocarbonyloxy" means the radical —OC(O)NRR', wherein R and R' are each hydrogen.

"Carbocycle" means a ring consisting of carbon atoms.

"Carbonyl" means the radical —C(=O)R, wherein R is hydrogen.

"Carboxamido" means the radical —C(=O)—NRR', wherein R and R' are each hydrogen.

"Carboxy" means the radical —C(=O)—OR, wherein R is hydrogen. It is noted that compounds of the invention containing carboxy moieties may include protected derivatives thereof, i.e., where the oxygen is substituted with a protecting group. Suitable protecting groups for carboxy moieties include benzyl, tent-butyl, and the like.

"Cyano" means the radical —CN.

"Cycloalkyl" means a non-aromatic, saturated or partially unsaturated, monocyclic, bicyclic or polycyclic ring assembly. $(C_X)$cycloalkyl and $(C_{X-Y})$cycloalkyl are typically used where X and Y indicate the number of carbon atoms in the ring assembly. For example, $(C_{3-10})$cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a $(C_{3-14})$cycloalkyl, a $(C_{3-10})$cycloalkyl, a $(C_{3-7})$cycloalkyl, a $(C_{8-10})$cycloalkyl or a $(C_{5-7})$cycloalkyl. Alternatively, "cycloalkyl," either alone or represented along with another radical, can be a $(C_5)$cycloalkyl, a $(C_6)$cycloalkyl, a $(C_7)$cycloalkyl, a $(C_8)$cycloalkyl, a $(C_9)$cycloalkyl or a $(C_{10})$cycloalkyl.

"Cycloalkylene" means a divalent, saturated or partially unsaturated, monocyclic, bicyclic or polycyclic ring assembly. $(C_X)$cycloalkylene and $(C_{X-Y})$cycloalkylene are typically used where X and Y indicate the number of carbon atoms in the ring assembly. In particular embodiments, "cycloalkylene," either alone or represented along with another radical, can be a $(C_{3-14})$cycloalkylene, a $(C_{3-10})$cycloalkylene, a $(C_{3-7})$cycloalkylene, a $(C_{8-10})$cycloalkylene or a $(C_{5-7})$cycloalkylene. Alternatively, "cycloalkylene," either alone or represented along with another radical, can be a $(C_5)$cycloalkylene, a $(C_6)$cycloalkylene, a $(C_7)$cycloalkylene, a $(C_8)$cycloalkylene., a $(C_9)$cycloalkylene or a $(C_{10})$cycloalkylene.

"Cyclyl" means a monocyclic, bicyclic or polycyclic monovalent ring radical where the ring may be aromatic, saturated or partially unsaturated, and polycyclic, wherein the ring atoms are all carbon atoms or optionally one or more of the ring atoms are heteroatoms.

"Disease" specifically includes any unhealthy condition of an animal or part thereof and includes an unhealthy condition that may be caused by, or incident to, medical or veterinary therapy applied to that animal, i.e., the "side effects" of such therapy.

"$EC_{50}$" means the molar concentration of an agonist that produces 50% of the maximal possible effect of that agonist. The action of the agonist may be stimulatory or inhibitory.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Heteroalkyl" means alkyl, as defined in this Application, provided that one or more of the atoms within the alkyl chain is a heteroatom. In particular embodiments, "heteroalkyl," either alone or represented along with another radical, can be a hetero($C_{1-20}$)alkyl, a hetero($C_{1-15}$)alkyl, a hetero($C_{1-10}$)alkyl, a hetero($C_{1-5}$)alkyl, a hetero($C_{1-3}$)alkyl or a hetero($C_{1-2}$)alkyl. Alternatively, "heteroalkyl," either alone or represented along with another radical, can be a hetero($C_1$)alkyl, a hetero($C_2$)alkyl or a hetero($C_3$)alkyl.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-a]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-c]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero($C_{1-13}$)aryl, a hetero($C_{2-13}$)aryl, a hetero($C_{2-6}$)aryl, a hetero($C_{3-9}$)aryl or a hetero($C_{5-9}$)aryl. Alternatively, "heteroaryl," either alone or represented along with another radical, can be a hetero($C_3$)aryl, a hetero($C_4$)aryl, a hetero($C_5$)aryl, a hetero($C_6$)aryl, a hetero($C_7$)aryl, a hetero($C_8$)aryl or a hetero($C_9$)aryl.

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —NR—, —N$^+$(=O$^-$)—, —O—, —S— or —S(O)$_2$—, wherein R is hydrogen or a further substituent.

"Heterobicycloalkyl" means bicycloalkyl, as defined in this Application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like. In particular embodiments, "heterobicycloalkyl," either alone or represented along with another radical, can be a hetero($C_{1-14}$)bicycloalkyl, a hetero($C_{4-14}$)bicycloalkyl, a hetero($C_{4-9}$)bicycloalkyl or a hetero($C_{5-9}$)bicycloalkyl. Alternatively, "heterobicycloalkyl," either alone or represented along with another radical, can be a hetero($C_5$)bicycloalkyl, hetero($C_6$)bicycloalkyl, hetero($C_7$)bicycloalkyl, hetero($C_8$)bicycloalkyl or a hetero($C_9$)bicycloalkyl.

"Heterobicycloaryl" means bicycloaryl, as defined in this Application, provided that one or more of the atoms within the ring is a heteroatom. For example, hetero($C_{4-12}$)bicycloaryl as used in this Application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero($C_{1-14}$)bicycloaryl, a hetero($C_{4-14}$)bicycloaryl, a hetero($C_{4-9}$)bicycloaryl or a hetero($C_{5-9}$)bicycloaryl. Alternatively, "heterobicycloaryl," either alone or represented along with another radical, can be a hetero($C_5$)bicycloaryl, hetero($C_6$)bicycloaryl, hetero($C_7$)bicycloaryl, hetero($C_8$)bicycloaryl or a hetero($C_9$)bicycloaryl.

"Heterocycloalkyl" means cycloalkyl, as defined in this Application, provided that one or more of the atoms forming the ring is a heteroatom selected, independently from N, O, or S, Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like. In particular embodiments, "heterocycloalkyl," either alone or represented along with another radical, can be a hetero($C_{1-13}$)cycloalkyl, a hetero($C_{1-9}$)cycloalkyl, a hetero($C_{1-6}$)cycloalkyl, a hetero($C_{5-9}$)cycloalkyl or a hetero($C_{2-6}$)cycloalkyl. Alternatively, "heterocycloalkyl," either alone or represented along with another radical, can be a hetero($C_2$)cycloalkyl, a hetero($C_3$)cycloalkyl, a hetero($C_4$)cycloalkyl, a hetero($C_5$)cycloalkyl, a hetero($C_6$)cycloalkyl, hetero($C_7$)cycloalkyl, hetero($C_8$)cycloalkyl or a hetero($C_9$)cycloalkyl.

"Heterocycloalkylene" means cycloalkylene, as defined in this Application, provided that one or more of the ring member carbon atoms is replaced by a heteroatom. In particular embodiments, "heterocycloalkylene," either alone or represented along with another radical, can be a hetero($C_{1-13}$) cycloalkylene, a hetero($C_{1-9}$)cycloalkylene, a hetero($C_{1-6}$) cycloalkylene, a hetero($C_{5-9}$)cycloalkylene or a hetero($C_{2-6}$) cycloalkylene. Alternatively, "heterocycloalkylene," either alone or represented along with another radical, can be a hetero($C_2$)cycloalkylene, a hetero($C_3$)cycloalkylene, a hetero ($C_4$)cycloalkylene, a hetero($C_5$)cycloalkylene, a hetero($C_6$) cycloalkylene, hetero($C_7$)cycloalkylene, hetero($C_8$)cycloalkylene or a hetero($C_9$)cycloalkylene.

"Heterocyclyl" means a monocyclic, bicyclic or polycyclic monovalent ring radical where the ring may be aromatic, saturated or partially unsaturated, and polycyclic, wherein at least one of the ring atoms is a heteroatom.

"Hydroxy" means the radical —OH.

"IC$_{50}$" means the molar concentration of an inhibitor that produces 50% inhibition of the target enzyme.

"Imino" means the radical —CR(=NR'), wherein R and R' are each hydrogen.

"Iminoketone derivative" means a derivative comprising the moiety —C(NR)—, wherein R is hydrogen or a further substituent.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 5th edition, March, Jerry, John Wiley & Sons, New York, 2001).

"Leaving group" means the group with the meaning conventionally associated with it in synthetic organic chemistry, i.e., an atom or group displaceable under reaction (e.g., alkylating) conditions. Examples of leaving groups include, but are not limited to, halo (e.g., F, Cl, Br and I), alkyl (e.g., methyl and ethyl) and sulfonyloxy (e.g., mesyloxy, ethanesulfonyloxy, benzenesulfonyloxy and tosyloxy), thiomethyl, thienyloxy, dihalophosphinoyloxy, tetrahalophosphoxy, benzyloxy, isopropyloxy, acyloxy, and the like.

"Nitro" means the radical —$NO_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa($C_{1-10}$)alkyl refers to a chain comprising between 1 and 10 carbons and one or more oxygen atoms.

"Oxoalkyl" means an alkyl, as defined above, except where one or more of the carbon atoms forming the alkyl chain are replaced with carbonyl groups (—C(=O)— or —C(=O)—R, wherein R is hydrogen or a further substituent). The carbonyl group may be an aldehyde, ketone, ester, amide, acid or acid halide. For example, an oxo($C_{1-10}$)alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Phosphonyl" means "the radical —P(O)(OR)(OR'), wherein R and R' are each hydrogen.

"Polycyclic ring" includes bicyclic and multi-cyclic rings. The individual rings comprising the polycyclic ring can be fused, spiro or bridging rings.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in P. G. M. Wuts and T. W. Greene, *"Greene's Protecting Groups in Organic Synthesis,* 4th edition, John Wiley & Sons, Inc. 2007.

"Ring" and "ring assembly" means a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" and "patient" includes humans, non-human mammals (e.g., dogs, cats, rabbits, cattle, horses, sheep, goats, swine, deer, and the like) and non-mammals (e.g., birds, and the like).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, ($C_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, phosphonyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, phosphonyl($C_{1-10}$) alkyl, ($C_{1-10}$)azaalkyl, imino($C_{1-10}$)alkyl, ($C_{3-12}$)cyclo alkyl ($C_{1-5}$)alkyl, hetero($C_{3-12}$)cycloalkyl($C_{1-10}$)alkyl, aryl($C_{1-10}$) alkyl, hetero($C_{1-10}$)aryl($C_{1-5}$)alkyl, ($C_{9-12}$)bicycloaryl($C_{1-5}$)

alkyl, hetero($C_{1-12}$)bicycloaryl($C_{1-5}$)alkyl, ($C_{3-12}$) cycloalkyl, hetero($C_{1-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$) alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl ($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl.

"Sulfamoyl," means the radical —OS(O)$_2$NRR', wherein R and R' are each hydrogen.

"Sulfinyl" means the radical —SO—R, wherein R is a further substituent. It is noted that the sulfinyl radical may be further substituted with a variety of substituents to form different sulfinyl groups including sulfinic acids, sulfinamides, sulfinyl esters, and sulfoxides.

"Sulfonamido" means the radical —S(O)$_2$—NRR', wherein R and R' are each hydrogen.

"Sulfonyl" means the radical —SO$_2$—R, wherein R is a further substituent. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes =S.

"Thioalkyl" means an alkyl, as defined above, except where one or more of the carbon atoms forming the alkyl chain are replaced with sulfur atoms. For example, a thio($C_{1-10}$)alkyl refers to a chain comprising between 1 and 10 carbons and one or more sulfur atoms.

"Thiocarbonyl" means the radical —C(=S)—R, wherein R is hydrogen.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a ($C_i$)alkyl comprises methyl (i.e., —CH$_3$) as well as —CRR'R" where R, R', and R" may each independently be hydrogen or a further substituent where the atom attached to the carbon is a heteroatom or cyano. Hence, CF$_3$, CH$_2$OH and CH$_2$CN, for example, are all ($C_1$)alkyls. Similarly, terms such as alkylamino and the like comprise dialkylamino and the like.

A compound having a formula that is represented with a dashed bond is intended to include the formulae optionally having zero, one or more double bonds, as exemplified and shown below:

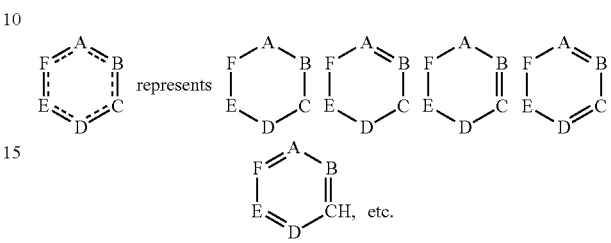

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

DETAILED DESCRIPTION OF THE INVENTION

The present invention relates to compounds that may be used to inhibit ASK1. The present invention also relates to pharmaceutical compositions, kits and articles of manufacture comprising such compounds. In addition, the present invention relates to methods and intermediates useful for making the compounds. Further, the present invention relates to methods of using said compounds.

It is noted that the compounds of the present invention may also possess activity for other members of the same protein family and thus may be used to address disease states associated with these other family members.

Compounds of the Invention

In one of its aspects, the present invention relates to compounds that are useful as ASK1 inhibitors.

In one embodiment, ASK1 inhibitors of the present invention consist of the formula:

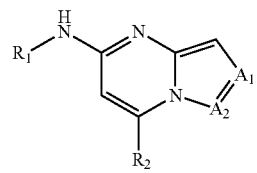

or a hydrate, solvate, tautomer, stereoisomer, or pharmaceutically acceptable salt thereof,
wherein
$A_1$ and $A_2$ are each selected from the group consisting of CR$_3$ and N, provided that only one of $A_1$ and $A_2$ is N;
$R_1$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)

alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or substituted with 1-3 substituents each independently selected from the group consisting of halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

$R_2$ is selected from the group consisting of nitro, cyano, thio, oxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{2-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or substituted with 1-3 substituents, provided that $R_2$ is not an unsubstituted n-($C_{1-3}$)alkyl;

wherein
each of said 1-3 substituents is independently selected from the group consisting of hydroxyl, halo, nitro, cyano, oxo, hydroxy, thio, ($C_{1-6}$)alkylthio, oxy, arylalkyloxy, carbonyloxy, ($C_{1-10}$)alkoxy, ($C_{4-12}$)aryloxy, hetero($C_{1-10}$)aryloxy, aminocarbonyloxy, carbonyl, ($C_{1-6}$)alkylcarbonyl, oxycarbonyl, aminocarbonyl, amino, amido, carboxamido, ($C_{1-10}$)alkylamino, acetylamino, sulfonamido, imino, sulfonyl, ($C_{1-6}$)alkylsulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or further substituted; and $R_3$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero ($C_{8-12}$)bicycloaryl($C_{1-5}$)alkyl, hetero($C_{1-10}$)alkyl, ($C_{3-12}$)cyclo alkyl, hetero($C_{3-12}$)cyclo alkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or substituted with 1-2 substituents each independently selected from the group consisting of hydroxyl, halo, halo($C_{1-6}$)alkyl, ($C_{1-6}$)alkyl, ($C_{3-6}$)cycloalkyl, hetero($C_{1-5}$)cycloalkyl, phenyl, and hetero ($C_{1-5}$)aryl;

provided that
when $R_2$ is an amino group, $R_1$ is not unsubstituted or substituted alkyl or unsubstituted or substituted cyclyl; and when $R_1$ is hydrogen, $R_2$ is an unsubstituted or substituted cyclyl.

In one particular variation of the above embodiment, the compounds of the invention are of formula I:

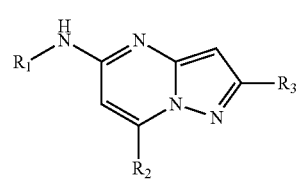

or a hydrate, solvate, tautomer, stereoisomer, or pharmaceutically acceptable salt thereof, and $R_1$, $R_2$ and $R_3$ are as previously defined.

$R_1$
In some variations of the above embodiment and variation, $R_1$ is hydrogen.

In some other variations, $R_1$ is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted with 1-3 substituents;

wherein
each of said 1-3 substituents is independently selected from the group consisting of halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted.

In some other variations of the above two embodiments, $R_1$ is selected from the group consisting of ($C_{4-12}$)aryl, hetero($C_{1-10}$)aryl, ($C_{9-12}$)bicycloaryl and hetero($C_{4-12}$)bicycloaryl, each unsubstituted or substituted with the 1-3 substituents.

In still other variations, $R_1$ is selected from the group consisting of furanyl, thienyl, pyrrolyl, oxazolyl, thiazolyl, imidazolyl, pyrazolyl, triazolyl, oxazolyl, isoxazolyl, oxadiazolyl, thiadiazolyl, phenyl, pyridinyl, pyrazinyl, pyrimidinyl, pyridazinyl, triazinyl, indolyl, isoindolyl, indolizinyl, benzimidazolyl, purinyl, naphthalenyl, quinolinyl, isoquinolinyl, cinnolinyl, phthalazinlyl, quinazolinyl, quinoxalinyl, naphthyridinyl, pteridinyl, pyrimidone, imidazolyl, and quinolinyl, each unsubstituted or substituted with the 1-3 substituents.

In still other variations, $R_1$ is selected from the group consisting of oxazolyl, isoxazolyl and oxadiazolyl, each unsubstituted or substituted with said 1-3 substituents.

In still other variations, $R_1$ is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, each unsubstituted or substituted with the 1-3 substituents.

In still other variations, $R_1$ is selected from the group consisting of pyrrolidinyl, pyridonyl, morpholino, thiomorpholino, piperazinyl, piperidinyl, pyranyl, cyclohexyl, cyclopentyl, cyclohexenyl, and cyclopentenyl, each unsubstituted or substituted with the 1-3 substituents.

In some variations of the above embodiments and variations, the 1-3 substituents on the $R_1$ groups are independently selected from the group consisting of halo, nitro, cyano, thio, mercapto, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, amido, carboxamido, carbamoyl, ($C_{1-10}$)alkylamino, sulfonamido, sulfamoyl, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cyclo alkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or substituted. In other variations, the 1-3 substituents on the $R_1$ groups are independently selected from the group consisting of halo, hydroxy, carbonyloxy, ($C_{1-10}$)alkoxy, carbonyl, oxycarbonyl, aminocarbonyl, amino, ($C_{1-10}$)alkylamino, sulfonamido, sulfonyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, and imino($C_{1-10}$)alkyl, each unsubstituted or substituted.

In another particular embodiment, where $R_1$ is a substituted carbonyl of the formula —C(O)$R_4$, such that the compounds of the invention consisting of the formula:

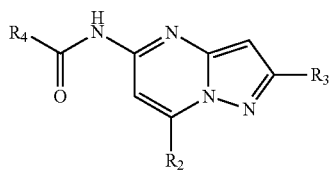

or a hydrate, solvate, tautomer, stereoisomer, or pharmaceutically acceptable salt thereof, where $R_2$ is selected from the group consisting of nitro, cyano, thio, oxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{2-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or substituted, provided that $R_2$ is not an unsubstituted n-($C_{1-3}$)alkyl; and $R_3$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cyclo alkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted; and $R_4$ is selected from the group consisting of oxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, ($C_{1-10}$)alkyl, halo($C_{1-10}$)alkyl, hydroxy($C_{1-10}$)alkyl, carbonyl($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or substituted with 1-3 substituents, where each of said 1-3 substituents is independently selected from the group consisting of halo, nitro, cyano, oxo, thio, mercapto, oxy, hydroxy, carbonyloxy, ($C_{1-10}$)alkoxy, ($C_{4-12}$)aryloxy, hetero($C_{1-10}$)aryloxy, carbonyl, oxycarbonyl, ($C_{1-10}$)alkyloxycarbonyl, ($C_{4-12}$)aryloxycarbonyl, hetero($C_{1-10}$)aryloxycarbonyl, aminocarbonyl, amino, $C_{1-10}$)alkylamino, amido, carboxamido, carbamoyl, ($C_{1-10}$)alkylamino, sulfonamido, sulfamoyl, imino, sulfonyl, sulfinyl, phosphonyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, phosphonyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or further substituted.

In yet another particular embodiment of the compounds of the invention, $R_1$ is a substituted carbonyl of the formula —C(O)$R_4$, such that the compounds of the invention consist of the formula:

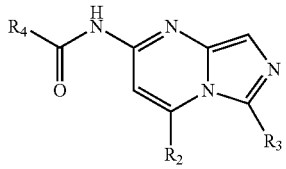

or a hydrate, solvate, tautomer, stereoisomer, or pharmaceutically acceptable salt thereof, where $R_2$ is selected from the group consisting of nitro, cyano, thio, oxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{2-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or substituted, provided that $R_2$ is not an unsubstituted n-($C_{1-3}$)alkyl; and $R_3$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted; and $R_4$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or substituted with 1-3 substituents, where each of said 1-3 substituents is independently selected from the group consisting of halo, nitro, cyano, oxo, thio, mercapto, oxy, hydroxy, carbonyloxy, ($C_{1-10}$)alkoxy, ($C_{4-12}$)aryloxy, hetero($C_{1-10}$)aryloxy, carbonyl, oxycarbonyl, ($C_{1-10}$)alkyloxycarbonyl, ($C_{4-12}$)aryloxycarbonyl, hetero($C_{1-10}$)aryloxycarbonyl, aminocarbonyl, amino, $C_{1-10}$)alkylamino, amido, carboxamido, carbamoyl, ($C_{1-10}$)alkylamino, sulfonamido, sulfamoyl, imino, sulfonyl, sulfinyl, phosphonyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, phosphonyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or further substituted.

$R_4$

In some variations of the two embodiments immediately above of the compounds of the invention, $R_4$ is selected from the group consisting of oxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, ($C_{1-10}$)alkyl, halo($C_{1-10}$)alkyl, hydroxy($C_{1-10}$)alkyl, carbonyl($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or substituted with said 1-3 substituents as defined above.

In some other variations, $R_4$ is selected from the group consisting of oxy, ($C_{1-6}$)alkoxy, ($C_{4-12}$)aryloxy, hetero($C_{1-10}$)aryloxy, amino, ($C_{1-6}$)alkylamino, ($C_{1-10}$)alkyl, halo($C_{1-6}$)alkyl, hydroxy($C_{1-6}$)alkyl, carbonyl($C_{1-10}$)alkyl, ($C_{3-6}$)cycloalkyl($C_{1-5}$)alkyl, hetero($C_{1-5}$)cycloalkyl($C_{1-6}$)alkyl, ($C_{4-6}$)aryl($C_{1-6}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each unsubstituted or substituted with said 1-3 substituents.

In other variations, $R_4$ is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted with said 1-3 substituents.

In another variation, $R_4$ comprises an alicyclic ring which is selected from the group consisting of cyclopropyl, cyclobutyl, cyclopentyl, cyclohexyl, piperidinyl, piperazinyl, morpholinyl, and admantanyl, each unsubstituted or substituted with said 1-3 substituents. Preferably, the alicyclic ring is cyclopropyl, each unsubstituted or substituted with said 1-3 substituents. Also preferrably, said 1-3 substituents is independently selected from the group consisting of $(C_{1-6})$alkyl, phenyl, pyridyl, —C(O)OC(CH$_3$)$_3$, —C(O)OCH(CH$_3$)OH, hetero$(C_{3-12})$bicycloalkyl$(C_{1-6})$alkyl, and hetero$(C_{1-10})$bicycloaryl$(C_{1-6})$alkyl, each unsubstituted or further substituted.

Preferred $R_4$ that are alicyclic, include, but are not limited to, the following

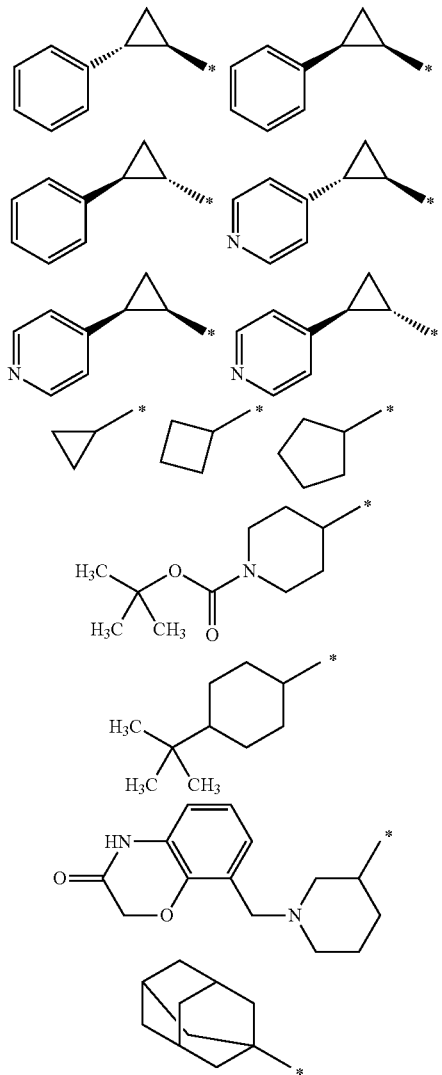

In some variations, $R_4$ is selected from a group consisting of $C_{4-6}$)aryl, hetero$(C_{1-5})$aryl, $(C_{8-12})$bicycloaryl, and hetero $(C_{4-12})$bicycloaryl, wherein the hetero$(C_{1-5})$aryl and hetero $(C_{4-12})$bicycloaryl contain optionally up to four heteroatoms that are independently selected from the group consisting of nitrogen, oxygen and sulfur, and wherein the aryls and heteroaryls are unsubstituted or substituted with said 1-3 substituents. In some variations, $R_4$ is a five-membered aryl or heteroaryl, where the heteroaryl contains optionally up to three heteroatoms that are independently selected from the group consisting of nitrogen, oxygen and sulfur, and where the aryl or heteroaryl is unsubstituted or substituted with 1-3 substituents.

In other variations, $R_4$ is selected from the group consisting of furanyl, thienyl, pyrrolyl, oxazolyl, thiazolyl, imidazolyl, pyrazolyl, triazolyl, isoxazolyl, isothiazolyl, oxadiazolyl, and thiadiazolyl, each unsubstituted or substituted with 1-3 substituents. In yet other variations, $R_4$ is selected from the group consisting of thiazolyl, isothiazolyl, furanyl, and theinyl, each unsubstituted or substituted with said 1-3 substituents. In other variations, $R_4$ is a thienyl, unsubstituted or substituted with 1-3 substituents.

In some other variations, $R_4$ is a six-membered aryl or heteroaryl, where the heteroaryl contains optionally up to four nitrogen atoms, and where the aryl or heteroaryl is unsubstituted or substituted with 1-3 substituents. In other variations, $R_4$ is selected from the group consisting of phenyl, pyridinyl, pyrazinyl, pyrimidinyl, pyridazinyl, and triazinyl, each unsubstituted or substituted with 1-3 substituents. In other particular variations, $R_4$ is phenyl, each unsubstituted or substituted with 1-3 substituents. In yet other particular variations, $R_4$ is pyridinyl, each unsubstituted or substituted with 1-3 substituents.

Preferred $R_4$ that are aryls or heteroaryls include, but are not limited to, the following:

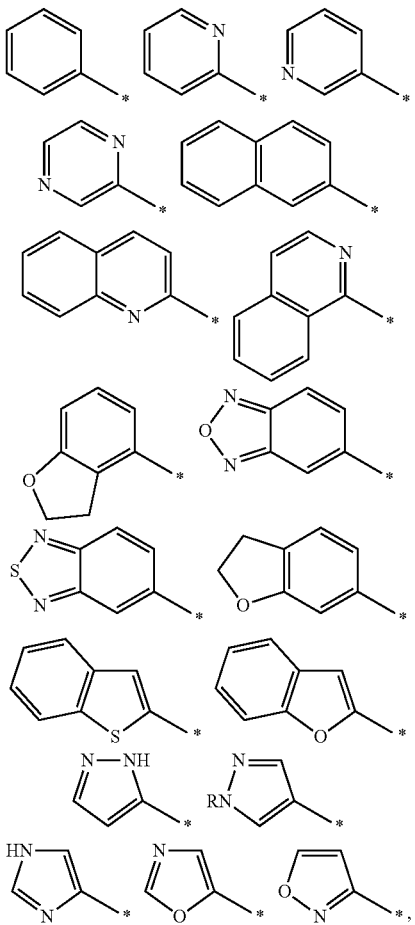

each unsubstituted or substituted with said 1-3 substituents, and where R is hydrogen or one of said 1-3 substituents.

In some variations of the embodiments of $R_4$ described above, the 1-3 substituents are independently selected from the group consisting of halo, nitro, cyano, thio, mercapto, oxy, hydroxy, carbonyloxy, $(C_{1-10})$alkoxy, $(C_{4-12})$aryloxy, hetero $(C_{1-10})$aryloxy, carbonyl, oxycarbonyl, aminocarbonyl, amino, amido, carboxamido, carbamoyl, $(C_{1-10})$alkylamino, sulfonamido, sulfamoyl, imino, sulfonyl, sulfinyl, ($C_{1-10}$) alkyl, halo($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl ($C_{1-10}$)alkyl, aza($C_{1-10}$)alkyl, ($C_{1-10}$)oxaalkyl, ($C_{1-10}$) oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero ($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{1-10}$)aryl, ($C_{9-12}$) bicycloaryl, and hetero($C_{4-12}$)bicycloaryl, each unsubstituted or substituted.

In some other variations, said 1-3 substituents of $R_4$ are independently selected from the group consisting of halo, oxy, hydroxy, cyano, ($C_{1-6}$)alkoxy, ($C_{4-12}$)aryloxy, hetero ($C_{1-10}$)aryloxy, ($C_{1-6}$)alkyl, halo($C_{1-6}$)alkyl, hydroxy($C_{1-6}$) alkyl, aza($C_{1-6}$)alkyl, oxa($C_{1-6}$)alkyl, oxo($C_{1-6}$)alkyl, ($C_{3-12}$) cycloalkyl($C_{1-5}$)alkyl, hetero($C_{3-6}$)cycloalkyl($C_{1-5}$)alkyl, aryl($C_{1-5}$)alkyl, hetero($C_{1-10}$)aryl($C_{1-5}$)alkyl, ($C_{3-7}$)cycloalkyl, hetero($C_{3-7}$)cycloalkyl, ($C_{4-12}$)aryl, and hetero ($C_{1-10}$)aryl, each substituted or unsubstituted.

In other variations, said 1-3 substituents of $R_4$ are each independently selected from the group consisting of halo, hydroxyl, nitro, thio, oxy, cyano, ($C_{1-6}$)alkyl, ($C_{2-6}$)alkenyl, ($C_{2-6}$)alkynyl, halo($C_{1-6}$)alkyl, ($C_{1-6}$)alkoxy, hydroxyl($C_{1-6}$) alkyl, mercapto, sulfinyl, sulfonyl, sulfamoyl, amino, amido, carboxamido, carbamoyl, carbonyl and carbonyloxy, each unsubstituted or substituted. In other variation, the 1-3 substituents on $R_4$ are each independently selected from the group consisting of halo, hydroxyl, nitro, thio, oxy, cyano, ($C_{1-6}$)alkyl, ($C_{2-6}$)alkenyl, ($C_{2-6}$)alkynyl, halo($C_{1-6}$)alkyl, ($C_{1-6}$)alkoxy, hydroxyl($C_{1-6}$)alkyl, phosphonylalkyl, mercapto, sulfinyl, sulfonyl, sulfamoyl, amino, amido, carboxamido, carbamoyl, carbonyl, oxycarbonyl, carbonyloxy, hetero($C_{1-5}$)aryl, and ($C_{4-6}$)aryl, each unsubstituted or further substituted.

In still other variations, said 1-3 substituents of $R_4$ are independently selected from the group consisting of hydroxyl, nitro, fluoro, chloro, bromo, cyano, ($C_{1-6}$)alkoxy, —OCHF$_2$, —OCF$_3$, furanyloxy, ($C_{1-6}$)alkyl, halo($C_{1-6}$)alkyl, hydroxyl ($C_{1-6}$)alkyl, —CF$_3$, —CH$_2$NHC(O)OC(CH$_3$)$_3$, —C(CH$_3$)(OH)CF$_3$, hetero($C_{1-5}$)aryl($C_{1-6}$)alkyl, —C(CH$_3$)═NOH, —CH$_2$OCH$_2$CF$_3$, —NC(O)CH$_3$, —NHS(O)$_2$CH$_3$, —N(CH$_3$)$_2$, —C(O)OCH$_3$, —OCH(CH$_3$)$_2$, —SCF$_3$, -sulfonylpyrrolidinyl, hetero($C_{1-5}$)aryl, hetero($C_{1-5}$)cycloalkyl,

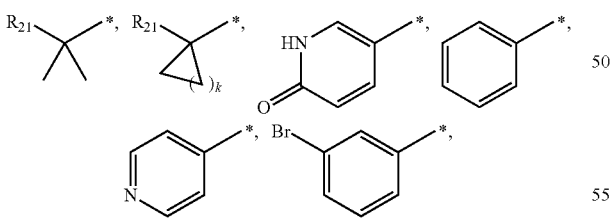

where
k is 1, 2, 3, or 4; and
each $R_{21}$ is selected from the group consisting of —(CH$_2$)$_n$OH, —C(O)OH, —C(O)OCH$_3$, cyano, —(CH$_2$)$_n$NH$_2$, —(CH$_2$)$_n$NHC(O)C(O)OH, —(CH$_2$)$_n$C(O)OH, —(CH$_2$)$_n$C(O)OCH$_3$, ($C_{1-4}$)alkyl, halo($C_{1-4}$)alkyl, —(CH$_2$)$_n$CN, —(CH$_2$)$_n$CONH$_2$, —(CH$_2$)$_n$aryl, —(CH$_2$)$_n$heteroaryl, —O(CH$_2$)$_n$aryl, —O(CH$_2$)$_n$heteroaryl, and —O(CH$_2$)$_n$CH(OH)CH$_2$OH, where n is 0, 1, 2, 3, or 4.

In some variation, $R_{21}$ is selected from the group consisting of cyano, hydroxyl, methyl, perfluorormethyl, hydroxylmethyl, —CH$_2$NH$_2$, —(CH$_2$)NHC(O)C(O)OH, —(CH$_2$)C(O)OH, —(CH$_2$)C(O)OCH$_3$, —O(CH$_2$)$_n$heteroaryl where n is 1 or 2, and —OCH$_2$CH(OH)CH$_2$OH.

In a particular variation, the 1-3 substituents is

where $R_{21}$ is selected from the group consisting of hydroxyl, ($C_{1-4}$alkyl, —CF$_3$, —(CH$_2$)OH, —(CH$_2$)CN, —(CH$_2$)C(O)OH, —(CH$_2$)CONH$_2$, —(CH$_2$)NH$_2$, —(CH$_2$)NHC(O)C(O)OH, —(CH$_2$)C(O)OCH$_3$, —O(CH$_2$)CH(OH)CH$_2$OH, —(CH$_2$)$_n$aryl, —O(CH$_2$)$_n$aryl, —(CH$_2$)$_n$heteroaryl, —O(CH$_2$)$_n$heteroaryl, where n is 0, 1, 2, 3, or 4.

Preferred $R_4$ that are aryls or heteroaryls include, but are not limited to, the following:

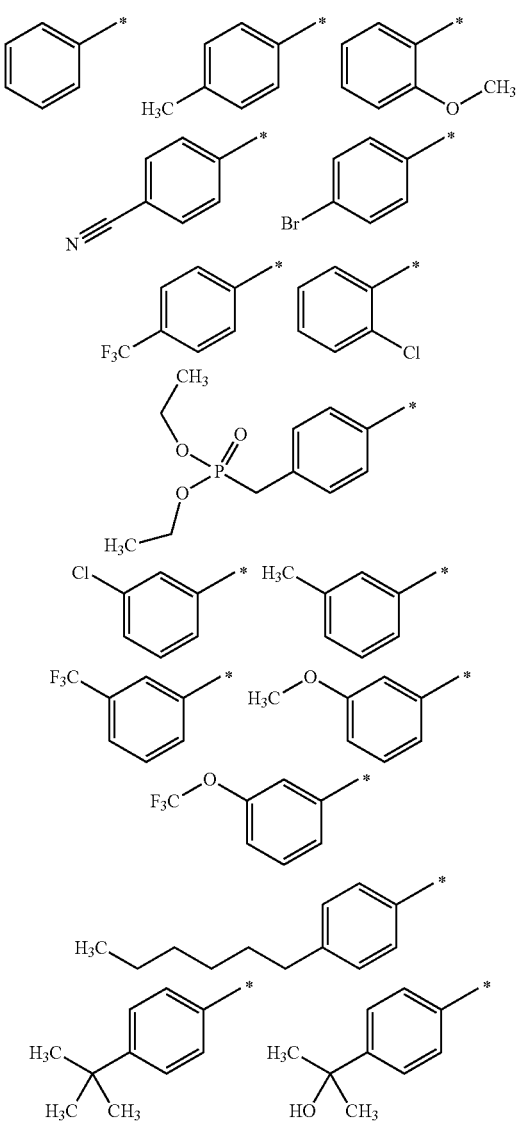

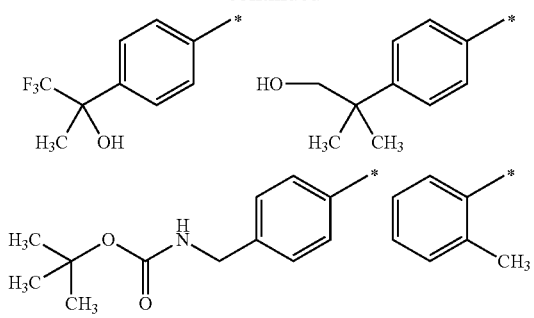
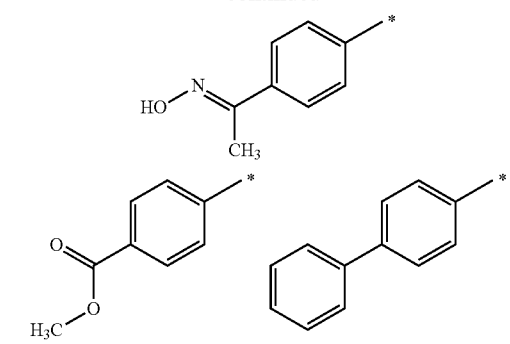
Preferred R$_4$ that are aryls or heteroaryls also include:
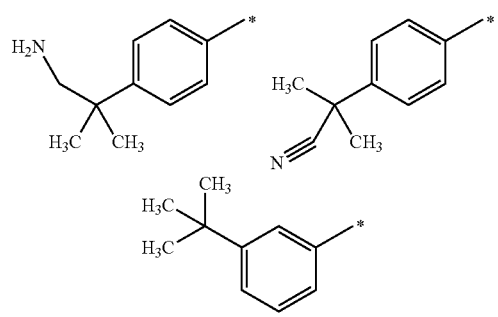
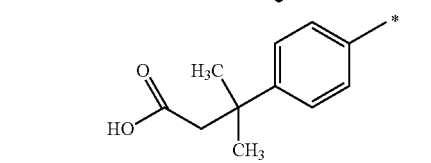
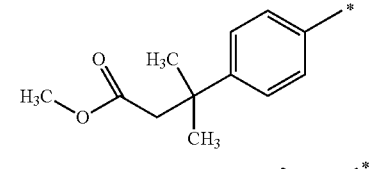
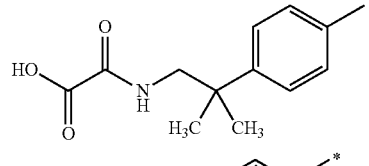
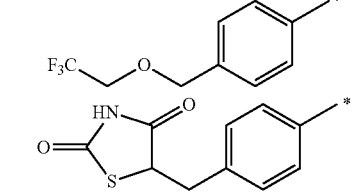
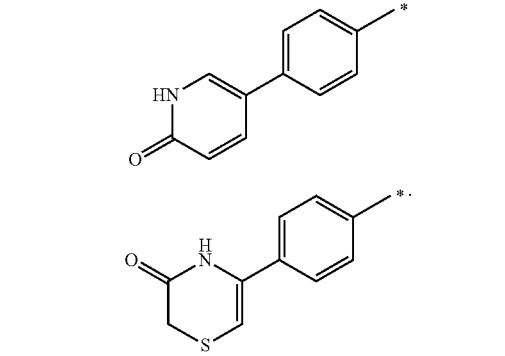
Preferred R$_4$ that are aryls or heteroaryls also include:
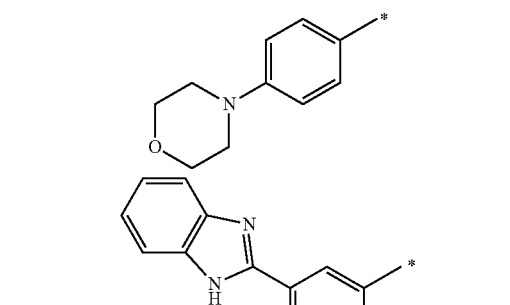
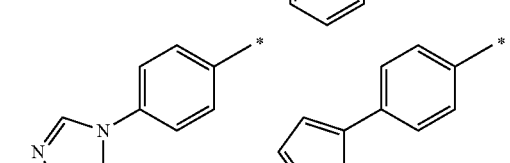
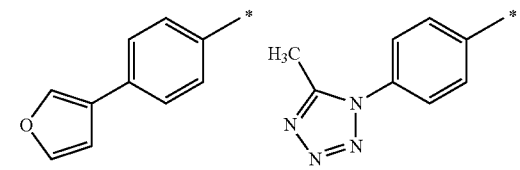
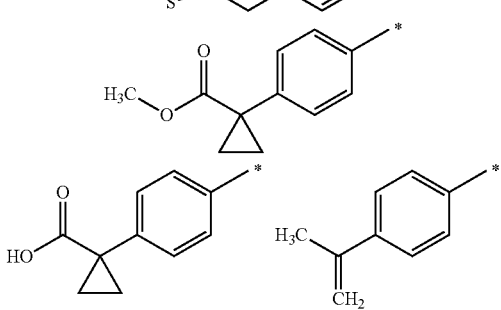
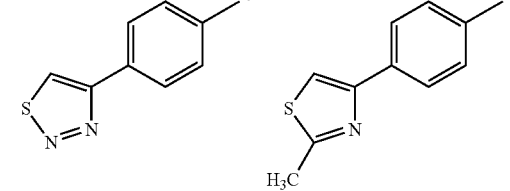

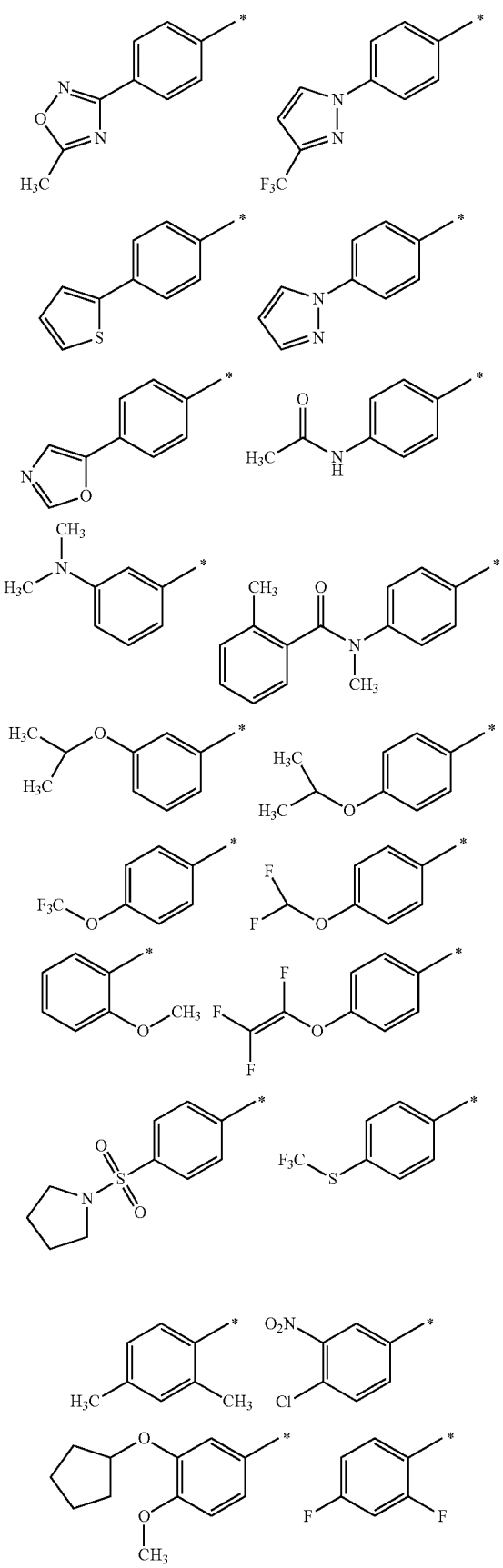
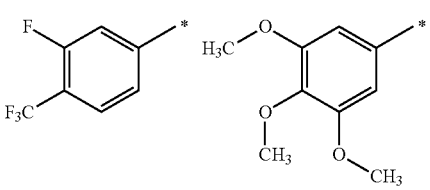
Preferred $R_4$ that are aryls or heteroaryls also include:
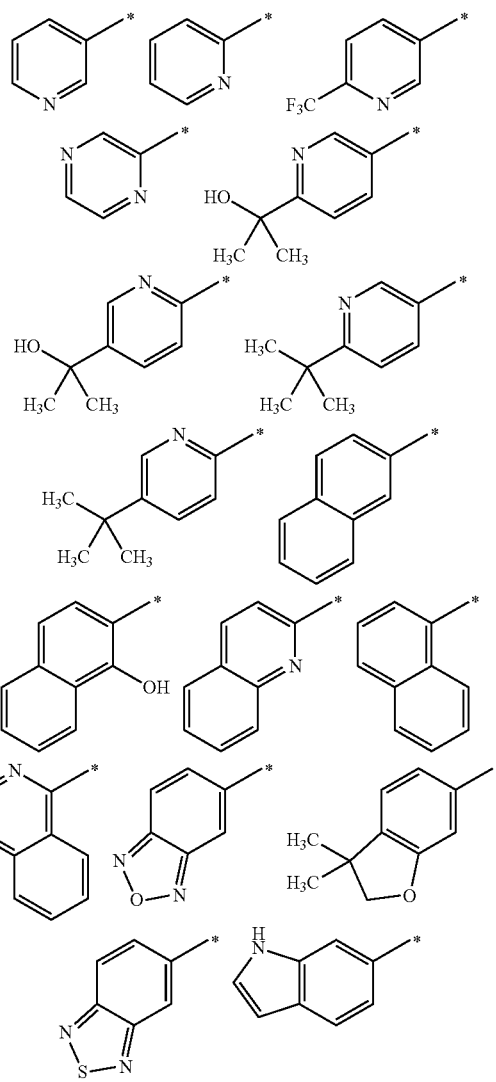
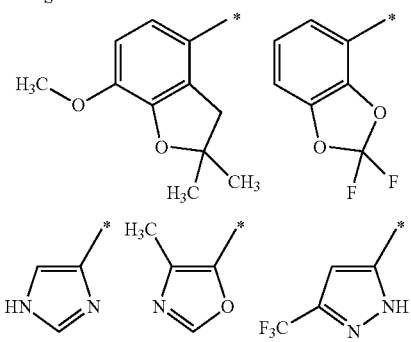

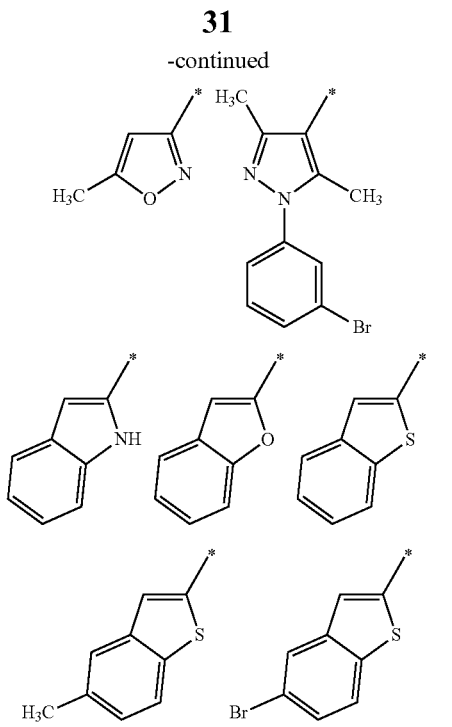
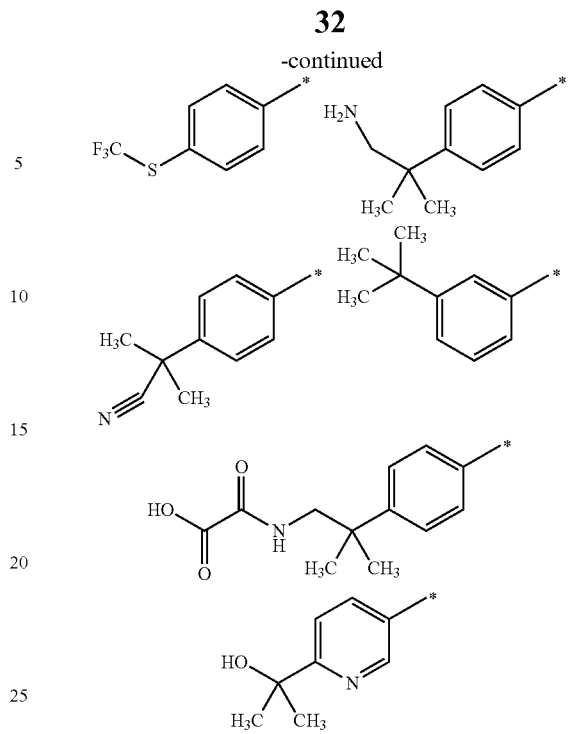

Preferred R₄ that are aryls or heteroaryls also include:

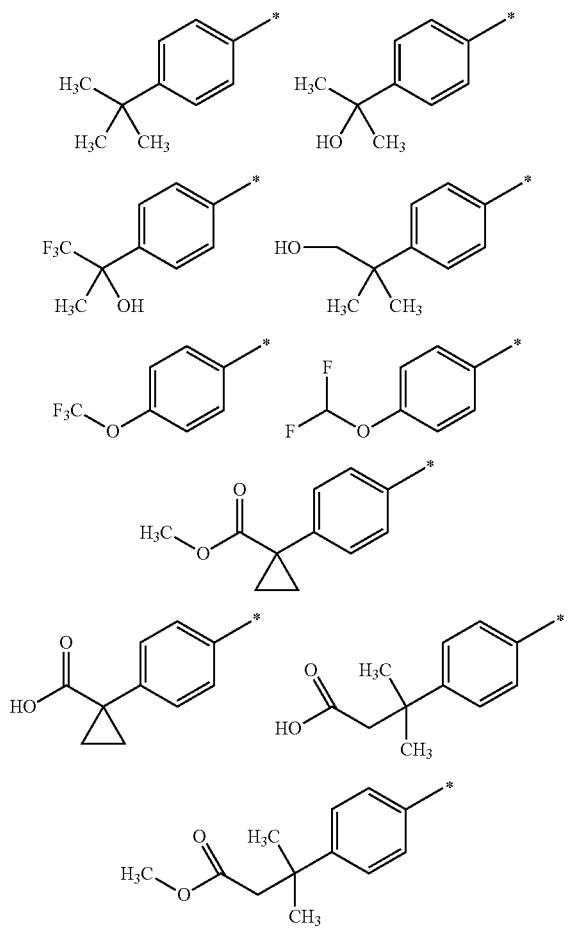

In another particular embodiment of the compound of the invention, $R_4$ is an amino consisting of the formula $—NR_{12}R_{13}$. In some variations, $R_{12}$ and $R_{13}$ are each independently selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted. In other variations, one of $R_{12}$ and $R_{13}$ is hydrogen. In other variations, both of $R_{12}$ and $R_{13}$ is hydrogen.

In another particular embodiment of the compound of the invention, $R_4$ is an oxy consisting of the formula $—OR_{14}$. In some variations, $R_{14}$ is selected from the group consisting of $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted. In other variations, $R_{14}$ is selected from the group consisting of $(C_{1-6})$alkyl, halo$(C_{1-6})$alkyl, hydroxy$(C_{1-6})$alkyl, $(C_{3-12})$cycloalkyl$(C_{1-5})$alkyl, hetero$(C_{3-12})$cycloalkyl$(C_{1-6})$alkyl, aryl$(C_{1-6})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero ($C_{4-12}$)bicycloaryl, each unsubstituted or substituted. In one preferred embodiment, $R_4$ is methoxy.

In still another particular embodiment of the compound of the invention, $R_4$ is an alkyl selected from the group selected from the group consisting of ($C_{1-6}$)alkyl or ($C_{1-6}$)alkenyl, each unsubstituted or substituted with said 1-3 substituents independently selected from the group consisting of hydroxyl, ($C_{1-6}$)alkyl, ($C_{1-6}$)alkenyl, ($C_{1-6}$)alkylthio, unsubstituted or substituted amino, unsubstituted or substituted ($C_{4-6}$)aryl, unsubstituted or substituted hetero($C_{1-5}$)aryl, unsubstituted or substituted ($C_{3-6}$)cycloalkyl, unsubstituted or substituted hetero($C_{1-5}$)cycloalkyl, unsubstituted or substituted amido, ($C_{1-6}$)alkoxy, ($C_{1-6}$)alkylcarbonyl, ($C_{4-6}$)aryloxy, and hetero($C_{1-5}$)aryloxy.

In some variation, $R_4$ is selected from the group consisting of methyl, ethyl, isopropyl, n-propyl, tert-butyl, pentyl, hexyl, ethenyl, pentenyl, each unsubstituted or substituted with 1-3 substituents independently selected from the group consisting of hydroxyl, fluoro, methyl, phenoxy, methoxy, isopropyloxy, methylthio, dimethylamino, pyridylamino, methylcarbonyl, cyclopentyl, cyclohexyl, furanyl, phenyl, 4-fluorophenyl, 4-cyanophenyl, 4-hydroxylphenyl, 4-perfluoromethylphenyl, pyridyl, biphenyl,

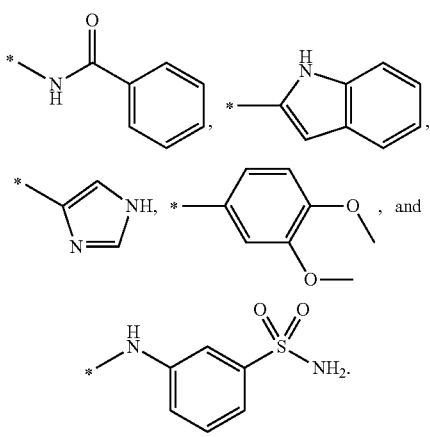

Preferred $R^4$ that are alkyls is selected from the group consisting of methyl,ethyl, isopropyl, tert-butyl, hexyl, hydroxyl ($C_{1-6}$)alkyl, —($CH_2)_2SCH_3$, —$CH_2CF_3$, —($CH_2)_2OCH_3$, —($CH_2)_3N(CH_2)_2$, —$CH_2C(CH_3)CH_2C(CH_3)_3$, —$C(CH_3)_2OH$, —($CH_2)_2C(O)CH_3$, —($CH_2)_5CH_3$, —($CH_2)_3$ $CH_2$=$CH_2$, and

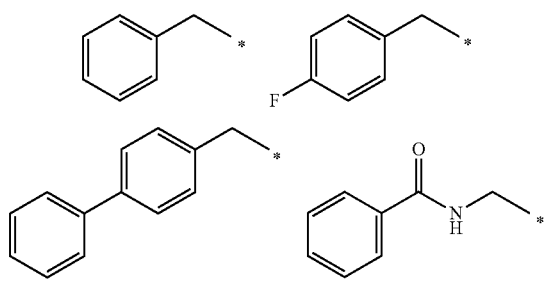

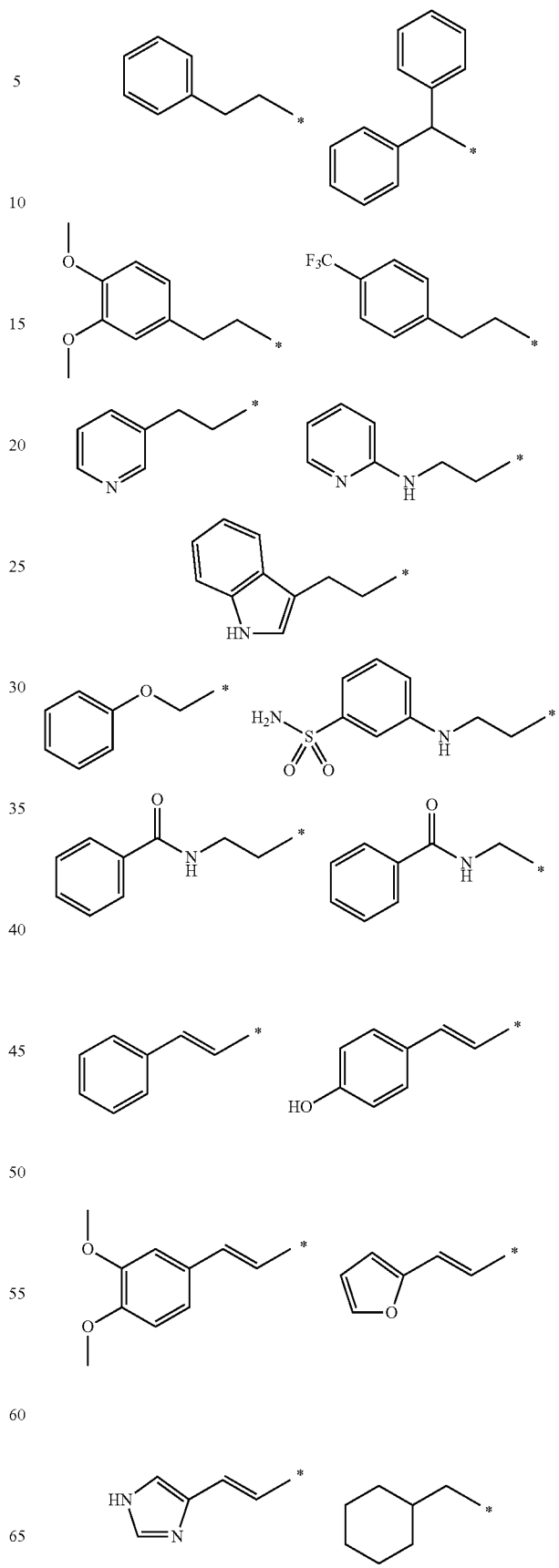

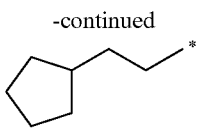

A preferred embodiment of R$_4$ is an unsubstituted or substituted phenyl consisting of the formula

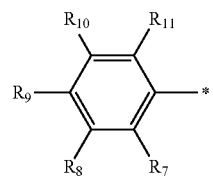

where
R$_7$, R$_8$, R$_9$, R$_{10}$, and R$_{11}$ are each independently selected from the group consisting of hydrogen, halo, hydroxyl, nitro, thio, oxy, cyano, (C$_{1-6}$)alkyl, (C$_{2-6}$)alkenyl, (C$_{2-6}$) alkynyl, halo(C$_{1-6}$)alkyl, (C$_{1-6}$)alkoxy, hydroxyl(C$_{1-6}$) alkyl, phosphonylalkyl, mercapto, sulfinyl, sulfonyl, sulfamoyl, amino, amido, carboxamido, carbamoyl, carbonyl, oxycarbonyl, carbonyloxy, hetero(C$_{1-5}$)aryl, and (C$_{4-6}$)aryl, and each unsubstituted or substituted; provided at least two of R$_7$, R$_8$, R$_9$, R$_{10}$, and R$_{11}$ are hydrogen.

In some variations of the above preferred embodiment of R$_4$, R$_7$, R$_8$, R$_9$, R$_{10}$, and R$_{11}$ are each independently selected from the group consisting of hydroxyl, nitro, fluoro, chloro, bromo, cyano, (C$_{1-6}$)alkoxy, —OCHF$_2$, —OCF$_3$, furanyloxy, (C$_{1-6}$)alkyl, halo(C$_{1-6}$)alkyl, hydroxyl(C$_{1-6}$)alkyl, —CF$_3$, —CH$_2$NHC(O)OC(CH$_3$)$_3$, —C(CH$_3$)(OH)CF$_3$, hetero(C$_{1-5}$) aryl(C$_{1-6}$)alkyl, —C(CH$_3$)=NOH, —CH$_2$OCH$_2$CF$_3$, —NC (O)CH$_3$, —NHS(O)$_2$CH$_3$, —N(CH$_3$)$_2$, —C(O)OCH$_3$, —OCH(CH$_3$)$_2$, —SCF$_3$, -sulfonylpyrrolidinyl, hetero(C$_{1-5}$) aryl, hetero(C$_{1-5}$)cycloalkyl,

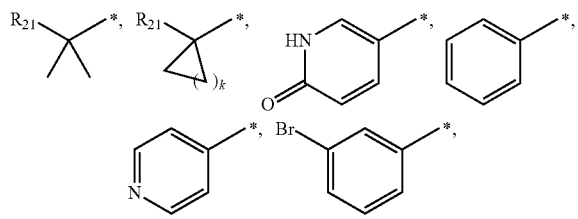

where
k is 1, 2, 3, or 4; and
R$_{21}$ is selected from the group consisting of —(CH$_2$)$_n$OH, —C(O)OH, —C(O)OCH$_3$, cyano, —(CH$_2$)$_n$NH$_2$, —(CH$_2$)$_n$NHC(O)C(O)OH, —(CH$_2$)$_n$C(O)OH, —(CH$_2$)$_n$C(O)OCH$_3$, (C$_{1-4}$)alkyl, halo(C$_{1-4}$)alkyl, —(CH$_2$)$_n$CN, —(CH$_2$)$_n$CONH$_2$, —(CH$_2$)$_n$aryl, —(CH$_2$)$_n$heteroaryl, —O(CH$_2$)$_n$aryl, —O(CH$_2$)$_n$heteroaryl, and —O(CH$_2$)$_n$CH(OH)CH$_2$OH, where n is 0, 1, 2, 3, or 4. In some variations, R$_{21}$ is selected from the group consisting of cyano, hydroxyl, methyl, perfluorormethyl, hydroxylmethyl, —CH$_2$NH$_2$, —(CH$_2$)C(O) OH, —(CH$_2$)C(O)OCH$_3$, —(CH$_2$)NHC(O)C(O)OH, —OCH$_2$CH(OH)CH$_2$OH, and —O(CH$_2$)$_n$heteroaryl where n is 1 or 2.

In other variation of the above preferred embodiment of R$_4$, R$_9$ is independently selected from the group consisting of hydrogen, tert-butyl, —CF$_3$, —C(CH$_3$)(OH)CF$_3$, —C(CH$_3$)$_2$CF$_3$, —C(CH$_3$)$_2$OH, —C(CH$_3$)$_2$(CH$_2$OH), —C(O)OCH$_3$,

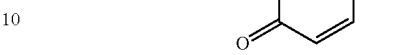

—C(CH$_3$)$_2$(OCH$_2$CH(OH)CH$_2$OH), —C(CH$_3$)$_2$CN, —C(CH$_3$)$_2$CH$_2$CN, —C(CH$_3$)$_2$O(CH$_2$)$_n$heteroaryl where n is 1 or 2, and R$_7$, R$_8$, R$_{10}$, and R$_{11}$ are each hydrogen. In some other variations, R$_9$ is selected from the group consisting of tert-butyl and —C(CH$_3$)$_2$OH. In still other variations, R$_9$ is tert-butyl. In still other variations, R$_9$ is —C(CH$_3$)$_2$OH.

In some preferred embodiments of the compounds of the invention, R$_4$ is selected from the group consisting of:

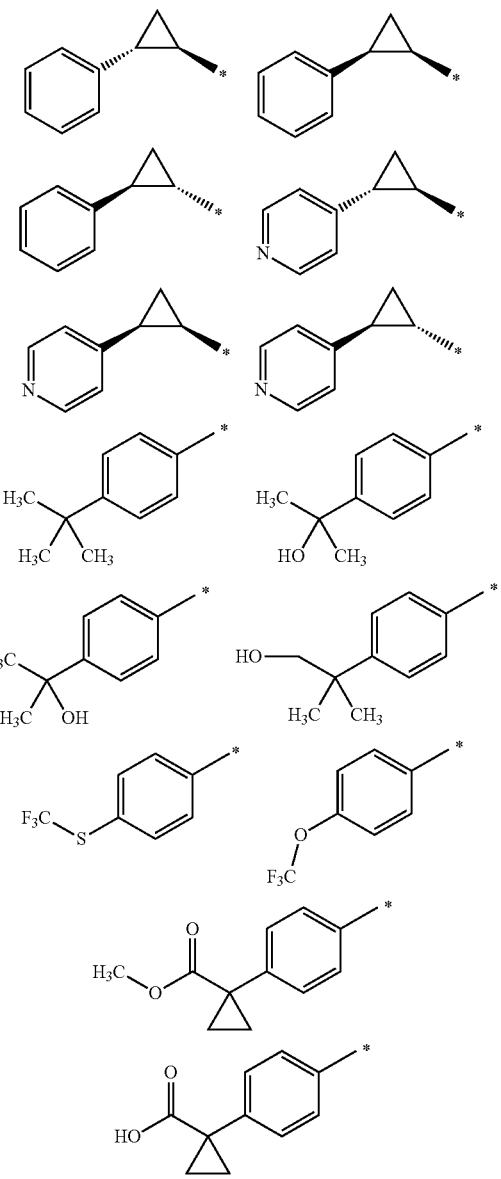

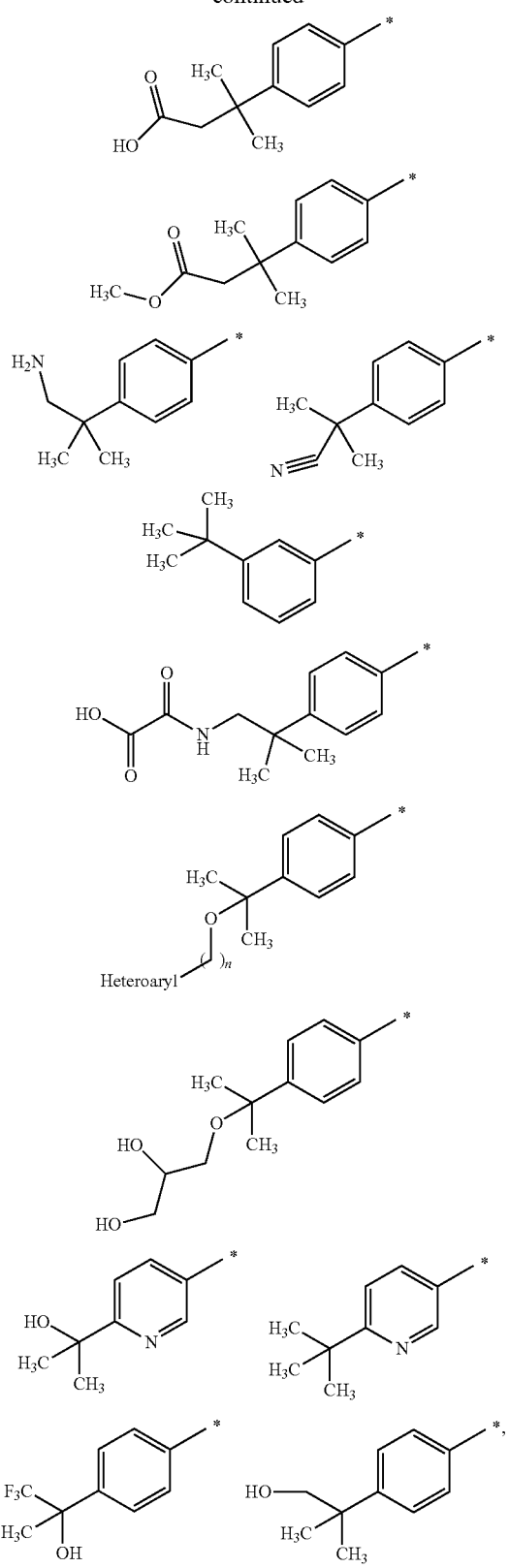

where n is 0, 1, 2, 3 or 4

In other preferred embodiments of the compounds of the invention, $R_4$ is selected from the group consisting of:

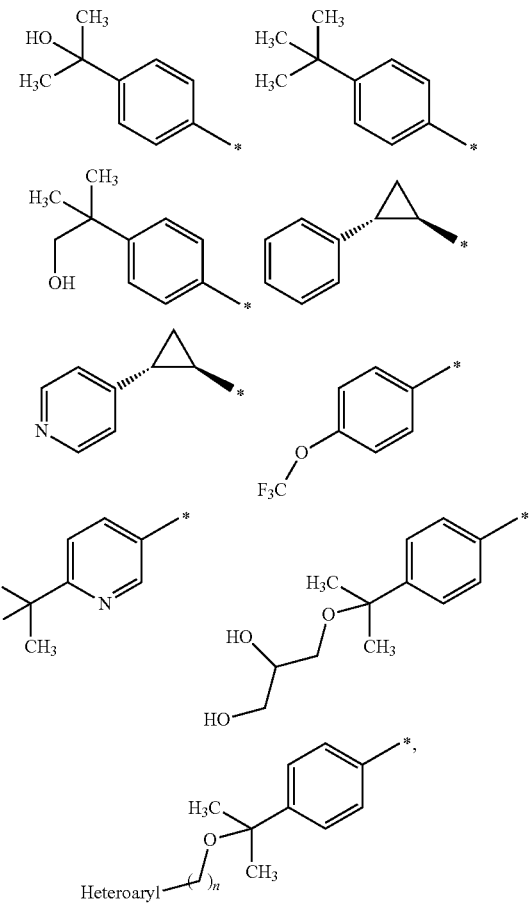

where n is 0, 1, 2, 3 or 4

$R_2$

In all the above embodiments and variations of the compounds of the invention, $R_2$ is selected from the group consisting of amino, oxy, thio, halo, $(C_{1-10})$alkylamino, $(C_{1-10})$alkyl, $(C_{1-10})$alkenyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted with 1-3 substituents, wherein each of said 1-3 substituents is independently selected from the group consisting of hydroxyl, halo, nitro, cyano, oxo, hydroxy, thio, $(C_{1-6})$alkylthio, oxy, arylalkyloxy, carbonyloxy, $(C_{1-10})$alkoxy, $(C_{4-12})$aryloxy, hetero$(C_{1-10})$aryloxy, aminocarbonyloxy, carbonyl, $(C_{1-6})$alkylcarbonyl, oxycarbonyl, aminocarbonyl, amino, amido, carboxamido, $(C_{1-10})$alkylamino, acetylamino, sulfonamido, imino, sulfonyl, $(C_{1-6})$alkylsulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or further substituted.

In some variations of the above embodiments and variations of the compounds of the invention, $R_2$ is a cyclic moiety selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10}$aryl, $(C_{9-12})$bicycloaryl and hetero$(C_{4-12})$bicycloaryl, each unsubstituted or substituted with said 1-3 substituents defined above.

In some other variations $R_2$ is selected from the group consisting of furanyl, thienyl, pyrrolyl, pyrrolidinyl, oxazolyl, thiazolyl, imidazolyl, pyrazolyl, triazolyl, isoxazolyl, oxadiazolyl, thiadiazolyl, phenyl, pyridyl, pyrazinyl, pyrimidinyl, pyranyl, thiopyranyl, tetrahydrothiopyranyl, piperidinyl, piperazinyl, pyridazinyl, triazinyl, indolyl, isoindolyl, indolizinyl, benzimidazolyl, purinyl, naphthalenyl, quinolinyl, isoquinolinyl, cinnolinyl, phthalazinlyl, quinazolinyl, quinoxalinyl, naphthyridinyl, pteridinyl, morpholino, thiomorpholinyl, cyclohexyl, cyclopentyl, cyclohexenyl, and cyclopentenyl, each unsubstituted or substituted with said 1-3 substituents.

In other variations, $R_2$ is selected from the group consisting of

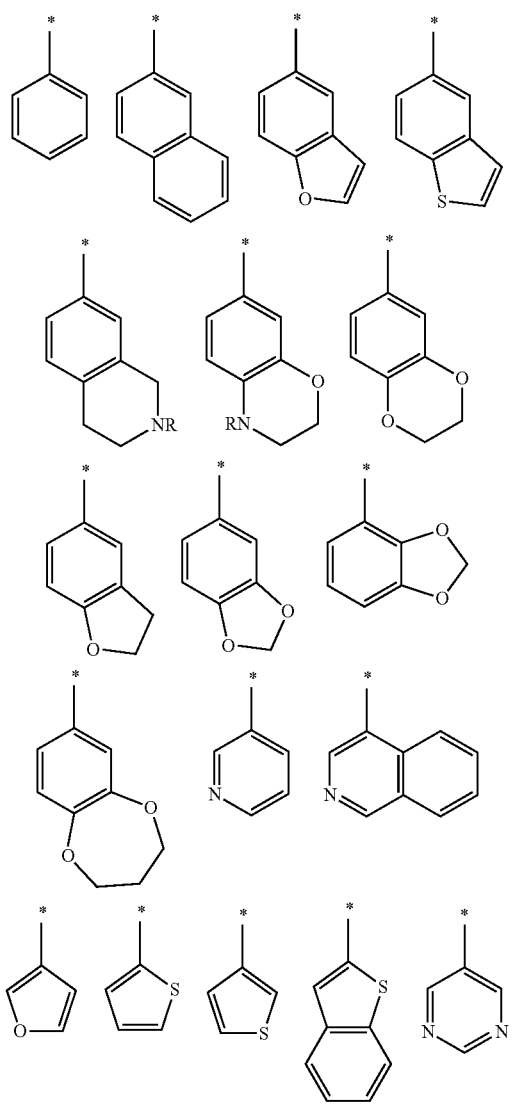

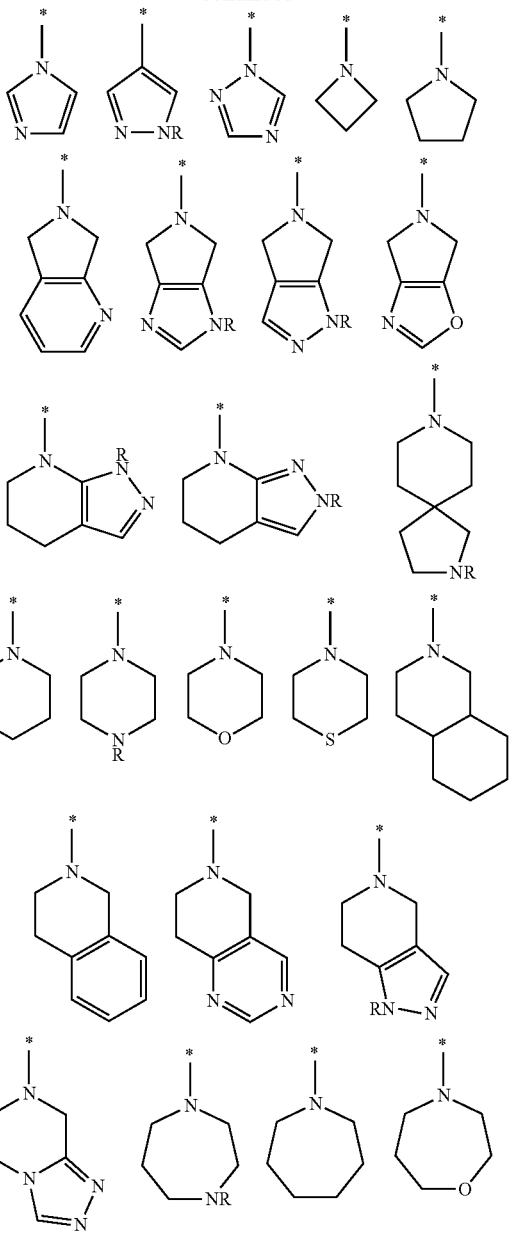

each of which is unsubstituted or substituted with said 1-3 substituents, wherein R is hydrogen or is one of the 1-3 substituents.

In still other variations $R_2$ is a phenyl, unsubstituted or substituted with 1-3 substituents. In yet still other variations, $R_2$ is a pyridyl, unsubstituted or substituted with 1-3 substituents. In yet still other variations, $R_2$ is a morpholinyl, unsubstituted or substituted with 1-3 substituents In all the above embodiments and variation of the compounds of the invention, where $R_2$ is a cyclic moiety, in some variations, the 1-3 substituents of $R_2$ are each independently selected from the group consisting of hydroxy, nitro, halo, cyano, oxo, oxy, $(C_{1-6})$alkoxy, $(C_{4-6})$aryloxy, $(C_{4-6})$aryl$(C_{1-6})$alkyloxy, aminocarbonyloxy, $(C_{1-6})$alkyl, $(C_{1-6})$haloalkyl, hydroxy$(C_{1-6})$alkyl, aminocarbonyl$(C_{1-6})$alkyl, cyanoalkyl, $(C_{1-6})$haloalkyloxy, $(C_{4-6})$aryl$(C_{1-6})$alkyloxy, thio, $(C_{1-6})$alkylthio, amino, sulfonylamino, $(C_{1-6})$alkylamino, $(C_{1-6})$alkylsulfonylamino, amido, aryl, aryl$(C_{1-6})$alkyl, $(C_{1-6})$alkylcarbonyl, $(C_{1-6})$alkyloxycarbonyl, carboxamido, hydroxycarbonyl, aminocarbonyl, and sulfonyl, $(C_{1-6})$alkylsulfonyl.

In some other variations, the 1-3 substituents of $R_2$ are each independently selected from the group consisting of hydroxy, nitro, halo, cyano, oxo, $(C_{1-6})$alkoxyl, $(C_{1-6})$alkyl, $(C_{1-6})$haloalkyl, hydroxy$(C_{1-6})$alkyl, cyanoalkyl, $(C_{1-6})$haloalkoxy, $(C_{1-6})$alkylthio, alkylsulfonylamino, amido, carboxamido, aryl and aryl$(C_{1-6})$alkyl, alkyloxycarbonyl, hydroxycarbonyl, aminocarbonyl, and alkylsulfonyl.

In still other variations, the 1-3 substituents of $R_2$ are each independently selected from the group consisting of hydroxyl, nitro, fluoro, chloro, cyano, oxo, methyl, perfluoromethyl, —CH(CH$_3$)CH$_2$CH$_3$, isobutyl, tert-butyl, hydroxy $(C_{1-6})$alkyl, cyanomethyl, methylthio, methoxy, perfluoromethyloxy, hydroxycarbonyl, aminocarbonyl, methylcarbonyl, ethyloxycarbonyl. methylcarboxamido, methylamido, methylsulfonyl, methylsulfonylamino, phenyl, and benzyl.

In still other variations, the 1-3 substituents of $R_2$ are each independently selected from the group consisting of hydroxyl, nitro, oxo, fluoro, chloro, cyano, cyanomethyl, methyl, isobutyl, tert-butyl, —CF$_3$, —C(CH$_3$)CH$_2$CH$_3$, —CH$_2$C(O)CH$_3$, —CH$_2$C(O)NH$_2$, —CH$_2$OH, —(CH$_2$)$_2$OH, —(CH$_2$)$_3$OH, —CH$_2$OCH$_3$, —C(O)CH$_3$, —C(O)CH$_3$, —C(O)CH$_2$CH$_3$, —C(O)NH$_2$, —NH$_2$, —N(CH$_3$)$_2$, —NHC(O)CH$_3$, —NHS(O)$_2$CH$_3$, —NHS(O)$_2$-phenyl, —OCH$_3$, —OCF$_3$, —OC(O)NHR where R is $(C_{1-6})$alkyl, $(C_{3-6})$cycloalkyl, hetero$(C_{1-5})$cycloalkyl, $(C_{4-6})$aryl, hetero$(C_{1-5})$aryl; —S(O)$_2$CH$_3$, —SCH$_3$, unsubstituted or substituted phenyl, and unsubstituted or substituted benzyl.

It is noted that the invention encompasses compounds where $R_2$ is an amino consisting of the formula —NR$_5$R$_6$.

In some variations where $R_2$ is —NR$_5$R$_6$, one of $R_5$ and $R_6$ is hydrogen and the other of $R_5$ and $R_6$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, cyano$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-5})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted with said 1-3 substituents.

In some other variations, $R_5$ and $R_6$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-3 substituents; provided that only one of $R_5$ and $R_6$ can be hydrogen.

In other variations, $R_5$ and $R_6$ are each independently selected from the group consisting of hydrogen, carbonyloxy, $(C_{1-10})$alkoxy, $(C_{4-12})$aryloxy, hetero$(C_{1-10})$aryloxy, sulfonyl, $(C_{1-10})$alkyl, hydroxy$(C_{1-10})$alkyl, carbonyl$(C_{1-10})$alkyl, sulfonyl$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-3 substituents; provided that only one of $R_5$ and $R_6$ can be hydrogen.

In still other variations, $R_5$ and $R_6$ are each independently selected from the group consisting of hydrogen, hydroxyl, methyl, n-butyl, isobutyl, tert-butyl, —(CH$_2$)$_2$OCH$_3$, —CH$_2$CH(CH$_3$)$_2$, —(CH$_2$)$_2$OH, —(CH$_2$)$_3$OH, —(CH$_2$)$_2$NHC(O)CH$_3$, —(CH$_2$)$_2$OCH(CH$_3$)$_2$, —(CH$_2$)$_3$SCH$_3$, —(CH$_2$)$_2$C(O)NH$_2$, —(CH$_2$)$_2$OCH$_3$, —CH(CH$_2$CH$_3$)$_2$, —CH$_2$C(O)NH$_2$, —(CH$_2$)$_2$N(CH$_3$)$_2$, and

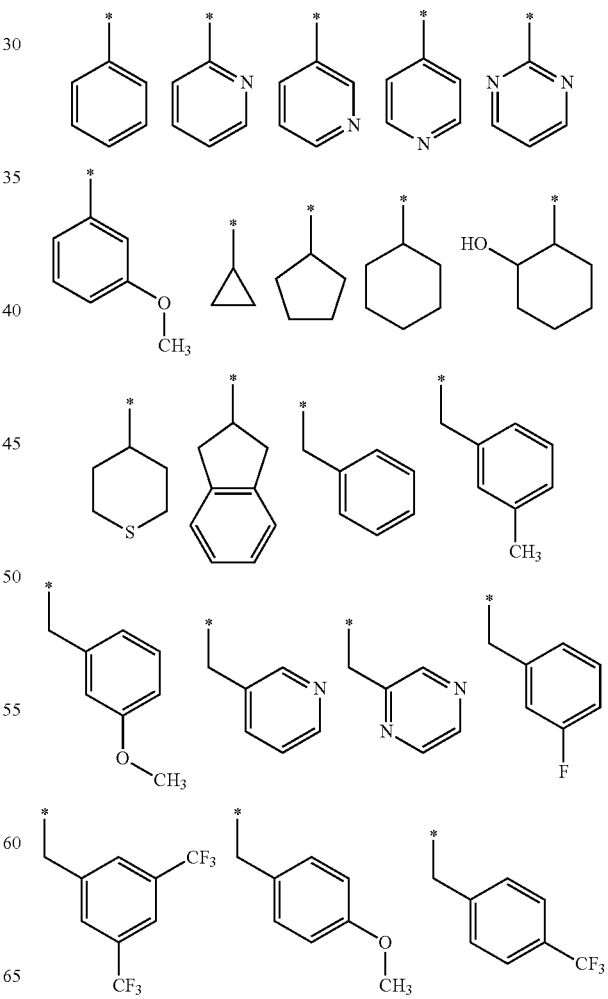

-continued

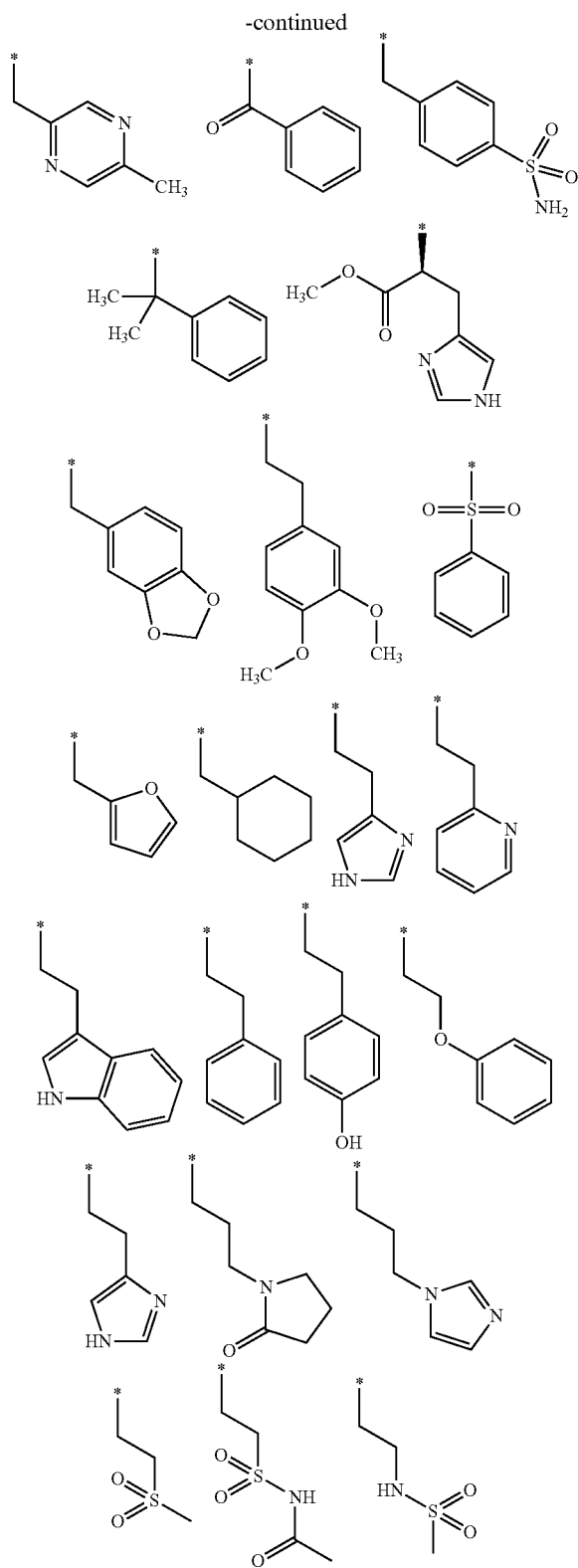

each unsubstituted or substituted with 1-3 substituents; provided that only one of $R_5$ and $R_6$ can be hydrogen.

In the above embodiments and variations where $R_2$ is $-NR_5R_6$, it is noted that $R_5$ and $R_6$ may be independently unsubstituted or substituted with 1-3 substituents. In some variations, the 1-3 substituents of $R_5$ and $R_6$, are each independently selected from the group consisting of hydroxyl, halo, nitro, cyano, thio, oxy, oxo, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, amido, carboxamido, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl $(C_{1-10})$alkyl, sulfinyl$(C_{1-10})$alkyl, aza$(C_{1-10})$alkyl, $(C_{1-10})$oxa alkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each unsubstituted or substituted.

In some other variations, the 1-3 substituents of $R_5$ or $R_6$, are each independently selected from the groups consisting of halo, nitro, cyano, thio, oxy, hydroxy, $(C_{1-10})$alkoxy, $(C_{4-12})$aryloxy, hetero$(C_{1-10})$aryloxy, carbonyl, oxycarbonyl, aminocarbonyl, amino, sulfonyl, $(C_{1-10})$alkyl, halo$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, hetero $(C_{1-10})$alkyl, $(C_{3-12})$cycloalkyl, hetero$(C_{3-12})$cycloalkyl, $(C_{4-12})$aryl, and hetero$(C_{1-10})$aryl, each unsubstituted or substituted.

In other variations, the 1-3 substituents of $R_5$ or $R_6$ are each independently selected from the group consisting of hydroxyl, nitro, fluoro, chloro, cyano, methyl, perfluoromethyl, isobutyl, tert-butyl, hydroxymethyl, hydroxyethyl, hydroxypropyl, cyanomethyl, methylthio, methoxy, perfluoromethyloxy, hydroxycarbonyl, aminocarbonyl, methylcarbonyl, ethyloxycarbonyl, methylcarboxamido, methylamido, methylsulfonyl, aminosulfonyl, methylsulfonylamino, phenyl, and benzyl, each unsubstituted or substituted.

In still other variation, the 1-3 substituents of $R_5$ and $R_6$ are each independently selected from the group consisting of fluoro, hydroxyl, methoxy, perfluoromethyl, and $-S(O)_2NH_2$.

It is noted that the invention encompasses compounds where $R_2$ is an alkyl.

In these embodiments and variations of compounds of the invention, $R_2$ is substituted $(C_{1-6})$alkyl or $(C_{1-6})$alkenyl, each substituted with 1-3 substituents, where the 1-3 substituents are each independently selected from the group consisting of $(C_{1-10})$alkoxy, $(C_{1-10})$alkyl, halo$(C_{1-10})$alkyl, hydroxy$(C_{1-10})$ alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each unsubstituted or substituted. In other variations, each of said 1-3 substituents is independently selected from the group consisting of $(C_{1-6})$cycloalkyl, hetero$(C_{1-5})$cycloalkyl, $(C_{4-6})$aryl, and hetero$(C_{1-5})$aryl, each unsubstituted or substituted with one or more substituents independently selected from the group consisting of halo, $(C_{1-6})$alkyl and $(C_{1-6})$alkoxy.

It is noted that the invention also encompasses compounds where $R_2$ is a thio moiety. In these embodiments and variations of the compounds, $R_2$ is a thio consisting of the formula $-SR_{15}$, where $R_{15}$ is selected from the group consisting of $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, $(C_{3-12})$cycloalkyl$(C_{1-5})$alkyl, hetero $(C_{3-12})$cycloalkyl$(C_{1-10})$alkyl, aryl$(C_{1-10})$alkyl, hetero$(C_{1-10})$ aryl$(C_{1-5})$alkyl, $(C_{9-12})$bicycloaryl$(C_{1-5})$alkyl, hetero$(C_{8-12})$ bicycloaryl$(C_{1-5})$alkyl, hetero$(C_{1-10})$alkyl, $(C_{3-12})$cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted.

It is noted that the invention also encompasses compounds where $R_2$ is a oxy moiety. In these embodiments and variations of the compounds, $R_2$ consisting the formula —$OR_{16}$, where $R_{16}$ is selected from the group consisting of carbonyl, ($C_{1-10}$)alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$)alkyl, sulfinyl($C_{1-10}$)alkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted. In other variations, $R_{16}$ is —$(CH_2)_2S(O)_2CH_3$, methyl, n-butyl and phenyl.

Preferred $R_2$ for the compounds of the invention include, but are not limited to, the following.

In some embodiments of the compounds of the invention where $R_2$ is cyclyl, $R_2$ is selected from the group consisting of

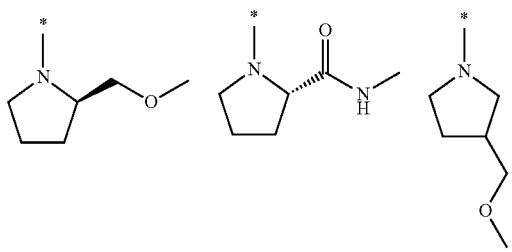

-continued

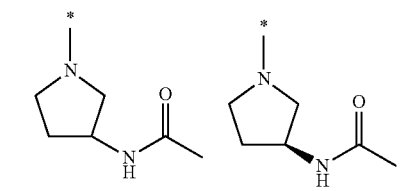

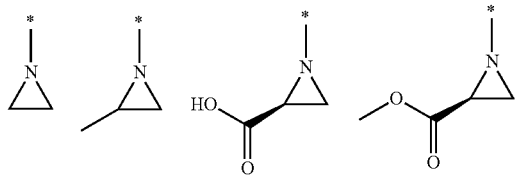

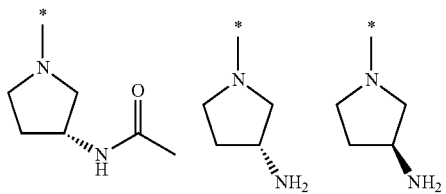

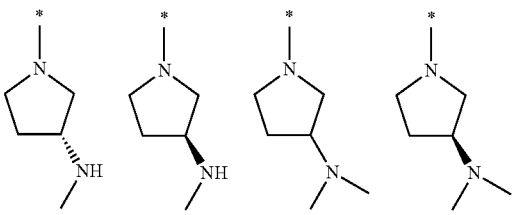

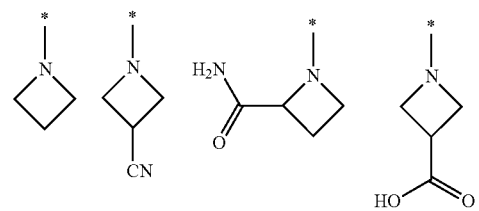

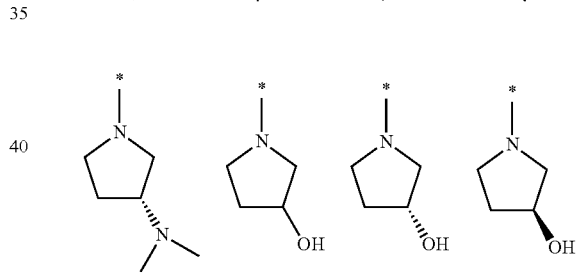

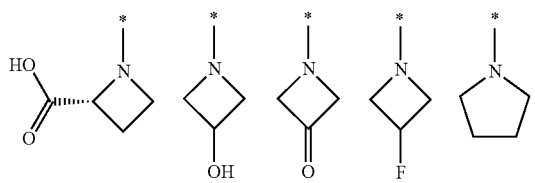

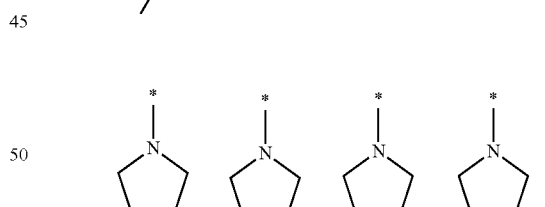

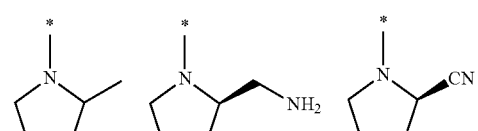

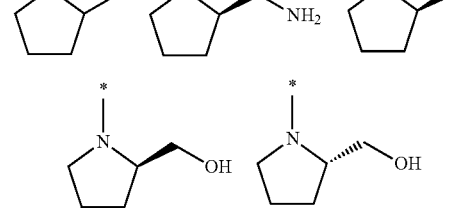

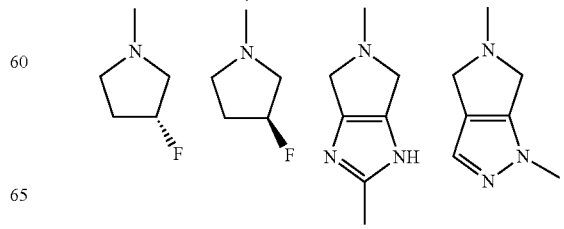

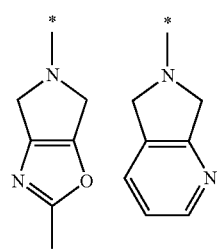
In some other embodiments where $R_2$ is cyclyl, $R_2$ is selected from the group consisting of
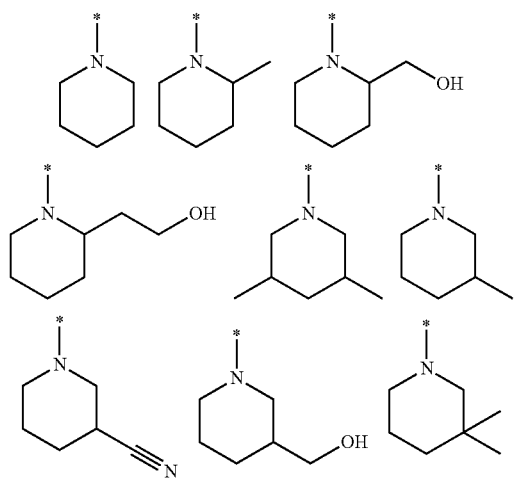
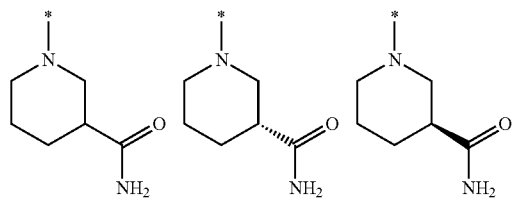
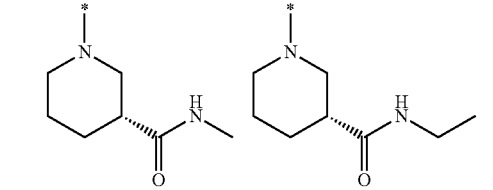
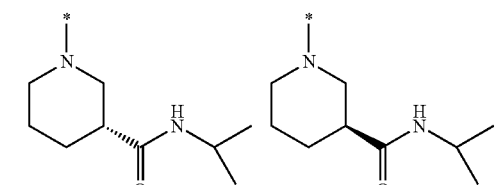
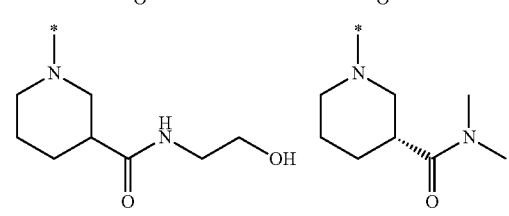
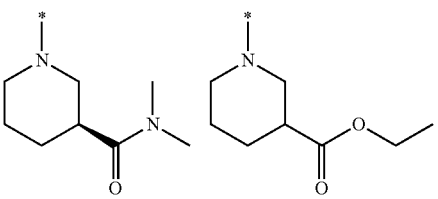
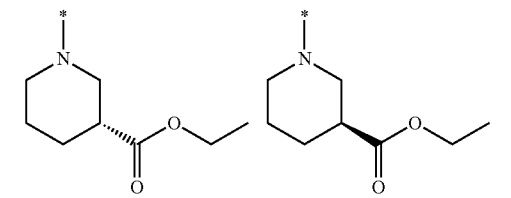
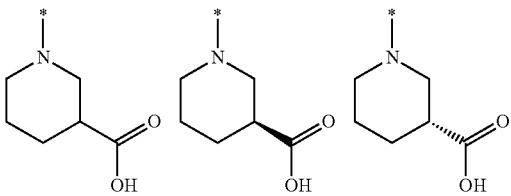
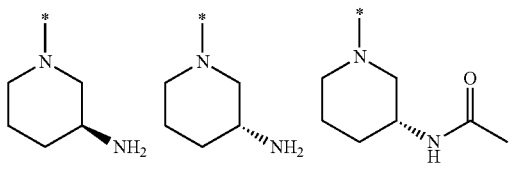
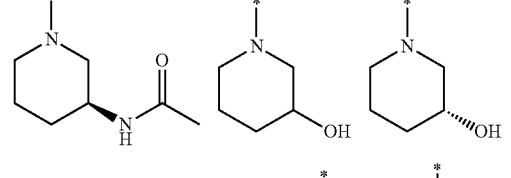
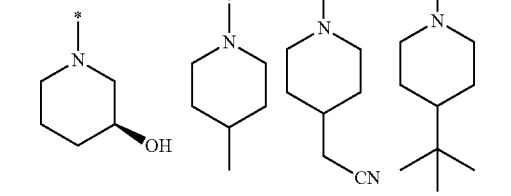
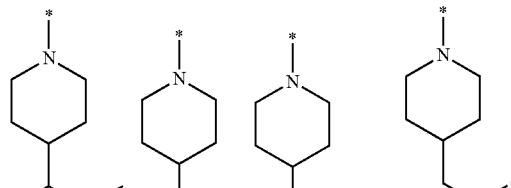

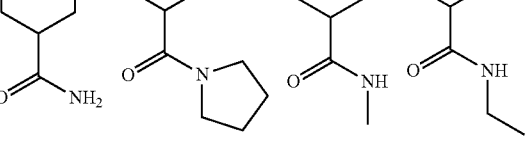

-continued
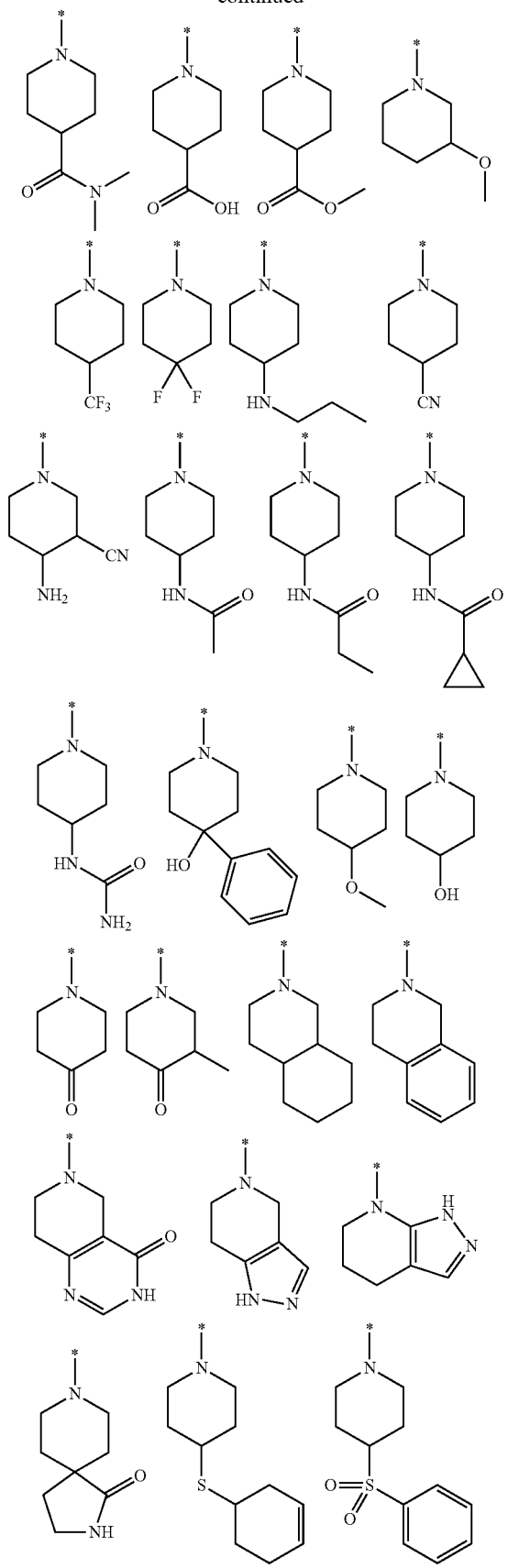
In other embodiments where $R_2$ is cyclyl, $R_2$ is selected from the group consisting of
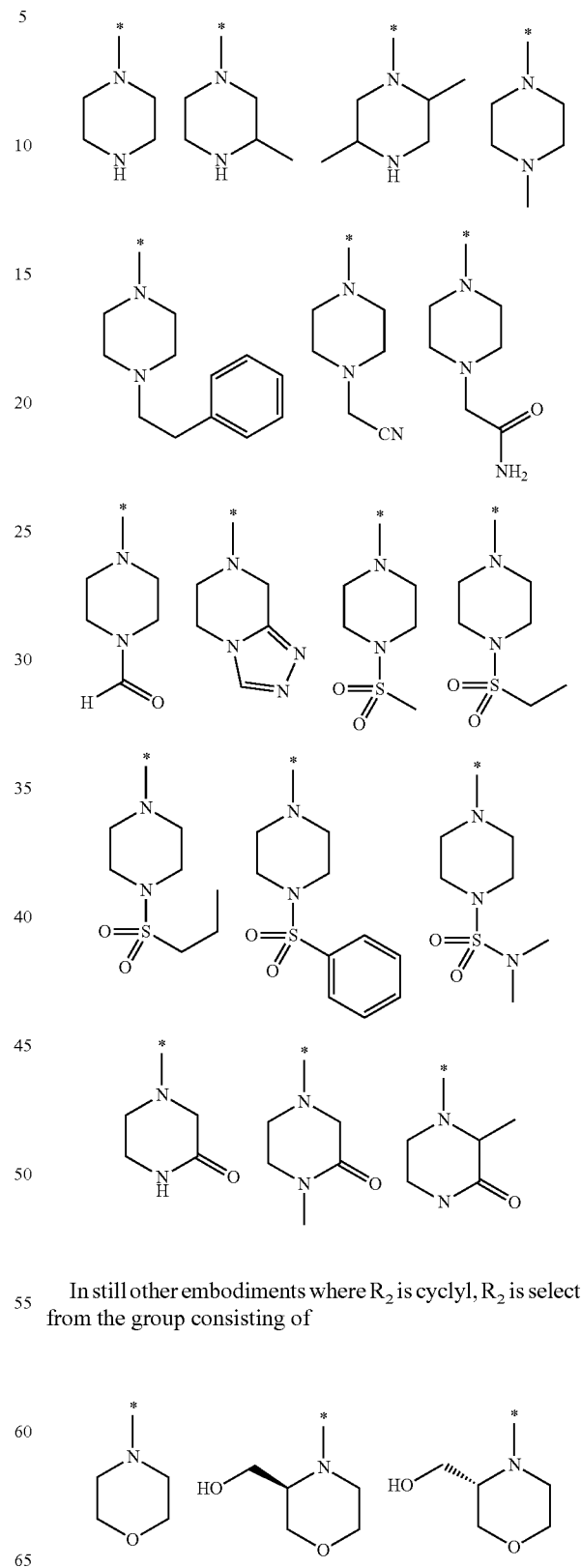
In still other embodiments where $R_2$ is cyclyl, $R_2$ is selected from the group consisting of

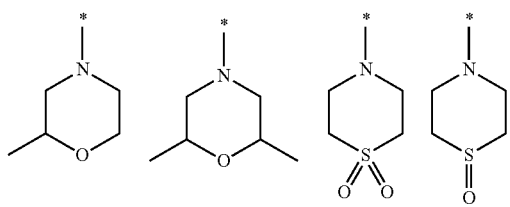
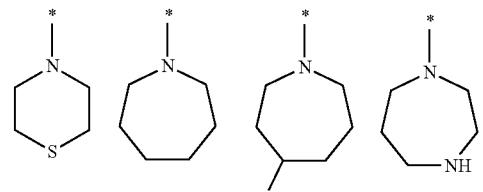
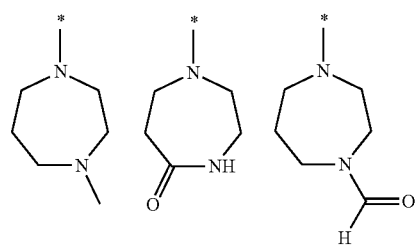
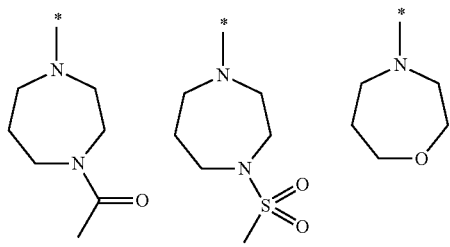
In still other embodiments where $R_2$ is cyclyl, $R_2$ is selected from the group consisting of
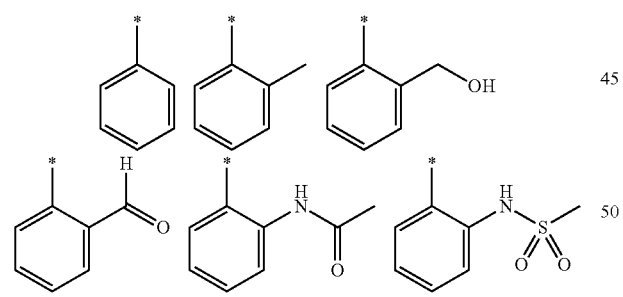
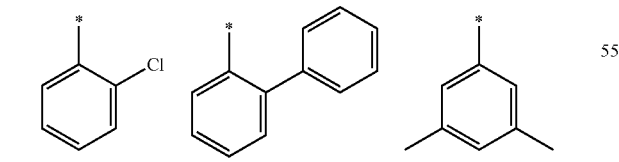
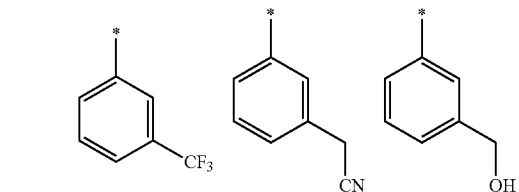
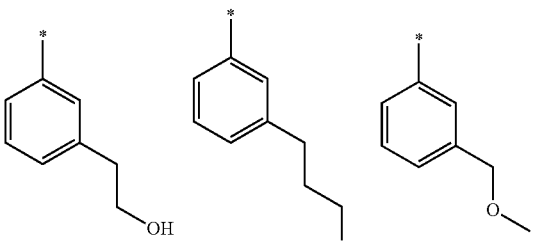
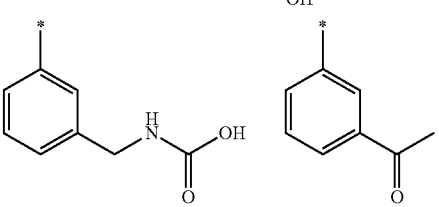
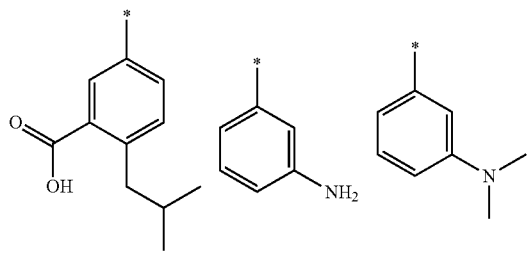
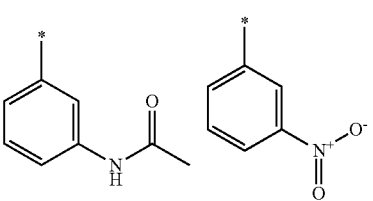
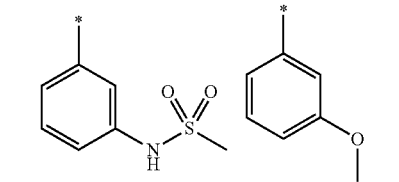
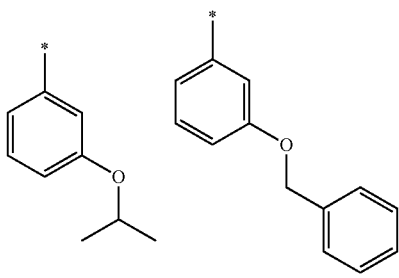
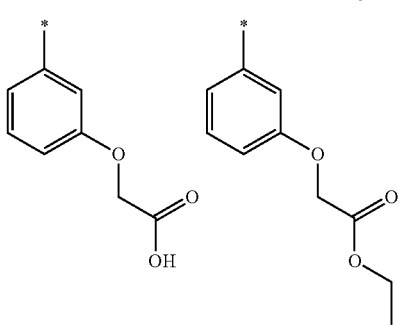

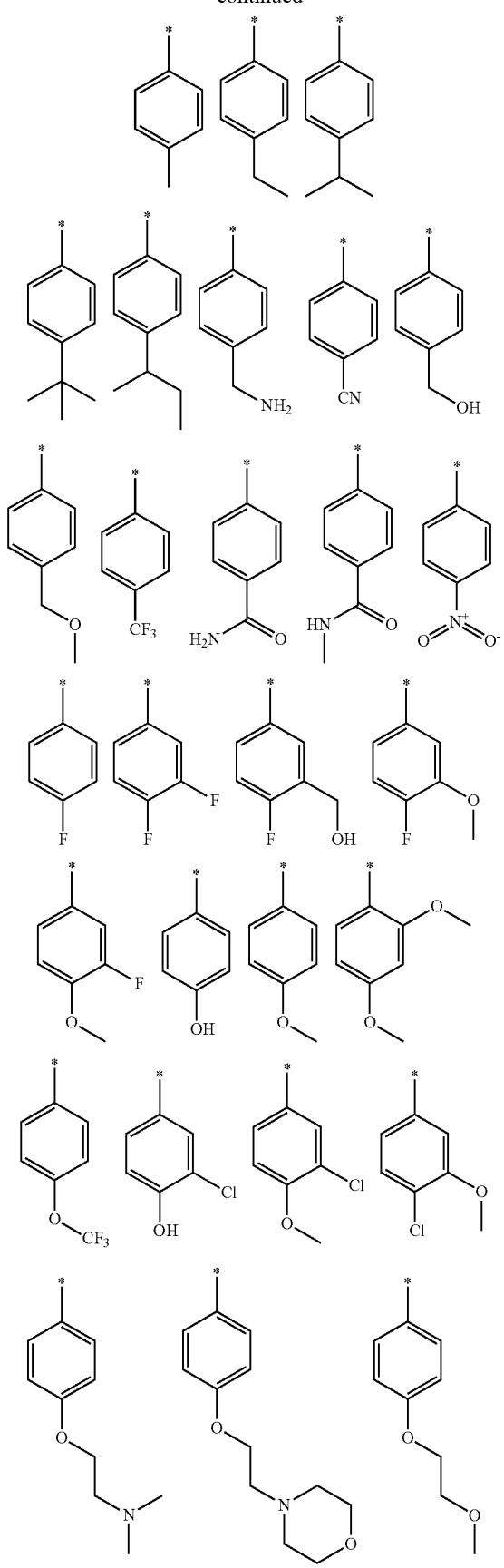
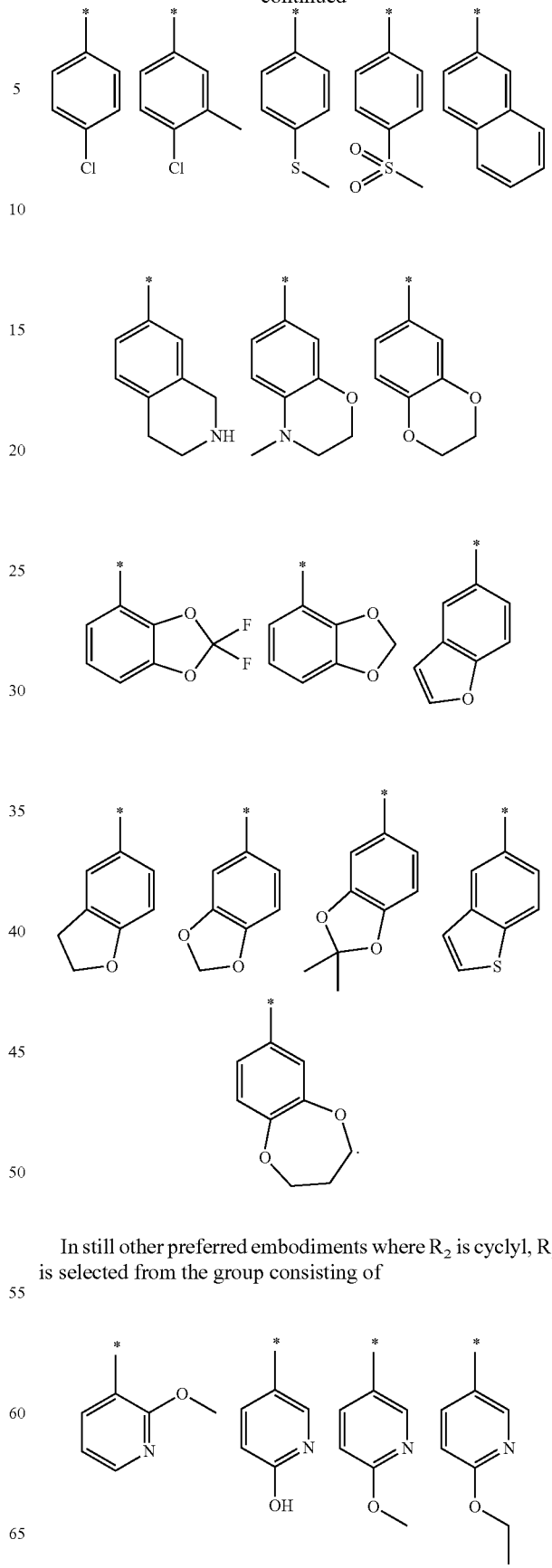
In still other preferred embodiments where $R_2$ is cyclyl, $R_2$ is selected from the group consisting of

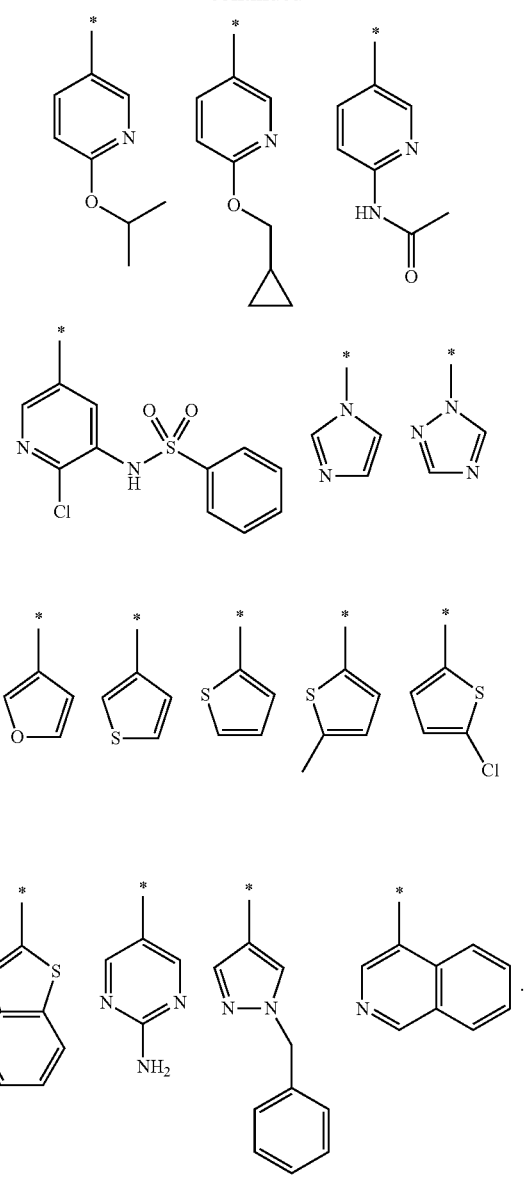

In still other embodiments where $R_2$ is an amino, $R_2$ is selected from the group consisting of —NH(CH$_3$)$_2$, —NHCH$_2$CH(CH$_3$)$_2$, —NHCH(CH$_2$CH$_3$)$_2$, —NH(CH$_2$)C(O)NH$_2$, —NH(CH$_2$)$_3$CH$_3$, —NHCH(CH$_3$)$_3$, —NH(CH$_2$)$_3$OH, —NH-cyclopropylmethyl, —NH(CH$_2$)$_3$SCH$_3$, —NH(CH$_2$)$_2$NHC(O)CH$_3$, —NH(CH$_2$)$_2$OCH(CH$_3$)$_2$, —NH(CH$_2$)$_2$OCH$_3$, —NH(CH$_2$)$_2$C(O)NH$_2$, —NH(CH$_2$)$_2$N(CH$_3$)$_2$.

In still other preferred embodiments where $R_2$ is an amino, $R_2$ is selected from the group consisting of

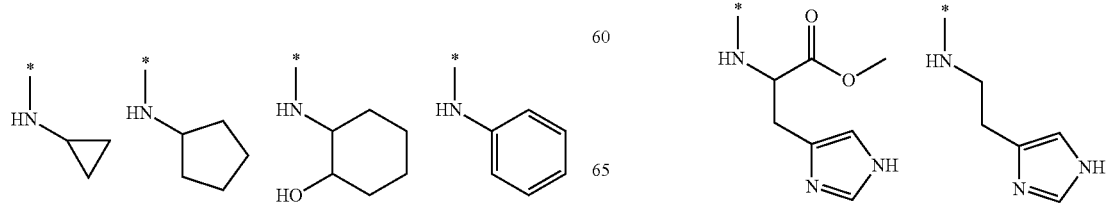

-continued

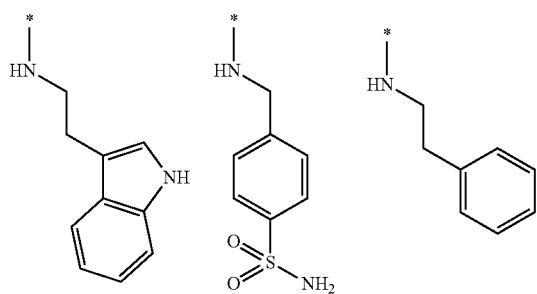
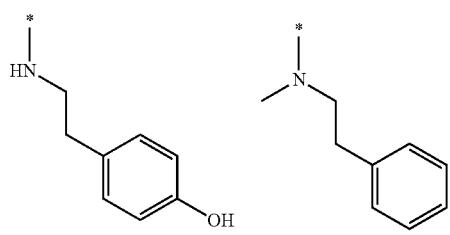
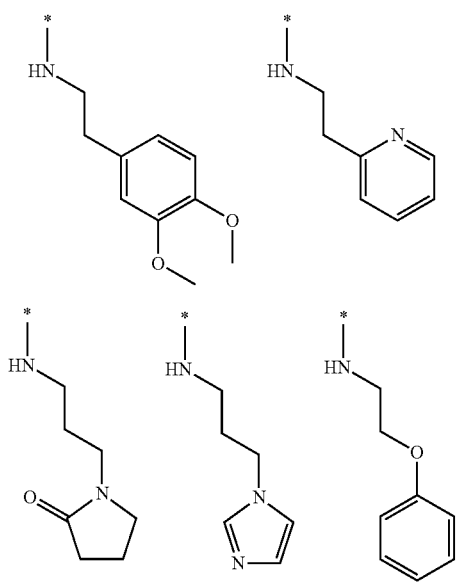
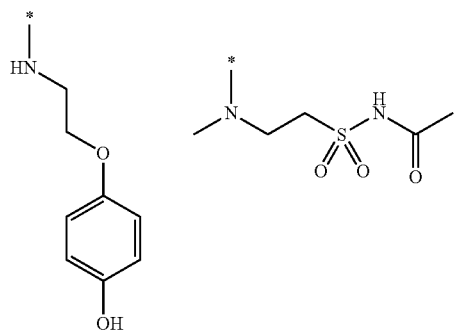
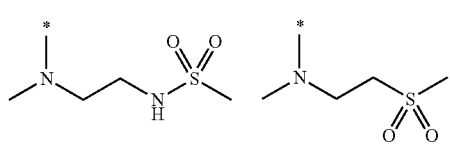

-continued

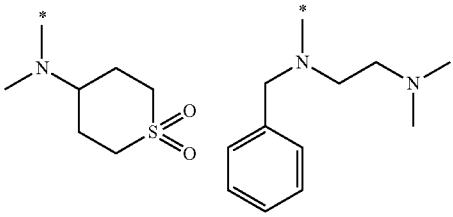
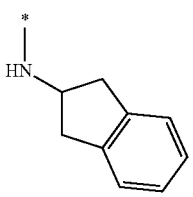

In the embodiments where $R_2$ is a substituted alkyl, $R_2$ is selected from the group consisting of

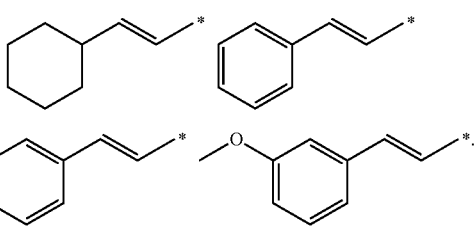

In the embodiments where $R_2$ is an oxy, $R_2$ is selected from the group consisting of —O($_c$H$_2$)$_3$CH$_3$, —O$_c$H$_3$, and phenoxy.

In some preferred embodiments and variations of the compounds of the invention, $R_2$ is selected from the group consisting of

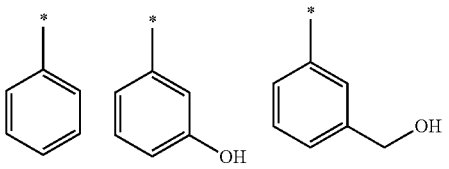
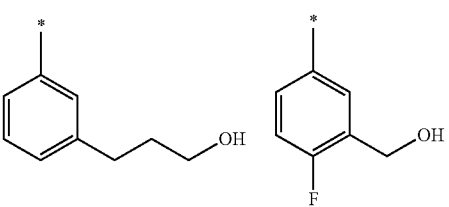
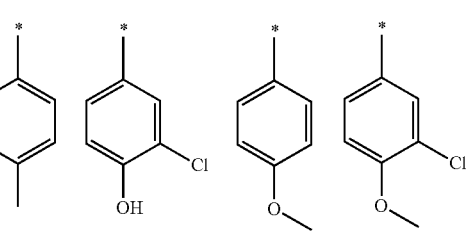

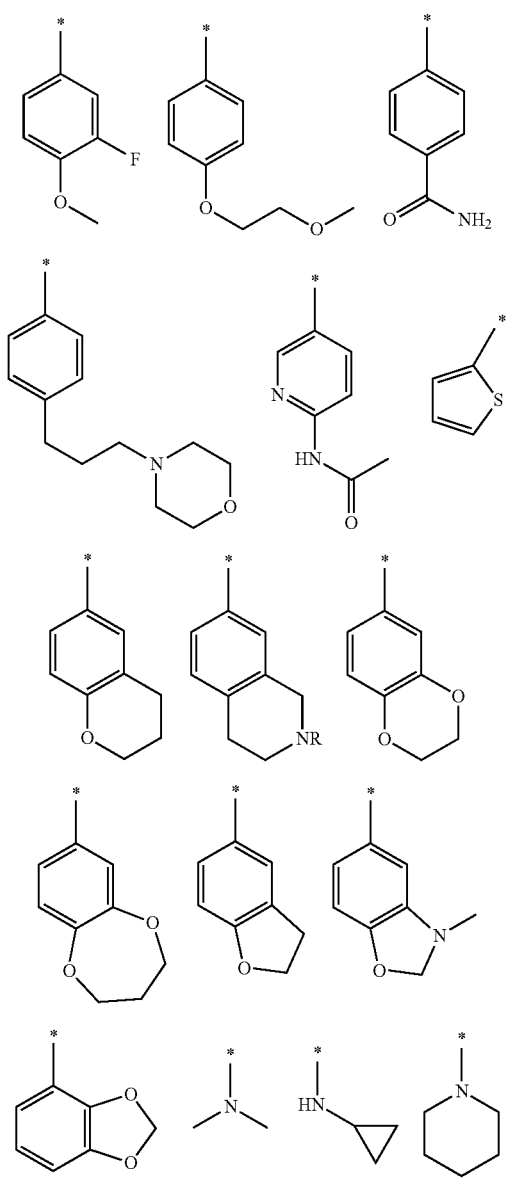
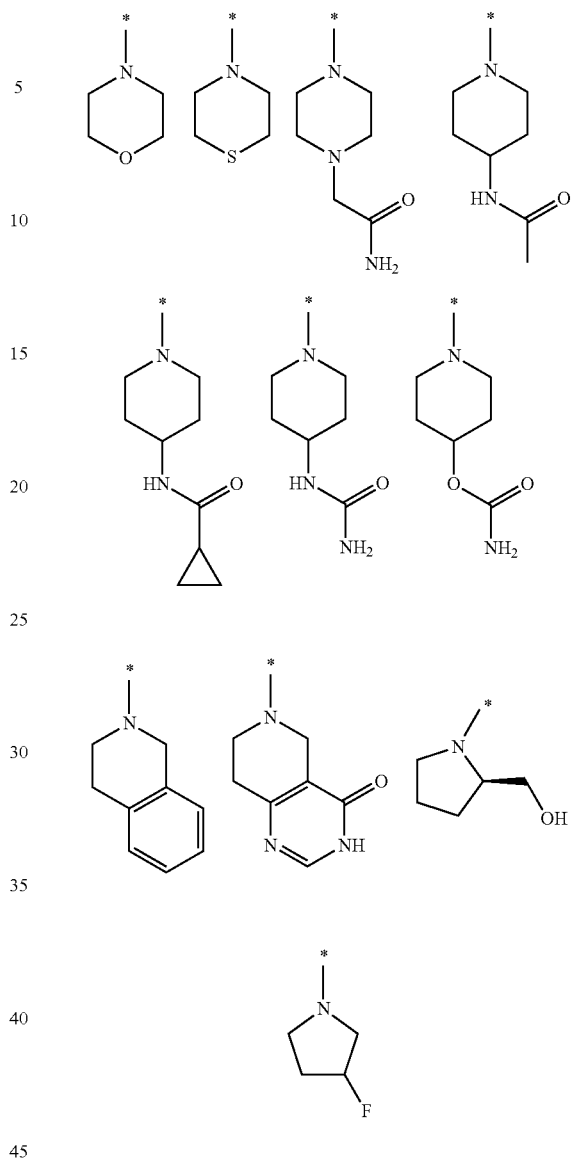
In some other preferred embodiments and variations of the compounds of the invention, R$_2$ is selected from the group consisting of
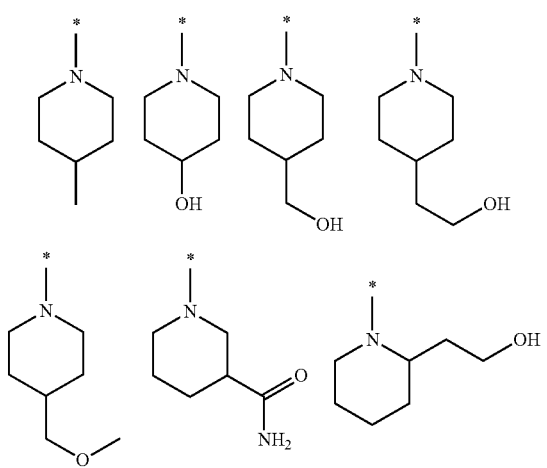

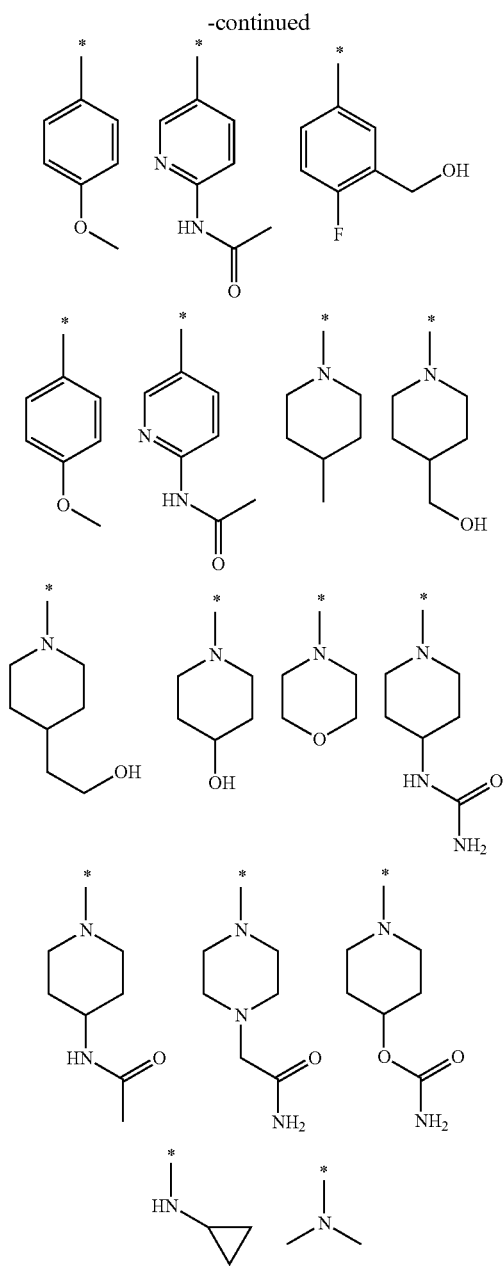

In some more preferred embodiments and variations of the compounds of the invention, R₂ is unsubstituted phenyl.

In some other more preferred embodiments and variations of the invention, R₂ is unsubstituted morphinyl.

R₃

In all the above embodiments and variations of the compound of the invention, in some variations, R₃ is selected from the group consisting of hydrogen, hydroxy, halo, nitro, cyano, thio, oxy, $(C_{1-10})$alkoxy, amino, halo$(C_{1-10})$alkyl, $(C_{1-10})$alkyl, carbonyl$(C_{1-10})$alkyl, hydroxy$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{3-12})$cycloalkyl, hetero$(C_{3-12})$cycloalkyl, each unsubstituted or substituted with 1-2 substituents, wherein said 1-2 substituents are each independently selected from the group consisting of hydroxyl, halo, halo$(C_{1-6})$alkyl, $(C_{1-6})$alkyl, $(C_{3-6})$cycloalkyl, hetero$(C_{1-5})$cycloalkyl, phenyl, and hetero$(C_{1-5})$aryl.

In some other variations, R₃ is selected from the group consisting of hydrogen, hydroxyl, amino, thio, oxy, $(C_{1-6})$alkyl, $(C_{1-6})$haloalkyl, $(C_{1-6})$cycloalkyl, and $(C_{1-6})$alkoxy, each unsubstituted or substituted with said 1-2 substituents.

In other variations, R₃ is selected from the group consisting of hydrogen, methyl, ethyl, perfluoromethyl, 2,2,2-trifluoroethyl, cyclopropyl, and methoxy, each unsubstituted or substituted with said 1-2 substituents.

In still other variations, R₃ is hydrogen. In yet still other variations, R₃ is methyl.

One preferred embodiment of the compounds of the invention is of Formula III:

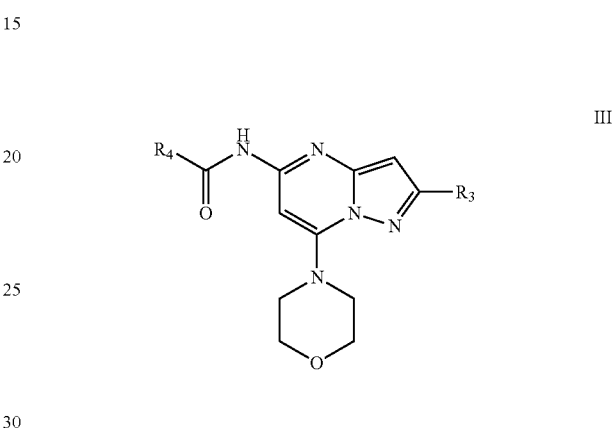

III and pharmaceutically acceptable salts thereof, wherein

R₃ is selected from the group consisting of hydrogen, hydroxyl, amino, thio, oxy, $(C_{1-6})$alkyl, $(C_{1-6})$haloalkyl, $(C_{1-6})$cycloalkyl, and $(C_{1-6})$alkoxy, each unsubstituted or substituted with 1-2 substituents independently selected from the group consisting of hydroxyl, halo, halo$(C_{1-6})$alkyl, $(C_{1-6})$alkyl, $(C_{3-6})$cycloalkyl, hetero$(C_{1-5})$cycloalkyl, phenyl, and hetero$(C_{1-5})$aryl; and R₄ is selected from the group consisting of $(C_{1-6})$alkyl, $(C_{1-6})$haloalkyl, $(C_{1-6})$alkenyl, $(C_{4-6})$aryl$(C_{1-6})$alkyl, hetero$(C_{1-5})$aryl$(C_{1-6})$alkyl, $(C_{3-6})$cycloalkyl$(C_{1-6})$alkyl, hetero$(C_{1-5})$cycloalkyl$(C_{1-6})$alkyl, $C_{4-6}$aryl, $(C_{1-5})$heteroaryl, $(C_{9-12})$bicycloaryl, hetero$(C_{4-12})$bicycloaryl, $(C_{3-6})$cycloalkyl, hetero$(C_{1-5})$cycloalkyl, hetero$(C_{9-12})$bicycloalkyl, each unsubstituted or substituted with 1-3 substituents independently selected from the group consisting of hydroxyl, chloro, fluoro, $(C_{1-3})$alkyl, $(C_{1-3})$alkoxy, phenyl, pyridyl, and heterobicycloaryl, each unsubstituted or further substituted.

In some variations of the immediately above embodiment of the compounds of the present invention, R₄ is selected from the group consisting of trifluoromethyl, methyl, ethyl, isopropyl, tert-butyl, n-hexyl, ethenyl, phenoxymethyl, methoxy, cyclopropyl, cyclobutyl, cyclopentyl, cyclohexyl, —$(CH_2)_3$N$(CH_3)_{25}$—$(CH_2)_5(CH_3)$, hydroxyl, —$(CH_2)_3CH_2$—$CH_2$, —$(CH_2)_2OCH_3$, —$C(O)OCH_3$, —$C(O)CH_3$, —$(CH_2)_2C(O)$CH₃, —$(CH_2)_2S(CH_3)$, —$CH_2CF_3$, —$CH_2CH(CH_3)CH_2C(CH_3)_3$, each unsubstituted or substituted with said 1-3 substituents each independently selected from the group consisting of furanyl, methylthio, fluoro, cyclohexyl, cyclopentyl, phenyl, 4-fluorophenyl, methoxy, methyl, hydroxyl, acetyl, —$N(CH_3)_2$, —$C(O)OCH_3$, —$C(O)CH_3$, hydroxyl, fluoro, methylthio, —$C(O)OCH_3$, and

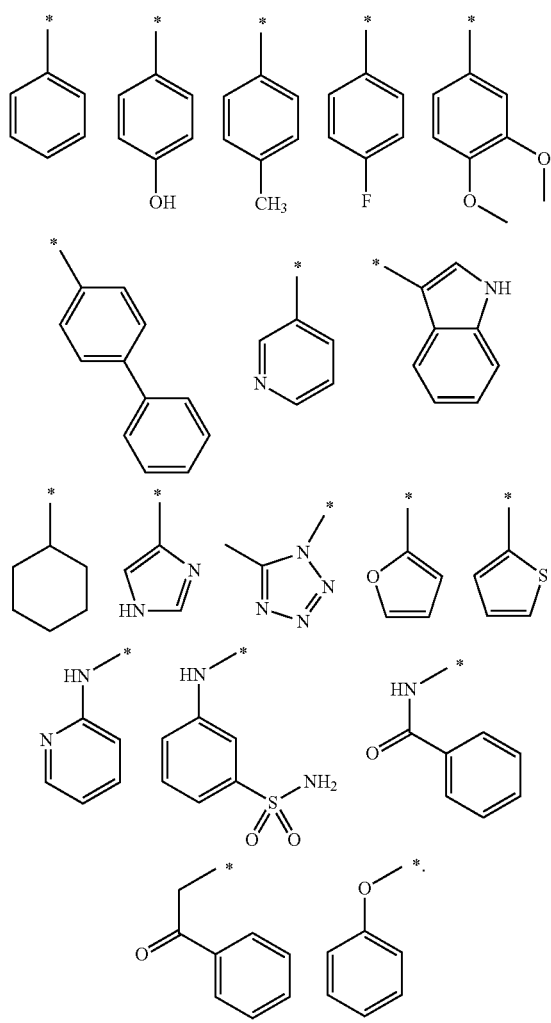

In some other variations, $R_4$ is selected from the group consisting of

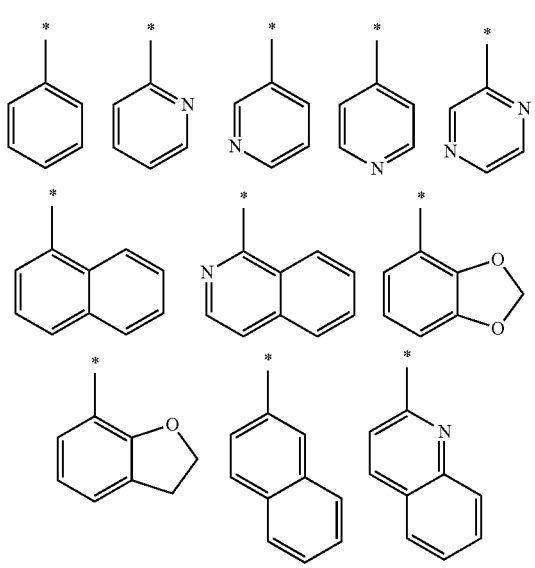

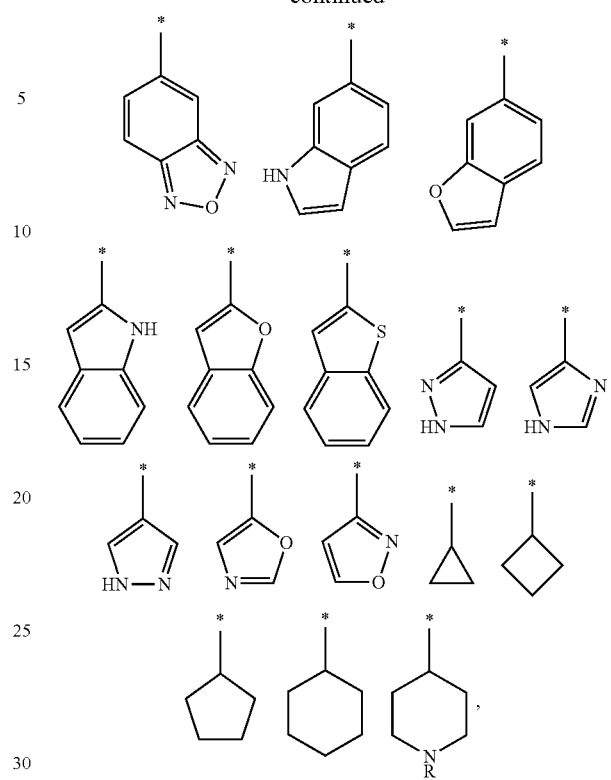

each unsubstituted or is substituted with 1-3 substituents, where R is hydrogen or one of said 1-3 substituents which are independently selected from the group consisting of —C(O)OC(CH$_3$)$_3$, phenyl, cyano, fluoro, —C(O)OCH$_3$, methyl, tert-butyl, hydroxyl, methoxy, fluoro, chloro, bromo, cyano, nitro, dimethylamino, —CH$_2$P(O)(OCH$_2$CH$_3$)$_2$, —NHC(O)CH$_3$, —CH$_2$NHC(O)OC(CH$_3$)$_3$, —C(CH$_3$)(=NOH), —C(OH)(CH$_3$)$_2$, —C(CH$_2$OH)(CH$_3$)$_2$, —OC(CH$_3$)$_3$, —SCF$_3$, —CF$_3$, —C(O)OC(CH$_3$)$_3$, —CH$_2$OCH$_2$CF$_3$, —OCHF$_2$, —C(CH$_3$)=NHOH, —NHC(O)OCH$_2$CH$_3$, and

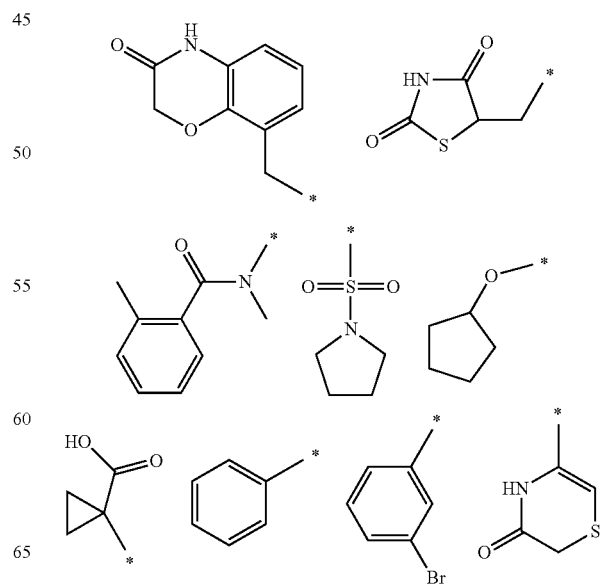

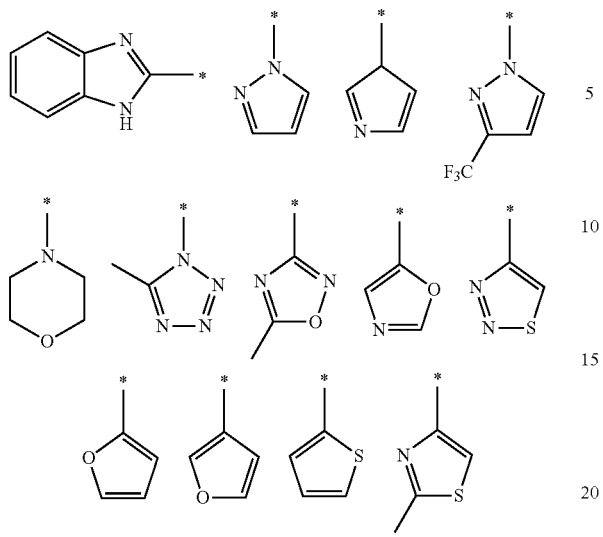
In some preferred variations, $R_4$ is selected from the group consisting of:
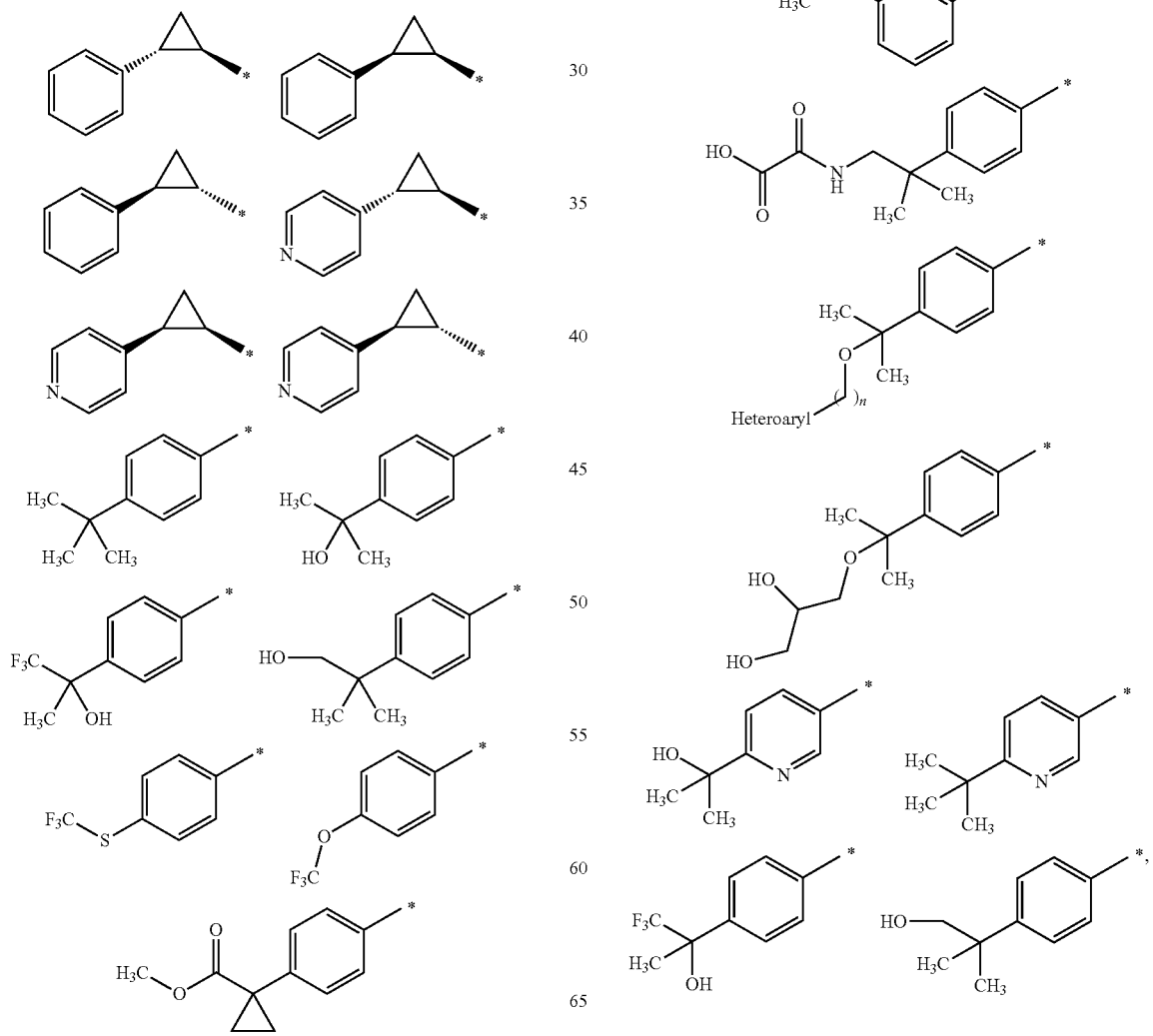
where n is 0, 1, 2, 3 or 4

In other preferred variations, $R_4$ is selected from the group consisting of:

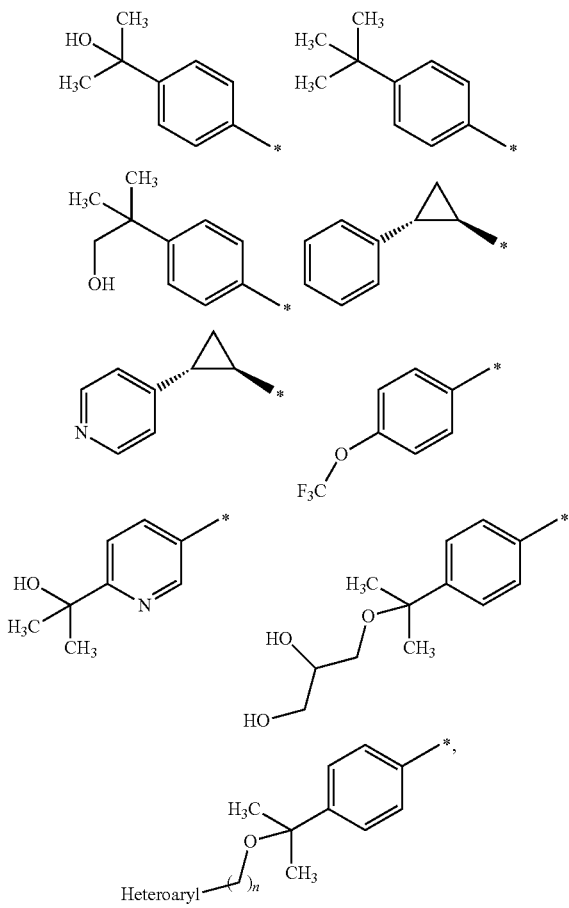

where n is 0, 1, 2, 3 or 4

In some variations of the above embodiments and variations of the compound of the invention, $R_3$ is selected from the group consisting of hydrogen, methyl, ethyl, perfluoromethyl, 2,2,2-trifluoroethyl, cyclopropyl, and methoxy, each unsubstituted or substituted with said 1-2 substituents. In other variations, $R_3$ is selected from the group consisting of hydrogen, methyl, ethyl, cyclopropyl, and methoxy, each unsubstituted or substituted with said 1-2 substituents. In still other variations, $R_3$ is hydrogen. In yet still other variations, $R_3$ is methyl.

Another preferred embodiment of the compounds of the present invention consisting of Formula IV:

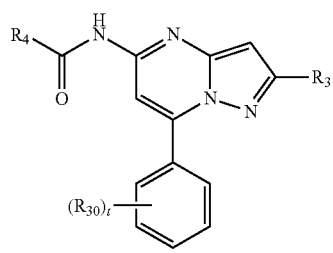

IV and pharmaceutically acceptable salts thereof, wherein t is 0, 1, 2 or 3;

$R_3$ is selected from the group consisting of hydrogen, hydroxyl, amino, thio, oxy, $(C_{1-6})$alkyl, $(C_{1-6})$haloalkyl, $(C_{1-6})$cycloalkyl, and $(C_{1-6})$alkoxy, each unsubstituted or substituted with 1-2 substituents independently selected from the group consisting of hydroxyl, halo, halo$(C_{1-6})$alkyl, $(C_{1-6})$alkyl, $(C_{3-6})$cycloalkyl, hetero$(C_{1-5})$cycloalkyl, phenyl, and hetero$(C_{1-5})$aryl;

$R_4$ is selected from the group consisting of $(C_{1-6})$alkyl, $(C_{1-6})$haloalkyl, $(C_{1-6})$alkenyl, $(C_{4-6})$aryl$(C_{1-6})$alkyl, hetero$(C_{1-5})$aryl$(C_{1-6})$alkyl, $(C_{3-6})$cycloalkyl$(C_{1-6})$alkyl, hetero$(C_{1-5})$cycloalkyl$(C_{1-6})$alkyl, $C_{4-6}$aryl, $(C_{1-5})$heteroaryl, $(C_{9-12})$bicycloaryl, hetero$(C_{4-12})$bicycloaryl, $(C_{3-6})$cycloalkyl, hetero$(C_{1-5})$cycloalkyl, each unsubstituted or substituted with 1-3 substituents independently selected from the group consisting of hydroxyl, chloro, fluoro, $(C_{1-3})$alkyl, $(C_{1-3})$alkoxy, phenyl, pyridyl, and heterobicycloaryl, each unsubstituted or further substituted; and each $R_{30}$ is independently selected from the group consisting of hydroxy, nitro, halo, cyano, oxo, oxy, $(C_{1-6})$alkoxyl, $(C_{4-6})$aryloxy, $(C_{4-6})$aryl$(C_{1-6})$alkyloxy, $(C_{1-6})$alkyl, $(C_{1-6})$haloalkyl, hydroxy$(C_{1-6})$alkyl, aminocarbonyl$(C_{1-6})$alkyl, cyanoalkyl, $(C_{1-6})$haloalkyloxy, $(C_{4-6})$aryl$(C_{1-6})$alkyloxy, thio, $(C_{1-6})$alkylthio, amino, sulfonylamino, $(C_{1-6})$alkylamino, $(C_{1-6})$alkylsulfonylamino, amido, aryl and aryl$(C_{1-6})$alkyl, $(C_{1-6})$alkylcarbonyl, $(C_{1-6})$alkyloxycarbonyl, carboxamido, hydroxycarbonyl, aminocarbonyl, and sulfonyl, $(C_{1-6})$alkylsulfonyl.

In some variations of the immediate above preferred embodiment of the compounds of the invention, $R_4$ is selected from the group consisting of:

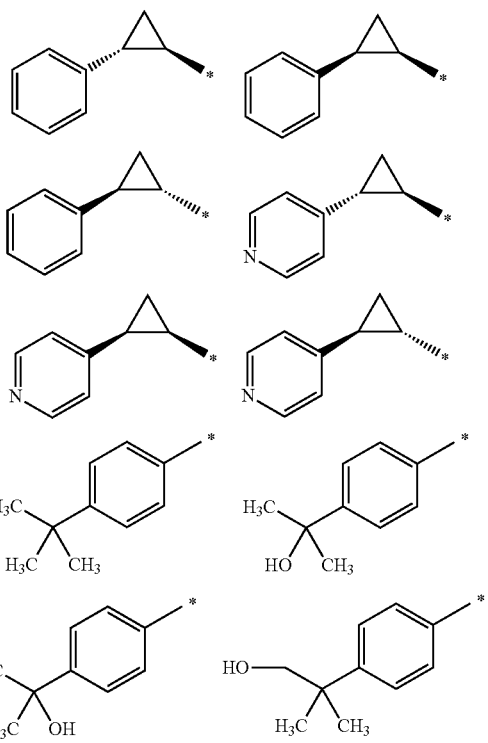

-continued
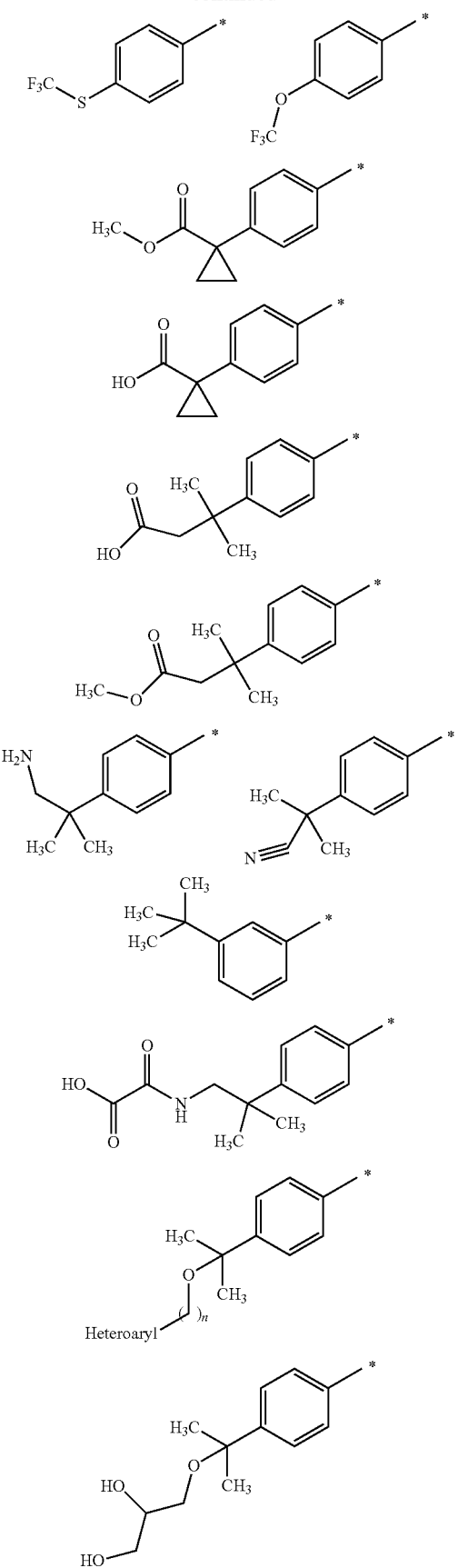
-continued
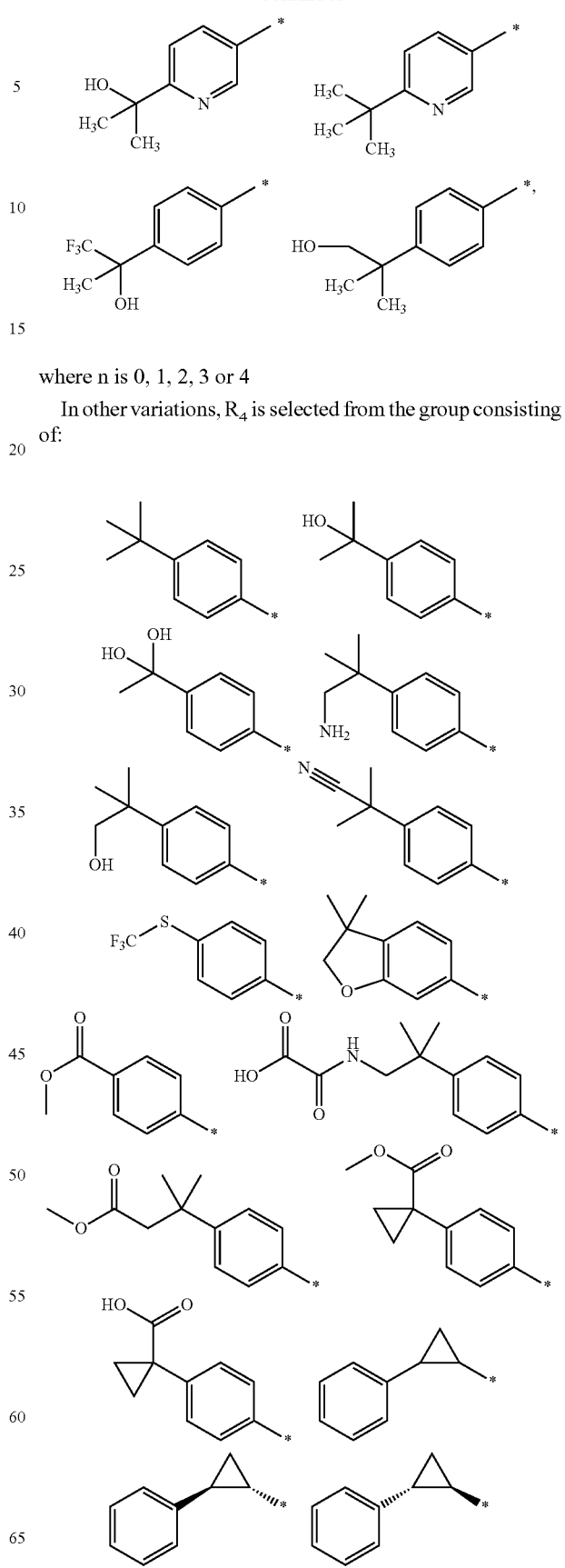
where n is 0, 1, 2, 3 or 4
In other variations, $R_4$ is selected from the group consisting of:

-continued

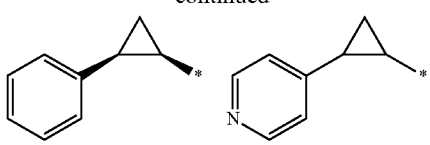

In still other variation, R$_4$ is selected from the group consisting of:

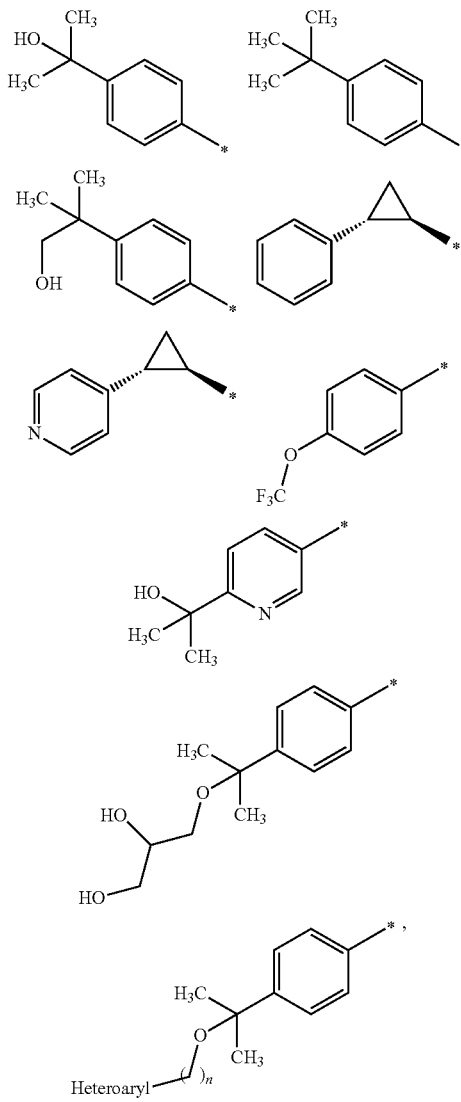

where n is 0, 1, 2, 3 or 4

In some variations of the immediately above embodiment of the compound of the invention, each R$_{30}$ is independently selected from the group consisting of hydroxyl, nitro, cyano, fluoro, chloro, methyl, cyanomethyl, —CH$_2$OCH$_3$, isobutyl, CF$_3$, —CH$_2$OH, —(CH$_2$)$_2$OH, —(CH$_2$)$_3$OH, —CH(CH$_3$)CH$_2$OH, —OCF$_3$, isopropyloxy, —OCH$_2$C(O)OH, benzloxy, —OCH$_2$C(O)OCH$_2$CH$_3$, —OCH$_2$CH$_2$N(CH$_3$)$_2$, —OCH$_2$CH$_2$-morpholinyl, —OCH$_2$CH$_2$OCH$_3$, —C(O)CH$_3$, —C(O)NH$_2$, —NHC(O)CH$_3$, —NHS(O)$_2$CH$_3$, —N(CH$_3$)$_2$, —SCH$_3$, —S(O)$_2$CH$_3$, and phenyl In some other variations, R$_{30}$ is selected from the group consisting of hydroxyl, —CH$_2$OH, —(CH$_2$)$_2$OH, —(CH$_2$)$_3$OH, —CH(CH$_3$)CH$_2$OH, and —OCH$_2$C(O)OH. In still other variations, t is 0.

In some variations of the above embodiments and variations of the compound of the invention, R$_3$ is selected from the group consisting of hydrogen, methyl, ethyl, perfluoromethyl, 2,2,2-trifluoroethyl, cyclopropyl, and methoxy, each unsubstituted or substituted with said 1-2 substituents. In other variations, R$_3$ is selected from the group consisting of hydrogen, methyl, ethyl, cyclopropyl, and methoxy, each unsubstituted or substituted with said 1-2 substituents. In still other variations, R$_3$ is hydrogen. In yet still other variations, R$_3$ is methyl.

Another preferred embodiment of the compound of the invention consisting of Formula V:

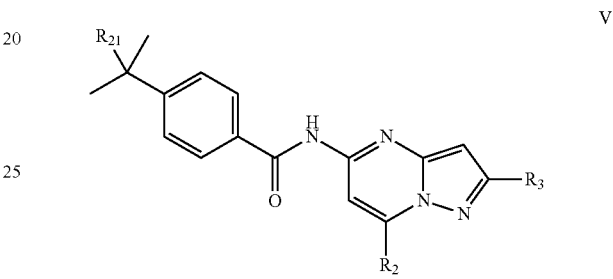

V and pharmaceutically acceptable salts thereof,
wherein
R$_2$ is selected from the group consisting of amino, oxy, thio, halo, (C$_{1-10}$)alkylamino, (C$_{1-10}$)alkyl, (C$_{1-10}$)alkenyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each unsubstituted or substituted with 1-3 substituents,
wherein
each of said 1-3 substituents is independently selected from the group consisting of hydroxyl, halo, nitro, cyano, thio, (C$_{1-6}$)alkylthio, oxy, arylalkyloxy, oxo, hydroxy, carbonyloxy, (C$_{1-10}$)alkoxy, (C$_{4-12}$)aryloxy, hetero(C$_{1-10}$)aryloxy, carbonyl, (C$_{1-6}$)alkylcarbonyl, oxycarbonyl, aminocarbonyl, amino, amido, carboxamido, (C$_{1-10}$)alkylamino, acetylamino (need definition), sulfonamido, imino, sulfonyl, (C$_{1-6}$)alkylsulfonyl, sulfinyl, (C$_{1-10}$)alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl (C$_{1-10}$)alkyl, sulfinyl(C$_{1-10}$)alkyl, (C$_{1-10}$)azaalkyl, (C$_{1-10}$)oxaalkyl, (C$_{1-10}$)oxoalkyl, imino(C$_{1-10}$) alkyl, (C$_{3-12}$)cycloalkyl(C$_{1-5}$)alkyl, hetero(C$_{3-12}$) cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$) alkyl, hetero(C$_{8-12}$)bicycloaryl(C$_{1-5}$)alkyl, hetero (C$_{1-10}$)alkyl, (C$_{3-12}$)cycloalkyl, hetero(C$_{3-12}$) cycloalkyl, (C$_{9-12}$)bicycloalkyl, hetero(C$_{3-12}$) bicycloalkyl, (C$_{4-12}$)aryl, hetero(C$_{1-10}$)aryl, (C$_{9-12}$) bicycloaryl, and hetero(C$_{4-12}$)bicycloaryl, each unsubstituted or further substituted;
R$_3$ is selected from the group consisting of hydrogen, hydroxyl, amino, thio, oxy, (C$_{1-6}$)alkyl, (C$_{1-6}$)haloalkyl, (C$_{1-6}$)cycloalkyl, and (C$_{1-6}$)alkoxy, each unsubstituted or substituted with 1-2 substituents independently selected from the group consisting of hydroxyl, halo, halo(C$_{1-6}$)alkyl, (C$_{1-6}$)alkyl, (C$_{3-6}$)cycloalkyl, hetero(C$_{1-5}$)cycloalkyl, phenyl, and hetero(C$_{1-5}$)aryl; and R$_{21}$ is selected from the group consisting of —(CH$_2$)$_n$OH, —C(O)OH, —C(O)OCH$_3$, cyano, —(CH$_2$)$_n$NH$_2$, —(CH$_2$)$_n$NHC(O)C(O)OH, —(CH$_2$)$_n$C(O)OH, —(CH$_2$)$_n$C(O)OCH$_3$, (C$_{1-4}$)alkyl, halo(C$_{1-4}$)alkyl, —(CH$_2$)$_n$CN, —(CH$_2$)$_n$CONH$_2$, —(CH$_2$)$_n$aryl, —(CH$_2$)$_n$heteroaryl, —O(CH$_2$)$_n$aryl, —O(CH$_2$)$_n$heteroaryl, and —O(CH$_2$)$_n$CH(OH)CH$_2$OH, where n is 0, 1, 2, 3, or 4.

In some variations of the immediately above embodiment, R$_{21}$ is selected from the group consisting of cyano, hydroxyl, methyl, perfluorormethyl, hydroxylmethyl, —CH$_2$NH$_2$, —(CH$_2$)NHC(O)C(O)OH, —(CH$_2$)C(O)OH, —(CH$_2$)C(O)OCH$_3$, —O(CH$_2$)$_n$heteroaryl where n is 1 or 2, and —OCH$_2$CH(OH)CH$_2$OH. In other variation, R$_{21}$ is OH. In yet another variation, R$_{21}$ is methyl.

In some variations of the immediately above embodiment and variations of the compound of the present invention, R$_2$ is selected from the group consisting of:

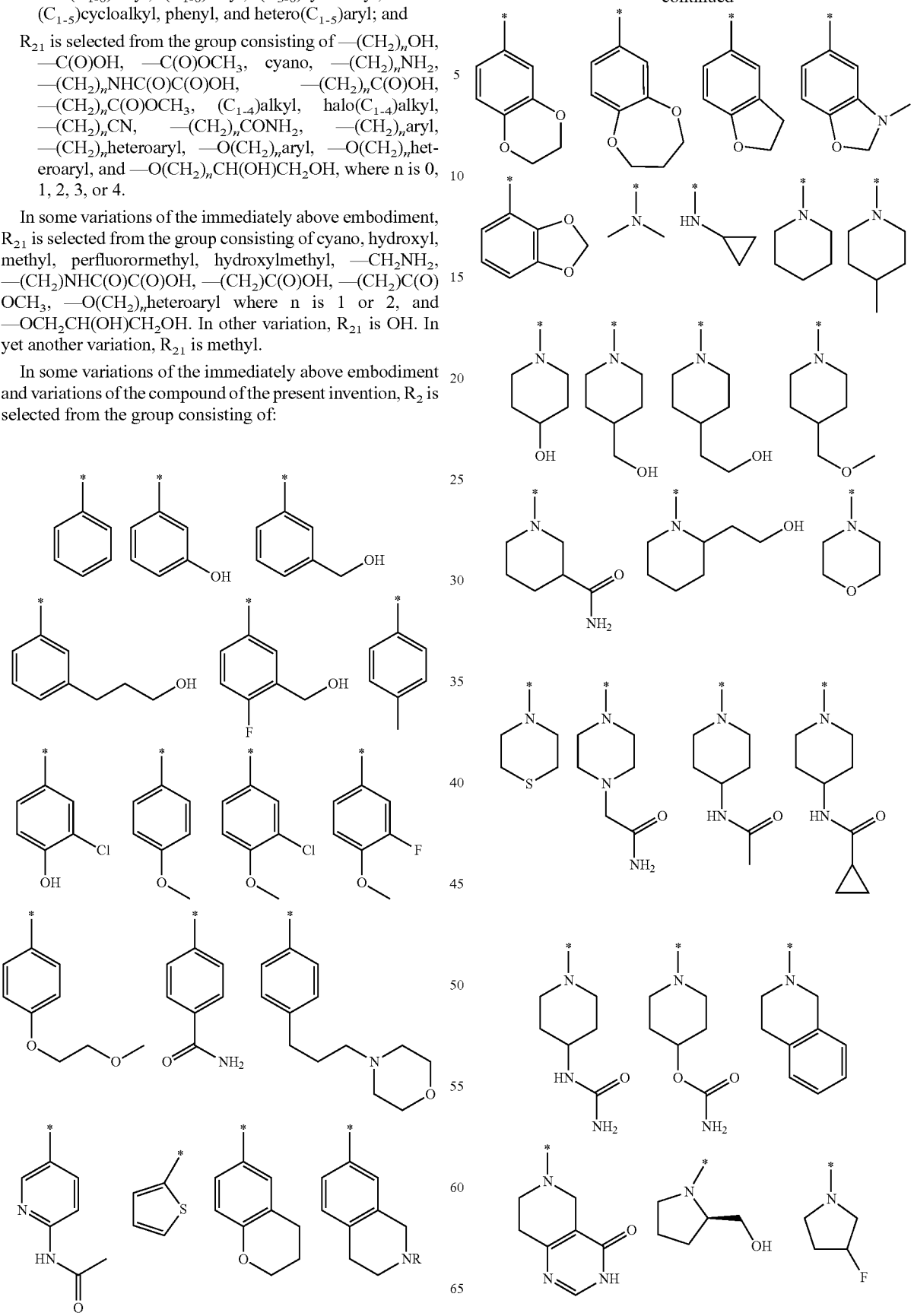

In other variations, R$_2$ is selected from the group consisting of:

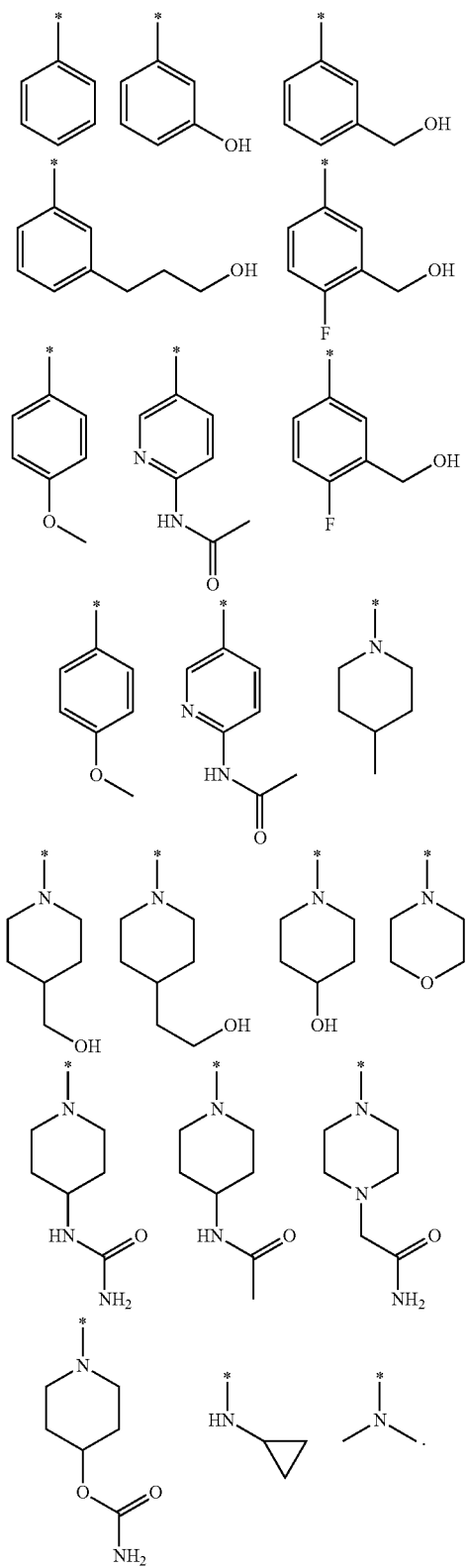

In a still other variation, R$_2$ is unsubstituted morpholinyl.
In yet still other variation, R$_2$ is unsubstituted phenyl.

In some variations of the above embodiments and variations of the compound of the invention, R$_3$ is selected from the group consisting of hydrogen, (C$_{1-6}$)alkyl, (C$_{1-6}$)haloalkyl, (C$_{1-6}$)cycloalkyl, and (C$_{1-6}$)alkoxy, each unsubstituted or substituted with 1-2 substituents each independently selected from the group consisting of hydroxyl, halo, halo(C$_{1-6}$)alkyl, (C$_{1-6}$)alkyl, (C$_{3-6}$)cycloalkyl, hetero(C$_{1-5}$)cycloalkyl, phenyl, and hetero(C$_{1-5}$)aryl. In some other variations, R$_3$ is selected from the group consisting of hydrogen, methyl, ethyl, perfluoromethyl, 2,2,2-trifluoroethyl, cyclopropyl, and methoxy, each unsubstituted or substituted with said 1-2 substituents. In other variations, R$_3$ is selected from the group consisting of hydrogen, methyl, ethyl, cyclopropyl, and methoxy, each unsubstituted or substituted with said 1-2 substituents. In still other variations, R$_3$ is hydrogen. In yet still other variations, R$_3$ is methyl Particular examples of compounds according to the present invention, and pharmaceutically acceptable salts thereof, include but are not limited to, the following:
4-tert-butyl-N-(7-(3-(hydroxymethyl)phenyl)-2-methylpyrazolo[1,5-a]pyrimidin-5-yl)benzamide;
4-tert-butyl-N-(7-(thiophen-2-yl)pyrazolo[1,5-a]pyrimidin-5-yl)benzamide;
4-tert-butyl-N-(7-(thiophen-2-yl)pyrazolo[1,5-a]pyrimidin-5-yl)benzamide;
4-tert-butyl-N-(7-(4-fluoro-3-(hydroxymethyl)phenyl)-2-methylpyrazolo[1,5-a]pyrimidin-5-yl)benzamide;
4-tert-butyl-N-(7-(3-(hydroxymethyl)phenyl)pyrazolo[1,5-a]pyrimidin-5-yl)benzamide;
N-(7-(3-(hydroxymethyl)phenyl)pyrazolo[1,5-a]pyrimidin-5-yl)-4-(2-hydroxypropan-2-yl)benzamide;
N-(7-(3-(hydroxymethyl)phenyl)pyrazolo[1,5-a]pyrimidin-5-yl)-4-(1,1,1-trifluoro-2-hydroxypropan-2-yl)benzamide;
4-tert-butyl-N-(7-(4-(methylsulfonyl)phenyl)pyrazolo[1,5-a]pyrimidin-5-yl)benzamide;
4-tert-butyl-N-(7-(4-methoxyphenyl)pyrazolo[1,5-a]pyrimidin-5-yl)benzamide;
4-tert-butyl-N-(7-(3-(2-hydroxyethyl)phenyl)pyrazolo[1,5-a]pyrimidin-5-yl)benzamide;
4-tert-butyl-N-(7-(3-(3-hydroxypropyl)phenyl)pyrazolo[1,5-a]pyrimidin-5-yl)benzamide;
N-(7-(3-acetylphenyl)pyrazolo[1,5-a]pyrimidin-5-yl)-4-tert-butylbenzamide;
4-tert-butyl-N-(7-(6-methoxypyridin-3-yl)pyrazolo[1,5-a]pyrimidin-5-yl)benzamide;
N-(7-(6-acetamidopyridin-3-yl)pyrazolo[1,5-a]pyrimidin-5-yl)-4-tert-butylbenzamide;
4-tert-butyl-N-(7-(3-methoxyphenyl)pyrazolo[1,5-a]pyrimidin-5-yl)benzamide;
4-(2-hydroxypropan-2-yl)-N-(7-phenylpyrazolo[1,5-a]pyrimidin-5-yl)benzamide;
4-(2-hydroxypropan-2-yl)-N-(7-(3-(methylsulfonamido)phenyl)pyrazolo[1,5-a]pyrimidin-5-yl)benzamide;
N-(7-(furan-3-yl)pyrazolo[1,5-a]pyrimidin-5-yl)-4-(2-hydroxypropan-2-yl)benzamide;
4-(2-hydroxypropan-2-yl)-N-(7-(4-methoxyphenyl)pyrazolo[1,5-a]pyrimidin-5-yl)benzamide;
4-(2-hydroxypropan-2-yl)-N-(7-p-tolylpyrazolo[1,5-a]pyrimidin-5-yl)benzamide;
N-(7-(3-(cyanomethyl)phenyl)pyrazolo[1,5-a]pyrimidin-5-yl)-4-(2-hydroxypropan-2-yl)benzamide;
N-(7-(4-carbamoylphenyl)pyrazolo[1,5-a]pyrimidin-5-yl)-4-(2-hydroxypropan-2-yl)benzamide;
4-(2-hydroxypropan-2-yl)-N-(7-(4-(methylthio)phenyl)pyrazolo[1,5-a]pyrimidin-5-yl)benzamide;

4-(2-hydroxypropan-2-yl)-N-(7-(4-(trifluoromethyl)phenyl) pyrazolo[1,5-a]pyrimidin-5-yl)benzamide;
N-(7-(3-acetamidophenyl)pyrazolo[1,5-a]pyrimidin-5-yl)-4-(2-hydroxypropan-2-yl)benzamide;
ethyl 2-(3-(5-(4-(2-hydroxypropan-2-yl)benzamido)pyrazolo[1,5-a]pyrimidin-7-yl)phenoxy)acetate;
2-(3-(5-(4-(2-hydroxypropan-2-yl)benzamido)pyrazolo[1,5-a]pyrimidin-7-yl)phenoxy)acetic acid;
4-(2-hydroxypropan-2-yl)-N-(7-(3-(methoxymethyl)phenyl)pyrazolo[1,5-a]pyrimidin-5-yl)benzamide;
4-(1-hydroxy-2-methylpropan-2-yl)-N-(2-methyl-7-phenylpyrazolo[1,5-a]pyrimidin-5-yl)benzamide;
4-(1-hydroxy-2-methylpropan-2-yl)-N-(7-(3-(hydroxymethyl)phenyl)-2-methylpyrazolo[1,5-a]pyrimidin-5-yl)benzamide;
4-(1-hydroxy-2-methylpropan-2-yl)-N-(7-(3-(methoxymethyl)phenyl)-2-methylpyrazolo[1,5-a]pyrimidin-5-yl)benzamide;
4-tert-butyl-N-[7-(4-fluorophenyl)pyrazolo[1,5-a]pyrimidin-5-yl]benzamide;
4-tert-butyl-N-[7-(4-tert-butylphenyl)pyrazolo[1,5-a]pyrimidin-5-yl]benzamide;
4-tert-butyl-N-{7-[3-(cyanomethyl)phenyl]pyrazolo[1,5-a]pyrimidin-5-yl}benzamide;
4-tert-butyl-N-(7-(furan-3-yl)pyrazolo[1,5-a]pyrimidin-5-yl)benzamide;
4-tert-butyl-N-(7-phenylpyrazolo[1,5-a]pyrimidin-5-yl)benzamide;
4-tert-butyl-N-(7-p-tolylpyrazolo[1,5-a]pyrimidin-5-yl)benzamide;
4-tert-butyl-N-(7-(4-cyanophenyl)pyrazolo[1,5-a]pyrimidin-5-yl)benzamide;
4-tert-butyl-N-(7-(3,5-dimethylphenyl)pyrazolo[1,5-a]pyrimidin-5-yl)benzamide;
4-tert-butyl-N-(7-(4-chlorophenyl)pyrazolo[1,5-a]pyrimidin-5-yl)benzamide;
4-tert-butyl-N-(7-(2-chlorophenyl)pyrazolo[1,5-a]pyrimidin-5-yl)benzamide;
4-tert-butyl-N-(7-(4-carbamoylphenyl)pyrazolo[1,5-a]pyrimidin-5-yl)benzamide;
4-tert-butyl-N-(7-(4-(methylthio)phenyl)pyrazolo[1,5-a]pyrimidin-5-yl)benzamide;
N-(7-(benzo[b]thiophen-2-yl)pyrazolo[1,5-a]pyrimidin-5-yl)-4-tert-butylbenzamide;
4-tert-butyl-N-(7-(2,4-dimethoxyphenyl)pyrazolo[1,5-a]pyrimidin-5-yl)benzamide;
4-tert-butyl-N-(7-(3-(trifluoromethyl)phenyl)pyrazolo[1,5-a]pyrimidin-5-yl)benzamide;
4-tert-butyl-N-(7-(4-(trifluoromethoxy)phenyl)pyrazolo[1,5-a]pyrimidin-5-yl)benzamide;
4-tert-butyl-N-(7-o-tolylpyrazolo[1,5-a]pyrimidin-5-yl)benzamide;
4-tert-butyl-N-(7-(2-(hydroxymethyl)phenyl)pyrazolo[1,5-a]pyrimidin-5-yl)benzamide;
N-(7-(2-acetamidophenyl)pyrazolo[1,5-a]pyrimidin-5-yl)-4-tert-butylbenzamide;
N-(7-(biphenyl-2-yl)pyrazolo[1,5-a]pyrimidin-5-yl)-4-tert-butylbenzamide;
4-tert-butyl-N-(7-(2-(methylsulfonamido)phenyl)pyrazolo[1,5-a]pyrimidin-5-yl)benzamide;
4-tert-butyl-N-(7-(2-methoxypyridin-3-yl)pyrazolo[1,5-a]pyrimidin-5-yl)benzamide;
4-tert-butyl-N-(7-(naphthalen-2-yl)pyrazolo[1,5-a]pyrimidin-5-yl)benzamide;
4-tert-butyl-N-(7-(3-nitrophenyl)pyrazolo[1,5-a]pyrimidin-5-yl)benzamide;
4-tert-butyl-N-(7-(4-nitrophenyl)pyrazolo[1,5-a]pyrimidin-5-yl)benzamide;
4-tert-butyl-N-(7-(3,4-difluorophenyl)pyrazolo[1,5-a]pyrimidin-5-yl)benzamide;
4-tert-butyl-N-(7-(4-sec-butylphenyl)pyrazolo[1,5-a]pyrimidin-5-yl)benzamide;
4-tert-butyl-N-(7-(isoquinolin-4-yl)pyrazolo[1,5-a]pyrimidin-5-yl)benzamide;
4-tert-butyl-N-(7-(4-isobutyl-3-nitrophenyl)pyrazolo[1,5-a]pyrimidin-5-yl)benzamide;
4-tert-butyl-N-(7-(2-formylphenyl)pyrazolo[1,5-a]pyrimidin-5-yl)benzamide;
4-tert-butyl-N-(7-(3-(methylsulfonamido)phenyl)pyrazolo[1,5-a]pyrimidin-5-yl)benzamide;
N-(7-(1-benzyl-1H-pyrazol-4-yl)pyrazolo[1,5-a]pyrimidin-5-yl)-4-tert-butylbenzamide;
N-(7-(3,4-dihydroisoquinolin-2(1H)-yl)pyrazolo[1,5-a]pyrimidin-5-yl)-4-(2-hydroxypropan-2-yl)benzamide;
4-tert-butyl-N-(7-morpholinopyrazolo[1,5-a]pyrimidin-5-yl)benzamide, trifluoroacetate salt;
4-tert-butyl-N-(7-(3,4-dihydroisoquinolin-2(1H)-yl)pyrazolo[1,5-a]pyrimidin-5-yl)benzamide;
(S)-N-(7-(2-(hydroxymethyl)pyrrolidin-1-yl)pyrazolo[1,5-a]pyrimidin-5-yl)-4-(2-hydroxypropan-2-yl)benzamide;
R)—N-(7-(2-(hydroxymethyl)pyrrolidin-1-yl)pyrazolo[1,5-a]pyrimidin-5-yl)-4-(2-hydroxypropan-2-yl)benzamide;
(R)-4-(2-hydroxypropan-2-yl)-N-(7-(3-hydroxypyrrolidin-1-yl)pyrazolo[1,5-a]pyrimidin-5-yl)benzamide;
(S)-4-(2-hydroxypropan-2-yl)-N-(7-(3-hydroxypyrrolidin-1-yl)pyrazolo[1,5-a]pyrimidin-5-yl)benzamide;
N-(7-(4-(2-hydroxyethyl)piperidin-1-yl)pyrazolo[1,5-a]pyrimidin-5-yl)-4-(2-hydroxypropan-2-yl)benzamide;
4-(2-hydroxypropan-2-yl)-N-(7-morpholinopyrazolo[1,5-a]pyrimidin-5-yl)benzamide;
N-(7-(4-hydroxypiperidin-1-yl)pyrazolo[1,5-a]pyrimidin-5-yl)-4-(2-hydroxypropan-2-yl)benzamide;
N-(7-(2-(2-hydroxyethyl)piperidin-1-yl)pyrazolo[1,5-a]pyrimidin-5-yl)-4-(2-hydroxypropan-2-yl)benzamide; and
(S)-4-tert-butyl-N-(7-(3-hydroxypiperidin-1-yl)pyrazolo[1,5-a]pyrimidin-5-yl)benzamide.

Particular examples of compounds according to the present invention and pharmaceutically acceptable salts thereof include, but are not limited to, the following:
(R)—N-(7-(3-hydroxypiperidin-1-yl)pyrazolo[1,5-a]pyrimidin-5-yl)-4-(2-hydroxypropan-2-yl)benzamide;
(R)-4-tert-butyl-N-(7-(3-hydroxypiperidin-1-yl)pyrazolo[1,5-a]pyrimidin-5-yl)benzamide;
(S)—N-(7-(3-hydroxypiperidin-1-yl)pyrazolo[1,5-a]pyrimidin-5-yl)-4-(2-hydroxypropan-2-yl)benzamide;
N-(7-(6,7-dihydro-1H-pyrazolo[4,3-c]pyridin-5(4H)-yl)pyrazolo[1,5-a]pyrimidin-5-yl)-4-(2-hydroxypropan-2-yl)benzamide;
4-(2-hydroxypropan-2-yl)-N-(7-(2-methylpiperidin-1-yl)pyrazolo[1,5-a]pyrimidin-5-yl)benzamide;

Particular examples of compounds according to the present invention and pharmaceutically acceptable salts thereof, include but are not limited to, the following:
1-yl)pyrazolo[1,5-a]pyrimidin-5-yl)benzamide;
4-(2-hydroxypropan-2-yl)-N-(7-(3-methylpiperidin-1-yl)pyrazolo[1,5-a]pyrimidin-5-yl)benzamide;
(R)-1-(5-(4-(2-hydroxypropan-2-yl)benzamido)pyrazolo[1,5-a]pyrimidin-7-yl)piperidine-3-carboxamide;
(R)-1-(5-(4-(2-hydroxypropan-2-yl)benzamido)pyrazolo[1,5-a]pyrimidin-7-yl)piperidine-3-carboxylic acid;
(S)-1-(5-(4-(2-hydroxypropan-2-yl)benzamido)pyrazolo[1,5-a]pyrimidin-7-yl)piperidine-3-carboxamide;

(S)-1-(5-(4-(2-hydroxypropan-2-yl)benzamido)pyrazolo[1,5-a]pyrimidin-7-yl)piperidine-3-carboxylic acid;
4-(2-hydroxypropan-2-yl)-N-(7-(pyrrolidin-1-yl)pyrazolo[1,5-a]pyrimidin-5-yl)benzamide;
N-(7-(cyclopropylamino)pyrazolo[1,5-a]pyrimidin-5-yl)-4-(2-hydroxypropan-2-yl)benzamide;
4-(2-hydroxypropan-2-yl)-N-(7-(4-oxo-3,4,7,8-tetrahydropyrido[4,3-d]pyrimidin-6(5H)-yl)pyrazolo[1,5-a]pyrimidin-5-yl)benzamide;
4-(2-hydroxypropan-2-yl)-N-(7-(4-(methylsulfonyl)piperazin-1-yl)pyrazolo[1,5-a]pyrimidin-5-yl)benzamide;
91-100
N-(7-(5,6-dihydro-[1,2,4]triazolo[4,3-a]pyrazin-7(8H)-yl)pyrazolo[1,5-a]pyrimidin-5-yl)-4-(2-hydroxypropan-2-yl)benzamide;
(S)-1-(5-(4-(2-hydroxypropan-2-yl)benzamido)pyrazolo[1,5-a]pyrimidin-7-yl)pyrrolidine-2-carboxamide;
4-(2-hydroxypropan-2-yl)-N-(7-(5-oxo-1,4-diazepan-1-yl)pyrazolo[1,5-a]pyrimidin-5-yl)benzamide;
4-(1-hydroxy-2-methylpropan-2-yl)-N-(2-methyl-7-(pyrrolidin-1-yl)pyrazolo[1,5-a]pyrimidin-5-yl)benzamide;
(S)-4-(1-hydroxy-2-methylpropan-2-yl)-N-(7-(2-(hydroxymethyl)pyrrolidin-1-yl)-2-methylpyrazolo[1,5-a]pyrimidin-5-yl)benzamide;
(R)-ethyl 1-(5-(4-(1-hydroxy-2-methylpropan-2-yl)benzamido)-2-methylpyrazolo[1,5-a]pyrimidin-7-yl)piperidine-3-carboxylate;
4-(1-hydroxy-2-methylpropan-2-yl)-N-(7-(3-hydroxyazetidin-1-yl)-2-methylpyrazolo[1,5-a]pyrimidin-5-yl)benzamide;
4-(1-hydroxy-2-methylpropan-2-yl)-N-(2-methyl-7-(4-oxo-3,4,7,8-tetrahydropyrido[4,3-d]pyrimidin-6(5H)-yl)pyrazolo[1,5-a]pyrimidin-5-yl)benzamide;
4-(1-hydroxy-2-methylpropan-2-yl)-N-(2-methyl-7-morpholinopyrazolo[1,5-a]pyrimidin-5-yl)benzamide;
(R)-4-(1-hydroxy-2-methylpropan-2-yl)-N-(7-(3-hydroxypyrrolidin-1-yl)-2-methylpyrazolo[1,5-a]pyrimidin-5-yl)benzamide;
4-(1-hydroxy-2-methylpropan-2-yl)-N-(7-(4-(2-hydroxyethyl)piperidin-1-yl)-2-methylpyrazolo[1,5-a]pyrimidin-5-yl)benzamide;
4-tert-butyl-N-(7-(piperidin-1-yl)pyrazolo[1,5-a]pyrimidin-5-yl)benzamide;
4-tert-butyl-N-(7-morpholinopyrazolo[1,5-a]pyrimidin-5-yl)benzamide;
1-(5-(4-tert-butylbenzamido)pyrazolo[1,5-a]pyrimidin-7-yl)piperidine-3-carboxamide;
4-tert-butyl-N-(7-(2-(2-hydroxyethyl)piperidin-1-yl)pyrazolo[1,5-a]pyrimidin-5-yl)benzamide;
4-tert-butyl-N-(7-(octahydroisoquinolin-2(1H)-yl)pyrazolo[1,5-a]pyrimidin-5-yl)benzamide;
4-tert-butyl-N-(7-(4-hydroxy-4-phenylpiperidin-1-yl)pyrazolo[1,5-a]pyrimidin-5-yl)benzamide;
4-tert-butyl-N-(7-(4-methylpiperazin-1-yl)pyrazolo[1,5-a]pyrimidin-5-yl)benzamide;
4-tert-butyl-N-(7-(4-phenethylpiperazin-1-yl)pyrazolo[1,5-a]pyrimidin-5-yl)benzamide;
4-tert-butyl-N-(7-(6,7-dihydro-2H-pyrazolo[4,3-c]pyridin-5(4H)-yl)pyrazolo[1,5-a]pyrimidin-5-yl)benzamide;
(S)-4-tert-butyl-N-(7-(2-(hydroxymethyl)pyrrolidin-1-yl)pyrazolo[1,5-a]pyrimidin-5-yl)benzamide;
4-tert-butyl-N-(7-(4-hydroxypiperidin-1-yl)pyrazolo[1,5-a]pyrimidin-5-yl)benzamide;
4-tert-butyl-N-(7-(3-hydroxypiperidin-1-yl)pyrazolo[1,5-a]pyrimidin-5-yl)benzamide;
1-(5-(4-tert-butylbenzamido)pyrazolo[1,5-a]pyrimidin-7-yl)piperidine-4-carboxamide;
N-(7-(3-acetamidopyrrolidin-1-yl)pyrazolo[1,5-a]pyrimidin-5-yl)-4-tert-butylbenzamide;
4-tert-butyl-N-(7-(4-(2-hydroxyethyl)piperidin-1-yl)pyrazolo[1,5-a]pyrimidin-5-yl)benzamide;
1-(5-(4-tert-butylbenzamido)pyrazolo[1,5-a]pyrimidin-7-yl)piperidine-3-carboxylic acid;
4-tert-butyl-N-(7-(3-hydroxypyrrolidin-1-yl)pyrazolo[1,5-a]pyrimidin-5-yl)benzamide;
(R)—N-(7-(3-acetamidopyrrolidin-1-yl)pyrazolo[1,5-a]pyrimidin-5-yl)-4-tert-butylbenzamide;
N-(7-(1H-imidazol-1-yl)pyrazolo[1,5-a]pyrimidin-5-yl)-4-tert-butylbenzamide;
N-(7-(1H-1,2,4-triazol-1-yl)pyrazolo[1,5-a]pyrimidin-5-yl)-4-tert-butylbenzamide;
4-tert-butyl-N-(7-(6,7-dihydro-1H-pyrazolo[4,3-b]pyridin-4(5H)-yl)pyrazolo[1,5-a]pyrimidin-5-yl)benzamide;
4-tert-butyl-N-(7-(pyrrolidin-1-yl)pyrazolo[1,5-a]pyrimidin-5-yl)benzamide;
(E)-4-tert-butyl-N-(7-(2-cyclohexylvinyl)pyrazolo[1,5-a]pyrimidin-5-yl)benzamide;
4-tert-butyl-N-(7-(dimethylamino)pyrazolo[1,5-a]pyrimidin-5-yl)benzamide, trifluoroacetate salt;
N-(7-(benzyl(2-(dimethylamino)ethyl)amino)pyrazolo[1,5-a]pyrimidin-5-yl)-4-tert-butylbenzamide;
4-(1-hydroxy-2-methylpropan-2-yl)-N-(2-methyl-7-(methyl(phenethyl)amino)pyrazolo[1,5-a]pyrimidin-5-yl)benzamide;
4-tert-butyl-N-[7-(cyclopropylamino)pyrazolo[1,5-a]pyrimidin-5-yl]benzamide;
4-tert-butyl-N-{7-[(4-methoxybenzyl)amino]pyrazolo[1,5-a]pyrimidin-5-yl}benzamide;
4-tert-butyl-N-{7-[(1-methyl-1-phenylethyl)amino]pyrazolo[1,5-a]pyrimidin-5-yl} benzamide;
131-140
4-tert-butyl-N-[7-(phenylamino)pyrazolo[1,5-a]pyrimidin-5-yl]benzamide;
4-tert-butyl-N-(7-(isobutylamino)pyrazolo[1,5-a]pyrimidin-5-yl)benzamide;
4-tert-butyl-N-(7-(butylamino)pyrazolo[1,5-a]pyrimidin-5-yl)benzamide;
4-tert-butyl-N-(7-(tert-butylamino)pyrazolo[1,5-a]pyrimidin-5-yl)benzamide;
4-tert-butyl-N-(7-(3-hydroxypropylamino)pyrazolo[1,5-a]pyrimidin-5-yl)benzamide;
4-tert-butyl-N-(7-(cyclopentylamino)pyrazolo[1,5-a]pyrimidin-5-yl)benzamide;
4-tert-butyl-N-(7-(furan-2-ylmethylamino)pyrazolo[1,5-a]pyrimidin-5-yl)benzamide;
N-(7-(2-acetamidoethylamino)pyrazolo[1,5-a]pyrimidin-5-yl)-4-tert-butylbenzamide;
4-tert-butyl-N-(7-(2-isopropoxyethylamino)pyrazolo[1,5-a]pyrimidin-5-yl)benzamide;
4-tert-butyl-N-(7-(3-(methylthio)propylamino)pyrazolo[1,5-a]pyrimidin-5-yl)benzamide;
N-(7-(benzylamino)pyrazolo[1,5-a]pyrimidin-5-yl)-4-tert-butylbenzamide;
4-tert-butyl-N-(7-(cyclohexylmethylamino)pyrazolo[1,5-a]pyrimidin-5-yl)benzamide;
4-tert-butyl-N-(7-(phenethylamino)pyrazolo[1,5-a]pyrimidin-5-yl)benzamide;
N-(7-(3-amino-3-oxopropylamino)pyrazolo[1,5-a]pyrimidin-5-yl)-4-tert-butylbenzamide;
4-tert-butyl-N-(7-(3-fluorobenzylamino)pyrazolo[1,5-a]pyrimidin-5-yl)benzamide;
4-tert-butyl-N-(7-(2,3-dihydro-1H-inden-2-ylamino)pyrazolo[1,5-a]pyrimidin-5-yl)benzamide;

4-tert-butyl-N-(7-(4-hydroxyphenethylamino)pyrazolo[1,5-a]pyrimidin-5-yl)benzamide;
4-tert-butyl-N-(7-(2-phenoxyethylamino)pyrazolo[1,5-a]pyrimidin-5-yl)benzamide;
4-tert-butyl-N-(7-(3-(2-oxopyrrolidin-1-yl)propylamino)pyrazolo[1,5-a]pyrimidin-5-yl)benzamide; and
N-(7-(benzo[d][1,3]dioxol-5-ylmethylamino)pyrazolo[1,5-a]pyrimidin-5-yl)-4-tert-butylbenzamide.

Particular examples of compounds according to the present invention and pharmaceutically acceptable salts thereof, include but are not limited to, the following:

N-(7-(2-(1H-indol-3-yl)ethylamino)pyrazolo[1,5-a]pyrimidin-5-yl)-4-tert-butylbenzamide;
4-tert-butyl-N-(7-(4-(trifluoromethyl)benzylamino)pyrazolo[1,5-a]pyrimidin-5-yl)benzamide;
4-tert-butyl-N-(7-(3,4-dimethoxyphenethylamino)pyrazolo[1,5-a]pyrimidin-5-yl)benzamide;
4-tert-butyl-N-(7-(4-sulfamoylbenzylamino)pyrazolo[1,5-a]pyrimidin-5-yl)benzamide;
N-(7-(3,5-bis(trifluoromethyl)benzylamino)pyrazolo[1,5-a]pyrimidin-5-yl)-4-tert-butylbenzamide;
4-tert-butyl-N-(7-(2-methoxyethylamino)pyrazolo[1,5-a]pyrimidin-5-yl)benzamide;
4-tert-butyl-N-(7-(pentan-3-ylamino)pyrazolo[1,5-a]pyrimidin-5-yl)benzamide;
N-(7-(2-amino-2-oxoethylamino)pyrazolo[1,5-a]pyrimidin-5-yl)-4-tert-butylbenzamide;
4-tert-butyl-N-(7-(3-methylbenzylamino)pyrazolo[1,5-a]pyrimidin-5-yl)benzamide;
4-tert-butyl-N-(7-(2-(dimethylamino)ethylamino)pyrazolo[1,5-a]pyrimidin-5-yl)benzamide;
4-tert-butyl-N-(7-(pyridin-3-ylmethylamino)pyrazolo[1,5-a]pyrimidin-5-yl)benzamide;
4-tert-butyl-N-(7-(2-(pyridin-2-yl)ethylamino)pyrazolo[1,5-a]pyrimidin-5-yl)benzamide;
4-tert-butyl-N-(7-((5-methylpyrazin-2-yl)methylamino)pyrazolo[1,5-a]pyrimidin-5-yl)benzamide;
N-(7-(3-(1H-imidazol-1-yl)propylamino)pyrazolo[1,5-a]pyrimidin-5-yl)-4-tert-butylbenzamide;
N-(7-(2-(1H-imidazol-5-yl)ethylamino)pyrazolo[1,5-a]pyrimidin-5-yl)-4-tert-butylbenzamide;
(S)-methyl 2-(5-(4-tert-butylbenzamido)pyrazolo[1,5-a]pyrimidin-7-ylamino)-3-(1H-imidazol-5-yl)propanoate;
4-tert-butyl-N-(7-(2-hydroxycyclohexylamino)pyrazolo[1,5-a]pyrimidin-5-yl)benzamide;
4-tert-butyl-N-(7-(pyridin-2-ylamino)pyrazolo[1,5-a]pyrimidin-5-yl)benzamide;
4-tert-butyl-N-(7-(pyridin-3-ylamino)pyrazolo[1,5-a]pyrimidin-5-yl)benzamide;
4-tert-butyl-N-(7-(pyrimidin-2-ylamino)pyrazolo[1,5-a]pyrimidin-5-yl)benzamide;
4-tert-butyl-N-(7-(pyrimidin-2-ylamino)pyrazolo[1,5-a]pyrimidin-5-yl)benzamide;
2-methyl-7-p-tolylpyrazolo[1,5-a]pyrimidin-5-amine;
(3-(5-amino-2-methylpyrazolo[1,5-a]pyrimidin-7-yl)phenyl)methanol;
7-p-tolylpyrazolo[1,5-a]pyrimidin-5-amine;
7-(thiophen-2-yl)pyrazolo[1,5-a]pyrimidin-5-amine;
7-(5-methylthiophen-2-yl)pyrazolo[1,5-a]pyrimidin-5-amine;
N-(5-(5-aminopyrazolo[1,5-a]pyrimidin-7-yl)pyridin-2-yl)acetamide;
(3-(5-aminopyrazolo[1,5-a]pyrimidin-7-yl)phenyl)methanol;
N-(7-(3-(benzyloxy)phenyl)pyrazolo[1,5-a]pyrimidin-5-yl)-4-(2-hydroxypropan-2-yl)benzamide;
N-(7-(2,3-dihydrobenzofuran-5-yl)pyrazolo[1,5-a]pyrimidin-5-yl)-4-(2-hydroxypropan-2-yl)benzamide;
4-(2-hydroxypropan-2-yl)-N-(7-(3-methoxyphenyl)pyrazolo[1,5-a]pyrimidin-5-yl)benzamide;
(E)-4-(2-hydroxypropan-2-yl)-N-(7-styrylpyrazolo[1,5-a]pyrimidin-5-yl)benzamide;
4-(2-hydroxypropan-2-yl)-N-(7-(thiophen-3-yl)pyrazolo[1,5-a]pyrimidin-5-yl)benzamide;
N-(7-(3-hydroxyazetidin-1-yl)pyrazolo[1,5-a]pyrimidin-5-yl)-4-(2-hydroxypropan-2-yl)benzamide;
4-(2-hydroxypropan-2-yl)-N-(7-(2-methylpyrrolidin-1-yl)pyrazolo[1,5-a]pyrimidin-5-yl)benzamide;
N-(7-(3-fluoropyrrolidin-1-yl)pyrazolo[1,5-a]pyrimidin-5-yl)-4-(2-hydroxypropan-2-yl)benzamide;
4-(2-hydroxypropan-2-yl)-N-(7-(3-oxopiperazin-1-yl)pyrazolo[1,5-a]pyrimidin-5-yl)benzamide;
4-(2-hydroxypropan-2-yl)-N-(7-(3-oxopiperazin-1-yl)pyrazolo[1,5-a]pyrimidin-5-yl)benzamide;
4-(2-hydroxypropan-2-yl)-N-(7-(3-methyl-4-oxopiperidin-1-yl)pyrazolo[1,5-a]pyrimidin-5-yl)benzamide;
N-(7-(3,3-dimethylpiperidin-1-yl)pyrazolo[1,5-a]pyrimidin-5-yl)-4-(2-hydroxypropan-2-yl)benzamide;
N-(7-(4-formylpiperazin-1-yl)pyrazolo[1,5-a]pyrimidin-5-yl)-4-(2-hydroxypropan-2-yl)benzamide;
(S)—N-(7-(3-(dimethylamino)pyrrolidin-1-yl)pyrazolo[1,5-a]pyrimidin-5-yl)-4-(2-hydroxypropan-2-yl)benzamide;
(R)-4-(2-hydroxypropan-2-yl)-N-(7-(2-(methoxymethyl)pyrrolidin-1-yl)pyrazolo[1,5-a]pyrimidin-5-yl)benzamide;
(R)—N-(7-(3-(dimethylamino)pyrrolidin-1-yl)pyrazolo[1,5-a]pyrimidin-5-yl)-4-(2-hydroxypropan-2-yl)benzamide;
N-(7-(2,5-dimethylpiperazin-1-yl)pyrazolo[1,5-a]pyrimidin-5-yl)-4-(2-hydroxypropan-2-yl)benzamide;
4-(2-hydroxypropan-2-yl)-N-(7-(4-methyl-1,4-diazepan-1-yl)pyrazolo[1,5-a]pyrimidin-5-yl)benzamide;
N-(7-(2,6-dimethylmorpholino)pyrazolo[1,5-a]pyrimidin-5-yl)-4-(2-hydroxypropan-2-yl)benzamide;
N-(7-(3-(hydroxymethyl)piperidin-1-yl)pyrazolo[1,5-a]pyrimidin-5-yl)-4-(2-hydroxypropan-2-yl)benzamide;
N-(7-(4-(hydroxymethyl)piperidin-1-yl)pyrazolo[1,5-a]pyrimidin-5-yl)-4-(2-hydroxypropan-2-yl)benzamide;
4-(2-hydroxypropan-2-yl)-N-(7-(4-methoxypiperidin-1-yl)pyrazolo[1,5-a]pyrimidin-5-yl)benzamide;
4-(2-hydroxypropan-2-yl)-N-(2-methyl-7-morpholinopyrazolo[1,5-a]pyrimidin-5-yl)benzamide;
4-(2-hydroxypropan-2-yl)-N-(2-methyl-7-phenylpyrazolo[1,5-a]pyrimidin-5-yl)benzamide;
(R)-4-(2-hydroxypropan-2-yl)-N-(7-(3-hydroxypyrrolidin-1-yl)-2-methylpyrazolo[1,5-a]pyrimidin-5-yl)benzamide;
4-(2-hydroxypropan-2-yl)-N-(2-methyl-7-(piperidin-1-yl)pyrazolo[1,5-a]pyrimidin-5-yl)benzamide;
N-(7-(benzo[d][1,3]dioxol-4-yl)pyrazolo[1,5-a]pyrimidin-5-yl)-4-(2-hydroxypropan-2-yl)benzamide;
4-(2-hydroxypropan-2-yl)-N-(2-methyl-7-(4-oxo-3,4,7,8-tetrahydropyrido[4,3-d]pyrimidin-6(5H)-yl)pyrazolo[1,5-a]pyrimidin-5-yl)benzamide;
4-(2-hydroxypropan-2-yl)-N-(2-methyl-7-thiomorpholinopyrazolo[1,5-a]pyrimidin-5-yl)benzamide;
4-[5-({[4-(1-hydroxy-1-methylethyl)phenyl]carbonyl}amino)-2-methylpyrazolo[1,5-a]pyrimidin-7-yl]thiomorpholin-1-ium-1-olate;
N-[7-(1,1-dioxidothiomorpholin-4-yl)-2-methylpyrazolo[1,5-a]pyrimidin-5-yl]-4-(1-hydroxy-1-methylethyl)benzamide;

N-(7-(4-(ethylsulfonyl)piperazin-1-yl)-2-methylpyrazolo[1,5-a]pyrimidin-5-yl)-4-(2-hydroxypropan-2-yl)benzamide;
N-(7-(4-(hydroxymethyl)piperidin-1-yl)-2-methylpyrazolo[1,5-a]pyrimidin-5-yl)-4-(2-hydroxypropan-2-yl)benzamide;
N-(7-(4-(hydroxymethyl)piperidin-1-yl)-2-methylpyrazolo[1,5-a]pyrimidin-5-yl)-4-(2-hydroxypropan-2-yl)benzamide;
N-(2-methyl-7-(4-oxo-3,4,7,8-tetrahydropyrido[4,3-d]pyrimidin-6(5H)-yl)pyrazolo[1,5-a]pyrimidin-5-yl)-6-(trifluoromethyl)nicotinamide;)
N-(2-cyclopropyl-7-phenylpyrazolo[1,5-a]pyrimidin-5-yl)-4-(2-hydroxypropan-2-yl)benzamide;
N-(2-cyclopropyl-7-(3-(hydroxymethyl)phenyl)pyrazolo[1,5-a]pyrimidin-5-yl)-4-(2-hydroxypropan-2-yl)benzamide;
N-(2-cyclopropyl-7-morpholinopyrazolo[1,5-a]pyrimidin-5-yl)-4-(2-hydroxypropan-2-yl)benzamide;
N-(2-cyclopropyl-7-(4-hydroxypiperidin-1-yl)pyrazolo[1,5-a]pyrimidin-5-yl)-4-(2-hydroxypropan-2-yl)benzamide;
methyl 4-(7-chloro-2-(trifluoromethyl)pyrazolo[1,5-a]pyrimidin-5-ylcarbamoyl)benzoate;
4-(2-hydroxypropan-2-yl)-N-(7-(4-(2-hydroxypropan-2-yl)piperidin-1-yl)-2-methylpyrazolo[1,5-a]pyrimidin-5-yl)benzamide; and
4-(2-hydroxypropan-2-yl)-N-(7-(4-methoxyphenyl)-2-methylpyrazolo[1,5-c]pyrimidin-5-yl)benzamide.
4-(2-hydroxypropan-2-yl)-N-(7-morpholino-2-(trifluoromethyl)pyrazolo[1,5-c]pyrimidin-5-yl)benzamide;
4-(2-hydroxypropan-2-yl)-N-(7-(4-(methoxymethyl)piperidin-1-yl)pyrazolo[1,5-c]pyrimidin-5-yl)benzamide;
4-(2-hydroxypropan-2-yl)-N-(7-(4-(2-hydroxypropan-2-yl)piperidin-1-yl)pyrazolo[1,5-a]pyrimidin-5-yl)benzamide;
N-(7-(2,3-dihydrobenzofuran-5-yl)-2-methylpyrazolo[1,5-a]pyrimidin-5-yl)-4-(2-hydroxypropan-2-yl)benzamide; and
methyl 4-(7-phenyl-2-(trifluoromethyl)pyrazolo[1,5-a]pyrimidin-5-ylcarbamoyl)benzoate.

Particular examples of compounds according to the present invention also include, but are not limited to, the following:
4-(2-hydroxypropan-2-yl)-N-(7-(4-(methoxymethyl)piperidin-1-yl)-2-methylpyrazolo[1,5-a]pyrimidin-5-yl)benzamide;
1-(5-(4-(2-hydroxypropan-2-yl)benzamido)-2-methylpyrazolo[1,5-a]pyrimidin-7-yl)piperidine-4-carboxylic acid;
N-(2-ethyl-7-(4-methoxyphenyl)pyrazolo[1,5-a]pyrimidin-5-yl)-4-(2-hydroxypropan-2-yl)benzamide;
N-(2-ethyl-7-phenylpyrazolo[1,5-a]pyrimidin-5-yl)-4-(2-hydroxypropan-2-yl)benzamide;
4-(2-hydroxypropan-2-yl)-N-(7-phenyl-2-(trifluoromethyl)pyrazolo[1,5-a]pyrimidin-5-yl)benzamide;
N-(2-ethyl-7-morpholinopyrazolo[1,5-a]pyrimidin-5-yl)-4-(2-hydroxypropan-2-yl)benzamide;
N-(7-(benzo[d][1,3]dioxol-5-yl)-2-methylpyrazolo[1,5-a]pyrimidin-5-yl)-4-(2-hydroxypropan-2-yl)benzamide;
N-(7-(4-(1-hydroxy-2-methylpropyl)piperidin-1-yl)pyrazolo[1,5-a]pyrimidin-5-yl)-4-(2-hydroxypropan-2-yl)benzamide;
N-(7-(4-formyl-1,4-diazepan-1-yl)pyrazolo[1,5-a]pyrimidin-5-yl)-4-(2-hydroxypropan-2-yl)benzamide;
N-(7-(4-acetyl-1,4-diazepan-1-yl)pyrazolo[1,5-a]pyrimidin-5-yl)-4-(2-hydroxypropan-2-yl)benzamide;
4-(2-hydroxypropan-2-yl)-N-(7-(3-hydroxypyrrolidin-1-yl)pyrazolo[1,5-a]pyrimidin-5-yl)benzamide;
N-(7-(4-acetyl-1,4-diazepan-1-yl)-2-ethylpyrazolo[1,5-a]pyrimidin-5-yl)-4-(2-hydroxypropan-2-yl)benzamide;

methyl 1-(5-(4-(2-hydroxypropan-2-yl)benzamido)-2-methylpyrazolo[1,5-a]pyrimidin-7-yl)piperidine-4-carboxylate;
4-(2-hydroxypropan-2-yl)-N-(7-(3-methoxyphenyl)-2-methylpyrazolo[1,5-a]pyrimidin-5-yl)benzamide;
N-(7-(4-(1-hydroxy-2-methylpropyl)piperidin-1-yl)-2-methylpyrazolo[1,5-a]pyrimidin-5-yl)-4-(2-hydroxypropan-2-yl)benzamide;
4-(2-hydroxypropan-2-yl)-N-(2-methyl-7-(1-oxo-2,8-diazaspiro[4.5]decan-8-yl)pyrazolo[1,5-a]pyrimidin-5-yl)benzamide;
4-(2-hydroxypropan-2-yl)-N-(2-methyl-7-(4-(pyrrolidine-1-carbonyl)piperidin-1-yl)pyrazolo[1,5-a]pyrimidin-5-yl)benzamide;
N-(7-(benzo[d][1,3]dioxol-5-yl)pyrazolo[1,5-a]pyrimidin-5-yl)-4-(2-hydroxypropan-2-yl)benzamide;
1-(5-(4-(2-hydroxypropan-2-yl)benzamido)pyrazolo[1,5-a]pyrimidin-7-yl)piperidine-4-carboxylic acid;
Methyl 1-(5-(4-(2-hydroxypropan-2-yl)benzamido)pyrazolo[1,5-a]pyrimidin-7-yl)piperidine-4-carboxylate;
4-(2-hydroxypropan-2-yl)-N-(2-methyl-7-(4-(phenylthio)piperidin-1-yl)pyrazolo[1,5-a]pyrimidin-5-yl)benzamide;
4-(2-hydroxypropan-2-yl)-N-(2-methyl-7-(4-(phenylsulfonyl)piperidin-1-yl)pyrazolo[1,5-a]pyrimidin-5-yl)benzamide;
4-(2-hydroxypropan-2-yl)-N-(2-methyl-7-(4-(phenylsulfonyl)piperazin-1-yl)pyrazolo[1,5-a]pyrimidin-5-yl)benzamide;
N-(7-(4-(N,N-dimethylsulfamoyl)piperazin-1-yl)-2-methylpyrazolo[1,5-a]pyrimidin-5-yl)-4-(2-hydroxypropan-2-yl)benzamide;
4-(2-hydroxypropan-2-yl)-N-(2-methyl-7-(4-(propylsulfonyl)piperazin-1-yl)pyrazolo[1,5-a]pyrimidin-5-yl)benzamide;
4-(2-hydroxypropan-2-yl)-N-(2-methyl-7-(4-(methylsulfonyl)-1,4-diazepan-1-yl)pyrazolo[1,5-a]pyrimidin-5-yl)benzamide;
4-(2-hydroxypropan-2-yl)-N-(7-(1,2,3,4-tetrahydroisoquinolin-7-yl)pyrazolo[1,5-c]pyrimidin-5-yl)benzamide, trifluoroacetate salt;
1-(5-(4-(2-hydroxypropan-2-yl)benzamido)-2-methylpyrazolo[1,5-a]pyrimidin-7-yl)piperidine-4-carboxamide;
4-(2-hydroxypropan-2-yl)-N-(2-methyl-7-(4-methylpiperidin-1-yl)pyrazolo[1,5-c]pyrimidin-5-yl)benzamide;
4-(2-hydroxypropan-2-yl)-N-(2-methyl-7-(1,4-oxazepan-4-yl)pyrazolo[1,5-c]pyrimidin-5-yl)benzamide;
N-(7-(4-formyl-1,4-diazepan-1-yl)-2-methylpyrazolo[1,5-a]pyrimidin-5-yl)-4-(2-hydroxypropan-2-yl)benzamide;
N-(7-(4-acetyl-1,4-diazepan-1-yl)-2-methylpyrazolo[1,5-a]pyrimidin-5-yl)-4-(2-hydroxypropan-2-yl)benzamide;
(S)—N-(7-(2-(hydroxymethyl)pyrrolidin-1-yl)-2-methylpyrazolo[1,5-a]pyrimidin-5-yl)-4-(2-hydroxypropan-2-yl)benzamide;
N-ethyl-1-(5-(4-(2-hydroxypropan-2-yl)benzamido)-2-methylpyrazolo[1,5-a]pyrimidin-7-yl)piperidine-4-carboxamide;
1-(5-(4-(2-hydroxypropan-2-yl)benzamido)-2-methylpyrazolo[1,5-a]pyrimidin-7-yl)-N-methylpiperidine-4-carboxamide;
1-(5-(4-(2-hydroxypropan-2-yl)benzamido)-2-methylpyrazolo[1,5-a]pyrimidin-7-yl)-N,N-dimethylpiperidine-4-carboxamide;
N-(7-(2,2-difluorobenzo[d][1,3]dioxol-4-yl)pyrazolo[1,5-a]pyrimidin-5-yl)-4-(2-hydroxypropan-2-yl)benzamide;
N-(7-(4,4-difluoropiperidin-1-yl)pyrazolo[1,5-a]pyrimidin-5-yl)-4-(2-hydroxypropan-2-yl)benzamide;

4-(2-hydroxypropan-2-yl)-N-(7-(4-(trifluoromethyl)piperidin-1-yl)pyrazolo[1,5-a]pyrimidin-5-yl)benzamide;
4-(2-hydroxypropan-2-yl)-N-(2-methyl-7-(1,2,3,4-tetrahydroisoquinolin-7-yl)pyrazolo[1,5-a]pyrimidin-5-yl)benzamide;
1-(5-(4-(2-hydroxypropan-2-yl)benzamido)pyrazolo[1,5-a]pyrimidin-7-yl)-N-methylpiperidine-4-carboxamide;
1-(5-(4-(2-hydroxypropan-2-yl)benzamido)pyrazolo[1,5-a]pyrimidin-7-yl)-N-isopropylpiperidine-4-carboxamide;
(R)-1-(5-(4-(2-hydroxypropan-2-yl)benzamido)pyrazolo[1,5-a]pyrimidin-7-yl)-N-methylpiperidine-3-carboxamide;
(R)-1-(5-(4-(2-hydroxypropan-2-yl)benzamido)pyrazolo[1,5-a]pyrimidin-7-yl)-N-methylpiperidine-3-carboxamide;
R)-1-(5-(4-(2-hydroxypropan-2-yl)benzamido)pyrazolo[1,5-a]pyrimidin-7-yl)-N,N-dimethylpiperidine-3-carboxamide;
4-(2-hydroxypropan-2-yl)-N-(7-phenoxypyrazolo[1,5-a]pyrimidin-5-yl)benzamide;
(R)-1-(5-(4-(2-hydroxypropan-2-yl)benzamido)pyrazolo[1,5-a]pyrimidin-7-yl)-N-isopropylpiperidine-3-carboxamide;
N-(7-(3-fluoropyrrolidin-1-yl)-2-methylpyrazolo[1,5-a]pyrimidin-5-yl)-4-(2-hydroxypropan-2-yl)benzamide;
N-(7-(4-(2-hydroxyethyl)piperidin-1-yl)-2-methylpyrazolo[1,5-a]pyrimidin-5-yl)-4-(2-hydroxypropan-2-yl)benzamide;
N-(7-(2,3-dihydrobenzo[b][1,4]dioxin-6-yl)-2-methylpyrazolo[1,5-a]pyrimidin-5-yl)-4-(2-hydroxypropan-2-yl)benzamide;
N-(7-morpholinopyrazolo[1,5-a]pyrimidin-5-yl)-4-(6-oxo-1,6-dihydropyridin-3-yl)benzamide;
(E)-4-(2-hydroxypropan-2-yl)-N-(2-methyl-7-styrylpyrazolo[1,5-a]pyrimidin-5-yl)benzamide;
(E)-N-(7-(4-fluorostyryl)-2-methylpyrazolo[1,5-a]pyrimidin-5-yl)-4-(2-hydroxypropan-2-yl)benzamide;
(E)-4-(2-hydroxypropan-2-yl)-N-(7-(3-methoxystyryl)-2-methylpyrazolo[1,5-c]pyrimidin-5-yl)benzamide;
N-(7-(4-acetamidopiperidin-1-yl)-2-methylpyrazolo[1,5-a]pyrimidin-5-yl)-4-(2-hydroxypropan-2-yl)benzamide;
(R)—N-ethyl-1-(5-(4-(2-hydroxypropan-2-yl)benzamido)pyrazolo[1,5-a]pyrimidin-7-yl)piperidine-3-carboxamide;
N-(7-(4-chlorophenyl)pyrazolo[1,5-a]pyrimidin-5-yl)-4-(2-hydroxypropan-2-yl)benzamide;
N-(7-(4-fluorophenyl)pyrazolo[1,5-a]pyrimidin-5-yl)-4-(2-hydroxypropan-2-yl)benzamide;
4-(furan-3-yl)-N-(7-morpholinopyrazolo[1,5-a]pyrimidin-5-yl)benzamide;
methyl 1-(4-(7-morpholinopyrazolo[1,5-a]pyrimidin-5-ylcarbamoyl)phenyl)cyclopropanecarboxylate;
N-(7-butoxypyrazolo[1,5-a]pyrimidin-5-yl)-4-(2-hydroxypropan-2-yl)benzamide;
methyl 1-(4-(2-methyl-7-phenylpyrazolo[1,5-a]pyrimidin-5-ylcarbamoyl)phenyl)cyclopropanecarboxylate;
1-(4-(7-morpholinopyrazolo[1,5-a]pyrimidin-5-ylcarbamoyl)phenyl)cyclopropanecarboxylic acid;
4-(2-hydroxypropan-2-yl)-N-(7-methoxypyrazolo[1,5-a]pyrimidin-5-yl)benzamide;
N-(7-(5,6-dihydro-[1,2,4]triazolo[4,3-a]pyrazin-7(8H)-yl)-2-methylpyrazolo[1,5-a]pyrimidin-5-yl)-4-(2-hydroxypropan-2-yl)benzamide;
N-(7-(3,4-dimethoxyphenyl)-2-methylpyrazolo[1,5-a]pyrimidin-5-yl)-4-(2-hydroxypropan-2-yl)benzamide;
N-(7-(3,4-dihydro-2H-benzo[b][1,4]dioxepin-7-yl)-2-methylpyrazolo[1,5-a]pyrimidin-5-yl)-4-(2-hydroxypropan-2-yl)benzamide;
N-(7-(2,2-difluorobenzo[d][1,3]dioxol-5-yl)-2-methylpyrazolo[1,5-a]pyrimidin-5-yl)-4-(2-hydroxypropan-2-yl)benzamide;
N-(7-(4-(2-hydroxyethyl)piperidin-1-yl)-2-methylpyrazolo[1,5-a]pyrimidin-5-yl)-2-phenylcyclopropanecarboxamide;
N-(7-(benzo[b]thiophen-5-yl)-2-methylpyrazolo[1,5-a]pyrimidin-5-yl)-4-(2-hydroxypropan-2-yl)benzamide;
4-(2-hydroxypropan-2-yl)-N-(2-methyl-7-(4-methyl-3,4-dihydro-2H-benzo[b][1,4]oxazin-7-yl)pyrazolo[1,5-a]pyrimidin-5-yl)benzamide;
4-(2-hydroxypropan-2-yl)-N-(7-(4-isopropoxyphenyl)-2-methylpyrazolo[1,5-a]pyrimidin-5-yl)benzamide;
(S)—N-(7-(3-acetamidopyrrolidin-1-yl)pyrazolo[1,5-a]pyrimidin-5-yl)-4-(2-hydroxypropan-2-yl)benzamide;
(R)—N-(7-(3-acetamidopyrrolidin-1-yl)pyrazolo[1,5-a]pyrimidin-5-yl)-4-(2-hydroxypropan-2-yl)benzamide; and
N-(7-((S)-3-fluoropyrrolidin-1-yl)-2-methylpyrazolo[1,5-a]pyrimidin-5-yl)-2-phenylcyclopropanecarboxamide.

Particular examples of compounds according to the present invention further include, but are not limited to, the following:
N-(7-((R)-3-fluoropyrrolidin-1-yl)-2-methylpyrazolo[1,5-a]pyrimidin-5-yl)-2-phenylcyclopropanecarboxamide;
N-(7-(4-methoxyphenyl)-2-methylpyrazolo[1,5-a]pyrimidin-5-yl)-2-phenylcyclopropanecarboxamide;
(S)-1-(5-(4-(2-hydroxypropan-2-yl)benzamido)pyrazolo[1,5-a]pyrimidin-7-yl)-N-methylpiperidine-3-carboxamide;
(S)—N-(7-(3-acetamidopiperidin-1-yl)pyrazolo[1,5-a]pyrimidin-5-yl)-4-(2-hydroxypropan-2-yl)benzamide;
(S)—N-(7-(3-aminopiperidin-1-yl)pyrazolo[1,5-a]pyrimidin-5-yl)-4-(2-hydroxypropan-2-yl)benzamide, trifluoroacetate salt;
(R)—N-(7-(3-acetamidopiperidin-1-yl)pyrazolo[1,5-a]pyrimidin-5-yl)-4-(2-hydroxypropan-2-yl)benzamide;
N-(7-(4-chlorophenyl)-2-methylpyrazolo[1,5-a]pyrimidin-5-yl)-4-(2-hydroxypropan-2-yl)benzamide;
N-(7-(4-fluoro-3-methoxyphenyl)-2-methylpyrazolo[1,5-a]pyrimidin-5-yl)-4-(2-hydroxypropan-2-yl)benzamide;
(R)—N-(7-(3-aminopiperidin-1-yl)pyrazolo[1,5-a]pyrimidin-5-yl)-4-(2-hydroxypropan-2-yl)benzamide, trifluoroacetate salt;
5-(2-hydroxypropan-2-yl)-N-(2-methyl-7-phenylpyrazolo[1,5-a]pyrimidin-5-yl)picolinamide;
N-(7-(5-chlorothiophen-2-yl)-2-methylpyrazolo[1,5-a]pyrimidin-5-yl)-4-(2-hydroxypropan-2-yl)benzamide;
N-(7-(4-acetamidopiperidin-1-yl)-2-methylpyrazolo[1,5-a]pyrimidin-5-yl)-2-phenylcyclopropanecarboxamide;
N-(7-(3-fluoro-4-methoxyphenyl)-2-methylpyrazolo[1,5-a]pyrimidin-5-yl)-4-(2-hydroxypropan-2-yl)benzamide;
N-(7-(3-chloro-4-methoxyphenyl)-2-methylpyrazolo[1,5-a]pyrimidin-5-yl)-4-(2-hydroxypropan-2-yl)benzamide;
6-(2-hydroxypropan-2-yl)-N-(2-methyl-7-phenylpyrazolo[1,5-a]pyrimidin-5-yl)nicotinamide;
6-(2-hydroxypropan-2-yl)-N-(7-morpholinopyrazolo[1,5-a]pyrimidin-5-yl)nicotinamide;
(R)-1-(5-(4-(2-hydroxypropan-2-yl)benzamido)-2-methylpyrazolo[1,5-c]pyrimidin-7-yl)-N-methylpiperidine-3-carboxamide;
N-(7-(4-chloro-3-methylphenyl)-2-methylpyrazolo[1,5-a]pyrimidin-5-yl)-4-(2-hydroxypropan-2-yl)benzamide;
N-(7-(3-chloro-4-hydroxyphenyl)-2-methylpyrazolo[1,5-a]pyrimidin-5-yl)-4-(2-hydroxypropan-2-yl)benzamide;
N-(7-(4-(2-(dimethylamino)ethoxy)phenyl)-2-methylpyrazolo[1,5-a]pyrimidin-5-yl)-4-(2-hydroxypropan-2-yl)benzamide;

4-(2-hydroxypropan-2-yl)-N-(2-methyl-7-(4-(2-morpholinoethoxy)phenyl)pyrazolo[1,5-a]pyrimidin-5-yl)benzamide;
4-(2-hydroxypropan-2-yl)-N-(7-(4-(2-methoxyethoxy)phenyl)-2-methylpyrazolo[1,5-a]pyrimidin-5-yl)benzamide;
4-(2-hydroxypropan-2-yl)-N-(2-methyl-7-(4-propionamidopiperidin-1-yl)pyrazolo[1,5-a]pyrimidin-5-yl)benzamide;
4-(2-hydroxypropan-2-yl)-N-(2-methyl-7-(4-ureidopiperidin-1-yl)pyrazolo[1,5-c]pyrimidin-5-yl)benzamide;
N-(7-(4-(2-amino-2-oxoethyl)piperidin-1-yl)-2-methylpyrazolo[1,5-a]pyrimidin-5-yl)-4-(2-hydroxypropan-2-yl)benzamide;
N-(7-(benzofuran-5-yl)-2-methylpyrazolo[1,5-a]pyrimidin-5-yl)-4-(2-hydroxypropan-2-yl)benzamide;
N-(7-(3-(dimethylamino)phenyl)-2-methylpyrazolo[1,5-a]pyrimidin-5-yl)-4-(2-hydroxypropan-2-yl)benzamide;
4-(2-hydroxypropan-2-yl)-N-(7-(6-hydroxypyridin-3-yl)-2-methylpyrazolo[1,5-c]pyrimidin-5-yl)benzamide;
4-(2-hydroxypropan-2-yl)-N-(7-(6-methoxypyridin-3-yl)-2-methylpyrazolo[1,5-c]pyrimidin-5-yl)benzamide;
3,3-dimethyl-N-(2-methyl-7-phenylpyrazolo[1,5-a]pyrimidin-5-yl)-2,3-dihydrobenzofuran-6-carboxamide;
N-(2-methyl-7-phenylpyrazolo[1,5-a]pyrimidin-5-yl)-2-(pyridin-4-yl)cyclopropanecarboxamide;
N-(7-(4-(cyclopropanecarboxamido)piperidin-1-yl)-2-methylpyrazolo[1,5-c]pyrimidin-5-yl)-4-(2-hydroxypropan-2-yl)benzamide;
4-(2-cyanopropan-2-yl)-N-(2-methyl-7-phenylpyrazolo[1,5-a]pyrimidin-5-yl)benzamide;
4-(1-amino-2-methylpropan-2-yl)-N-(2-methyl-7-phenylpyrazolo[1,5-a]pyrimidin-5-yl)benzamide;
2-(2-methyl-2-(4-(2-methyl-7-phenylpyrazolo[1,5-a]pyrimidin-5-ylcarbamoyl)phenyl)propylamino)-2-oxoacetic acid;
N-(7-(4-acetamidopiperidin-1-yl)-2-methylpyrazolo[1,5-a]pyrimidin-5-yl)-2-(pyridin-4-yl)cyclopropanecarboxamide;
N-(2-methyl-7-(4-ureidopiperidin-1-yl)pyrazolo[1,5-a]pyrimidin-5-yl)-2-(pyridin-4-yl)cyclopropanecarboxamide;
6-(2-hydroxypropan-2-yl)-N-(7-(4-methoxyphenyl)-2-methylpyrazolo[1,5-c]pyrimidin-5-yl)nicotinamide, trifluoroacetate salt;
N-(7-(benzo[d][1,3]dioxol-5-yl)-2-methylpyrazolo[1,5-a]pyrimidin-5-yl)-6-(2-hydroxypropan-2-yl)nicotinamide, trifluoroacetate salt;
N-(7-(2,3-dihydrobenzofuran-5-yl)-2-methylpyrazolo[1,5-a]pyrimidin-5-yl)-6-(2-hydroxypropan-2-yl)nicotinamide, trifluoroacetate salt;
N-(7-(4-acetamidopiperidin-1-yl)-2-methylpyrazolo[1,5-a]pyrimidin-5-yl)-6-(2-hydroxypropan-2-yl)nicotinamide, trifluoroacetate salt;
6-(2-hydroxypropan-2-yl)-N-(2-methyl-7-(4-ureidopiperidin-1-yl)pyrazolo[1,5-c]pyrimidin-5-yl)nicotinamide, trifluoroacetate salt;
N-(7-(4-(2-amino-2-oxoethyl)piperazin-1-yl)-2-methylpyrazolo[1,5-a]pyrimidin-5-yl)-4-(2-hydroxypropan-2-yl)benzamide, trifluoroacetate salt;
N-(7-(4-(2-amino-2-oxoethyl)piperazin-1-yl)-2-methylpyrazolo[1,5-a]pyrimidin-5-yl)-4-(2-hydroxypropan-2-yl)benzamide, trifluoroacetate salt;
methyl 3-methyl-3-(4-(2-methyl-7-phenylpyrazolo[1,5-a]pyrimidin-5-ylcarbamoyl)phenyl)butanoate;
(1S,2S)—N-(2-methyl-7-phenylpyrazolo[1,5-a]pyrimidin-5-yl)-2-phenylcyclopropanecarboxamide;
(1R,2R)—N-(2-methyl-7-phenylpyrazolo[1,5-a]pyrimidin-5-yl)-2-phenylcyclopropanecarboxamide;
(1R,2S)—N-(2-methyl-7-phenylpyrazolo[1,5-a]pyrimidin-5-yl)-2-phenylcyclopropanecarboxamide;
N-(7-(4-chloro-3-methoxyphenyl)-2-methylpyrazolo[1,5-a]pyrimidin-5-yl)-4-(2-hydroxypropan-2-yl)benzamide;
N-(2-methyl-7-morpholinopyrazolo[1,5-a]pyrimidin-5-yl)-4-(trifluoromethoxy)benzamide;
N-(2-hydroxyethyl)-1-(5-(4-(2-hydroxypropan-2-yl)benzamido)-2-methylpyrazolo[1,5-a]pyrimidin-7-yl)piperidine-3-carboxamide;
N-(7-(6-ethoxypyridin-3-yl)-2-methylpyrazolo[1,5-a]pyrimidin-5-yl)-4-(2-hydroxypropan-2-yl)benzamide;
4-(2-hydroxypropan-2-yl)-N-(7-(6-isopropoxypyridin-3-yl)-2-methylpyrazolo[1,5-a]pyrimidin-5-yl)benzamide;
N-(7-(6-(cyclopropylmethoxy)pyridin-3-yl)-2-methylpyrazolo[1,5-a]pyrimidin-5-yl)-4-(2-hydroxypropan-2-yl)benzamide;
N-(2-methyl-7-phenylpyrazolo[1,5-a]pyrimidin-5-yl)-4-(trifluoromethylthio)benzamide;
(1R,2R)—N-(7-(4-acetamidopiperidin-1-yl)-2-methylpyrazolo[1,5-a]pyrimidin-5-yl)-2-phenylcyclopropanecarboxamide;
(1R,2R)—N-(2-methyl-7-(4-ureidopiperidin-1-yl)pyrazolo[1,5-a]pyrimidin-5-yl)-2-phenylcyclopropanecarboxamide;
(1S,2S)—N-(7-(4-acetamidopiperidin-1-yl)-2-methylpyrazolo[1,5-a]pyrimidin-5-yl)-2-phenylcyclopropanecarboxamide;
2-(4-fluorophenyl)-N-(2-methyl-7-phenylpyrazolo[1,5-a]pyrimidin-5-yl)cyclopropanecarboxamide;
cis-2-(4-fluorophenyl)-N-(2-methyl-7-phenylpyrazolo[1,5-a]pyrimidin-5-yl)cyclopropanecarboxamide;
N-(7-(4-acetamidopiperidin-1-yl)-2-methylpyrazolo[1,5-a]pyrimidin-5-yl)-2-(4-fluorophenyl)cyclopropanecarboxamide;
2-(4-fluorophenyl)-N-(2-methyl-7-(4-ureidopiperidin-1-yl)pyrazolo[1,5-a]pyrimidin-5-yl)cyclopropanecarboxamide;
N-(2-methyl-7-(4-ureidopiperidin-1-yl)pyrazolo[1,5-a]pyrimidin-5-yl)-4-(trifluoromethoxy)benzamide;
N-(7-(4-(2-amino-2-oxoethyl)piperidin-1-yl)-2-methylpyrazolo[1,5-a]pyrimidin-5-yl)-4-(trifluoromethoxy)benzamide;
N-(7-(4-acetamidopiperidin-1-yl)-2-methylpyrazolo[1,5-a]pyrimidin-5-yl)-4-(trifluoromethoxy)benzamide; and
N-(7-(4-acetamidopiperidin-1-yl)-2-methylpyrazolo[1,5-a]pyrimidin-5-yl)-2-(pyridin-4-yl)cyclopropanecarboxamide.

Particular examples of compounds according to the present invention further include, but are not limited to, the following:
N-(7-morpholinopyrazolo[1,5-a]pyrimidin-5-yl)cyclopropanecarboxamide;
N-(7-morpholinopyrazolo[1,5-a]pyrimidin-5-yl)isobutyramide;
N-(7-morpholinopyrazolo[1,5-a]pyrimidin-5-yl)cyclopentanecarboxamide;
3-(methylthio)-N-(7-morpholinopyrazolo[1,5-a]pyrimidin-5-yl)propanamide;
3,3,3-trifluoro-N-(7-morpholinopyrazolo[1,5-a]pyrimidin-5-yl)propanamide;
(E)-3-(furan-2-yl)-N-(7-morpholinopyrazolo[1,5-a]pyrimidin-5-yl)acrylamide;
2-cyclohexyl-N-(7-morpholinopyrazolo[1,5-a]pyrimidin-5-yl)acetamide;
N-(7-morpholinopyrazolo[1,5-a]pyrimidin-5-yl)cinnamamide;
N-(7-morpholinopyrazolo[1,5-a]pyrimidin-5-yl)-3-phenylpropanamide;

2-(4-fluorophenyl)-N-(7-morpholinopyrazolo[1,5-a]pyrimidin-5-yl)acetamide;
N-(2-(7-morpholinopyrazolo[1,5-a]pyrimidin-5-ylamino)-2-oxoethyl)benzamide;
3-(1H-indol-3-yl)-N-(7-morpholinopyrazolo[1,5-a]pyrimidin-5-yl)propanamide;
N-(3-(7-morpholinopyrazolo[1,5-a]pyrimidin-5-ylamino)-3-oxopropyl)benzamide;
3-(3,4-dimethoxyphenyl)-N-(7-morpholinopyrazolo[1,5-a]pyrimidin-5-yl)propanamide;
2-(biphenyl-4-yl)-N-(7-morpholinopyrazolo[1,5-a]pyrimidin-5-yl)acetamide;
N-(7-morpholinopyrazolo[1,5-a]pyrimidin-5-yl)-2,2-diphenylacetamide;
tert-butyl 4-(7-morpholinopyrazolo[1,5-a]pyrimidin-5-ylcarbamoyl)piperidine-1-carboxylate;
N-(7-morpholinopyrazolo[1,5-a]pyrimidin-5-yl)cyclobutanecarboxamide;
N-(7-morpholinopyrazolo[1,5-a]pyrimidin-5-yl)pivalamide;
3-methoxy-N-(7-morpholinopyrazolo[1,5-a]pyrimidin-5-yl)propanamide;
2-hydroxy-2-methyl-N-(7-morpholinopyrazolo[1,5-a]pyrimidin-5-yl)propanamide;
N-(7-morpholinopyrazolo[1,5-a]pyrimidin-5-yl)-4-oxopentanamide;
N-(7-morpholinopyrazolo[1,5-a]pyrimidin-5-yl)heptanamide;
N-(7-morpholinopyrazolo[1,5-a]pyrimidin-5-yl)-2-phenoxyacetamide;
trans-N-(7-morpholinopyrazolo[1,5-a]pyrimidin-5-yl)-2-phenylcyclopropane carboxamide;
(E)-3-(4-hydroxyphenyl)-N-(7-morpholinopyrazolo[1,5-a]pyrimidin-5-yl)acrylamide;
(E)-3-(3,4-dimethoxyphenyl)-N-(7-morpholinopyrazolo[1,5-a]pyrimidin-5-yl)acrylamide;
N-(7-morpholinopyrazolo[1,5-a]pyrimidin-5-yl)-3-(4-(trifluoromethyl)phenyl)propanamide;
N-(7-morpholinopyrazolo[1,5-a]pyrimidin-5-yl)hex-5-enamide;
4-cyano-N-(7-morpholinopyrazolo[1,5-a]pyrimidin-5-yl)benzamide;
2,4-difluoro-N-(7-morpholinopyrazolo[1,5-a]pyrimidin-5-yl)benzamide;
N-(7-morpholinopyrazolo[1,5-a]pyrimidin-5-yl)-1H-indole-2-carboxamide;
N-(7-morpholinopyrazolo[1,5-a]pyrimidin-5-yl)-1H-indole-6-carboxamide;
N-(7-morpholinopyrazolo[1,5-a]pyrimidin-5-yl)-1-naphthamide;
methyl 4-(7-morpholinopyrazolo[1,5-a]pyrimidin-5-ylcarbamoyl)benzoate;
N-(7-morpholinopyrazolo[1,5-a]pyrimidin-5-yl)biphenyl-4-carboxamide;
2,4-dimethyl-N-(7-morpholinopyrazolo[1,5-a]pyrimidin-5-yl)benzamide;
1-hydroxy-N-(7-morpholinopyrazolo[1,5-a]pyrimidin-5-yl)-2-naphthamide;
4-methyl-N-(7-morpholinopyrazolo[1,5-a]pyrimidin-5-yl)benzamide;
3-methyl-N-(7-morpholinopyrazolo[1,5-a]pyrimidin-5-yl)benzamide;
2-methoxy-N-(7-morpholinopyrazolo[1,5-a]pyrimidin-5-yl)benzamide;
N-(7-morpholinopyrazolo[1,5-a]pyrimidin-5-yl)-2-naphthamide;
4-bromo-N-(7-morpholinopyrazolo[1,5-a]pyrimidin-5-yl)benzamide;
N-(7-morpholinopyrazolo[1,5-a]pyrimidin-5-yl)-1H-imidazole-4-carboxamide;
N-(7-morpholinopyrazolo[1,5-a]pyrimidin-5-yl)nicotinamide;
N-(7-morpholinopyrazolo[1,5-a]pyrimidin-5-yl)picolinamide;
N-(7-morpholinopyrazolo[1,5-a]pyrimidin-5-yl)pyrazine-2-carboxamide;
(E)-3-(1H-imidazol-4-yl)-N-(7-morpholinopyrazolo[1,5-a]pyrimidin-5-yl)acrylamide;
N-(7-morpholinopyrazolo[1,5-a]pyrimidin-5-yl)-3-(pyridin-3-yl)propanamide;
4-(dimethylamino)-N-(7-morpholinopyrazolo[1,5-a]pyrimidin-5-yl)butanamide;
N-(7-morpholinopyrazolo[1,5-a]pyrimidin-5-yl)quinoline-2-carboxamide;
N-(7-morpholinopyrazolo[1,5-a]pyrimidin-5-yl)isoquinoline-1-carboxamide;
1-(3-bromophenyl)-3,5-dimethyl-N-(7-morpholinopyrazolo[1,5-a]pyrimidin-5-yl)-1H-pyrazole-4-carboxamide;
N-(7-morpholinopyrazolo[1,5-a]pyrimidin-5-yl)-1-((3-oxo-3,4-dihydro-2H-benzo[b][1,4]oxazin-8-yl)methyl)piperidine-3-carboxamide;
N-(7-morpholinopyrazolo[1,5-a]pyrimidin-5-yl)-3-(pyridin-2-ylamino)propanamide;
N-(7-morpholinopyrazolo[1,5-a]pyrimidin-5-yl)-3-(3-sulfamoylphenylamino)propanamide;
diethyl 4-(7-morpholinopyrazolo[1,5-a]pyrimidin-5-ylcarbamoyl)benzylphosphonate;
tert-butyl 4-(7-morpholinopyrazolo[1,5-a]pyrimidin-5-ylcarbamoyl)benzylcarbamate;
N-(7-morpholinopyrazolo[1,5-a]pyrimidin-5-yl)-4-(thiophen-2-yl)benzamide;
4-(5-methyl-1H-tetrazol-1-yl)-N-(7-morpholinopyrazolo[1,5-a]pyrimidin-5-yl)benzamide;
N-(7-morpholinopyrazolo[1,5-a]pyrimidin-5-yl)-4-(oxazol-5-yl)benzamide;
4-morpholino-N-(7-morpholinopyrazolo[1,5-a]pyrimidin-5-yl)benzamide;
4-(1H-imidazol-1-yl)-N-(7-morpholinopyrazolo[1,5-a]pyrimidin-5-yl)benzamide;
N-(7-morpholinopyrazolo[1,5-a]pyrimidin-5-yl)-4-(3-oxo-3,4-dihydro-2H-1,4-thiazin-5-yl)benzamide;
N-(7-morpholinopyrazolo[1,5-a]pyrimidin-5-yl)-4-(3-(trifluoromethyl)-1H-pyrazol-1-yl)benzamide;
2,2-difluoro-N-(7-morpholinopyrazolo[1,5-a]pyrimidin-5-yl)benzo[d][1,3]dioxole-4-carboxamide;
4-(2-methylthiazol-4-yl)-N-(7-morpholinopyrazolo[1,5-a]pyrimidin-5-yl)benzamide;
N,2-dimethyl-N-(4-(7-morpholinopyrazolo[1,5-a]pyrimidin-5-ylcarbamoyl)phenyl)benzamide;
4((2,4-dioxothiazolidin-5-yl)methyl)-N-(7-morpholinopyrazolo[1,5-a]pyrimidin-5-yl)benzamide;
3-(1H-benzo[d]imidazol-2-yl)-N-(7-morpholinopyrazolo[1,5-a]pyrimidin-5-yl)benzamide;
7-methoxy-2,2-dimethyl-N-(7-morpholinopyrazolo[1,5-a]pyrimidin-5-yl)-2,3-dihydrobenzofuran-4-carboxamide;
4-(5-methyl-1,2,4-oxadiazol-3-yl)-N-(7-morpholinopyrazolo[1,5-a]pyrimidin-5-yl)benzamide;
N-(7-morpholinopyrazolo[1,5-a]pyrimidin-5-yl)-4-(1,2,3-thiadiazol-4-yl)benzamide;
(E)-4-(1-(hydroxyimino)ethyl)-N-(7-morpholinopyrazolo[1,5-a]pyrimidin-5-yl)benzamide;
4-(furan-2-yl)-N-(7-morpholinopyrazolo[1,5-a]pyrimidin-5-yl)benzamide;
4-(furan-3-yl)-N-(7-morpholinopyrazolo[1,5-a]pyrimidin-5-yl)benzamide;

4-tert-butyl-N-(7-(1-oxo-thiomorpholino)pyrazolo[1,5-a]pyrimidin-5-yl)benzamide;
4-tert-butyl-N-(7-(methyl(1,1-dioxo(tetrahydro-thiopyran-4-yl))amino)pyrazolo[1,5-a]pyrimidin-5-yl)benzamide;
4-tert-butyl-N-(7-(methyl(2-(methylsulfonyl)ethyl)amino)pyrazolo[1,5-a]pyrimidin-5-yl)benzamide;
N-(7-((2-(N-acetylsulfamoyl)ethyl)(methyl)amino)pyrazolo[1,5-a]pyrimidin-5-yl)-4-tert-butylbenzamide;
4-tert-butyl-N-(7-(methyl(2-(methylsulfonamido)ethyl)amino)pyrazolo[1,5-a]pyrimidin-5-yl)benzamide; and
4-tert-butyl-N-(7-(2-(methylsulfonyl)ethoxy)pyrazolo[1,5-a]pyrimidin-5-yl)benzamide.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent such as hydrogen.

It is further noted that the compound may be present as a mixture of stereoisomers, or the compound may present as a single stereoisomer.

In another of its aspects, there is provided a pharmaceutical composition comprising as an active ingredient a compound according to any one of the above embodiments and variations. In one particular variation, the composition is a solid formulation adapted for oral administration. In another particular variation, the composition is a liquid formulation adapted for oral administration. In yet another particular variation, the composition is a tablet. In still another particular variation, the composition is a liquid formulation adapted for parenteral administration.

The present invention also provides a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of the above embodiments and variations to a subject.

In another of its aspects, there is provided a method of inhibiting ASK1 comprising contacting ASK1 with a compound of any one of the above embodiments and variations.

In yet another of its aspects, there is provided a method of inhibiting ASK1 comprising causing a compound of any one of the above embodiments and variations to be present in a subject in order to inhibit ASK1 in vivo.

In a further of its aspects, there is provided a method of inhibiting ASK1 comprising administering a first compound to a subject that is converted in vivo to a second compound wherein the second compound inhibits ASK1 in vivo, the second compound being a compound according to any one of the above embodiments and variations.

In another of its aspects, there is provided a method of treating a disease state for which ASK1 possesses activity that contributes to the pathology and/or symptomology of the disease state, the method comprising causing a compound of any one of the above embodiments and variations to be present in a subject in a therapeutically effective amount for the disease state.

In yet another of its aspects, there is provided a method of treating a disease state for which ASK1 possesses activity that contributes to the pathology and/or symptomology of the disease state, the method comprising administering a compound of any one of the above embodiments and variations to a subject, wherein the compound is present in the subject in a therapeutically effective amount for the disease state.

In a further of its aspects, there is provided a method of treating a disease state for which ASK1 possesses activity that contributes to the pathology and/or symptomology of the disease state, the method comprising administering a first compound to a subject that is converted in vivo to a second compound wherein the second compound inhibits ASK1 in vivo, the second compound being a compound according to any one of the above embodiments and variations.

In some variations of each of the above treatment methods, the disease state is selected from the group consisting of metabolic diseases, inflammatory diseases, neurodegenerative diseases, autoimmune diseases, destructive bone disorders, infectious diseases, diseases and conditions that are mediated by inducible pro-inflammatory proteins, reperfusion/ischemia in stroke, cardiac hypertrophy, respiratory diseases, heart attacks, myocardial ischemia, organ hypoxia, vascular hyperplasia, cardiac hypertrophy, hepatic ischemia, liver disease, congestive heart failure, pathologic immune responses, thrombin-induced platelet aggregation, gastroenterological diseases, hematological diseases, and urological diseases.

In some other variations of each of the above treatment methods, the disease state is selected from the group consisting of the disease state is selected from the group consisting of diabetes, type 2 diabetes mellitus, diabetic dyslipidemia, impaired glucose tolerance (IGT), impaired fasting plasma glucose (IFG), metabolic acidosis, ketosis, appetite regulation, obesity and complications associated with diabetes including diabetic neuropathy, diabetic retinopathy, inflammatory bowel disease, Crohn's disease, chemotherapy-induced enteritis, oral mucositis, Shortened Bowel Syndrome, kidney disease, hyperlipidemia, arteriosclerosis; hypertension; myocardial infarction, angina pectoris, cerebral infarction, cerebral apoplexy and metabolic syndrome.

In some other variations of each of the above treatment methods, the disease state is selected from the group consisting of acute pancreatitis, chronic pancreatitis, asthma, allergies, chronic obstructive pulmonary disease, adult respiratory distress syndrome.

In still some other variations of each of the above treatment methods, the disease state is selected from the group consisting of Alzheimer's disease, Parkinson's disease, amyotrophic lateral sclerosis (ALS), epilepsy, seizures, Huntington's disease, polyglutamine diseases, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

In still other variations of each of the above treatment methods, the disease state is selected from the group consisting of glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, multiple sclerosis, or Sjoegren's syndrome.

In still other variations of each of the above treatment methods, the disease state is selected from the group consisting of osteoporosis, osteoarthritis and multiple myeloma-related bone disorder.

In yet still other variations of each of the above treatment methods, the disease state is selected from the group consisting of sepsis, septic shock, and Shigellosis.

In yet still other variations of each of the above treatment methods, the disease state is selected from the group consisting of edema, analgesia, fever and pain, such as neuromuscular pain, headache, cancer pain, dental pain and arthritis pain.

In yet still other variations of each of the above treatment methods, the disease state is selected from the group consisting of ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T cell activation and thrombin-induced platelet aggregation.

Another aspect of the invention is directed to method of preparing the inhibitor of the invention.

One embodiment of the preparation method comprises:
coupling a compound of Formula A

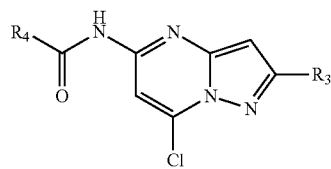

A to a compound of the formula $R_2B(OH)_2$, under conditions that form a reaction product of formula B

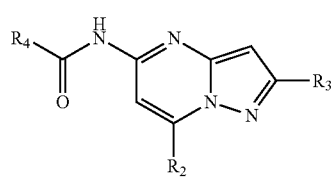

B wherein $R_2$ is selected from the group consisting of amino, oxy, thio, halo, $(C_{1-10})$alkylamino, $(C_{1-10})$alkyl, $(C_{1-10})$alkenyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted with 1-3 substituents,
where
each of said 1-3 substituents is independently selected from the group consisting of hydroxyl, halo, nitro, cyano, oxo, hydroxy, thio, $(C_{1-6})$alkylthio, oxy, arylalkyloxy, carbonyloxy, $(C_{1-10})$alkoxy, $(C_{4-12})$aryloxy, hetero$(C_{1-10})$aryloxy, aminocarbonyloxy, carbonyl, $(C_{1-6})$alkylcarbonyl, oxycarbonyl, aminocarbonyl, amino, amido, carboxamido, $(C_{1-10})$alkylamino, methylcarbonylamino, sulfonamido, imino, sulfonyl, $(C_{1-6})$alkylsulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or further substituted;

$R_3$ is selected from the group consisting of hydrogen, hydroxyl, amino, thio, oxy, $(C_{1-6})$alkyl, $(C_{1-6})$haloalkyl, $(C_{1-6})$cycloalkyl, and $(C_{1-6})$alkoxy, each unsubstituted or substituted with 1-2 substituents independently selected from the group consisting of hydroxyl, halo, halo$(C_{1-6})$alkyl, $(C_{1-6})$alkyl, $(C_{3-6})$cycloalkyl, hetero$(C_{1-5})$cycloalkyl, phenyl, and hetero$(C_{1-5})$aryl; and $R_4$ is selected from the group consisting of oxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, $(C_{1-10})$alkyl, halo$(C_{1-10})$alkyl, hydroxy$(C_{1-10})$alkyl, carbonyl$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted with 1-3 substituents,
where
each of said 1-3 substituents is independently selected from the group consisting of halo, nitro, cyano, oxo, thio, mercapto, oxy, hydroxy, carbonyloxy, $(C_{1-10})$alkoxy, $(C_{4-12})$aryloxy, hetero$(C_{1-10})$aryloxy, carbonyl, oxycarbonyl, $(C_{1-10})$alkyloxycarbonyl, $(C_{4-12})$aryloxycarbonyl, hetero$(C_{1-10})$aryloxycarbonyl, aminocarbonyl, amino, $C_{1-10})$alkylamino, amido, carboxamido, carbamoyl, $(C_{1-10})$alkylamino, sulfonamido, sulfamoyl, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or further substituted.

In some variations the above embodiment of the preparation method of the invention, $R_2$ is selected from the group consisting of:
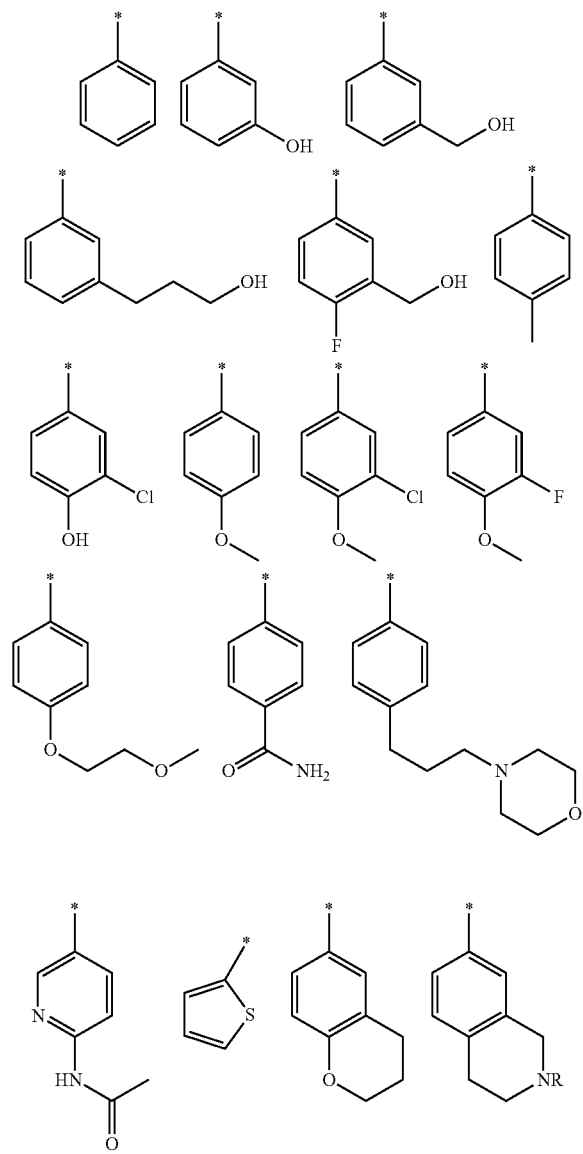
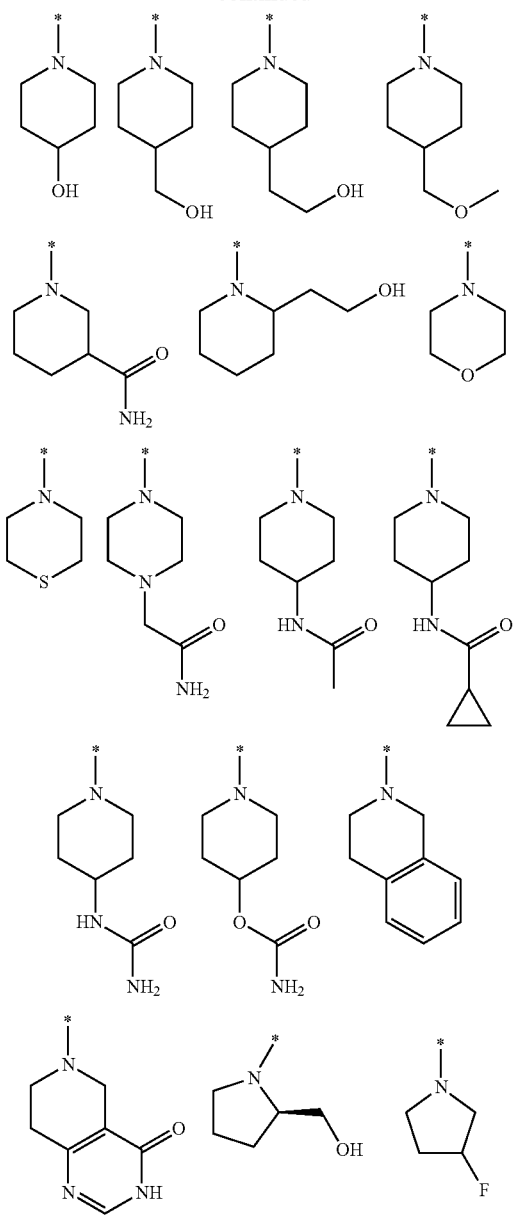
In other variations, $R_2$ is selected from the group consisting of
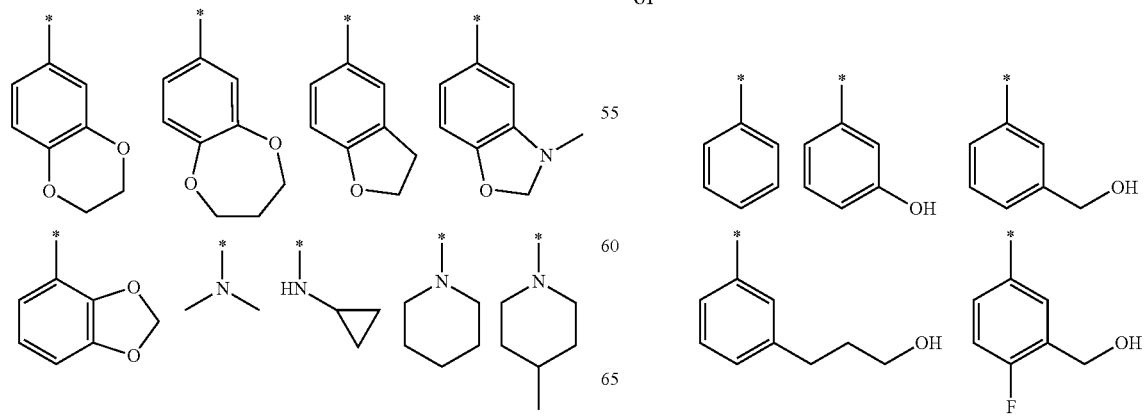

-continued

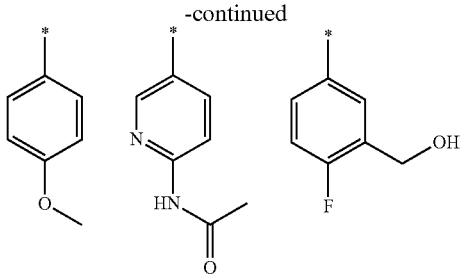

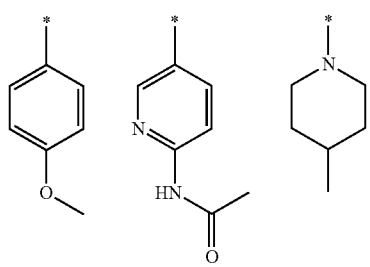

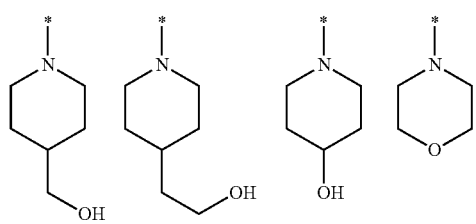

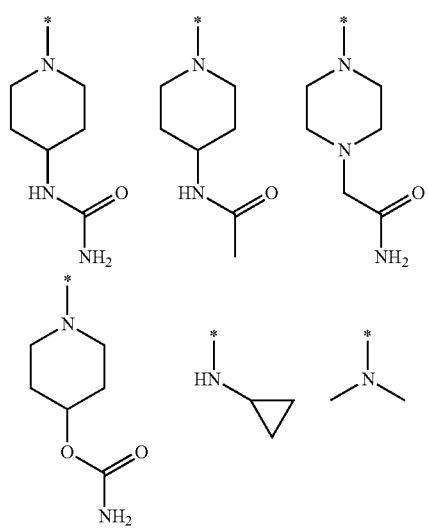

In some variation of the above process of the invention, $R_3$ is selected from the group consisting of hydrogen, $(C_{1-6})$alkyl, $(C_{1-6})$haloalkyl, and $(C_{1-6})$cycloalkyl, each unsubstituted or substituted with said 1-2 substituents. In other variations, $R_3$ is selected from the group consisting of hydrogen and methyl.

In some variation of the above process of the invention, $R_4$ is an unsubstituted or substituted phenyl of the formula:

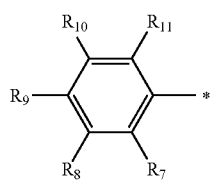

where $R_7$, $R_8$, $R_9$, $R_{10}$, and $R_{11}$ are each independently selected from the group consisting of hydrogen, halo, hydroxyl, nitro, thio, oxy, cyano, $(C_{1-6})$alkyl, $(C_{2-6})$alkenyl, $(C_{2-6})$alkynyl, halo$(C_{1-6})$alkyl, $(C_{1-6})$alkoxy, hydroxyl$(C_{1-6})$alkyl, phosphonylalkyl, mercapto, sulfinyl, sulfonyl, sulfamoyl, amino, amido, carboxamido, carbamoyl, carbonyl, oxycarbonyl, carbonyloxy, hetero$(C_{1-5})$aryl, and $(C_{4-6})$aryl, and each unsubstituted or substituted; provided at least two of $R_7$, $R_8$, $R_9$, $R_{10}$, and $R_{11}$ are hydrogen.

In other variations, $R_7$, $R_9$, $R_9$, $R_{10}$, and $R_{11}$ are each independently selected from the group consisting of hydroxyl, nitro, fluoro, chloro, bromo, cyano, $(C_{1-6})$alkoxy, —OCHF$_2$, —OCF$_3$, furanyloxy, $(C_{1-6})$alkyl, halo$(C_{1-6})$alkyl, hydroxyl $(C_{1-6})$alkyl, —CF$_3$, —CH$_2$NHC(O)OC(CH$_3$)$_3$, —C(CH$_3$)(OH)CF$_3$, hetero$(C_{1-5})$aryl$(C_{1-6})$alkyl, —C(CH$_3$)=NOH, —CH$_2$OCH$_2$CF$_3$, —NC(O)CH$_3$, —NHS(O)$_2$CH$_3$, —N(CH$_3$)$_2$, —C(O)OCH$_3$, —OCH(CH$_3$)$_2$, —SCF$_3$, -sulfonylpyrrolidinyl, hetero$(C_{1-5})$aryl, hetero$(C_{1-5})$cycloalkyl,

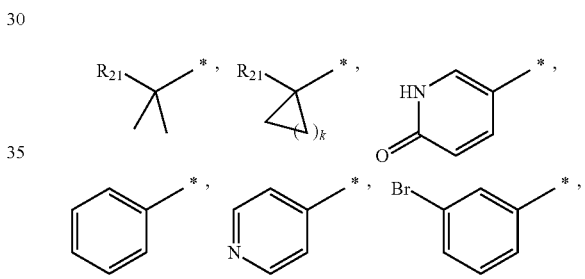

where k is 1, 2, 3, or 4; and $R_{21}$ is selected from the group consisting of —(CH$_2$)$_n$OH, —C(O)OH, —C(O)OCH$_3$, cyano, —(CH$_2$)$_n$NH$_2$, —(CH$_2$)$_n$NHC(O)C(O)OH, —(CH$_2$)$_n$C(O)OH, —(CH$_2$)$_n$C(O)OCH$_3$, $(C_{1-4})$alkyl, halo$(C_{1-4})$alkyl, —(CH$_2$)$_n$CN, —(CH$_2$)$_n$CONH$_2$, —(CH$_2$)$_n$aryl, —(CH$_2$)$_n$heteroaryl, —O(CH$_2$)$_n$ aryl, —O(CH$_2$)$_n$heteroaryl, and —O(CH$_2$)$_n$CH(OH)CH$_2$OH, where n is 0, 1, 2, 3, or 4. In some other variations, $R_{21}$ is selected from the group consisting of methyl, perfluororm-ethyl, hydroxyl, hydroxylmethyl, cyano, —CH$_2$NH$_2$, —(CH$_2$)C(O)OH, —(CH$_2$)NHC(O)C(O)OH, —(CH$_2$)C(O)OCH$_3$ and —O(CH$_2$)$_n$heteroaryl where n is 1 or 2, and —OCH$_2$CH(OH)CH$_2$OH.

In still other variations, $R_9$ is independently selected from the group consisting of hydrogen, tert-butyl, —CF$_3$, —CH(CH$_3$)(OH)CF$_3$, —CH(OH)(CH$_3$)$_2$, —CH(CH$_2$OH)(CH$_3$)$_2$, —C(O)OCH$_3$,

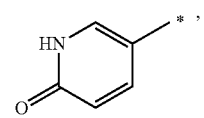

and —C(OCH$_2$CH(OH)CH$_2$OH)(CH$_3$)$_2$; and R$_7$, R$_8$, R$_{10}$, and R$_{11}$ are each hydrogen. In still further variations, R$_9$ is selected from the group consisting of tert-butyl and —CH(OH)(CH$_3$)$_2$.

In some preferred variations of the above embodiment of the process of the invention, R$_4$ is selected from the group consisting of:

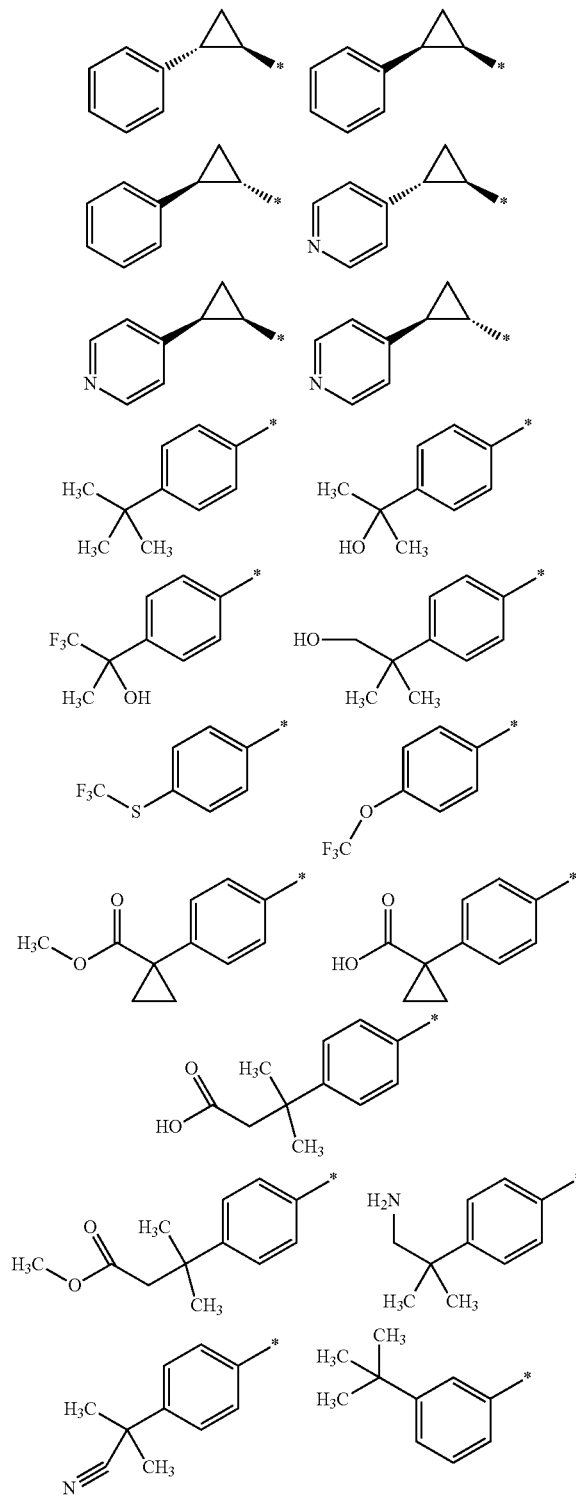

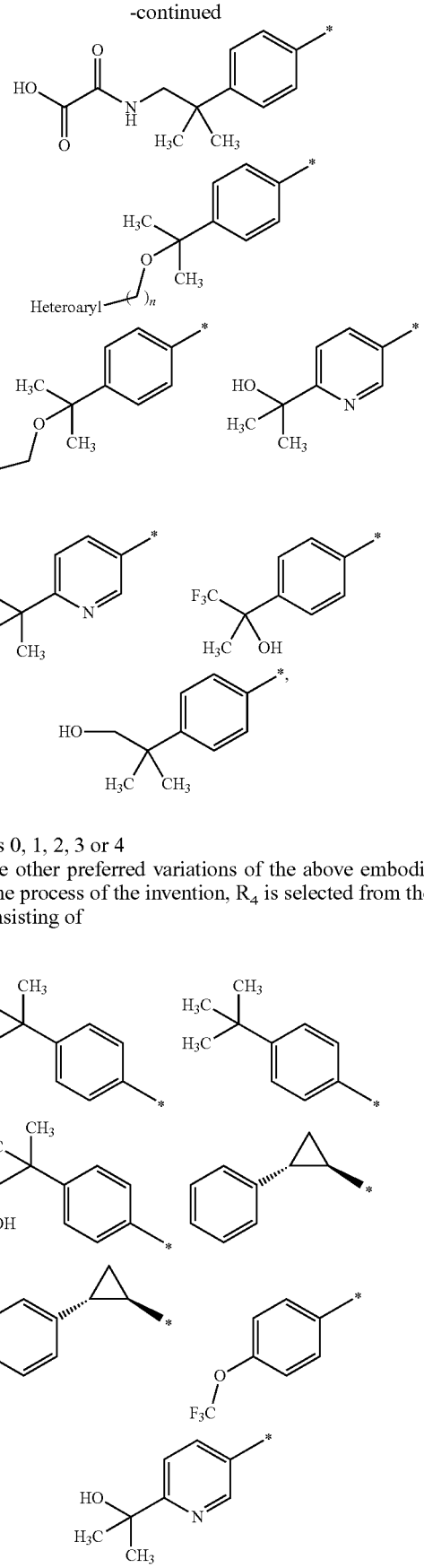

where n is 0, 1, 2, 3 or 4

In some other preferred variations of the above embodiment of the process of the invention, R$_4$ is selected from the group consisting of -continued

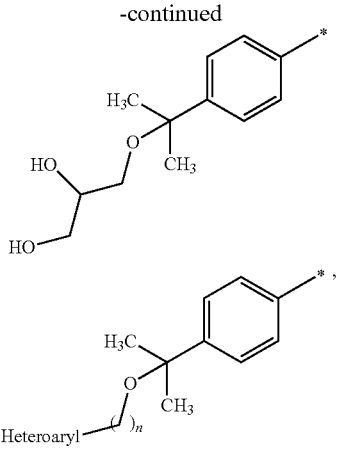

where n is 0, 1, 2, 3 or 4

Another aspect of the present invention relates to a process of preparing intermediate for the preparation of the compounds of the invention. In one embodiment, the process comprising:

converting a compound of Formula D, or a tautomer thereof

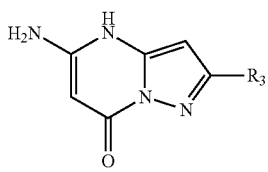

under conditions that form a compound of Formula E,

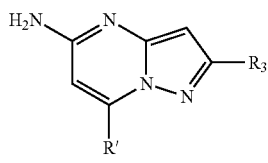

wherein $R_3$ is selected from the group consisting of hydrogen, hydroxyl, amino, thio, oxy, $(C_{1-6})$alkyl, $(C_{1-6})$haloalkyl, $(C_{1-6})$cycloalkyl, and $(C_{1-6})$alkoxy, each unsubstituted or substituted with 1-2 substituents independently selected from the group consisting of hydroxyl, halo, halo $(C_{1-6})$alkyl, $(C_{1-6})$alkyl, $(C_{3-6})$cycloalkyl, hetero $(C_{1-5})$ cycloalkyl, phenyl, and hetero $(C_{1-5})$ aryl; and R' is selected from the group consisting of halogen.

In some variations of the immediately above embodiment of the process $R_3$, is selected from the group consisting of hydrogen, $(C_{1-6})$alkyl, $(C_{1-6})$haloalkyl, $(C_{1-6})$cycloalkyl, and $(C_{1-6})$alkoxy, each unsubstituted or substituted with said 1-2 substituents. In some other variations, $R_3$ is selected from the group consisting of hydrogen, methyl, ethyl, perfluoromethyl, 2,2,2-trifluoroethyl, cyclopropyl, and methoxy, each unsubstituted or substituted with said 1-2 substituents. In still other variations, $R_3$ is selected from the group consisting of hydrogen and methyl. In still other variations, $R_3$ is hydrogen. In yet still other variations, $R_3$ is methyl.

In some variations of the immediately above embodiment of the process of the invention, wherein R' is chloro.

Another aspect of the invention relates to novel intermediates.

In one embodiment, the intermediate is of formula E:

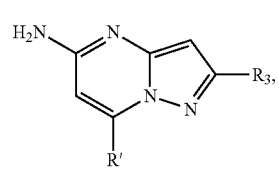

and a pharmaceutically acceptable salts thereof,
wherein $R_3$ is selected from the group consisting of hydrogen, hydroxyl, amino, thio, oxy, $(C_{1-6})$alkyl, $(C_{1-6})$haloalkyl, $(C_{1-6})$cycloalkyl, and $(C_{1-6})$alkoxy, each unsubstituted or substituted with 1-2 substituents independently selected from the group consisting of hydroxyl, halo, halo$(C_{1-6})$alkyl, $(C_{1-6})$alkyl, $(C_{3-6})$cycloalkyl, hetero$(C_{1-5})$cycloalkyl, phenyl, and hetero$(C_{1-5})$aryl; and R' is selected from the group consisting of halogen.

In some variations of the intermediate compound of the invention, In other variations, $R_3$ is selected from the group consisting of hydrogen, $(C_{1-6})$alkyl, $(C_{1-6})$haloalkyl, $(C_{1-6})$ cycloalkyl, and $(C_{1-6})$alkoxy, each unsubstituted or substituted with said 1-2 substituents. In still other variations, $R_3$ is selected from the group consisting of hydrogen, methyl, ethyl, perfluoromethyl, 2,2,2-trifluoroethyl, cyclopropyl, and methoxy, each unsubstituted or substituted with said 1-2 substituents. In still other variations, $R_3$ is selected from the group consisting of hydrogen and methyl. In yet still other variations, $R_3$ is methyl. In yet still other variations, $R_3$ is hydrogen.

Particular examples of the intermediate compounds according to the present invention include, but are not limited to, the following:

7-chloropyrazolo[1,5-a]pyrimidin-5-amine;
7-chloro-2-methylpyrazolo[1,5-a]pyrimidin-5-amine;
7-chloro-2-ethylpyrazolo[1,5-a]pyrimidin-5-amine;
7-chloro-2-(trifluoromethyl)pyrazolo[1,5-a]pyrimidin-5-amine;
7-chloro-2-(2,2,2-trifluoroethyl)pyrazolo[1,5-a]pyrimidin-5-amine;
7-chloro-2-methoxypyrazolo[1,5-a]pyrimidin-5-amine; and
7-chloro-2-cyclopropylpyrazolo[1,5-a]pyrimidin-5-amine.

Salts, Hydrates, and Prodrugs of ASK1 Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptonate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen containing groups may be quaternized with such agents as ($C_{1-4}$) alkyl halides, e.g., methyl, ethyl, iso-propyl and tert-butyl chlorides, bromides and iodides; di ($C_{1-4}$) alkyl sulfates, e.g., dimethyl, diethyl and diamyl sulfates; ($C_{10-18}$) alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al., (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in P. G. M. Wuts and T. W. Greene in "*Greene's Protective Groups in Organic Synthesis*" 4th edition, John Wiley and Sons, 2007.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Uses for the Compounds of the Invention

ASK1 activates the p38 and JNK pro-apoptotic pathways in response to environmental stresses. Wang et al. *J. Biol.*

Chem. 1996, 271, 31607-31611; Ichijo et al. *Science* 1997, 275, 90-94. ASK1 induces apoptosis through ASK1-p38/JNK cascades in response to pro-apoptotic stresses (e.g. oxidative stress and TNF) and pathogenic stresses (e.g. ER stress, GPCR- and Aβ-induced ROS production). Overexpression of wild-type or constitutively active ASK1 induces apoptosis in various cells through mitochondria-dependent caspase activation. Saitoh et al *EMBO J.* 1998, 17:2596-2606; Kanamoto et al. *Mol. Cell. Biol.* 2000, 20, 196-204; Hatai et al. *J. Biol. Chem.* 2000, 275, 26576-2658.

Apoptosis plays an essential role in normal development and tissue homeostasis; such that when dysregulated, it contributes to multiple diseases including, but are not limited to, amyloidosis, hypercholesterolemia, diabetes mellitus, cancers, inflammatory diseases, autoimmune diseases, destructive bone disorders, infectious diseases, neurodegenerative diseases, reperfusion/ischemia in stroke, cardiac hypertrophy respiratory diseases, metabolic diseases, gastroenterological diseases, hematological diseases, and urological diseases. Thompson, *Science* 1995, 267, 1456-1462; Yuan and Yanker *Nature* 2000, 407, 802-809; Los et al. *Immunity* 1999, 10, 629-639; Aridor and Balch, *Nat. Med.* 1999, 5, 745-751; Kopito and Ron, *Nat. Cell Biol.* 2000, 2, E207-E209; Nakagawa et al. *Nature* 2000, 403, 98-103; Imai et al. *Cell* 2001, 105, 891-902; Harding et al. *Mol Cell* 2001, 7, 1153-1163; and Nishitoh et al. *Genes Dev.* 2002, 16, 1345-1355.

Recent studies revealed that ASK1 contributes not only to regulation of cell death but also has diverse functions in the decision of cell fate such as cytokine responses, cell differentiation, and innate immune responses. Matsukawa et al. *J Biochem.* (Toyko) 2004, 136, 261-265. Sayama et al. *J. Biol. Chem.* 2000, 276:999-1004; Takeda et al. *J. Biol. Chem.* 2000, 275:9805-9813; Sagasti et al. *Cell* 2001, 105:221-232; Kim at al. *Science* 2002, 297:623-626; Nishitoh et al. *Genes Dev.* 2002, 16:1345-1355; Matsukawa et al. *Nat Immunol* 2005, 6, 587-592; Tobiume et al. *EMBO Rep.* 2001, 2:222-228; Imoto, et al. *Diabetes* 2006, 55:1197-1204. Constitutively active ASK1 induces neurite outgrowth in PC12 cells. ASK1 is activated by CaMKII, which activates ASK1-p38 pathway in neurons, suggesting that ASK1 might play critical roles in synaptic plasticity. Moreover, TRAF6-ASK1-p38 pathway plays an essential role in inflammatory and innate immune responses. Hayakaw et al. *Microbes and Infection* 2006, 8, 1098-1107. It has also been demonstrated that ASK1 has a role in the pathogenesis of TNF-α-induced insulin resistance. Overexpression of wild-type ASK1 increases serine phosphorylation of insulin receptor substrate (IRS)-1, and decreases insulin-stimulated tyrosine phosphorylation of IRS-1, leading to impair insulin signaling. Imoto, et al. *Diabetes* 2006, 55:1197-1204.

Accordingly, modulating the activity of ASK1 by the compounds of the invention would have impact of a multiple of diseases and condition; in particularly, metabolic diseases, inflammatory diseases, neurodegenerative diseases, autoimmune diseases, destructive bone disorders, infectious diseases, diseases and conditions that are mediated by inducible pro-inflammatory proteins, reperfusion/ischemia in stroke, cardiac hypertrophy, respiratory diseases, heart attacks, myocardial ischemia, organ hypoxia, vascular hyperplasia, cardiac hypertrophy, hepatic ischemia, liver disease, congestive heart failure, pathologic immune responses, thrombin-induced platelet aggregation, gastroenterological diseases, hematological diseases, and urological diseases.

Metabolic diseases which may be treated or prevented by the compounds of this invention include, but are not limited to, diabetes, particularly, type 2 diabetes mellitus, diabetic dislipidemia, impaired glucose tolerance (IGT), impaired fasting plasma glucose (IFG), metabolic acidosis, ketosis, appetite regulation, obesity and complications associated with diabetes including diabetic neuropathy, diabetic retinopathy, inflammatory bowel disease, Crohn's disease, chemotherapy-induced enteritis, oral mucositis, Shortened Bowel Syndrome and kidney disease. The conditions mediated by ASK1 inhibitors of the invention further include hyperlipidemia such as hypertriglyceridemia, hypercholesteremia, hypoHDLemia and postprandial hyperlipidemia; arteriosclerosis; hypertension; myocardial infarction, angina pectoris, cerebral infarction, cerebral apoplexy and metabolic syndrome.

Inflammatory diseases which may be treated or prevented by the compounds of this invention include, but are not limited to, acute pancreatitis, chronic pancreatitis, asthma, allergies, chronic obstructive pulmonary disease, adult respiratory distress syndrome.

Neurodegenerative diseases which may be treated or prevented by the compounds of this invention include, but are not limited to, Alzheimer's disease (Nakagawa et al. *Nature* 2000, 403, 98-103), Parkinson's disease (Imai et al. *Cell* 2001, 105, 891-902), amyotrophic lateral sclerosis (ALS), epilepsy, seizures, Huntington's disease, polyglutamine diseases (Nishitoh et al. *Genes Dev.* 2002, 16, 1345-1355), traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

Autoimmune diseases which may be treated or prevented by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, multiple sclerosis, or Sjoegren's syndrome.

Destructive bone disorders which may be treated or prevented by the compounds of this invention include, but are not limited to, osteoporosis, osteoarthritis and multiple myeloma-related bone disorder.

Infectious diseases which may be treated or prevented by the compounds of this invention include, but are not limited to, sepsis, septic shock, and Shigellosis.

Diseases and conditions that are mediated by inducible pro-inflammatory proteins which may be treated or prevented by the compounds of this invention include, but are not limited to, edema, analgesia, fever and pain, such as neuromuscular pain, headache, cancer pain, dental pain and arthritis pain.

Other conditions that are mediated by ASK1 and may be treated or prevented by the compounds of this invention include, but are not limited to, ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T cell activation, and thrombin-induced platelet aggregation.

Combination Therapy

A wide variety of therapeutic agents may have a therapeutic additive or synergistic effect with ASK1 inhibitors according to the present invention. Combination therapies that comprise one or more compounds of the present invention with one or more other therapeutic agents can be used, for example, to: 1) enhance the therapeutic effect(s) of the one or more compounds of the present invention and/or the one or more other therapeutic agents; 2) reduce the side effects exhibited by the one or more compounds of the present invention and/or the one or more other therapeutic agents; and/or 3) reduce the effective dose of the one or more compounds of the present invention and/or the one or more other therapeutic agents. It is noted that combination therapy is intended to cover when agents are administered before or after each other (sequential therapy) as well as when the agents are administered at the same time.

The present invention particularly relates to the use of the compounds of the invention in combination with one or more other antidiabetic agents. Examples of such other antidiabetic agents include, but are not limited to insulin signaling pathway modulators, like protein tyrosine phosphatase (PTPase) inhibitors, and glutamine-fructose-6-phosphate amidotransferase (GFAT) inhibitors; compounds influencing a dysregulated hepatic glucose production, like glucose-6-phosphatase (G6 Pase) inhibitors, fructose-1,6-bisphosphatase (F-1,6-BPase) inhibitors, glycogen phosphorylase (GP) inhibitors, glucagon receptor antagonists and phosphoenolpyruvate carboxykinase (PEPCK) inhibitors; pyruvate dehydrogenase kinase (PDHK) inhibitors; insulin sensitivity enhancers (insulin sensitizers); insulin secretion enhancers (insulin secretagogues); alpha-glucosidase inhibitors; inhibitors of gastric emptying; glucokinase activators, GLP-1 receptor agonists, GLP-2 receptor agonists, UCP modulators, RXR modulators, GSK-3 inhibitors, PPAR modulators, metformin, insulin; and $\alpha_2$-adrenergic antagonists. ASK1 inhibitors may be administered with such at least one other antidiabetic compound either simultaneously as a single dose, at the same time as separate doses, or sequentially (i.e., where one is administered before or after the other is administered).

Examples of PTPase inhibitors that may be used in combination with ASK1 inhibitors of the invention include, but are not limited to those disclosed in U.S. Pat. Nos. 6,057,316, 6,001,867, and PCT Publication Nos. WO 99/58518, WO 99/58522, WO 99/46268, WO 99/46267, WO 99/46244, WO 99/46237, WO 99/46236, and WO 99/15529.

Examples of GFAT inhibitors that may be used in combination with ASK1 inhibitors of the invention include, but are not limited to those disclosed in Mol. Cell. Endocrinol. 1997, 135(1), 67-77.

Examples of G6 Pase inhibitors that may be used in combination with ASK1 inhibitors of the invention include, but are not limited to those disclosed in PCT Publication Nos. WO 00/14090, WO 99/40062 and WO 98/40385, European Patent Publication No. EP682024 and Diabetes 1998, 47, 1630-1636.

Examples of F-1,6-BPase inhibitors that may be used in combination with ASK1 inhibitors of the invention include, but are not limited to those disclosed in PCT Publication Nos. WO 00/14095, WO 99/47549, WO 98/39344, WO 98/39343 and WO 98/39342.

Examples of GP inhibitors that may be used in combination with ASK1 inhibitors of the invention include, but are not limited to those disclosed in U.S. Pat. No. 5,998,463, PCT Publication Nos. WO 99/26659, WO 97/31901, WO 96/39384 and WO9639385 and European Paternt Publication Nos. EP 978279 and EP 846464.

Examples of glucagon receptor antagonists that may be used in combination with ASK1 inhibitors of the invention include, but are not limited to those disclosed in U.S. Pat. Nos. 5,880,139 and 5,776,954, PCT Publication Nos. WO 99/01423, WO 98/22109, WO 98/22108, WO 98/21957, WO 97/16442 and WO 98/04528 and those described in *Bioorg Med. Chem. Lett* 1992, 2, 915-918, *J. Med. Chem.* 1998, 41, 5150-5157, and *J. Biol. Chem.* 1999, 274, 8694-8697.

Examples of PEPCK inhibitors that may be used in combination with ASK1 inhibitors of the invention include, but are not limited to those disclosed in U.S. Pat. No. 6,030,837 and *Mol. Biol. Diabetes* 1994, 2, 283-99.

Examples of PDHK inhibitors that may be used in combination with ASK1 inhibitors of the invention include, but are not limited to those disclosed in *J. Med. Chem.* 1999, 42, 2741-2746.

Examples of insulin sensitivity enhancers that may be used in combination with ASK1 inhibitors of the invention include, but are not limited to GSK-3 inhibitors, retinoid X receptor (RXR) agonists, Beta-3 AR agonists, UCP modulators, antidiabetic thiazolidinediones (glitazones), non-glitazone type PPAR gamma agonists, dual PPAR gamma/PPAR alpha agonists, antidiabetic vanadium containing compounds and biguanides such as metformin.

Examples of GSK-3 inhibitors include, but are not limited to those disclosed in PCT Publication Nos. WO 00/21927 and WO 97/41854.

Examples of RXR modulators include, but are not limited to those disclosed in U.S. Pat. Nos. 4,981,784, 5,071,773, 5,298,429 and 5,506,102 and PCT Publication Nos. WO89/05355, WO91/06677, WO92/05447, WO93/11235, WO95/18380, WO94/23068, and WO93/23431.

Examples of Beta-3 AR agonists include, but are not limited to CL-316,243 (Lederle Laboratories) and those disclosed in U.S. Pat. No. 5,705,515 and PCT Publication Nos. WO 99/29672, WO 98/32753, WO 98/20005, WO 98/09625, WO 97/46556, and WO 97/37646.

Examples of UCP modulators include agonists of UCP-1, UCP-2 and UCP-3. Examples of UCP modulators include, but are not limited to those disclosed in Vidal-Puig et al., *Biochem. Biophys. Res. Commun.,* 1997, 235(1), 79-82.

Examples of antidiabetic, PPAR modulating thiazolidinediones (glitazones) include, but are not limited to, (S)-((3,4-dihydro-2-(phenyl-methyl)-2H-1-benzopyran-6-yl) methyl-thiazolidine-2,4-dione (englitazone), 5-{[4-(3-(5-methyl-2-phenyl-4-oxazolyl)-1-oxo-propyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazoly)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)-methyl]phenyl}methane (YM268), 5-{4-[2-(5-methyl-2-phenyl-4-oxazolyl)-2-hydroxyethoxy]-benzyl}-1-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenylmethyl)-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl) thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}-thiazolidine-2,4-dione (pioglitazone; marketed under the trademark ACTOS™), 5-[6-(2-fluoro-benzyloxy)-naphthalen-2-ylmethyl]-thiazolidine-2,4-dione (MCC555), 5-([2-(2-naphthyl])-benzoxazol-5-yl]-methyl}thiazolidine-2, 4-dione (T-174), edaglitazone (BM-13-1258), rivoglitazone (CS-011), and 5-(2,4-dioxothiazolidin-5-ylmethyl)-2-methoxy-N-(4-trifluoromethyl-benzyl)benzamide (KRP297).

Examples of non-glitazone type PPAR gamma agonists include, but are not limited to N-(2-benzoylphenyl)-L-tyrosine analogues, such as GI-262570, reglixane (JTT501), and FK-614 and metaglidasen (MBX-102).

Examples of dual PPAR gamma/PPAR alpha agonists include, but are not limited to omega.-[(oxoquinazolinylalkoxy)phenyl]alkanoates and analogs thereof including those described in PCT Publication No. WO 99/08501 and *Diabetes* 2000, 49(5), 759-767; tesaglitazar, muraglitazar, and naveglitazar.

Examples of antidiabetic vanadium containing compounds include, but are not limited to those disclosed in the U.S. Pat. No. 5,866,563.

Metformin (dimethyldiguanide) and its hydrochloride salt is marketed under the trademark GLUCOPHAGE™.

Examples of insulin secretion enhancers include but are not limited to glucagon receptor antagonists (as described above), sulphonyl urea derivatives, incretin hormones or mimics thereof, especially glucagon-like peptide-1 (GLP-1) or GLP-1 agonists, beta-cell imidazoline receptor antagonists, and short-acting insulin secretagogues, like antidiabetic phenylacetic acid derivatives, antidiabetic D-phenylalanine derivatives, and mitiglinide and pharmaceutical acceptable salts thereof.

Examples of sulphonyl urea derivatives include, but are not limited to, glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide; glimepiride and gliclazide. Tolbutamide, glibenclamide, gliclazide, glibornuride, gliquidone, glisoxepid and glimepiride can be administered in the form that they are marketed under the trademarks RASTINON HOECHST™, AZUGLUCON™, DIAMICRONT™, GLUBORID™, GLURENORM™, PRO-DIABAN™ and AMARYL™, respectively.

Examples of GLP-1 agonists include, but are not limited to those disclosed in U.S. Pat. Nos. 5,120,712, 5,118,666 and 5,512,549, and PCT Publication No. WO 91/11457. In particular, GLP-1 agonists include those compounds like GLP-1 (7-37) in which compound the carboxy-terminal amide functionality of Arg$^{36}$ is displaced with Gly at the 37$^{th}$ position of the GLP-1 (7-36)NH$_2$ molecule and variants and analogs thereof including GLN$^9$-GLP-1 (7-37), D-GLN$^9$-GLP-1 (7-37), acetyl LYS$^9$-GLP-1 (7-37), LYS$^{18}$-GLP-1 (7-37) and, in particular, GLP-1 (7-37)OH, VAL$^8$-GLP-1 (7-37), GLY$^8$-GLP-1(7-37), THR$^8$-GLP-1 (7-37), GLP-1 (7-37) and 4-imidazopropionyl-GLP-1.

One particular example of a GLP-1 agonist is Exendatide, a 39-amino acid peptide amide, which is marketed under the trademark BYETTA™. Extendatide has the empirical formula C$_{184}$H$_{282}$N$_{50}$O$_{60}$S and molecular weight of 4186.6 Daltons. The amino acid sequence for Extendatide is as follows: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$.

Examples of glucagon-like peptide-2 (GLP-2) or GLP-2 agonists include, but are not limited to those disclosed in U.S. Pat. No. 7,056,886 and PCT Publication Nos. WO 00/53208, WO 01/49314 and WO 03/099854. One particular example of a GLP-2 agonist is TEDUGLUTIDE™, a 39-amino acid peptide amide (NPS Pharmaceuticals, Inc.).

Examples of beta-cell imidazoline receptor antagonists include, but are not limited to those described in PCT Publication No. WO 00/78726 and *J. Pharmacol. Exp. Ther.* 1996, 278, 82-89.

An example of an antidiabetic phenylacetic acid derivative is repaglinide and pharmaceutically acceptable salts thereof.

Examples of antidiabetic D-phenylalanine derivatives include, but are not limited to nateglinide (N-[(trans-4-isopropylcyclohexyl)-carbonyl]-D-phenylalanine, EP 196222 and EP 526171) and repaglinide ((S)-2-ethoxy-4-{2-[[3-methyl-1-1-[2-(1-piperidinyl)phenyl]butyl]-amino]-2-oxoethyl}benzoic acid, EP 0 147 850 A2 and EP 0 207 331 A1). Nateglinide is intended to include the particular crystal forms (polymorphs) disclosed in U.S. Pat. No. 5,488,510 and European Patert Publication No. EP 0526171 B1. Repaglinide and nateglinide may be administered in the form as they are marketed under the trademarks NOVONORM™ and STARLIX™, respectively.

Examples of alpha-Glucosidase inhibitors include, but are not limited to, acarbose, N-(1,3-dihydroxy-2-propyl)valiolamine (voglibose) and the 1-deoxynojirimycin derivative miglitol. Acarbose is 4",6"-dideoxy-4'-[(1S)-(1,4,6/5)-4,5,6-trihydroxy-3-hydroxymethyl-2-cyclo-hexenylamino)maltotriose. The structure of acarbose can as well be described as 0-4,6-dideoxy-4-{[1S,4R,5 S,6S]-4,5,6-trihydroxy-3-(hydroxymethyl)-2-cyclohexen-1-yl]-amino)-alpha-D-glucopyranosyl-(1-4)-O-alpha-D-glucopyranosyl-(1-4)-D-glucopyranose. (U.S. Pat. No. 4,062,950 and European Patert Publication No. EP 0 226 121). Acarbose and miglitol may be administered in the forms that they are marketed under the trademarks GLUCOBAY™ and DIASTABOL 50™ respectively.

Examples of inhibitors of gastric emptying other than GLP-1 include, but are not limited to those disclosed in *J. Clin. Endocrinol. Metab.* 2000, 85(3), 1043-1048, and *Diabetes Care* 1998, 21, 897-893, especially Amylin and analogs thereof such as pramlintide. Amylin is described in *Diabetologia*, 1996, 39, 492-499.

Examples of $\alpha_2$-adrenergic antagonists include, but are not limited to midaglizole which is described in *Diabetes* 1987, 36, 216-220. The insulin that may be used in combination with ASK1 inhibitors of the invention include, but are not limited to animal insulin preparations extracted from the pancreas of bovine and pig; human insulin preparations genetically synthesized using *Escherichia coli* or yeast; zinc insulin; protamine zinc insulin; fragment or derivative of insulin (e.g., INS-1) and an oral insulin preparation.

In one particular embodiment, the antidiabetic compound administered in combination with ASK1 inhibitors of the invention is selected from the group consisting of nateglinide, mitiglinide, repaglinide, metformin, extendatide, rosiglitazone, tesaglitazar, pioglitazone, glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide, glimepiride and gliclazide, including any pharmaceutically acceptable salts thereof.

Examples of the preparation and formulation of PTPase inhibitors, GSK-3 inhibitors, non-small molecule mimetic compounds, GFAT inhibitors, G6 Pase inhibitors, glucagon receptor antagonists, PEPCK inhibitors, F-1,6-BPase inhibitors, GP inhibitors, RXR modulators, Beta-3 AR agonists, PDHK inhibitors, inhibitors of gastric emptying and UCP modulators are disclosed in the paterts, applications and references provided herein.

In the case of combination therapy with Compound I, the other antidiabetic compound may be administered (e.g., route and dosage form) in a manner known per se for such compound. ASK1 inhibitors of the invention and the other antidiabetic compound may be administered sequentially (i.e., at separate times) or at the same time, either one after the other separately in two separate dose forms or in one combined, single dose form. In one particular embodiment, the other antidiabetic compound is administered with ASK1 inhibitors of the invention as a single, combined dosage form. The dose of the antidiabetic compound may be selected from the range known to be clinically employed for such compound. Any therapeutic compounds of diabetic complications, antihyperlipemic compounds, antiobestic compounds or antihypertensive compounds can be used in combination with ASK1 inhibitors of the invention in the same manner as the above antidiabetic compounds. Examples of therapeutic compounds of diabetic complications include, but are not limited to, aldose reductase inhibitors such as tolrestat, epalrestat, zenarestat, zopolrestat, minalrestat, fidarestat, CT-112 and ranirestat; neurotrophic factors and increasing compounds thereof such as NGF, NT-3, BDNF and neurotrophin production-secretion promoters described in WO01/14372 (e.g., 4-(4-chlorophenyl)-2-(2-methyl-1-imidazolyl)-5-[3-(2-methylphenoxy)propyl]oxazole); neuranagenesis stimulators such as Y-128; PKC inhibitors such as ruboxistaurin mesylate; AGE inhibitors such as ALT946, pimagedine, N-phenacylthiazolium bromide (ALT766), ALT-711, EXO-226, pyridorin and pyridoxamine; reactive oxygen scavengers such as thioctic acid; cerebral vasodilators such as tiapride and mexiletine; somatostatin receptor agonists such as BIM23190; and apoptosis signal regulating kinase-1 (ASK-1) inhibitors. Examples of antihyperlipemic compounds include, but are not limited to, HMG-CoA reductase inhibitors such as pravastatin, simvastatin, lovastatin, atorvastatin, fluvastatin, rosuvastatin and pitavastatin; squalene synthase inhibitors such as compounds described in WO97/10224 (e.g., N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]-piperidine-4-acetic acid); fibrate compounds such as bezafibrate, clofibrate, simfibrate and clinofibrate; ACAT inhibitors such as avasimibe and eflucimibe; anion exchange resins such as colestyramine; probucol; nicotinic acid drugs such as nicomol and niceritrol; ethyl icosapentate; and plant sterols such as soysterol and γ-oryzanol. Examples of antiobestic compounds include, but are not limited to, dexfenfluramine, fenfluramine, phentermine, sibutramine, amfepramone, dexamphetamine, mazindol, phenylpropanolamine, clobenzorex; MCH receptor antagonists such as SB-568849 and SNAP-7941; neuropeptide Y antagonists such as CP-422935; cannabinoid receptor antagonists such as SR-141716 and SR-147778; ghrelin antagonist; 11β-hydroxysteroid dehydrogenase inhibitors such as BVT-3498; pancreatic lipase inhibitors such as orlistat and ATL-962; Beta-3 AR agonists such as AJ-9677; peptidic anorexiants such as leptin and CNTF (Ciliary Neurotropic Factor); cholecystokinin agonists such as lintitript and FPL-15849; and feeding deterrent such as P-57. Examples of the antihypertensive compounds include angiotensin converting enzyme inhibitors such as captopril, enalapril and delapril; angiotensin II antagonists such as candesartan cilexetil, losartan, eprosartan, valsartan, telmisartan, irbesartan, olmesartan medoxomil, tasosartan and 1-[[2'-(2,5-dihydro-5-oxo-4H-1,2,4-oxadiazol-3-yl)biphenyl-4-yl]methyl]-2-ethoxy-1H-benzimidazole-7-carboxylic acid; calcium channel blockers such as manidipine, nifedipine, nicardipine, amlodipine and efonidipine; potassium channel openers such as levcromakalim, L-27152, AL0671 and NIP-121; and clonidine.

The structure of the active agents identified herein by code nos., generic or trade names may be taken from the actual edition of the standard compendium "The Merck Index" or from databases, e.g. Paterts International (e.g. IMS World Publications). The corresponding contert thereof is hereby incorporated by reference. Any person skilled in the art is fully enabled to identify the active agents and, based on these references, likewise enabled to manufacture and test the pharmaceutical indications and properties in standard test models, both in vitro and in vivo.

Compositions Comprising ASK1 Inhibitors

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stert), subcutaneously, intraadiposally, intraarticularly, or intrathecally. The compounds and/or compositions according to the invention may also be administered or coadministered in slow release dosage forms.

The ASK1 inhibitors and compositions comprising them may be administered or coadministered in any conventional dosage form. Co-administration in the context of this invention is intended to mean the administration of more than one therapeutic agent, one of which includes a ASK1 inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington: The Science and Practices of Pharmacy, Lippincott Williams, and Wilkins Publisher, $21^{st}$ edition, 2005. The composition or formulation to be administered will, in any event, contain a sufficient quantity of an inhibitor of the present invention to reduce ASK1 activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more ASK1 inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

A. Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358, 603.

B. Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of the ASK1 inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The ASK1 inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

C. Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a ASK1 inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

D. Formulation for Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The ASK1 inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the ASK1 inhibitor alone or in combination with other pharmaceutically acceptable excipients can also be administered.

E. Formulations for Other Routes of Administration

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

F. Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of the Present Invention | 1% |
| Microcrystalline Cellulose | 73% |
| Stearic Acid | 25% |
| Colloidal Silica | 1%. |

Dosage, Host and Safety

The compounds of the present invention are stable and can be used safely. In particular, the compounds of the present invention are useful as ASK1 inhibitors for a variety of subjects (e.g., humans, non-human mammals and non-mammals).

The optimal dose may vary depending upon such conditions as, for example, the type of subject, the body weight of the subject, on the severity of the condition, the route of administration, and specific properties of the particular compound being used. Generally, acceptable and effective daily doses are amounts sufficient to effectively slow or eliminate the condition being treated. Typically, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Kits and Articles of Manufacture Comprising ASK1 Inhibitors

The invention is also directed to kits and other articles of manufacture for treating diseases associated with ASK1. It is noted that diseases are intended to cover all conditions for which the ASK1 possess activity that contributes to the pathology and/or symptomology of the condition.

In one embodiment, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Preparation of ASK1 Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see P. G. M. Wuts and T. W. Greene in "*Greene's Protective Groups in Organic Synthesis*" 4<sup>th</sup> edition, John Wiley and Sons, 2007.

Scheme A: General Synthetic Route I

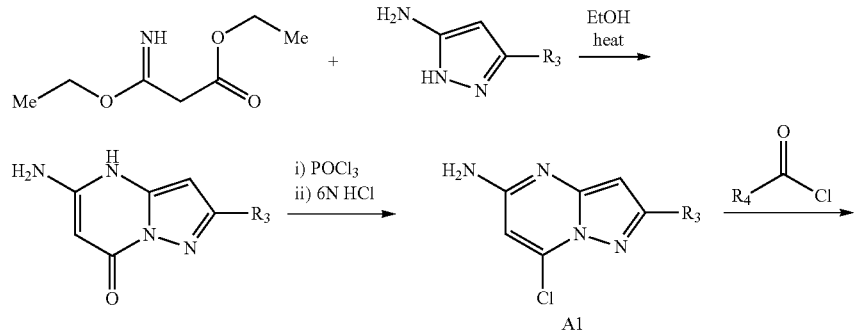

A1

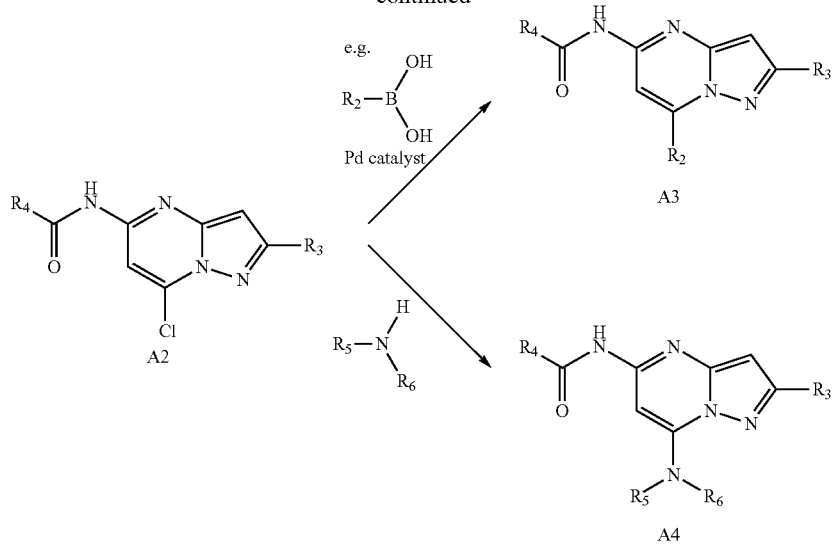

A general synthetic route for producing compounds of the present invention is shown in Scheme A. Reaction of commercially available ethyl 3-ethoxy-3-iminopropionate with an aminopyrazole in ethanol at reflux temperature would afford hydroxylated bicyclic intermediate. Chlorination of the product by heating in excess $POCl_3$ would afford chloro intermediate A1. Acylation of A1 in pyridine or in another aprotic solvent would give intermediate A2. Subsequent reaction of A2 with a boronic acid, boronic ester or a potassium trifluoroborate under Pd-catalyzed reaction conditions would afford compounds of the formula A3. Alternatively, when A2 is reacted with a primary or secondary amine with heating, compounds for the formula A4 would be obtained.

Scheme B: General Synthetic Route II

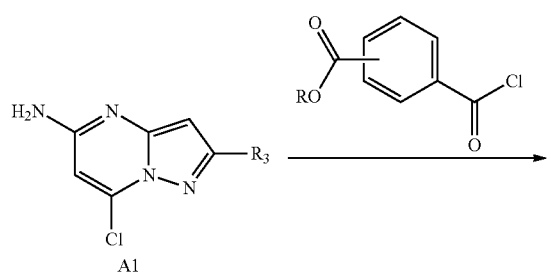

Another general synthetic route for producing compounds of the present invention is shown in Scheme B. Chloro intermediate A1 (see Scheme A) can be coupled with a carboxy-substituted benzoyl chloride. This is followed by a double addition reaction with a Grignard reagent to give alcohol intermediate B1. As with intermediate A2 in Scheme A, B1 can further react with a boronic acid or an amine to give the corresponding final products under Suzuki and displacement reaction conditions, respectively.

Scheme C: General Synthetic Route III

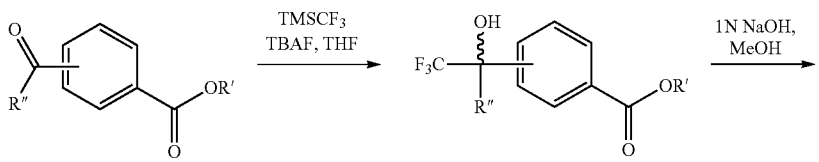

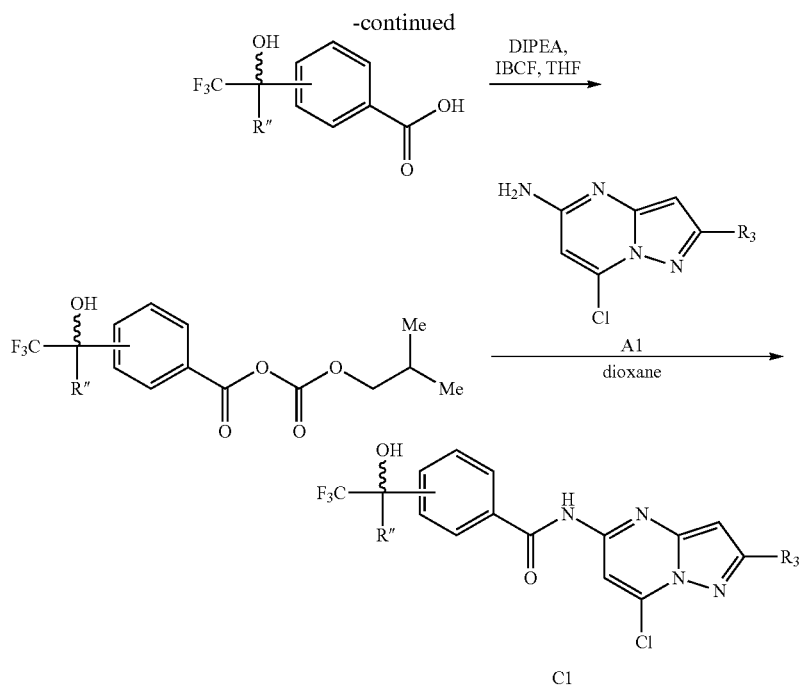

Alternatively compounds of the present invention can be prepared as shown in Scheme C. Carboxy-substituted phenyl ketone can be reacted with TMSCF$_3$ to give alkyl-, CF$_3$-disubstituted benzyl alcohol. Saponification followed by reaction with IBCF would afford acylcarbonate intermediate. Subsequent coupling reaction with intermediate A1 (see Scheme A) would afford intermediate C1. As with intermediate A2 in Scheme A, C1 can further react with a boronic acid or an amine to give the corresponding final products under Suzuki and displacement reaction conditions, respectively.

Scheme D: General Synthetic Route IV

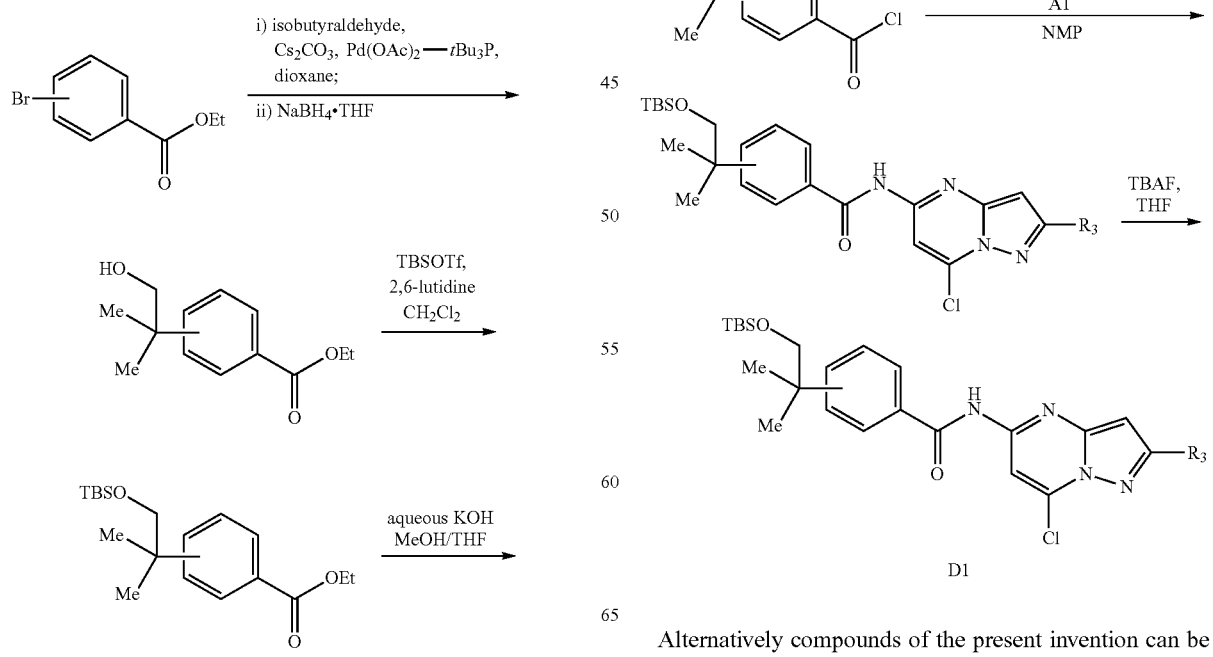

Alternatively compounds of the present invention can be prepared as shown in Scheme D. Isobutyraldehyde can be α-arylated by ethyl bromobenzoate under Pd-catalyzed conditions. Reduction of the aldehyde by NaBH$_4$ would give the corresponding alcohol. Protection of the primary alcohol as the TBS ether followed by saponification and chlorination would afford the desired acid chloride. Coupling with intermediate A1 from Scheme A followed by fluoride-mediated deprotection of the TBS group would afford intermediate D1. As with intermediate A2 in Scheme A, D1 can further react with a boronic acid or an amine to give the corresponding final products under Suzuki and displacement reaction conditions, respectively.

Scheme E: General Synthetic Route V

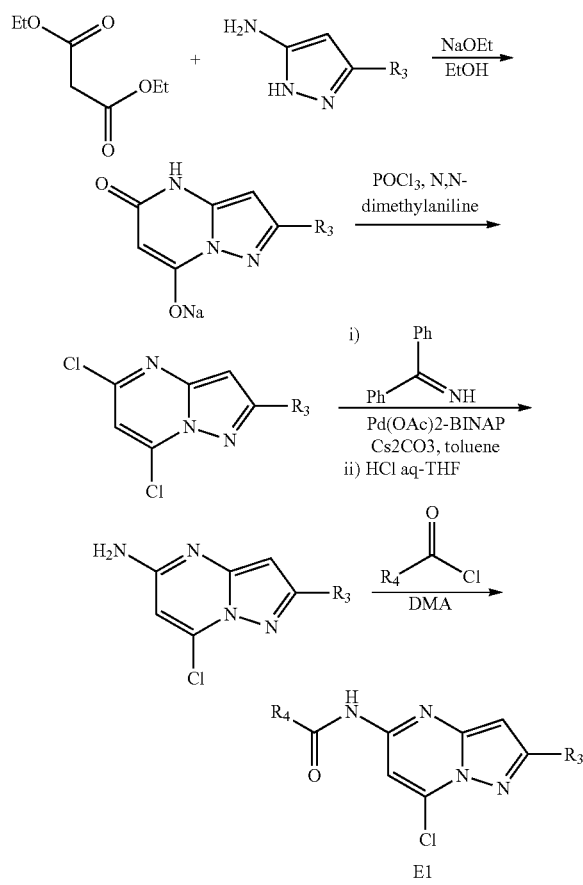

E1

Alternatively compounds of the present invention can be prepared as shown in Scheme E. Malonate can be reacted with an aminopyrazole in the presence of sodium ethoxide in ethanol at reflux temperature to afford the bicyclic intermediate. The dihydroxylated product can then be chlorinated in excess POCl$_3$ to form the corresponding dichloro derivative. Pd-catalyzed conditions using benzophenone imine would then allow mono-amination at the desired position after acid hydrolysis of the imine protecting group. Reaction of the resulting product with an acid chloride would then afford the desired intermediate E1. As with intermediate A2 in Scheme A, E1 can further react with a boronic acid or an amine to give the corresponding final products under Suzuki and displacement reaction conditions, respectively.

General Procedures

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in P. G. M. Wuts and T. W. Greene, "Greene's Protecting Groups in Organic Synthesis", 4$^{th}$ edition, John Wiley & Sons, Inc. 2007.

Compounds according to the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

As used herein the symbols and conventions used in these processes, schemes and examples are consistert with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60E-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-23, John Wiley and Sons, New York, N.Y., 2006; Rodd's Chemistry of Carbon Compounds, vols. 1-5 and supps., Elsevier Science Publishers, 1998; Organic Reactions, vols. 1-68, John Wiley and Sons, New York, N.Y., 2007; March J.: Advanced Organic Chemistry, 5th ed., 2001, John Wiley and Sons, New York, N.Y.; and Larock: Comprehen- μL (microliters)
atm (atmosphere)
BOC (tert-butyloxycarbonyl)

BSA (Bovine Serum Albumin)
CDI (1,1-carbonyldiimidazole)
DCE (dichloroethane)
DMAP (4-dimethylaminopyridine)
DMF (N,N-dimethylformamide)
DMSO (dimethylsulfoxide)
EDTA (Ethylenediaminetetraacetic acid)
Et$_2$O (diethyl ether)
FMOC (9-fluorenylmethoxycarbonyl)
h (hours)
HOBT (1-hydroxybenzotriazole)
HPLC (high pressure liquid chromatography)
i.v. (intravenous)
i-PrOH (isopropanol)
M (molar)
Me (methyl)
mg (milligrams)
min (minutes)
mM (millimolar)
mol (moles)
mp (melting point)
OMe (methoxy)
RP (reverse phase)
SPA (Scintillation Proximity Assay)
TBS (t-butyldimethylsilyl)
TEA (triethylamine)
TFAA (trifluoroacetic anhydride)
TIPS (triisopropylsilyl)
TMS (trimethylsilyl)
Tr (retention time)

Ac (acetyl)
ATP (Adenosine Triphosphatase)
BOP (bis(2-oxo-3-oxazolidinyl)phosphinic chloride)
CBZ (benzyloxycarbonyl)
DCC (dicyclohexylcarbodiimide)
DCM (dichloromethane)
DME (1,2-dimethoxyethane)
DMPU (N,N'-dimethylpropyleneurea)
EDCI (ethylcarbodiimide hydrochloride)
Et (ethyl)
EtOAc (ethyl acetate)
g (grams)
HOAc or AcOH (acetic acid)
HOSu (N-hydroxysuccinimide)
Hz (Hertz)
IBCF (isobutyl chloroformate)
L (liters)
mCPBA (meta-chloroperbenzoic acid)
MeOH (methanol)
MHz (megahertz)
mL (milliliters)
mmol (millimoles)
MOPS (Morpholinepropanesulfonic acid)
NaOAc (sodium acetate)
psi (pounds per square inch)
r.t. (ambient temperature)
TBAF (tetra-n-butylammonium fluoride)
tBu (tert-butyl)
TFA (trifluoroacetic acid)
THF (tetrahydrofuran)
TLC (thin layer chromatography)
TMSE (2-(trimethylsilyl)ethyl)
Brij35 (polyoxyethyleneglycol dodecyl ether)

All references to ether or Et$_2$O are to diethyl ether; and brine refers to a saturated aqueous solution of NaCl. Unless otherwise indicated, all temperatures are expressed in ° C. (degrees Centigrade). All reactions are conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

sive Organic Transformations, 2$^{nd}$ edition, John Wiley and Sons, New York, 1999. The entire disclosures of all documents cited throughout this application are incorporated herein by reference.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques, Andre Collet, and Samuel H. Wilen, Enantiomers, Racemates and Resolutions, John Wiley & Sons, Inc. (1981).

Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, and Samuel H. Wilen, Enantiomers, Racemates and Resolutions, John Wiley & Sons, Inc. (1981).

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Waters ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (54μ, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 104 in methanol at 0.1 mg/mL in concentration.

In another variation, preparative chiral separations are performed using a Berger MultiGram II SFC purification system. For example, samples can be loaded onto a ChiralPak AD column (21×250 mm, 104 In particular variations, the flow rate for separation can be 70 mL/min, the injection volume up to 2 mL, and the inlet pressure set at 130 bar. Stacked injections can be applied to increase the efficiency.

Descriptions of the syntheses of particular compounds according to the present invention based on the above reaction schemes and variations thereof are set forth in the Example section.

Assaying the Biological Activity of the Compounds of the Invention

The inhibitory effect of the compound of the invention on ASK1 may be evaluated by a variety of binding assays and functional assays.

ASK1 protein for the assay may be prepared by standard PCR cloning and expression in a vector. Example A discloses such a method of preparing the enzyme. However, it should be noted that ASK1 is commercially available through Millipore (Cat. #14-606).

The inhibitory effect of the compound of the invention on ASK1 may be evaluated by evaluating the phosphorylating activity of the enzyme on a known substrate with or without the presence of the test compound. Example B provides such an assay where myelin basic protein (Wako) is used as substrate and detection is by scintillation counting. It should be understood other substrates and detection mechanism may be used. A commercially available a kit, Cisbio's HTRF® KinEASE™ STK kit, has shown to be useful for evaluating ASK1 activity. The assay uses an anti-phosphoseric specific, Eu3+-Cryptate labeled antibody to mark the phosphorylated product of ASK1 on a biotinylated kinase substrate, and detection is by time resolved fluorescence using XL665 labeled streptavidin. The fluorescence intensity is proportional to the amount of product formation. Example C provides the assay protocol.

$IC_{50}$ values of selected compounds of the invention were measured using the assay described in Example B. Some of the exemplified compounds were shown to have $IC_{50}$ of greater than 1 μM, some others less than about 1 μM, and most others of the compounds have an $IC_{50}$ value of less than about 0.1 μM. The $IC_{50}$ values of selected compounds of the present invention are given in Table 1.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

EXAMPLES

Example 1

Preparation of Intermediates 1E, 1F, 1J, 1K, 1O and 1S

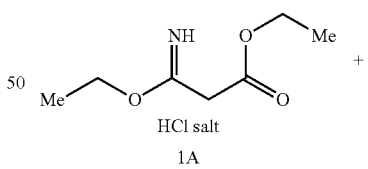

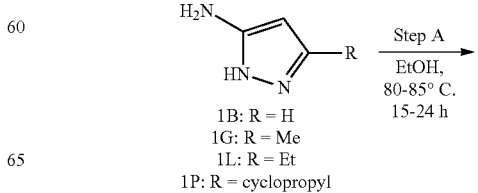

1B: R = H
1G: R = Me
1L: R = Et
1P: R = cyclopropyl

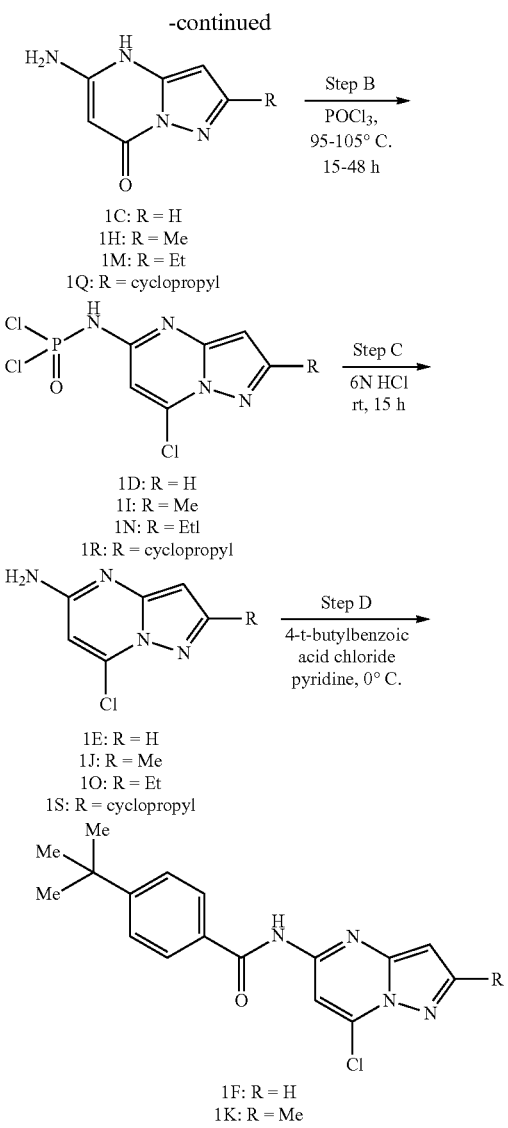

1C: R = H
1H: R = Me
1M: R = Et
1Q: R = cyclopropyl

1D: R = H
1I: R = Me
1N: R = Et
1R: R = cyclopropyl

1E: R = H
1J: R = Me
1O: R = Et
1S: R = cyclopropyl

1F: R = H
1K: R = Me

Step A: Commercially available HCl salt of ethyl 3-ethoxy-3-iminopropionate 1A (25 g, 1.0 equivalent) was neutralized by adding it portion wise to a mixture of ice, saturated NaHCO$_3$ and EtOAc with vigorous stirring for 5-10 minutes. The bi-layer was separated and the aqueous layer was extracted with EtOAc. Combined organic layers were washed with brine, dried over MgSO$_4$, filtered and dried in vacuo. The colorless oil was dissolved in EtOH (1.0 M) and the solution was added to an ethanolic solution (0.5 M) of 1H-pyrazol-5-amine (1B) (1.0 equivalent), 3-methyl-1H-pyrazol-5-amine (1G) (1.0 equivalent), 3-ethyl-1H-pyrazol-5-amine (1L) (1.0 equivalent) or 3-cyclopropyl-1H-pyrazol-5-amine (1P) (1.0 equivalent). The mixture was heated to 80-85° C. under nitrogen for 15-24 h. The mixture was then filtered warm on a fritted funnel under nitrogen. The collected precipitate was washed once with cold EtOH and then Et$_2$O under nitrogen. The product 1C (87%), 1H (72%), 1M (74%) or 1Q (88%), respectively, was dried under vacuum and then used without further purification.

1C: $^1$H NMR (400 MHz, DMSO-d$_6$) δ ppm 4.73 (s, 1 H) 5.91 (d, J=1.77 Hz, 1 H) 6.54 (s, 2 H) 7.62 (d, J=1.77 Hz, 1 H) 11.42 (br. s., 1 H).

1H: $^1$H NMR (400 MHz, DMSO-d$_6$) δ ppm 2.20 (s, 3 H) 4.70 (s, 1 H) 5.75 (s, 1 H) 6.54 (s, 2 H) 11.39 (br. s., 1 H); ESI-MS: m/z 164.9 (M+H)$^+$.

1M: $^1$H NMR (400 MHz, DMSO-d$_6$) δ: 5.66 (s, 1H), 2.57 (q, J=7.6 Hz, 2H), 1.10-1.22 (m, 3H).

1Q: $^1$H NMR (400 MHz, DMSO-d$_6$) δ: 11.29 (br. s., 1H), 6.44 (s, 2H), 5.63 (s, 1H), 4.67 (s, 1H), 1.82-1.94 (m, 1H), 0.85-0.95 (m, 2H), 0.65-0.75 (m, 2H).

Step B: 5-Aminopyrazolo[1,5-a]pyrimidin-7(4H)-one (1C), 5-amino-2-methylpyrazolo[1,5-a]pyrimidin-7(4H)-one (1H), 5-amino-2-ethylpyrazolo[1,5-a]pyrimidin-7(4H)-one (1M), or 5-amino-2-cyclopropylpyrazolo[1,5-a]pyrimidin-7(4H)-one (1Q) was added portion wise to ice-cooled POCl$_3$ (0.3 M). The mixture was then heated to 95-105° C. for 48 h or until the mixture is homogeneous, and then cooled to 0° C. for 6 h. For 1C or 1H, the resulting fine precipitate was collected on a fritted glass funnel under nitrogen, and was washed twice with Et$_2$O; after drying under a stream of nitrogen for 1 h, the intermediate, 1D or 1I, respectively, was obtained as a light yellow solid to be used in the next step without further purification. For 1M or 1Q, POCl$_3$ was removed in vacuo to give the crude product 1N or 1R for use in the next step without further purification.

Step C: Phosphorylated intermediate 1D, 1I, 1N or 1R was suspended in 6-12 N HCl (0.6 M) at 0° C. The mixture was then warmed to room temperature and was stirred for 15-24 h. At 0° C., a 6-14 N aqueous solution of NaOH was added to adjust the pH of the reaction mixture to 9. For 1D and 1I, the resulting precipitate was collected by filtration and was washed twice with water; after having been dried under a stream of nitrogen, the off-white solid was further washed with Et$_2$O and dried to give analytically pure 1E (74%) or 1.1 (48%). For 1D and 1I, the resulting mixture was extracted with EtOAc twice; combined organic layers were washed with brine, dried over MgSO$_4$, concentrated in vacuo and filtered to collect the product 1O (44%) and 1S (56%) as a light yellow solid.

1E: NMR (400 MHz, DMSO-d$_6$) δ ppm 5.11 (br. s.) 6.25 (d, J=2.27 Hz, 1 H) 6.71 (s, 1 H) 8.02 (d, J=2.27 Hz, 1 H).

1.1: $^1$H NMR (400 MHz, DMSO-d$_6$) δ ppm 2.28 (s, 3 H) 5.86 (s, 1 H) 6.37 (s, 1 H) 6.88 (br. s., 1 H); ESI-MS: m/z 183.0 (M+H)$^+$.

1O: $^1$H NMR (400 MHz, DMSO-d$_6$) δ: 6.86 (s, 2 H), 6.37 (s, 1 H), 5.88 (s, 1 H), 2.64 (q, J=7.6 Hz, 2 H), 1.21 (t, J=7.6 Hz, 3 H); ESI-MS: m/z 197.1 (M+H)$^+$.

1S: $^1$H NMR (400 MHz, DMSO-d$_6$) δ: 6.84 (s, 1H), 6.34 (s, 1H), 5.74 (s, 1H), 1.89-1.99 (m, 1H), 0.91-0.98 (m, 2H), 0.72-0.79 (m, 2H); ESI-MS: m/z 209.1 (M+H)$^+$.

Step D: 7-Chloropyrazolo[1,5-a]pyrimidin-5-amine 1E (1.0 equivalent) or 7-chloro-2-methylpyrazolo[1,5-a]pyrimidin-5-amine (1J, 1.0 equivalent) was dissolved in anhydrous pyridine (0.35 M). 4-t-Butylbenzoic acid chloride (1.05 equivalents) was added at 0° C., and the mixture was stirred for two hours. The reaction was then quenched with saturated NaHCO$_3$; pyridine was removed in vacuo and the residue was extracted with EtOAc. Combined organic layers were washed twice with 0.2 N HCl to remove residual pyridine, dried over MgSO$_4$, filtered and concentrated. Crude product was purified by column chromatography (SiO$_2$, gradient of 15 to 30% EtOAc/hexanes). The purified product was triturated with Et$_2$O to give 4-tert-butyl-N-(7-chloropyrazolo[1,5-a]pyrimidin-5-yl)benzamide (1F, 47%) or 4-tert-butyl-N-(7-chloro-2-methylpyrazolo[1,5-a]pyrimidin-5-yl)benzamide (1K) of the product as a solid.

1F: $^1$H NMR (400 MHz, DMSO-d$_6$) δ ppm 1.33 (s, 9 H) 6.65 (d, J=2.27 Hz, 1 H) 7.56 (d, J=8.59 Hz, 1 H) 8.01 (d, J=8.59 Hz, 1 H) 8.15 (s, 1 H) 8.28 (d, J=2.27 Hz, 1 H) 11.37 (s, 1H); ESI-MS: m/z 329.0 (M+H)+.

1K: $^1$H NMR (400 MHz, CDCl$_3$) δ ppm 1.37 (s, 9H) 2.25 (s, 3H) 6.31 (s, 1H) 7.55 (d, J=8.3 Hz, 2H) 7.86 (d, J=8.3 Hz, 2H) 8.26 (s, 1H) 8.56 (s, 1H).

Example 2

Preparation of Intermediate 2D, 2F, 2H and 2J

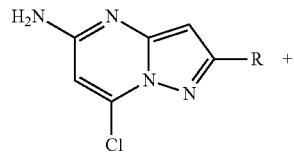

1E: R = H
1J: R = Me
1O: R = Et
1S: R = cyclopropyl

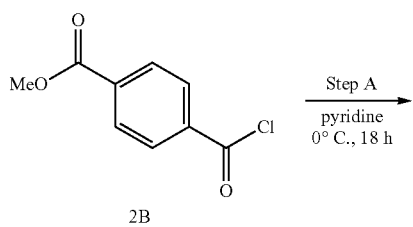

2B

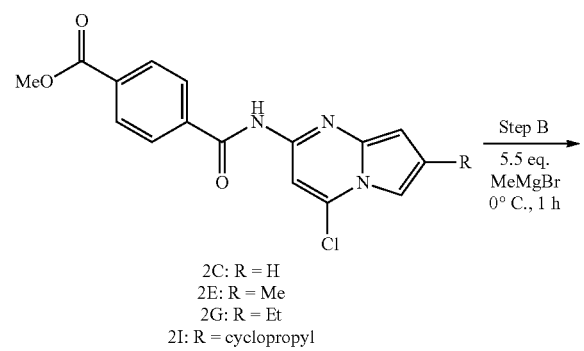

2C: R = H
2E: R = Me
2G: R = Et
2I: R = cyclopropyl

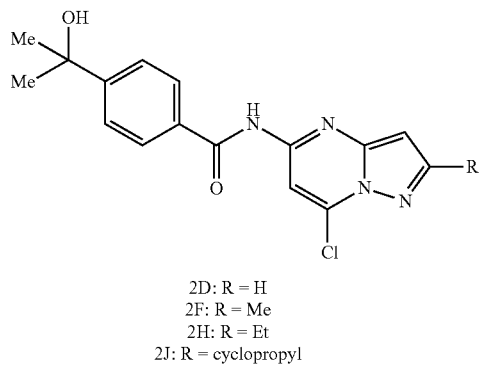

2D: R = H
2F: R = Me
2H: R = Et
2J: R = cyclopropyl

Step A: 7-Chloropyrazolo[1,5-a]pyrimidin-5-amine (1E, 1.0 equivalent), 7-chloro-2-methylpyrazolo[1,5-a]pyrimidin-5-amine (1J, 1.0 equivalent), 7-chloro-2-ethylpyrazolo[1,5-a]pyrimidin-5-amine (1O, 1.0 equivalent), or 7-chloro-2-cyclopropylpyrazolo[1,5-a]pyrimidin-5-amine (1S, 1.0 equivalent) was suspended in pyridine (0.3 M). At 0° C. was added terephthalic acid monomethylester chloride (2B, 1.3 equivalents), and the mixture was stirred vigorously at 0° C. for 4-18 h. The reaction was quenched with saturated NaHCO$_3$ and stirred for another 0.5 h; pyridine was removed in vacuo and the residue was suspended in water. The precipitate was collected on a fritted glass funnel and was washed twice with water. After drying under a stream of N$_2$ for 15 h, the crude product methyl 4-(7-chloropyrazolo[1,5-a]pyrimidin-5-ylcarbamoyl)benzoate 2C (92%), methyl 4-(7-chloro-2-methylpyrazolo[1,5-a]pyrimidin-5-ylcarbamoyl)benzoate 2E (72%), methyl 4-(7-chloro-2-ethylpyrazolo[1,5-a]pyrimidin-5-ylcarbamoyl)benzoate 2G (84%) or methyl 4-(7-chloro-2-cyclopropylpyrazolo[1,5-a]pyrimidin-5-ylcarbamoyl)benzoate 2I (98%) was obtained as an orange solid and was used without further purification.

2C: $^1$H NMR (400 MHz, DMSO-d$_6$) δ ppm 3.90 (s, 3 H) 6.67 (d, J=2.27 Hz, 2 H) 8.05-8.11 (m, 4 H) 8.11-8.19 (m, 6 H) 8.30 (d, J=2.27 Hz, 2 H) 11.67 (s, 2 H); ESI-MS: m/z 331.0 (M+H)+.

Step B: Methyl 4-(7-chloropyrazolo[1,5-a]pyrimidin-5-ylcarbamoyl)benzoate 2C (1.0 equivalent), methyl 4-(7-chloro-2-methylpyrazolo[1,5-a]pyrimidin-5-ylcarbamoyl)benzoate 2E (1.0 equivalent), methyl 4-(7-chloro-2-ethylpyrazolo[1,5-a]pyrimidin-5-ylcarbamoyl)benzoate 2G (1.0 equivalent), or methyl 4-(7-chloro-2-cyclopropylpyrazolo[1,5-a]pyrimidin-5-ylcarbamoyl)benzoate 2I (1.0 equivalent) was suspended in THF (0.2 M). At 0° C. methyl magnesium bromide (3.0 M solution in diethyl ether, 5.5 equivalents) was added via a dropping funnel. The mixture was stirred at 0° C. for another one hour before being quenched at 0° C. with saturated NH$_4$Cl. Volatiles were removed in vacuo and the residue was diluted with brine and extracted with EtOAc. Combined organic layers were dried over MgSO$_4$, filtered and concentrated. For 2C, or 2G, the crude product was purified by chromatography (SiO$_2$, gradient of 30 to 50% EtOAc/hexanes) to afford N-(7-chloropyrazolo[1,5-a]pyrimidin-5-yl)-4-(2-hydroxypropan-2-yl)benzamide 2D (44%), or N-(7-chlorop-2-ethylpyrazolo[1,5-a]pyrimidin-5-yl)-4-(2-hydroxypropan-2-yl)benzamide 2H (69%), respectively, as a solid. For 2E or 2I crude product was purified by recrystallization from EtOH and ether to give the pure product N-(7-chloro-2-methylpyrazolo[1,5-a]pyrimidin-5-yl)-4-(2-hydroxypropan-2-yl)benzamide 2F (54%) or N-(7-chloro-2-cyclopropylpyrazolo[1,5-a]pyrimidin-5-yl)-4-(2-hydroxypropan-2-yl)benzamide 2J (54%), respectively, as pale yellow solid.

2F: $^1$H NMR (400 MHz, DMSO-d$_6$) δ: 11.32 (s, 1H), 8.06 (s, 1H), 7.96-8.04 (m, 2H), 7.58-7.65 (m, 2H), 6.46 (s, 1H), 5.20 (s, 1H), 2.44 (s, 3H), 1.44-1.49 (m, 6H); ESI-MS: m/z 345.2 (M+H)+.

2H: $^1$H NMR (400 MHz, DMSO-d$_6$) δ: 11.33 (s, 1 H), 8.07 (s, 1 H), 8.03-7.94 (m, 2 H), 7.69-7.58 (m, 2 H), 6.49 (s, 1 H), 5.21 (s, 1 H), 2.81 (q, J=7.6 Hz, 3 H), 1.46 (s, 7 H), 1.30 (t, J=7.6 Hz, 4 H); ESI-MS: m/z 359.0 (M+H)+.

2J: $^1$H NMR (400 MHz, DMSO-d$_6$) δ: 11.30 (s, 1H), 8.04 (s, 2 H), 7.99 (d, J=8.6 Hz, 2 H), 7.61 (d, J=8.8 Hz, 2 H), 6.36

(s, 1 H), 5.20 (s, 1 H), 2.12 (s, 1 H), 1.45 (s, 6 H), 1.06 (dd, J=2.5, 8.3 Hz, 2 H), 0.89 (dd, J=2.5, 5.1 Hz, 2 H); ESI-MS: m/z 371.1 (M+H)+.

Example 3

Preparation of Intermediate 3E

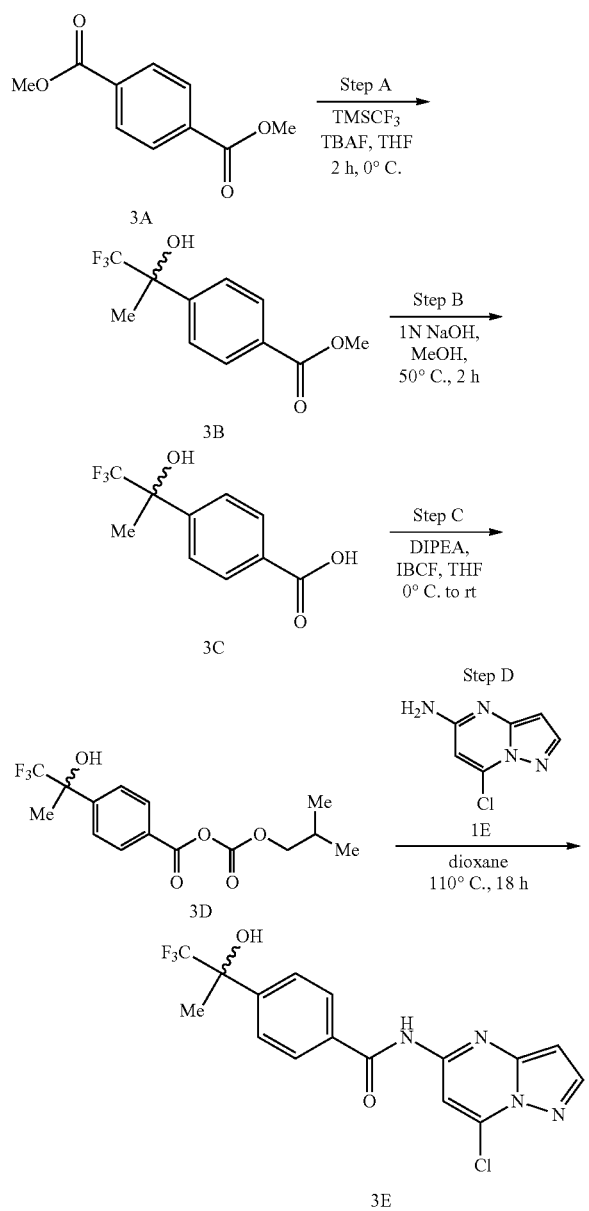

Step A: Methyl 4-acetyl benzoate (3A, 10 g, 1.0 equivalent) was dissolved in THF (0.25 M) along with TMSCF$_3$ (3.0 equivalents). At 0° C., TBAF (1.0 M in THF, 2.5 equivalents) was added via a dropping funnel over 1 h. The mixture was stirred for another hour at 0° C. Volatiles were removed in vacuo, and the residue was diluted in Et$_2$O and washed with saturated NaHCO$_3$ solution and brine. Organic layer was dried over MgSO$_4$, filtered and concentrated. The crude product was purified by chromatography (SiO$_2$) to give 3B (80%) as a colorless oil.

Step B: Methyl 4-(1,1,1-trifluoro-2-hydroxypropan-2-yl)benzoate (3B, 1.0 equivalent) was dissolved in methanol (1.0 M). A 1 N solution of NaOH (5.0 equivalents) was added and the mixture was heated to 50° C. for 2 h. At room temperature, the mixture was then acidified with 2 N HCl solution. Methanol was removed in vacuo, and the residue was extracted with EtOAc. Combined organic layers were dried over MgSO$_4$, filtered and concentrated. The crude product was purified by recrystallization from hexanes/Et$_2$O to give 3C (32%) as a colorless solid. $^1$H NMR (400 MHz, MeOD) δ ppm 1.77 (s, 3 H) 7.75 (d, J=8.34 Hz, 2 H) 8.05 (d, J=8.34 Hz, 2 H).

Step C: 4-(1,1,1-Trifluoro-2-hydroxypropan-2-yl)benzoic acid (3C, 1.0 equivalent) and DIPEA (1.05 equivalents) were dissolved in THF (0.3 M). At 0° C., ICBF (1.05 equivalents) was added and the mixture was allowed to warm to room temperature. After 4 h, brine was added, and the mixture was extracted with Et$_2$O. Combined organic layers were dried over MgSO$_4$, filtered and concentrated. The crude product was purified by chromatography (SiO$_2$, gradient of 15 to 30% EtOAc/hexanes) to give 3D (72%) as a colorless oil. $^1$H NMR (400 MHz, CHLOROFORM-d) δ ppm 1.01 (d, J=6.82 Hz, 6 H) 1.82 (s, 3 H) 2.03-2.14 (m, 1 H) 2.89-3.03 (m, 1 H) 4.14 (d, J=6.57 Hz, 2 H) 7.73 (d, J=7.58 Hz, 2 H) 8.08 (d, J=8.34 Hz, 2 H).

Step D: 4-(1,1,1-Trifluoro-2-hydroxypropan-2-yl)benzoic (isobutyl carbonic) anhydride 3D (1.0 equivalent) and 7-chloropyrazolo[1,5-a]pyrimidin-5-amine (1E, 1.0 equivalent) were dissolved in dioxane (0.15 M) and the mixture was heated to 110° C. for 18 h. After cooling to room temperature, brine was added and the mixture was extracted with EtOAc. Combined organic layers were dried over MgSO$_4$, filtered and concentrated. The crude product was purified by chromatography (SiO$_2$, gradient of 40 to 50% EtOAc/hexanes) to give N-(7-chloropyrazolo[1,5-a]pyrimidin-5-yl)-4-(1,1,1-trifluoro-2-hydroxypropan-2-yl)benzamide (3E, 48%) as a colorless oil.

Example 4

Preparation of Intermediate 4G

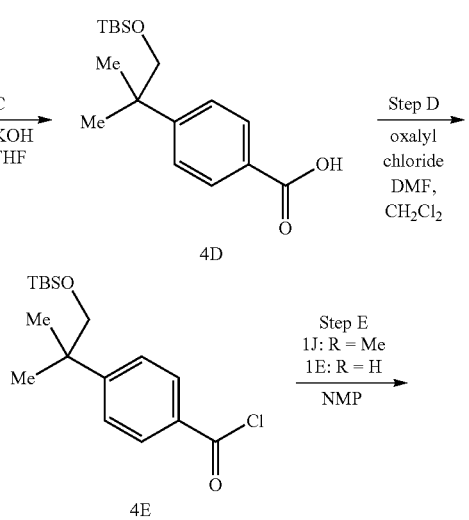

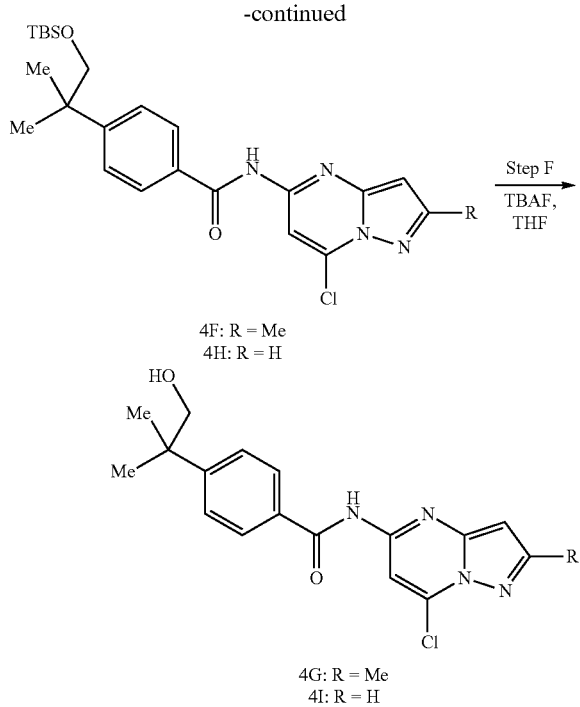

4F: R = Me
4H: R = H

4G: R = Me
4I: R = H

Step A: Anhydrous cesium carbonate (7.8 g, 1.2 equivalents) was suspended in dixoane (0.25 M). Ethyl 4-bromobenzoate (4A, 1.0 equivalent), isobutyraldehyde (2.0 equivalents), Pd(OAc)$_2$ (0.05 equivalent) and tri-tert-butylphosphine (0.1 equivalent) were added. The resulting mixture was heated to 110° C. for 2 h. After cooling, water was added and the mixture was extracted with ethyl acetate. Combined organic layers were dried over MgSO$_4$, filtered and concentrated. The crude product was purified by chromatography (SiO$_2$) to give 4B (15%) as a colorless oil. $^1$H NMR (400 MHz, CHLOROFORM-d) δ ppm 1.32-1.44 (m, 9H) 2.04 (s, 1H) 3.65 (d, J=6.2 Hz, 2H) 4.37 (q, J=7.2 Hz, 2H), 7.41-7.52 (m, 2H), 7.96-8.06 (m, 2H).

Step B: To a solution of ethyl 4-(1,1-dimethyl-2-oxoethyl) benzoate (4B, 680 mg, 1.0 equivalent) and 2,6-lutidine (2.0 equivalents) in CH$_2$Cl$_2$ (0.03 M) was added TBSOTf (1.5 equivalents) at 0° C. With gradual warming to room temperature, the reaction mixture was stirred for 1 h. Water was then added, and the mixture was extracted with CH$_2$Cl$_2$. Combined organic layers were dried over MgSO$_4$, filtered and concentrated. The crude product was purified by chromatography (SiO$_2$) to give 4C (99%) as a colorless oil. $^1$H NMR (CHLOROFORM-d) δ ppm −0.07 (s, 6H) 0.83 (s, 9H) 1.31 (s, 6H) 1.39 (t, J=7.2 Hz, 3H) 3.55 (s, 2H) 4.36 (q, J=7.2 Hz, 2H) 7.44 (d, J=8.4 Hz, 2H) 7.96 (d, J=8.4 Hz, 2H).

Step C: To a solution of ethyl 4-(2-{[tert-butyl(dimethyl) silyl]oxy}-1,1-dimethylethyl)benzoate (4C, 1.0 g, 1.0 equivalents) in a 3:1 mixture of THF/MeOH (0.78 M) was added 0.9 M aqueous solution of KOH (2.9 equivalents). The reaction mixture was heated to 70° C. for 1 h. After stirring, the solvents were evaporated, and the residue was acidified with dilute aqueous HCl and then extracted with CH$_2$Cl$_2$. Combined organic layers were dried over MgSO$_4$, filtered and concentrated. The crude product was purified by chromatography (SiO$_2$) to give 4D (82%) as a white solid: $^1$H NMR (CHLOROFORM-d) δ ppm −0.07 (s, 6H) 0.82 (s, 9H) 1.32 (s, 6H) 3.56 (s, 2H) 7.47 (d, J=8.7 Hz, 2H) 8.01 (d, J=8.7 Hz, 2H).

Step D: A solution of 4-(1-(tert-butyldimethylsilyloxy)-2-methylpropan-2-yl)benzoic acid (4D, 4.0 g, 1.0 equivalent) and CH$_2$Cl$_2$ (0.20 M) was treated with oxalyl chloride (2.0 M in CH$_2$Cl$_2$, 3.8 equivalents). After 15 min, DMF (0.10 equivalents) was added. The mixture was stirred for another two hours and then the volatiles were removed in vacuo. The white residue of crude 4-(1-(tert-butyldimethylsilyloxy)-2-methylpropan-2-yl)benzoyl chloride (4E) was used in the next step without further purification.

Step E: 4-(1-(tert-Butyldimethylsilyloxy)-2-methylpropan-2-yl)benzoyl chloride (4E, 1.0 equivalent) was suspended in NMP and treated with 7-chloro-2-methylpyrazolo [1,5-c]pyrimidin-5-amine (1.1, 1.0 equivalent). After 14 hours, the reaction mixture was partitioned between EtOAc and water. The organic layer was washed with 0.33M HCl, water, NaHCO$_3$, and brine and was then dried over Na$_2$SO$_4$, filtered, and concentrated in vacuo. Crude 4-(1-(tert-butyldimethylsilyloxy)-2-methylpropan-2-yl)-N-(7-chloro-2-methylpyrazolo[1,5-a]pyrimidin-5-yl)benzamide (4F), a viscous yellow oil, was in the next step without further purification.

Step F: 4-(1-(tert-Butyldimethylsilyloxy)-2-methylpropan-2-yl)-N-(7-chloro-2-methylpyrazolo[1,5-a]pyrimidin-5-yl)benzamide (4F, 3.9 g, 1.0 equivalent) was dissolved in THF (0.13 M) and treated with TBAF (1.0 M in THF, 4.0 equivalents). After 60 hours, pH 7 phosphate buffer was added and the mixture was extracted with EtOAc. The organic layer was dried over Na$_2$SO$_4$, filtered, and concentrated in vacuo. The residue was purified by chromatography (SiO$_2$, gradient of 25 to 50% EtOAc/hexanes) to give N-(7-chloro-2-methylpyrazolo[1,5-a]pyrimidin-5-yl)-4-(1-hydroxy-2-methylpropan-2-yl)benzamide (4G) as a white solid. $^1$H NMR (400 MHz, DMSO-d$_6$) δ ppm 1.25 (s, 6 H), 2.44 (s, 3 H), 3.46 (d, J=5.05 Hz, 2 H), 4.76 (t, J=5.31 Hz, 1 H), 6.45 (s, 1 H), 7.52 (d, J=8.59 Hz, 2 H), 7.99 (d, J=8.59 Hz, 2 H), 8.06 (s, 1 H), 11.30 (s, 1 H).

Example 5

Preparation of Intermediates 5F and 5G

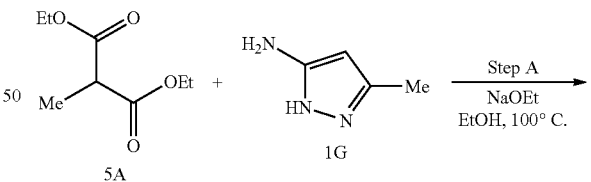

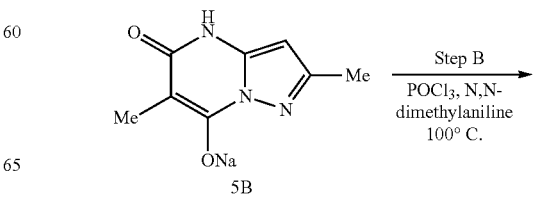

-continued

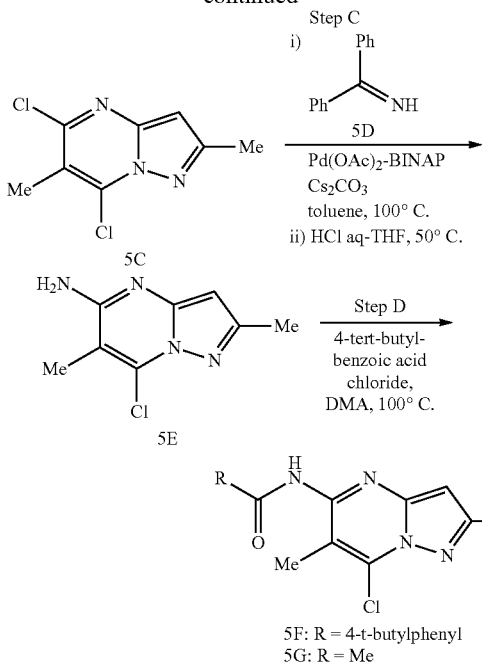

Step A: A 21% ethanolic solution of NaOEt (12 ml, 2.0 equivalents) was added to 3-methyl-1H-pyrazol-5-amine (1G, 1.0 equivalent) in EtOH (0.35 M). Diethyl 2-methylmalonate (5A, 1.1 equivalent) was then added. The resulting mixture was mechanically stirred at 100° C. overnight for 3 h. After cooling, a white precipitate appeared. The solid was filtered, washed with EtOH and then dried. Compound 5B (79%) was obtained as a white solid.

Step B: Sodium 2,6-dimethyl-5-oxo-4,5-dihydropyrazolo[1,5-a]pyrimidin-7-olate (5B, 1.0 equivalent) was added POCl$_3$ (0.8 M) slowly, and then N,N-dimethylaniline (0.5 equivalent) was added. The suspension was mechanically stirred at 100° C. for 18 h. POCl$_3$ was removed by evaporation. The residue was extracted with EtOAc from the residue after being neutralized with aqueous NaOH (pH 9-10). Combined organic layers were dried over MgSO$_4$, filtered and concentrated. The crude product was purified by chromatography (SiO$_2$) to give 5C (58%) as a white solid. $^1$H NMR (400 MHz, CDCl$_3$) δ ppm 2.52 (s, 3H) 2.55 (s, 3H) 6.48 (s, 1H).

Step C: 5,7-Dichloro-2,6-dimethylpyrazolo[1,5-a]pyrimidine (5C, 1.0 equivalent), diphenylmethanimine (5D, 1.0 equivalent), Pd(OAc)$_2$ (0.1 equivalent), BINAP (0.1 equivalent) and anhydrous Cs$_2$CO$_3$ (2.0 equivalents) are added to toluene (0.2 M). The mixture was stirred at 100° C. for 18 h. After cooling, toluene was removed by evaporation. The residue was extracted with EtOAc from brine. Combined organic layers were dried over MgSO$_4$, filtered and concentrated. The residue was dissolved in THF (0.25 M) and then concentrated HCl (10% by volume) was added. The resulting mixture was stirred at 50° C. for 18 h. The solvent was removed and the residue neutralized with aqueous NaOH (pH 9-10) and then extracted with EtOAc. Combined organic layers were dried over MgSO$_4$, filtered and concentrated. The crude product was purified by chromatography (SiO$_2$, gradient of 20 to 60% EtOAc/hexanes) to give 5E (23%) as a white solid. $^1$H NMR (400 MHz, DMSO-d$_6$) δ ppm 2.16 (s, 3H) 2.27 (s, 3H) 5.83 (s, 1H) 6.79 (s, 2H).

Step D: 7-Chloro-2,6-dimethylpyrazolo[1,5-a]pyrimidin-5-amine (5E, 1.0 equivalent) and 4-t-butylbenzoic acid chloride (2.0 equivalents) were dissolved in DMA (0.5 M with respect to 5E) and were heated to 100° C. for 18 h. After cooling to room temperature, saturated NaHCO$_3$ was added and the mixture was extracted with EtOAc. Combined organic layers were dried over MgSO$_4$, filtered and concentrated. The crude product was purified by chromatography (SiO$_2$) to give 4-tert-butyl-N-(7-chloro-2,6-dimethylpyrazolo[1,5-a]pyrimidin-5-yl)benzamide (5F, 31%) and N-(7-chloro-2,6-dimethylpyrazolo[1,5-a]pyrimidin-5-yl)acetamide (5G, 9%) as white solids.

5F: $^1$H NMR (400 MHz, CHLOROFORM-d) δ ppm 1.37 (s, 9 H) 2.40 (s, 3 H) 2.55 (s, 3 H) 6.40 (s, 1 H) 7.54 (d, J=8.34 Hz, 2 H) 7.89 (d, J=8.59 Hz, 2 H) 8.21 (s, 1 H).

5G: $^1$H NMR (400 MHz, CHLOROFORM-d) δ ppm 2.37 (s, 3 H) 2.46 (s, 3 H) 2.53 (s, 2 H) 6.35 (s, 1 H).

Example 6

Preparation of Intermediates 6B

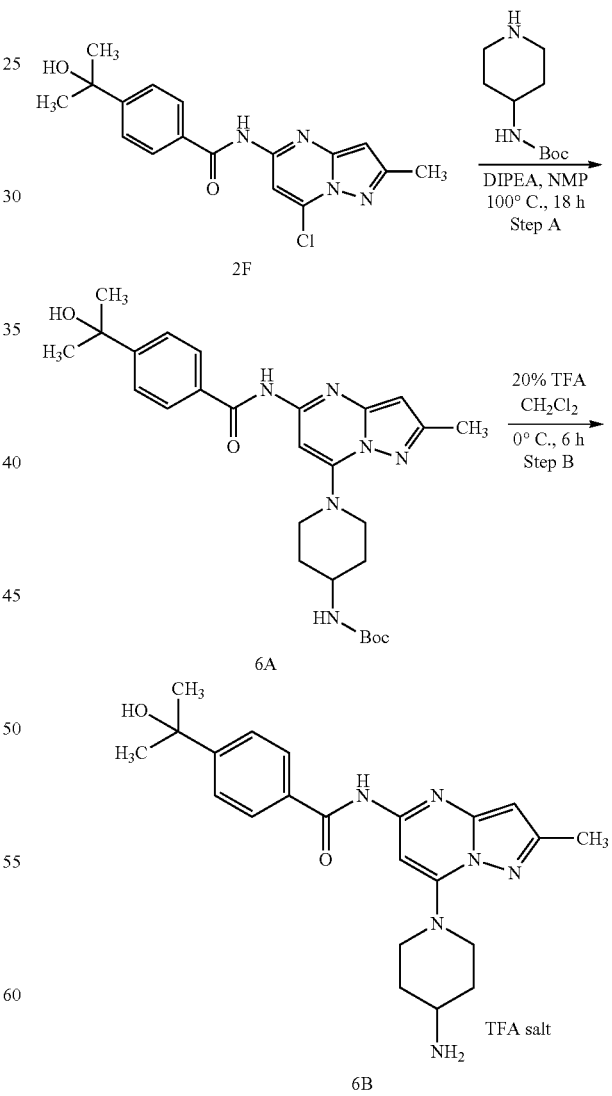

Step A: In a 100 mL round-bottomed flask were placed N-(7-chloro-2-methylpyrazolo[1,5-a]pyrimidin-5-yl)-4-(2- hydroxypropan-2-yl)benzamide (2F, 0.5 g, 1.450 mmol) and tert-butyl piperidin-4-ylcarbamate (0.305 g, 1.523 mmol) in N-methyl-2-pyrrolidinone (Volume: 14.50 ml). Diisopropylethylamine (0.253 ml, 1.450 mmol) was added. The reaction was heated overnight at 100° C. The reaction mixture was partitioned between ethyl acetate and brine. The organic was dried MgSO$_4$, filtered and concentrated in vacuo. The compound was chromatographed on silica using 30-50% EtOAc/Hexane silica column to give tert-butyl 1-(5-(4-(2-hydroxypropan-2-yl)benzamido)-2-methylpyrazolo[1,5-a]pyrimidin-7-yl)piperidin-4-ylcarbamate (6A, 0.576 mg, 78%) as a yellow solid. $^1$H NMR (METHANOL-d$_4$) δ: 7.79-8.02 (m, 2H), 7.60-7.73 (m, 2H), 7.33 (s, 1H), 6.83 (br. s., 1H), 6.13 (s, 1H), 4.39 (d, J=12.6 Hz, 2H), 3.57-3.78 (m, 1H), 3.11-3.23 (m, 2H), 2.43 (s, 3H), 1.73 (d, J=8.8 Hz, 2H), 1.56 (s, 6H), 1.46 (s, 9H); resonances of the three piperidine peaks are obscured by diisopropylethylamine. ESI-MS: m/z 509.0 (M+H)$^+$.

Step B: In a 100 mL round-bottomed flask was placed tert-butyl 1-(5-(4-(2-hydroxypropan-2-yl)benzamido)-2-methylpyrazolo[1,5-a]pyrimidin-7-yl)piperidin-4-ylcarbamate (0.576 g, 1.13 mmol). Trifluoroacetic acid (2 ml) in CH$_2$Cl$_2$ (9 ml) was added at 0° C. for 6 hours. The reaction was concentrated in vacuo and residual TFA was removed azeotropically with toluene (3×). Elimination product was observed in the crude product mixture containing N-(7-(4-aminopiperidin-1-yl)-2-methylpyrazolo[1,5-a]pyrimidin-5-yl)-4-(2-hydroxypropan-2-yl)benzamide (6B), which was used without further purification.

Example 7

Preparation of Intermediates 7D and 7E

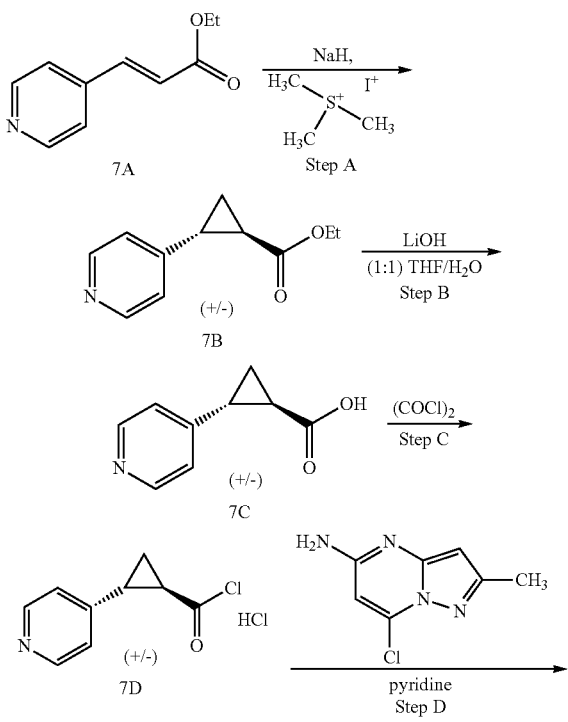

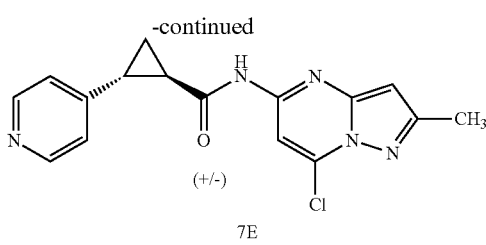

Step A: Trimethylsulfonium iodide (1.50 g, 7.34 mmol) and sodium hydride (0.293 g, 7.34 mmol) were placed into a dry round bottom under nitrogen. DMSO (25 mL) was added and the mixture was stirred for 40 min. The solution turned cloudy. 3-Pyridin-4-yl-acrylic acid ethyl ester (7A, 1.0 g, 5.6 mmol) in DMSO (40 ml) was added dropwise at room temperature. The mixture was left to stir overnight and product was observed the next day by analytical HPLC. The reaction was quenched with 10 mL of water and the mixture was partitioned between ethyl acetate and water. The separated organic layer was dried over Mg$_2$SO$_4$, filtered, and concentrated under reduced pressure. The crude mixture was chromatographed on silica using 10-20% methanol/CH$_2$Cl$_2$ gradient, to give trans-ethyl 2-(pyridin-4-yl)cyclopropanecarboxylate (7B, 0.20 g, 18%) as a cream solid. $^1$H NMR (METHANOL-d$_4$) δ: 8.39 (d, J=6.1 Hz, 2H), 7.21 (d, J=6.1 Hz, 2H), 4.17 (q, J=7.1 Hz, 2H), 2.42-2.55 (m, 1H), 2.02-2.13 (m, 1H), 1.59-1.69 (m, 1H), 1.42-1.51 (m, 1H), 1.27 (t, 3H). ESI-MS: m/z 192.0 (M+H)$^+$.

Step B: trans-Ethyl 2-(pyridin-4-yl)cyclopropanecarboxylate and LiOH were combined in 1:1 THF/H$_2$O at room temperature and the mixture was stirred overnight. The product was observed by HPLC/MS the next day. The reaction was quenched with 1N of HCl (5 mL) and was concentrated in vacuo. Then, residual water was removed azeotropically with toluene (3×). After drying under reduced pressure, the crude product trans-2-(pyridin-4-yl)cyclopropanecarboxylic acid (7C) was used in the next step without further purification.

Step C: In a 250 mL round-bottomed flask, oxalyl chloride (30.8 ml, 61.7 mmol) was added to trans-2-(pyridin-4-yl)cyclopropanecarboxylic acid (7C) give a yellow suspension. After 40 minutes, the reaction was complete. The reaction mixture was concentrated and residual volatiles were removed azeotropically with toluene (3×). The crude product trans-2-(pyridin-4-yl)cyclopropanecarbonyl chloride, HCl salt (7D) was used without further purification.

Step D: In a 100 mL round-bottomed flask was added 7-chloro-2-methylpyrazolo[1,5-a]pyrimidin-5-amine (1J, 2.74 g, 15.02 mmol) in pyridine (75 ml) to give a yellow solution. Then, at 0° C., 2-(pyridin-4-yl)cyclopropanecarbonyl chloride (7D, 0.19 g, 1.046 mmol) in pyridine (1 ml) was added to give a suspension. After the reaction was complete, saturated NaHCO$_3$ solution was added and the mixture was extracted with EtOAc. The organic layer was dried over MgSO$_4$, filtered and concentrated. The residue was chromatographed on silica using 20% MeOH/CH$_2$Cl$_2$ to provide trans-N-(7-chloro-2-methylpyrazolo[1,5-a]pyrimidin-5-yl)-2-(pyridin-4-yl)cyclopropanecarboxamide (7E, 213 mg, 4% for 3 steps) as a yellow solid. $^1$H NMR (DMSO-d$_6$) δ: 11.43 (s, 1H), 8.46 (d, J=6.1 Hz, 2H), 7.97 (s, 1H), 7.15-7.27 (m, 2H), 6.40 (s, 1H), 2.39-2.46 (m, 4H), 2.28-2.35 (m, 1H), 1.46-1.67 (m, 2H). ESI-MS: m/z 328.0 (M+H)$^+$.

Example 8

Preparation of Intermediates 8C, 8E, and 8G

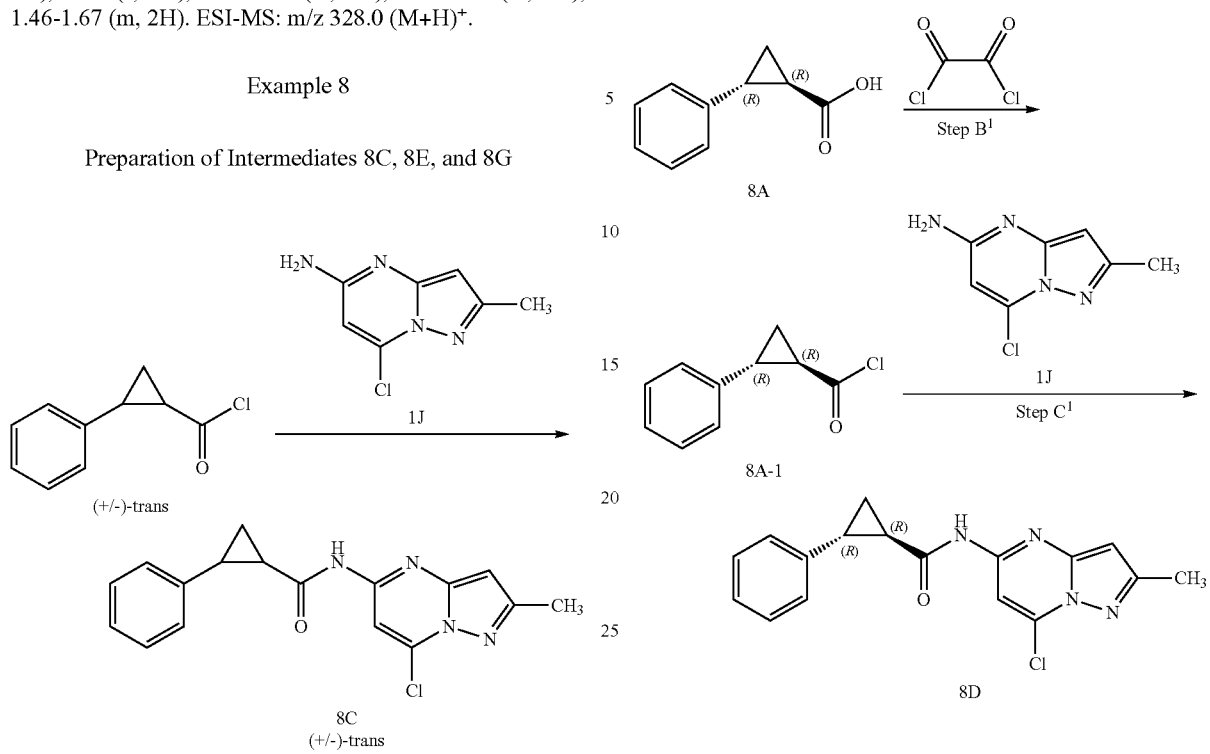

In a 250 ml round-bottomed flask was added (+/−)-trans-2-phenylcyclopropanecarbonyl chloride (1.9 g, 10 mmol) in pyridine (94 ml) to give a yellow suspension. 7-Chloro-2-methylpyrazolo[1,5-a]pyrimidin-5-amine (1J, 1.7 g, 9.4 mmol) was added portionwise at 0° C. The temperature was slowly raised to room temperature. After 30 min, reaction was complete and was quenched with saturated sodium bicarbonate solution. The layers were extracted with ethyl acetate (3×100 mL), and the organic layers were washed with saturated sodium bicarbonate solution and concentrated in vacuo. The residue was suspended in methanol and filtered. The filtrate was concentrated to obtain the product N-(7-chloro-2-methylpyrazolo[1,5-a]pyrimidin-5-yl)-2-phenylcyclopropanecarboxamide (8C, 1.9 g, 62%) as an orange solid. $^1$H NMR (DMSO-d$_6$) δ: 11.39 (s, 1H), 7.99 (s, 1H), 7.27-7.34 (m, 2H), 7.15-7.25 (m, 3H), 6.39 (s, 1H), 2.46 (td, 1H), 2.41 (s, 3H), 2.30-2.37 (m, 1H), 1.50-1.58 (m, 1H), 1.46 (ddd, J=8.2, 6.6, 4.2 Hz, 1H). ESI-MS: m/z 327.2 (M+H)$^+$.

Step A: Enantiomers (1R,2R)- and (1S,2S)-2-phenylcyclopropanecarboxylic acid (8A, and 8B, respectively) were separated from 1 gram of a commercially available racemic mixture on a Waters System using Chiralcel AD-H 250×21 mm at a flow rate of 20 mL/min in 96-4% Hexane:iPrOH. Each injection was 50 mg/mL. Only the first peak was separated out but the second and third peak eluted concurrently. The first peak, (1S,2S)-2-phenylcyclopropanecarboxylic acid (8B), and the third peak, (1R,2R)-2-phenylcyclopropanecarboxylic acid (8A), were in a 1:1 ratio and composed the majority of mixture. The second peak is the cis diastereomers. The separation yielded 420 mg (41% recovery) for 8B, and 750 mg for the mixture of 8A and cis diastereomers. Optical rotation for the first peak, (1S,2S)-2-phenylcyclopropanecarboxylic acid (8B), is +337° (c=0.761, CHCl$_3$).

Step B$^1$: In a dry 250 ml round-bottomed flask was added oxalyl chloride (0.90 ml, 1.8 mmol) to 8A (0.60 g, 3.5 mmol) in CH$_2$Cl$_2$ at room temperature to give a yellow solution. In 2 hours, the reaction was complete. The crude mixture was concentrated in vacuo and residual TFA was removed azeotropically with toluene 3 times to give the desired product (1R,2R)-2-phenylcyclopropanecarbonyl chloride (8A-1), which was used in the next step without further purification.

Step C$^1$: In a 250 ml round-bottomed flask was added 8A-1 (0.66 g, 3.5 mmol) in pyridine (12 ml) to give a yellow suspension. 7-Chloro-2-methylpyrazolo[1,5-a]pyrimidin-5-amine (1.1, 0.32 g, 1.7 mmol) was added portionwise at 0° C. The temperature was slowly raised to room temperature. After 30 minutes, reaction was complete and was quenched with saturated sodium bicarbonate. The layers were extracted with ethyl acetate and washed with saturated sodium bicarbonate. The organic layer was dried over MgSO$_4$, filtered and concentrated. The crude product was purified by prepatory HPLC (65-76% MeCN/H$_2$O gradient+0.01% TFA) to give (1R,2R)—N-(7-chloro-2-methylpyrazolo[1,5-a]pyrimidin-5-yl)-2-phenylcyclopropanecarboxamide (8D, 189 mg, 33%) as an orange solid. $^1$H NMR (DMSO-d$_6$) δ: 11.39 (s, 1H), 7.99 (s, 1H), 7.27-7.36 (m, 2H), 7.15-7.25 (m, 3H), 6.39 (s, 1H), 2.46 (td, J=6.2, 3.3 Hz, 1H), 2.41 (s, 3H), 2.29-2.37 (m, 1H), 1.54 (dt, J=9.2, 4.6 Hz, 1H), 1.46 (ddd, J=8.1, 6.5, 4.3 Hz, 1H). ESI-MS: m/z 327.0 (M+H)$^+$.

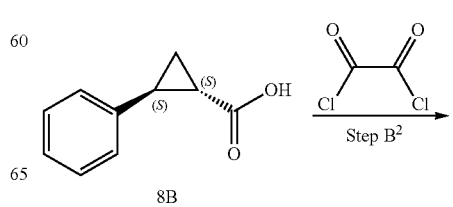

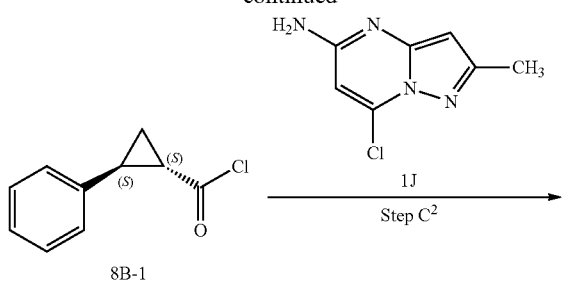

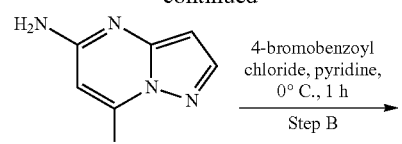

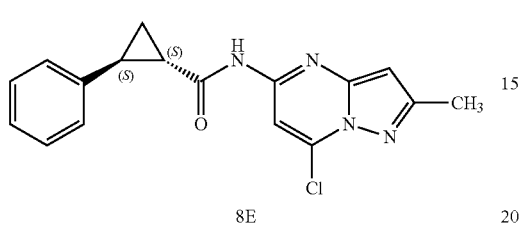

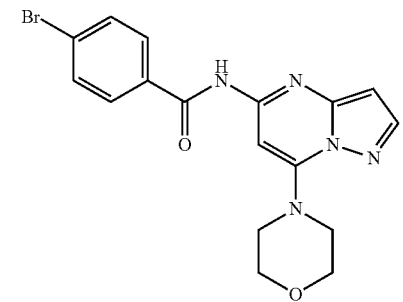

Step B[2]: In a dry 100 ml round-bottomed flask was added oxalyl chloride (2.0 ml, 23 mmol) to 8B (0.25 g, 1.5 mmol) in CH$_2$Cl$_2$ at room temperature to give a yellow solution. In 2.5 hours, the reaction was complete. The crude mixture was concentrated in vacuo and residual TFA was removed azeotropically with toluene 3 times to give the desired product (1S,2S)-2-phenylcyclopropanecarbonyl chloride (8B-1), which was used in the next step without further purification.

Step C[2]: In a 100 ml round-bottomed flask was added 8B-1 (0.28 g, 1.5 mmol) added in pyridine (5.1 ml) to give a yellow suspension. 7-Chloro-2-methylpyrazolo[1,5-a]pyrimidin-5-amine (1J, 0.14 g, 0.77 mmol) was added portionwise at 0° C. The temperature was slowly raised to room temperature. After reaction was complete, it was quenched with saturated sodium bicarbonate. The layers were extracted with ethyl acetate and the combined organic layers were dried over MgSO$_4$, filtered and concentrated. The crude product was purified by column chromatography (SiO$_2$, 20%-100% ethyl acetate/hexane gradient) to give (1S,2S)—N-(7-chloro-2-methylpyrazolo[1,5-a]pyrimidin-5-yl)-2-phenylcyclopropanecarboxamide (8E, 220 mg, 67%) as a yellow solid. $^1$H NMR (DMSO-d$_6$) δ: 11.39 (s, 1H), 7.99 (s, 1H), 7.25-7.33 (m, 2H), 7.16-7.24 (m, 3H), 6.39 (s, 1H), 2.43-2.49 (m, 1H), 2.41 (s, 3H), 2.30-2.37 (m, 1H), 1.51-1.58 (m, 1H), 1.46 (ddd, J=8.2, 6.4, 4.3 Hz, 1H). ESI-MS: m/z 327.0 (M+H)$^+$.

Example 9

Preparation of Intermediates 9A and 9B

Step A: 7-Chloropyrazolo[1,5-a]pyrimidin-5-amine (1E, 10 g, 30 mmol) and morpholine were added to NMP (20 ml) and dioxane (80 ml). The mixture was heated to 100° C. and the resulting suspension was concentrated in vacuo to remove most of the dioxane. Brine was added and the mixture was extracted with EtOAc five times. Combined organics were washed with brine, dried over MgSO$_4$, filtered and concentrated in vacuo. Trituration of the residue with Et$_2$O gave the desired product 7-morpholinopyrazolo[1,5-a]pyrimidin-5-amine (9A, 5.0 g, 38%) as an off-white solid.

Step B: 7-Morpholinopyrazolo[1,5-a]pyrimidin-5-amine (9A, 1.0 g, 4.6 mmol) was suspended in pyridine (10 ml), and 4-bromobenzoyl chloride (1.1 g, 4.8 mmol) was then added at 0° C. After 1 hour, water (200 ml) was added and the resulting precipitate was collected on a fritted glass funnel, washed with water twice, and then dried under a stream of nitrogen for 3 hours to give analytically pure product 4-bromo-N-(7-morpholinopyrazolo[1,5-a]pyrimidin-5-yl)benzamide (9B, 1.6 g, 87%). $^1$H NMR (400 MHz, DMSO-d$_6$) δ=11.13 (s, 1 H), 8.10 (d, J=2.3 Hz, 1 H), 8.01-7.93 (m, 2 H), 7.77-7.71 (m, 2 H), 7.37 (s, 1 H), 6.38 (d, J=2.3 Hz, 1 H), 3.88-3.81 (m, 4 H), 3.77-3.70 (m, 4 H); ESI-MS: m/z 402.2 (M+H)$^+$.

Example 10

Preparation of Intermediate 10A

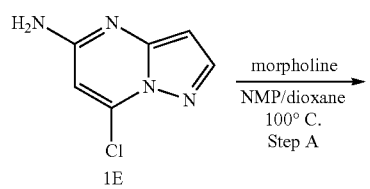

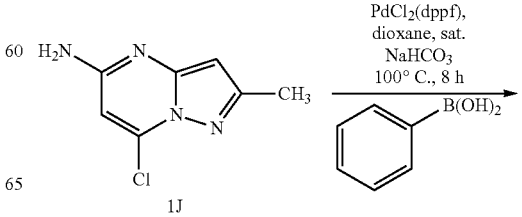

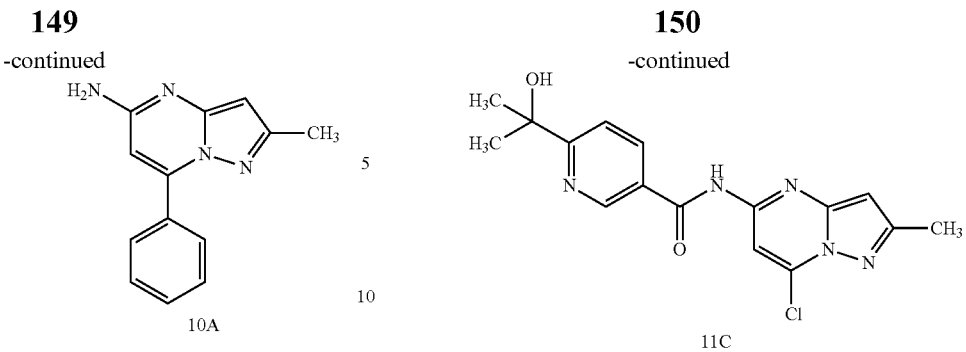

7-Chloro-2-methylpyrazolo[1,5-a]pyrimidin-5-amine (1J, 10 g, 55 mmol), phenylboronic acid (7.3 g, 60 mmol), and [1,1'-bis(diphenylphosphino)ferrocene]-dichloropalladium (II) (1.0 g, 1.4 mmol) were mixed in dioxane (120 ml) and saturated NaHCO₃ (60 ml). The mixture was then heated at 100° C. for 4 hours. After cooling to room temperature, Brine was added and the mixture was extracted with EtOAc five times. Combined organics were washed with brine, dried over MgSO₄, filtered and concentrated in vacuo. The crude product was purified by column chromatography (SiO₂) to give 2-methyl-7-phenylpyrazolo[1,5-c]pyrimidin-5-amine (10A, 2.2 g, 18%) as a solid. $^1$H NMR (400 MHz, DMSO-d₆) δ=7.95-7.85 (m, 2 H), 7.62-7.50 (m, 3 H), 6.70 (s, 2 H), 6.22 (s, 1 H), 5.81 (s, 1 H), 2.24 (s, 3 H).

Example 11

Preparation of Intermediates 11A and 11C

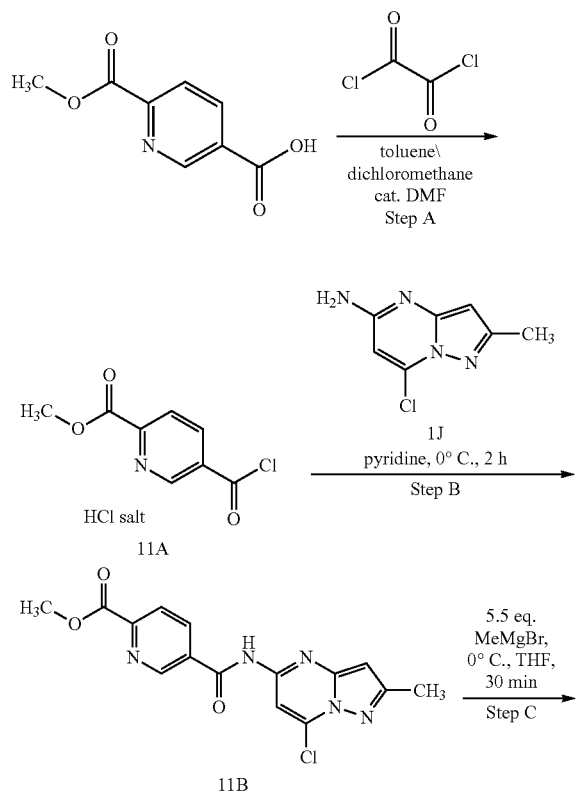

Step A: In a 250 ml round-bottomed flask was added 6-(methoxycarbonyl)nicotinic acid (3.0 g, 17 mmol) in toluene (30 ml) to give a suspension. To this was then added oxalyl chloride (2.0 M in DCM) (17 ml, 33 mmol) and 2 drops of DMF. Gas evolution was observed. The resulting suspension was heated to 60° C. for 2.5 hours, after which the mixture turned into a clear yellow solution and gas evolution ceased. The mixture was cooled to room temperature, and then concentrated in vacuo. To the crude product was added toluene (50 mL), and the mixture was concentrated once more to remove residual volatiles. After drying under vacuum for 1 hour, the resulting light-yellow-colored powder methyl 5-(chlorocarbonyl)picolinate, HCl salt (11A, 3.8 g, 96% yield) was used in the next steps without further purification.

Step B: In a 200 ml pear flask was added 7-chloro-2-methylpyrazolo[1,5-a]pyrimidin-5-amine (1J, 1.4 g, 7.67 mmol) in pyridine (20 ml) to give a light yellow solution. At 0° C., methyl 5-(chlorocarbonyl)picolinate, HCl salt (11A, 1.8 g, 7.63 mmol) was added as a solid. The mixture gradually turned very thick; an additional 20 ml of pyridine was added to free up the stirring. The mixture was stirred at 0° C. for 30 minutes, and HPLC/MS showed almost complete conversion of starting materials to the desired product. Little was changed after an additional 2 hours of stirring at 0° C. Brine (150 ml) was then added, and the precipitate was collected by vacuum filtration on a fritted-glass funnel. The filtrate was basified and some more precipitate was formed and was collected. The collected off-white solids were washed with water, and then dried under a stream of nitrogen overnight to give the desired methyl 5-(7-chloro-2-methylpyrazolo[1,5-a]pyrimidin-5-ylcarbamoyl)picolinate (11B, 1.5 g, 55% yield). ESI-MS: m/z 346.1 (M+H)⁺.

Step C: In a 250 ml round-bottomed flask was added methyl 5-(7-chloro-2-methylpyrazolo[1,5-a]pyrimidin-5-ylcarbamoyl)picolinate (11B, 1.36 g, 3.93 mmol) in tetrahydrofuran (30 ml). At −30° C., methylmagnesium bromide (3.0 M in ether) (6.7 ml, 20 mmol) was added and the mixture was warmed slowly from −30 to 0° C. for 4 h. The mixture was then poured into saturated ammonium chloride mixed with ice (total volume of 300 ml). After vigorous stirring, the mixture was extracted with was extracted three times with ethyl acetate. Combined organic layers were dried over MgSO₄, filtered and concentrated. The crude product was purified by column chromatography (SiO₂, 65-80% ethyl acetate/hexanes) to give the desired product N-(7-chloro-2- methylpyrazolo[1,5-a]pyrimidin-5-yl)-6-(2-hydroxypropan-2-yl)nicotinamide (11C, 780 mg, 2.2 mmol, 57% yield) as a pink/orange solid.

Example 12

Preparation of Intermediates 12A

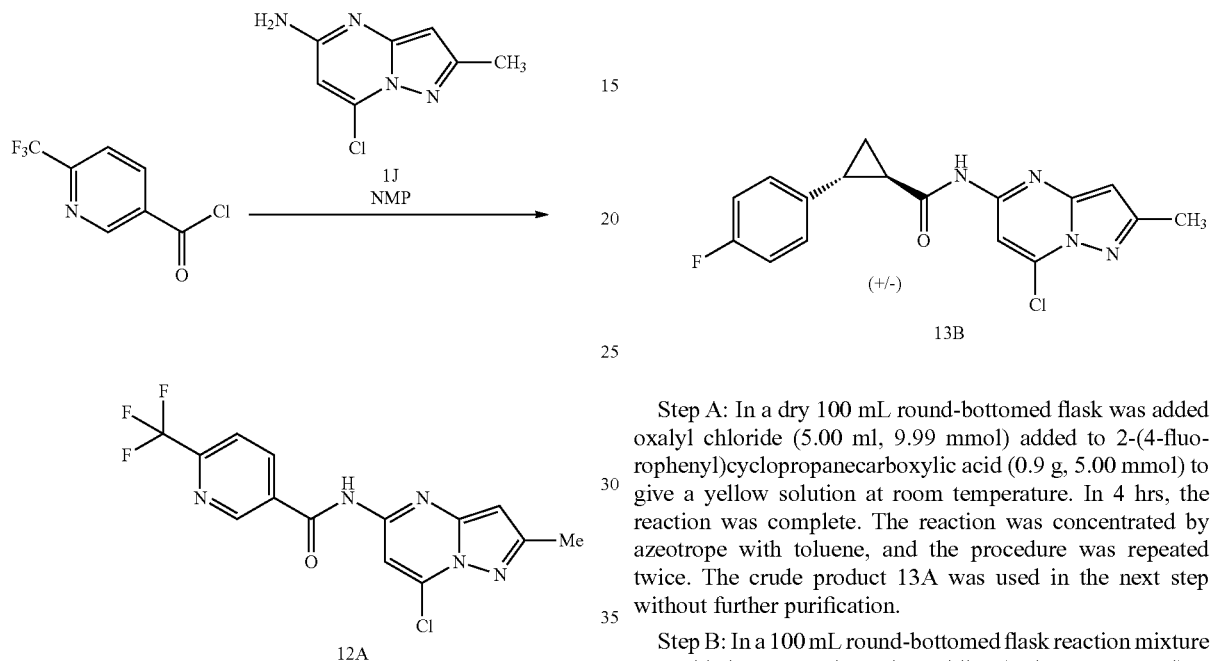

To a 20 ml scintillation vial was added 7-chloro-2-methylpyrazolo[1,5-a]pyrimidin-5-amine (1.1, 237 mg, 1.30 mmol), 6-(trifluoromethyl)nicotinoyl chloride (328 mg, 1.57 mmol), and NMP (5 mL) and the reaction mixture was stirred at rt for 1 hr. The reaction mixture was then diluted with water, filtered, and the filter cake rinsed thoroughly with water. Drying with suction under a stream of dry nitrogen resulted in the desired product N-(7-chloro-2-methylpyrazolo[1,5-a]pyrimidin-5-yl)-6-(trifluoromethyl)nicotinamide (12A) as a pink solid. $^1$H NMR (DMSO-d$_6$) δ: 11.87 (s, 1H), 9.29 (d, J=2.3 Hz, 1H), 8.62 (dd, J=8.0, 1.9 Hz, 1H), 8.11 (d, J=8.3 Hz, 1H), 8.04 (s, 1H), 6.51 (s, 1H), 2.46 (s, 3H); ESI-MS: m/z 356.1 (M+H)$^+$.

Example 13

Preparation of Intermediates 13A and 13B

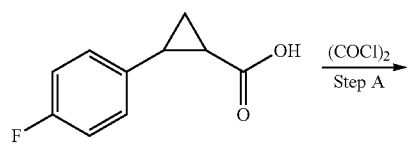

Step A: In a dry 100 mL round-bottomed flask was added oxalyl chloride (5.00 ml, 9.99 mmol) added to 2-(4-fluorophenyl)cyclopropanecarboxylic acid (0.9 g, 5.00 mmol) to give a yellow solution at room temperature. In 4 hrs, the reaction was complete. The reaction was concentrated by azeotrope with toluene, and the procedure was repeated twice. The crude product 13A was used in the next step without further purification.

Step B: In a 100 mL round-bottomed flask reaction mixture was added compound 13A in pyridine (Volume: 16.65 ml) to give a yellow suspension. 7-Chloro-2-methylpyrazolo[1,5-a]pyrimidin-5-amine (1J, 0.456 g, 2.498 mmol) was added portionwise at 0° C. The temperature was slowly raised to room temperature. Chromatography on SiO$_2$ using a gradient of 20-50% ethyl acetate/hexane provided the desired product 13B as a racemate and a white solid (739 mg, 86% total yield). The solid was triturated with ether and the majority of the filtered solid is the trans isomer. $^1$H NMR (DMSO-d$_6$) δ: 11.38 (s, 1H), 7.98 (s, 1H), 7.20-7.27 (m, 2H), 7.10-7.17 (m, 2H), 6.39 (s, 1H), 2.47 (dd, J=6.7, 3.9 Hz, 1H), 2.41 (s, 3H), 2.25-2.33 (m, 1H), 1.52 (dt, J=9.3, 4.7 Hz, 1H), 1.44 (ddd, J=8.1, 6.6, 4.3 Hz, 1H); ESI-MS: m/z 345.0 (M+H)$^+$.

Example 14

Preparation of Intermediates 14A

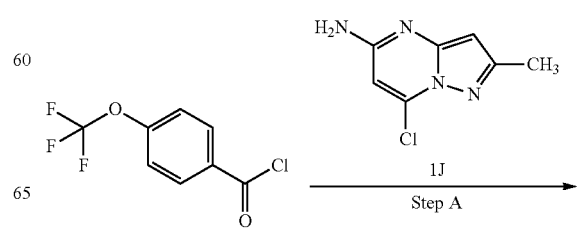

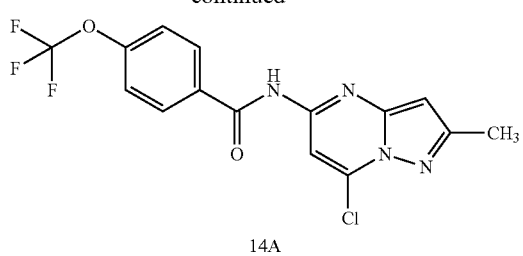

14A

To a 20 mL scintillation vial was added 7-chloro-2-methylpyrazolo[1,5-a]pyrimidin-5-amine (1.1, 0.207 g, 1.131 mmol) and pyridine (2.84 ml, 35.1 mmol) and the solution was cooled to 0° C. To the yellow solution was added 4-(trifluoromethoxy)benzoyl chloride (0.508 g, 2.262 mmol) to give an orange suspension. The reaction mixture was stirred for one hour, quenched by the addition of saturated aqueous sodium bicarbonate, and extracted with ethyl acetate. The organic extracts were dried over sodium sulfate, filtered, and concentrated under reduced pressure in the presence of silica gel. The silica-adsorbed material was then purified by silica gel chromatography (25-75% ethyl acetate/hexanes gradient) to afford the desired compound N-(7-chloro-2-methylpyrazolo[1,5-a]pyrimidin-5-yl)-4-(trifluoromethoxy)benzamide 14A as an orange solid (215 mg, 51% yield); ESI-MS: m/z 370.0 (M+H)$^+$.

Example 15

4-tert-butyl-N-(7-(3-(hydroxymethyl)phenyl)-2-methylpyrazolo[1,5-a]pyrimidin-5-yl)benzamide

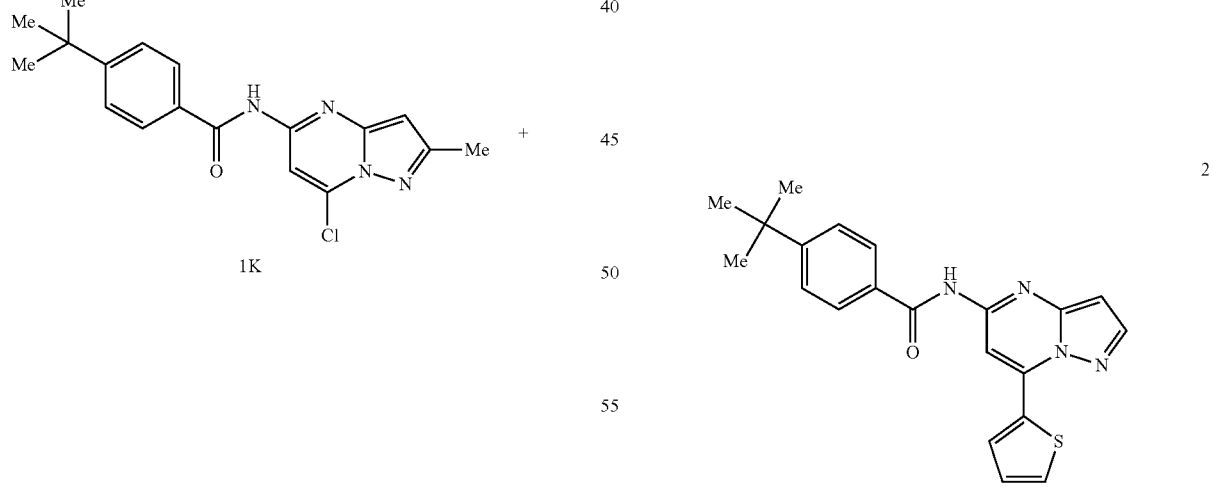

A suspension of 4-tert-butyl-N-(7-chloro-2-methylpyrazolo[1,5-a]pyrimidin-5-yl)benzamide (1K, 40 mg, 1.0 equivalent), 3-(hydroxymethyl)phenylboronic acid (1.9 equivalents), Pd(PPh$_3$)$_4$ (0.10 equivalent), and Na$_2$CO$_3$ (4.0 equivalents) in N$_2$-saturated 5:1 DMF/H$_2$O (0.05 M with respect to 1K) was stirred at 100° C. overnight. After cooling, the mixture was diluted with brine and extracted with EtOAc. Combined organic layers were dried over MgSO$_4$, filtered and concentrated. The crude product was purified by chromatography (SiO$_2$, gradient of 40 to 50% EtOAc/hexanes). The product was then recrystallized from CH$_2$Cl$_2$-hexanes to give the titled compound (62%) as a white solid. $^1$H NMR (400 MHz, CDCl$_3$) δ ppm 1.37 (s, 9H) 2.50 (s, 3H) 4.83 (d, J=6.1 Hz, 2H) 6.29 (s, 1H) 7.44-7.71 (m, 5H) 7.88 (d, J=8.3 Hz, 2H) 8.03 (s, 1H) 8.15 (s, 1H) 8.59 (s, 1H).

Example 16

4-tert-butyl-N-(7-(thiophen-2-yl)pyrazolo[1,5-a]pyrimidin-5-yl)benzamide (2)

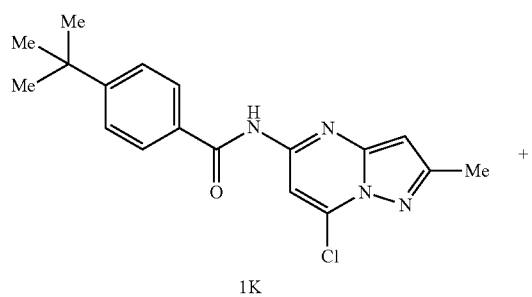

The titled compound was prepared using a procedure analogous to that described in connection with Example 15 using thiophen-2-ylboronic acid as starting material. $^1$H NMR (400 MHz, CDCl$_3$) δ ppm 1.38 (s, 9H), 6.51 (s, 1H), 7.28-7.32 (m, 1H), 7.56 (d, J=8.3 Hz, 2H), 7.76 (d, J=5.1 Hz, 1H), 7.91 (d, J=8.3 Hz, 2H), 8.21 (s, 1H), 8.42 (d, J=3.8 Hz, 1H), 8.66 (br, 2H).

Example 17

4-(tert-butyl)-N-(7-(3-(3-hydroxypropyl)phenyl)-2-methylpyrazolo[1,5-a]pyrimidin-5-yl)benzamide (3)

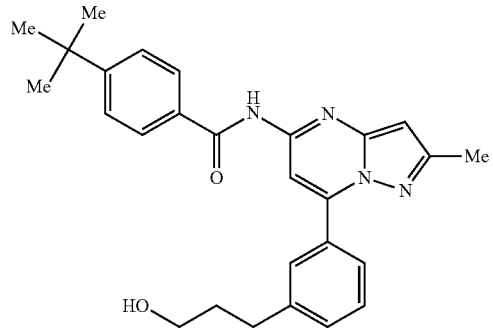

The titled compound was prepared using a procedure analogous to that described in connection with Example 15 using 3-(3-hydroxypropyl)phenylboronic acid as starting material. ¹H NMR (400 MHz, CDCl₃) δ ppm 1.37 (s, 9H), 1.88-2.02 (m, 2H), 2.50 (s, 3H), 2.85 (t, J=7.6 Hz, 2H), 3.72 (q, J=6.0 Hz, 2H), 6.28 (s, 1H), 7.34-7.42 (m, 1H), 7.48 (t, J=7.8 Hz, 1H), 7.55 (d, J=8.3 Hz, 2H), 7.88 (d, J=8.3 Hz, 2H), 7.91-7.99 (m, 2H), 8.14 (s, 1H), 8.59 (s, 1H).

Example 18

4-tert-butyl-N-(7-(4-fluoro-3-(hydroxymethyl)phenyl)-2-methylpyrazolo[1,5-a]pyrimidin-5-yl)benzamide (4)

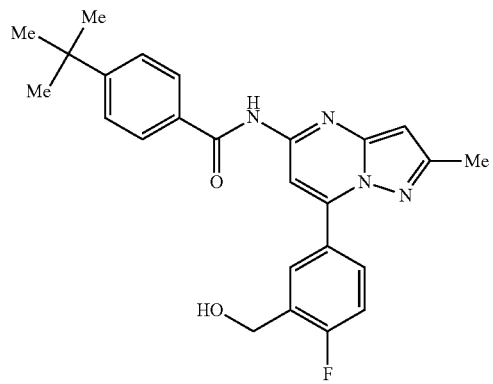

The titled compound was prepared using a procedure analogous to that described in connection with Example 15 using 4-fluoro-3-(hydroxymethyl)phenylboronic acid as starting material. ¹H NMR (400 MHz, CDCl₃) δ ppm 1.37 (s, 9H), 2.50 (s, 3H), 4.88 (d, J=6.3 Hz, 2H), 6.29 (s, 1H), 7.34-7.47 (m, 1H), 7.55 (d, J=8.3 Hz, 2H), 7.66-7.77 (m, 1H), 8.08 (br, 1H), 8.14 (s, 1H), 8.22 (s, 1H), 8.60 (s, 1H).

Example 19

4-tert-butyl-N-(7-(3-(hydroxymethyl)phenyl)pyrazolo[1,5-a]pyrimidin-5-yl)benzamide (5)

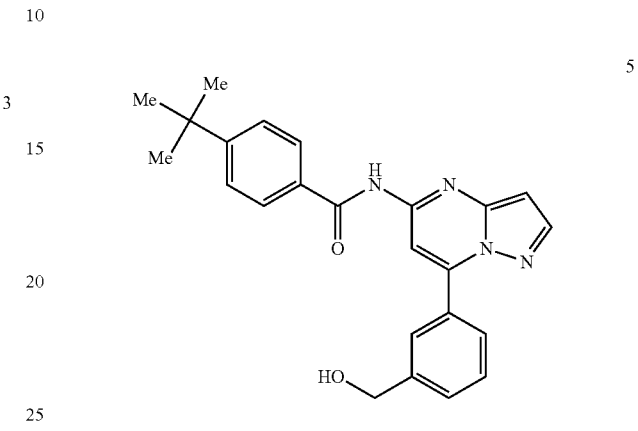

The titled compound was prepared using a procedure analogous to that described in connection with Example 15 except that 4-tert-butyl-N-(7-chloropyrazolo[1,5-a]pyrimidin-5-yl)benzamide (1F) was used instead of 1K as starting material. ¹H NMR (400 MHz, DMSO-d₆) δ ppm 1.33 (s, 9 H) 4.64 (d, J=5.81 Hz, 2 H) 5.42 (t, J=5.81 Hz, 1 H) 6.59 (d, J=2.27 Hz, 1 H) 7.54-7.60 (m, 3 H) 7.98 (td, J=3.66, 1.52 Hz, 1 H) 8.00-8.08 (m, 3 H) 8.20 (d, J=2.27 Hz, 1 H) 11.25 (s, 1 H). ESI-MS: m/z 401.0 (M+H)⁺.

Example 20

N-(7-(3-(hydroxymethyl)phenyl)pyrazolo[1,5-a]pyrimidin-5-yl)-4-(2-hydroxypropan-2-yl)benzamide (6)

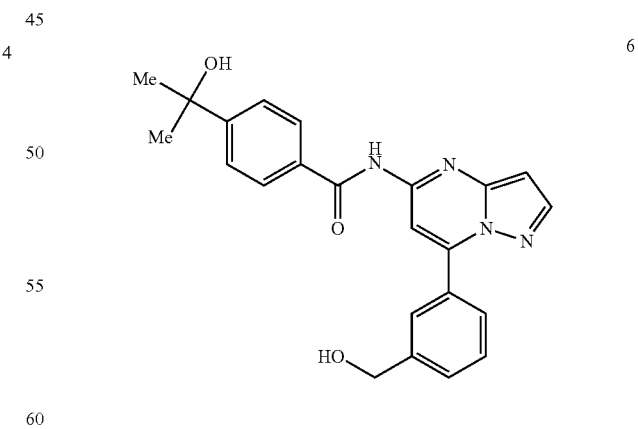

The titled compound was prepared using a procedure analogous to that described in connection with Example 15 except that N-(7-chloropyrazolo[1,5-a]pyrimidin-5-yl)-4-(2-hydroxypropan-2-yl)benzamide (2D) was used instead of 1K as starting material. ¹H NMR (400 MHz, DMSO-d₆) δ ppm 1.46 (s, 6 H) 4.63 (d, J=5.81 Hz, 2 H) 5.20 (s, 1 H) 5.40 (t, J=5.56 Hz, 1 H) 6.59 (d, J=2.27 Hz, 1 H) 7.96-8.00 (m, 1 H)

8.00-8.03 (m, 2 H) 8.03-8.05 (m, 1 H) 8.06 (s, 1 H) 8.20 (d, J=2.27 Hz, 1 H) 11.27 (s, 1 H). ESI-MS: m/z 403.1 (M+H)⁺.

Example 21

N-(7-(3-(hydroxymethyl)phenyl)pyrazolo[1,5-a]pyrimidin-5-yl)-4-(1,1,1-trifluoro-2-hydroxypropan-2-yl)benzamide (7)

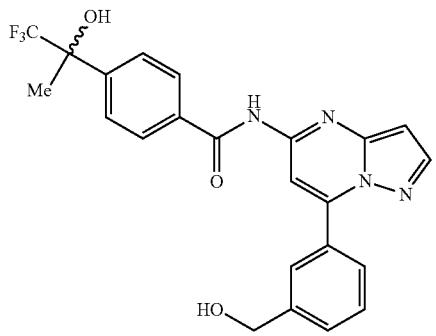

The titled compound was prepared using a procedure analogous to that described in connection with Example 15 except that N-(7-chloropyrazolo[1,5-a]pyrimidin-5-yl)-4-(1,1,1-trifluoro-2-hydroxypropan-2-yl)benzamide (3E) was used instead of 1K as starting material. ¹H NMR (400 MHz, DMSO-d₆) δ ppm 1.74 (br. s., 3 H) 4.64 (d, J=5.05 Hz, 2 H) 5.40 (t, J=5.31 Hz, 1 H) 6.61 (br. s., 1 H) 6.80 (s, 1 H) 7.58 (d, J=4.04 Hz, 2 H) 7.76 (d, J=7.83 Hz, 2 H) 7.97 (br. s., 1 H) 8.00-8.07 (m, 2 H) 8.10 (d, J=8.08 Hz, 2 H) 8.21 (br. s., 1 H) 11.39 (br. s., 1 H). ESI-MS: m/z 457.0 (M+H)⁺.

Example 22

4-tert-butyl-N-(7-(4-(methylsulfonyl)phenyl)pyrazolo[1,5-a]pyrimidin-5-yl)benzamide (8)

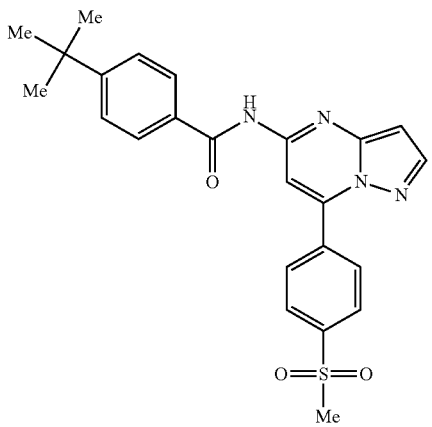

The titled compound was prepared using a procedure analogous to that described in connection with Example 15 except that 4-tert-butyl-N-(7-chloropyrazolo[1,5-a]pyrimidin-5-yl)benzamide (1F) and the corresponding boronic acid or ester were used as starting materials. The product was obtained as a yellow solid (19%). ¹H NMR (400 MHz, MeOD) δ ppm 1.38 (s, 9 H) 3.22 (s, 3 H) 6.59 (s, 1 H) 7.57-7.65 (m, 2 H) 7.92-8.01 (m, 2 H) 8.08-8.23 (m, 4 H) 8.29-8.39 (m, 2 H). ESI-MS: m/z 449.3 (M+H)⁺.

Example 23

4-tert-Butyl-N-(7-(4-methoxyphenyl)pyrazolo[1,5-a]pyrimidin-5-yl)benzamide (9)

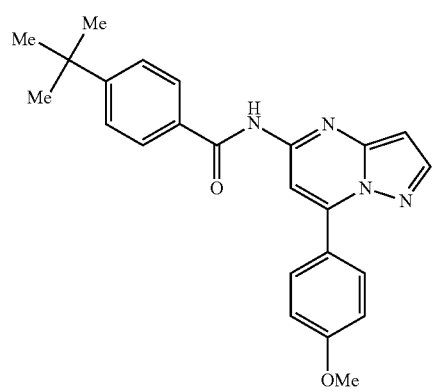

The titled compound was prepared using a procedure analogous to that described in connection with Example 15 except that 4-tert-butyl-N-(7-chloropyrazolo[1,5-a]pyrimidin-5-yl)benzamide (1F) and the corresponding boronic acid or ester were used as starting material. This product was obtained as a yellow solid (3%). ¹H NMR (400 MHz, MeOD) δ ppm 1.38 (s, 9H) 3.91 (s, 3 H) 6.53 (s, 1 H) 7.11-7.18 (m, 2 H) 7.57-7.64 (m, 2 H) 7.88-8.17 (m, 6 H). ESI-MS: m/z 401.3 (M+H)⁺.

Example 24

4-tert-butyl-N-(7-(3-(2-hydroxyethyl)phenyl)pyrazolo[1,5-a]pyrimidin-5-yl)benzamide (10)

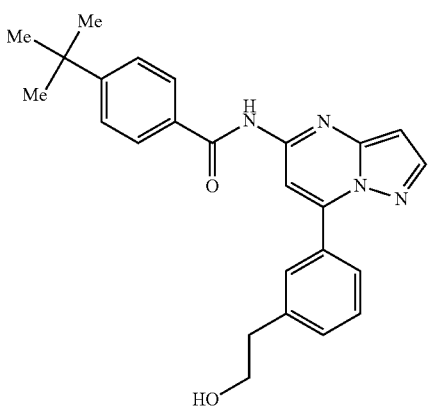

The titled compound was prepared using a procedure analogous to that described in connection with Example 15 except that 4-tert-butyl-N-(7-chloropyrazolo[1,5-a]pyrimidin-5-yl)benzamide (1F) and the corresponding boronic acid or ester were used as starting material. The product was obtained as a yellow solid (8%). ¹H NMR (400 MHz, MeOD) δ ppm 1.38 (s, 9H) 2.96 (t, J=6.82 Hz, 2 H) 3.85 (t, J=6.82 Hz, 2 H) 6.55 (s, 1 H) 7.46-7.65 (m, 4 H) 7.84-7.99 (m, 4 H) 8.03-8.12 (m, 2 H). ESI-MS: m/z 415.0 (M+H)⁺.

Example 25

4-tert-Butyl-N-(7-(3-(3-hydroxypropyl)phenyl)pyrazolo[1,5-a]pyrimidin-5-yl)benzamide (11)

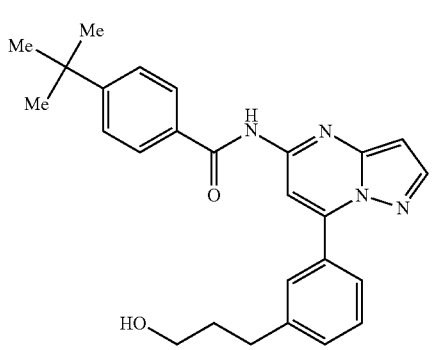

The titled compound was prepared using a procedure analogous to that described in connection with Example 15 except that 4-tert-butyl-N-(7-chloropyrazolo[1,5-a]pyrimidin-5-yl)benzamide (1F) and the corresponding boronic acid or ester were used as starting material.

This product was obtained as a yellow solid (30%). ¹H NMR (400 MHz, MeOD) δ ppm 1.38 (s, 9 H) 1.87-1.98 (m, 2 H) 2.83 (t, J=7.83 Hz, 2 H) 3.63 (t, J=6.44 Hz, 2 H) 6.55 (s, 1 H) 7.42-7.65 (m, 4 H) 7.81-8.00 (m, 4 H) 8.03-8.12 (m, 2 H). ESI-MS: m/z 429.0 (M+H)⁺.

Example 26

N-(7-(3-Acetylphenyl)pyrazolo[1,5-a]pyrimidin-5-yl)-4-tert-butylbenzamide (12)

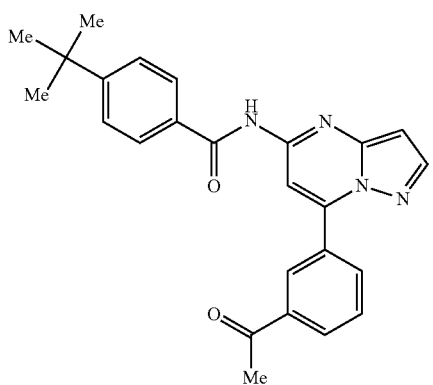

The titled compound was prepared using a procedure analogous to that described in connection with Example 15 except that 4-tert-butyl-N-(7-chloropyrazolo[1,5-a]pyrimidin-5-yl)benzamide (1F) and the corresponding boronic acid or ester were used as starting material. This product was obtained as a yellow solid (13%). ¹H NMR (400 MHz, MeOD) δ ppm 1.38 (s, 9 H) 2.70 (s, 3 H) 6.58 (s, 1 H) 7.52-7.83 (m, 3 H) 7.92-8.02 (m, 2 H) 8.07-8.33 (m, 4 H) 8.70 (s, 1 H). ESI-MS: m/z 413.3 (M+H)⁺.

Example 27

4-tert-Butyl-N-(7-(6-methoxypyridin-3-yl)pyrazolo[1,5-a]pyrimidin-5-yl)benzamide (13)

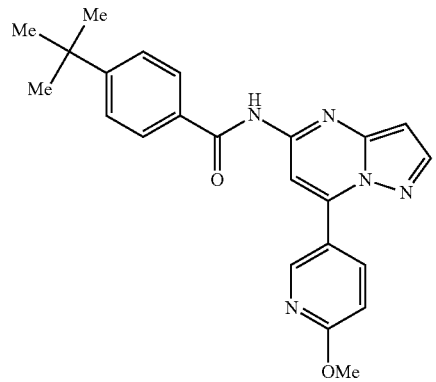

The titled compound was prepared using a procedure analogous to that described in connection with Example 15 except that 4-tert-butyl-N-(7-chloropyrazolo[1,5-a]pyrimidin-5-yl)benzamide (1F) and the corresponding boronic acid or ester were used as starting material. This product was obtained as a yellow solid (1%). ¹H NMR (400 MHz, MeOD) δ ppm 1.35-1.42 (m, 9 H) 4.03 (s, 3 H) 6.53-6.56 (m, 1 H) 6.99-7.04 (m, 1 H) 7.58-7.63 (m, 2 H) 7.88-8.01 (m, 2 H) 8.06-8.14 (m, 2 H) 8.38-8.50 (m, 1 H) 8.94 (s, 1 H). ESI-MS: m/z 402.2 (M+H)⁺.

Example 28

N-(7-(6-Acetamidopyridin-3-yl)pyrazolo[1,5-a]pyrimidin-5-yl)-4-tert-butylbenzamide (14)

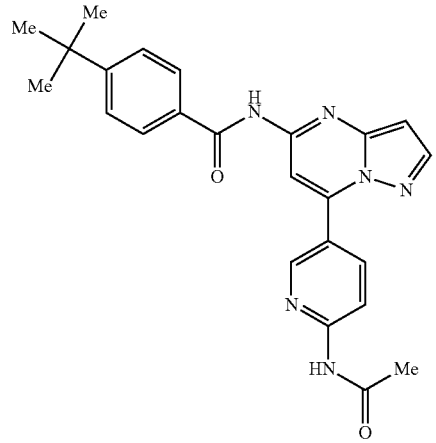

The titled compound was prepared using a procedure analogous to that described in connection with Example 15 except that 4-tert-butyl-N-(7-chloropyrazolo[1,5-a]pyrimidin-5-yl)benzamide (1F) and the corresponding boronic acid or ester were used as starting material. This product was obtained as a yellow solid (18%). $^1$H NMR (400 MHz, MeOD) δ ppm 1.38 (s, 9 H) 2.25 (s, 3 H) 6.55 (s, 1 H) 7.60 (d, J=8.08 Hz, 2 H) 7.96 (d, 2 H) 8.08-8.16 (m, 2 H) 8.24-8.33 (m, 1 H) 8.54-8.64 (m, 1 H) 9.09 (br. s., 1 H). ESI-MS: m/z 429.2 (M+H)$^+$.

Example 29

4-tert-Butyl-N-(7-(3-methoxyphenyl)pyrazolo[1,5-a]pyrimidin-5-yl)benzamide (15)

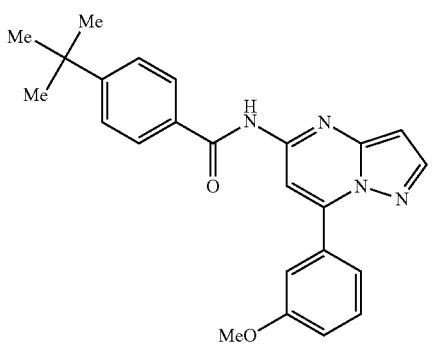

15

The titled compound was prepared using a procedure analogous to that described in connection with Example 15 except that 4-tert-butyl-N-(7-chloropyrazolo[1,5-a]pyrimidin-5-yl)benzamide (1F) and the corresponding boronic acid or ester were used as starting material. This product was obtained as a white solid (20%). $^1$H NMR (400 MHz, MeOD) δ ppm 1.37 (s, 9H) 3.89 (s, 3 H) 6.51-6.57 (m, 1 H) 7.13-7.22 (m, 1 H) 7.46-7.71 (m, 5 H) 7.88-8.16 (m, 4 H). ESI-MS: m/z 401.2 (M+H)$^+$.

Example 30

4-(2-Hydroxypropan-2-yl)-N-(7-phenylpyrazolo[1,5-a]pyrimidin-5-yl)benzamide (16)

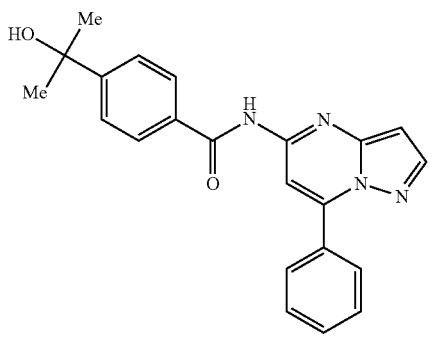

16

The titled compound was prepared using a procedure analogous to that described in connection with Example 15 except that N-(7-chloropyrazolo[1,5-a]pyrimidin-5-yl)-4-(2-hydroxypropan-2-yl)benzamide (2D) and the corresponding boronic acid or ester were used as starting material. The product was obtained a yellow solid (16%). $^1$H NMR (400 MHz, MeOD) δ ppm 1.57 (s, 6 H) 6.55 (d, J=2.27 Hz, 1 H) 7.57-7.63 (m, 3 H) 7.68 (d, J=8.59 Hz, 2 H) 7.99 (d, J=8.84 Hz, 2 H) 8.04-8.08 (m, 3 H) 8.09 (d, J=2.27 Hz, 1 H). ESI-MS: m/z 373.0 (M+H)$^+$.

Example 31

4-(2-Hydroxypropan-2-yl)-N-(7-(3-(methylsulfonamido)phenyl)pyrazolo[1,5-a]pyrimidin-5-yl)benzamide (17)

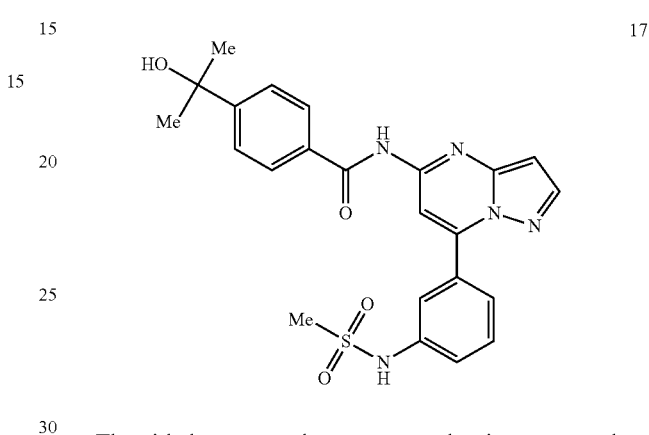

17

The titled compound was prepared using a procedure analogous to that described in connection with Example 15 except that N-(7-chloropyrazolo[1,5-a]pyrimidin-5-yl)-4-(2-hydroxypropan-2-yl)benzamide (2D) and the corresponding boronic acid or ester were used as starting material. After cooling to room temperature, the crude mixture was filtered and the filtrate was purified by preparatory LC-MS to give the TFA salt of the titled compound as a yellow solid (36%). $^1$H NMR (400 MHz, DMSO-d$_6$) δ ppm 1.46 (s, 6 H) 3.10 (s, 3 H) 5.20 (br. s., 1 H) 6.60 (d, J=2.27 Hz, 1 H) 7.42-7.49 (m, 1 H) 7.55-7.66 (m, 3 H) 7.77-7.83 (m, 1 H) 7.92-7.96 (m, 1 H) 7.99-8.08 (m, 3 H) 8.21 (d, J=2.27 Hz, 1 H) 10.08 (s, 1 H) 11.29 (s, 1 H). ESI-MS: m/z 466.2 (M+H)$^+$.

Example 32

N-(7-(Furan-3-yl)pyrazolo[1,5-a]pyrimidin-5-yl)-4-(2-hydroxypropan-2-yl)benzamide (18)

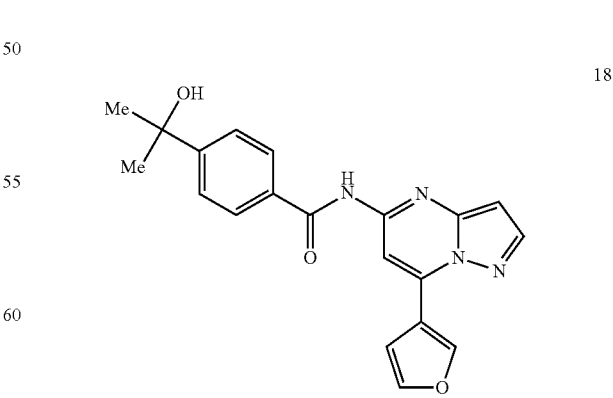

18

The titled compound was prepared using a procedure analogous to that described in connection with Example 15 except that N-(7-chloropyrazolo[1,5-a]pyrimidin-5-yl)-4-(2- hydroxypropan-2-yl)benzamide (2D) and the corresponding boronic acid or ester were used as starting material. The product was obtained as a pale yellow solid (43%). ¹H NMR (400 MHz, DMSO-d₆) δ ppm 1.47 (s, 6 H) 5.20 (br. s., 1 H) 6.62 (d, J=2.27 Hz, 1 H) 7.24-7.38 (m, 1 H) 7.56-7.71 (m, 2 H) 7.98-8.13 (m, 3 H) 8.27 (s, 1 H) 8.31 (d, J=2.27 Hz, 1 H) 9.15 (s, 1 H) 11.23 (s, 1 H). ESI-MS: m/z 363.2 (M+H)⁺.

Example 33

4-(2-Hydroxypropan-2-yl)-N-(7-(4-methoxyphenyl)pyrazolo[1,5-a]pyrimidin-5-yl)benzamide (19)

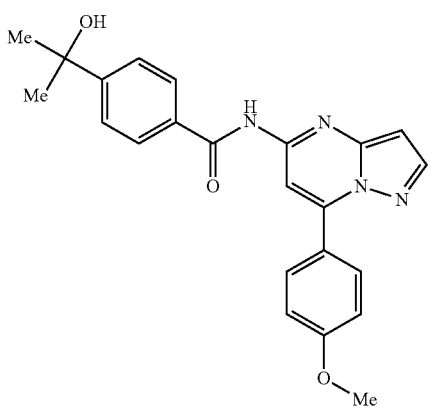

19

The titled compound was prepared using a procedure analogous to that described in connection with Example 15 except that N-(7-chloropyrazolo[1,5-a]pyrimidin-5-yl)-4-(2-hydroxypropan-2-yl)benzamide (2D) and the corresponding boronic acid or ester were used as starting material. The product was obtained as a pale yellow solid (23%). Melting point (199.0-203° C.). ¹H NMR (400 MHz, MeOD) δ ppm 1.57 (s, 6 H) 3.92 (s, 3 H) 6.53 (d, J=2.27 Hz, 1 H) 7.12-7.16 (m, 2 H) 7.65-7.69 (m, 2 H) 7.96-8.01 (m, 2 H) 8.05 (s, 1 H) 8.08-8.13 (m, 3 H). ESI-MS: m/z 403.3 (M+H)⁺.

Example 34

4-(2-Hydroxypropan-2-yl)-N-(7-p-tolylpyrazolo[1,5-a]pyrimidin-5-yl)benzamide (20)

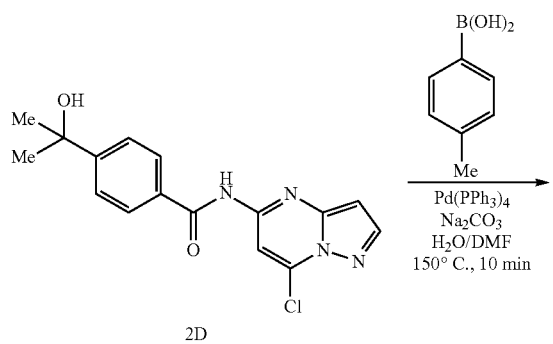

20

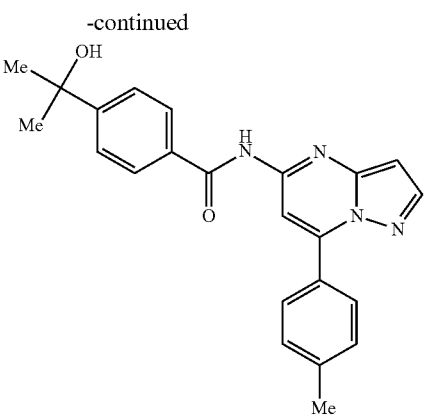

20

A suspension of N-(7-chloropyrazolo[1,5-a]pyrimidin-5-yl)-4-(2-hydroxypropan-2-yl)benzamide (2D, 50 mg, 1.0 equivalent), p-tolylboronic acid (2.0 equivalents), Pd(PPh₃)₄ (0.05 equivalent), and Na₂CO₃ (4.0 equivalents) in N₂-saturated 4:1 DMF/H₂O (0.1 M with respect to 2D) was heated at 150° C. in microwave for 10 minutes. After cooling to room temperature, the crude mixture was filtered and the filtrate was purified by PREP LC-MS to give the TFA salt of the titled compound (35%) as a pale yellow solid. ¹H NMR (400 MHz, DMSO-d₆) δ ppm 1.47 (s, 6 H) 2.44 (s, 3 H) 6.58 (d, J=2.27 Hz, 1 H) 7.45 (d, J=8.34 Hz, 2 H) 7.62 (d, J=8.34 Hz, 2 H) 7.99-8.09 (m, 5 H) 8.20 (d, J=2.27 Hz, 1 H) 11.23 (s, 1 H). ESI-MS: m/z 387.2 (M+H)⁺.

Example 35

N-(7-(3-(cyanomethyl)phenyl)pyrazolo[1,5-a]pyrimidin-5-yl)-4-(2-hydroxypropan-2-yl)benzamide (21)

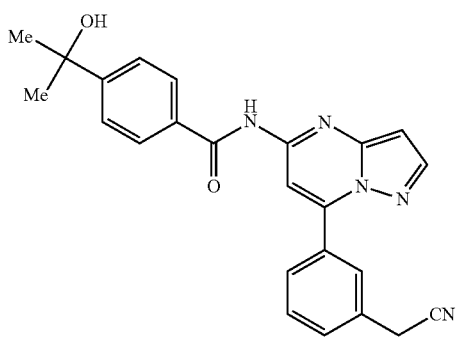

21

The titled compound was prepared using a procedure analogous to that described in connection with Example 34 except that 3-(cyanomethyl)phenylboronic acid was used. After cooling to room temperature, the crude mixture was filtered and the filtrate was purified by preparatory LC-MS, and then extracted from saturated NaHCO₃ solution into EtOAc to give the free base of the titled compound (11%) as a yellow solid. ¹H NMR (400 MHz, DMSO-d₆) δ ppm 1.47 (s, 6 H) 4.23 (s, 2 H) 5.19 (s, 1 H) 6.61 (d, J=2.27 Hz, 1 H)

7.60-7.72 (m, 4 H) 8.00-8.09 (m, 5 H) 8.21 (d, J=2.27 Hz, 1 H) 11.28 (s, 1 H). ESI-MS: m/z 412.2 (M+H)+.

Example 36

N-(7-(4-carbamoylphenyl)pyrazolo[1,5-a]pyrimidin-5-yl)-4-(2-hydroxypropan-2-yl)benzamide (22)

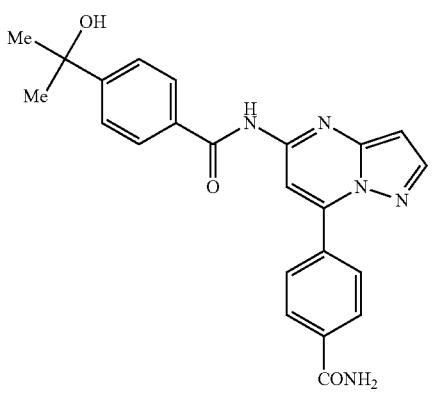

The titled compound was prepared using a procedure analogous to that described in connection with Example 34 except that 4-carbamoylphenylboronic acid was used. After cooling to room temperature, the crude mixture was filtered and the filtrate was purified by preparatory LC-MS to give the TFA salt of the titled compound (5%) as a yellow solid. $^1$H NMR (400 MHz, DMSO-$d_6$) δ ppm 1.46 (s, 6 H) 5.18 (s, 1 H) 6.60 (d, J=2.27 Hz, 1 H) 7.56 (br. s., 1 H) 7.62 (d, J=8.34 Hz, 2 H) 8.02 (d, J=8.34 Hz, 2 H) 8.06-8.13 (m, 3 H) 8.17 (d, J=8.34 Hz, 3 H) 8.20 (d, J=2.02 Hz, 1 H) 11.28 (s, 1 H). ESI-MS: m/z 416.2 (M+H)+.

Example 37

4-(2-hydroxypropan-2-yl)-N-(7-(4-(methylthio)phenyl)pyrazolo[1,5-a]pyrimidin-5-yl)benzamide (23)

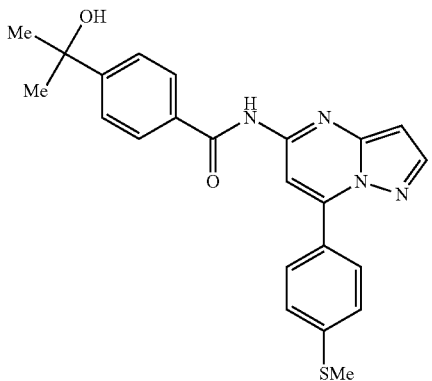

The titled compound was prepared using a procedure analogous to that described in connection with Example 34 except that 4-(methylthio)phenylboronic acid was used. After cooling to room temperature, the crude mixture was filtered and the filtrate was purified by preparatory LC-MS to give the TFA salt of the titled compound (30%) as a pale yellow solid. $^1$H NMR (400 MHz, DMSO-$d_6$) δ ppm 1.46 (s, 6 H) 2.58 (s, 3 H) 5.19 (br. s., 1 H) 6.58 (d, J=2.27 Hz, 1 H) 7.49 (d, J=8.59 Hz, 2 H) 7.62 (d, J=8.34 Hz, 2 H) 8.03 (d, J=8.59 Hz, 2 H) 8.06-8.13 (m, 3 H) 8.20 (d, J=2.27 Hz, 1 H) 11.23 (s, 1 H); ESI-MS: m/z 419.2 (M+H)+.

Example 38

4-(2-hydroxypropan-2-yl)-N-(7-(4-(trifluoromethyl)phenyl)pyrazolo[1,5-a]pyrimidin-5-yl)benzamide (24)

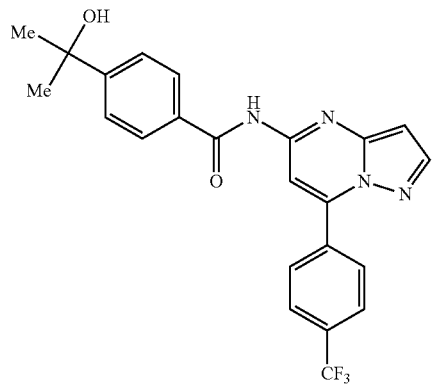

The titled compound was prepared using a procedure analogous to that described in connection with Example 34 except that 4-(trifluoromethyl)phenylboronic acid was used. After cooling to room temperature, the crude mixture was filtered and purified by preparatory LC-MS to give the TFA salt of the titled compound (39%) as a yellow solid. $^1$H NMR (400 MHz, DMSO-$d_6$) δ ppm 1.46 (s, 6 H) 5.20 (s, 1 H) 6.63 (d, J=2.27 Hz, 1 H) 7.61-7.63 (m, 2 H) 7.98-8.06 (m, 4 H) 8.12 (s, 1 H) 8.21 (d, J=2.27 Hz, 1 H) 8.31 (d, J=8.08 Hz, 2 H) 11.34 (s, 1 H); ESI-MS: m/z 441.2 (M+H)+.

Example 39

N-(7-(3-acetamidophenyl)pyrazolo[1,5-a]pyrimidin-5-yl)-4-(2-hydroxypropan-2-yl)benzamide (25)

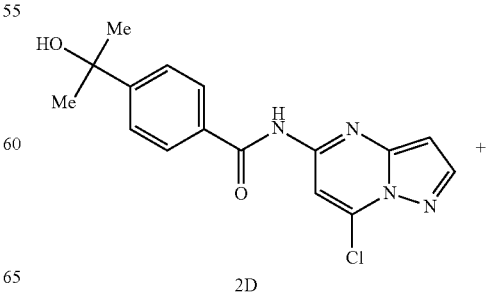

-continued

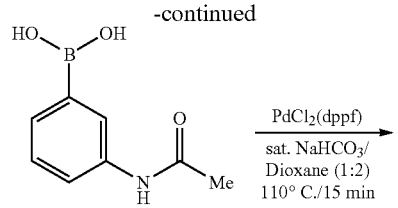

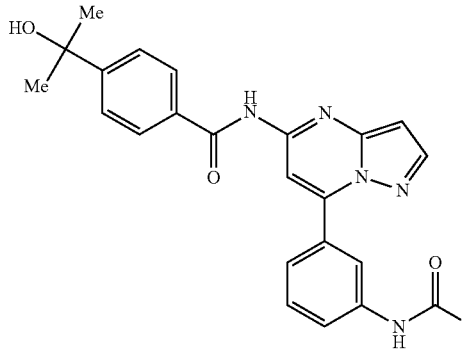

A mixture of N-(7-chloropyrazolo[1,5-a]pyrimidin-5-yl)-4-(2-hydroxypropan-2-yl)benzamide (2D, 50 mg, 1.0 equivalent), 3-acetamidophenylboronic acid (2.0 equivalents), and PdCl$_2$(dppf) (0.08 equivalent) in 1:2 saturated NaHCO$_3$/dioxane (0.15 M with respect to 2D) was heated at 110° C. for 15 minutes in the microwave. After cooling to room temperature, the crude mixture was filtered and the filtrate was purified by preparatory LC-MS to give the titled compound (35%) as a pink solid. $^1$H NMR (400 MHz, DMSO-d$_6$) δ ppm 1.46 (s, 6 H) 2.09 (s, 3H) 5.20 (s, 1 H) 6.60 (d, J=2.27 Hz, 1 H) 7.52-7.57 (m, 1 H) 7.60-7.64 (m, 2 H) 7.73-7.77 (m, 1 H) 7.84-7.89 (m, 1 H) 7.99-8.07 (m, 2 H) 8.20 (d, J=2.27 Hz, 1 H) 8.28 (t, J=1.77 Hz, 1 H) 10.24 (s, 1 H) 11.28 (s, 1 H). ESI-MS: m/z 430.3 (M+H)$^+$.

Example 40 ethyl 2-(3-(5-(4-(2-hydroxypropan-2-yl)benzamido)pyrazolo[1,5-a]pyrimidin-7-yl)phenoxy)acetate (26)

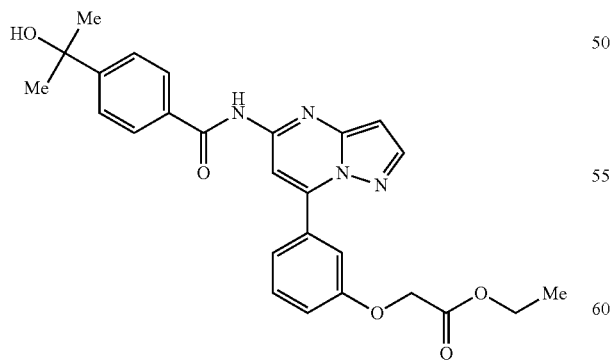

The titled compound was prepared using a procedure analogous to that described in connection with Example 39 except the corresponding boronic acid, ester or trifluoro salt was used as starting material. After cooling to room temperature, the crude mixture was filtered and the filtrate was purified by preparatory LC-MS to give the titled compound (15%) as a yellow solid. $^1$H NMR (400 MHz, DMSO-d$_6$) δ ppm 1.23 (t, 3 H) 1.46 (s, 6 H) 4.21 (q, J=7.16 Hz, 2 H) 4.90 (s, 2 H) 6.59 (d, J=2.27 Hz, 1 H) 7.18-7.24 (m, 1 H) 7.51-7.70 (m, 5 H) 8.00-8.07 (m, 3H) 8.20 (d, J=2.27 Hz, 1 H) 11.27 (s, 1 H). ESI-MS: m/z 475.0 (M+H)$^+$.

Example 41

2-(3-(5-(4-(2-hydroxypropan-2-yl)benzamido)pyrazolo[1,5-a]pyrimidin-7-yl)phenoxy)acetic acid (27)

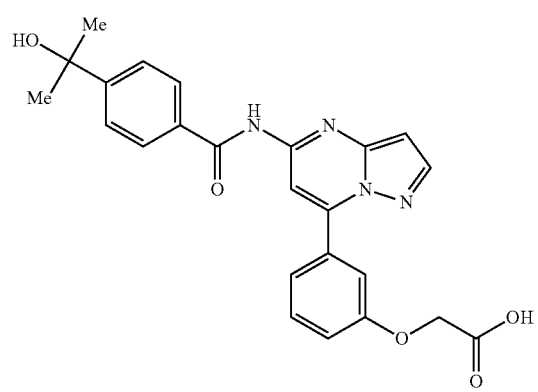

The titled compound was prepared using a procedure analogous to that described in connection with Example 39 except the corresponding boronic acid, ester or trifluoro salt was used as starting material. After cooling to room temperature, the crude mixture was filtered and the filtrate was purified by preparatory LC-MS to give the titled compound (19%) as a white solid as a side product. $^1$H NMR (400 MHz, DMSO-d$_6$) δ ppm 1.46 (s, 6 H) 3.53 (br. s., 1 H) 4.79 (s, 2 H) 6.59 (d, J=2.27 Hz, 1 H) 7.17-7.22 (m, 1 H) 7.51-7.57 (m, 1 H) 7.60-7.70 (m, 4 H) 8.00-8.07 (m, 3 H) 8.19 (d, J=2.53 Hz, 1 H) 11.27 (s, 1 H) 13.09 (br. s., 1 H). ESI-MS: m/z 447.3 (M+H)$^+$.

Example 42

4-(2-hydroxypropan-2-yl)-N-(7-(3-(methoxymethyl)phenyl)pyrazolo[1,5-a]pyrimidin-5-yl)benzamide (28)

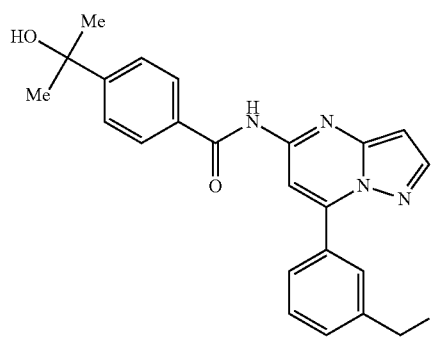

The titled compound was prepared using a procedure analogous to that described in connection with Example 39 except the corresponding boronic acid, ester or trifluoro salt was used as starting material. After cooling to room temperature, the crude mixture was filtered and the filtrate was purified by preparatory LC-MS to give the titled compound (17%) as a tan solid. $^1$H NMR (400 MHz, DMSO-d$_6$) δ ppm 1.46 (s, 6 H) 3.36 (s, 3 H) 4.55 (s, 2 H) 5.20 (s, 1 H) 6.54 (s, 1 H) 6.59 (d, J=2.27 Hz, 1 H) 7.54-7.67 (m, 5 H) 7.98-8.08 (m, 3 H) 8.21 (d, J=2.27 Hz, 1 H) 11.27 (s, 1 H). ESI-MS: m/z 417.0 (M+H)$^+$.

Example 43

4-(1-hydroxy-2-methylpropan-2-yl)-N-(2-methyl-7-phenylpyrazolo[1,5-a]pyrimidin-5-yl)benzamide (29)

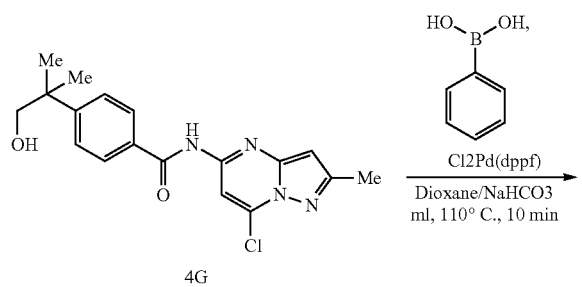

A suspension of N-(7-chloro-2-methylpyrazolo[1,5-a]pyrimidin-5-yl)-4-(1-hydroxy-2-methylpropan-2-yl)benzamide (4G, 44 mg, 1.0 equivalent), phenylboronic acid (1.5 equivalents) and [1,1'-bis(diphenylphosphino)ferrocene]dichloropalladium(II) (0.09 equivalents) in 2:1 dioxane/saturated aqueous NaHCO$_3$ (0.125 M with respect to 4G) was warmed to 110° C. in a microwave reactor. The reaction mixture was cooled to room temperature, diluted with methanol, filtered, and purified via preparative HPLC to afford the title compound (49%) as a yellow solid. $^1$H NMR (400 MHz, DMSO-d$_6$) δ ppm 1.26 (s, 6 H), 2.40 (s, 3 H), 3.47 (s, 2 H), 4.76 (br. s., 1 H), 6.40 (s, 1 H), 7.53 (d, J=8.59 Hz, 2 H), 7.58-7.68 (m, 3 H), 7.94-8.04 (m, 3 H), 8.04-8.10 (m, 2 H), 11.19 (s, 1 H). ESI-MS: m/z 401.1 (M+H)$^+$.

Example 44

4-(1-hydroxy-2-methylpropan-2-yl)-N-(7-(3-(hydroxymethyl)phenyl)-2-methylpyrazolo[1,5-a]pyrimidin-5-yl)benzamide (30)

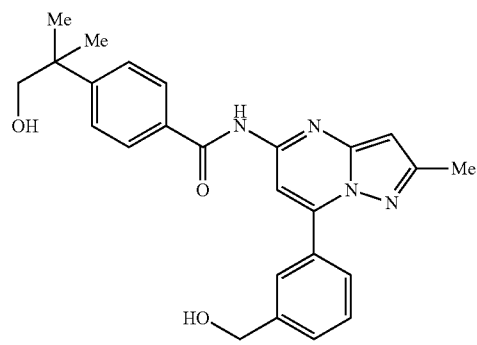

The title compound was prepared using a procedure analogous to that described in connection with Example 43 except that 3-(hydroxymethyl)phenylboronic acid (1.5 equivalents) was used instead of phenylboronic acid as starting material to afford the titled compound (31%) as a yellow solid. $^1$H NMR (400 MHz, DMSO-d$_6$) δ ppm 1.26 (s, 6 H), 2.40 (s, 3 H), 3.48 (br. s., 2 H), 4.63 (br. s., 2 H), 4.76 (br. s., 1 H), 5.40 (br. s., 1 H), 6.39 (s, 1 H), 7.53 (d, J=8.84 Hz, 2 H), 7.55-7.60 (m, 2 H), 7.92-7.98 (m, 3 H), 8.02 (d, J=8.59 Hz, 2 H), 11.19 (s, 1 H). ESI-MS: m/z 431.1 (M+H)$^+$.

Example 45

4-(1-hydroxy-2-methylpropan-2-yl)-N-(7-(3-(methoxymethyl)phenyl)-2-methylpyrazolo[1,5-a]pyrimidin-5-yl)benzamide (31)

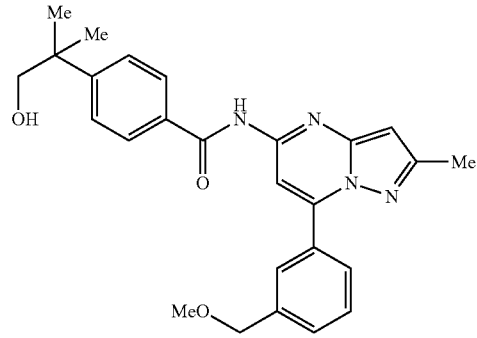

The title compound was prepared using a procedure analogous to that described in connection with Example 43 except that 3-(methoxymethyl)phenylboronic acid (1.5 equivalents) was used instead of phenylboronic acid as starting material to afford the title compound (44%) as a yellow solid. $^1$H NMR (400 MHz, DMSO-d$_6$) δ ppm 1.26 (s, 6 H), 2.40 (s, 3 H), 3.36 (s, 3 H), 3.47 (s, 2 H), 4.55 (s, 2 H), 6.39 (s, 1 H), 7.53 (d, J=8.84 Hz, 2 H), 7.55-7.65 (m, 2 H), 7.92-7.98 (m, 2 H), 7.99-8.05 (m, 3 H), 11.19 (s, 1 H). ESI-MS: m/z 445.0 (M+H)⁺.

Example 46

4-tert-butyl-N-[7-(4-fluorophenyl)pyrazolo[1,5-a]pyrimidin-5-yl]benzamide (32)

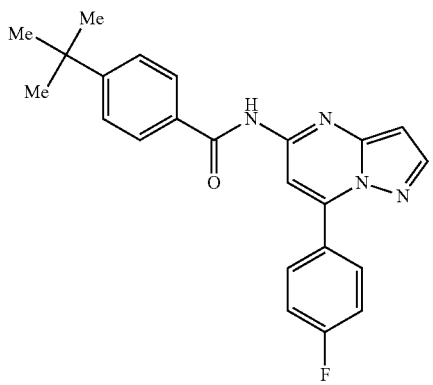

32

A suspension of N-(7-chloro-2-methylpyrazolo[1,5-a]pyrimidin-5-yl)-4-(1-hydroxy-2-methylpropan-2-yl)benzamide (4G, 44 mg, 1.0 equivalent), 4-fluorophenylboronic acid (1.2 equivalents), Pd(OAc)₂ (0.05 equivalent), and K₂CO₃ (4.0 equivalents) in DME/H₂O was warmed to 110° C. in a microwave reactor. The reaction mixture was cooled to room temperature, diluted with methanol, filtered, and purified via preparative HPLC to afford the title compound. ¹H NMR (400 MHz, CHLOROFORM-d) δ ppm 1.37 (s, 9 H) 6.50 (d, J=2.26 Hz, 1 H) 7.23-7.32 (m, 1 H) 7.56 (d, J=8.29 Hz, 2 H) 7.89 (d, J=8.29 Hz, 2 H) 8.11 (d, J=2.26 Hz, 1 H) 8.12-8.18 (m, 2 H) 8.25 (s, 1 H) 8.67 (s, 1 H); ESI-MS: m/z 389 (M+H)⁺.

Example 47

4-tert-butyl-N-[7-(4-tert-butylphenyl)pyrazolo[1,5-a]pyrimidin-5-yl]benzamide (33)

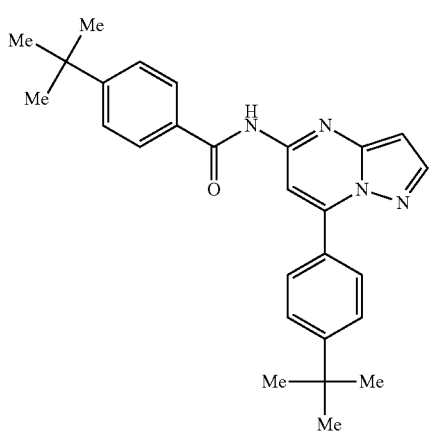

33

The titled compound was prepared using a procedure analogous to that described in connection with Example 46 except that 4-tert-butylphenylboronic acid (1.5 equivalents) was used instead of phenylboronic acid as starting material to afford the title compound. ¹H NMR (400 MHz, CHLOROFORM-d) δ ppm 1.37 (s, 9 H) 1.39 (s, 9 H) 6.49 (d, J=2.26 Hz, 1 H) 7.55 (d, J=8.48 Hz, 2 H) 7.59 (d, J=8.48 Hz, 2 H) 7.89 (d, J=8.48 Hz, 2 H) 8.05 (d, J=8.48 Hz, 2 H) 8.11 (d, J=2.26 Hz, 1 H) 8.25 (s, 1 H) 8.64 (s, 1 H); ESI-MS: m/z 427 (M+H)⁺.

Example 48

4-tert-butyl-N-{7-[3-(cyanomethyl)phenyl]pyrazolo[1,5-a]pyrimidin-5-yl}benzamide (34)

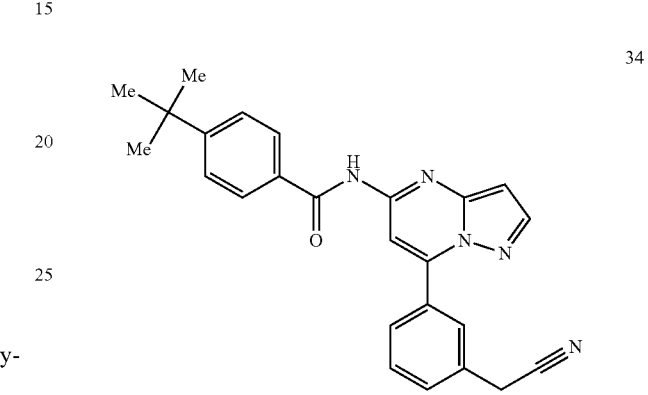

34

The titled compound was prepared using a procedure analogous to that described in connection with Example 46 except that 4-(cyanomethyl)phenylboronic acid (1.5 equivalents) was used instead of phenylboronic acid as starting material to afford the title compound. ¹H NMR (400 MHz, CHLOROFORM-d) δ ppm 1.37 (s, 9 H) 3.90 (s, 2 H) 6.51 (d, J=2.26 Hz, 1 H) 7.56 (d, J=8.29 Hz, 2 H) 7.59-7.65 (m, 2 H) 7.89 (d, J=8.48 Hz, 2 H) 8.04 (d, J=6.78 Hz, 1 H) 8.07 (s, 1 H) 8.11 (d, J=2.26 Hz, 1 H) 8.26 (s, 1 H) 8.67 (s, 1 H); ESI-MS: m/z 410 (M+H)⁺.

Example 49

4-tert-butyl-N-(7-(furan-3-yl)pyrazolo[1,5-a]pyrimidin-5-yl)benzamide (35)

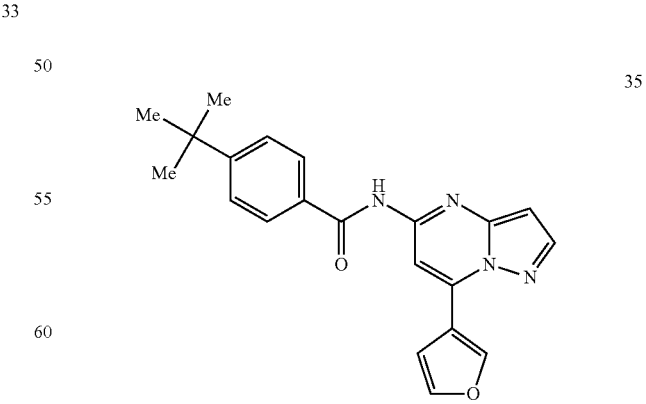

35

The titled compound was prepared using a procedure analogous to that described in connection with Example 46 except that furan-3-ylboronic acid (1.5 equivalents) was used instead of phenylboronic acid as starting material to afford the title compound. ESI-MS: m/z 361 (M+H)+.

Example 50

4-tert-butyl-N-(7-phenylpyrazolo[1,5-a]pyrimidin-5-yl)benzamide (36)

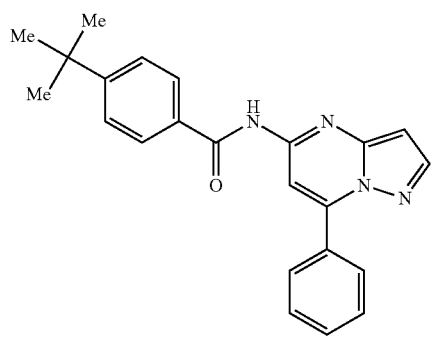

36

The titled compound was prepared using a procedure analogous to that described in connection with Example 46 except the corresponding boronic acid, ester or trifluoroborate salt was used as starting material. ESI-MS: m/z 371 (M+H)+.

Example 51

4-tert-butyl-N-(7-p-tolylpyrazolo[1,5-a]pyrimidin-5-yl)benzamide (37)

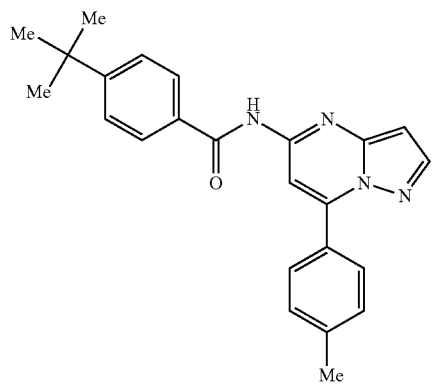

37

The titled compound was prepared using a procedure analogous to that described in connection with Example 46 except the corresponding boronic acid, ester or trifluoroborate salt was used as starting material. ESI-MS: m/z 385 (M+H)+.

Example 52

4-tert-butyl-N-(7-(4-cyanophenyl)pyrazolo[1,5-a]pyrimidin-5-yl)benzamide (38)

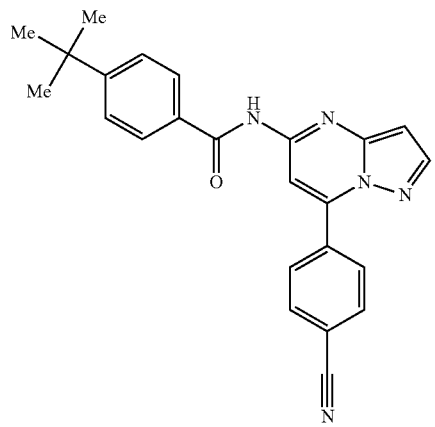

38

The titled compound was prepared using a procedure analogous to that described in connection with Example 46 except the corresponding boronic acid, ester or trifluoroborate salt was used as starting material. ESI-MS: m/z 396 (M+H)+.

Example 53

4-tert-butyl-N-(7-(3,5-dimethylphenyl)pyrazolo[1,5-a]pyrimidin-5-yl)benzamide (39)

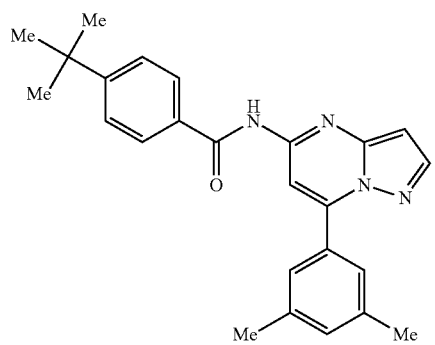

39

The titled compound was prepared using a procedure analogous to that described in connection with Example 46 except the corresponding boronic acid, ester or trifluoroborate salt was used as starting material. ESI-MS: m/z 399 (M+H)+.

Example 54

4-tert-butyl-N-(7-(4-chlorophenyl)pyrazolo[1,5-a]pyrimidin-5-yl)benzamide (40)

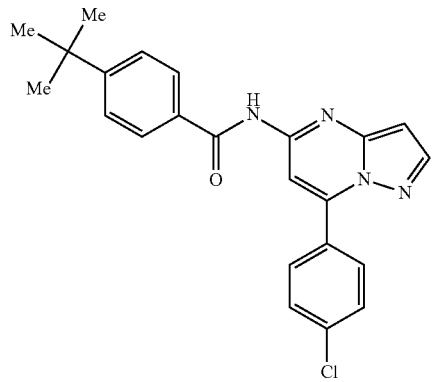

The titled compound was prepared using a procedure analogous to that described in connection with Example 46 except the corresponding boronic acid, ester or trifluoroborate salt was used as starting material. ESI-MS: m/z 405 (M+H)+.

Example 55

4-tert-butyl-N-(7-(2-chlorophenyl)pyrazolo[1,5-a]pyrimidin-5-yl)benzamide (41)

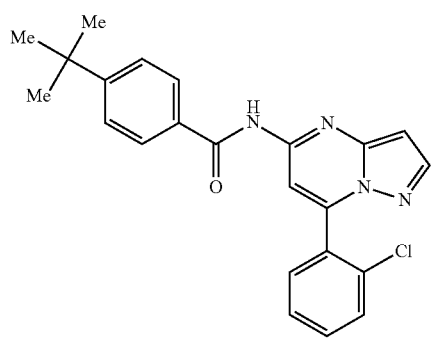

The titled compound was prepared using a procedure analogous to that described in connection with Example 46 except the corresponding boronic acid, ester or trifluoroborate salt was used as starting material. ESI-MS: m/z 405 (M+H)+.

Example 56

4-tert-butyl-N-(7-(4-carbamoylphenyl)pyrazolo[1,5-a]pyrimidin-5-yl)benzamide (42)

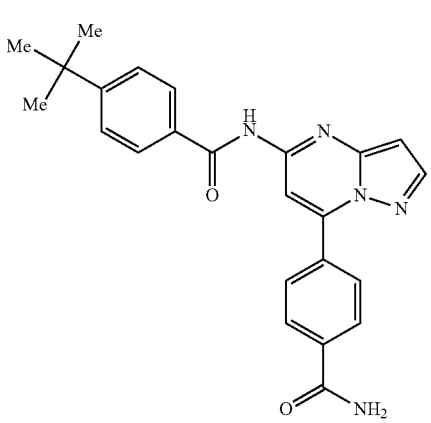

The titled compound was prepared using a procedure analogous to that described in connection with Example 46 except the corresponding boronic acid, ester or trifluoroborate salt was used as starting material. ESI-MS: m/z 414 (M+H)+.

Example 57

4-tert-butyl-N-(7-(4-(methylthio)phenyl)pyrazolo[1,5-a]pyrimidin-5-yl)benzamide (43)

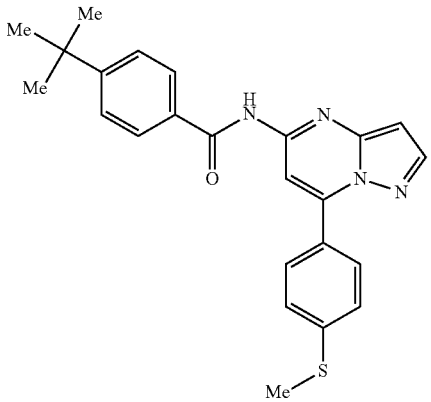

The titled compound was prepared using a procedure analogous to that described in connection with Example 46 except the corresponding boronic acid, ester or trifluoroborate salt was used as starting material. ESI-MS: m/z 417 (M+H)+.

Example 58

N-(7-(benzo[b]thiophen-2-yl)pyrazolo[1,5-a]pyrimidin-5-yl)-4-tert-butylbenzamide (44)

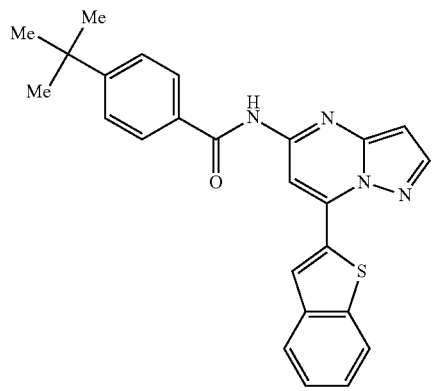

The titled compound was prepared using a procedure analogous to that described in connection with Example 46 except the corresponding boronic acid, ester or trifluoroborate salt was used as starting material. ESI-MS: m/z 427 (M+H)+.

Example 59

4-tert-butyl-N-(7-(2,4-dimethoxyphenyl)pyrazolo[1,5-a]pyrimidin-5-yl)benzamide (45)

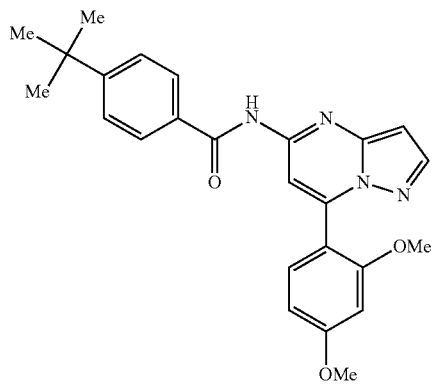

The titled compound was prepared using a procedure analogous to that described in connection with Example 46 except the corresponding boronic acid, ester or trifluoroborate salt was used as starting material. ESI-MS: m/z 431 (M+H)+.

Example 60

4-tert-butyl-N-(7-(3-(trifluoromethyl)phenyl)pyrazolo[1,5-a]pyrimidin-5-yl)benzamide (46)

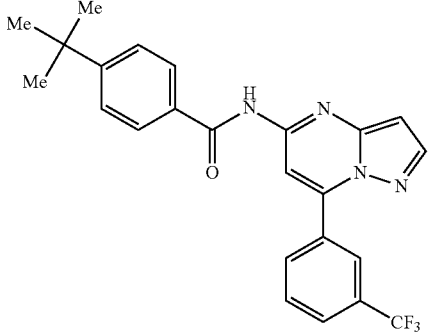

The titled compound was prepared using a procedure analogous to that described in connection with Example 46 except the corresponding boronic acid, ester or trifluoroborate salt was used as starting material. ESI-MS: m/z 439 (M+H)+.

Example 61

4-tert-butyl-N-(7-(4-(trifluoromethoxy)phenyl)pyrazolo[1,5-a]pyrimidin-5-yl)benzamide (47)

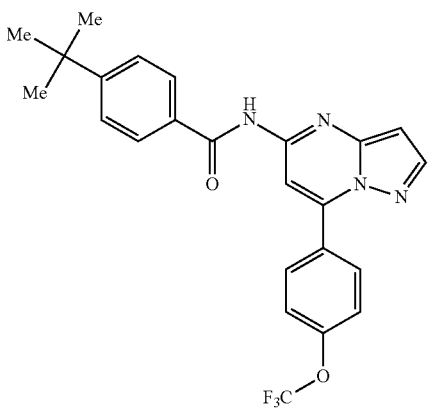

The titled compound was prepared using a procedure analogous to that described in connection with Example 46 except the corresponding boronic acid, ester or trifluoroborate salt was used as starting material. ESI-MS: m/z 455 (M+H)⁺.

Example 62

4-tert-butyl-N-(7-o-tolylpyrazolo[1,5-a]pyrimidin-5-yl)benzamide (48)

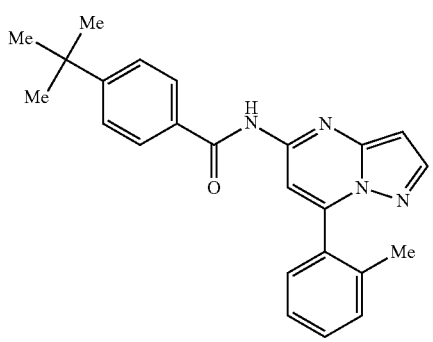

The titled compound was prepared using a procedure analogous to that described in connection with Example 46 except the corresponding boronic acid, ester or trifluoroborate salt was used as starting material. ESI-MS: m/z 385 (M+H)⁺.

Example 63

4-tert-butyl-N-(7-(2-(hydroxymethyl)phenyl)pyrazolo[1,5-a]pyrimidin-5-yl)benzamide (49)

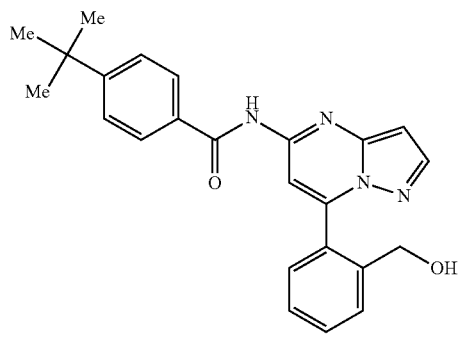

The titled compound was prepared using a procedure analogous to that described in connection with Example 46 except the corresponding boronic acid, ester or trifluoroborate salt was used as starting material. ESI-MS: m/z 401 (M+H)⁺.

Example 64

N-(7-(2-acetamidophenyl)pyrazolo[1,5-a]pyrimidin-5-yl)-4-tert-butylbenzamide (50)

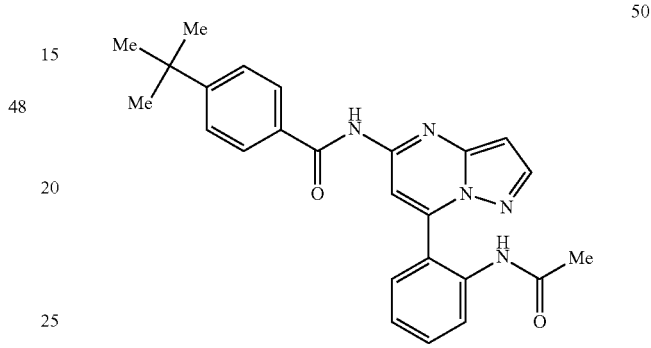

The titled compound was prepared using a procedure analogous to that described in connection with Example 46 except the corresponding boronic acid, ester or trifluoroborate salt was used as starting material. ESI-MS: m/z 428 (M+H)⁺.

Example 65

N-(7-(biphenyl-2-yl)pyrazolo[1,5-a]pyrimidin-5-yl)-4-tert-butylbenzamide (51)

The titled compound was prepared using a procedure analogous to that described in connection with Example 46 except the corresponding boronic acid, ester or trifluoroborate salt was used as starting material. ESI-MS: m/z 447 (M+H)⁺.

Example 66

4-tert-butyl-N-(7-(2-(methylsulfonamido)phenyl)pyrazolo[1,5-a]pyrimidin-5-yl)benzamide (52)

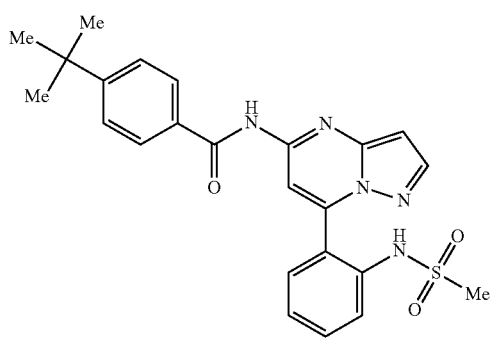

The titled compound was prepared using a procedure analogous to that described in connection with Example 46 except the corresponding boronic acid, ester or trifluoroborate salt was used as starting material. ESI-MS: m/z 464 (M+H)⁺.

Example 67

4-tert-butyl-N-(7-(2-methoxypyridin-3-yl)pyrazolo[1,5-a]pyrimidin-5-yl)benzamide (53)

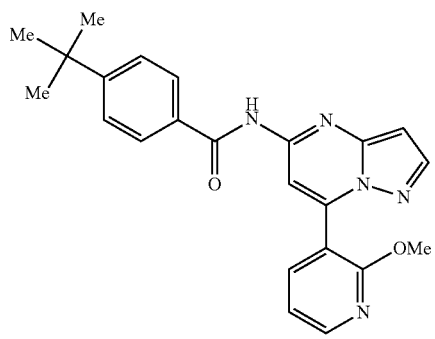

The titled compound was prepared using a procedure analogous to that described in connection with Example 46 except the corresponding boronic acid, ester or trifluoroborate salt was used as starting material. ESI-MS: m/z 402 (M+H)⁺.

Example 68

4-tert-butyl-N-(7-(naphthalen-2-yl)pyrazolo[1,5-a]pyrimidin-5-yl)benzamide (54)

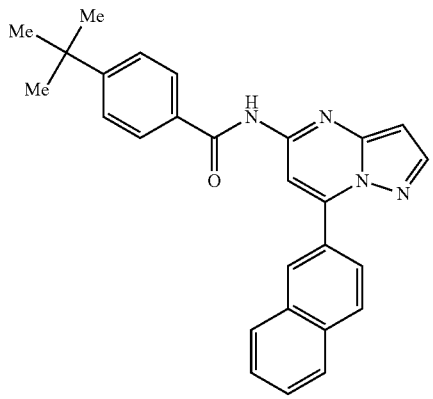

The titled compound was prepared using a procedure analogous to that described in connection with Example 46 except the corresponding boronic acid, ester or trifluoroborate salt was used as starting material. ESI-MS: m/z 421 (M+H)⁺.

Example 69

4-tert-butyl-N-(7-(3-nitrophenyl)pyrazolo[1,5-a]pyrimidin-5-yl)benzamide (55)

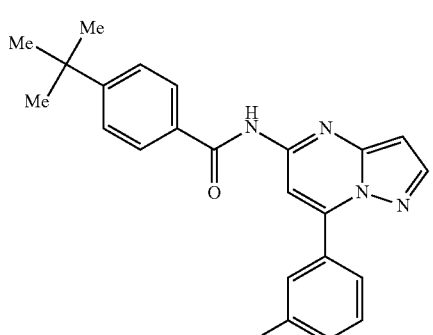

The titled compound was prepared using a procedure analogous to that described in connection with Example 46 except the corresponding boronic acid, ester or trifluoroborate salt was used as starting material. ESI-MS: m/z 416 (M+H)+.

Example 70

4-tert-butyl-N-(7-(4-nitrophenyl)pyrazolo[1,5-a]pyrimidin-5-yl)benzamide (56)

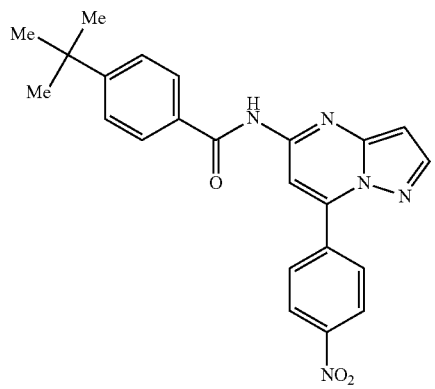

The titled compound was prepared using a procedure analogous to that described in connection with Example 46 except the corresponding boronic acid, ester or trifluoroborate salt was used as starting material. ESI-MS: m/z 416 (M+H)+.

Example 71

4-tert-butyl-N-(7-(3,4-difluorophenyl)pyrazolo[1,5-a]pyrimidin-5-yl)benzamide (57)

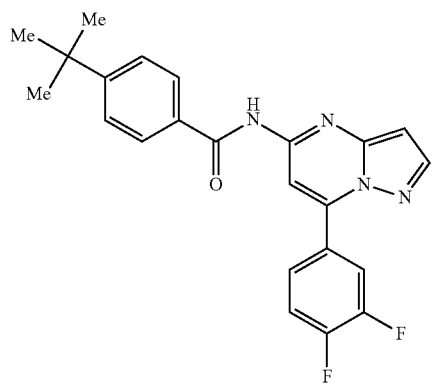

The titled compound was prepared using a procedure analogous to that described in connection with Example 46 except the corresponding boronic acid, ester or trifluoroborate salt was used as starting material. ESI-MS: m/z 407 (M+H)+.

Example 72

4-tert-butyl-N-(7-(4-sec-butylphenyl)pyrazolo[1,5-a]pyrimidin-5-yl)benzamide (58)

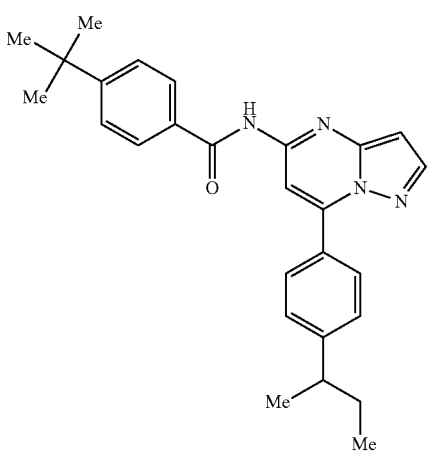

The titled compound was prepared using a procedure analogous to that described in connection with Example 46 except the corresponding boronic acid, ester or trifluoroborate salt was used as starting material. ESI-MS: m/z 427 (M+H)+.

Example 73

4-tert-butyl-N-(7-(isoquinolin-4-yl)pyrazolo[1,5-a]pyrimidin-5-yl)benzamide (59)

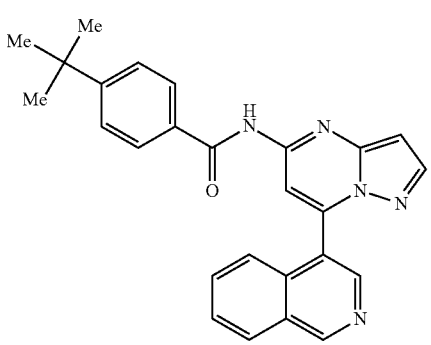

The titled compound was prepared using a procedure analogous to that described in connection with Example 46 except the corresponding boronic acid, ester or trifluoroborate salt was used as starting material. ESI-MS: m/z 422 (M+H)$^+$.

Example 74

4-tert-butyl-N-(7-(4-isobutyl-3-nitrophenyl)pyrazolo[1,5-a]pyrimidin-5-yl)benzamide (60)

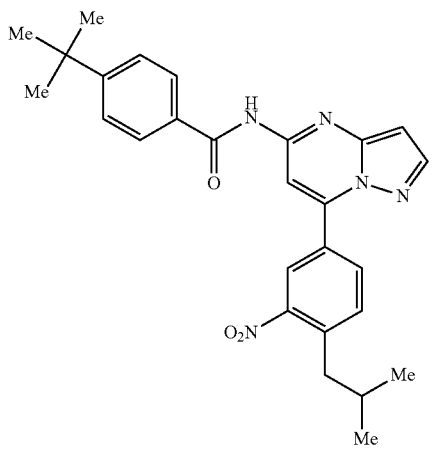

The titled compound was prepared using a procedure analogous to that described in connection with Example 46 except the corresponding boronic acid, ester or trifluoroborate salt was used as starting material. ESI-MS: m/z 472 (M+H)$^+$.

Example 75

4-tert-butyl-N-(7-(2-formylphenyl)pyrazolo[1,5-a]pyrimidin-5-yl)benzamide (61)

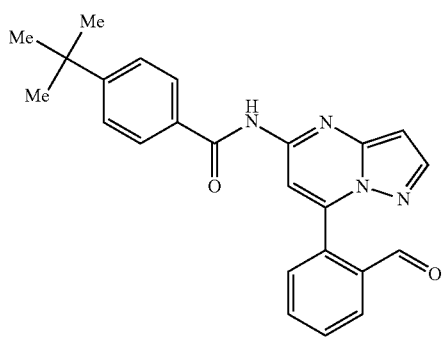

The titled compound was prepared using a procedure analogous to that described in connection with Example 46 except the corresponding boronic acid, ester or trifluoroborate salt was used as starting material. ESI-MS: m/z 399 (M+H)$^+$.

Example 76

4-tert-butyl-N-(7-(3-(methylsulfonamido)phenyl)pyrazolo[1,5-a]pyrimidin-5-yl)benzamide (62)

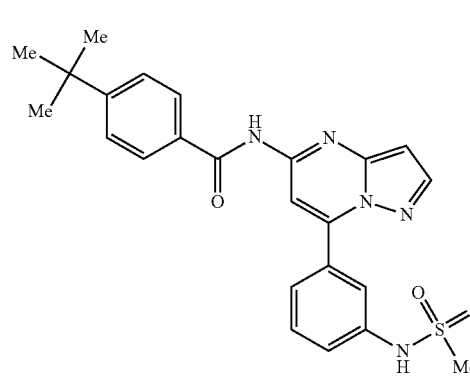

The titled compound was prepared using a procedure analogous to that described in connection with Example 46 except the corresponding boronic acid, ester or trifluoroborate salt was used as starting material. ESI-MS: m/z 464 (M+H)$^+$.

Example 77

N-(7-(1-benzyl-1H-pyrazol-4-yl)pyrazolo[1,5-a]pyrimidin-5-yl)-4-tert-butylbenzamide (63)

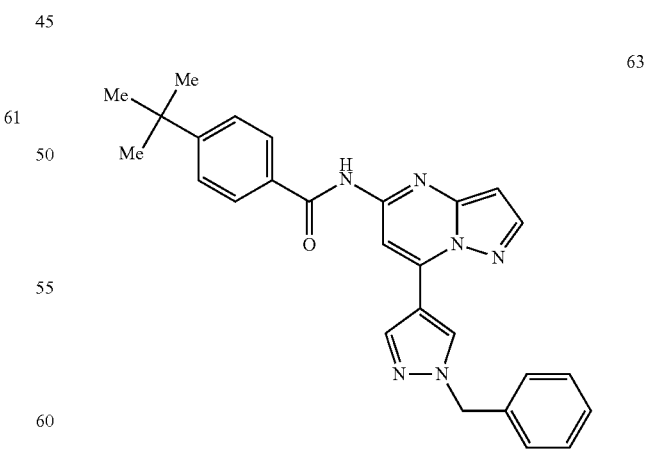

The titled compound was prepared using a procedure analogous to that described in connection with Example 46 except the corresponding boronic acid, ester or trifluoroborate salt was used as starting material. ESI-MS: m/z 451 (M+H)$^+$.

Example 78

N-(7-(3,4-dihydroisoquinolin-2(1H)-yl)pyrazolo[1,5-a]pyrimidin-5-yl)-4-(2-hydroxypropan-2-yl)benzamide (64)

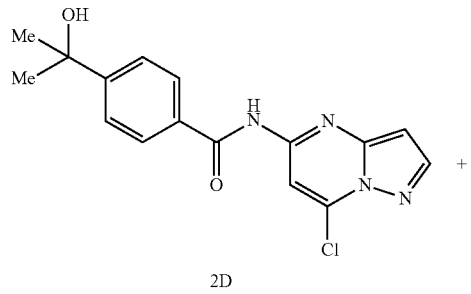

2D

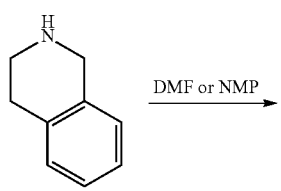

DMF or NMP →

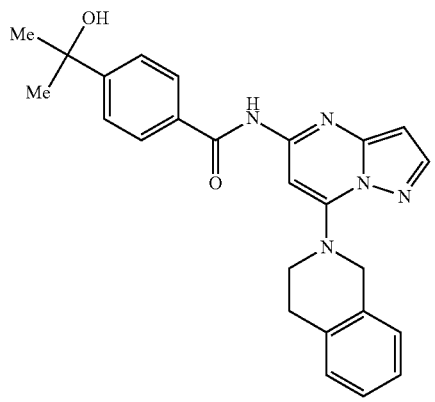

64

N-(7-chloropyrazolo[1,5-a]pyrimidin-5-yl)-4-(2-hydroxypropan-2-yl)benzamide (2D, 50 mg, 1.0 equivalent) and 1,2,3,4-tetrahydroisoquinoline (2.0 equivalent) were dissolved in dry DMF (0.1 M) or NMP (0.1 M) under nitrogen. Triethylamine (6.0 equivalents) was added if the starting amine was used as an acid salt. The mixture was heated for 3 hours at 100° C. The mixture was then filtered and the filtrate was purified by preparatory LC-MS. TFA salt of the titled compound (66%) was obtained as a white solid. $^1$H NMR (400 MHz, MeOD) δ ppm 1.57 (s, 6 H) 3.11-3.20 (m, 2 H) 4.27-4.41 (m, 2 H) 5.08-5.17 (m, 2 H) 6.49 (br. s., 1 H) 6.90 (br. s., 1 H) 7.20-7.27 (m, 4 H) 7.70 (d, 2 H) 7.99 (d, 2 H) 8.08-8.12 (m, 1 H). ESI-MS: m/z 428.0 (M+H)$^+$.

Example 79

4-tert-butyl-N-(7-morpholinopyrazolo[1,5-a]pyrimidin-5-yl)benzamide, trifluoroacetate salt (65)

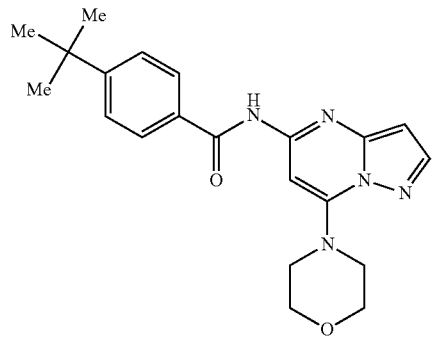

65

The titled compound was prepared using a procedure analogous to that described in connection with Example 78 except that 4-tert-butyl-N-(7-chloropyrazolo[1,5-a]pyrimidin-5-yl)benzamide (1F) and morpholine were used as starting materials. TFA salt of the titled compound was obtained as a white solid (19%). $^1$H NMR (400 MHz, MeOD) δ ppm 1.37 (s, 9 H) 3.65-3.82 (m, 4 H) 3.87-4.00 (m, 4 H) 6.35 (d, 1 H) 7.40 (s, 1 H) 7.57 (d, 2 H) 7.91 (d, 2 H) 8.01 (d, 1 H). ESI-MS: m/z 382.0 (M+H)$^+$.

Example 80

4-tert-butyl-N-(7-(3,4-dihydroisoquinolin-2(1H)-yl)pyrazolo[1,5-a]pyrimidin-5-yl)benzamide (66)

1F

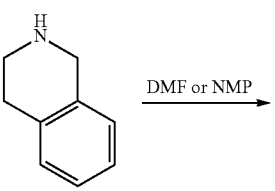

DMF or NMP →

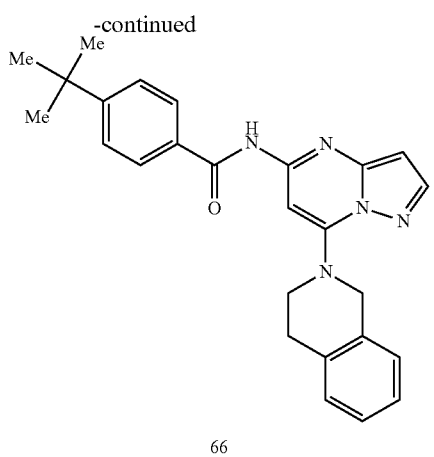

66

The titled compound was prepared using a procedure analogous to that described in connection with Example 78 except that 4-tert-butyl-N-(7-chloropyrazolo[1,5-a]pyrimidin-5-yl)benzamide (1F) was used as starting materials. TFA salt of the titled compound was obtained as a white solid. $^1$H NMR (400 MHz, MeOD) δ ppm 1.37 (s, 9 H) 3.09-3.23 (m, 2 H) 4.25-4.40 (m, 2 H) 5.04-5.19 (m, 2 H) 6.50 (br. s., 1 H) 6.86 (br. s., 1 H) 7.17-7.28 (m, 4 H) 7.62 (d, J=8.59 Hz, 2 H) 7.97 (d, J=8.34 Hz, 2 H) 8.06-8.15 (m, 1 H). ESI-MS: m/z 426.0. (M+H)$^+$.

Example 81

(S)-N-(7-(2-(hydroxymethyl)pyrrolidin-1-yl)pyrazolo[1,5-a]pyrimidin-5-yl)-4-(2-hydroxypropan-2-yl)benzamide (67)

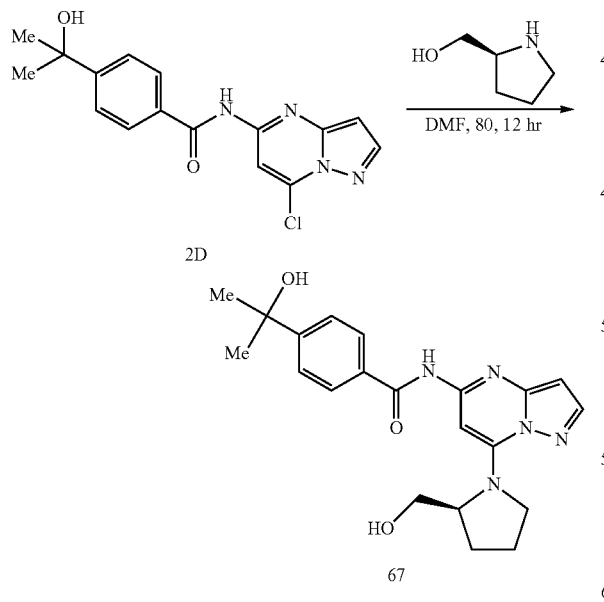

67

N-(7-chloropyrazolo[1,5-a]pyrimidin-5-yl)-4-(2-hydroxypropan-2-yl)benzamide (2D, 1.0 equivalent) and (S)-pyrrolidin-2-ylmethanol (2.0 equivalents) were dissolved in DMF (0.1 M with respect to 2D) and heated to 80° C. for 18 h. After cooling to room temperature, the crude mixture was filtered and the filtrate was purified by preparatory LC-MS to give the TFA salt of the titled compound (71%) as a white solid. $^1$H NMR (400 MHz, DMSO-d$_6$) δ ppm 1.46 (s, 6 H) 1.96 (br. s., 1 H) 2.10 (br. s., 3 H) 3.42-3.52 (m, 1 H) 3.55-3.64 (m, 1 H) 3.81 (br. s., 1 H) 3.95 (br. s., 1 H) 5.06 (br. s., 1 H) 6.30-6.36 (m, 1 H) 6.95 (s, 1 H) 7.59-7.67 (m, 2 H) 7.96-8.02 (m, 2 H) 8.02-8.09 (m, 1 H) 10.92 (br. s., 1 H). ESI-MS: m/z 396.2 (M+H)$^+$.

Example 82

(R)-N-(7-(2-(hydroxymethyl)pyrrolidin-1-yl)pyrazolo[1,5-a]pyrimidin-5-yl)-4-(2-hydroxypropan-2-yl)benzamide (68)

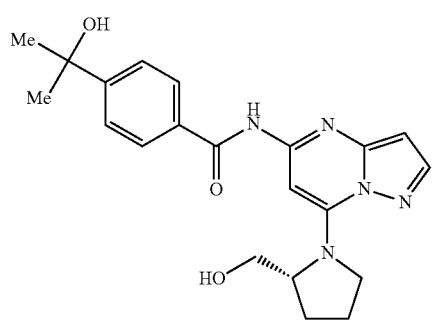

68

The titled compound was prepared using a procedure analogous to that described for Example 78 except that N-(7-chloropyrazolo[1,5-a]pyrimidin-5-yl)-4-(2-hydroxypropan-2-yl)benzamide (2D) and (R)-pyrrolidin-2-ylmethanol were used as starting materials. After cooling to room temperature, the crude mixture was filtered and the filtrate was purified by preparatory LC-MS to give the TFA salt of the titled compound (54%) as a white solid. $^1$H NMR (400 MHz, DMSO-d$_6$) δ ppm 1.47 (s, 6 H) 1.96 (br. s., 1 H) 2.08 (br. s., 3 H) 3.46 (dd, J=10.74, 6.44 Hz, 1 H) 3.53-3.62 (m, 1 H) 3.79 (br. s., 1 H) 3.93 (br. s., 1 H) 5.05 (br. s., 1 H) 6.30 (d, J=2.27 Hz, 1 H) 6.96 (s, 1 H) 7.61 (d, J=8.34 Hz, 2 H) 7.98 (d, J=8.34 Hz, 2 H) 8.03 (d, J=2.27 Hz, 1 H) 10.88 (s, 1 H). ESI-MS: m/z 396.2 (M+H)$^+$.

Example 83

(R)-4-(2-hydroxypropan-2-yl)-N-(7-(3-hydroxypyrrolidin-1-yl)pyrazolo[1,5-a]pyrimidin-5-yl)benzamide (69)

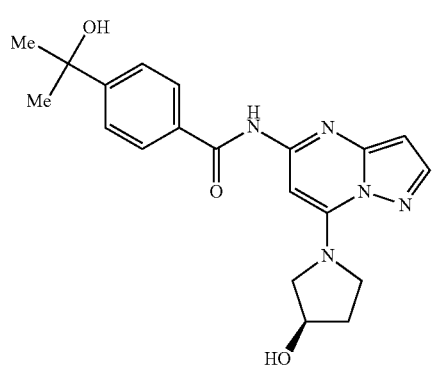

69

The titled compound was prepared using a procedure analogous to that described for Example 81 except that (R)-pyrrolidin-3-ol was used as starting material. After cooling to room temperature, the crude mixture was filtered and the filtrate was purified by preparatory LC-MS to give the TFA salt of the titled compound (78%) as a white solid. ¹H NMR (400 MHz, DMSO-d₆) δ ppm 1.39 (s, 6 H) 1.93 (d, J=3.03 Hz, 2 H) 3.94 (br. s., 4 H) 4.38 (br. s., 1 H) 6.24 (br. s., 1 H) 6.76 (br. s., 1 H) 7.49-7.64 (m, 2 H) 7.85-8.04 (m, 3 H) 10.85 (br. s., 1 H). ESI-MS: m/z 382.1 (M+H)⁺.

Example 84

(S)-4-(2-hydroxypropan-2-yl)-N-(7-(3-hydroxypyrrolidin-1-yl)pyrazolo[1,5-a]pyrimidin-5-yl)benzamide (70)

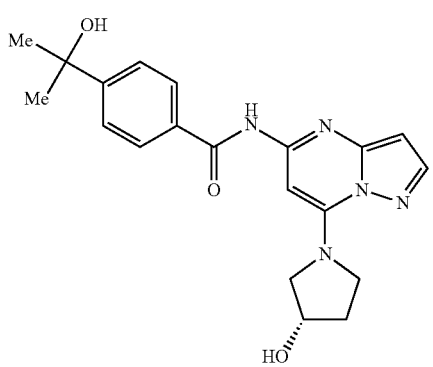

70

The titled compound was prepared using a procedure analogous to that described for Example 78 except that N-(7-chloropyrazolo[1,5-a]pyrimidin-5-yl)-4-(2-hydroxypropan-2-yl)benzamide (2D) and (S)-pyrrolidin-3-ol were used as starting materials. After cooling to room temperature, the crude mixture was filtered and the filtrate was purified by PREP LC-MS to give the TFA salt of the titled compound (75%) as a white solid. ¹H NMR (400 MHz, DMSO-d₆) δ ppm 1.47 (s, 6 H) 1.94-2.10 (m, 2 H) 3.88-4.13 (m, 4 H) 4.44 (br. s., 2 H) 6.27 (br. s., 1 H) 6.90 (br. s., 1 H) 7.61 (br. s., 2 H) 8.01 (br. s., 3 H) 10.81 (br. s., 1 H). ESI-MS: m/z 382.1 (M+H)⁺.

Example 85

N-(7-(4-(2-hydroxyethyl)piperidin-1-yl)pyrazolo[1,5-a]pyrimidin-5-yl)-4-(2-hydroxypropan-2-yl)benzamide (71)

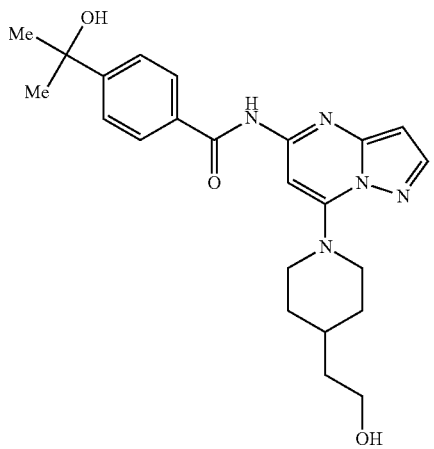

71

The titled compound was prepared using a procedure analogous to that described for Example 78 except that 2-(piperidin-4-yl)ethanol was used as starting material. After cooling to room temperature, the crude mixture was filtered and the filtrate was purified by preparatory LC-MS to give the TFA salt of the titled compound (78%) as a white solid. ¹H NMR (400 MHz, DMSO-d₆) δ ppm 1.30-1.39 (m, 4 H) 1.45 (s, 6 H) 1.75 (br. s., 1 H) 1.85 (d, J=13.39 Hz, 2 H) 3.07 (t, J=12.38 Hz, 2 H) 3.42-3.58 (m, 2 H) 4.49 (d, J=11.62 Hz, 2 H) 6.33-6.42 (m, 1 H) 7.34 (d, J=3.28 Hz, 1 H) 7.57-7.64 (m, 2 H) 7.96-8.05 (m, 2 H) 8.05-8.14 (m, 1 H) 10.90 (d, J=2.02 Hz, 1 H). ESI-MS: m/z 424.2 (M+H)⁺.

Example 86

4-(2-hydroxypropan-2-yl)-N-(7-morpholinopyrazolo[1,5-a]pyrimidin-5-yl)benzamide (72)

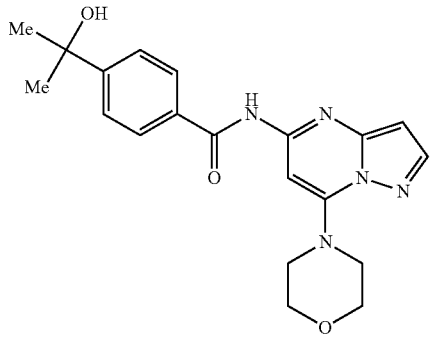

72

N-(7-Chloropyrazolo[1,5-a]pyrimidin-5-yl)-4-(2-hydroxypropan-2-yl)benzamide (2D) (1.0 equivalent) and morpholine (2.0 equivalent) were dissolved in dry n-butanol (0.1 M) under nitrogen. The mixture was heated to 100° C. for 18 h. Next day, lower temperature to room temperature, and product precipitates. The precipitate was collected by filtration and then washed with diethyl ether to give the titled compound (54%) as a pink solid. Melting point (225.0-229° C.). $^1$H NMR (400 MHz, MeOD) δ ppm 3.31 (s, 6 H) 3.70-3.79 (m, 4 H) 3.90-3.98 (m, 4 H) 6.35 (d, J=2.27 Hz, 1 H) 7.40 (s, 1 H) 7.66 (d, J=8.59 Hz, 2 H) 7.94 (d, J=8.59 Hz, 2 H) 8.01 (d, J=2.27 Hz, 1 H). ESI-MS: m/z 382.2 (M+H)$^+$.

Example 87

N-(7-(4-hydroxypiperidin-1-yl)pyrazolo[1,5-a]pyrimidin-5-yl)-4-(2-hydroxypropan-2-yl)benzamide (73)

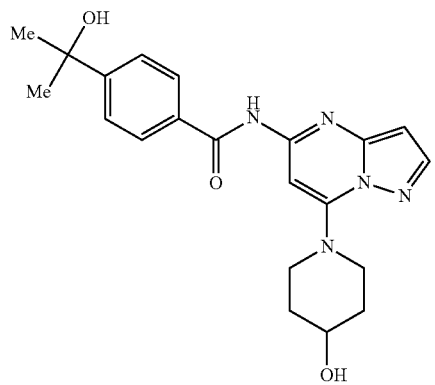

73

The titled compound was prepared using a procedure analogous to that described for Example 78 except that piperidin-4-ol was used as starting materials. After cooling to room temperature, the crude mixture was filtered and the filtrate was purified by silica gel column to give the titled compound (13%) as a white solid. $^1$H NMR (400 MHz, MeOD) δ ppm 1.56 (s, 6 H) 1.70-1.84 (m, 2 H) 2.01-2.13 (m, 2 H) 3.36-3.47 (m, 2 H) 3.88-3.97 (m, 1 H) 4.13-4.26 (m, 2 H) 6.33 (d, J=2.02 Hz, 1 H) 7.38 (s, 1 H) 7.66 (d, 2 H) 7.94 (d, 2 H) 7.98-8.01 (m, J=2.02 Hz, 1 H). ESI-MS: m/z 396.2 (M+H)$^+$.

Example 88

N-(7-(2-(2-hydroxyethyl)piperidin-1-yl)pyrazolo[1,5-a]pyrimidin-5-yl)-4-(2-hydroxypropan-2-yl)benzamide (74)

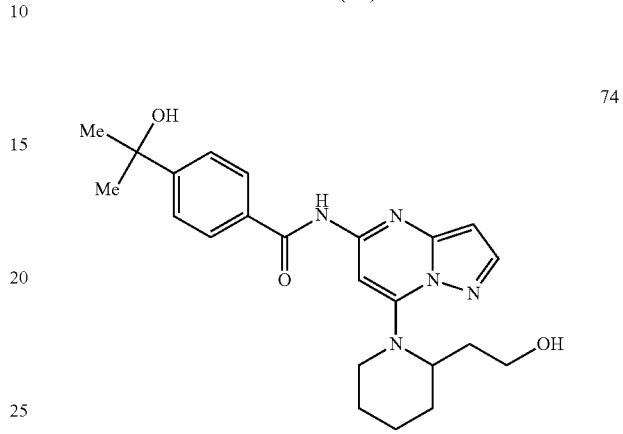

74

The titled compound was prepared using a procedure analogous to that described for Example 78 except that 2-(piperidin-2-yl)ethanol was used as starting materials. After cooling to room temperature, the crude mixture was filtered and the filtrate was purified by silica gel column to give the titled compound (33%) as a white solid. $^1$H NMR (400 MHz, MeOD) δ ppm 1.57 (s, 6 H) 1.67-2.05 (m, 7 H) 2.30 (dd, J=14.15, 8.59 Hz, 1 H) 3.46-3.60 (m, 1 H) 3.66 (t, J=5.94 Hz, 2 H) 4.35-4.54 (m, 1 H) 5.24 (br. s., 1 H) 6.51 (d, J=2.02 Hz, 1 H) 6.88 (br. s., 1 H) 7.70 (d, J=8.34 Hz, 2 H) 8.00 (d, J=8.34 Hz, 2 H) 8.07 (d, J=1.26 Hz, 1 H). ESI-MS: m/z 424.3 (M+H)$^+$.

Example 89

(S)-4-tert-butyl-N-(7-(3-hydroxypiperidin-1-yl)pyrazolo[1,5-a]pyrimidin-5-yl)benzamide (75)

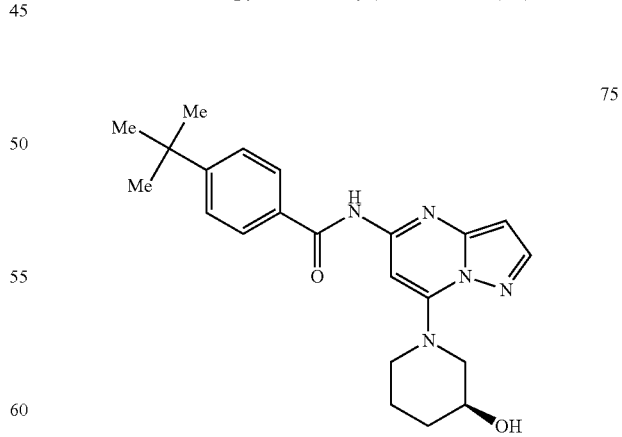

75

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. The titled compound was obtained as a TFA salt that was a white solid (42%). $^1$H NMR (400 MHz, MeOD) δ ppm 1.37 (s, 9 H) 1.60-1.84 (m, 2 H) 2.00-2.19 (m, 2 H) 3.72-3.84 (m, 1 H) 3.89-4.01 (m, 2 H) 4.02-4.13 (m, 1 H) 4.25-4.36 (m, 1 H) 6.51 (br. s., 1 H) 6.81 (br. s., 1 H) 7.63 (d, 2 H) 7.97 (d, 2 H) 8.06-8.12 (m, 1 H). ESI-MS: m/z 394.2 (M+H)$^+$.

Example 90

(R)-N-(7-(3-hydroxypiperidin-1-yl)pyrazolo[1,5-a]pyrimidin-5-yl)-4-(2-hydroxypropan-2-yl)benzamide (76)

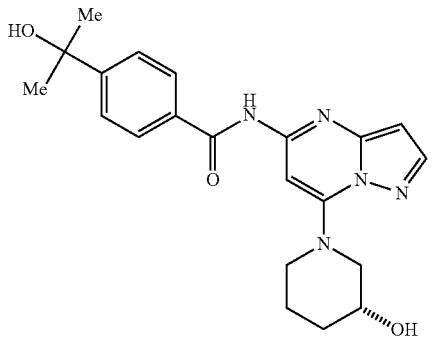

76

The titled compound was prepared using a procedure analogous to that described for Example 78 except that (R)-piperidin-3-ol was used as starting materials. After cooling to room temperature, the crude mixture was filtered and the filtrate was purified by preparatory LC-MS to give the TFA salt of the titled compound (42%) as a white solid. $^1$H NMR (400 MHz, MeOD) δ ppm 1.53-1.61 (m, 6 H) 1.68-1.85 (m, 2 H) 2.00-2.19 (m, 2 H) 3.84-4.14 (m, 4 H) 4.28-4.38 (m, 1 H) 6.52-6.57 (m, J=2.02 Hz, 1 H) 6.71 (s, 1 H) 7.71 (d, J=8.59 Hz, 2 H) 8.01 (d, J=8.84 Hz, 2 H) 8.08-8.12 (m, J=1.77 Hz, 1 H). ESI-MS: m/z 396.2 (M+H)$^+$.

Example 91

(R)-4-tert-butyl-N-(7-(3-hydroxypiperidin-1-yl)pyrazolo[1,5-a]pyrimidin-5-yl)benzamide (77)

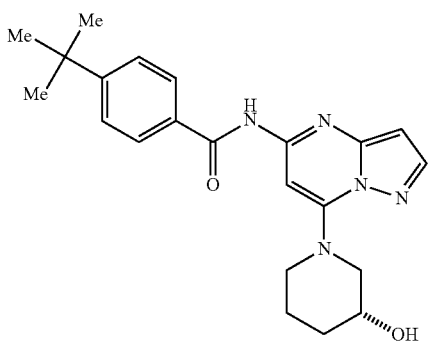

77

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. The product was obtained as a TFA salt that was a white solid (35%). $^1$H NMR (400 MHz, MeOD) δ ppm 1.38 (s, 9 H) 1.65-1.90 (m, 2 H) 2.00-2.21 (m, 2 H) 3.70-4.17 (m, 4 H) 4.33 (d, J=10.36 Hz, 1 H) 6.54 (d, J=2.02 Hz, 1 H) 6.75 (s, 1 H) 7.59-7.67 (m, 2 H) 7.97 (d, 2 H) 8.10 (d, J=1.77 Hz, 1 H). ESI-MS: m/z 394.3 (M+H)$^+$.

Example 92

(S)-N-(7-(3-hydroxypiperidin-1-yl)pyrazolo[1,5-a]pyrimidin-5-yl)-4-(2-hydroxypropan-2-yl)benzamide (78)

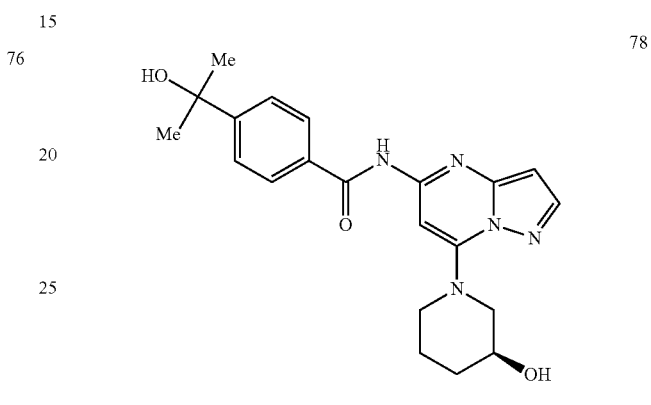

78

The titled compound was prepared using a procedure analogous to that described for Example 78 except that N-(7-chloropyrazolo[1,5-a]pyrimidin-5-yl)-4-(2-hydroxypropan-2-yl)benzamide (2D) and (S)-piperidin-3-ol were used as starting materials. After cooling to room temperature, the crude mixture was filtered and the filtrate was purified by preparatory LC-MS to give the TFA salt of the titled compound (43%) as a white solid. $^1$H NMR (400 MHz, MeOD) δ ppm 1.52-1.60 (m, 6 H) 1.67-1.85 (m, 2 H) 1.95-2.22 (m, 3 H) 3.85 (d, J=8.08 Hz, 1 H) 3.92-4.16 (m, 3 H) 4.33 (d, J=10.11 Hz, 1 H) 6.76 (br. s., 1 H) 7.71 (d, J=8.34 Hz, 2 H) 8.01 (d, J=8.59 Hz, 2 H) 8.10 (s, 1 H). ESI-MS: m/z 396.2 (M+H)$^+$.

Example 93

N-(7-(6,7-dihydro-1H-pyrazolo[4,3-c]pyridin-5(4H)-yl)pyrazolo[1,5-a]pyrimidin-5-yl)-4-(2-hydroxypropan-2-yl)benzamide (79)

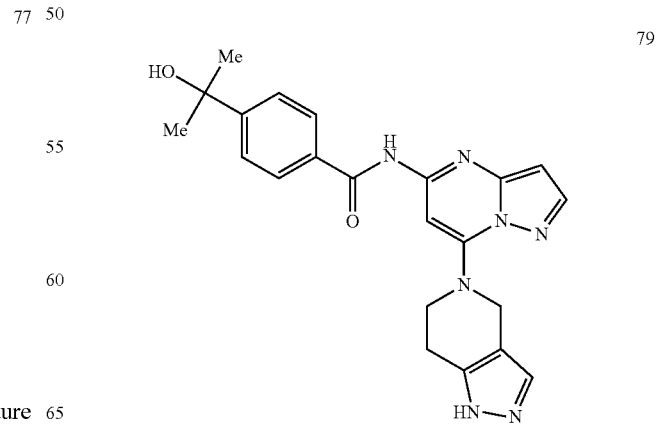

79

The titled compound was prepared using a procedure analogous to that described for Example 78 except that N-(7-chloropyrazolo[1,5-a]pyrimidin-5-yl)-4-(2-hydroxypropan-2-yl)benzamide (2D) and (S)-pyrrolidin-3-ol were used as starting materials. After cooling to room temperature, the crude mixture was filtered and the filtrate was purified by preparatory LC-MS to give the TFA salt of the titled compound (15%) as a yellow solid. $^1$H NMR (400 MHz, MeOD) δ ppm 1.57 (s, 6 H) 3.09-3.16 (m, 2 H) 4.45 (t, J=5.68 Hz, 2 H) 5.02 (s, 2 H) 6.55 (d, J=2.27 Hz, 1 H) 6.85 (s, 1 H) 7.61 (s, 1 H) 7.68-7.74 (m, 2 H) 7.98-8.04 (m, 2 H) 8.13 (d, J=2.27 Hz, 1 H). ESI-MS: m/z 418.0 (M+H)$^+$.

Example 94

4-(2-hydroxypropan-2-yl)-N-(7-(2-methylpiperidin-1-yl)pyrazolo[1,5-a]pyrimidin-5-yl)benzamide (80)

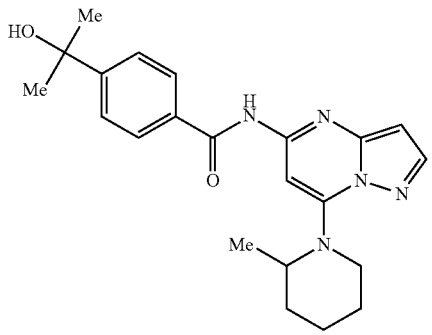

The titled compound was prepared using a procedure analogous to that described for Example 78 except that N-(7-chloropyrazolo[1,5-a]pyrimidin-5-yl)-4-(2-hydroxypropan-2-yl)benzamide (2D) and 2-methylpiperidine were used as starting materials. After cooling to room temperature, the crude mixture was filtered and the filtrate was purified by preparatory LC-MS to give the TFA salt of the titled compound (63%) as a white solid. $^1$H NMR (400 MHz, DMSO-d$_6$) δ ppm 1.22 (d, 3 H) 1.46 (s, 6 H) 1.55-1.96 (m, 6 H) 3.31-3.43 (m, 1 H) 3.88 (br. s., 1 H) 5.15 (br. s., 1 H) 6.34 (d, J=2.27 Hz, 1 H) 7.35 (s, 1 H) 7.60 (d, J=8.59 Hz, 2 H) 7.99 (d, J=8.59 Hz, 2 H) 8.07 (d, J=2.27 Hz, 1 H) 10.88 (s, 1 H). ESI-MS: m/z 394.4 (M+H)$^+$.

Example 95

N-(7-(3,5-dimethylpiperidin-1-yl)pyrazolo[1,5-a]pyrimidin-5-yl)-4-(2-hydroxypropan-2-yl)benzamide (81)

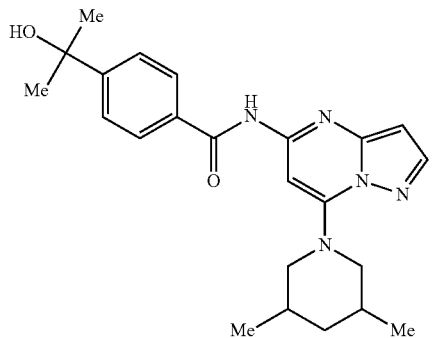

The titled compound was prepared using a procedure analogous to that described for Example 78 except that N-(7-chloropyrazolo[1,5-a]pyrimidin-5-yl)-4-(2-hydroxypropan-2-yl)benzamide (2D) and 3,5-dimethylpiperidine were used as starting materials. After cooling to room temperature, the crude mixture was filtered and the filtrate was purified by preparatory LC-MS to give the TFA salt of the titled compound (77%) as a yellow solid. $^1$H NMR (400 MHz, DMSO-d$_6$) δ ppm 0.94 (d, J=6.57 Hz, 6 H) 1.46 (s, 7 H) 1.85 (br. s., 3 H) 2.55 (s, 2 H) 4.37-4.46 (m, 2 H) 6.35 (d, J=2.27 Hz, 1 H) 7.38 (s, 1 H) 7.60 (d, J=8.59 Hz, 2 H) 8.00 (d, J=8.59 Hz, 2 H) 8.09 (d, J=2.27 Hz, 1 H) 10.89 (s, 1 H). ESI-MS: m/z 408.4 (M+H)$^+$.

Example 96

4-(2-hydroxypropan-2-yl)-N-(7-(3-methylpiperidin-1-yl)pyrazolo[1,5-a]pyrimidin-5-yl)benzamide (82)

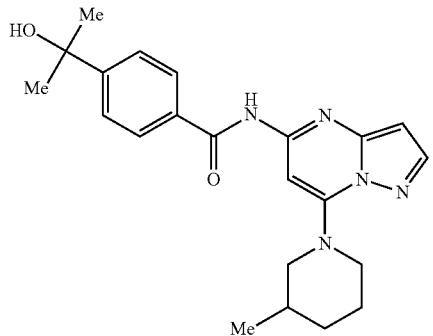

The titled compound was prepared using a procedure analogous to that described for Example 78 except that N-(7-chloropyrazolo[1,5-a]pyrimidin-5-yl)-4-(2-hydroxypropan-2-yl)benzamide (2D) and 3-methylpiperidine were used as starting materials. After cooling to room temperature, the crude mixture was filtered and the filtrate was purified by preparatory LC-MS to give the TFA salt of the titled compound (87%) as a white solid. ¹H NMR (400 MHz, DMSO-d₆) δ ppm 0.95 (d, J=6.32 Hz, 3 H) 1.19-1.32 (m, 1 H) 1.45 (s, 6 H) 1.57-1.92 (m, 4 H) 2.65-2.82 (m, 1 H) 2.95-3.13 (m, 1 H) 4.23-4.43 (m, 3 H) 6.34 (d, J=2.27 Hz, 1 H) 7.38 (s, 1 H) 7.60 (d, J=8.84 Hz, 2 H) 8.00 (d, J=8.59 Hz, 2 H) 8.08 (d, J=2.27 Hz, 1 H) 10.88 (s, 1 H); ESI-MS: m/z 394.4 (M+H)⁺.

Example 97

(R)-1-(5-(4-(2-hydroxypropan-2-yl)benzamido)pyrazolo[1,5-a]pyrimidin-7-yl)piperidine-3-carboxamide (83)

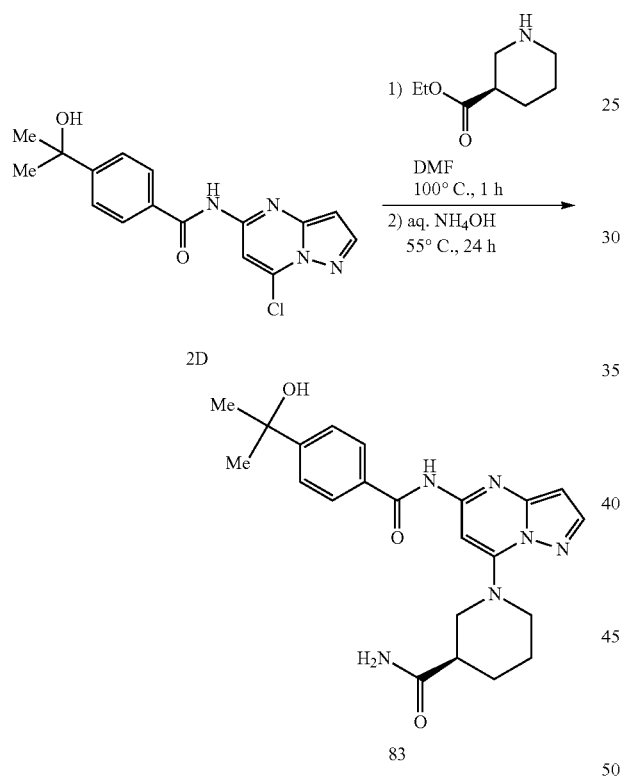

N-(7-chloropyrazolo[1,5-a]pyrimidin-5-yl)-4-(2-hydroxypropan-2-yl)benzamide (2D) and (R)-ethyl piperidine-3-carboxylate were dissolved in DMF (0.15 M with respect to 2D) and heated to 100° C. for 1 hr. After cooling to room temperature, 30% aqueous ammonium hydroxide (excess) was added and the mixture was heated to 55° C. for 18 h. After cooling to room temperature, reaction mixture was neutralized with 2N HCl and was extracted with EtOAc. Combined organic layers were dried over Na₂SO₄, filtered and concentrated. The crude product was purified by preparatory LC-MS to give the TFA salt of the titled compound (24%) as a white solid. ¹H NMR (400 MHz, DMSO-d₆) δ ppm 1.45 (s, 6 H) 1.71 (br. s., 2 H) 1.84 (br. s., 1 H) 1.99 (br. s., 1 H) 2.55 (br. s., 1 H) 2.98-3.12 (m, 1 H) 3.17-3.30 (m, 1 H) 4.30-4.37 (m, 2 H) 6.36 (s, 1 H) 6.96 (br. s., 1 H) 7.39 (s, 1 H) 7.50 (br. s., 1 H) 7.60 (d, J=5.31 Hz, 2 H) 7.96-8.04 (m, 2 H) 8.09 (s, 1 H) 10.89 (s, 1 H). ESI-MS: m/z 423.2 (M+H)⁺.

Example 98

(R)-1-(5-(4-(2-hydroxypropan-2-yl)benzamido)pyrazolo[1,5-a]pyrimidin-7-yl)piperidine-3-carboxylic acid (84)

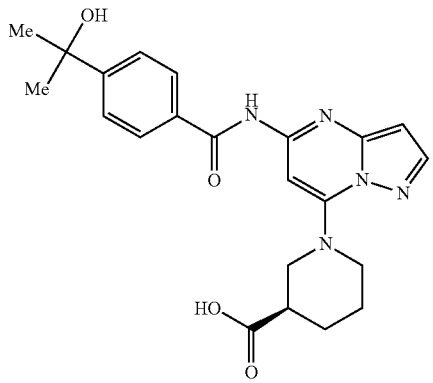

The titled compound was prepared using the same procedure as that described for Example 97. After purification by preparatory LC-MS, the TFA salt of the titled compound (5%) was obtained as a by-product as a white solid. ¹H NMR (400 MHz, DMSO-d₆) δ ppm 1.39 (s, 6 H) 1.61-1.71 (m, 2 H) 1.79 (br. s., 1 H) 2.01 (br. s., 1 H) 2.56-2.67 (m, 1 H) 3.13-3.28 (m, 2 H) 4.10 (d, J=11.37 Hz, 1 H) 4.41 (d, J=12.88 Hz, 1 H) 6.25-6.31 (m, 1 H) 7.35 (s, 1 H) 7.53 (d, J=8.34 Hz, 2 H) 7.93 (d, J=7.58 Hz, 2 H) 7.99-8.05 (m, 1 H) 10.80 (s, 1 H). ESI-MS: m/z 424.2 (M+H)⁺.

Example 99

(S)-1-(5-(4-(2-hydroxypropan-2-yl)benzamido)pyrazolo[1,5-a]pyrimidin-7-yl)piperidine-3-carboxamide (85)

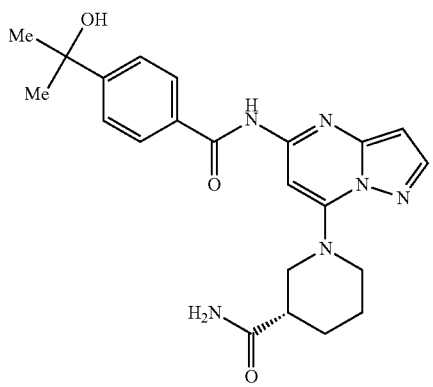

The titled compound was prepared using the same procedure as that described for Example 97 except that (S)-ethyl piperidine-3-carboxylate was used as starting material. After purification by preparatory LC-MS, the TFA salt of the titled compound (24%) was obtained as a white solid. ¹H NMR (400 MHz, DMSO-d₆) δ ppm 1.45 (s, 6 H) 1.71 (br. s., 2 H) 1.84 (br. s., 1 H) 1.98 (br. s., 1 H) 2.56 (br. s., 1 H) 3.01-3.12 (m, 1 H) 3.19-3.31 (m, 1 H) 4.28-4.43 (m, 2 H) 6.32-6.40 (m, 1 H) 6.96 (br. s., 1 H) 7.38 (s, 1 H) 7.49 (br. s., 1 H) 7.60 (d, J=8.08 Hz, 2 H) 8.00 (d, J=8.08 Hz, 2 H) 8.06-8.13 (m, 1 H) 10.90 (s, 1 H). ESI-MS: m/z 423.2 (M+H)⁺.

Example 100

(S)-1-(5-(4-(2-hydroxypropan-2-yl)benzamido)pyrazolo[1,5-a]pyrimidin-7-yl)piperidine-3-carboxylic acid (86)

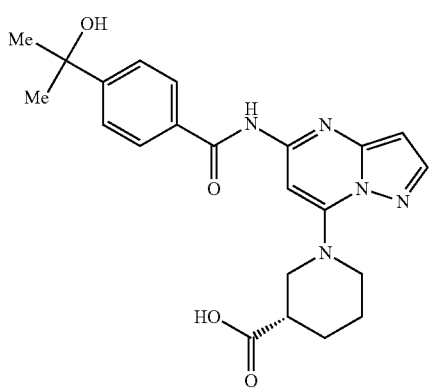

86

The titled compound was prepared using the same procedure as that described for Example 99. After purification by preparatory LC-MS, the TFA salt of the titled compound (14%) was obtained as a by-product as a white solid. ¹H NMR (400 MHz, DMSO-d₆) δ ppm 1.45 (s, 6 H) 1.67-1.79 (m, 2 H) 1.88 (br. s., 1 H) 2.08 (br. s., 1 H) 2.69 (br. s., 1 H) 3.19-3.39 (m, 2 H) 4.17 (d, J=13.14 Hz, 1 H) 4.48 (d, J=12.38 Hz, 1 H) 6.33-6.40 (m, 1 H) 7.39 (d, J=3.54 Hz, 1 H) 7.57-7.65 (m, 2 H) 7.97-8.05 (m, 2 H) 8.07-8.12 (m, 1 H) 10.89 (br. s., 1 H). ESI-MS: m/z 423.2 (M+H)⁺.

Example 101

4-(2-hydroxypropan-2-yl)-N-(7-(pyrrolidin-1-yl)pyrazolo[1,5-a]pyrimidin-5-yl)benzamide (87)

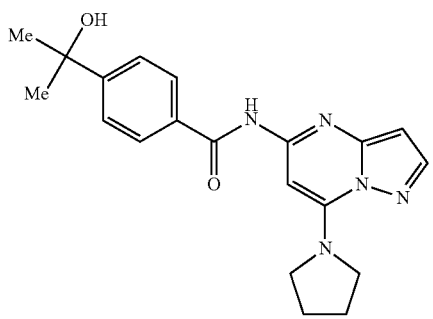

87

The titled compound was prepared using a procedure described for Example 78 except that N-(7-chloropyrazolo[1,5-a]pyrimidin-5-yl)-4-(2-hydroxypropan-2-yl)benzamide (2D) and the corresponding amine were used as starting materials. After cooling to room temperature, the crude mixture was filtered and the filtrate was purified by preparatory LC-MS to give the TFA salt of the titled compound (51%) as a white solid. ¹H NMR (400 MHz, DMSO-d₆) δ ppm 1.46 (s, 6 H) 1.90-2.08 (m, 4 H) 3.96 (br. s., 4 H) 6.27 (d, J=2.27 Hz, 1 H) 6.89 (s, 1 H) 7.54-7.69 (m, 2 H) 7.89-8.05 (m, 3 H) 10.84 (s, 1 H). ESI-MS: m/z 366.2 (M+H)⁺.

Example 102

N-(7-(cyclopropylamino)pyrazolo[1,5-a]pyrimidin-5-yl)-4-(2-hydroxypropan-2-yl)benzamide (88)

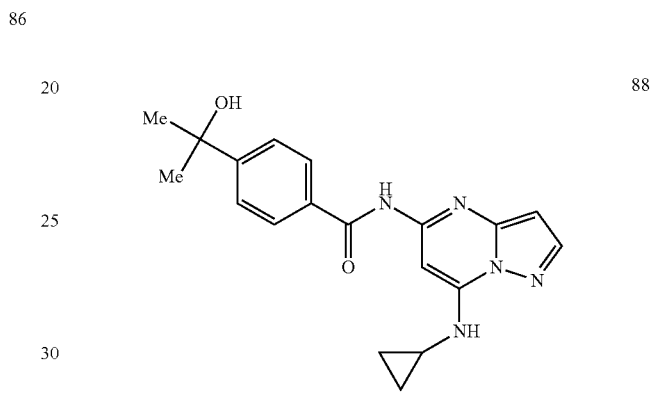

88

The titled compound was prepared using a procedure described for Example 78 except that N-(7-chloropyrazolo[1,5-a]pyrimidin-5-yl)-4-(2-hydroxypropan-2-yl)benzamide (2D) and the corresponding amine were used as starting materials. After cooling to room temperature, the crude mixture was filtered and the filtrate was purified by preparatory LC-MS to give the TFA salt of the titled compound (34%) as a white solid. ¹H NMR (400 MHz, DMSO-d₆) δ ppm 0.74-0.81 (m, 2 H) 0.84-0.92 (m, 2 H) 1.46 (s, 6 H) 2.72 (br. s., 1 H) 6.32 (d, J=2.27 Hz, 1 H) 7.32 (s, 1 H) 7.58-7.66 (m, 2 H) 7.97-8.03 (m, 2 H) 8.06 (d, J=2.27 Hz, 1 H) 8.61 (s, 1 H) 10.92 (s, 1 H). ESI-MS: m/z 352.2 (M+H)⁺.

Example 103

4-(2-hydroxypropan-2-yl)-N-(7-(4-oxo-3,4,7,8-tetrahydropyrido[4,3-d]pyrimidin-6(5H)-yl)pyrazolo[1,5-a]pyrimidin-5-yl)benzamide (89)

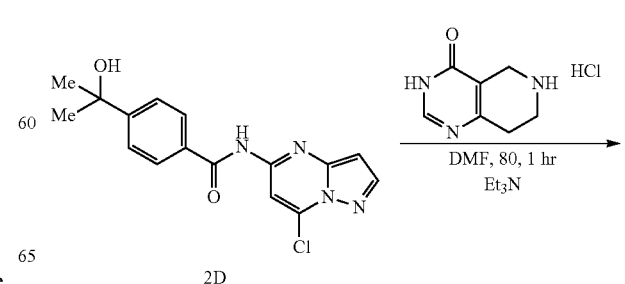

2D

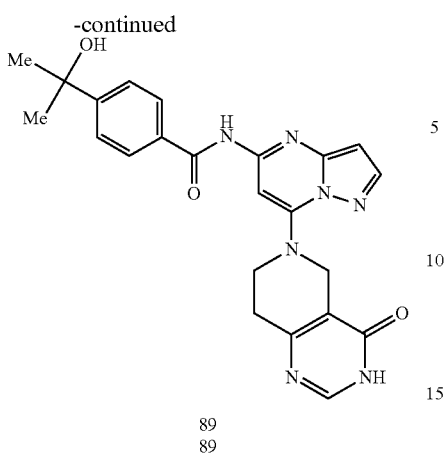

89

N-(7-chloropyrazolo[1,5-a]pyrimidin-5-yl)-4-(2-hydroxypropan-2-yl)benzamide (2D) (1.0 equivalent), 5,6,7,8-tetrahydropyrido[4,3-d]pyrimidin-4(3H)-one hydrochloride (2.0 equivalents), and triethylamine (6.0 eq) were dissolved in DMF (0.1 M with respect to 2D) and heated to 80° C. The reaction was completed after 1 hr. After cooling to room temperature, the crude mixture was filtered and the filtrate was purified by preparatory LC-MS to give the TFA salt of the titled compound (48%) as a white solid. $^1$H NMR (400 MHz, DMSO-d$_6$) δ ppm 1.46 (s, 6 H) 2.89 (t, J=5.56 Hz, 2 H) 4.13 (t, J=5.81 Hz, 2 H) 4.51 (s, 2 H) 6.38 (d, J=2.27 Hz, 1 H) 7.53 (s, 1 H) 7.59-7.62 (m, 2 H) 8.00-8.03 (m, 2 H) 8.11-8.17 (m, 2 H) 10.93 (s, 1 H). ESI-MS: m/z 446.2 (M+H)$^+$.

Example 104

4-(2-hydroxypropan-2-yl)-N-(7-(4-(methylsulfonyl)piperazin-1-yl)pyrazolo[1,5-a]pyrimidin-5-yl)benzamide (90)

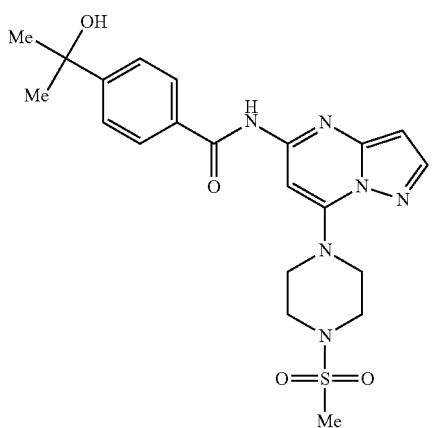

90

The titled compound was prepared using a procedure analogous to that described for Example 81 except that 1-(methylsulfonyl)piperazine was used as starting materials and the reaction was completed in 1 hr. After cooling to room temperature, the crude mixture was filtered and the filtrate was purified by preparatory LC-MS to give the TFA salt of the titled compound (59%) as a white solid. $^1$H NMR (400 MHz, DMSO-d$_6$) δ ppm 1.45 (s, 6 H) 2.98 (s, 3 H) 3.34-3.44 (m, 4 H) 3.79-3.90 (m, 4 H) 6.39 (d, J=2.27 Hz, 1 H) 7.44 (s, 1 H) 7.57-7.64 (m, 2 H) 7.95-8.03 (m, 2 H) 8.11 (d, J=2.27 Hz, 1 H) 10.96 (s, 1 H). ESI-MS: m/z 459.2 (M+H)$^+$.

Example 105

N-(7-(5,6-dihydro-[1,2,4]triazolo[4,3-a]pyrazin-7(8H)-yl)pyrazolo[1,5-a]pyrimidin-5-yl)-4-(2-hydroxypropan-2-yl)benzamide (91)

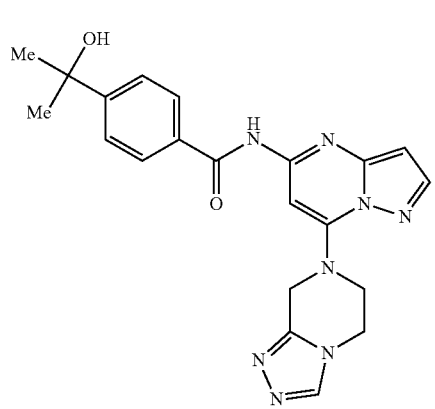

91

The titled compound was prepared using a procedure analogous to that described for Example 81 except that 5,6,7,8-tetrahydro-[1,2,4]triazolo[4,3-a]pyrazine was used as starting material and the reaction was completed in 1 hr. After cooling to room temperature, the crude mixture was filtered and purified by preparatory LC-MS to give the TFA salt of the titled compound (19%) as a white solid. $^1$HNMR (400 MHz, DMSO-d$_6$) δ ppm 1.46 (s, 6 H) 4.32 (t, J=5.18 Hz, 2 H) 4.40 (t, J=5.05 Hz, 2 H) 5.22 (s, 2 H) 6.43 (d, J=2.27 Hz, 1 H) 7.57 (s, 1 H) 7.59-7.62 (m, 2 H) 7.99-8.02 (m, 2 H) 8.16 (d, J=2.27 Hz, 1 H) 8.93 (s, 1 H) 11.02 (s, 1 H). ESI-MS: m/z 419.2 (M+H)$^+$.

Example 106

(S)-1-(5-(4-(2-hydroxypropan-2-yl)benzamido)pyrazolo[1,5-a]pyrimidin-7-yl)pyrrolidine-2-carboxamide (92)

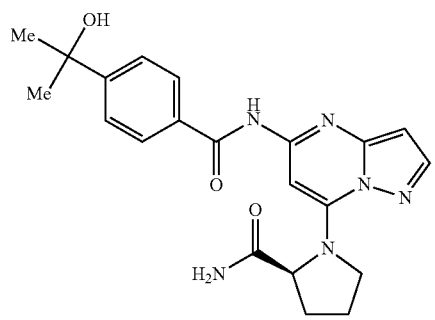

92

The titled compound was prepared using a procedure analogous to that described for Example 81 except that (S)-pyrrolidine-2-carboxamide was used as starting material and the reaction was completed in 12 hr. After cooling to room temperature, the crude mixture was filtered and the filtrate was purified by preparatory LC-MS to give the TFA salt of the titled compound (64%) as a white solid. $^1$H NMR (400 MHz, DMSO-d$_6$) δ ppm 1.45 (s, 6 H) 1.90-2.05 (m, 3 H) 2.23-2.34 (m, 1 H) 2.54 (d, J=4.55 Hz, 3 H) 3.82 (br. s., 1 H) 3.89 (br. s., 1 H) 5.45 (br. s., 1 H) 6.26 (d, J=2.27 Hz, 1 H) 6.95 (s, 1 H) 7.57-7.66 (m, 2 H) 7.95 (d, J=2.27 Hz, 2 H) 7.96-8.01 (m, 2 H) 10.90 (s, 1 H). ESI-MS: m/z 423.2 (M+H)$^+$.

Example 107

4-(2-hydroxypropan-2-yl)-N-(7-(5-oxo-1,4-diazepan-1-yl)pyrazolo[1,5-a]pyrimidin-5-yl)benzamide (93)

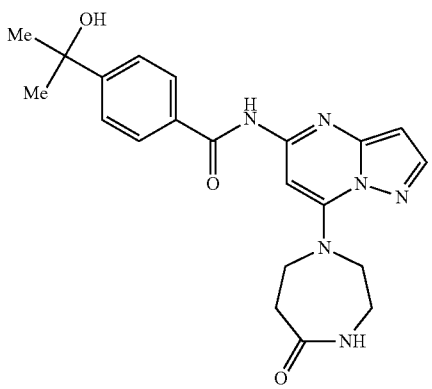

93

The titled compound was prepared using a procedure described for Example 78 except that N-(7-chloropyrazolo[1,5-a]pyrimidin-5-yl)-4-(2-hydroxypropan-2-yl)benzamide (2D) and 1,4-diazepan-5-one were used as starting materials and the reaction was completed in 2 hr. After cooling to room temperature, the crude mixture was filtered and the filtrate was purified by preparatory LC-MS to give the TFA salt of the titled compound (75%) as a white solid. $^1$H NMR (400 MHz, DMSO-d$_6$) δ ppm 1.46 (s, 6 H) 2.77 (br. s., 2 H) 3.41 (br. s., 2 H) 3.91 (br. s., 2 H) 3.96 (br. s., 2 H) 6.37 (d, J=2.27 Hz, 1 H) 7.35 (s, 1 H) 7.61 (m, 2 H) 7.75 (t, J=5.56 Hz, 1 H) 8.00 (m, 2 H) 8.10 (d, J=2.27 Hz, 1 H) 10.92 (s, 1 H). ESI-MS: m/z 409.2 (M+H)$^+$.

Example 108

4-(1-hydroxy-2-methylpropan-2-yl)-N-(2-methyl-7-(pyrrolidin-1-yl)pyrazolo[1,5-a]pyrimidin-5-yl)benzamide (94)

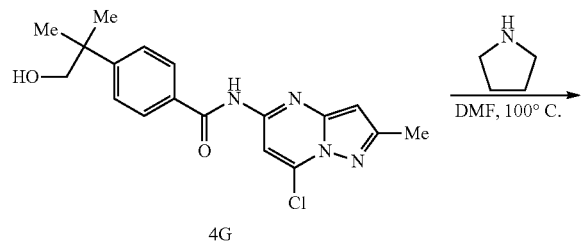

4G

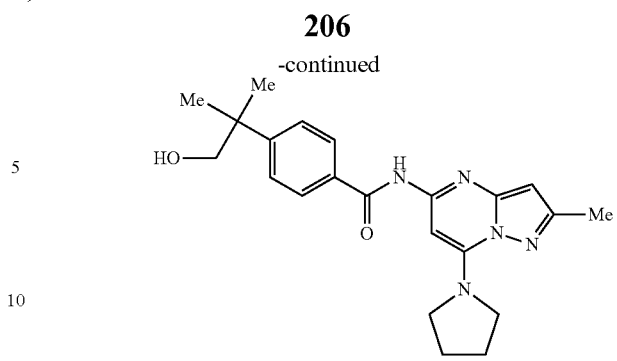

94

A solution of N-(7-chloro-2-methylpyrazolo[1,5-a]pyrimidin-5-yl)-4-(1-hydroxy-2-methylpropan-2-yl)benzamide (4G, 44 mg, 1.0 equivalent) and pyrrolidine (4.0 equivalents) in DMF (0.10 M with respect to 4G) was stirred at 80° C. for 1 h. After cooling, the mixture was diluted with methanol and purified by preparative LC-MS to afford the titled compound (76%) as a white solid. $^1$H NMR (400 MHz, DMSO-d$_6$) δ ppm 1.26 (s, 6 H), 1.85-2.07 (m, 4 H), 2.33 (s, 3 H), 3.47 (s, 2 H), 3.96 (br. s., 4 H), 6.13 (s, 1 H), 6.75 (s, 1 H), 7.53 (d, J=8.59 Hz, 2 H), 7.97 (d, J=8.59 Hz, 2 H), 10.89 (s, 1 H). ESI-MS: m/z 394.3 (M+H)$^+$.

Example 109

(S)-4-(1-hydroxy-2-methylpropan-2-yl)-N-(7-(2-(hydroxymethyl)pyrrolidin-1-yl)-2-methylpyrazolo[1,5-a]pyrimidin-5-yl)benzamide (95)

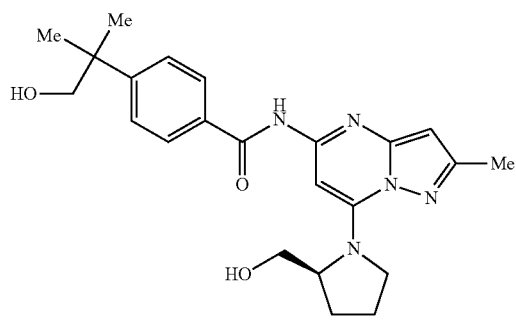

95

The title compound was prepared using a procedure analogous to that described in connection with Example 108 except that (S)-prolinol (3.0 equivalents) was used instead of pyrrolidine as a starting material to afford the title compound as a white solid. $^1$H NMR (400 MHz, DMSO-d$_6$) δ ppm 1.26 (s, 6 H), 1.86-2.00 (m, 1 H), 2.02-2.19 (m, 3 H), 2.35 (s, 3 H), 3.41-3.51 (m, 3 H), 3.53-3.63 (m, 1 H), 3.75-3.89 (m, 1 H), 3.97 (t, J=7.96 Hz, 1 H), 5.01 (br. s., 1 H), 6.18 (s, 1 H), 6.83

(s, 1 H), 7.54 (d, J=8.59 Hz, 2 H), 7.97 (d, J=8.59 Hz, 2 H), 10.96 (s, 1 H). ESI-MS: m/z 324.3 (M+H)⁺.

Example 110

(R)-ethyl 1-(5-(4-(1-hydroxy-2-methylpropan-2-yl) benzamido)-2-methylpyrazolo[1,5-a]pyrimidin-7-yl) piperidine-3-carboxylate (96)

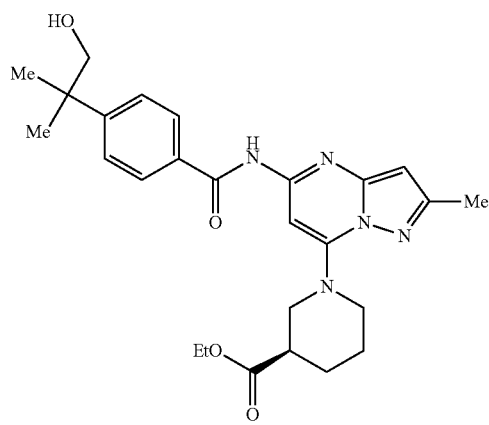

The title compound was prepared using a procedure analogous to that described in connection with Example 108 except that (R)-ethyl nipecotate (2.0 equivalents) was used instead of pyrrolidine as a starting material to afford the title compound as a white solid. ¹H NMR (400 MHz, DMSO-d₆) δ ppm 1.12 (t, J=7.07 Hz, 3 H), 1.25 (s, 6 H), 1.71-1.79 (m, 2 H), 1.82-1.90 (m, 1 H), 2.01-2.09 (m, 1 H), 2.37 (s, 3 H), 2.72-2.81 (m, 1 H), 3.28 (dd, J=12.76, 9.22 Hz, 1 H), 3.56 (dd, 1 H), 4.04 (dd, 2 H), 4.07-4.13 (m, 3 H), 4.38 (dd, J=12.63, 4.04 Hz, 2 H), 6.15 (s, 1 H), 7.34 (s, 1 H), 7.50 (d, J=8.59 Hz, 2 H), 7.98 (d, J=8.84 Hz, 2 H), 10.81 (s, 1 H). ESI-MS: m/z 480.3 (M+H)⁺.

Example 111

4-(1-hydroxy-2-methylpropan-2-yl)-N-(7-(3-hydroxyazetidin-1-yl)-2-methylpyrazolo[1,5-a]pyrimidin-5-yl)benzamide (97)

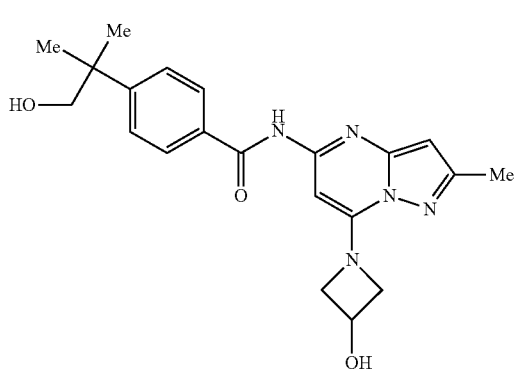

The title compound was prepared using a procedure analogous to that described in connection with Example 108 except that azetidin-3-ol (3.0 equivalents) was used instead of pyrrolidine as a starting material to afford the title compound as a white solid. ¹H NMR (400 MHz, DMSO-d₆) δ ppm 1.26 (s, 6 H), 2.33 (s, 3 H), 3.47 (s, 2 H), 4.21 (br. s., 2 H), 4.60-4.67 (m, 1 H), 4.73 (br. s., 2 H), 6.10 (s, 1 H), 6.57 (s, 1 H), 7.53 (d, J=8.59 Hz, 2 H), 7.97 (d, J=8.59 Hz, 2 H), 10.86 (s, 1 H). ESI-MS: m/z 396.2 (M+H)⁺.

Example 112

4-(1-hydroxy-2-methylpropan-2-yl)-N-(2-methyl-7-(4-oxo-3,4,7,8-tetrahydropyrido[4,3-d]pyrimidin-6 (5H)-yl)pyrazolo[1,5-a]pyrimidin-5-yl)benzamide (98)

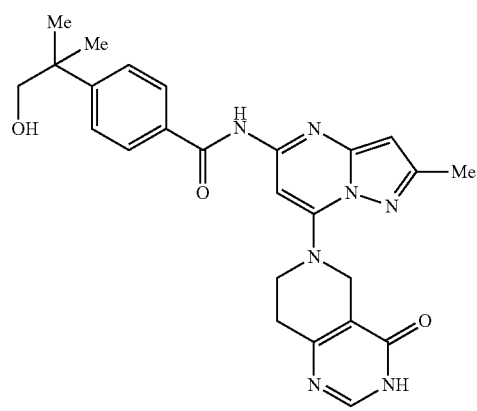

The title compound was prepared using a procedure analogous to that described in connection with Example 108 except that 5,6,7,8-tetrahydropyrido[4,3-d]pyrimidin-4(3H)-one (2.0 equivalents) was used instead of pyrrolidine as starting material to afford the title compound as a white solid. ¹H NMR (400 MHz, DMSO-d₆) δ ppm 1.26 (s, 6 H), 2.40 (s, 3 H), 2.88 (t, J=5.94 Hz, 2 H), 3.47 (d, J=5.31 Hz, 2 H), 4.10 (t, J=5.43 Hz, 2 H), 4.49 (s, 2 H), 4.75 (t, J=5.31 Hz, 1 H), 6.18 (s, 1 H), 7.46 (s, 1 H), 7.51 (d, J=8.84 Hz, 2 H), 8.00 (d, J=8.59

Hz, 2 H), 8.13 (d, J=3.03 Hz, 1 H), 10.85 (s, 1 H), 12.59 (br. s., 1 H). ESI-MS: m/z 474.1 (M+H)+.

Example 113

4-(1-hydroxy-2-methylpropan-2-yl)-N-(2-methyl-7-morpholinopyrazolo[1,5-a]pyrimidin-5-yl)benzamide (99)

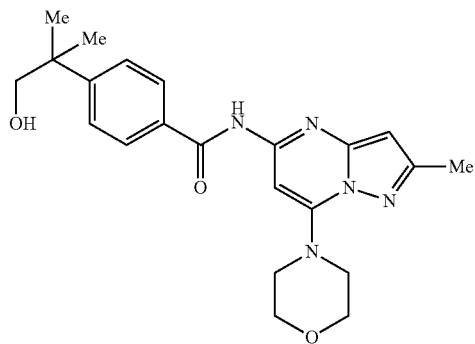

The title compound was prepared using a procedure analogous to that described in connection with Example 108 except that morpholine (4.0 equivalents) was used instead of pyrrolidine as starting material to afford the titled compound as a white solid. $^1$H NMR (400 MHz, DMSO-d$_6$) δ ppm 1.25 (s, 6 H), 2.38 (s, 3 H), 3.46 (d, J=5.31 Hz, 2 H), 3.72 (dd, J=5.81, 3.28 Hz, 4 H), 3.79-3.88 (m, 4 H), 4.75 (t, J=5.31 Hz, 1 H), 6.17 (s, 1 H), 7.36 (s, 1 H), 7.50 (d, J=8.84 Hz, 2 H), 7.99 (d, J=8.59 Hz, 2 H), 10.85 (s, 1 H). ESI-MS: m/z 410.0 (M+H)+.

Example 114

(R)-4-(1-hydroxy-2-methylpropan-2-yl)-N-(7-(3-hydroxypyrrolidin-1-yl)-2-methylpyrazolo[1,5-a]pyrimidin-5-yl)benzamide (100)

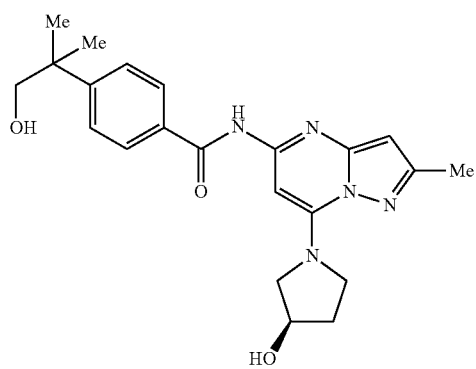

The title compound was prepared using a procedure analogous to that described in connection with Example 108 except that (R)-pyrrolidin-3-ol (4.00 equivalents) was used instead of pyrrolidine as starting material to afford the title compound (43%) as a pink solid. $^1$H NMR (400 MHz, DMSO-d$_6$) δ ppm 1.25 (s, 6 H), 1.89-2.09 (m, 2 H), 2.32 (s, 3 H), 3.46 (d, J=5.31 Hz, 2 H), 3.83-4.07 (m, 4 H), 4.41 (br. s., 1 H), 4.74 (t, J=5.31 Hz, 1 H), 5.08 (d, J=3.54 Hz, 1 H), 5.97 (s, 1 H), 6.99 (s, 1 H), 7.49 (d, J=8.59 Hz, 2 H), 7.97 (d, J=8.84 Hz, 2 H), 10.55 (s, 1 H). ESI-MS: m/z 410.0 (M+H)+.

Example 115

4-(1-hydroxy-2-methylpropan-2-yl)-N-(7-(4-(2-hydroxyethyl)piperidin-1-yl)-2-methylpyrazolo[1,5-a]pyrimidin-5-yl)benzamide (101)

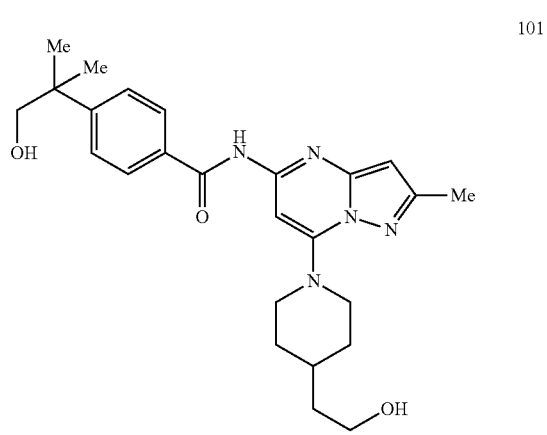 [SMILES: Cc1cc2nc(NC(=O)c3ccc(C(C)(C)CO)cc3)cc(N3CCC(CCO)CC3)n2n1]

The title compound was prepared using a procedure analogous to that described in connection with Example 108 except that 2-(piperidin-4-yl)ethanol (4.00 equivalents) was used instead of pyrrolidine as starting material to afford the titled compound (76%) as a white solid. $^1$H NMR (400 MHz, DMSO-d$_6$) δ ppm 1.26 (s, 6 H), 1.29-1.41 (m, 2 H), 1.44 (q, J=6.57 Hz, 2 H), 1.69-1.80 (m, 1 H), 1.84 (d, J=13.39 Hz, 2 H), 2.38 (s, 3 H), 2.99-3.12 (m, 2 H), 3.47 (s, 2 H), 3.50 (t, J=6.57 Hz, 2 H), 4.49 (d, J=12.38 Hz, 2 H), 6.18 (s, 1 H), 7.23 (s, 1 H), 7.52 (d, J=8.84 Hz, 2 H), 7.98 (d, J=8.59 Hz, 2 H), 10.88 (s, 1 H); ESI-MS: m/z 452.1 (M+H)+.

Example 116

4-tert-butyl-N-(7-(piperidin-1-yl)pyrazolo[1,5-a]pyrimidin-5-yl)benzamide (102)

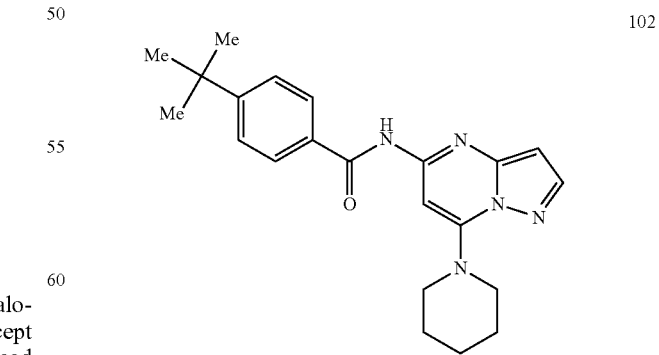

The titled compound was prepared using a procedure analogous to that described in connection with Example 78 except that 4-tert-butyl-N-(7-chloropyrazolo[1,5-a]pyrimi-

Example 117

4-tert-butyl-N-(7-morpholinopyrazolo[1,5-a]pyrimidin-5-yl)benzamide (103)

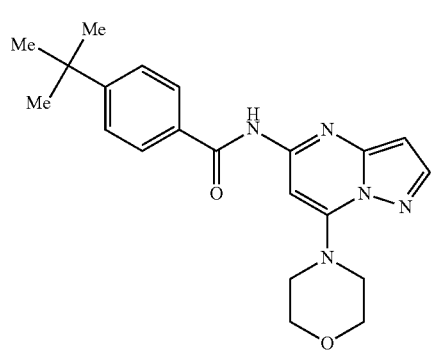

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 380 (M+H)$^+$.

Example 118

1-(5-(4-tert-butylbenzamido)pyrazolo[1,5-a]pyrimidin-7-yl)piperidine-3-carboxamide (104)

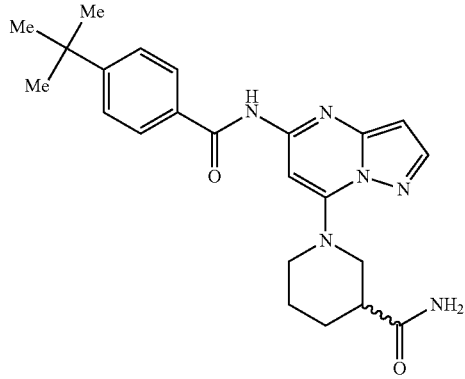

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 378 (M+H)$^+$.

Example 119

4-tert-butyl-N-(7-(2-(2-hydroxyethyl)piperidin-1-yl)pyrazolo[1,5-a]pyrimidin-5-yl)benzamide (105)

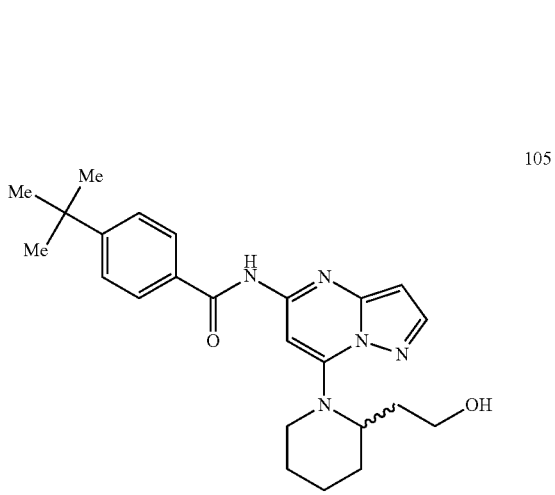 [SMILES: CC(C)(C)c1ccc(C(=O)Nc2cc(N3CCCCC3CCO)n3nccc3n2)cc1]

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 422 (M+H)$^+$.

Example 120

4-tert-butyl-N-(7-(octahydroisoquinolin-2(1H)-yl)pyrazolo[1,5-a]pyrimidin-5-yl)benzamide (106)

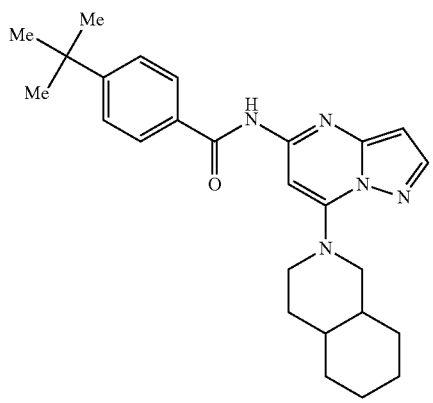

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 432 (M+H)$^+$.

Example 121

4-tert-butyl-N-(7-(4-hydroxy-4-phenylpiperidin-1-yl)pyrazolo[1,5-a]pyrimidin-5-yl)benzamide (107)

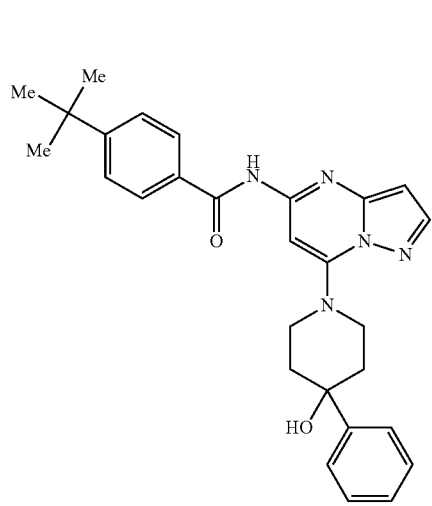

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 470 (M+H)$^+$.

Example 122

4-tert-butyl-N-(7-(4-methylpiperazin-1-yl)pyrazolo[1,5-a]pyrimidin-5-yl)benzamide (108)

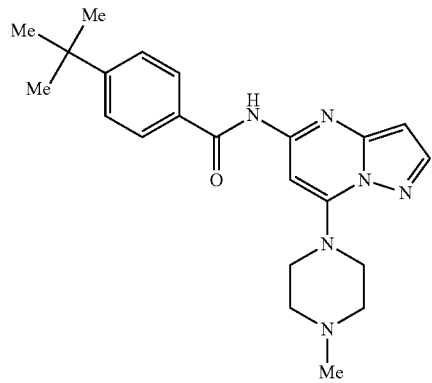

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 393 (M+H)$^+$.

Example 123

4-tert-butyl-N-(7-(4-phenethylpiperazin-1-yl)pyrazolo[1,5-a]pyrimidin-5-yl)benzamide (109)

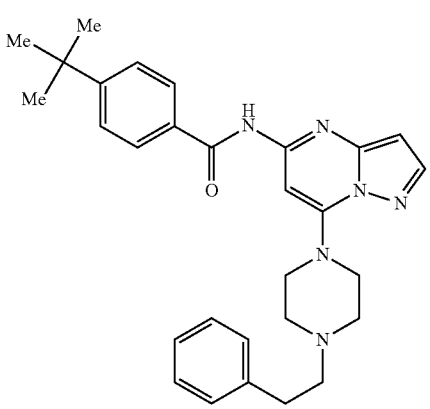

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 483 (M+H)$^+$.

Example 124

4-tert-butyl-N-(7-(6,7-dihydro-2H-pyrazolo[4,3-c]pyridin-5(4H)-yl)pyrazolo[1,5-a]pyrimidin-5-yl)benzamide (110)

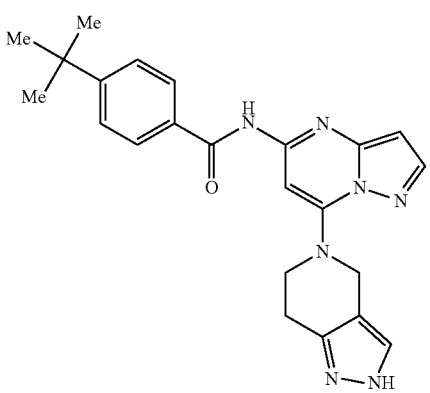

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 416 (M+H)+.

Example 125

(S)-4-tert-butyl-N-(7-(2-(hydroxymethyl)pyrrolidin-1-yl)pyrazolo[1,5-a]pyrimidin-5-yl)benzamide (111)

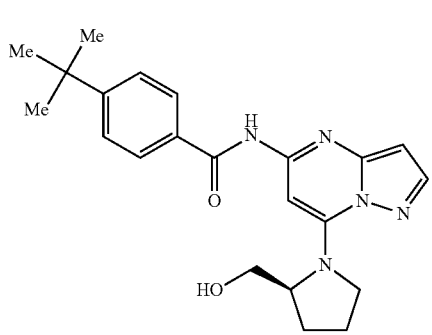

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 394 (M+H)+.

Example 126

4-tert-butyl-N-(7-(4-hydroxypiperidin-1-yl)pyrazolo[1,5-a]pyrimidin-5-yl)benzamide (112)

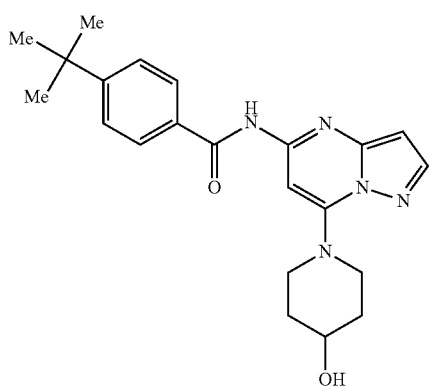

The titled compound was prepared using a procedure analogous to that described in connection with Example 78 except that 4-tert-butyl-N-(7-chloropyrazolo[1,5-a]pyrimi-din-5-yl)benzamide (1F) and the corresponding amine were used as starting materials. ESI-MS: m/z 394 (M+H)+.

Example 127

4-tert-butyl-N-(7-(3-hydroxypiperidin-1-yl)pyrazolo[1,5-a]pyrimidin-5-yl)benzamide (113)

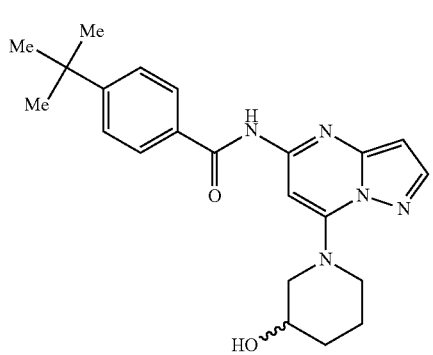

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 393 (M+H)+.

Example 128

1-(5-(4-tert-butylbenzamido)pyrazolo[1,5-a]pyrimidin-7-yl)piperidine-4-carboxamide (114)

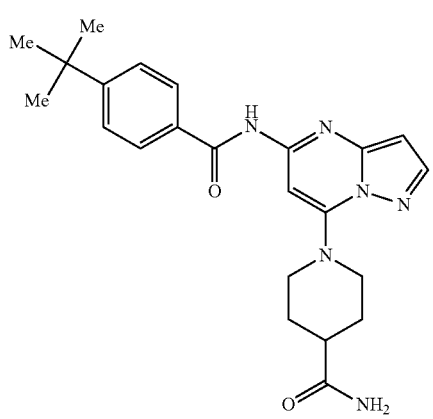

The titled compound was prepared using a procedure analogous to that described in connection with Example 78 except that 4-tert-butyl-N-(7-chloropyrazolo[1,5-a]pyrimi- Example 129

N-(7-(3-acetamidopyrrolidin-1-yl)pyrazolo[1,5-a]pyrimidin-5-yl)-4-tert-butylbenzamide (115)

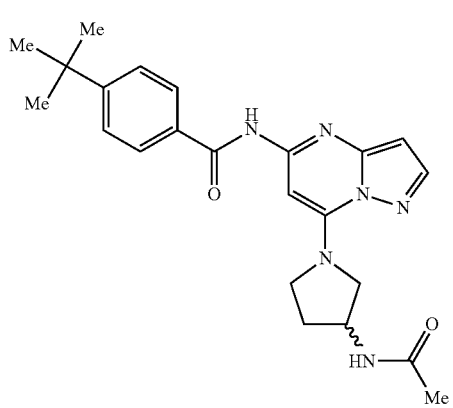

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 421 (M+H)⁺.

Example 130

4-tert-butyl-N-(7-(4-(2-hydroxyethyl)piperidin-1-yl)pyrazolo[1,5-a]pyrimidin-5-yl)benzamide (116)

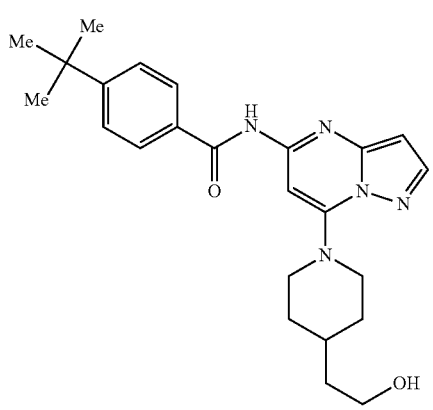

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 422 (M+H)⁺.

Example 131

1-(5-(4-tert-butylbenzamido)pyrazolo[1,5-a]pyrimidin-7-yl)piperidine-3-carboxylic acid (117)

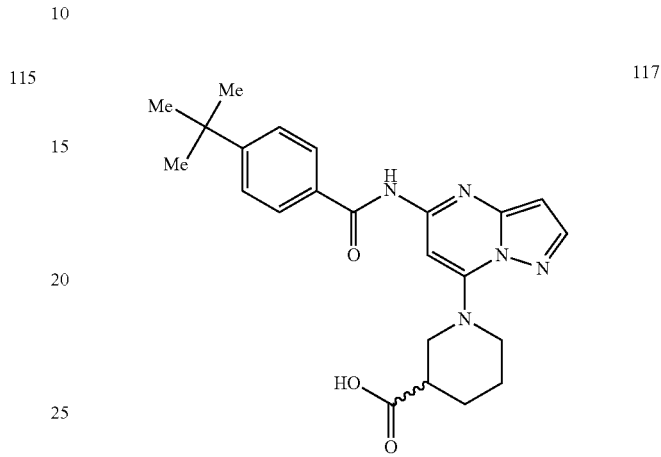

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 422 (M+H)⁺.

Example 132

4-tert-butyl-N-(7-(3-hydroxypyrrolidin-1-yl)pyrazolo[1,5-a]pyrimidin-5-yl)benzamide (118)

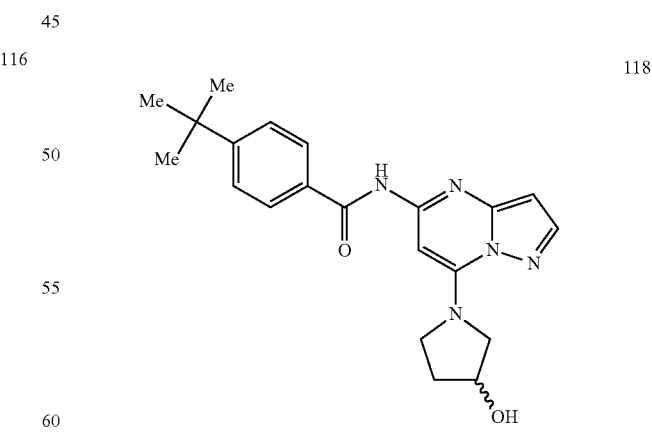

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 380 (M+H)$^+$.

Example 133

(R)-N-(7-(3-acetamidopyrrolidin-1-yl)pyrazolo[1,5-a]pyrimidin-5-yl)-4-tert-butylbenzamide (119)

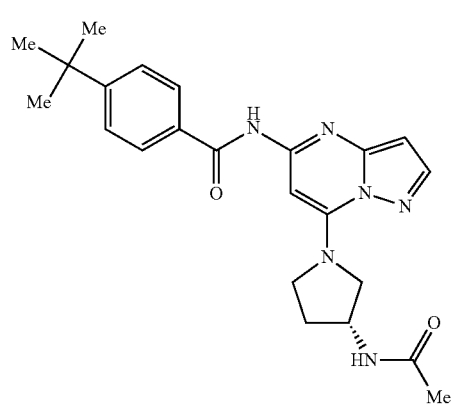

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 421 (M+H)$^+$.

Example 134

N-(7-(1H-imidazol-1-yl)pyrazolo[1,5-a]pyrimidin-5-yl)-4-tert-butylbenzamide (120)

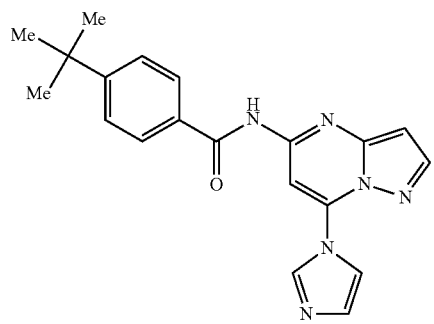

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 361 (M+H)$^+$.

Example 135

N-(7-(1H-1,2,4-triazol-1-yl)pyrazolo[1,5-a]pyrimidin-5-yl)-4-tert-butylbenzamide (121)

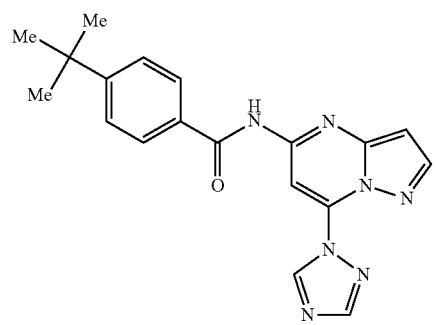

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 362 (M+H)$^+$.

Example 136

4-tert-butyl-N-(7-(6,7-dihydro-1H-pyrazolo[4,3-b]pyridin-4(5H)-yl)pyrazolo[1,5-a]pyrimidin-5-yl)benzamide (122)

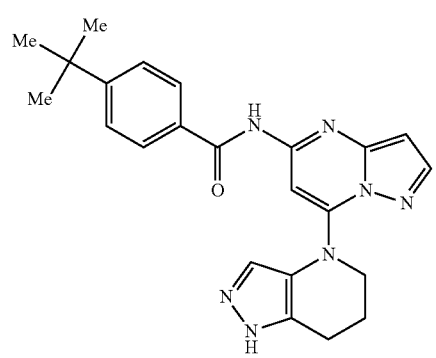

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 416 (M+H)+.

Example 137

4-tert-butyl-N-(7-(pyrrolidin-1-yl)pyrazolo[1,5-a]pyrimidin-5-yl)benzamide (123)

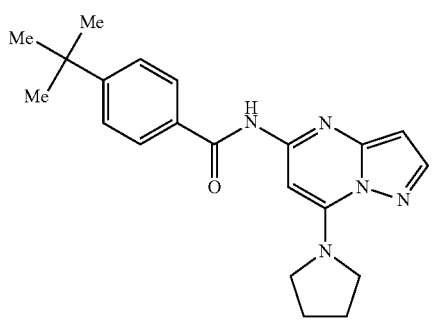

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 364 (M+H)+.

Example 138

(E)-4-tert-butyl-N-(7-(2-cyclohexylvinyl)pyrazolo[1,5-a]pyrimidin-5-yl)benzamide (124)

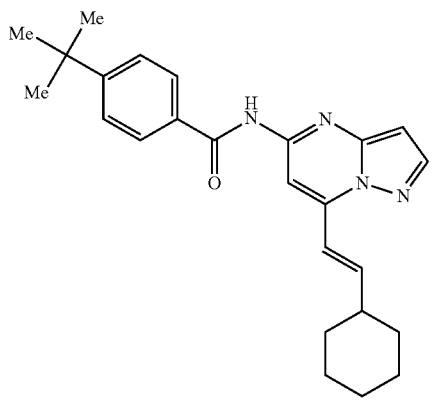

The titled compound was prepared using a procedure analogous to that described in connection with Example 46 except the corresponding boronic acid, ester or trifluoroborate salt was used as starting material. ESI-MS: m/z 403 (M+H)+.

Example 139

4-tert-butyl-N-(7-(dimethylamino)pyrazolo[1,5-a]pyrimidin-5-yl)benzamide, trifluoroacetate salt (125)

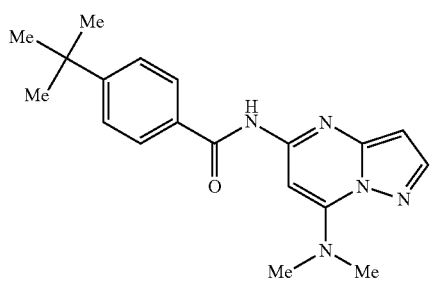

The titled compound was prepared using a procedure analogous to that described in connection with Example 78 except that 4-tert-butyl-N-(7-chloropyrazolo[1,5-a]pyrimidin-5-yl)benzamide (1F) and dimethylamine were used as starting materials. This product was obtained as a white solid. $^1$H NMR (400 MHz, DMSO-$d_6$) δ ppm 1.32 (s, 9 H) 3.36 (s, 6 H) 6.32 (d, J=2.27 Hz, 1 H) 7.22 (s, 1 H) 7.55 (d, 2 H) 8.00 (d, J=8.34 Hz, 2 H) 8.06 (d, J=2.27 Hz, 1 H) 10.84 (s, 1 H); ESI-MS: m/z 338.1 (M+H)+.

Example 140

N-(7-(benzyl(2-(dimethylamino)ethyl)amino)pyrazolo[1,5-a]pyrimidin-5-yl)-4-tert-butylbenzamide (126)

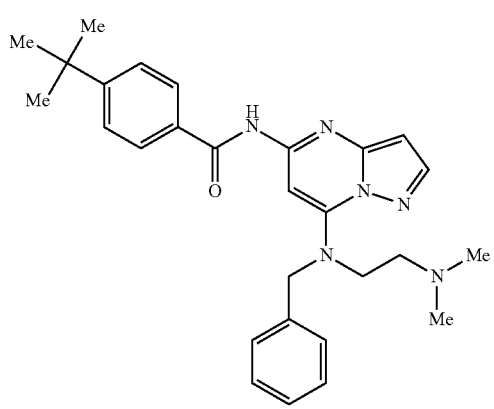

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 471 (M+H)⁺.

Example 141

4-(1-hydroxy-2-methylpropan-2-yl)-N-(2-methyl-7-(methyl(phenethyl)amino)pyrazolo[1,5-a]pyrimidin-5-yl)benzamide (127)

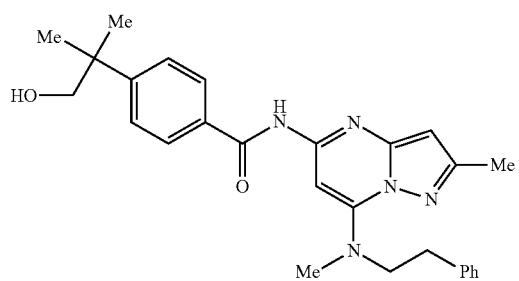

The title compound was prepared using a procedure analogous to that described in connection with Example 108 except that N-methyl-2-phenylethanamine (3.0 equivalents) was used instead of pyrrolidine as a starting material to afford the title compound as a white solid. $^1$H NMR (400 MHz, DMSO-d$_6$) δ ppm 1.25 (s, 6 H), 2.41 (s, 3 H), 3.00 (dd, J=9.47, 6.19 Hz, 2 H), 3.23 (s, 3 H), 3.46 (s, 2 H), 4.20 (dd, J=9.73, 6.19 Hz, 2 H), 6.10 (s, 1 H), 7.14-7.22 (m, 2 H), 7.24-7.34 (m, 4 H), 7.50 (d, J=8.84 Hz, 2 H), 7.98 (d, J=8.59 Hz, 2 H), 10.72 (s, 1 H). ESI-MS: m/z 458.3 (M+H)⁺.

Example 142

4-tert-butyl-N-[7-(cyclopropylamino)pyrazolo[1,5-a]pyrimidin-5-yl]benzamide (128)

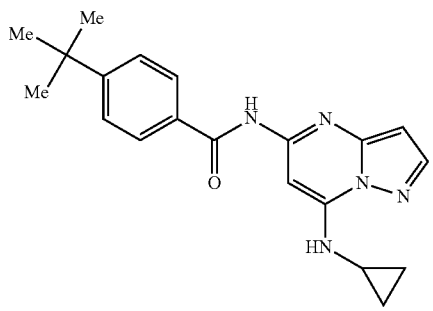

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. $^1$H NMR (400 MHz, CHLOROFORM-d) δ ppm 0.79-0.84 (m, 2 H) 0.99-1.06 (m, J=6.03, 6.03 Hz, 2 H) 2.82 (dd, J=3.39, 1.88 Hz, 1 H) 6.25 (d, J=2.26 Hz, 1 H) 6.60 (s, 1 H) 7.52 (d, J=8.48 Hz, 2 H) 7.65 (s, 1 H) 7.88 (d, J=8.29 Hz, 2 H) 7.93 (d, J=2.26 Hz, 1 H) 8.55 (s, 1 H). ESI-MS: m/z 350 (M+H)⁺.

Example 143

4-tert-butyl-N-{7-[(4-methoxybenzyl)amino]pyrazolo[1,5-a]pyrimidin-5-yl}benzamide (129)

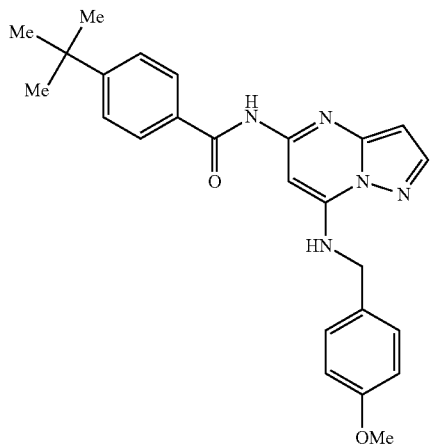

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. $^1$H NMR (400 MHz, CHLOROFORM-d) δ ppm 1.36 (s, 9 H) 3.81 (s, 3 H) 4.60 (d, J=5.65 Hz, 2 H) 6.24 (d, J=2.07 Hz, 1 H) 6.67 (t, J=5.37 Hz, 1 H) 6.92 (d, J=8.48 Hz, 2 H) 7.36 (d, J=8.48 Hz, 2 H) 7.47 (s, 1 H) 7.52 (d, J=8.29 Hz, 2 H) 7.86 (d, J=8.29 Hz, 2 H) 7.93 (d, J=2.07 Hz, 1 H) 8.56 (s, 1 H). ESI-MS: m/z 430 (M+H)⁺.

Example 144

4-tert-butyl-N-{7-[(1-methyl-1-phenylethyl)amino]pyrazolo[1,5-a]pyrimidin-5-yl}benzamide (130)

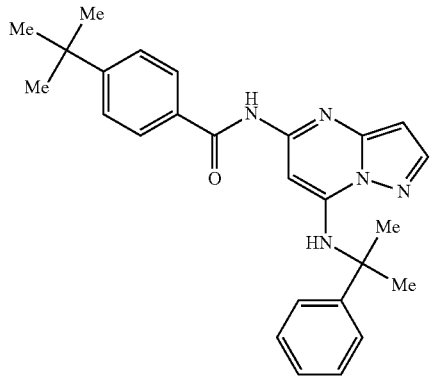

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ¹H NMR (400 MHz, CHLOROFORM-d) δ ppm 1.32 (s, 9 H) 1.92 (s, 6 H) 6.24 (d, J=2.26 Hz, 1 H) 6.81 (s, 1 H) 6.93 (s, 1 H) 7.26-7.30 (m, 1 H) 7.39 (t, J=7.72 Hz, 1 H) 7.44 (d, J=8.48 Hz, 2 H) 7.54 (d, J=7.91 Hz, 2 H) 7.73 (d, J=8.48 Hz, 2 H) 7.96 (d, J=2.26 Hz, 1 H) 8.30 (s, 1 H). ESI-MS: m/z 428 (M+H)⁺.

Example 145

4-tert-butyl-N-[7-(phenylamino)pyrazolo[1,5-a]pyrimidin-5-yl]benzamide (131)

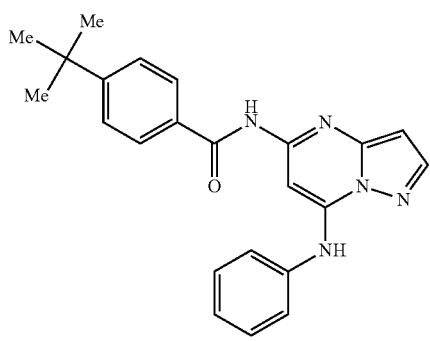

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ¹H NMR (400 MHz, CHLOROFORM-d) d ppm 1.35 (s, 9 H) 6.33 (d, J=2.26 Hz, 1 H) 7.29 (t, J=7.25 Hz, 1 H) 7.43-7.56 (m, 6 H) 7.82 (d, J=3.20 Hz, 2 H) 7.84 (s, 1 H) 8.02 (d, J=2.26 Hz, 1 H) 8.21 (s, 1 H) 8.54 (s, 1 H). ESI-MS: m/z 386 (M+H)⁺.

Example 146

4-tert-butyl-N-(7-(isobutylamino)pyrazolo[1,5-a]pyrimidin-5-yl)benzamide (132)

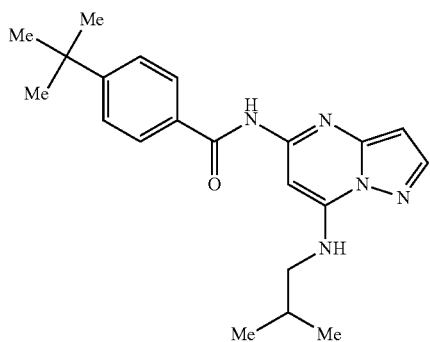

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 366 (M+H)⁺.

Example 147

4-tert-butyl-N-(7-(butylamino)pyrazolo[1,5-a]pyrimidin-5-yl)benzamide (133)

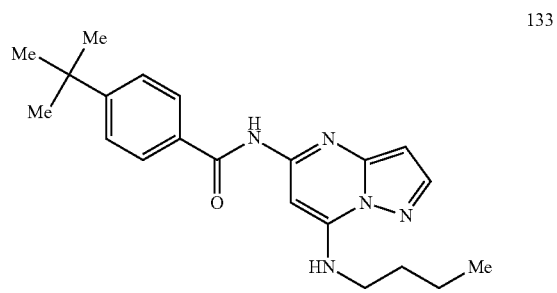 [SMILES: CC(C)(C)c1ccc(C(=O)Nc2cc(NCCCO)n3nccc3n2)cc1]

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 366 (M+H)⁺.

Example 148

4-tert-butyl-N-(7-(tert-butylamino)pyrazolo[1,5-a]pyrimidin-5-yl)benzamide (134)

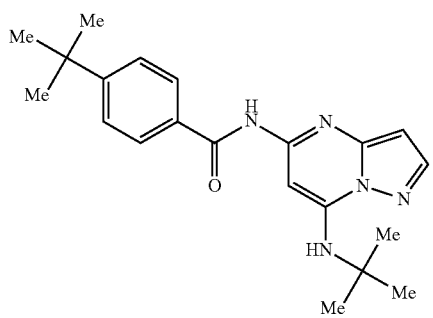

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 366 (M+H)⁺.

Example 149

4-tert-butyl-N-(7-(3-hydroxypropylamino)pyrazolo[1,5-a]pyrimidin-5-yl)benzamide (135)

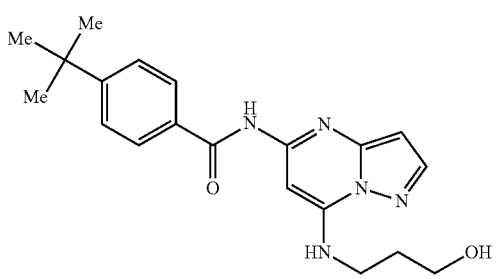

135

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 368 (M+H)⁺.

Example 150

4-tert-butyl-N-(7-(cyclopentylamino)pyrazolo[1,5-a]pyrimidin-5-yl)benzamide (136)

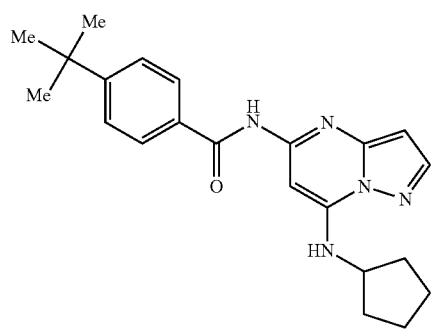

136

The titled compound was prepared using a procedure analogous to that described in connection with Example 64 except that 4-tert-butyl-N-(7-chloropyrazolo[1,5-a]pyrimidin-5-yl)benzamide (1F) and the corresponding amine were used as starting materials. ESI-MS: m/z 378 (M+H)⁺.

Example 151

4-tert-butyl-N-(7-(furan-2-ylmethylamino)pyrazolo[1,5-a]pyrimidin-5-yl)benzamide (137)

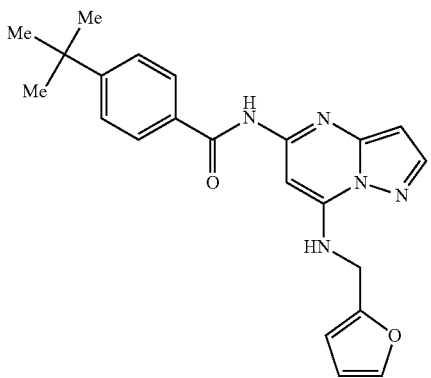

137

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 390 (M+H)⁺.

Example 152

N-(7-(2-acetamidoethylamino)pyrazolo[1,5-a]pyrimidin-5-yl)-4-tert-butylbenzamide (138)

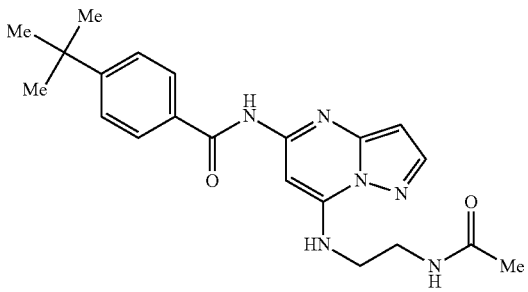

138

The titled compound was prepared using a procedure analogous to that described in connection with Example 78 except that 4-tert-butyl-N-(7-chloropyrazolo[1,5-a]pyrimi-

Example 153

4-tert-butyl-N-(7-(2-isopropoxyethylamino)pyrazolo[1,5-a]pyrimidin-5-yl)benzamide (139)

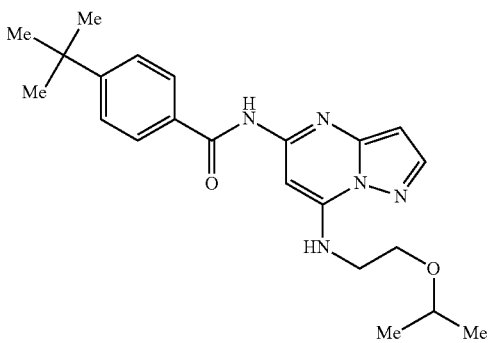

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 396 (M+H)$^+$.

Example 154

4-tert-butyl-N-(7-(3-(methylthio)propylamino)pyrazolo[1,5-a]pyrimidin-5-yl)benzamide (140)

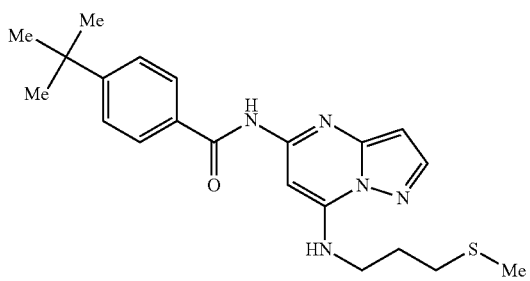

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 398 (M+H)$^+$.

Example 155

N-(7-(benzylamino)pyrazolo[1,5-a]pyrimidin-5-yl)-4-tert-butylbenzamide (141)

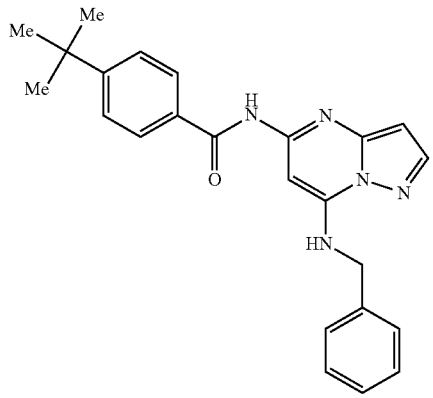

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 400 (M+H)$^+$.

Example 156

4-tert-butyl-N-(7-(cyclohexylmethylamino)pyrazolo[1,5-a]pyrimidin-5-yl)benzamide (142)

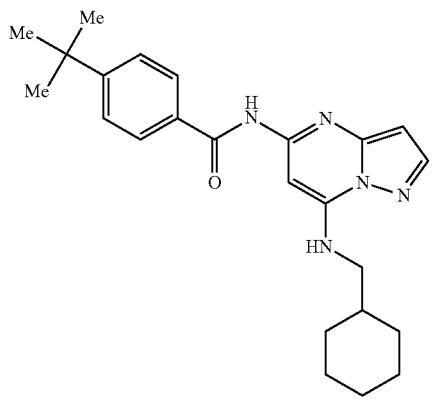

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 406 (M+H)$^+$.

Example 157

4-tert-butyl-N-(7-(phenethylamino)pyrazolo[1,5-a]pyrimidin-5-yl)benzamide (143)

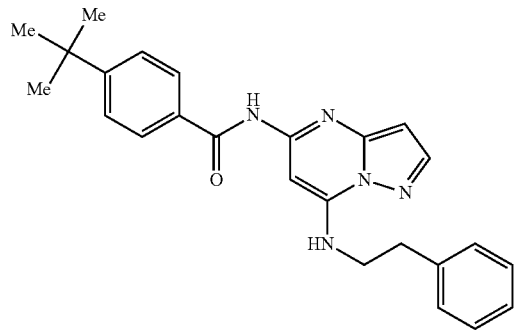

143

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 414 (M+H)$^+$.

Example 158

N-(7-(3-amino-3-oxopropylamino)pyrazolo[1,5-a]pyrimidin-5-yl)-4-tert-butylbenzamide (144)

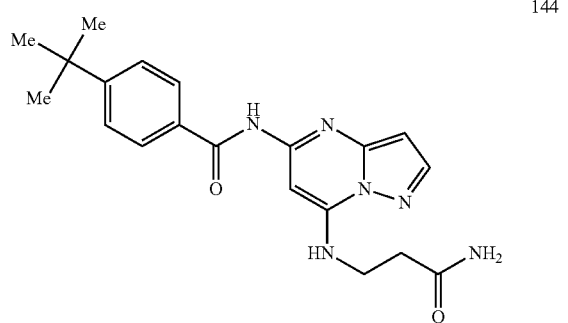 [SMILES: CC(C)(C)c1ccc(C(=O)Nc2cc(NCCC(N)=O)n3nccc3n2)cc1]

144

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 381 (M+H)$^+$.

Example 159

4-tert-butyl-N-(7-(3-fluorobenzylamino)pyrazolo[1,5-a]pyrimidin-5-yl)benzamide (145)

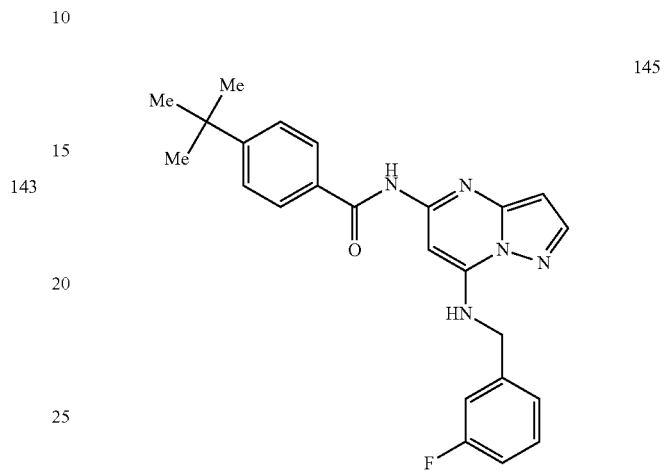

145

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 418 (M+H)$^+$.

Example 160

4-tert-butyl-N-(7-(2,3-dihydro-1H-inden-2-ylamino)pyrazolo[1,5-a]pyrimidin-5-yl)benzamide (146)

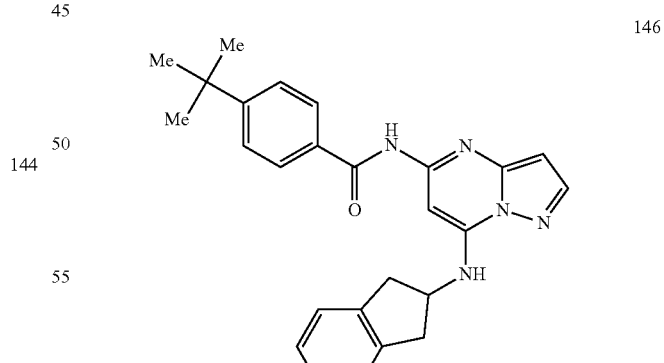

146

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 426 (M+H)⁺.

Example 161

4-tert-butyl-N-(7-(4-hydroxyphenethylamino)pyrazolo[1,5-a]pyrimidin-5-yl)benzamide (147)

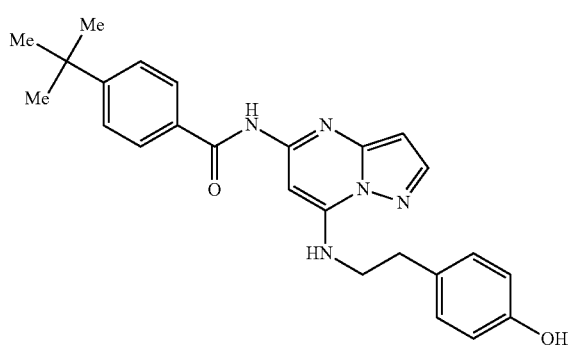

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 430 (M+H)⁺.

Example 162

4-tert-butyl-N-(7-(2-phenoxyethylamino)pyrazolo[1,5-a]pyrimidin-5-yl)benzamide (148)

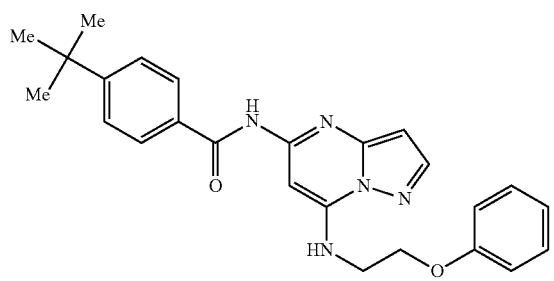

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 430 (M+H)⁺.

Example 163

4-tert-butyl-N-(7-(3-(2-oxopyrrolidin-1-yl)propylamino)pyrazolo[1,5-a]pyrimidin-5-yl)benzamide (149)

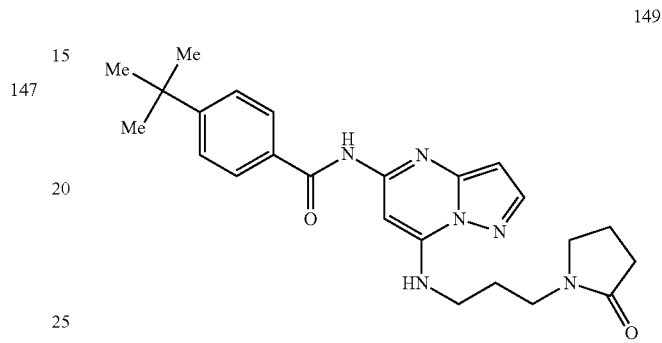

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 435 (M+H)⁺.

Example 164

N-(7-(benzo[d][1,3]dioxol-5-ylmethylamino)pyrazolo[1,5-a]pyrimidin-5-yl)-4-tert-butylbenzamide (150)

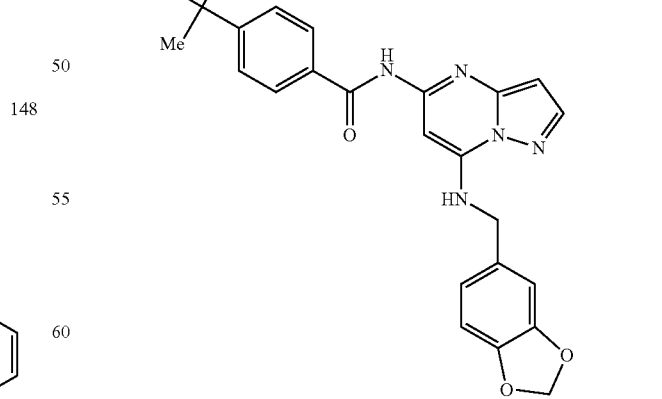

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 444 (M+H)$^+$.

Example 165

N-(7-(2-(1H-indol-3-yl)ethylamino)pyrazolo[1,5-a]pyrimidin-5-yl)-4-tert-butylbenzamide (151)

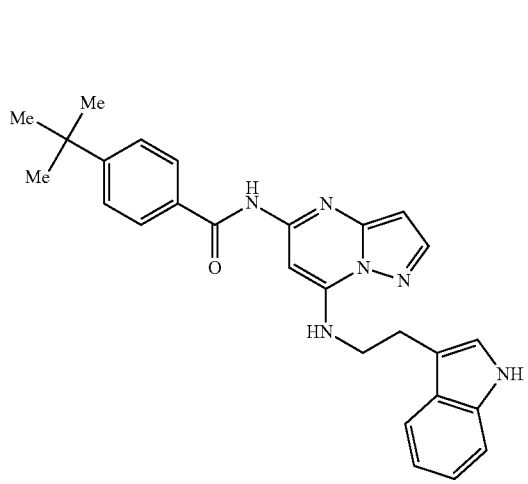

151

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 453 (M+H)$^+$.

Example 166

4-tert-butyl-N-(7-(4-(trifluoromethyl)benzylamino)pyrazolo[1,5-a]pyrimidin-5-yl)benzamide (152)

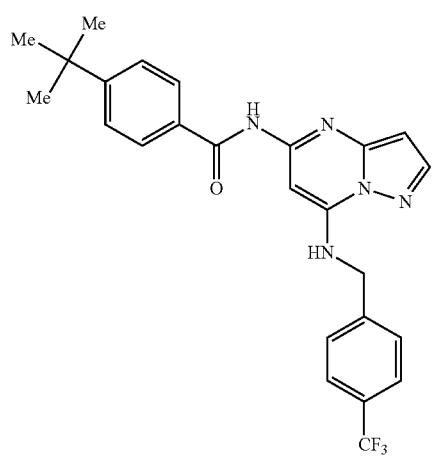

152

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 468 (M+H)$^+$.

Example 167

4-tert-butyl-N-(7-(3,4-dimethoxyphenethylamino)pyrazolo[1,5-a]pyrimidin-5-yl)benzamide (153)

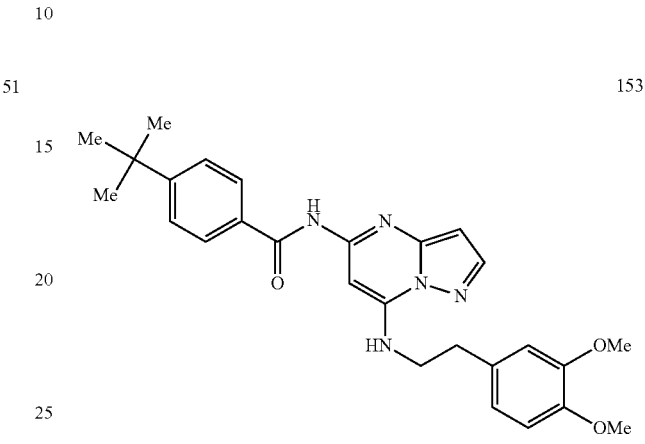

153

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 474 (M+H)$^+$.

Example 168

4-tert-butyl-N-(7-(4-sulfamoylbenzylamino)pyrazolo[1,5-a]pyrimidin-5-yl)benzamide (154)

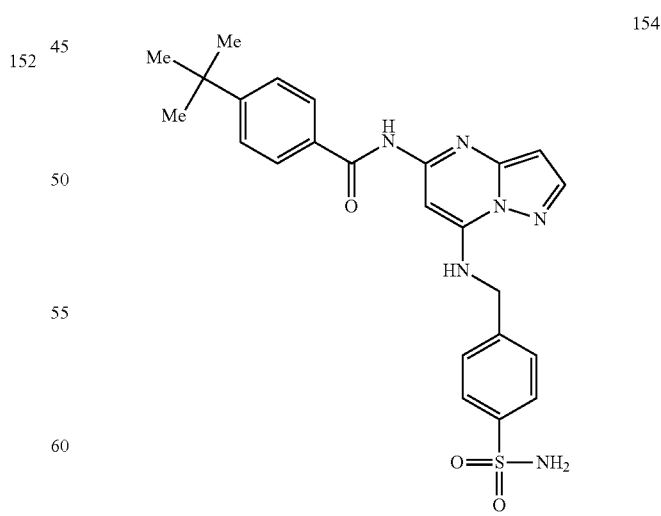

154

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 479 (M+H)$^+$.

Example 169

N-(7-(3,5-bis(trifluoromethyl)benzylamino)pyrazolo[1,5-a]pyrimidin-5-yl)-4-tert-butylbenzamide (155)

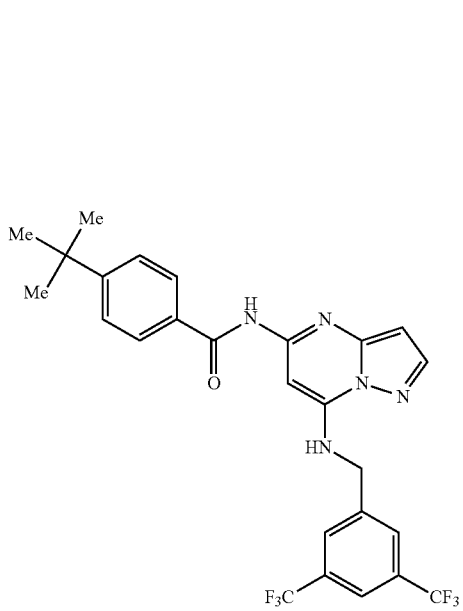

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 536 (M+H)$^+$.

Example 170

4-tert-butyl-N-(7-(2-methoxyethylamino)pyrazolo[1,5-a]pyrimidin-5-yl)benzamide (156)

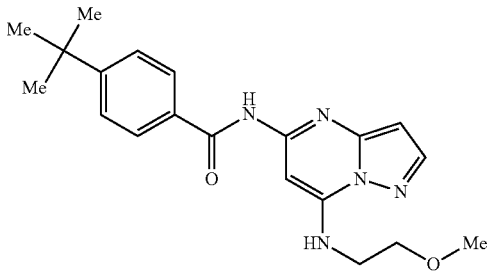

The titled compound was prepared using a procedure analogous to that described in connection with Example 78 except that 4-tert-butyl-N-(7-chloropyrazolo[1,5-a]pyrimi-din-5-yl)benzamide (1F) and the corresponding amine were used as starting materials. ESI-MS: m/z 368 (M+H)$^+$.

Example 171

4-tert-butyl-N-(7-(pentan-3-ylamino)pyrazolo[1,5-a]pyrimidin-5-yl)benzamide (157)

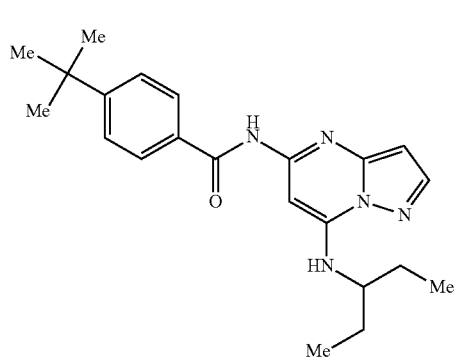

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 380 (M+H)$^+$.

Example 172

N-(7-(2-amino-2-oxoethylamino)pyrazolo[1,5-a]pyrimidin-5-yl)-4-tert-butylbenzamide (158)

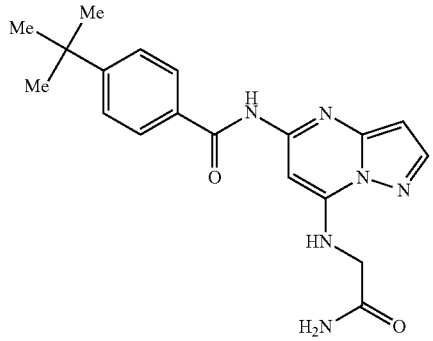

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 367 (M+H)+.

Example 173

4-tert-butyl-N-(7-(3-methylbenzylamino)pyrazolo[1,5-a]pyrimidin-5-yl)benzamide (159)

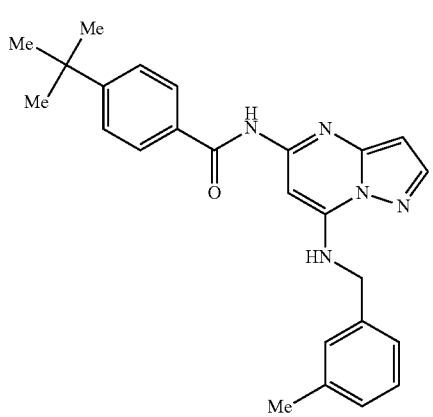

159

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 414 (M+H)+.

Example 174

4-tert-butyl-N-(7-(2-(dimethylamino)ethylamino)pyrazolo[1,5-a]pyrimidin-5-yl)benzamide (160)

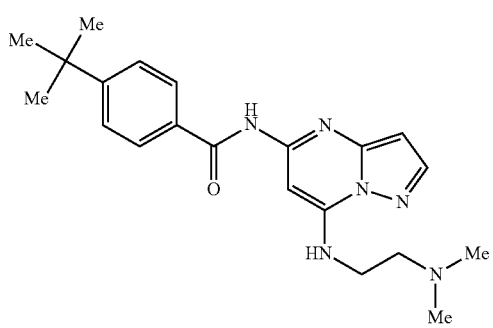

160

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 381 (M+H)+.

Example 175

4-tert-butyl-N-(7-(pyridin-3-ylmethylamino)pyrazolo[1,5-a]pyrimidin-5-yl)benzamide (161)

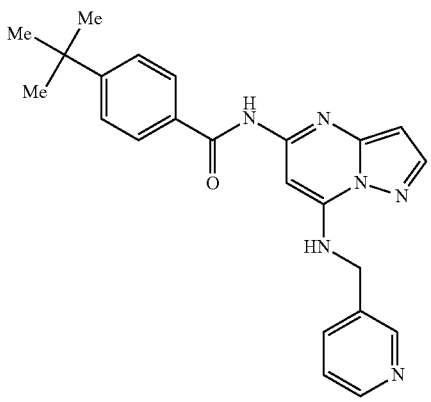

161

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 401 (M+H)+.

Example 176

4-tert-butyl-N-(7-(2-(pyridin-2-yl)ethylamino)pyrazolo[1,5-a]pyrimidin-5-yl)benzamide (162)

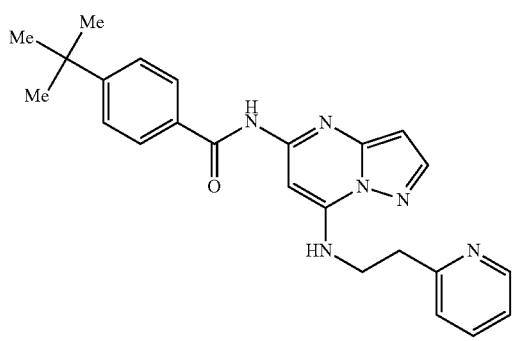

162

The titled compound was prepared using a procedure analogous to that described in connection with Example 78 except that 4-tert-butyl-N-(7-chloropyrazolo[1,5-a]pyrimi-

Example 177

4-tert-butyl-N-(7-((5-methylpyrazin-2-yl)methylamino)pyrazolo[1,5-a]pyrimidin-5-yl)benzamide (163)

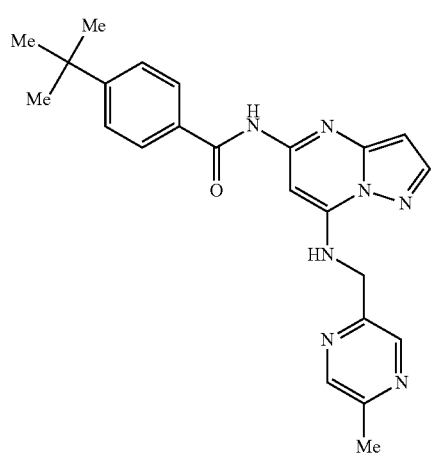

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 416 (M+H)$^+$.

Example 178

N-(7-(3-(1H-imidazol-1-yl)propylamino)pyrazolo[1,5-a]pyrimidin-5-yl)-4-tert-butylbenzamide (164)

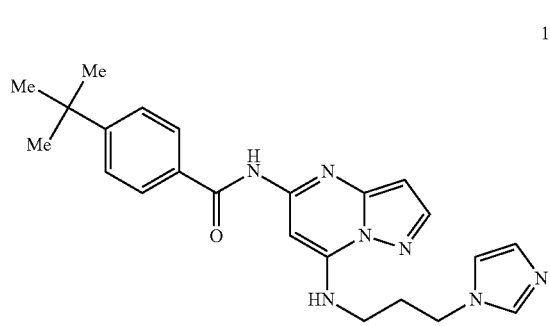

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 418 (M+H)$^+$.

Example 179

N-(7-(2-(1H-imidazol-5-yl)ethylamino)pyrazolo[1,5-a]pyrimidin-5-yl)-4-tert-butylbenzamide (165)

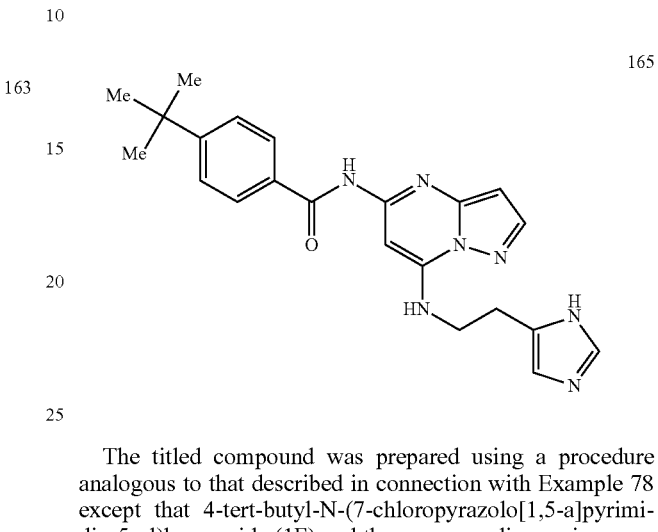

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 404 (M+H)$^+$.

Example 180

(S)-methyl 2-(5-(4-tert-butylbenzamido)pyrazolo[1,5-a]pyrimidin-7-ylamino)-3-(1H-imidazol-5-yl)propanoate (166)

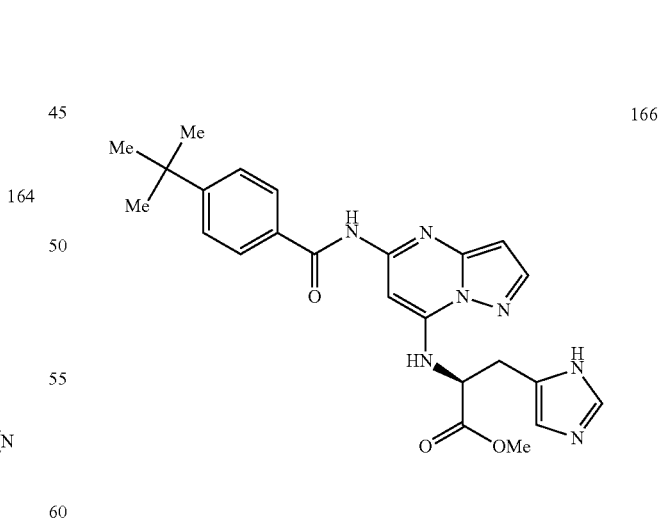

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 462 (M+H)+.

Example 181

4-tert-butyl-N-(7-(2-hydroxycyclohexylamino)pyrazolo[1,5-a]pyrimidin-5-yl)benzamide (167)

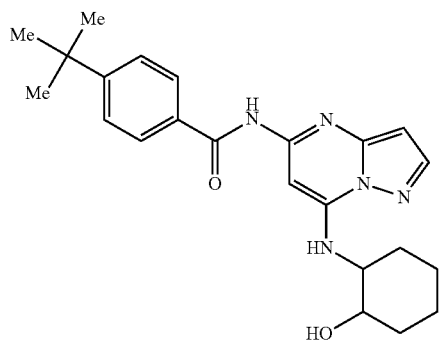

167

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 408 (M+H)+.

Example 182

4-tert-butyl-N-(7-(pyridin-2-ylamino)pyrazolo[1,5-a]pyrimidin-5-yl)benzamide (168)

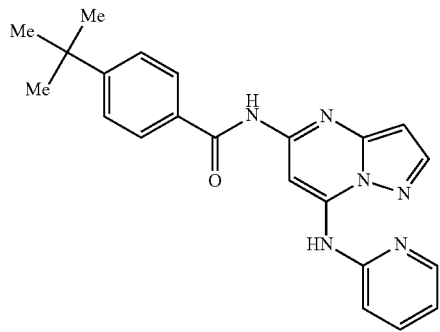

168

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 387 (M+H)+.

Example 183

4-tert-butyl-N-(7-(pyridin-3-ylamino)pyrazolo[1,5-a]pyrimidin-5-yl)benzamide (169)

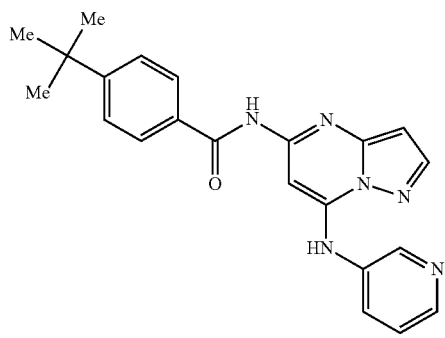

169

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 387 (M+H)+.

Example 184

4-tert-butyl-N-(7-(pyridin-4-ylamino)pyrazolo[1,5-a]pyrimidin-5-yl)benzamide (170)

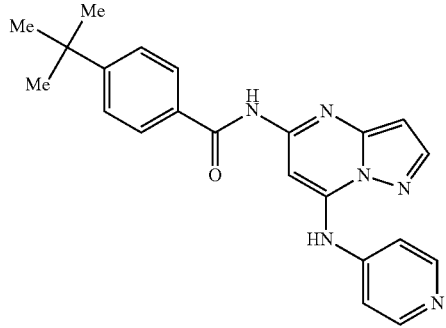

170

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 387 (M+H)+.

Example 185

4-tert-butyl-N-(7-(pyrimidin-2-ylamino)pyrazolo[1,5-a]pyrimidin-5-yl)benzamide (171)

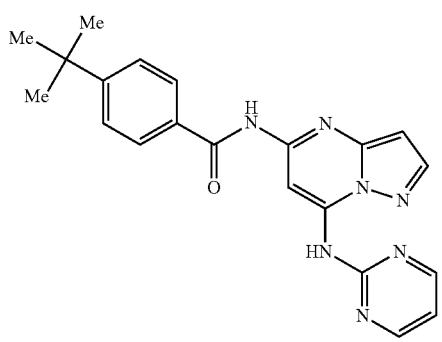

171

The titled compound was prepared using a procedure analogous to that described in connection with Example 78 except that 4-tert-butyl-N-(7-chloropyrazolo[1,5-a]pyrimidin-5-yl)benzamide (1F) and the corresponding amine were used as starting materials. ESI-MS: m/z 388 (M+H)+.

Example 186

2-methyl-7-p-tolylpyrazolo[1,5-a]pyrimidin-5-amine (172)

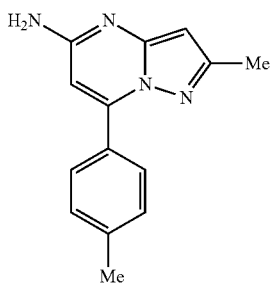

172

The titled compound was prepared using a procedure analogous to that described in connection with Example 15 except that 7-chloro-2-methylpyrazolo[1,5-a]pyrimidin-5-amine (1J) and p-tolylboronic acid were used as starting materials.

Example 187

(3-(5-amino-2-methylpyrazolo[1,5-a]pyrimidin-7-yl)phenyl)methanol (173)

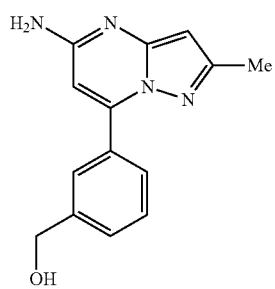

173

The titled compound was prepared using a procedure analogous to that described in connection with Example 15 except that 2-methylpyrazolo[1,5-a]pyrimidin-5-amine (1J) and 3-(hydroxymethyl)phenylboronic acid were used as starting materials. ¹H NMR (400 MHz, CHLOROFORM-d) δ 2.40 (s, 3 H), 4.79 (s, 2 H), 4.90 (br, 2 H), 6.03 (s, 1 H), 6.09 (s, 1 H), 7.51-7.54 (m, 2 H), 7.82-7.85 (m, 1 H), 7.94 (s, 1 H).

Example 188

7-p-tolylpyrazolo[1,5-a]pyrimidin-5-amine (174)

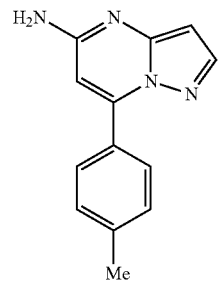

174

The titled compound was prepared using a procedure analogous to that described in connection with Example 15 except that 7-chloropyrazolo[1,5-a]pyrimidin-5-amine (1E) and p-tolylboronic acid were used as starting materials. ¹H NMR (400 MHz, CHLOROFORM-d) δ 2.44 (s, 3H), 4.82 (s, 2H), 6.16 (s, 1H), 6.20 (d, J=2.0 Hz, 1H), 7.34 (d, J=8.1 Hz, 2H), 7.81 (d, J=8.1 Hz, 2H), 7.91 (d, J=2.0 Hz, 1H).

Example 189

7-(thiophen-2-yl)pyrazolo[1,5-a]pyrimidin-5-amine (175)

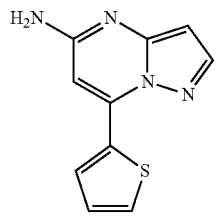

175

The titled compound was prepared using a procedure analogous to that described in connection with Example 15 except that 7-chloropyrazolo[1,5-a]pyrimidin-5-amine (1E) and thiophen-2-ylboronic acid were used as starting materials. $^1$H NMR (400 MHz, CHLOROFORM-d) δ 4.82 (s, 2H), 6.24 (d, J=1.7 Hz, 1H), 6.52 (s, 1H), 7.21-7.25 (m, 1H), 7.66 (d, J=5.1 Hz, 1H), 8.02 (d, J=1.7 Hz, 1H), 8.22 (d, J=3.8 Hz, 1H).

Example 190

7-(5-methylthiophen-2-yl)pyrazolo[1,5-a]pyrimidin-5-amine (176)

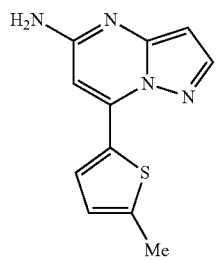

176

The titled compound was prepared using a procedure analogous to that described in connection with Example 15 except that 7-chloropyrazolo[1,5-a]pyrimidin-5-amine (1E) and 5-methylthiophen-2-ylboronic acid were used as starting materials. $^1$H NMR (400 MHz, CHLOROFORM-d) δ 2.59 (s, 3H), 4.76 (s, 2H), 6.21 (d, J=1.8 Hz, 1H), 6.44 (s, 1H), 6.89 (d, J=3.5 Hz, 1H), 7.99-8.04 (m, 2H).

Example 191

N-(5-(5-aminopyrazolo[1,5-a]pyrimidin-7-yl)pyridin-2-yl)acetamide (177)

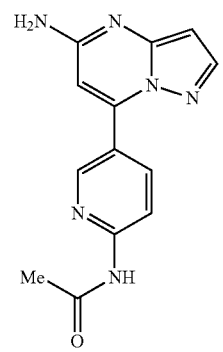

177

The titled compound was prepared using a procedure analogous to that described in connection with Example 15 except that 7-chloropyrazolo[1,5-a]pyrimidin-5-amine (1E) and 5-methylthiophen-2-ylboronic acid were used as starting materials. $^1$H NMR (400 MHz, DMSO-d6) δ 2.15 (s, 3H), 6.01 (d, J=2.0 Hz, 1H), 6.40 (s, 1H), 6.81 (s, 2H), 7.84 (d, J=1.8 Hz, 1H), 8.23 (d, J=8.8 Hz, 1H), 8.37 (d, J=8.8 Hz, 1H), 8.90 (d, J=2.0 Hz, 1H), 10.82 (s, 1H).

Example 192

(3-(5-aminopyrazolo[1,5-a]pyrimidin-7-yl)phenyl)methanol (178)

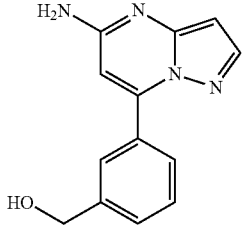

178

The titled compound was prepared using a procedure analogous to that described in connection with Example 15 except that 7-chloropyrazolo[1,5-a]pyrimidin-5-amine (1E) and 3-(hydroxymethyl)phenylboronic acid were used as starting materials. $^1$H NMR (400 MHz, MeOD) δ ppm 4.72 (s, 2 H) 6.27-6.31 (m, 1 H) 6.47 (s, 1 H) 7.56 (t, J=7.58 Hz, 1 H) 7.62 (d, J=7.58 Hz, 1 H) 7.84 (d, J=7.33 Hz, 1 H) 7.91-7.97 (m, 2 H).

Example 193

N-(7-(3-(benzyloxy)phenyl)pyrazolo[1,5-a]pyrimidin-5-yl)-4-(2-hydroxypropan-2-yl)benzamide (179)

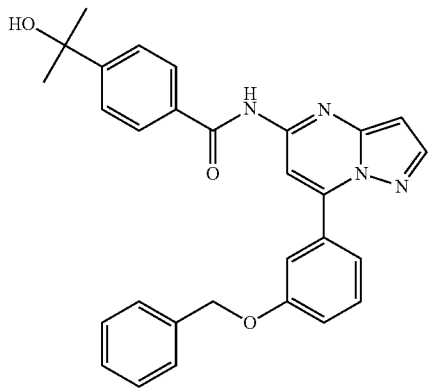

179

A suspension of N-(7-chloropyrazolo[1,5-a]pyrimidin-5-yl)-4-(2-hydroxypropan-2-yl)benzamide (2D, 50 mg, 150 mmol), 3-Benzyloxyphenylboronic Acid (70 mg, 302 mmol), and [1,1'-bis(diphenylphosphino)ferrocene]dichloropalladium(II) (9 mg, 12 µmol) in 2:1 1,4-dioxane/saturated aqueous NaHCO$_3$ (670 microliters of 1,4-dioxane and 0.5 microliters of saturated aqueous NaHCO$_3$) was prepared in a 10 mL microwave reaction vessel and the sealed reaction vessel warmed to 110° C. for 20 minutes. The reaction mixture was cooled to rt, diluted with methanol, filtered, and purified via preparative HPLC, 60-80% (MeCN/H$_2$O gradient+0.01% TFA). Lyophilization of the combined fractions gave the titled compound as a yellow solid (9.7 mg, 13%). $^1$H NMR (400 MHz, DMSO-d$_6$) δ ppm 1.46 (s, 6 H) 5.21 (s, 2 H) 6.59 (d, J=2.27 Hz, 1 H) 7.27-7.32 (m, 1 H) 7.36 (d, J=7.33 Hz, 1 H) 7.39-7.44 (m, 1 H) 7.49-7.54 (m, 2 H) 7.49-7.57 (m, 1 H) 7.54-7.59 (m, 1 H) 7.60-7.67 (m, 3 H) 7.75-7.79 (m, 1 H) 8.01-8.06 (m, 3 H) 8.19 (d, J=2.27 Hz, 1 H) 11.26 (s, 1 H). ESI-MS: m/z 479.4 (M+H)$^+$.

Example 194

SYR154205Z: N-(7-(2,3-dihydrobenzofuran-5-yl)pyrazolo[1,5-a]pyrimidin-5-yl)-4-(2-hydroxypropan-2-yl)benzamide (180)

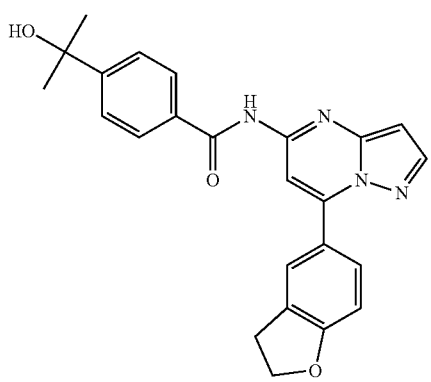

180

A suspension of N-(7-chloropyrazolo[1,5-a]pyrimidin-5-yl)-4-(2-hydroxypropan-2-yl)benzamide (2D, 50 mg, 151 mmol), 3-dihydrobenzofuran-5-ylboronic acid (50 mg, 305 mmol), and [1,1'-bis(diphenylphosphino)ferrocene]dichloropalladium(II) (9 mg, 12 mmol) in 2:1 1,4-dioxane/saturated aqueous NaHCO$_3$ (670 microliters of 1,4-dioxane and 330 microliters of saturated aqueous NaHCO$_3$) was prepared in a 2 mL microwave reaction vessel and the sealed reaction vessel warmed to 110° C. for 20 minutes. The reaction mixture was cooled to rt, diluted with methanol, filtered, and purified via preparative HPLC, 45-70% (MeCN/H$_2$O gradient+0.01% TFA). Lyophilization of the combined fractions gave the titled compound as a yellow solid (16.8 mg, 27%). Melting point (174.2.0-184.3° C.). $^1$HNMR (400 MHz, DMSO-d$_6$) δ ppm 1.46 (s, 6 H) 3.32 (t, J=8.59 Hz, 2 H) 4.67 (t, J=8.72 Hz, 2 H) 6.56 (d, J=2.27 Hz, 1 H) 7.01 (d, J=8.59 Hz, 1 H) 7.62 (d, J=8.34 Hz, 2 H) 7.95 (dd, J=8.46, 1.64 Hz, 1 H) 8.00-8.08 (m, 4 H) 8.19 (d, J=2.02 Hz, 1 H) 11.20 (s, 1 H). ESI-MS: m/z 415.3 (M+H)$^+$.

Example 195

4-(2-hydroxypropan-2-yl)-N-(7-(3-methoxyphenyl)pyrazolo[1,5-a]pyrimidin-5-yl)benzamide (181)

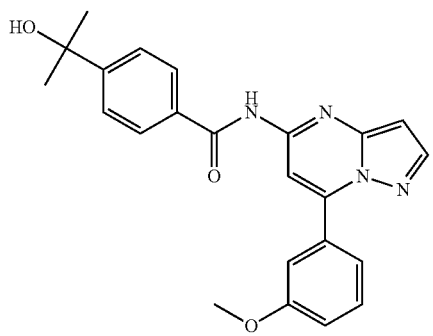

181

A suspension of N-(7-chloropyrazolo[1,5-a]pyrimidin-5-yl)-4-(2-hydroxypropan-2-yl)benzamide (2D, 50 mg, 151 mmol), 3-methoxyphenylboronic acid (46 mg, 302 mmol), and [1,1'-bis(diphenylphosphino)ferrocene]dichloropalladium(II) (9 mg, 12 µmol) in 2:1 1,4-dioxane/saturated aqueous NaHCO$_3$ (670 microliters of 1,4-dioxane and 330 microliters of saturated aqueous NaHCO$_3$) was prepared in a 2 mL microwave reaction vessel and the sealed reaction vessel warmed to 110° C. for 20 minutes. The reaction mixture was cooled to rt, diluted with methanol, filtered, and purified via preparative HPLC, 45-70% (MeCN/H$_2$O gradient+0.01% TFA). Lyophilization of the combined fractions gave the titled compound as a yellow solid (5.2 mg, 9%). $^1$H NMR (400 MHz, DMSO-d$_6$) δ ppm 1.46 (s, 6 H) 3.85 (s, 3 H) 6.59 (d, J=2.27 Hz, 1 H) 7.22 (dd, J=8.08, 1.77 Hz, 1 H) 7.55 (t, J=7.83 Hz, 1 H) 7.59-7.70 (m, 4 H) 7.98-8.09 (m, 3 H) 8.20 (d, J=2.02 Hz, 1 H) 11.27 (s, 1 H). ESI-MS: m/z 403.3 (M+H)$^+$.

Example 196

(E)-4-(2-hydroxypropan-2-yl)-N-(7-styrylpyrazolo[1,5-a]pyrimidin-5-yl)benzamide (182)

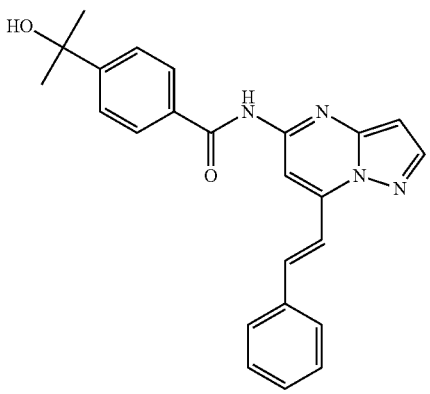

182

A suspension of N-(7-chloropyrazolo[1,5-a]pyrimidin-5-yl)-4-(2-hydroxypropan-2-yl)benzamide (2D, 50 mg, 151 mmol), (E)-styrylboronic acid (45 mg, 302 mmol), and [1,1'-bis(diphenylphosphino)ferrocene]dichloropalladium(II) (9 mg, 12 μmol) in 2:1 1,4-dioxane/saturated aqueous NaHCO₃ (670 microliters of 1,4-dioxane and 330 microliters of saturated aqueous NaHCO₃) was prepared in a 2 mL microwave reaction vessel and the sealed reaction vessel warmed to 110° C. for 20 minutes. The reaction mixture was cooled to rt, diluted with methanol, filtered, and purified via preparative HPLC, 50-80% (MeCN/H₂O gradient+0.01% TFA). Lyophilization of the combined fractions gave the titled compound as a yellow solid (5.8 mg, 10%). ¹H NMR (400 MHz, DMSO-d₆) δ ppm 1.46 (s, 6 H) 3.85 (s, 3 H) 6.59 (d, J=2.27 Hz, 1 H) 7.22 (dd, J=8.08, 1.77 Hz, 1 H) 7.55 (t, J=7.83 Hz, 1 H) 7.59-7.70 (m, 4 H) 7.98-8.09 (m, 3 H) 8.20 (d, J=2.02 Hz, 1 H) 11.27 (s, 1 H). ESI-MS: m/z 399.3 (M+H)⁺.

Example 197

4-(2-hydroxypropan-2-yl)-N-(7-(thiophen-3-yl)pyrazolo[1,5-a]pyrimidin-5-yl)benzamide (183)

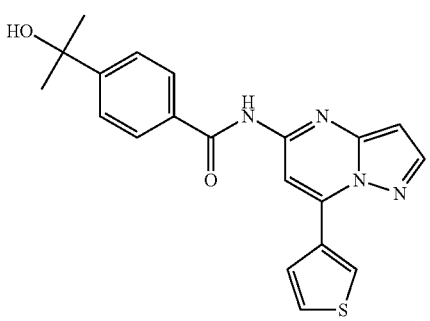

183

A suspension of N-(7-chloropyrazolo[1,5-a]pyrimidin-5-yl)-4-(2-hydroxypropan-2-yl)benzamide (2D, 50 mg, 151 mmol), thiophen-3-ylboronic acid (64 mg, 302 mmol), and [1,1'-bis(diphenylphosphino)ferrocene]dichloropalladium (II) (9 mg, 12 μmol) in 2:1 1,4-dioxane/saturated aqueous NaHCO₃ (670 microliters of 1,4-dioxane and 330 microliters of saturated aqueous NaHCO₃) was prepared in a 2 mL microwave reaction vessel and the sealed reaction vessel warmed to 110° C. for 20 minutes. The reaction mixture was cooled to rt, diluted with methanol, filtered, and purified via preparative HPLC, 40-70% (MeCN/H₂O gradient+0.01% TFA). Lyophilization of the combined fractions gave the titled compound as a yellow solid (6.4 mg, 11%). ¹H NMR (400 MHz, DMSO-d₆) δ ppm 1.46 (s, 6 H) 6.61 (d, 1 H) 7.63 (d, J=8.34 Hz, 2 H) 7.84 (dd, J=5.18, 2.91 Hz, 1 H) 7.93 (dd, J=5.18, 1.14 Hz, 1 H) 8.04 (d, J=8.34 Hz, 2 H) 8.23-8.40 (m, 2 H) 9.12 (dd, J=3.03, 1.26 Hz, 1 H) 11.24 (s, 1 H). ESI-MS: m/z 379.2 (M+H)⁺.

Example 198

N-(7-(3-hydroxyazetidin-1-yl)pyrazolo[1,5-a]pyrimidin-5-yl)-4-(2-hydroxypropan-2-yl)benzamide [TFA salt] (184)

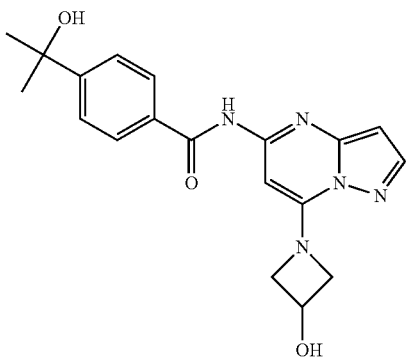

184

A solution of N-(7-chloropyrazolo[1,5-a]pyrimidin-5-yl)-4-(2-hydroxypropan-2-yl)benzamide (2D, 50 mg, 151 mmol) and azetidin-3-ol (22 mg, 0.302 mmol) in NMP (0.950 mL) was stirred at 85° C. overnight. After cooling to room temperature, the mixture was diluted with a few drops of DMSO and methanol, and was then purified by preparatory HPLC, 15-40% (MeCN/H₂O gradient+0.01% TFA). Lyophilization of the combined fractions gave the titled compound as a white solid (17 mg, 32%). ¹H NMR (400 MHz, DMSO-d₆) δ ppm 1.45 (s, 6 H) 4.21 (br. s., 2 H) 4.52-4.89 (m, 3 H) 6.22 (d, J=2.27 Hz, 1 H) 6.74 (s, 1 H) 7.60 (d, J=8.59 Hz, 2 H) 7.91-8.10 (m, 3 H) 10.79 (s, 1 H). ESI-MS: m/z 368.2 (M+H)$^+$.

Example 199

4-(2-hydroxypropan-2-yl)-N-(7-(2-methylpyrrolidin-1-yl)pyrazolo[1,5-a]pyrimidin-5-yl)benzamide [TFA salt] (185)

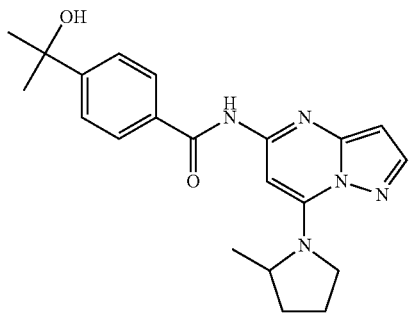

185

A solution of N-(7-chloropyrazolo[1,5-a]pyrimidin-5-yl)-4-(2-hydroxypropan-2-yl)benzamide (2D, 50 mg, 151 mmol) and 2-methylpyrrolidine (26 mg, 0.302 mmol) in NMP (0.950 mL) was stirred at 85° C. overnight. After cooling to room temperature, the mixture was diluted with a few drops of DMSO and methanol, and was then purified by preparatory HPLC, 25-50% (MeCN/H$_2$O gradient+0.01% TFA). Lyophilization of the combined fractions gave the titled compound as a orange solid (34 mg, 59%). $^1$H NMR (400 MHz, DMSO-d$_6$) δ ppm 1.26 (d, J=6.06 Hz, 3 H) 1.45 (s, 6 H) 1.71-1.81 (m, 1 H) 1.90-2.01 (m, 1 H) 2.03-2.26 (m, 2 H) 3.75-3.91 (m, 1 H) 3.96-4.12 (m, 1 H) 4.96 (br. s., 1 H) 6.27 (d, J=2.27 Hz, 1 H) 6.98 (s, 1 H) 7.61 (d, J=8.34 Hz, 2 H) 7.91-8.09 (m, 3 H) 10.81 (s, 1 H). ESI-MS: m/z 380.3 (M+H)$^+$.

Example 200

N-(7-(3-fluoropyrrolidin-1-yl)pyrazolo[1,5-a]pyrimidin-5-yl)-4-(2-hydroxypropan-2-yl)benzamide [TFA salt] (186)

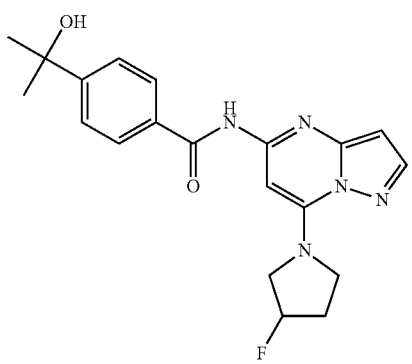

186

A solution of N-(7-chloropyrazolo[1,5-a]pyrimidin-5-yl)-4-(2-hydroxypropan-2-yl)benzamide (2D, 50 mg, 0.151 mmol) and 3-fluoropyrrolidine (27 mg, 0.302 mmol) in NMP (0.950 mL) was stirred at 85° C. overnight. After cooling to room temperature, the mixture was diluted with a few drops of DMSO and methanol, and was then purified by preparatory HPLC, 25-50% (MeCN/H$_2$O gradient+0.01% TFA). Lyophilization of the combined fractions gave the titled compound as a white solid (31 mg, 54%). $^1$H NMR (400 MHz, DMSO-d$_6$) δ ppm 1.45 (s, 6 H) 2.02-2.45 (m, 2 H) 3.86-4.02 (m, 1 H) 4.05-4.47 (m, 3 H) 5.35-5.64 (m, 1 H) 6.26 (s, 1 H) 7.01 (br. s., 1 H) 7.60 (d, J=8.34 Hz, 2 H) 7.88-8.10 (m, 3 H) 10.80 (br. s., 1 H). ESI-MS: m/z 384.2 (M+H)$^+$.

Example 201

4-(2-hydroxypropan-2-yl)-N-(7-(3-oxopiperazin-1-yl)pyrazolo[1,5-a]pyrimidin-5-yl)benzamide [TFA salt] (187)

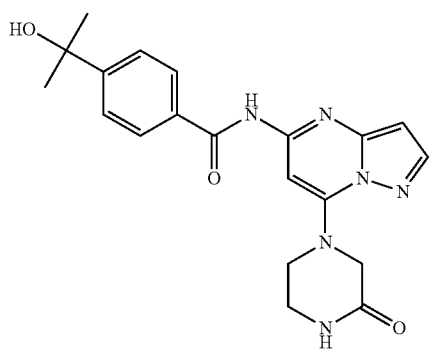

187

A solution of N-(7-chloropyrazolo[1,5-a]pyrimidin-5-yl)-4-(2-hydroxypropan-2-yl)benzamide (2D, 50 mg, 151 mmol) and piperazin-2-one (30 mg, 0.302 mmol) in NMP (0.950 mL) was stirred at 85° C. overnight. After cooling to room temperature, the mixture was diluted with a few drops of DMSO and methanol, and was then purified by preparatory HPLC, 20-45% (MeCN/H$_2$O gradient+0.01% TFA). Lyophilization of the combined fractions gave the titled compound as a orange solid (17 mg, 29%). $^1$H NMR (400 MHz, DMSO-d$_6$) δ ppm 1.46 (s, 6 H) 3.43 (br. s., 2 H) 4.08 (t, J=5.18 Hz, 2 H) 4.27 (s, 2 H) 6.38 (d, J=2.27 Hz, 1 H) 7.41 (s, 1 H) 7.60 (d, J=8.59 Hz, 2 H) 8.00 (d, J=8.34 Hz, 2 H) 8.11 (d, J=2.27 Hz, 1 H) 8.23 (br. s., 1 H) 10.93 (s, 1 H). ESI-MS: m/z 395.2 (M+H)$^+$.

Example 202

N-(7-(3-cyanopiperidin-1-yl)pyrazolo[1,5-a]pyrimidin-5-yl)-4-(2-hydroxypropan-2-yl)benzamide [TFA salt] (188)

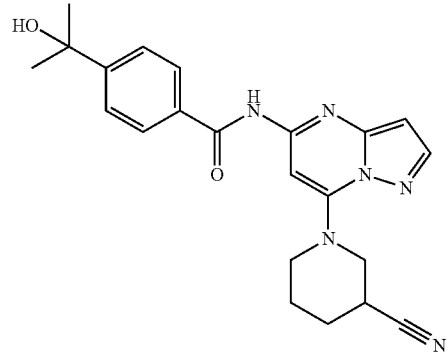

188

A solution of N-(7-chloropyrazolo[1,5-a]pyrimidin-5-yl)-4-(2-hydroxypropan-2-yl)benzamide (2D, 50 mg, 0.151 mmol) and piperidine-3-carbonitrile (33 mg, 0.302 mmol) in NMP (0.950 mL) was stirred at 85° C. overnight. After cooling to room temperature, the mixture was diluted with a few drops of DMSO and methanol, and was then purified by preparatory HPLC, 35-60% (MeCN/H$_2$O gradient+0.01% TFA). Lyophilization of the combined fractions gave the titled compound as a orange solid (52 mg, 85%). $^1$H NMR (400 MHz, DMSO-d$_6$) δ ppm 1.45 (s, 6 H) 1.73-2.11 (m, 4 H) 3.25-3.34 (m, 1 H) 3.53-3.63 (m, 1 H) 3.68-3.79 (m, 1 H) 3.98 (dd, J=12.51, 2.65 Hz, 1 H) 4.12-4.23 (m, 1 H) 6.38 (d, J=2.27 Hz, 1 H) 7.46 (s, 1 H) 7.60 (d, J=8.59 Hz, 2 H) 8.00 (d, J=8.59 Hz, 2 H) 8.12 (d, J=2.27 Hz, 1 H) 10.93 (s, 1 H). ESI-MS: m/z 405.3 (M+H)$^+$.

Example 203

4-(2-hydroxypropan-2-yl)-N-(7-(3-methyl-4-oxopiperidin-1-yl)pyrazolo[1,5-a]pyrimidin-5-yl)benzamide [TFA salt] (189)

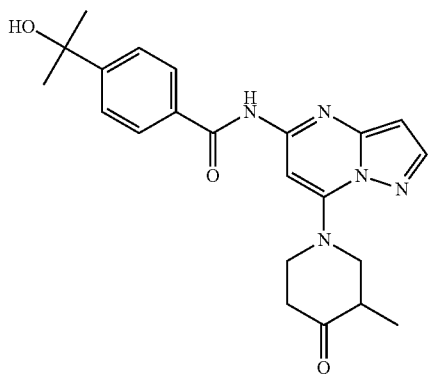

189

A solution of N-(7-chloropyrazolo[1,5-a]pyrimidin-5-yl)-4-(2-hydroxypropan-2-yl)benzamide (2D, 50 mg, 0.151 mmol) and 3-methylpiperidin-4-one (34 mg, 0.302 mmol) in NMP (0.950 mL) was stirred at 85° C. overnight. After cooling to room temperature, the mixture was diluted with a few drops of DMSO and methanol, and was then purified by preparatory HPLC, 30-55% (MeCN/H2O gradient+0.01% TFA). Lyophilization of the combined fractions gave the titled compound as a white solid (34 mg, 56%). $^1$H NMR (400 MHz, DMSO-d$_6$) δ ppm 1.02 (d, J=6.57 Hz, 3 H) 1.46 (s, 6 H) 2.74-2.97 (m, 2 H) 3.30 (t, J=11.87 Hz, 1 H) 3.57-3.69 (m, 1 H) 4.56-4.70 (m, 2 H) 6.38 (d, J=2.27 Hz, 1 H) 7.48 (s, 1 H) 7.60 (d, J=8.59 Hz, 2 H) 8.00 (d, J=8.59 Hz, 2 H) 8.13 (d, J=2.27 Hz, 1 H) 10.93 (s, 1 H). ESI-MS: m/z 408.2 (M+H)$^+$.

Example 204

N-(7-(3,3-dimethylpiperidin-1-yl)pyrazolo[1,5-a]pyrimidin-5-yl)-4-(2-hydroxypropan-2-yl)benzamide [TFA salt] (190)

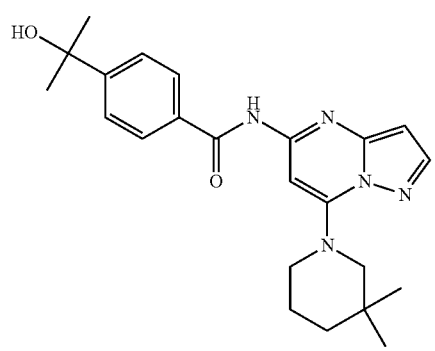

190

A solution of N-(7-chloropyrazolo[1,5-a]pyrimidin-5-yl)-4-(2-hydroxypropan-2-yl)benzamide (2D, 50 mg, 0.151 mmol) and 3,3-dimethylpiperidine (34 mg, 0.302 mmol) in NMP (0.950 mL) was stirred at 85° C. overnight. After cooling to room temperature, the mixture was diluted with a few drops of DMSO and methanol, and was then purified by preparatory HPLC, 40-65% (MeCN/H$_2$O gradient+0.01% TFA). Lyophilization of the combined fractions gave the titled compound as a white solid (33 mg, 54%). $^1$H NMR (400 MHz, DMSO-d$_6$) δ ppm 0.99 (s, 6 H) 1.45 (s, 6 H) 1.50 (t, J=6.06 Hz, 2 H) 1.80 (br. s., 2 H) 3.51 (s, 2 H) 3.65 (t, J=5.05 Hz, 2 H) 6.33 (d, J=2.02 Hz, 1 H) 7.39 (s, 1 H) 7.60 (d, J=8.34 Hz, 2 H) 8.00 (d, J=8.34 Hz, 2 H) 8.08 (d, J=2.02 Hz, 1 H) 10.85 (s, 1 H). ESI-MS: m/z 408.3 (M+H)$^+$.

Example 205

N-(7-(4-formylpiperazin-1-yl)pyrazolo[1,5-a]pyrimidin-5-yl)-4-(2-hydroxypropan-2-yl)benzamide [TFA salt] (191)

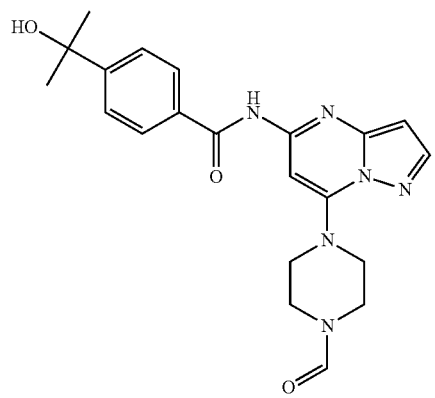

191

A solution of N-(7-chloropyrazolo[1,5-a]pyrimidin-5-yl)-4-(2-hydroxypropan-2-yl)benzamide (2D, 50 mg, 0.151 mmol) and piperazine-1-carbaldehyde (34 mg, 0.302 mmol) in NMP (0.950 mL) was stirred at 85° C. overnight. After cooling to room temperature, the mixture was diluted with a few drops of DMSO and methanol, and was then purified by preparatory HPLC, 20-45% (MeCN/H₂O gradient+0.01% TFA). Lyophilization of the combined fractions gave the titled compound as a white solid (35 mg, 57%). ¹H NMR (400 MHz, DMSO-d₆) δ ppm 1.45 (s, 6 H) 3.59-3.82 (m, 8 H) 6.39 (d, J=2.02 Hz, 1 H) 7.43 (s, 1 H) 7.60 (d, J=8.59 Hz, 2 H) 8.00 (d, J=8.34 Hz, 2 H) 8.08-8.15 (m, 2 H) 10.94 (s, 1 H). ESI-MS: m/z 409.2 (M+H)⁺.

Example 206

(S)-N-(7-(3-(dimethylamino)pyrrolidin-1-yl)pyrazolo[1,5-a]pyrimidin-5-yl)-4-(2-hydroxypropan-2-yl)benzamide (192)

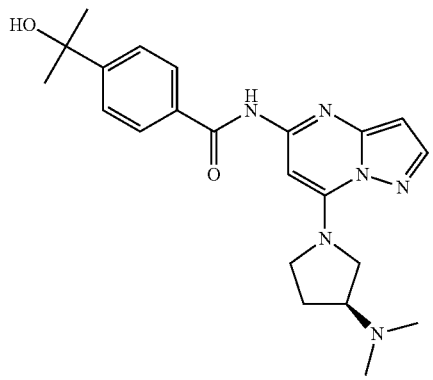

192

A solution of N-(7-chloropyrazolo[1,5-a]pyrimidin-5-yl)-4-(2-hydroxypropan-2-yl)benzamide (2D, 50 mg, 0.151 mmol) and (S)-N,N-dimethylpyrrolidin-3-amine (34 mg, 0.302 mmol) in NMP (0.950 mL) was stirred at 85° C. overnight. After cooling to room temperature, the mixture was diluted with a few drops of DMSO and methanol, and was then purified by preparatory HPLC, 10-35% (MeCN/H₂O gradient+0.01% TFA). Lyophilization of the combined fractions gave the titled compound as a white solid (60 mg, 97%). ¹H NMR (400 MHz, DMSO-d₆) δ ppm 1.45 (s, 6 H) 2.20-2.37 (m, 1 H) 2.61-2.71 (m, 1 H) 2.90 (d, J=3.79 Hz, 6 H) 3.79-3.91 (m, 1 H) 4.02-4.19 (m, 2 H) 4.35 (d, J=6.57 Hz, 2 H) 6.26 (d, J=2.27 Hz, 1 H) 7.15 (s, 1 H) 7.60 (d, J=8.59 Hz, 2 H) 7.99 (d, J=8.59 Hz, 2 H) 8.04 (d, J=2.02 Hz, 1 H) 9.87 (br. s., 1 H) 10.77 (s, 1 H). ESI-MS: m/z 409.3 (M+H)⁺.

Example 207

(R)-4-(2-hydroxypropan-2-yl)-N-(7-(2-(methoxymethyl)pyrrolidin-1-yl)pyrazolo[1,5-a]pyrimidin-5-yl)benzamide [TFA salt] (193)

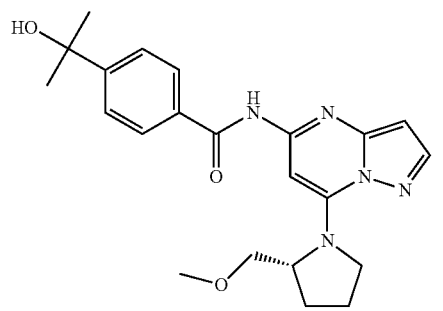

193

A solution of N-(7-chloropyrazolo[1,5-a]pyrimidin-5-yl)-4-(2-hydroxypropan-2-yl)benzamide (2D, 50 mg, 0.151 mmol) and (R)-2-(methoxymethyl)pyrrolidine (35 mg, 0.302 mmol) in NMP (0.950 mL) was stirred at 85° C. overnight. After cooling to room temperature, the mixture was diluted with a few drops of DMSO and methanol, and was then purified by preparatory HPLC, 20-45% (MeCN/H₂O gradient+0.01% TFA). Lyophilization of the combined fractions gave the titled compound as a orange solid (44 mg, 72%). ¹H NMR (400 MHz, DMSO-d₆) δ ppm 1.46 (s, 6 H) 1.90-2.18 (m, 4 H) 3.24 (s, 3 H) 3.37 (dd, J=9.47, 7.20 Hz, 1 H) 3.54 (dd, J=9.73, 3.66 Hz, 1 H) 3.68-3.79 (m, 1 H) 3.83-3.98 (m, 1 H) 5.25 (br. s., 1 H) 6.28 (d, J=2.27 Hz, 1 H) 7.06 (s, 1 H) 7.61 (d, J=8.59 Hz, 2 H) 7.98 (d, J=8.59 Hz, 2 H) 8.04 (d, J=2.02 Hz, 1 H) 10.81 (s, 1 H). ESI-MS: m/z 410.3 (M+H)⁺.

Example 208

(R)-N-(7-(3-(dimethylamino)pyrrolidin-1-yl)pyrazolo[1,5-a]pyrimidin-5-yl)-4-(2-hydroxypropan-2-yl)benzamide [TFA salt] (194)

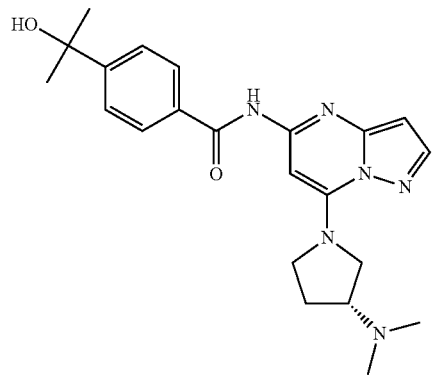

194

A solution of N-(7-chloropyrazolo[1,5-a]pyrimidin-5-yl)-4-(2-hydroxypropan-2-yl)benzamide (2D, 50 mg, 0.151 mmol) and (R)-N,N-dimethylpyrrolidin-3-amine (34 mg, 0.302 mmol) in NMP (0.950 mL) was stirred at 85° C. overnight. After cooling to room temperature, the mixture was diluted with a few drops of DMSO and methanol, and was then purified by preparatory HPLC, 10-35% (MeCN/H₂O gradient+0.01% TFA). Lyophilization of the combined fractions gave the titled compound as a white solid (60 mg, 97%). ¹H NMR (400 MHz, DMSO-d₆) δ ppm 1.45 (s, 6 H) 2.22-2.35 (m, 2 H) 2.90 (d, J=3.79 Hz, 6 H) 3.78-3.91 (m, 1 H) 4.01-4.16 (m, 2 H) 4.35 (d, J=6.57 Hz, 2 H) 6.26 (d, J=2.27 Hz, 1 H) 7.15 (s, 1 H) 7.60 (d, J=8.34 Hz, 2 H) 7.99 (d, J=8.34 Hz, 2 H) 8.04 (d, J=2.27 Hz, 1 H) 9.88 (br. s., 1 H) 10.77 (s, 1 H). ESI-MS: m/z 409.3 (M+H)⁺.

Example 209

N-(7-(2,5-dimethylpiperazin-1-yl)pyrazolo[1,5-a]pyrimidin-5-yl)-4-(2-hydroxypropan-2-yl)benzamide [TFA salt] (195)

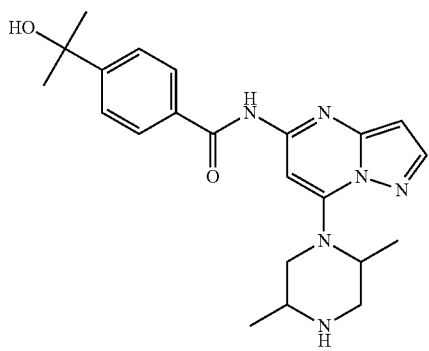

A solution of N-(7-chloropyrazolo[1,5-a]pyrimidin-5-yl)-4-(2-hydroxypropan-2-yl)benzamide (2D, 50 mg, 0.151 mmol) and 2,5-dimethylpiperazine (34 mg, 0.302 mmol) in NMP (0.950 mL) was stirred at 85° C. overnight. After cooling to room temperature, the mixture was diluted with a few drops of DMSO and methanol, and was then purified by preparatory HPLC, 15-40% (MeCN/H₂O gradient+0.01% TFA). Lyophilization of the combined fractions gave the titled compound as a white solid (41 mg, 66%). ¹H NMR (400 MHz, DMSO-d₆) δ ppm 1.30 (d, J=6.57 Hz, 3 H) 1.36 (d, J=6.82 Hz, 3 H) 1.46 (s, 6 H) 3.17 (d, J=5.81 Hz, 1 H) 3.60 (dd, J=13.14, 5.31 Hz, 2 H) 3.73 (br. s., 1 H) 3.93 (dd, J=13.14, 2.78 Hz, 1 H) 4.62 (d, J=4.55 Hz, 1 H) 6.44 (d, J=2.27 Hz, 1 H) 7.51 (s, 1 H) 7.61 (d, J=8.59 Hz, 2 H) 8.00 (d, J=8.34 Hz, 2 H) 8.13 (d, J=2.27 Hz, 1 H) 8.94 (br. s., 1 H) 9.04 (br. s., 1 H) 11.04 (s, 1 H). ESI-MS: m/z 409.3 (M+H)⁺.

Example 210

4-(2-hydroxypropan-2-yl)-N-(7-(4-methyl-1,4-diazepan-1-yl)pyrazolo[1,5-a]pyrimidin-5-yl)benzamide [TFA salt] (196)

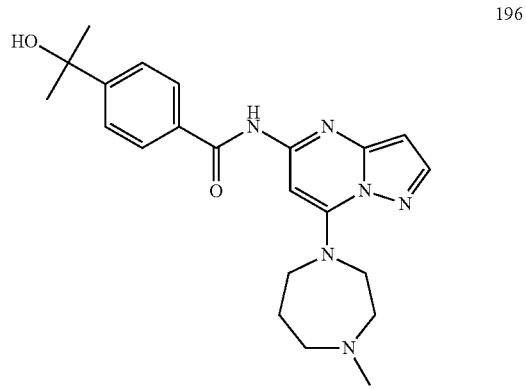 [SMILES: CN1CCCN(c2cc(NC(=O)c3ccc(C(C)(C)O)cc3)nc3ccnn23)CC1]

A solution of N-(7-chloropyrazolo[1,5-a]pyrimidin-5-yl)-4-(2-hydroxypropan-2-yl)benzamide (2D, 50 mg, 0.151 mmol) and 1-methyl-1,4-diazepane (34 mg, 0.302 mmol) in NMP (0.950 mL) was stirred at 85° C. overnight. After cooling to room temperature, the mixture was diluted with a few drops of DMSO and methanol, and was then purified by preparatory HPLC, 15-40% (MeCN/H₂O gradient+0.01% TFA). Lyophilization of the combined fractions gave the titled compound as a white solid (61 mg, 99%). ¹H NMR (400 MHz, DMSO-d₆) δ ppm 1.45 (s, 6 H) 2.33 (d, J=1.77 Hz, 2 H) 2.91 (d, J=4.55 Hz, 3 H) 3.32-3.46 (m, 1 H) 3.51-3.64 (m, 2 H) 3.64-3.86 (m, 4 H) 4.65 (dd, J=15.54, 4.42 Hz, 1 H) 6.33 (d, J=2.27 Hz, 1 H) 7.32 (s, 1 H) 7.60 (d, J=8.59 Hz, 2 H) 7.99 (d, J=8.34 Hz, 2 H) 8.08 (d, J=2.27 Hz, 1 H) 9.62 (br. s., 1 H) 10.85 (s, 1 H). ESI-MS: m/z 409.3 (M+H)⁺.

Example 211

N-(7-(2,6-dimethylmorpholino)pyrazolo[1,5-a]pyrimidin-5-yl)-4-(2-hydroxypropan-2-yl)benzamide [TFA salt] (197)

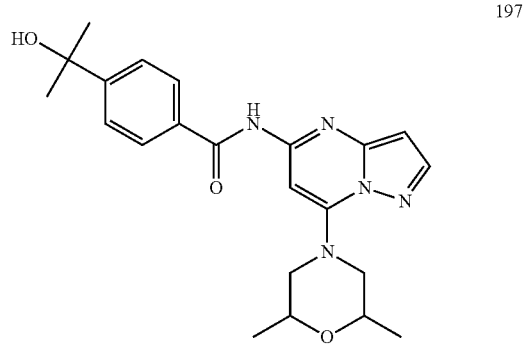 [SMILES: CC1CN(c2cc(NC(=O)c3ccc(C(C)(C)O)cc3)nc3ccnn23)CC(C)O1]

A solution of N-(7-chloropyrazolo[1,5-a]pyrimidin-5-yl)-4-(2-hydroxypropan-2-yl)benzamide (2D, 50 mg, 0.151 mmol) and 2,6-dimethylmorpholine (35 mg, 0.302 mmol) in NMP (0.950 mL) was stirred at 85° C. overnight. After cooling to room temperature, the mixture was diluted with a few drops of DMSO and methanol, and was then purified by preparatory HPLC, 35-65% (MeCN/H₂O gradient+0.01% TFA). Lyophilization of the combined fractions gave the titled compound as a white solid (41 mg, 66%). ¹H NMR (400 MHz, DMSO-d₆) δ ppm 1.19 (d, J=6.06 Hz, 6 H) 1.46 (s, 6 H) 2.68 (t, J=11.24 Hz, 2 H) 3.80-3.91 (m, 2 H) 4.38 (d, J=11.62 Hz, 2 H) 6.37 (d, J=2.27 Hz, 1 H) 7.40 (s, 1 H) 7.60 (d, J=8.34 Hz, 2 H) 8.00 (d, J=8.59 Hz, 2 H) 8.10 (d, J=2.27 Hz, 1 H) 10.91 (s, 1 H). ESI-MS: m/z 410.3 (M+H)⁺.

Example 212

N-(7-(3-(hydroxymethyl)piperidin-1-yl)pyrazolo[1,5-a]pyrimidin-5-yl)-4-(2-hydroxypropan-2-yl)benzamide [TFA salt] (198)

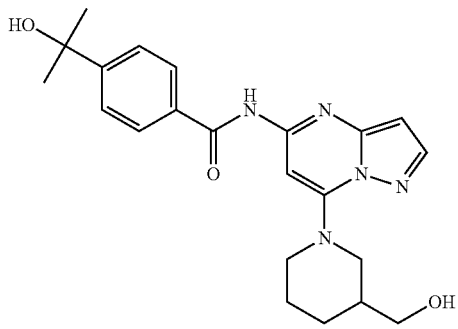

A solution of N-(7-chloropyrazolo[1,5-a]pyrimidin-5-yl)-4-(2-hydroxypropan-2-yl)benzamide (2D, 50 mg, 0.151 mmol) and piperidin-3-ylmethano (35 mg, 0.302 mmol) in NMP (0.950 mL) was stirred at 85° C. overnight. After cooling to room temperature, the mixture was diluted with a few drops of DMSO and methanol, and was then purified by preparatory HPLC, 20-45% (MeCN/H₂O gradient+0.01% TFA). Lyophilization of the combined fractions gave the titled compound as a white solid (15 mg, 24%). ¹H NMR (400 MHz, DMSO-d₆) δ ppm 1.45 (s, 6 H) 1.58-1.74 (m, 2 H) 2.00-2.10 (m, 2 H) 3.31 (s, 3 H) 3.42-3.55 (m, 3 H) 4.01-4.14 (m, 2 H) 6.34 (d, J=2.27 Hz, 1 H) 7.41 (s, 1 H) 7.60 (d, J=8.34 Hz, 2 H) 7.99 (d, J=8.34 Hz, 2 H) 8.08 (d, J=2.27 Hz, 1 H) 10.87 (s, 1 H). ESI-MS: m/z 410.3 (M+H)⁺.

Example 213

N-(7-(4-(hydroxymethyl)piperidin-1-yl)pyrazolo[1,5-a]pyrimidin-5-yl)-4-(2-hydroxypropan-2-yl)benzamide [TFA salt] (199)

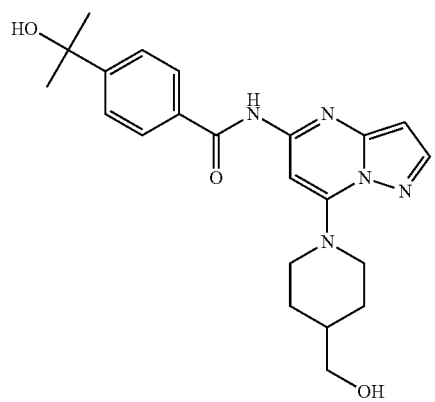

A solution of N-(7-chloropyrazolo[1,5-a]pyrimidin-5-yl)-4-(2-hydroxypropan-2-yl)benzamide (2D, 50 mg, 0.151 mmol) and piperidin-4-ylmethanol (35 mg, 0.302 mmol) in NMP (0.950 mL) was stirred at 85° C. overnight. After cooling to room temperature, the mixture was diluted with a few drops of DMSO and methanol, and was then purified by preparatory HPLC, 20-50% (MeCN/H₂O gradient+0.01% TFA). Lyophilization of the combined fractions gave the titled compound as a white solid (55 mg, 89%). ¹H NMR (400 MHz, DMSO-d₆) δ ppm 1.46 (s, 8 H) 1.65-1.95 (m, 3 H) 2.96-3.15 (m, 2 H) 3.34 (d, J=6.06 Hz, 2 H) 4.39-4.56 (m, 2 H) 6.35 (d, J=2.02 Hz, 1 H) 7.38 (s, 1 H) 7.60 (d, J=8.59 Hz, 2 H) 8.00 (d, J=8.59 Hz, 2 H) 8.08 (d, J=2.27 Hz, 1 H) 10.87 (s, 1 H). ESI-MS: m/z 410.3 (M+H)⁺.

Example 214

4-(2-hydroxypropan-2-yl)-N-(7-(4-methoxypiperidin-1-yl)pyrazolo[1,5-a]pyrimidin-5-yl)benzamide (200)

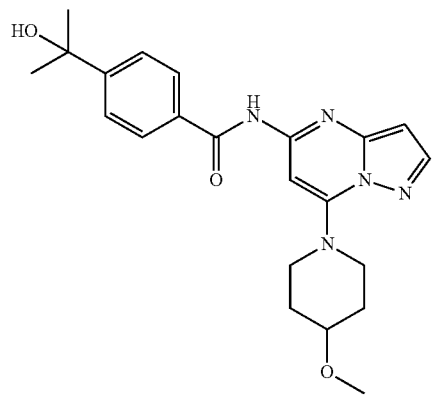

A solution of N-(7-chloro-2-methylpyrazolo[1,5-a]pyrimidin-5-yl)-4-(2-hydroxypropan-2-yl)benzamide (2D, 50 mg, 0.151 mmol) and 4-methoxypiperidine (27 mg, 0.302 mmol) in NMP (0.950 mL) was stirred at 85° C. overnight. After cooling to room temperature, the mixture was diluted with a few drops of DMSO and methanol, and was then purified by preparatory HPLC, 5-95% (MeCN/H$_2$O gradient+0.01% TFA). Lyophilization of the combined fractions gave the titled compound as a white solid (16 mg, 26%). $^1$H NMR (400 MHz, DMSO-d$_6$) δ ppm 1.45 (s, 6 H) 1.59-1.75 (m, 2 H) 1.98-2.12 (m, 2 H) 3.31 (s, 3 H) 3.41-3.58 (m, 3 H) 3.97-4.15 (m, 2 H) 6.35 (d, J=2.27 Hz, 1 H) 7.40 (s, 1 H) 7.60 (m, J=8.34 Hz, 2 H) 7.99 (m, J=8.59 Hz, 2 H) 8.08 (d, J=2.27 Hz, 1 H) 10.88 (s, 1 H). ESI-MS: m/z 410.3 (M+H)$^+$.

Example 215

4-(2-hydroxypropan-2-yl)-N-(2-methyl-7-morpholinopyrazolo[1,5-a]pyrimidin-5-yl)benzamide (201)

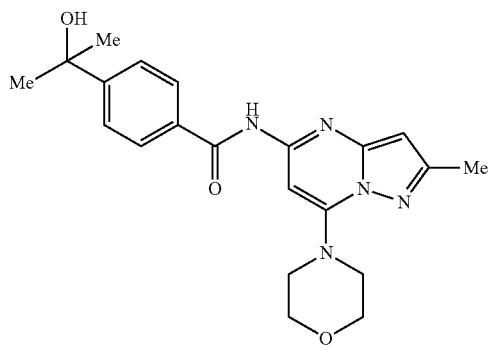

A solution of N-(7-chloro-2-methylpyrazolo[1,5-a]pyrimidin-5-yl)-4-(2-hydroxypropan-2-yl)benzamide (2F, 43 mg, 0.125 mmol) and morpholine (43 mg, 0.499 mmol) in DMF (0.5 mL) was stirred at 100° C. for 3 h. After cooling to room temperature, the mixture was diluted with DMF and then purified by preparatory HPLC (20-35% MeCN/H$_2$O+ 0.01% TFA). Lyophilization of the combined fractions gave the titled compound as a white solid (22.4 mg, 45%). Melting point (242.8-242.9° C.). $^1$H NMR (400 MHz, DMSO-d$_6$) δ ppm 1.45 (s, 6 H), 2.38 (s, 3 H), 3.69-3.78 (m, 4 H), 3.80-3.88 (m, 4 H), 6.18 (s, 1 H), 7.34 (s, 1 H), 7.60 (d, J=8.84 Hz, 2 H), 7.99 (d, J=8.84 Hz, 2 H), 10.87 (s, 1 H); ESI-MS: m/z 396.2 (M+H)$^+$.

Example 216

4-(2-hydroxypropan-2-yl)-N-(2-methyl-7-phenylpyrazolo[1,5-a]pyrimidin-5-yl)benzamide (202)

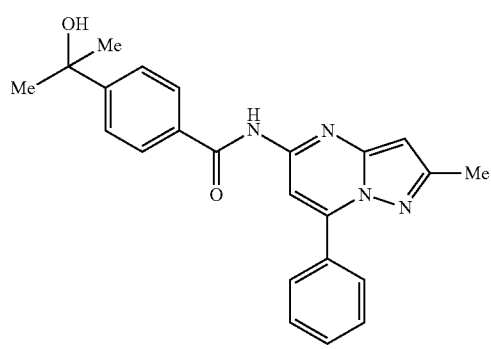

A suspension of N-(7-chloro-2-methylpyrazolo[1,5-a]pyrimidin-5-yl)-4-(2-hydroxypropan-2-yl)benzamide (2F, 49 mg, 0.142 mmol), phenylboronic acid (23 mg, 0.189 mmol), and [1,1'-bis[1,1'-Bis(diphenylphosphino)ferrocene]-dichloropalladium(II) (9.3 mg, 13 mmol) in 2:1 1,4-dioxane/saturated aqueous NaHCO$_3$ (0.76 mL of 1,4-dioxane and 0.38 mL of saturated aqueous NaHCO$_3$) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (65-75% MeCN/H$_2$O+0.01% TFA). Lyophilization of the combined fractions gave the titled compound as a yellow solid (13.9 mg, 25%). Decomposition observed at 199.8° C. $^1$H NMR (400 MHz, DMSO-d$_6$) δ ppm 1.46 (s, 6 H), 2.40 (s, 3 H), 5.20 (br. s., 1 H), 6.40 (s, 1 H), 7.58-7.66 (m, 5 H), 7.97 (s, 1 H), 8.02 (d, J=8.59 Hz, 2 H), 8.06 (dd, J=6.57, 3.03 Hz, 2 H), 11.20 (s, 1 H); ESI-MS: m/z 387.2 (M+H)$^+$.

Example 217

(R)-4-(2-hydroxypropan-2-yl)-N-(7-(3-hydroxypyrrolidin-1-yl)-2-methylpyrazolo[1,5-a]pyrimidin-5-yl)benzamide (203)

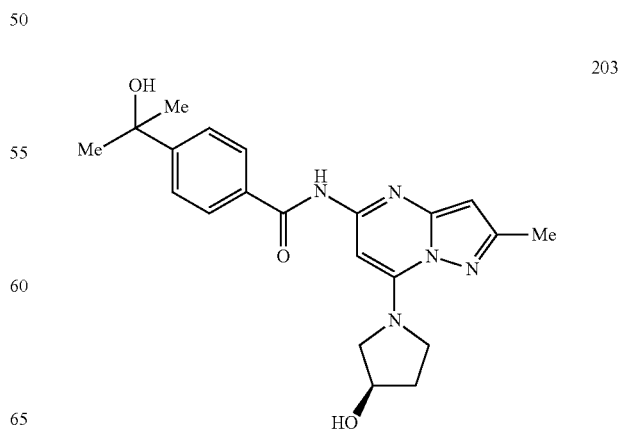

A solution of N-(7-chloro-2-methylpyrazolo[1,5-a]pyrimidin-5-yl)-4-(2-hydroxypropan-2-yl)benzamide (2F, 52 mg, 0.151 mmol) and (R)-pyrrolidin-3-ol (53 mg, 0.603 mmol) in DMF (0.5 mL) was stirred at 100° C. for 3 h. After cooling to room temperature, the mixture was diluted with a few drops of DMSO and methanol, and was then purified by preparatory HPLC (25-25% MeCN/H$_2$O+0.01% TFA). Lyophilization of the combined fractions gave the titled compound as a white solid (21.1 mg, 35%). $^1$H NMR (400 MHz, DMSO-d$_6$) δ ppm 1.46 (s, 6 H), 1.91-2.12 (m, 2 H), 2.34 (s, 3 H), 3.82-4.13 (m, 5 H), 4.44 (br. s., 1 H), 6.16 (s, 1 H), 6.71 (s, 1 H), 7.63 (d, J=8.59 Hz, 2 H), 7.98 (d, J=8.34 Hz, 2 H), 10.95 (s, 1 H); ESI-MS: m/z 396.2 (M+H)$^+$.

Example 218

4-(2-hydroxypropan-2-yl)-N-(2-methyl-7-(piperidin-1-yl)pyrazolo[1,5-a]pyrimidin-5-yl)benzamide (204)

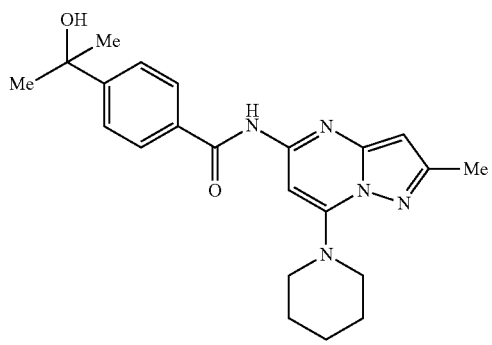

204

A solution of N-(7-chloro-2-methylpyrazolo[1,5-a]pyrimidin-5-yl)-4-(2-hydroxypropan-2-yl)benzamide (2F, 52 mg, 0.151 mmol) and piperidine (52 mg, 0.603 mmol) in DMF (0.5 mL) was stirred at 100° C. for 3 h. After cooling to room temperature, the mixture was diluted with a few drops of DMSO and methanol, and was then purified by preparatory HPLC (35-45% MeCN/H$_2$O+0.01% TFA). Lyophilization of the combined fractions gave the titled compound as a white solid (31.2 mg, 52%). $^1$H NMR (400 MHz, DMSO-d$_6$) δ ppm 1.45 (s, 6 H), 1.70 (br. s., 6 H), 2.37 (s, 3 H), 3.73 (br. s., 4 H), 6.16 (s, 1 H), 7.28 (s, 1 H), 7.60 (d, J=8.59 Hz, 2 H), 7.99 (d, J=8.59 Hz, 2 H), 10.84 (s, 1 H); ESI-MS: m/z 394.3 (M+H)$^+$.

Example 219

N-(7-(benzo[d][1,3]dioxol-4-yl)pyrazolo[1,5-a]pyrimidin-5-yl)-4-(2-hydroxypropan-2-yl)benzamide (205)

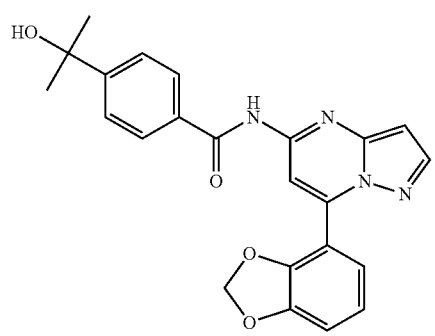

205

A suspension of N-(7-chloro-2-methylpyrazolo[1,5-a]pyrimidin-5-yl)-4-(2-hydroxypropan-2-yl)benzamide (2D, 50 mg, 0.151 mmol), benzo[d][1,3]dioxol-4-ylboronic acid (50 mg, 0.302 mmol), and [1,1'-bis(diphenylphosphino)ferrocene]dichloropalladium(II) (9 mg, 12 μmol) in 2:1 1,4-dioxane/saturated aqueous NaHCO$_3$ (330 microliters of 1,4-dioxane and 670 microliters of saturated aqueous NaHCO$_3$) was prepared in a 2 mL microwave reaction vessel and the sealed reaction vessel warmed to 110° C. for 20 minutes. The reaction mixture was cooled to rt, diluted with methanol, filtered, and purified via preparative HPLC, 5-95% (MeCN/H$_2$O gradient+0.01% TFA). Lyophilization of the combined fractions gave the titled compound as a yellow solid (2.8 mg, 4%). $^1$H NMR (400 MHz, DMSO-d$_6$) δ ppm 1.46 (s, 6 H) 5.20 (s, 1 H) 6.18 (s, 2 H) 6.57 (d, J=2.27 Hz, 1 H) 7.17 (d, J=8.34 Hz, 1 H) 7.56-7.69 (m, 3 H) 7.72 (d, J=1.77 Hz, 1 H) 7.98-8.10 (m, 3 H) 8.19 (d, J=2.27 Hz, 1 H) 11.23 (s, 1 H). ESI-MS: m/z 417.0 (M+H)$^+$.

Example 220

4-(2-hydroxypropan-2-yl)-N-(2-methyl-7-(4-oxo-3,4,7,8-tetrahydropyrido[4,3-d]pyrimidin-6(5H)-yl)pyrazolo[1,5-a]pyrimidin-5-yl)benzamide (206)

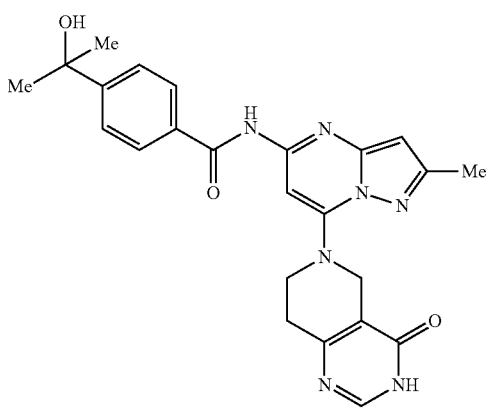

206

A solution of N-(7-chloro-2-methylpyrazolo[1,5-a]pyrimidin-5-yl)-4-(2-hydroxypropan-2-yl)benzamide (2F, 52 mg, 0.151 mmol), 5,6,7,8-tetrahydropyrido[4,3-c/]pyrimidin-4(3H)-one hydrochloride (78 mg, 0.395 mmol), and N,N-diisopropylethylamine (60 mg, 0.467 mmol) in DMF (0.5 mL) was stirred at 100° C. for 3 h. After cooling to room temperature, the mixture was filtered and the crude material recrystallized from hot methanol, providing the titled compound as a white solid (26.9 mg, 39%). $^1$H NMR (DMSO-d$_6$) δ: 8.13 (br. s., 1H), 8.00 (d, J=8.6 Hz, 2H), 7.60 (d, J=8.6 Hz, 2H), 7.45 (s, 1H), 6.18 (s, 1H), 5.18 (s, 1H), 4.49 (br. s., 2H), 4.10 (t, J=6.7 Hz, 2H), 2.87 (t, J=6.7 Hz, 2H), 2.40 (s, 3H), 1.45 (s, 6H); ESI-MS: m/z 460.2 (M+H)$^+$.

Example 221

4-(2-hydroxypropan-2-yl)-N-(2-methyl-7-thiomorpholinopyrazolo[1,5-a]pyrimidin-5-yl)benzamide (207)

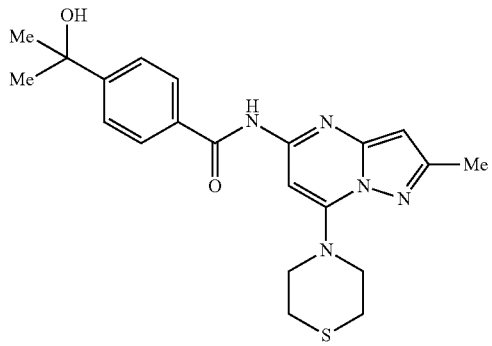

207

A solution of N-(7-chloro-2-methylpyrazolo[1,5-a]pyrimidin-5-yl)-4-(2-hydroxypropan-2-yl)benzamide (2F, 99 mg, 0.287 mmol) and thiomorpholine (91 mg, 0.861 mmol) in DMF (1.11 mL) was stirred at 100° C. for 2 h. After cooling to room temperature, the mixture was diluted with methanol and then purified by preparatory HPLC (35-60% MeCN/H$_2$O gradient+0.01% TFA). Lyophilization of the combined fractions gave the titled compound as a white solid (26.9 mg, 39%). Melting point (229.1-229.2° C.). $^1$H NMR (400 MHz, DMSO-d$_6$) δ ppm 1.45 (s, 6H), 2.38 (s, 3H), 2.75-2.90 (m, 4H), 4.02 (dt, J=4.67, 2.46 Hz, 4H), 6.16 (s, 1H), 7.35 (s, 1H), 7.60 (d, J=8.34 Hz, 2H), 7.99 (d, J=8.34 Hz, 2H), 10.86 (s, 1H); ESI-MS: m/z 412.2 (M+H)$^+$.

Example 222

4-[5-({[4-(1-hydroxy-1-methylethyl)phenyl]carbonyl}amino)-2-methylpyrazolo[1,5-a]pyrimidin-7-yl]thiomorpholin-1-ium-1-olate (208)

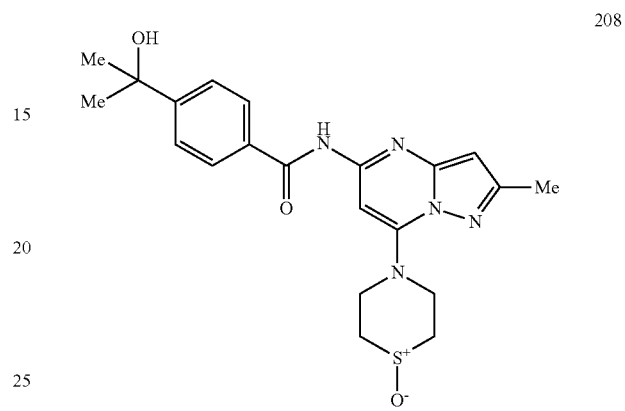

208

A solution of N-(7-chloro-2-methylpyrazolo[1,5-a]pyrimidin-5-yl)-4-(2-hydroxypropan-2-yl)benzamide (2F, 52 mg, 0.151 mmol), thiomorpholine-S-oxide hydrochloride (91 mg, 0.557 mmol), and N,N-diisopropylethylamine (79 mg, 0.467 mmol) in DMF (1.11 mL) was stirred at 100° C. for 3.5 h. After cooling to room temperature, the mixture was diluted with methanol, and was then purified by preparatory HPLC (25-30% MeCN/H$_2$O gradient+0.01% TFA). Lyophilization of the combined fractions gave the titled compound as a white solid (29.3 mg, 24%). $^1$H NMR (400 MHz, DMSO-d$_6$) δ ppm 1.45 (s, 6H), 2.39 (s, 3H), 2.93 (dd, J=12.13, 1.77 Hz, 2H), 3.09-3.22 (m, 2H), 3.99-4.09 (m, 2H), 4.40 (d, J=14.40 Hz, 2H), 6.19 (s, 1H), 7.43 (s, 1H), 7.60 (d, J=8.59 Hz, 2H), 8.00 (d, J=8.59 Hz, 2H), 10.89 (s, 1H); ESI-MS: m/z 428.3 (M+H)$^+$.

Example 223

N-[7-(1,1-dioxidothiomorpholin-4-yl)-2-methylpyrazolo[1,5-a]pyrimidin-5-yl]-4-(1-hydroxy-1-methylethyl)benzamide (209)

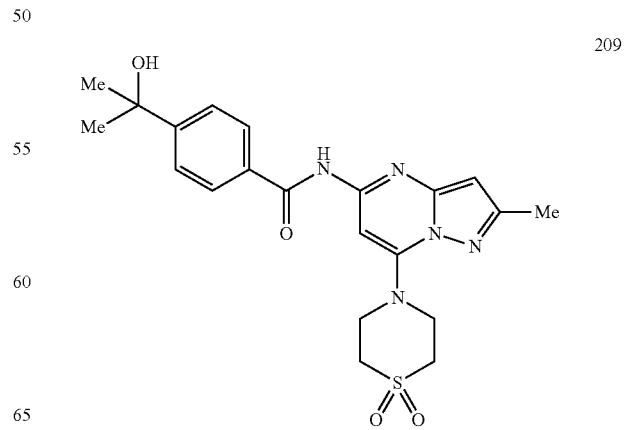

209

A solution of N-(7-chloro-2-methylpyrazolo[1,5-a]pyrimidin-5-yl)-4-(2-hydroxypropan-2-yl)benzamide (2F, 110 mg, 0.319 mmol), S,S-dioxidothiomorpholine hydrochloride (164 mg, 0.957 mmol) and N,N-diisopropylethylamine (181 mg, 1.40 mmol) in DMF (1.28 mL) was stirred at 100° C. for 3 h. After cooling to room temperature, the mixture was diluted with methanol, and was then purified by preparatory HPLC (20-30% MeCN/H₂O gradient+0.01% TFA). Lyophilization of the combined fractions gave the titled compound as a white solid (52.4 mg, 37%). ¹H NMR (DMSO-d₆) δ: 10.92 (s, 1H), 8.00 (d, J=8.8 Hz, 2H), 7.60 (d, J=8.6 Hz, 2H), 7.42 (s, 1H), 6.21 (s, 1H), 4.25 (br. s., 4H), 3.41 (br. s., 4H), 2.39 (s, 3H), 1.45 (s, 6H); ESI-MS: m/z 444.2 (M+H)⁺.

Example 224

N-(7-(4-(ethylsulfonyl)piperazin-1-yl)-2-methylpyrazolo[1,5-a]pyrimidin-5-yl)-4-(2-hydroxypropan-2-yl)benzamide (210)

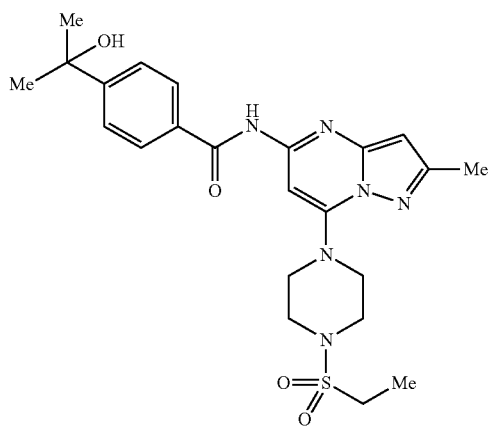

210

A solution of N-(7-chloro-2-methylpyrazolo[1,5-a]pyrimidin-5-yl)-4-(2-hydroxypropan-2-yl)benzamide (2F, 110 mg, 0.315 mmol) and 1-(ethylsulfonyl)piperazine (174 mg, 0.957 mmol) in DMF (1.28 mL) was stirred at 100° C. for 3 h. After cooling to room temperature, the mixture was diluted with a few drops of DMSO and methanol, and was then purified by preparatory HPLC (35-45% MeCN/H₂O gradient+0.01% TFA). Lyophilization of the combined fractions gave the titled compound as a white solid (59.9 mg, 39%). Melting point (176.4-180.4° C.). ¹H NMR (DMSO-d₆) δ: 10.91 (s, 1H), 8.00 (d, J=8.6 Hz, 2H), 7.60 (d, J=8.6 Hz, 2H), 7.36 (s, 1H), 6.20 (s, 1H), 3.69-3.93 (m, 4H), 3.34-3.55 (m, 4H), 3.16 (q, J=7.3 Hz, 2H), 2.39 (s, 3H), 1.45 (s, 6H), 1.26 (t, J=7.3 Hz, 3H); ESI-MS: m/z 487.3 (M+H)⁺.

Example 225

N-(7-(4-(hydroxymethyl)piperidin-1-yl)-2-methylpyrazolo[1,5-a]pyrimidin-5-yl)-4-(2-hydroxypropan-2-yl)benzamide (211)

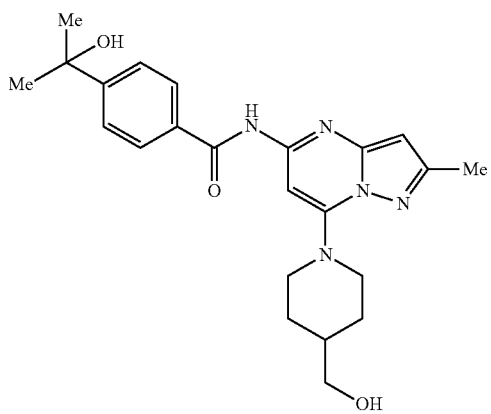

211

A solution of N-(7-chloro-2-methylpyrazolo[1,5-a]pyrimidin-5-yl)-4-(2-hydroxypropan-2-yl)benzamide (2F, 81 mg, 0.235 mmol) and piperidin-4-ylmethanol (35 mg, 0.294 mmol) in DMF (1 mL) was stirred at 100° C. for 3 h. After cooling to room temperature, the mixture was diluted with a few drops of DMSO and methanol, and was then purified by preparatory HPLC (25-35% MeCN/H₂O gradient+0.01% TFA). Lyophilization of the combined fractions gave the titled compound as a white solid (62.1 mg, 62%). Melting point (164.0-169.5° C.). ¹H NMR (DMSO-d₆) δ: 10.86 (s, 1H), 7.99 (d, J=8.6 Hz, 2H), 7.60 (d, J=8.6 Hz, 2H), 7.27 (s, 1H), 6.17 (s, 1H), 4.50 (d, J=12.1 Hz, 2H), 3.33 (d, J=6.3 Hz, 2H), 2.99-3.11 (m, 2H), 2.38 (s, 3H), 1.79-1.87 (m, 2H), 1.67-1.78 (m, 1H), 1.45 (s, 6H), 1.28-1.42 (m, 2H); ESI-MS: m/z 424.3 (M+H)⁺.

Example 226

N-(2-methyl-7-morpholinopyrazolo[1,5-a]pyrimidin-5-yl)-6-(trifluoromethyl)nicotinamide (212)

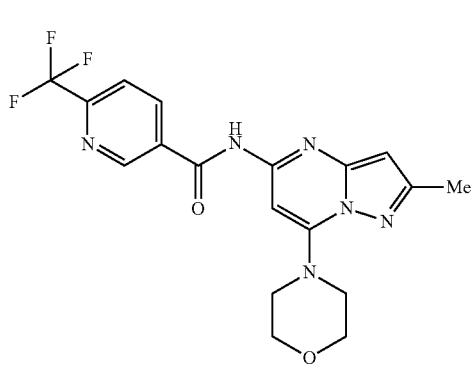

212

A solution of N-(7-chloro-2-methylpyrazolo[1,5-a]pyrimidin-5-yl)-6-(trifluoromethyl)nicotinamide (12A, 81 mg, 0.228 mmol) and morpholine (67 mg, 0.761 mmol) in DMF (0.912 mL) was stirred at 100° C. for 90 min, then cooled to rt and maintained overnight. The mixture was filtered and the crude material recrystallized from hot methanol, providing the titled compound as a white solid (50.2 mg, 54%). $^1$H NMR (DMSO-$d_6$) δ: 11.45 (s, 1H), 9.28 (d, 1H), 8.59-8.63 (m, 1H), 8.09 (d, J=8.1 Hz, 1H), 7.31 (s, 1H), 6.21 (s, 1H), 3.80-3.89 (m, 4H), 3.68-3.80 (m, 4H), 2.39 (s, 3H); ESI-MS: m/z 407.2 (M+H)$^+$.

Example 227

N-(2-methyl-7-(4-oxo-3,4,7,8-tetrahydropyrido[4,3-d]pyrimidin-6(5H)-yl)pyrazolo[1,5-a]pyrimidin-5-yl)-6-(trifluoromethyl)nicotinamide (213)

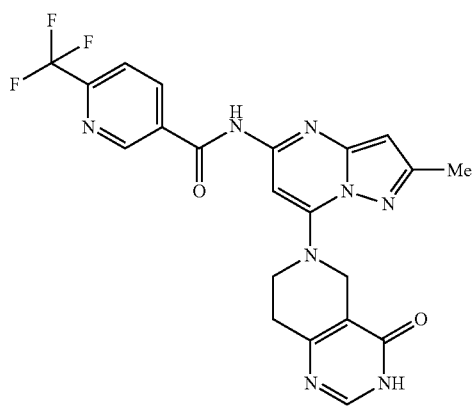

A solution of N-(7-chloro-2-methylpyrazolo[1,5-a]pyrimidin-5-yl)-6-(trifluoromethyl)nicotinamide (12A, 90 mg, 0.253 mmol), 5,6,7,8-tetrahydropyrido[4,3-d]pyrimidin-4(3H)-one hydrochloride (134 mg, 0.633 mmol), and N,N-diisopropylethylamine (98 mg, 0.757 mmol) in DMF (1.012 mL) was stirred at 100° C. for 90 min, then cooled to rt and maintained overnight. The mixture was filtered and the crude material recrystallized from hot methanol, providing the titled compound as a yellow solid (76.6 mg, 64%). $^1$H NMR (DMSO-$d_6$) δ: 12.63 (br. s., 1H), 11.45 (s, 1H), 9.29 (s, 1H), 8.53-8.69 (m, 1H), 8.13 (s, 1H), 8.09 (dd, J=8.3, 0.8 Hz, 1H), 7.40 (s, 1H), 6.21 (s, 1H), 4.51 (s, 2H), 4.13 (t, J=5.7 Hz, 2H), 2.73 (s, 2H), 2.41 (s, 3H); ESI-MS: m/z 471.1 (M+H)$^+$.

Example 228

N-(2-cyclopropyl-7-phenylpyrazolo[1,5-a]pyrimidin-5-yl)-4-(2-hydroxypropan-2-yl)benzamide (214)

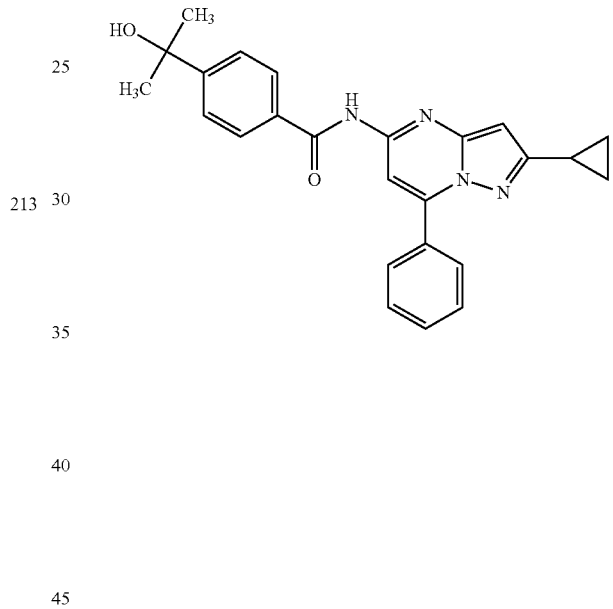

In a 2 mL microwave vial was placed N-(7-chloro-2-cyclopropylpyrazolo[1,5-c]pyrimidin-5-yl)-4-(2-hydroxypropan-2-yl)benzamide (2J, 100 mg, 0.27 mmol), phenylboronic acid (41 mg, 0.34 mmol) and [1,1'-bis(diphenylphosphino)ferrocene]-dichloropalladium(II) (9.9 mg, 14 μmmol). To the sealed vial was then added 1,4-dioxane (1 ml) and saturated aqueous NaHCO$_3$ (0.5 ml) to give a suspension. The mixture was then heated in the microwave at 110° C. for 20 minutes. After cooling to room temperature, the reaction mixture was partitioned between brine and EtOAc. The aqueous layer was extracted once more with EtOAc, and the combined organic layers were dried over MgSO$_4$, filtered and concentrated in vacuo. The crude product was purified by preparatory HPLC (40-60% ACN/water, TFA mode). Neutralization with saturated NaHCO$_3$ solution and concentration of the collected fractions produced a precipitate, which was collected on a fritted funnel, washed with water and dried under a stream of nitrogen to give the titled compound (49 mg, 44% yield) as an off-white powder. $^1$H NMR (400 MHz, DMSO-$d_6$) δ=11.19 (s, 1 H), 8.11-8.05 (m, 2 H), 8.01 (d, J=8.6 Hz, 2 H), 7.96 (s, 1 H), 7.66-7.58 (m, 5 H), 6.28 (s, 1 H), 5.19 (s, 1 H), 2.13-2.00 (m, 1 H), 1.46 (s, 5 H), 1.07-0.98 (m, 2 H), 0.88-0.80 (m, 2 H); ESI-MS: m/z 413.2 (M+H)+.

Example 229

N-(2-cyclopropyl-7-(3-(hydroxymethyl)phenyl)pyrazolo[1,5-a]pyrimidin-5-yl)-4-(2-hydroxypropan-2-yl)benzamide (215)

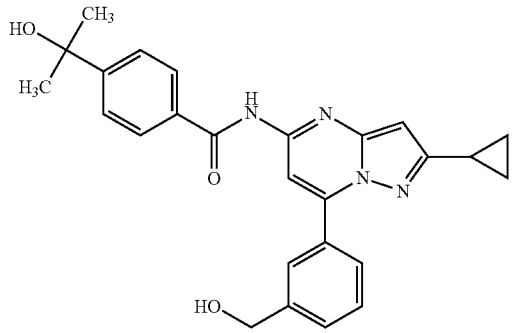

In a 2 mL microwave vial were placed N-(7-chloro-2-cyclopropylpyrazolo[1,5-a]pyrimidin-5-yl)-4-(2-hydroxypropan-2-yl)benzamide (2J, 100 mg, 0.27 mmol), 3-(hydroxymethyl)phenylboronic acid (51 mg, 0.34 mmol) and [1,1'-bis(diphenylphosphino)ferrocene]-dichloropalladium (II) (9.9 mg, 14 µmol). To the sealed vial was then added 1,4-dioxane (1 ml) and saturated aqueous NaHCO₃ (0.5 ml) to give a suspension. The mixture was then heated in the microwave at 110° C. for 20 minutes. After cooling to room temperature, the reaction mixture was partitioned between brine and EtOAc. The aqueous layer was extracted once more with EtOAc, and the combined organic layers were dried over MgSO₄, filtered and concentrated in vacuo. The crude product was purified by recrystallization from ether and EtOAC to give the titled compound (52 mg, 44% yield) as an off-white solid. ¹H NMR (400 MHz, DMSO-d₆) δ=11.18 (s, 1 H), 8.02 (d, J=8.6 Hz, 2 H), 8.00-7.96 (m, 2 H), 7.95 (s, 1 H), 7.61 (d, J=8.6 Hz, 2 H), 7.59-7.54 (m, 2 H), 6.28 (s, 1 H), 5.44-5.37 (m, 1 H), 5.19 (s, 1 H), 4.63 (d, J=5.6 Hz, 2 H), 2.12-2.03 (m, 1 H), 1.04-0.98 (m, 2 H), 0.88-0.81 (m, 2 H); ESI-MS: m/z 443.3 (M+H)+.

Example 230

N-(2-cyclopropyl-7-morpholinopyrazolo[1,5-a]pyrimidin-5-yl)-4-(2-hydroxypropan-2-yl)benzamide (216)

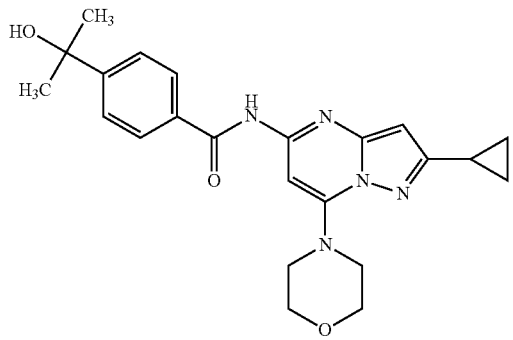

In a 2 mL microwave vial was placed N-(7-chloro-2-cyclopropylpyrazolo[1,5-a]pyrimidin-5-yl)-4-(2-hydroxypropan-2-yl)benzamide (2J, 100 mg, 0.27 mmol) and morpholine (47.0 mg, 0.54 mmol). To the sealed vial was then added NMP (2 ml) and the mixture was then heated in the microwave at 120° C. for 15 minutes. After cooling to room temperature, DMF (1 ml) was added. The crude product mixture was filtered by syringe filter and purified by preparatory HPLC (35-45% ACN/water, TFA mode). Lyophilization of the collected fractions gave the titled compound product (42 mg, 37% yield) as an off-white powder. ¹H NMR (400 MHz, DMSO-d₆) δ=10.84 (s, 1 H), 7.99 (d, J=8.1 Hz, 2 H), 7.59 (d, J=7.8 Hz, 2 H), 7.34 (s, 1 H), 6.06 (s, 1 H), 5.18 (s, 1 H), 3.97-3.58 (m, 8 H), 2.15-1.96 (m, 1 H), 1.45 (s, 5 H), 1.08-0.92 (m, 2 H), 0.88-0.74 (m, 2 H); ESI-MS: m/z 422.2 (M+H)+.

Example 231

N-(2-cyclopropyl-7-(4-hydroxypiperidin-1-yl)pyrazolo[1,5-a]pyrimidin-5-yl)-4-(2-hydroxypropan-2-yl)benzamide (217)

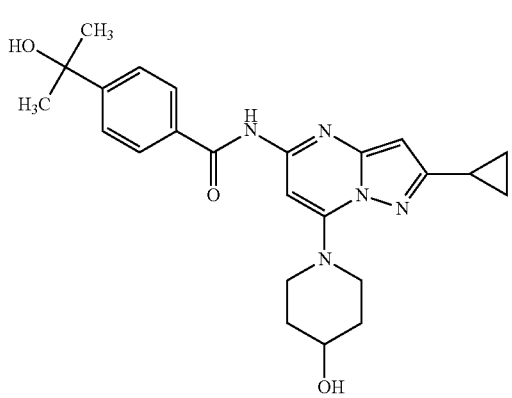

In a 2 mL microwave vial was placed N-(7-chloro-2-cyclopropylpyrazolo[1,5-a]pyrimidin-5-yl)-4-(2-hydroxypropan-2-yl)benzamide (2J, 100 mg, 0.27 mmol) and 4-hydroxypiperidine (55.0 mg, 0.54 mmol). To the sealed vial was then added NMP (2 ml) and the mixture was then heated in the microwave at 120° C. for 15 minutes. After cooling to room temperature, DMF (1 ml) was added. The crude product mixture was filtered by syringe filter and purified by preparatory HPLC (20-40% ACN/water, TFA mode). Lyophilization of the collected fractions gave the titled compound product (30 mg, 26% yield) as an off-white powder. ¹H NMR (400 MHz, DMSO-d₆) δ=10.78 (s, 1 H), 7.98 (d, J=8.6 Hz, 2 H), 7.59 (d, J=8.6 Hz, 2 H), 7.34 (s, 1 H), 6.02 (s, 1 H), 5.18 (s, 1 H), 4.84 (d, J=4.3 Hz, 1 H), 4.12 (d, J=12.6 Hz, 2 H), 3.79 (dd, J=4.2, 8.5 Hz, 1 H), 3.41-3.36 (m, 1 H), 2.11-2.00 (m, 1 H), 1.91 (br. s., 2 H), 1.65-1.51 (m, 2 H), 1.45 (s, 6 H), 1.04-0.94 (m, 2 H), 0.88-0.75 (m, 2 H); ESI-MS: m/z 436.3 (M+H)+.

Example 232

Methyl 4-(7-chloro-2-(trifluoromethyl)pyrazolo[1,5-a]pyrimidin-5-ylcarbamoyl)benzoate (218)

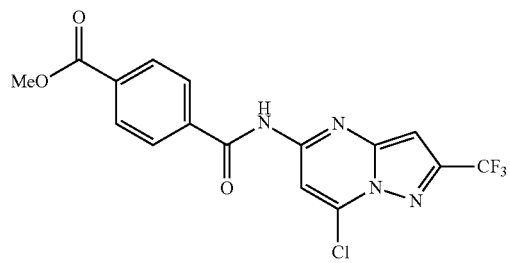

218

7-chloro-2-(trifluoromethyl)pyrazolo[1,5-a]pyrimidin-5-amine (0.5 g, 1.0 equivalent) was suspended in pyridine (0.2 M) in a round bottom flask. At 0° C. was added a solution of terephthalic acid monomethylester chloride (2.0 equivalents) pre-dissolved in pyridine (0.8M), and followed by addition of N,N-dimethylpyridin-4-amine (0.1 equivalent). The mixture was stirred vigorously at 0° C. for 48 h. The reaction was quenched with saturated NaHCO₃; pyridine was removed in vacuo and the residue was extracted with EtOAc twice and the combined organic layers were dried over Na₂SO₄. The organic layers were concentrated in vacuo and the crude mixture was purified using chromatography (SiO₂, gradient of 10 to 50% EtOAc/hexanes) to afford the titled compound (10%) as a solid. Melting point (191.0-195.0° C.). $^1$H NMR (400 MHz, DMSO-d$_6$) δ ppm 3.90 (s, 3 H) 7.20 (s, 1 H) 8.06-8.11 (m, 2 H) 8.12-8.18 (m, 2 H) 8.32 (s, 1 H) 11.88 (s, 1 H); ESI-MS: m/z 399.0 (M+H)⁺.

Example 233

4-(2-hydroxypropan-2-yl)-N-(7-(4-(2-hydroxypropan-2-yl)piperidin-1-yl)-2-methylpyrazolo[1,5-a]pyrimidin-5-yl)benzamide (219)

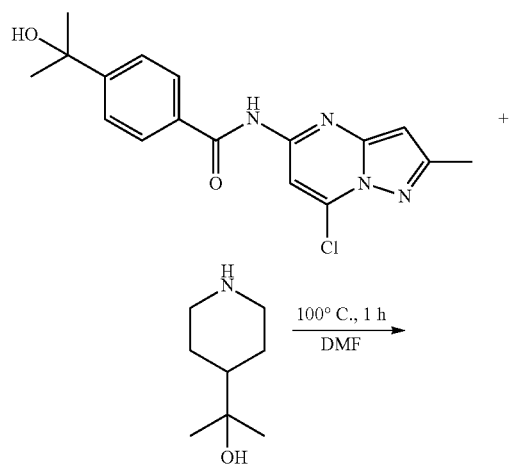

N-(7-chloro-2-methylpyrazolo[1,5-a]pyrimidin-5-yl)-4-(2-hydroxypropan-2-yl)benzamide (2F, 0.2 g, 1.0 equivalent) in DMF (0.1M) was added 2-(piperidin-4-yl)propan-2-ol (2.0 equivalents) and heated to 100° C. for 1 h. The solvent was removed in vacuo and the crude mixture was purified by preparatory HPLC (15-45% ACN/water, TFA mode) to afford the TFA salt of the titled compound 219 (75%) as a light yellow solid. $^1$H NMR (400 MHz, DMSO-d$_6$) δ ppm 1.09 (s, 6 H) 1.39-1.56 (m, 9 H) 1.86 (d, J=12.13 Hz, 2 H) 2.37 (s, 3 H) 2.85-3.00 (m, 2 H) 4.57 (d, J=13.64 Hz, 2 H) 6.16 (s, 1 H) 7.27 (s, 1 H) 7.56-7.64 (m, 2 H) 7.95-8.02 (m, 2 H) 10.84 (s, 1 H); ESI-MS: m/z 452.3 (M+H)⁺.

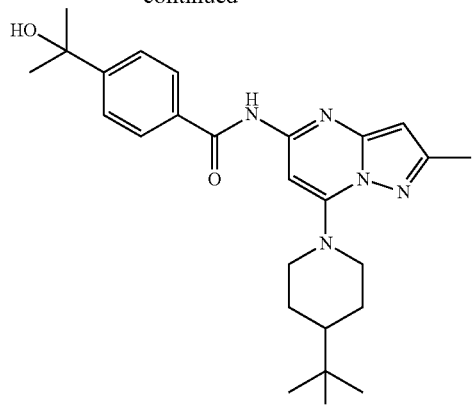

219

Example 234

4-(2-hydroxypropan-2-yl)-N-(7-(4-methoxyphenyl)-2-methylpyrazolo[1,5-a]pyrimidin-5-yl)benzamide (220)

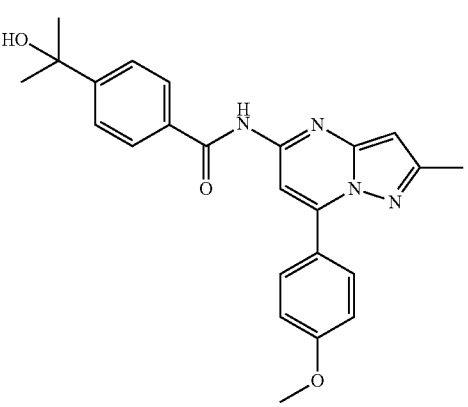

220

A mixture of N-(7-chloro-2-methylpyrazolo[1,5-a]pyrimidin-5-yl)-4-(2-hydroxypropan-2-yl)benzamide (2F, 0.05 g, 1.0 equivalent), 4-methoxyphenylboronic acid (2.0 equivalents), and PdCl₂(dppf)/DCM (0.10 equivalent) in 2N Na₂CO₃ (0.3 M), dioxane (0.1M) and DMF (0.5M) was heated at 120° C. for 10 minutes in the microwave. After cooling to room temperature, the mixture was added water and EtOAc; and extracted with EtOAc twice and the combined organic layers were dried over Na₂SO₄. The solvent was removed in vacuo and the crude mixture was purified by preparatory HPLC (40-65% ACN/water, TFA mode) to afford the TFA salt of the titled compound 220 (51%) as an off white solid. Melting point (48.8-48.9° C.). $^1$H NMR (400 MHz, DMSO-d$_6$) δ ppm 1.45 (s, 6 H) 2.40 (s, 3 H) 3.87 (s, 3 H) 5.19 (s, 1 H) 6.36 (s, 1 H) 7.18 (d, J=9.09 Hz, 2 H) 7.60 (m, J=8.34 Hz, 2 H) 7.96 (s, 1 H) 8.01 (m, J=8.59 Hz, 2 H) 8.10 (d, J=8.84 Hz, 2 H) 11.14 (s, 1 H); ESI-MS: m/z 417.2 (M+H)$^+$.

Example 235

4-(2-hydroxypropan-2-yl)-N-(7-morpholino-2-(trifluoromethyl)pyrazolo[1,5-a]pyrimidin-5-yl)benzamide (221)

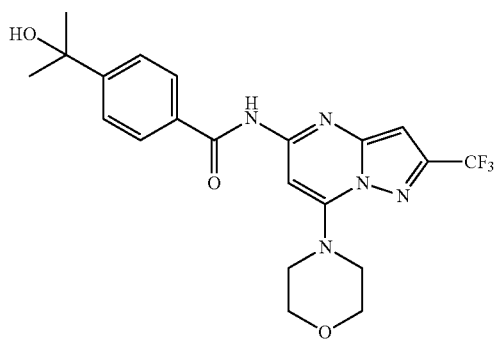

221

Methyl 4-(7-chloro-2-(trifluoromethyl)pyrazolo[1,5-a]pyrimidin-5-ylcarbamoyl)benzoate (0.08 g, 1.0 equivalent) was suspended in THF (0.2 M) in a round bottom flask. At 0° C., methyl magnesium bromide (3.0 M solution in diethyl ether, 5.5 equivalents) was added drop wise. The mixture was stirred at 0° C. for another 3 h before being quenched at 0° C. with saturated NH$_4$Cl. The mixture was extracted three times with EtOAc, and the combined organic layers were dried over Na$_2$SO$_4$, filtered and concentrated. Crude product was purified by preparatory HPLC (40-60% ACN/water, TFA mode) to afford the TFA salt of N-(7-chloro-2-(trifluoromethyl)pyrazolo[1,5-a]pyrimidin-5-yl)-4-(2-hydroxypropan-2-yl)benzamide (32%) as a solid for the next step. N-(7-chloro-2-(trifluoromethyl)pyrazolo[1,5-a]pyrimidin-5-yl)-4-(2-hydroxypropan-2-yl)benzamide (0.025 mg, 1.0 equivalent) was suspended in n-BuOH (0.1M), and followed by addition of morpholine (2.0 equivalents). The mixture was heated to 100° C. for 1 h, and the crude mixture was purified by preparatory HPLC (40-60% ACN/water, TFA mode) to afford the TFA salt of the titled compound 221 (96%) as a white solid. $^1$H NMR (400 MHz, DMSO-d$_6$) δ ppm 1.45 (s, 6 H) 3.69-3.76 (m, 4 H) 3.81-3.91 (m, 4 H) 6.85 (s, 1 H) 7.56-7.65 (m, 3 H) 8.00 (d, J=8.34 Hz, 2 H) 11.14 (s, 1 H); ESI-MS: m/z 450.2 (M+H)$^+$.

Example 236

4-(2-hydroxypropan-2-yl)-N-(7-(4-(methoxymethyl)piperidin-1-yl)pyrazolo[1,5-a]pyrimidin-5-yl)benzamide (222)

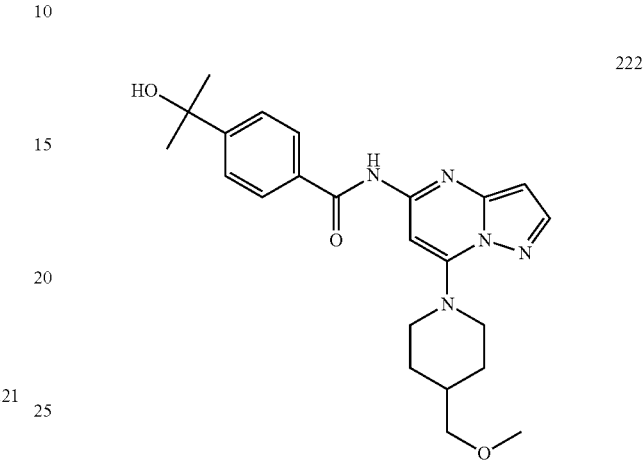

222

A solution of N-(7-chloropyrazolo[1,5-a]pyrimidin-5-yl)-4-(2-hydroxypropan-2-yl)benzamide (2D, 200 mg, 0.604 mmol) and 4-(methoxymethyl)piperidine (117 mg, 0.906 mmol) in Dioxane (6 mL) was stirred at 85° C. overnight. After cooling to room temperature, the mixture was diluted with a few drops of DMSO and methanol, and was then purified by preparatory HPLC, 5-95% (MeCN/H$_2$O gradient+0.01% TFA). Lyophilization of the combined fractions gave the titled compound as a yellow solid (50 mg, 20%). $^1$H NMR (400 MHz, DMSO-d$_6$) δ ppm 1.45 (s, 6 H) 1.59-1.75 (m, 2 H) 1.98-2.12 (m, 2 H) 3.31 (s, 3 H) 3.41-3.58 (m, 3 H) 3.97-4.15 (m, 2 H) 6.35 (d, J=2.27 Hz, 1 H) 7.40 (s, 1 H) 7.60 (m, J=8.34 Hz, 2 H) 7.99 (m, J=8.59 Hz, 2 H) 8.08 (d, J=2.27 Hz, 1 H) 10.88 (s, 1 H). ESI-MS: m/z 424.2 (M+H)$^+$.

Example 237

4-(2-hydroxypropan-2-yl)-N-(7-(4-(2-hydroxypropan-2-yl)piperidin-1-yl)pyrazolo[1,5-a]pyrimidin-5-yl)benzamide (223)

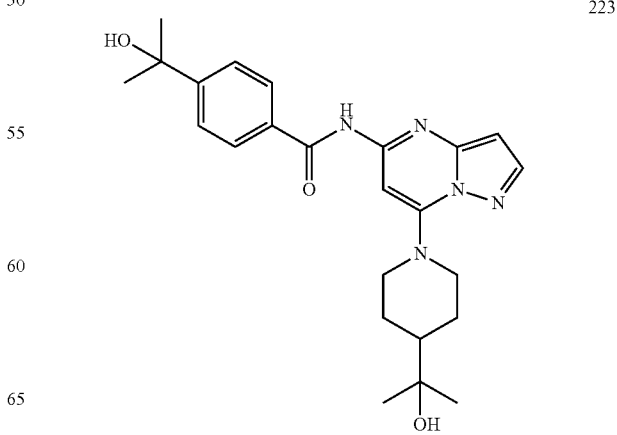

223

A solution of N-(7-chloro-pyrazolo[1,5-a]pyrimidin-5-yl)-4-(2-hydroxypropan-2-yl)benzamide (2D, 200 mg, 0.604 mmol) and 2-(piperidin-4-yl)propan-2-ol (130 mg, 0.906 mmol) in Dioxane (6 mL) was stirred at 85° C. overnight. After cooling to room temperature, the mixture was diluted with a few drops of DMSO and methanol, and was then purified by preparatory HPLC, 5-95% (MeCN/H$_2$O gradient+0.01% TFA). Lyophilization of the combined fractions gave the titled compound as a white solid (105 mg, 41%). $^1$H NMR (METHANOL-d$_4$) δ: 8.00 (d, J=2.3 Hz, 1H), 7.95 (d, 2H), 7.66 (d, J=8.3 Hz, 2H), 7.39 (s, 1H), 6.33 (d, J=1.5 Hz, 1H), 4.59 (d, J=11.6 Hz, 2H), 2.97 (t, 2H), 1.95 (d, J=9.1 Hz, 2H), 1.61-1.69 (m, 3H), 1.56 (s, 6H), 1.21 (s, 6H). ESI-MS: m/z 438.0 (M+H)$^+$.

Example 238

N-(7-(2,3-dihydrobenzofuran-5-yl)-2-methylpyrazolo[1,5-a]pyrimidin-5-yl)-4-(2-hydroxypropan-2-yl)benzamide (224)

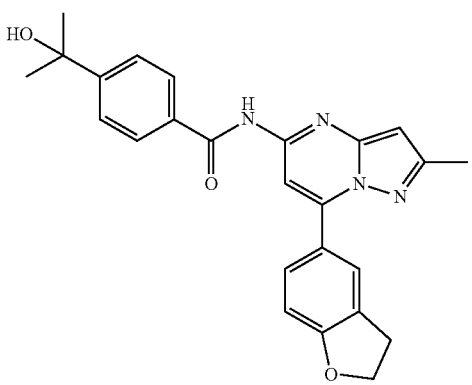

224

A mixture of N-(7-chloro-2-methylpyrazolo[1,5-a]pyrimidin-5-yl)-4-(2-hydroxypropan-2-yl)benzamide (2F, 0.05 g, 1.0 equivalent), 2,3-dihydrobenzofuran-5-ylboronic acid (2.0 equivalents), and PdCl$_2$(dppf)/DCM (0.10 equivalent) in 2N Na$_2$CO$_3$ (0.3 M), dioxane (0.1M) and DMF (0.5M) was heated at 120° C. for 10 minutes in the microwave. After cooling to room temperature, the mixture was added water and EtOAc; and extracted with EtOAc twice and the combined organic layers were dried over Na$_2$SO$_4$. The solvent was removed in vacuo and the crude mixture was purified by preparatory HPLC (40-55% ACN/water, TFA mode) to afford the TFA salt of the titled compound 224 (35%) as a yellow solid. $^1$H NMR (400 MHz, DMSO-d$_6$) δ ppm 1.46 (s, 6 H) 2.41 (s, 3 H) 3.29-3.33 (m, 2 H) 4.67 (t, J=8.72 Hz, 2 H) 5.19 (s, 1 H) 6.36 (s, 1 H) 7.00 (d, J=8.59 Hz, 1 H) 7.61 (d, J=8.59 Hz, 2 H) 7.91-7.97 (m, 2 H) 7.97-8.05 (m, 3 H) 11.13 (s, 1 H); ESI-MS: m/z 429.2 (M+H)$^+$.

Example 239

Methyl 4-(7-phenyl-2-(trifluoromethyl)pyrazolo[1,5-a]pyrimidin-5-ylcarbamoyl)benzoate (225)

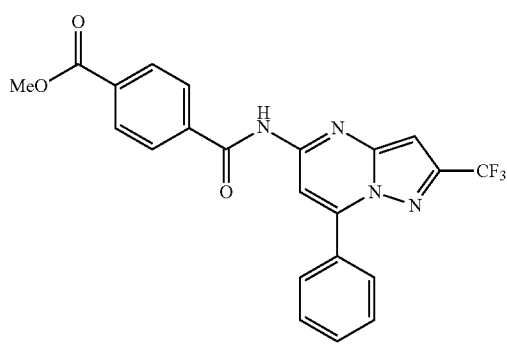

225

Methyl 4-(7-phenyl-2-(trifluoromethyl)pyrazolo[1,5-a]pyrimidin-5-ylcarbamoyl)benzoate (0.01 g, 1.0 equivalent) was suspended in pyridine (0.4 M). At 0° C. was added a solution of terephthalic acid monomethylester chloride (2.0 equivalents) pre-dissolved in pyridine (0.4M). The mixture was stirred vigorously at 0° C. for 2 h, then the reaction was quenched with saturated NaHCO$_3$ and pyridine was removed in vacuo. The mixture was then filtered on a fritted funnel and the collected precipitate was washed once with water then twice with cold 10% EtOH in Et$_2$O. The precipitate was dried under vacuum to afford a white solid as the product (40%) and it was used without further purification. $^1$H NMR (400 MHz, DMSO-d$_6$) δ ppm 3.90 (s, 3 H) 7.12 (s, 1 H) 7.65-7.70 (m, 3 H) 8.01-8.07 (m, 2 H) 8.07-8.12 (m, 2 H) 8.15-8.22 (m, 3 H) 11.79 (s, 1 H); ESI-MS: m/z 441.1 (M+H)$^+$.

Example 240

4-(2-hydroxypropan-2-yl)-N-(7-(4-(methoxymethyl)piperidin-1-yl)-2-methylpyrazolo[1,5-a]pyrimidin-5-yl)benzamide (226)

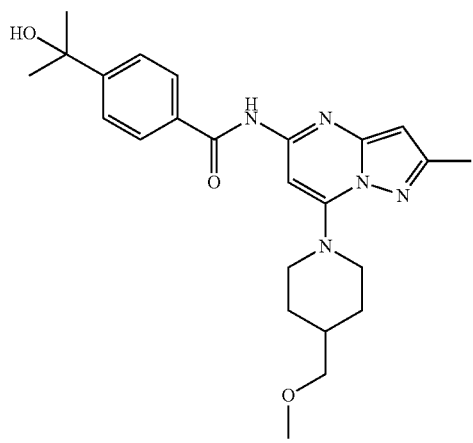

226

N-(7-chloro-2-methylpyrazolo[1,5-a]pyrimidin-5-yl)-4-(2-hydroxypropan-2-yl)benzamide (2F, 0.05 g, 1.0 equivalent) and 4-(methoxymethyl)piperidine HCl salt (1.6 equivalents) in DMF (0.1M) was heated to 100° C. for 1 h. Then Et$_3$N (6.0 equivalents) was added and the mixture was heated to 80° C. for 8 h. The solvent was removed in vacuo and the crude mixture was purified by preparatory HPLC (20-45% ACN/water, TFA mode) to afford the TFA salt of the titled compound 226 (47%) as a beige solid. $^1$H NMR (400 MHz, DMSO-d$_6$) δ ppm 1.39 (dd, J=12.38, 3.54 Hz, 2 H) 1.44 (s, 6 H) 1.81 (d, J=16.42 Hz, 2 H) 1.89 (br. s., 1 H) 2.36 (s, 3 H) 2.94-3.10 (m, 2 H) 3.24 (s, 2 H) 3.26 (s, 3 H) 4.44 (br. s., 2 H) 6.14 (s, 1 H) 7.30 (s, 1 H) 7.59 (m, 2 H) 7.98 (m, 2 H) 10.81 (s, 1 H); ESI-MS: m/z 438.2 (M+H)$^+$.

Example 241

1-(5-(4-(2-hydroxypropan-2-yl)benzamido)-2-methylpyrazolo[1,5-a]pyrimidin-7-yl)piperidine-4-carboxylic acid (227)

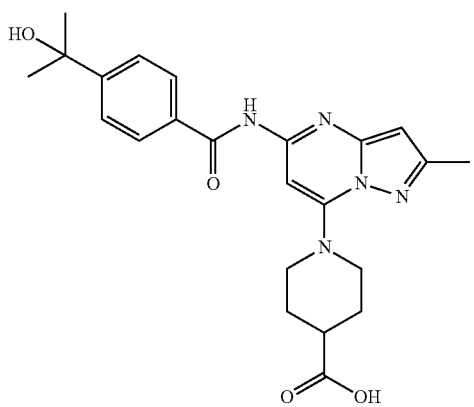

227

N-(7-Chloro-2-methylpyrazolo[1,5-a]pyrimidin-5-yl)-4-(2-hydroxypropan-2-yl)benzamide (2F, 0.05 g, 1.0 equivalent) and piperidine-4-carboxylic acid (2.0 equivalents) in DMF (0.1M) was heated to 100° C. for 3 h. Then the solvent was removed in vacuo and the crude mixture was purified by preparatory HPLC (20-35% ACN/water, TFA mode) to afford the TFA salt of the titled compound 227 (39%) as a white solid. $^1$H NMR (400 MHz, DMSO-d$_6$) δ ppm 1.44 (s, 6 H) 1.68-1.81 (m, 2 H) 1.99 (d, J=12.13 Hz, 2 H) 2.37 (s, 3 H) 2.54-2.64 (m, 1 H) 3.17 (t, J=13.01 Hz, 2 H) 4.34 (d, J=12.63 Hz, 2 H) 6.14 (s, 1 H) 7.33 (s, 1 H) 7.55-7.60 (m, 2 H) 7.93-8.02 (m, 2 H) 10.81 (s, 1 H); ESI-MS: m/z 438.2 (M+H)$^+$.

Example 242

N-(2-ethyl-7-(4-methoxyphenyl)pyrazolo[1,5-a]pyrimidin-5-yl)-4-(2-hydroxypropan-2-yl)benzamide (228)

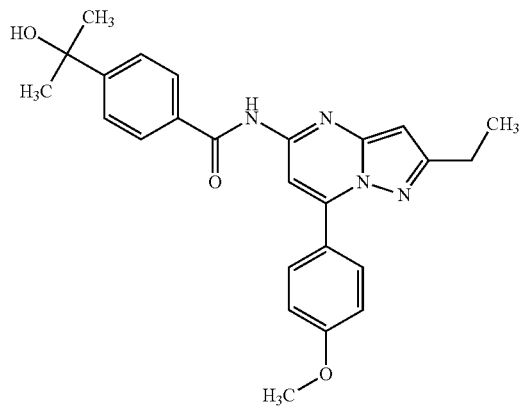

228

In a 2 mL microwave vial were placed N-(7-chlorop-2-ethylpyrazolo[1,5-a]pyrimidin-5-yl)-4-(2-hydroxypropan-2-yl)benzamide (2H, 75 mg, 0.21 mmol), 4-methoxyphenylboronic acid (40 mg, 0.26 mmol) and [1,1'-bis(diphenylphosphino)ferrocene]-dichloropalladium(II) (8 mg, 10 μmol). To the sealed vial was then added 1,4-dioxane (1.5 ml) and saturated aqueous NaHCO$_3$ (0.75 ml) to give a suspension. The mixture was then heated in the microwave at 110° C. for 30 minutes. After cooling to room temperature, the reaction mixture was partitioned between brine and EtOAc. The aqueous layer was extracted once more with EtOAc, and the combined organic layers were dried over MgSO$_4$, filtered and concentrated in vacuo. The crude product was purified by recrystallization from ether and EtOAC to give the titled compound (25 mg, 28% yield) as an off-white solid. $^1$H NMR (400 MHz, DMSO-d$_6$) δ=11.16 (s, 1 H), 8.16-8.10 (m, 2 H), 8.02 (d, J=8.6 Hz, 2 H), 7.98 (s, 1 H), 7.61 (d, J=8.6 Hz, 2 H), 7.19 (d, J=9.1 Hz, 2 H), 6.40 (s, 1 H), 5.19 (s, 1 H), 3.88 (s, 3 H), 2.78 (q, J=7.6 Hz, 2 H), 1.46 (s, 6 H), 1.29 (t, J=7.7 Hz, 3 H); ESI-MS: m/z 431 (M+H)$^+$.

Example 243

N-(2-ethyl-7-phenylpyrazolo[1,5-a]pyrimidin-5-yl)-4-(2-hydroxypropan-2-yl)benzamide (229)

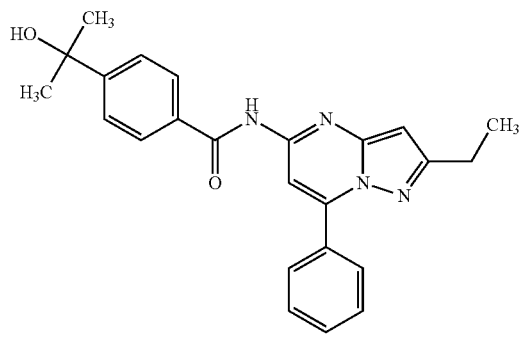

229

In a 2 mL microwave vial were placed N-(7-chlorop-2-ethylpyrazolo[1,5-a]pyrimidin-5-yl)-4-(2-hydroxypropan-2-yl)benzamide (2H, 75 mg, 0.21 mmol), phenylboronic acid (32 mg, 0.26 mmol) and [1,1'-bis(diphenylphosphino)ferrocene]-dichloropalladium(II) (8 mg, 10 μmmol). To the sealed vial was then added 1,4-dioxane (1.5 ml) and saturated aqueous NaHCO₃ (0.75 ml) to give a suspension. The mixture was then heated in the microwave at 110° C. for 30 minutes. After cooling to room temperature, the reaction mixture was partitioned between brine and EtOAc. The aqueous layer was extracted once more with EtOAc, and the combined organic layers were dried over MgSO₄, filtered and concentrated in vacuo. The crude product was purified by recrystallization from ether and EtOAC to give the titled compound (20 mg, 24% yield) as an off-white solid. $^1$H NMR (400 MHz, DMSO-d$_6$) δ=11.22 (s, 3 H), 8.13-8.05 (m, 6 H), 8.02 (d, J=8.6 Hz, 2 H), 7.99 (s, 1 H), 7.69-7.57 (m, 5 H), 6.43 (s, 1 H), 5.20 (s, 1 H), 2.77 (q, J=7.6 Hz, 2 H), 1.46 (s, 6 H), 1.28 (t, J=7.7 Hz, 3 H); ESI-MS: m/z 401 (M+H)$^+$.

Example 244

4-(2-hydroxypropan-2-yl)-N-(7-phenyl-2-(trifluoromethyl)pyrazolo[1,5-a]pyrimidin-5-yl)benzamide (230)

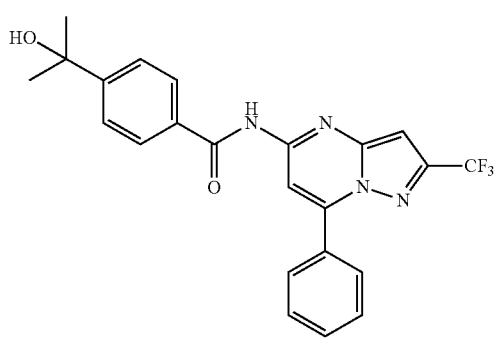

230

Methyl 4-(7-chloro-2-(trifluoromethyl)pyrazolo[1,5-a]pyrimidin-5-ylcarbamoyl)benzoate (0.06 g, 1.0 equivalent) was suspended in THF (0.2 M). At 0° C., methyl magnesium bromide (3.0 M solution in diethyl ether, 11.0 equivalents) was added drop wise. The mixture was stirred at 0° C. for another 6 h before being quenched at 0° C. with saturated NH₄Cl. The mixture was extracted twice with EtOAc, and the combined organic layers were dried over Na₂SO₄, filtered and concentrated. Crude product was purified by preparatory HPLC (50-65% ACN/water, TFA mode) to afford the TFA salt of 4-(2-hydroxypropan-2-yl)-N-(7-phenyl-2-(trifluoromethyl)pyrazolo[1,5-a]pyrimidin-5-yl)benzamide (20%) as a grey solid. $^1$H NMR (400 MHz, DMSO-d$_6$) δ ppm 1.46 (s, 6 H) 5.21 (br. s., 1 H) 7.09 (s, 1 H) 7.60-7.70 (m, 5H) 8.01-8.07 (m, 4 H) 8.24 (s, 1 H) 11.50 (s, 1 H); ESI-MS: m/z 441.2 (M+H)$^+$.

Example 245

N-(2-ethyl-7-morpholinopyrazolo[1,5-a]pyrimidin-5-yl)-4-(2-hydroxypropan-2-yl)benzamide (231)

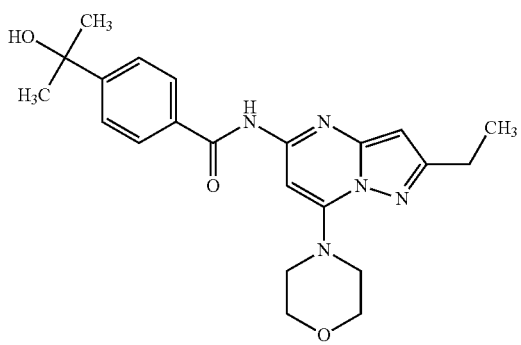

231

In a 2 mL microwave vial was placed N-(7-chloro-2-cyclopropylpyrazolo[1,5-c]pyrimidin-5-yl)-4-(2-hydroxypropan-2-yl)benzamide (2H, 75 mg, 0.21 mmol) and morpholine (36 mg, 0.42 mmol). To the sealed vial was then added NMP (2 ml) and the mixture was then heated in the microwave at 120° C. for 30 minutes. After cooling to room temperature, the reaction mixture was partitioned between brine and EtOAc. The aqueous layer was extracted once more with EtOAc, and the combined organic layers were dried over MgSO₄, filtered and concentrated in vacuo. The crude product was purified by recrystallization from ether and EtOAC to give the titled compound (43 mg, 50% yield) as an off-white solid. $^1$H NMR (400 MHz, DMSO-d$_6$) δ=10.87 (s, 2 H), 8.05-7.92 (m, 2 H), 7.59 (d, J=8.6 Hz, 2 H), 7.36 (s, 1 H), 6.19 (s, 1 H), 5.18 (s, 1 H), 3.91-3.79 (m, 4 H), 3.77-3.69 (m, 4 H), 2.74 (q, J=7.6 Hz, 2 H), 1.45 (s, 6 H), 1.35-1.23 (m, 3 H); ESI-MS: m/z 410 (M+H)$^+$.

Example 246

N-(7-(benzo[d][1,3]dioxol-5-yl)-2-methylpyrazolo[1,5-a]pyrimidin-5-yl)-4-(2-hydroxypropan-2-yl)benzamide (232)

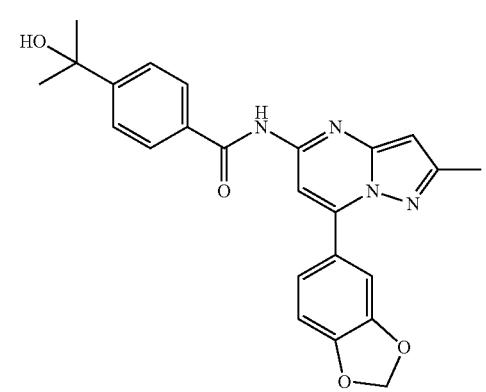

232

N-(7-chloro-2-methylpyrazolo[1,5-a]pyrimidin-5-yl)-4-(2-hydroxypropan-2-yl)benzamide (2F, 0.07 g, 1.0 equivalent) and benzo[d][1,3]dioxol-5-ylboronic acid (2.0 equivalents) and PdCl$_2$(dppf)/DCM (0.10 equivalent) in 2N Na$_2$CO$_3$ (0.2 M), dioxane (0.1M) and DMF (0.5M) was heated at 120° C. for 10 minutes in the microwave. After cooling to room temperature, the mixture was added water and EtOAc; and extracted with EtOAc twice and the combined organic layers were dried over Na$_2$SO$_4$. Then the solvent was removed in vacuo and the crude mixture was purified by preparatory HPLC (40-55% ACN/water, TFA mode) to afford the TFA salt of the titled compound, which was further purified by EtOAc wash and filtered to afford the titled compound 232 (8%) as a white solid. $^1$H NMR (400 MHz, DMSO-d$_6$) δ ppm 1.46 (s, 6 H) 2.41 (s, 3 H) 5.19 (s, 1 H) 6.18 (s, 2 H) 6.37 (s, 1 H) 7.17 (d, J=8.34 Hz, 1 H) 7.58-7.64 (m, 3 H) 7.70 (d, J=1.52 Hz, 1 H) 7.94 (s, 1 H) 8.01 (d, J=8.59 Hz, 2 H) 11.16 (s, 1 H); ESI-MS: m/z 431.2 (M+H)$^+$.

Example 247

N-(7-(4-(1-hydroxy-2-methylpropyl)piperidin-1-yl)pyrazolo[1,5-a]pyrimidin-5-yl)-4-(2-hydroxypropan-2-yl)benzamide (233)

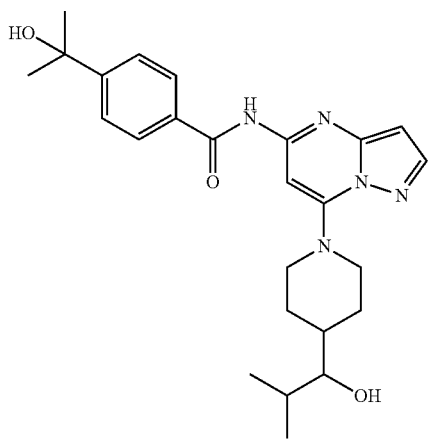

233

A solution of N-(7-chloropyrazolo[1,5-a]pyrimidin-5-yl)-4-(2-hydroxypropan-2-yl)benzamide (2D, 200 mg, 0.604 mmol) and 2-methyl-1-(piperidin-4-yl)propan-1-ol (142 mg, 0.604 mmol) in Dioxane (6 mL) was stirred at 85° C. overnight. After cooling to room temperature, the mixture was diluted with a few drops of DMSO and methanol, and was then purified by preparatory HPLC, 5-95% (MeCN/H$_2$O gradient+0.01% TFA). Lyophilization of the combined fractions gave the titled compound as a yellow solid (59 mg, 23%). $^1$H NMR (METHANOL-d$_4$) δ: 7.99 (d, J=2.3 Hz, 1H), 7.92-7.97 (m, 2H), 7.61-7.69 (m, 2H), 7.39 (s, 1H), 6.32 (d, J=2.5 Hz, 1H), 4.55 (d, J=12.4 Hz, 2H), 2.93-3.14 (m, 3H), 2.02 (d, J=1.0 Hz, 1H), 1.58-1.89 (m, 5H), 1.57 (s, 6H), 0.96 (dd, 6H). ESI-MS: m/z 452.0 (M+H)$^+$.

Example 248

N-(7-(4-formyl-1,4-diazepan-1-yl)pyrazolo[1,5-a]pyrimidin-5-yl)-4-(2-hydroxypropan-2-yl)benzamide (234)

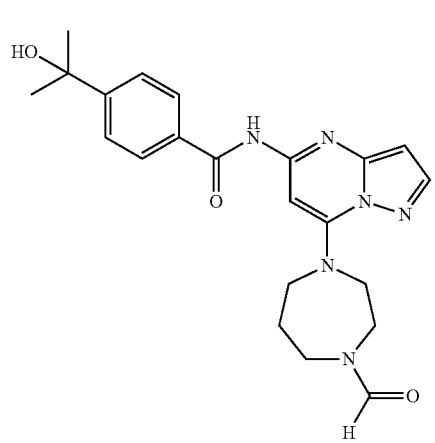

234

A solution of N-(7-chloropyrazolo[1,5-a]pyrimidin-5-yl)-4-(2-hydroxypropan-2-yl)benzamide (2D, 200 mg, 0.604 mmol) and 1,4-diazepane-1-carbaldehyde (116 mg, 0.906 mmol) in Dioxane (6 mL) was stirred at 85° C. overnight. After cooling to room temperature, the mixture was diluted with a few drops of DMSO and methanol, and was then purified by preparatory HPLC, 5-95% (MeCN/H$_2$O gradient+0.01% TFA). Lyophilization of the combined fractions gave the titled compound as a yellow solid (127.7 mg, 50%). $^1$H NMR (METHANOL-d$_4$) δ: 8.12 (s, 1H), 7.89-7.99 (m, 3H), 7.63-7.69 (m, 2H), 7.34 (s, 1H), 6.24-6.29 (m, 1H), 4.43 (t, J=5.8 Hz, 1H), 4.32-4.37 (m, 1H), 4.09 (t, J=6.2 Hz, 1H), 3.98-4.04 (m, 1H), 3.78 (t, J=5.9 Hz, 2H), 3.60-3.71 (m, 2H), 2.13-2.22 (m, 1H), 2.06 (t, 1H), 1.56 (s, 6H). ESI-MS: m/z 423.1 (M+H)$^+$.

Example 249

N-(7-(4-acetyl-1,4-diazepan-1-yl)pyrazolo[1,5-a]pyrimidin-5-yl)-4-(2-hydroxypropan-2-yl)benzamide (235)

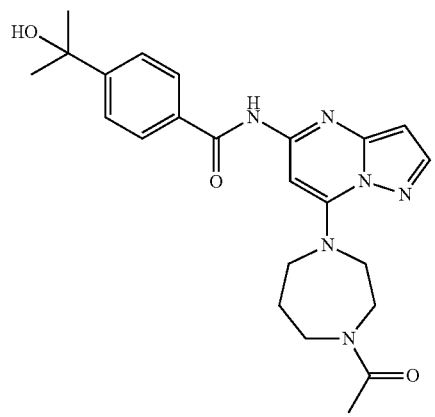

235

A solution of N-(7-chloropyrazolo[1,5-a]pyrimidin-5-yl)-4-(2-hydroxypropan-2-yl)benzamide (2D, 200 mg, 0.604 mmol) and 1-(1,4-diazepan-1-yl)ethanone (130 mg, 0.906 mmol) in Dioxane (6 mL) was stirred at 85° C. overnight. After cooling to room temperature, the mixture was diluted with a few drops of DMSO and methanol, and was then purified by preparatory HPLC, 5-95% (MeCN/H₂O gradient+0.01% TFA). Lyophilization of the combined fractions gave the titled compound as a white solid (182.5 mg, 70%). ¹H NMR (METHANOL-d₄) δ: 7.89-7.99 (m, 6H), 7.62-7.68 (m, 4H), 7.34 (d, J=8.6 Hz, 2H), 6.26 (t, J=2.3 Hz, 2H), 4.47 (t, J=5.7 Hz, 2H), 4.18-4.30 (m, 2H), 4.05 (dt, J=16.2, 6.0 Hz, 4H), 3.82 (dt, J=11.6, 5.8 Hz, 4H), 3.67 (dt, J=8.7, 6.0 Hz, 4H), 2.19 (t, J=5.9 Hz, 2H), 2.13 (s, 3H), 2.03-2.11 (m, 2H), 1.90 (s, 3H), 1.56 (s, 12H). ESI-MS: m/z 437.1 (M+H)⁺.

Example 250

4-(2-hydroxypropan-2-yl)-N-(7-(3-hydroxypyrrolidin-1-yl)pyrazolo[1,5-a]pyrimidin-5-yl)benzamide (236)

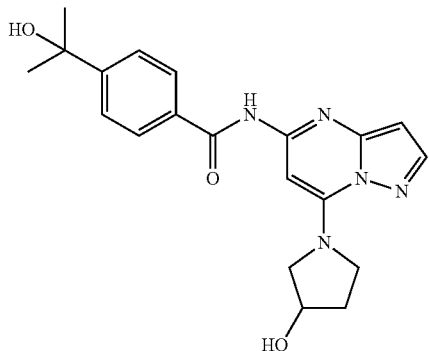

236

A solution of N-(7-chloropyrazolo[1,5-a]pyrimidin-5-yl)-4-(2-hydroxypropan-2-yl)benzamide (2D, 200 mg, 0.604 mmol) and pyrrolidin-3-ol (80 mg, 0.906 mmol) in Dioxane (6 mL) was stirred at 85° C. overnight. After cooling to room temperature, the mixture was diluted with a few drops of DMSO and methanol, and was then purified by preparatory HPLC, 5-95% (MeCN/H₂O gradient+0.01% TFA). Lyophilization of the combined fractions gave the titled compound as a white solid (52.5 mg, 23%). ¹H NMR (400 MHz, DMSO-d₆) δ: 10.63 (s, 1H), 7.82-8.10 (m, 3H), 7.58 (d, 2H), 7.05 (s, 1H), 6.17 (d, J=2.3 Hz, 1H), 5.17 (s, 1H), 5.10 (d, J=3.3 Hz, 1H), 4.43 (br. s., 1H), 3.87-4.13 (m, 4H), 1.87-2.12 (m, 2H), 1.45 (s, 6H). ESI-MS: m/z 382.0 (M+H)⁺.

Example 251

N-(7-(4-acetyl-1,4-diazepan-1-yl)-2-ethylpyrazolo[1,5-a]pyrimidin-5-yl)-4-(2-hydroxypropan-2-yl)benzamide (237)

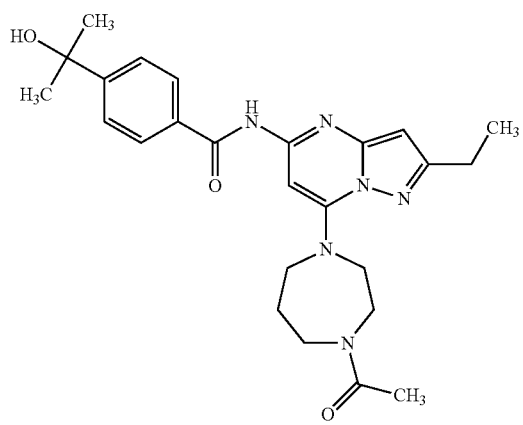

237

In a 2 mL microwave vial was placed N-(7-chloro-2-cyclopropylpyrazolo[1,5-c]pyrimidin-5-yl)-4-(2-hydroxypropan-2-yl)benzamide (2H, 75 mg, 0.21 mmol) and N-acetylhomopiperazine (59 mg, 0.42 mmol). To the sealed vial was then added NMP (2 ml) and the mixture was then heated in the microwave at 120° C. for 30 minutes. After cooling to room temperature, the reaction mixture was partitioned between brine and EtOAc. The aqueous layer was extracted once more with EtOAc, and the combined organic layers were dried over MgSO₄, filtered and concentrated in vacuo. The crude product was purified by recrystallization from ether and EtOAc to give the titled compound (50 mg, 51% yield) as an off-white solid. ESI-MS: m/z 465 (M+H)⁺.

Example 252

Methyl 1-(5-(4-(2-hydroxypropan-2-yl)benzamido)-2-methylpyrazolo[1,5-a]pyrimidin-7-yl)piperidine-4-carboxylate (238)

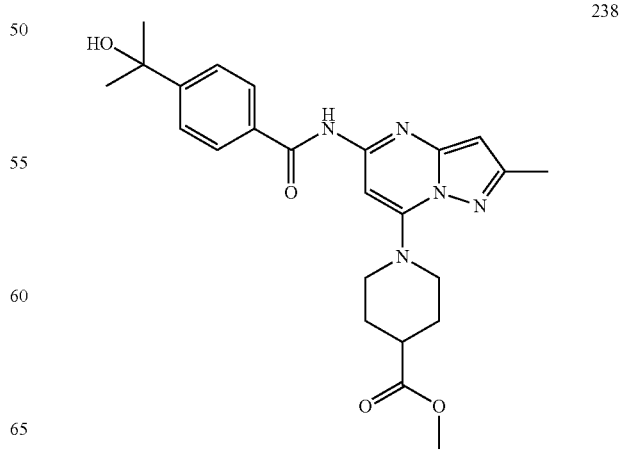

238

N-(7-chloro-2-methylpyrazolo[1,5-a]pyrimidin-5-yl)-4-(2-hydroxypropan-2-yl)benzamide (2F, 0.05 g, 1.0 equivalent) and methyl piperidine-4-carboxylate (2.0 equivalents) in DMF (0.1M) was heated to 80° C. for 2 h. Then the solvent was removed in vacuo and the crude mixture was purified by preparatory HPLC (30-45% ACN/water, TFA mode) to afford the TFA salt of the titled compound 238 (61%) as a white solid. $^1$HNMR (400 MHz, DMSO-d$_6$) δ ppm 1.44 (s, 6 H) 1.70-1.84 (m, 2 H) 2.01 (d, J=13.14 Hz, 2 H) 2.36 (s, 3 H) 2.69-2.78 (m, 1H) 3.10-3.23 (m, 2 H) 3.64 (s, 3 H) 4.30-4.40 (m, 2 H) 6.14 (s, 1 H) 7.34 (s, 1 H) 7.55-7.63 (m, 2 H) 7.93-8.02 (m, 2 H) 10.82 (s, 1 H); ESI-MS: m/z 452.2 (M+H)$^+$.

Example 253

4-(2-Hydroxypropan-2-yl)-N-(7-(3-methoxyphenyl)-2-methylpyrazolo[1,5-a]pyrimidin-5-yl)benzamide (239)

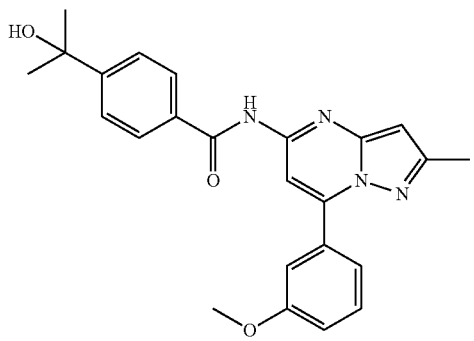

239

N-(7-chloro-2-methylpyrazolo[1,5-a]pyrimidin-5-yl)-4-(2-hydroxypropan-2-yl)benzamide (2F, 0.07 g, 1.0 equivalent), 3-methoxyphenylboronic acid (2.0 equivalents) and PdCl$_2$(dppf)/DCM (0.10 equivalent) in 2N Na$_2$CO$_3$ (0.2 M), dioxane (0.1M) and DMF (0.5M) was heated at 120° C. for 10 minutes in the microwave. After cooling to room temperature, the mixture was added water and EtOAc; and extracted with EtOAc twice and the combined organic layers were dried over Na$_2$SO$_4$. Then the solvent was removed in vacuo and the crude mixture was purified by preparatory HPLC (50-50% ACN/water, TFA mode) to afford the TFA salt of the titled compound, which was further purified by EtOAc wash and filtered to afford the titled compound 239 (24%) as a white solid. $^1$H NMR (400 MHz, DMSO-d$_6$) δ ppm 1.45 (s, 6 H) 2.40 (s, 3 H) 3.85 (s, 3 H) 5.19 (s, 1 H) 6.39 (s, 1 H) 7.21 (ddd, J=7.83, 2.65, 1.39 Hz, 1 H) 7.50-7.67 (m, 5 H) 7.96 (s, 1 H) 8.01 (d, J=8.34 Hz, 2 H) 11.19 (s, 1 H); ESI-MS: m/z 417.2 (M+H)$^+$.

Example 254

N-(7-(4-(1-hydroxy-2-methylpropyl)piperidin-1-yl)-2-methylpyrazolo[1,5-a]pyrimidin-5-yl)-4-(2-hydroxypropan-2-yl)benzamide (240)

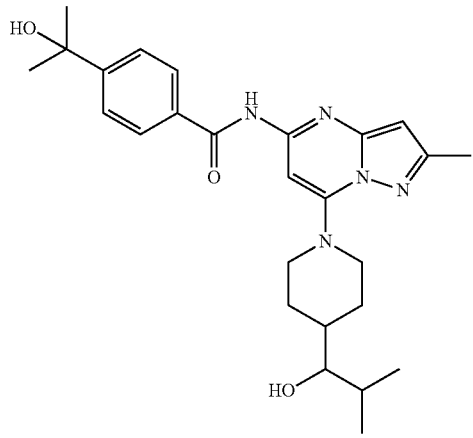

240

N-(7-chloro-2-methylpyrazolo[1,5-a]pyrimidin-5-yl)-4-(2-hydroxypropan-2-yl)benzamide (0.07 g, 1.0 equivalent) and 2-methyl-1-(piperidin-4-yl)propan-1-ol (2.0 equivalents)) in DMF (0.1M) was heated to 100° C. for 1 h. Then the solvent was removed in vacuo and the crude mixture was purified by preparatory HPLC (30-40% ACN/water, TFA mode) to afford the TFA salt of the titled compound 240 (71%) as a white solid. $^1$H NMR (400 MHz, DMSO-d$_6$) δ ppm 0.88 (dd, J=10.99, 6.69 Hz, 6 H) 1.45 (s, 6 H) 1.47-1.76 (m, 5 H) 1.90 (d, J=14.65 Hz, 1 H) 2.37 (s, 3 H) 2.90-3.06 (m, 3 H) 4.51 (t, J=16.04 Hz, 2 H) 6.14 (s, 1 H) 7.30 (s, 1 H) 7.54-7.63 (m, 2 H) 7.93-8.03 (m, 2 H) 10.81 (s, 1 H); ESI-MS: m/z 466.3 (M+H)$^+$.

Example 255

4-(2-hydroxypropan-2-yl)-N-(2-methyl-7-(1-oxo-2,8-diazaspiro[4.5]decan-8-yl)pyrazolo[1,5-a]pyrimidin-5-yl)benzamide (241)

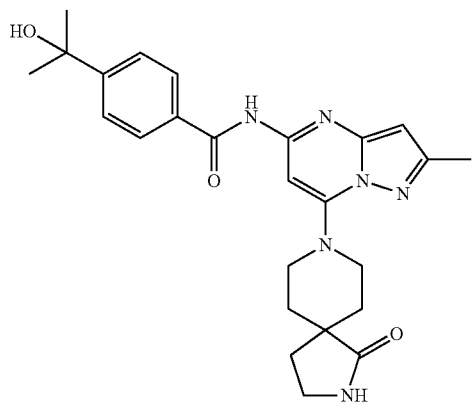

241

N-(7-Chloro-2-methylpyrazolo[1,5-a]pyrimidin-5-yl)-4-(2-hydroxypropan-2-yl)benzamide (2F, 0.05 g, 1.0 equivalent) and 2,8-diazaspiro[4.5]decan-1-one hydrochloride (2.0 equivalents) in DMF (0.1M) was added Et₃N (6.0 equivalents). The mixture was heated to 80° C. for 2.5 h. Then the solvent was removed in vacuo and the crude mixture was purified by preparatory HPLC (20-35% ACN/water, TFA mode) to afford the TFA salt of the titled compound 241 (85%) as a white solid. $^1$H NMR (400 MHz, DMSO-d$_6$) δ ppm 1.45 (s, 6 H) 1.56 (d, J=13.64 Hz, 2 H) 1.84-1.94 (m, 2 H) 2.08 (t, J=6.82 Hz, 2 H) 2.38 (s, 3 H) 3.23 (t, J=6.82 Hz, 2 H) 3.31 (t, J=12.00 Hz, 2 H) 4.34 (ddd, J=12.76, 3.54, 3.41 Hz, 2 H) 6.16 (s, 1 H) 7.35 (s, 1 H) 7.57-7.62 (m, 2 H) 7.67 (s, 1 H) 7.96-8.01 (m, 2 H) 10.85 (s, 1 H); ESI-MS: m/z 463.2 (M+H)⁺.

Example 256

4-(2-hydroxypropan-2-yl)-N-(2-methyl-7-(4-(pyrrolidine-1-carbonyl)piperidin-1-yl)pyrazolo[1,5-a]pyrimidin-5-yl)benzamide (242)

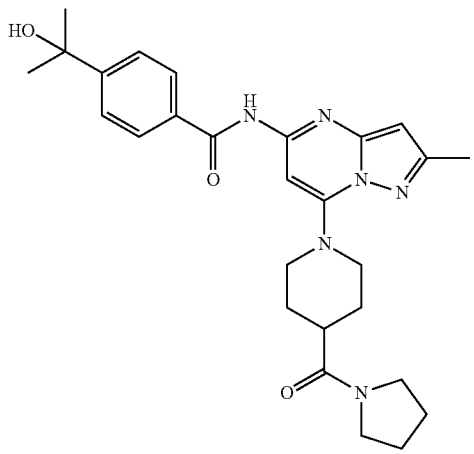

242

N-(7-chloro-2-methylpyrazolo[1,5-a]pyrimidin-5-yl)-4-(2-hydroxypropan-2-yl)benzamide (2F, 0.05 g, 1.0 equivalent) and piperidin-4-yl(pyrrolidin-1-yl)methanone nitrate (2.0 equivalents) in DMF (0.1 M) was added Et₃N (6.0 equivalents). The mixture was heated to 80° C. for 2 h. Then the mixture was added water and EtOAc; and extracted with EtOAc twice and the combined organic layers were dried over Na₂SO₄. Then the solvent was removed in vacuo and the crude mixture was purified by preparatory HPLC (20-60% ACN/water, TFA mode) to afford the TFA salt of the titled compound 242 (48%) as a white solid. $^1$H NMR (400 MHz, DMSO-d$_6$) δ ppm 1.45 (s, 6 H) 1.72-1.84 (m, 5 H) 1.90 (t, J=6.57 Hz, 3 H) 2.37 (s, 3 H) 2.77-2.86 (m, 1 H) 3.08-3.19 (m, 2 H) 3.29 (t, J=6.82 Hz, 2 H) 3.54 (t, J=6.69 Hz, 2 H) 4.49 (d, J=13.14 Hz, 2 H) 6.15 (s, 1 H) 7.34 (s, 1 H) 7.56-7.62 (m, 2 H) 7.95-8.02 (m, 2 H) 10.83 (s, 1 H); ESI-MS: m/z 491.3 (M+H)⁺.

Example 257

N-(7-(benzo[d][1,3]dioxol-5-yl)pyrazolo[1,5-a]pyrimidin-5-yl)-4-(2-hydroxypropan-2-yl)benzamide (243)

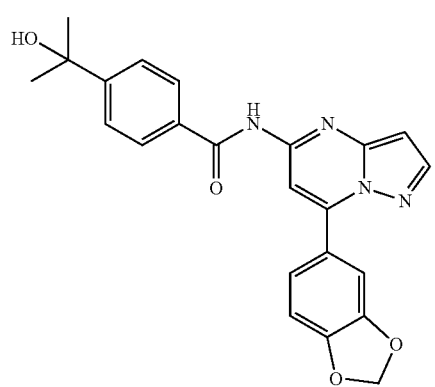

243

A suspension of N-(7-chloropyrazolo[1,5-a]pyrimidin-5-yl)-4-(2-hydroxypropan-2-yl)benzamide (2D, 200 mg, 0.604 mmol), benzo[d][1,3]dioxol-5-ylboronic acid (200 mg, 1.21 mmol), and [1,1'-bis(diphenylphosphino)ferrocene]dichloropalladium(II) (35 mg, 48 μmol) in 2:1 1,4-dioxane/saturated aqueous NaHCO₃ (2 mL of 1,4-dioxane and 1 mL of saturated aqueous NaHCO₃) was prepared in a 2 mL microwave reaction vessel and the sealed reaction vessel warmed to 100° C. for 20 minutes. The reaction mixture was cooled to rt, diluted with methanol, filtered, and purified via preparative HPLC, 5-95% (MeCN/H₂O gradient+0.01% TFA). Lyophilization of the combined fractions gave the titled compound as a green solid (119 mg, 47%). $^1$H NMR (DMSO-d$_6$) δ: 11.23 (s, 1H), 8.19 (d, J=2.3 Hz, 1H), 7.94-8.10 (m, 3H), 7.72 (d, J=1.5 Hz, 1H), 7.57-7.67 (m, 3H), 7.17 (d, J=8.3 Hz, 1H), 6.57 (d, J=2.3 Hz, 1H), 6.18 (s, 2H), 5.20 (s, 1H), 1.46 (s, 6H). ESI-MS: m/z 417.0 (M+H)⁺.

Example 258

1-(5-(4-(2-hydroxypropan-2-yl)benzamido)pyrazolo[1,5-a]pyrimidin-7-yl)piperidine-4-carboxylic acid [TFA salt] (244)

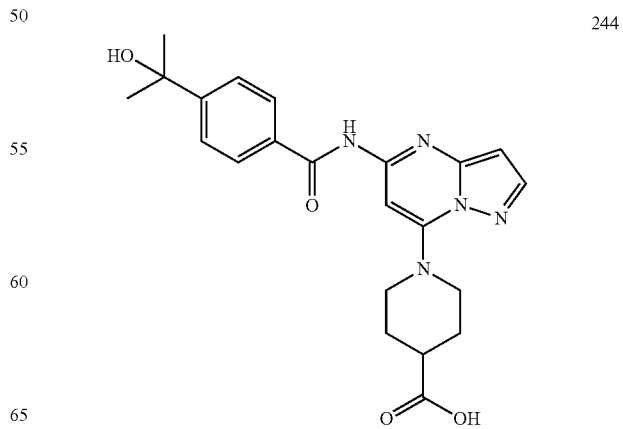

244

A solution of N-(7-chloropyrazolo[1,5-a]pyrimidin-5-yl)-4-(2-hydroxypropan-2-yl)benzamide (2D, 500 mg, 1.51 mmol) and piperidine-4-carboxylic acid (390 mg, 3.02 mmol) in Dioxane (15 mL) was stirred at 85° C. overnight. After cooling to room temperature, the mixture was diluted with a few drops of DMSO and methanol, and was then purified by preparatory HPLC, 30-40% (MeCN/H$_2$O gradient+0.01% TFA). Lyophilization of the combined fractions gave the titled compound as a white solid (59 mg, 50%). $^1$H NMR (DMSO-d$_6$) δ: 10.89 (s, 1H), 8.09 (d, J=2.3 Hz, 1H), 8.00 (d, 2H), 7.60 (d, 2H), 7.42 (s, 1H), 6.35 (d, J=2.3 Hz, 1H), 4.30-4.39 (m, 2H), 3.20 (td, J=11.7, 1.6 Hz, 2H), 2.57-2.69 (m, 1H), 1.97-2.07 (m, 2H), 1.70-1.83 (m, 2H), 1.45 (s, 6H). ESI-MS: m/z 424.0 (M+H)$^+$.

Example 259

Methyl 1-(5-(4-(2-hydroxypropan-2-yl)benzamido)pyrazolo[1,5-a]pyrimidin-7-yl)piperidine-4-carboxylate (245)

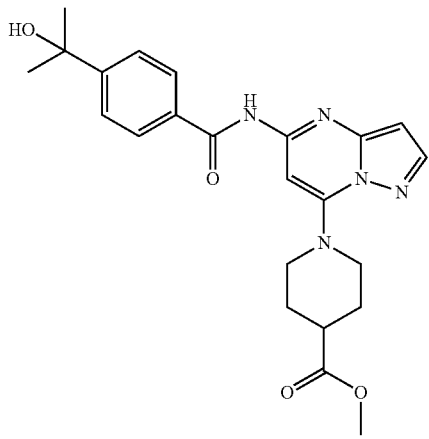

245

A solution of N-(7-chloropyrazolo[1,5-a]pyrimidin-5-yl)-4-(2-hydroxypropan-2-yl)benzamide (2D, 500 mg, 1.51 mmol) and methyl piperidine-4-carboxylate (390 mg, 3.05 mmol) in Dioxane (15 mL) was stirred at 100° C. overnight. After cooling to room temperature, the mixture was diluted with a few drops of DMSO and methanol, and was then purified by preparatory HPLC, 30-40% (MeCN/H$_2$O gradient+0.01% TFA). Lyophilization of the combined fractions gave the titled compound as a yellow solid (75 mg, 28%). $^1$H NMR (DMSO-d$_6$) δ: 10.89 (s, 1H), 8.09 (d, J=2.3 Hz, 1H), 8.00 (d, J=8.6 Hz, 2H), 7.60 (d, J=8.6 Hz, 2H), 7.44 (s, 1H), 6.35 (d, J=2.3 Hz, 1H), 5.18 (s, 1H), 4.29-4.44 (m, 2H), 3.65 (s, 3H), 3.17 (d, J=5.3 Hz, 2H), 2.67-2.82 (m, 1H), 1.98-2.11 (m, 2H), 1.70-1.88 (m, 2H), 1.46 (s, 6H). ESI-MS: m/z 438.0 (M+H)$^+$.

Example 260

4-(2-hydroxypropan-2-yl)-N-(2-methyl-7-(4-(phenylthio)piperidin-1-yl)pyrazolo[1,5-a]pyrimidin-5-yl)benzamide (246)

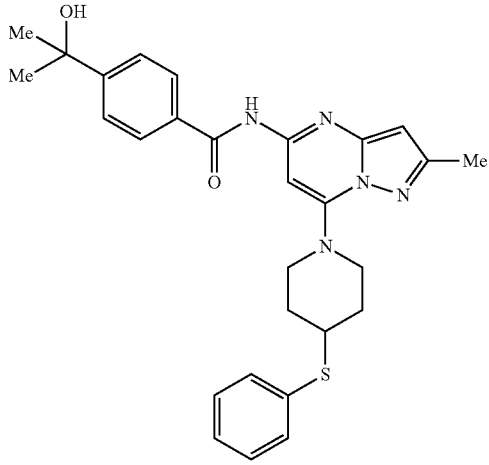

246

A solution of N-(7-chloro-2-methylpyrazolo[1,5-a]pyrimidin-5-yl)-4-(2-hydroxypropan-2-yl)benzamide (2F, 86 mg, 0.25 mmol), 4-(phenylthio)piperidine hydrochloride (128 mg, 0.50 mmol), and N,N-diisopropylethylamine (116 mg, 0.90 mmol) in DMF (1.0 mL) was stirred at 100° C. for 2 h. After cooling to room temperature, the mixture was diluted with a few drops of DMSO and methanol, and was then purified by preparatory HPLC (55-55% MeCN/H$_2$O gradient+0.01% TFA). Lyophilization of the combined fractions gave the titled compound as a white solid (82.0 mg, 65%). $^1$H NMR (DMSO-d$_6$) δ: 10.83 (s, 1H), 7.99 (d, J=8.6 Hz, 2H), 7.60 (d, J=8.3 Hz, 2H), 7.47 (d, 2H), 7.33-7.42 (m, 3H), 7.26-7.33 (m, 1H), 6.15 (s, 1H), 4.33 (d, J=12.6 Hz, 2H), 3.27 (t, J=10.9 Hz, 2H), 2.37 (s, 3H), 2.03-2.18 (m, 2H), 1.63-1.79 (m, 2H), 1.46 (s, 6H); ESI-MS: m/z 502.3 (M+H)$^+$.

Example 261

4-(2-hydroxypropan-2-yl)-N-(2-methyl-7-(4-(phenylsulfonyl)piperidin-1-yl)pyrazolo[1,5-a]pyrimidin-5-yl)benzamide (247)

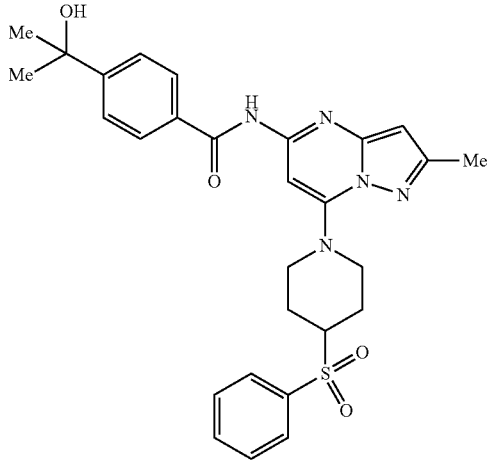

247

A solution of N-(7-chloro-2-methylpyrazolo[1,5-a]pyrimidin-5-yl)-4-(2-hydroxypropan-2-yl)benzamide (2F, 86 mg, 0.25 mmol), 4-(phenylsulfonyl)piperidine hydrochloride (145 mg, 0.50 mmol), and N,N-diisopropylethylamine (116 mg, 0.90 mmol) in DMF (1.0 mL) was stirred at 100° C. for 2 h. After cooling to room temperature, the mixture was diluted with a few drops of DMSO and methanol, and was then purified by preparatory HPLC (40-55% MeCN/H₂O gradient+0.01% TFA). Lyophilization of the combined fractions gave the titled compound as a white solid (97.2 mg, 73%). ¹H NMR (DMSO-d₆) δ: 10.90 (s, 1H), 7.99 (d, J=8.8 Hz, 2H), 7.89-7.95 (m, 2H), 7.78-7.85 (m, 1H), 7.68-7.76 (m, 2H), 7.60 (d, 2H), 7.28 (s, 1H), 6.18 (s, 1H), 4.53 (d, J=12.6 Hz, 2H), 3.69 (tt, J=11.8, 3.7 Hz, 1H), 3.00-3.11 (m, 2H), 2.37 (s, 3H), 2.04 (d, J=10.9 Hz, 2H), 1.75 (qd, J=12.3, 3.8 Hz, 2H), 1.45 (s, 6H); ESI-MS: m/z 534.2 (M+H)⁺.

Example 262

4-(2-hydroxypropan-2-yl)-N-(2-methyl-7-(4-(phenylsulfonyl)piperazin-1-yl)pyrazolo[1,5-a]pyrimidin-5-yl)benzamide (248)

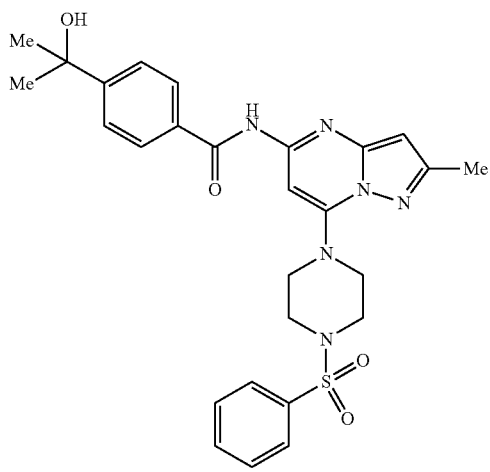

A solution of N-(7-chloro-2-methylpyrazolo[1,5-a]pyrimidin-5-yl)-4-(2-hydroxypropan-2-yl)benzamide (2F, 86 mg, 0.25 mmol) and 1-(phenylsulfonyl)piperazine (170 mg, 0.75 mmol) in DMF (1.0 mL) was stirred at 100° C. for 2 h. After cooling to room temperature, the mixture was diluted with a few drops of DMSO and methanol, and was then purified by preparatory HPLC (40-65% MeCN/H₂O gradient+0.01% TFA). Lyophilization of the combined fractions gave the titled compound as a white solid (103.0 mg, 77%). ¹H NMR (DMSO-d₆) δ: 10.88 (s, 1H), 7.98 (d, J=8.6 Hz, 2H), 7.81-7.85 (m, 2H), 7.75-7.80 (m, 1H), 7.68-7.74 (m, 2H), 7.59 (d, 2H), 7.30 (s, 1H), 6.16 (s, 1H), 3.76-3.81 (m, 4H), 3.09-3.18 (m, 4H), 2.34 (s, 3H), 1.45 (s, 6H); ESI-MS: m/z 535.0 (M+H)⁺.

Example 263

N-(7-(4-(N,N-dimethylsulfamoyl)piperazin-1-yl)-2-methylpyrazolo[1,5-a]pyrimidin-5-yl)-4-(2-hydroxypropan-2-yl)benzamide (249)

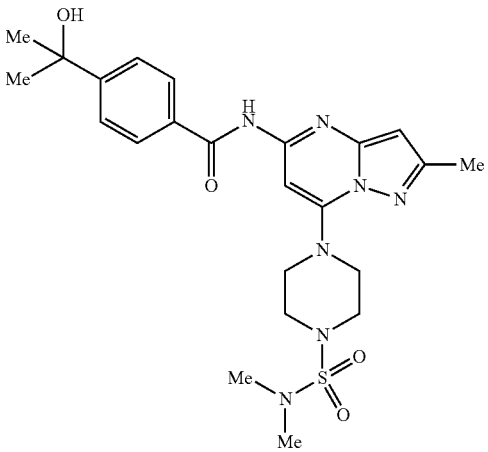

A solution of N-(7-chloro-2-methylpyrazolo[1,5-a]pyrimidin-5-yl)-4-(2-hydroxypropan-2-yl)benzamide (2F, 86 mg, 0.25 mmol) and N,N-dimethylpiperazine-1-sulfonamide (145 mg, 0.75 mmol) in DMF (1.0 mL) was stirred at 100° C. for 2 h. After cooling to room temperature, the mixture was diluted with a few drops of DMSO and methanol, and was then purified by preparatory HPLC (35-60% MeCN/H₂O gradient+0.01% TFA). Lyophilization of the combined fractions gave the titled compound as a white solid (101.3 mg, 81%). ¹H NMR (DMSO-d₆) δ: 10.90 (s, 1H), 8.00 (d, J=8.8 Hz, 2H), 7.60 (d, J=8.6 Hz, 2H), 7.36 (s, 1H), 6.20 (s, 1H), 3.79-3.82 (m, 4H), 3.39-3.48 (m, 4H), 3.07-3.16 (m, 2H), 2.39 (s, 3H), 1.66-1.82 (m, 2H), 1.45 (s, 6H), 1.01 (t, 3H); ESI-MS: m/z 502.3 (M+H)⁺.

Example 264

4-(2-hydroxypropan-2-yl)-N-(2-methyl-7-(4-(propylsulfonyl)piperazin-1-yl)pyrazolo[1,5-a]pyrimidin-5-yl)benzamide (250)

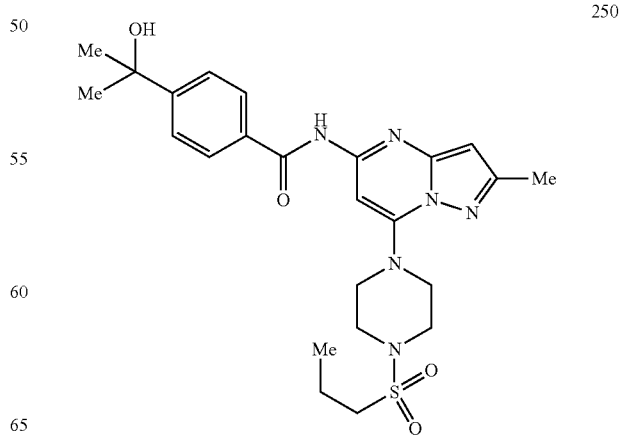

A solution of N-(7-chloro-2-methylpyrazolo[1,5-a]pyrimidin-5-yl)-4-(2-hydroxypropan-2-yl)benzamide (2F, 86 mg, 0.25 mmol), 1-(propylsulfonyl)piperazine hydrochloride (144 mg, 0.75 mmol), and N,N-diisopropylethylamine (116 mg, 0.90 mmol) in DMF (1.0 mL) was stirred at 100° C. for 2 h. After cooling to room temperature, the mixture was diluted with a few drops of DMSO and methanol, and was then purified by preparatory HPLC (40-55% MeCN/H$_2$O gradient+0.01% TFA). Lyophilization of the combined fractions gave the titled compound as a white solid (111.6 mg, 89%). $^1$H NMR (DMSO-d$_6$) δ: 10.87 (s, 1H), 7.99 (d, J=8.8 Hz, 2H), 7.61 (d, J=8.6 Hz, 2H), 7.16 (s, 1H), 6.16 (s, 1H), 4.32 (t, J=5.3 Hz, 2H), 4.00 (t, J=5.9 Hz, 2H), 3.53 (t, J=5.3 Hz, 2H), 3.36-3.45 (m, 2H), 2.90 (s, 3H), 2.37 (s, 3H), 1.95-2.15 (m, 2H), 1.45 (s, 6H); ESI-MS: m/z 501.3 (M+H)$^+$.

Example 265

4-(2-hydroxypropan-2-yl)-N-(2-methyl-7-(4-(methylsulfonyl)-1,4-diazepan-1-yl)pyrazolo[1,5-a]pyrimidin-5-yl)benzamide (251)

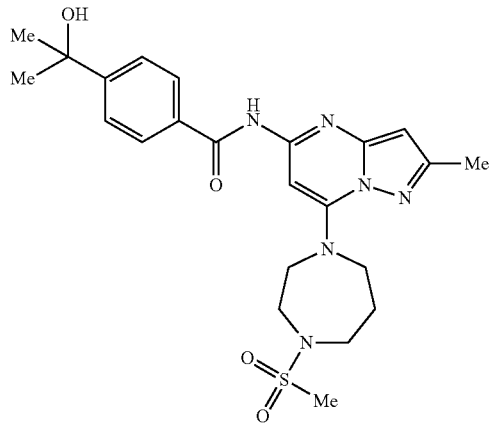

251

A solution of N-(7-chloro-2-methylpyrazolo[1,5-a]pyrimidin-5-yl)-4-(2-hydroxypropan-2-yl)benzamide (2F, 86 mg, 0.25 mmol), 1-(methylsulfonyl)-1,4-diazepane hydrochloride (107 mg, 0.50 mmol), and N,N-diisopropylethylamine (116 mg, 0.90 mmol) in DMF (1.0 mL) was stirred at 100° C. for 2 h. After cooling to room temperature, the mixture was diluted with a few drops of DMSO and methanol, and was then purified by preparatory HPLC (30-30% MeCN/H$_2$O gradient+0.01% TFA). Lyophilization of the combined fractions gave the titled compound as a white solid (93.0 mg, 76%). $^1$H NMR (DMSO-d$_6$) δ: 10.87 (s, 1H), 7.99 (d, J=8.8 Hz, 2H), 7.61 (d, J=8.6 Hz, 2H), 7.16 (s, 1H), 6.16 (s, 1H), 4.32 (t, J=5.3 Hz, 2H), 4.00 (t, J=5.9 Hz, 2H), 3.53 (t, J=5.3 Hz, 2H), 3.36-3.45 (m, 2H), 2.90 (s, 3H), 2.37 (s, 3H), 1.95-2.15 (m, 2H), 1.45 (s, 6H); ESI-MS: m/z 487.3 (M+H)$^+$.

Example 266

4-(2-hydroxypropan-2-yl)-N-(7-(1,2,3,4-tetrahydroisoquinolin-7-yl)pyrazolo[1,5-a]pyrimidin-5-yl)benzamide, trifluoroacetate salt (252)

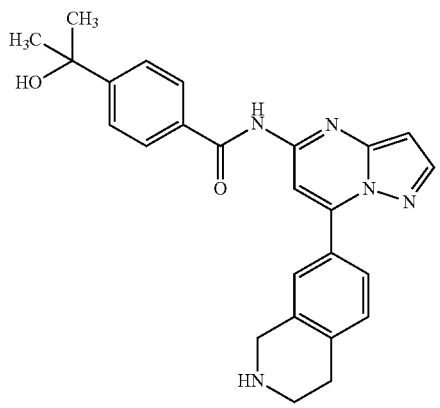

252

Step A: In a 2 mL microwave vial were placed N-(7-chloropyrazolo[1,5-a]pyrimidin-5-yl)-4-(2-hydroxypropan-2-yl)benzamide (2D, 75 mg, 0.23 mmol), 2-(tert-butoxycarbonyl)-1,2,3,4-tetrahydroisoquinolin-7-ylboronic acid (79 mg, 0.28 mmol) and [1,1'-bis(diphenylphosphino)ferrocene]-dichloropalladium(II) (8 mg, 11 μmmol). To the sealed vial were then added 1,4-dioxane (1.5 ml) and saturated aqueous NaHCO$_3$ (0.75 ml) to give a suspension. The mixture was then heated in the microwave at 110° C. for 30 minutes. After cooling to room temperature, the reaction mixture was partitioned between brine and EtOAc. The aqueous layer was extracted once more with EtOAc, and the combined organic layers were dried over MgSO$_4$, filtered and concentrated in vacuo. The crude product tert-butyl 7-(5-(4-(2-hydroxypropan-2-yl)benzamido)pyrazolo[1,5-a]pyrimidin-7-yl)-3,4-dihydroisoquinoline-2(1H)-carboxylate was used in the next step without further purification.

Step B: tert-Butyl 7-(5-(4-(2-hydroxypropan-2-yl)benzamido)pyrazolo[1,5-a]pyrimidin-7-yl)-3,4-dihydroisoquinoline-2(1H)-carboxylate from Step A was dissolved in CH$_2$Cl$_2$ (2 ml). Trifluoroacetic acid (2 ml) was then added at 0° C. The mixture was stirred for 30 minutes at that temperature before being concentrated in vacuo. Residual trifluoroacetic acid was removed azeotropically with toluene twice. The residue was then dissolved in acetonitrile before being purified by preparatory HPLC (20-30% MeCN/H$_2$O gradient+0.01% TFA) to give the titled compound as a white powder (50 mg, 41% yield). $^1$H NMR (400 MHz, DMSO-d$_6$) δ=11.30 (s, 1 H), 9.14 (br. s., 2 H), 8.21 (d, J=2.5 Hz, 1 H), 8.07 (s, 1 H), 8.05-8.01 (m, 2 H), 8.00-7.95 (m, 1 H), 7.65-7.60 (m, 2 H), 7.50 (d, J=8.1 Hz, 1 H), 6.60 (d, J=2.3 Hz, 1 H), 4.47-4.40 (m, 2 H), 3.47 (br. s., 2 H), 3.13 (t, J=6.2 Hz, 2 H), 1.46 (s, 6 H).

Example 267

1-(5-(4-(2-hydroxypropan-2-yl)benzamido)-2-methylpyrazolo[1,5-a]pyrimidin-7-yl)piperidine-4-carboxamide (253)

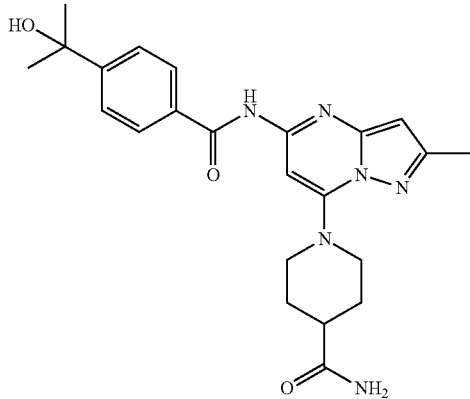

N-(7-chloro-2-methylpyrazolo[1,5-a]pyrimidin-5-yl)-4-(2-hydroxypropan-2-yl)benzamide (2F, 0.05 g, 1.0 equivalent) and piperidine-4-carboxamide (2.0 equivalents) in DMF (0.1M) was heated to 100° C. for 1 h. Then the solvent was removed in vacuo and the crude mixture was purified by preparatory HPLC (5-50% ACN/water, TFA mode) to afford the TFA salt of the titled compound 253 (46%) as a white solid. $^1$H NMR (400 MHz, DMSO-$d_6$) δ ppm 1.45 (s, 6 H) 1.69-1.83 (m, 2 H) 1.84-1.94 (m, 2 H) 2.38 (s, 3 H) 2.40-2.47 (m, 1 H) 3.03-3.14 (m, 2 H) 4.45 (d, J=12.63 Hz, 2 H) 6.15 (s, 1 H) 6.86 (s, 1 H) 7.34 (s, 1 H) 7.36 (br. s., 1 H) 7.57-7.62 (m, 2 H) 7.96-8.01 (m, 2 H) 10.83 (s, 1 H); ESI-MS: m/z 437.2 (M+H)$^+$.

Example 268

4-(2-hydroxypropan-2-yl)-N-(2-methyl-7-(4-methylpiperidin-1-yl)pyrazolo[1,5-a]pyrimidin-5-yl)benzamide (254)

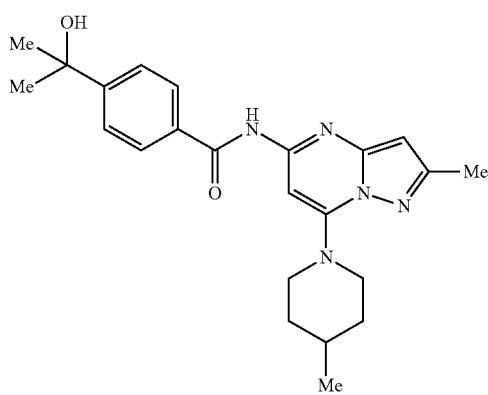

A solution of N-(7-chloro-2-methylpyrazolo[1,5-a]pyrimidin-5-yl)-4-(2-hydroxypropan-2-yl)benzamide (2F, 86 mg, 0.25 mmol) and 4-methylpiperidine (77 mg, 0.75 mmol) in DMF (1.0 mL) was stirred at 100° C. for 2 h. After cooling to room temperature, the mixture was diluted with a few drops of DMSO and methanol, and was then purified by preparatory HPLC (45-45% MeCN/H$_2$O gradient+0.01% TFA). Lyophilization of the combined fractions gave the titled compound as a white solid (88.6 mg, 87%). Melting point (154.0-158.0° C.). $^1$H NMR (DMSO-$d_6$) δ: 10.85 (s, 1H), 7.99 (d, J=8.3 Hz, 2H), 7.60 (d, J=8.6 Hz, 2H), 7.29 (s, 1H), 6.16 (s, 1H), 4.46 (d, J=12.1 Hz, 2H), 2.98-3.10 (m, 2H), 2.37 (s, 3H), 1.78 (d, J=12.9 Hz, 2H), 1.61-1.74 (m, 1H), 1.46 (s, 6H), 1.28-1.39 (m, 2H), 0.98 (d, 3H); ESI-MS: m/z 408.3 (M+H)$^+$.

Example 269

4-(2-hydroxypropan-2-yl)-N-(2-methyl-7-(1,4-oxazepan-4-yl)pyrazolo[1,5-a]pyrimidin-5-yl)benzamide (255)

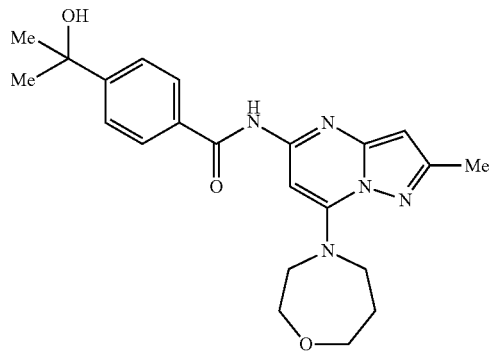

A solution of N-(7-chloro-2-methylpyrazolo[1,5-a]pyrimidin-5-yl)-4-(2-hydroxypropan-2-yl)benzamide (2F, 86 mg, 0.25 mmol), 1-(propylsulfonyl)piperazine hydrochloride (144 mg, 0.75 mmol), and N,N-diisopropylethylamine (116 mg, 0.90 mmol) in DMF (1.0 mL) was stirred at 100° C. for 2 h. After cooling to room temperature, the mixture was diluted with a few drops of DMSO and methanol, and was then purified by preparatory HPLC (30-30% MeCN/H$_2$O gradient+0.01% TFA). Lyophilization of the combined fractions gave the titled compound as a white solid (111.6 mg, 89%). $^1$H NMR (DMSO-$d_6$) δ: 10.87 (s, 1H), 7.99 (d, J=8.8 Hz, 2H), 7.61 (d, J=8.6 Hz, 2H), 7.15 (s, 1H), 6.16 (s, 1H), 4.27 (t, J=4.9 Hz, 2H), 4.00 (t, J=6.2 Hz, 2H), 3.79-3.85 (m, 2H), 3.72-3.78 (m, 2H), 2.36 (s, 3H), 2.05 (quin, J=5.8 Hz, 2H), 1.46 (s, 6H); ESI-MS: m/z 410.3 (M+H)$^+$.

Example 270

N-(7-(4-formyl-1,4-diazepan-1-yl)-2-methylpyrazolo[1,5-a]pyrimidin-5-yl)-4-(2-hydroxypropan-2-yl)benzamide (256)

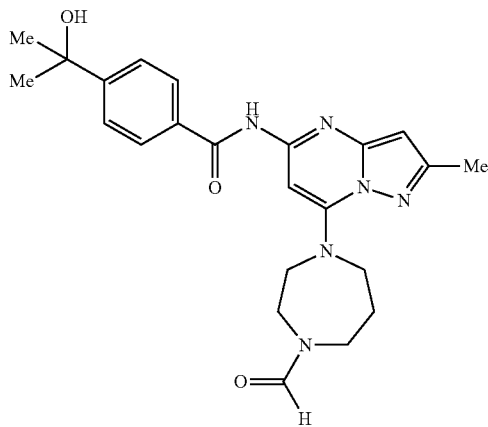

A solution of N-(7-chloro-2-methylpyrazolo[1,5-a]pyrimidin-5-yl)-4-(2-hydroxypropan-2-yl)benzamide (2F, 86 mg, 0.25 mmol) and 1,4-diazepane-1-carbaldehyde (97 mg, 0.75 mmol) in DMF (1.0 mL) was stirred at 100° C. for 2 h. After cooling to room temperature, the mixture was diluted with a few drops of DMSO and methanol, and was then purified by preparatory HPLC (25-35% MeCN/H$_2$O gradient+0.01% TFA). Lyophilization of the combined fractions gave the titled compound as a white solid (84.4 mg, 77%). $^1$H NMR (DMSO-d$_6$) δ: 10.86 (s, 1H), [1:1 ratio of rotamers: 8.09 (s, 1H); 7.93 (s, 1H)], 7.98 (d, J=8.3 Hz, 2H), 7.61 (d, J=8.6 Hz, 2H), 7.14 (d, J=2.8 Hz, 1H), 6.16 (s, 1H), 4.25-4.39 (m, 3H), 3.55-3.71 (m, 4H), 3.46-3.54 (m, 1H), 2.37 (s, 3H), 1.97-2.09 (m, 1H), 1.86-1.97 (m, 1H), 1.45 (s, 6H); ESI-MS: m/z 437.3 (M+H)$^+$.

Example 271

N-(7-(4-acetyl-1,4-diazepan-1-yl)-2-methylpyrazolo[1,5-a]pyrimidin-5-yl)-4-(2-hydroxypropan-2-yl)benzamide (257)

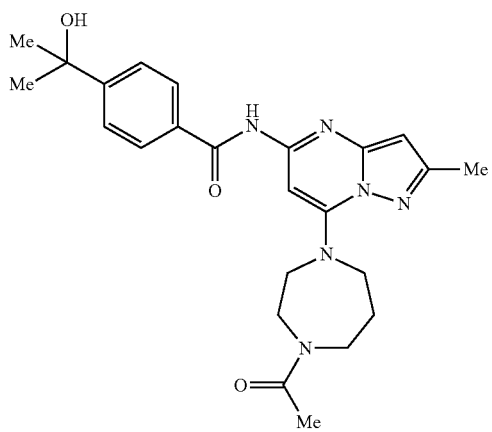

A solution of N-(7-chloro-2-methylpyrazolo[1,5-a]pyrimidin-5-yl)-4-(2-hydroxypropan-2-yl)benzamide (2F, 86 mg, 0.25 mmol) and 1-(1,4-diazepan-1-yl)ethanone (101 mg, 0.75 mmol) in DMF (1.0 mL) was stirred at 100° C. for 2 h. After cooling to room temperature, the mixture was diluted with a few drops of DMSO and methanol, and was then purified by preparatory HPLC (25-40% MeCN/H$_2$O gradient+0.01% TFA). Lyophilization of the combined fractions gave the titled compound as a white solid (87.7 mg, 78%). $^1$H NMR (DMSO-d$_6$) [1:1 ratio of rotamers: δ: 10.93 (s, 1H); 10.91 (s, 1H)], 7.99 (d, J=8.3 Hz, 2H), 7.62 (dd, 2H), [1:1 ratio of rotamers: 7.13 (s, 1H); 7.07 (s, 1H)], [1:1 ratio of rotamers: 6.19 (s, 1H); 6.18 (s, 1H)], [1:1 ratio of rotamers: 4.37 (t, J=5.6 Hz, 2H); 4.20 (t, J=5.4 Hz, 2H)], [1:1 ratio of rotamers: 4.03 (t, J=5.6 Hz, 2H); 3.97 (t, J=5.9 Hz, 2H)], 3.63-3.78 (m, 2H), [1:1 ratio of rotamers: 3.58 (t, J=5.9 Hz, 2H); 3.52 (t, J=5.8 Hz, 2H)], 2.37 (s, 3H), [1:1 ratio of rotamers: 2.03-2.11 (m, 2H); 1.94 (quin, J=5.9 Hz, 2H)], [1:1 ratio of rotamers: 2.02 (s, 3H); 1.89 (s, 3H)], 1.46 (s, 6H); ESI-MS: m/z 451.3 (M+H)$^+$.

Example 272

(S)-N-(7-(2-(hydroxymethyl)pyrrolidin-1-yl)-2-methylpyrazolo[1,5-a]pyrimidin-5-yl)-4-(2-hydroxypropan-2-yl)benzamide (258)

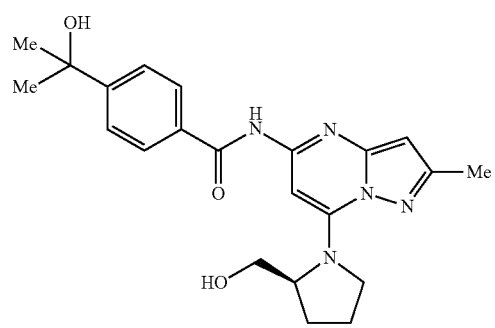

A solution of N-(7-chloro-2-methylpyrazolo[1,5-a]pyrimidin-5-yl)-4-(2-hydroxypropan-2-yl)benzamide (2F, 86 mg, 0.25 mmol) and (S)-pyrrolidin-2-ylmethanol (78 mg, 0.75 mmol) in DMF (1.0 mL) was stirred at 100° C. for 2 h. After cooling to room temperature, the mixture was diluted with a few drops of DMSO and methanol, and was then purified by preparatory HPLC (25-25% MeCN/H$_2$O gradient+0.01% TFA). Lyophilization of the combined fractions gave the titled compound as a white solid (82.8 mg, 81%). Melting point (167.0-197.7° C.). $^1$H NMR (DMSO-d$_6$) δ: 11.06 (s, 1H), 7.99 (d, J=8.6 Hz, 2H), 7.64 (d, J=8.6 Hz, 2H), 6.80 (s, 1H), 6.21 (s, 1H), 5.01 (br. s., 1H), 3.99 (t, J=8.2 Hz, 1H), 3.77-3.92 (m, 1H), 3.55-3.62 (m, 1H), 3.49 (dd, J=10.9, 6.6 Hz, 1H), 2.36 (s, 3H), 2.02-2.18 (m, 3H), 1.88-2.00 (m, 1H), 1.46 (s, 6H); ESI-MS: m/z 410.3 (M+H)⁺.

Example 273

N-ethyl-1-(5-(4-(2-hydroxypropan-2-yl)benzamido)-2-methylpyrazolo[1,5-a]pyrimidin-7-yl)piperidine-4-carboxamide (259)

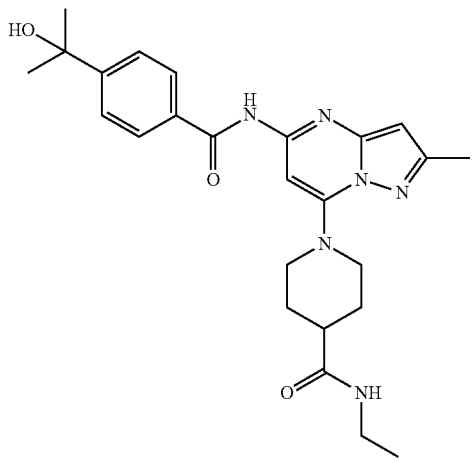

259

N-(7-chloro-2-methylpyrazolo[1,5-a]pyrimidin-5-yl)-4-(2-hydroxypropan-2-yl)benzamide (2F, 0.05 g, 1.0 equivalent) and N-ethylpiperidine-4-carboxamide (2.0 equivalents) in DMF (0.1M) was heated to 100° C. for 7 h. Then the solvent was removed in vacuo and the crude mixture was purified by preparatory HPLC (20-40% ACN/water, TFA mode) to afford the TFA salt of the titled compound, which was further purified by EtOAc wash and filtered to afford the titled compound 259 (42%) as a white solid. ¹H NMR (400 MHz, DMSO-d₆) δ ppm 1.03 (t, J=7.20 Hz, 3 H) 1.46 (s, 6 H) 1.71-1.91 (m, 4 H) 2.38 (s, 3 H) 2.41-2.48 (m, 1 H) 3.00-3.17 (m, 4 H) 4.47 (d, J=14.40 Hz, 2 H) 6.15 (s, 1 H) 7.36 (s, 1 H) 7.57-7.64 (m, 2 H) 7.88 (t, J=5.31 Hz, 1 H) 7.99 (d, J=8.59 Hz, 2 H) 10.83 (s, 1 H); ESI-MS: m/z 465.3 (M+H)⁺.

Example 274

1-(5-(4-(2-hydroxypropan-2-yl)benzamido)-2-methylpyrazolo[1,5-a]pyrimidin-7-yl)-N-methylpiperidine-4-carboxamide (260)

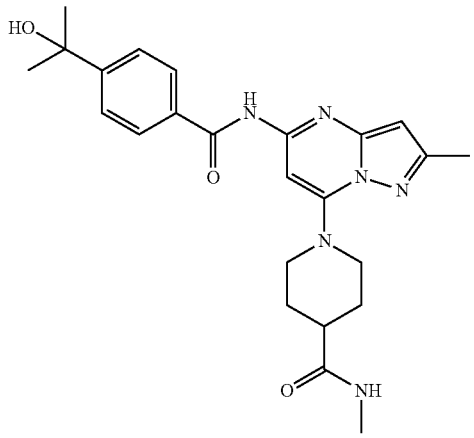

260

N-(7-chloro-2-methylpyrazolo[1,5-a]pyrimidin-5-yl)-4-(2-hydroxypropan-2-yl)benzamide (2F, 0.05 g, 1.0 equivalent) and N-methylpiperidine-4-carboxamide (2.0 equivalents) in DMF (0.1M) was heated to 100° C. for 6 h. Then another 2.0 equivalents of N-methylpiperidine-4-carboxamide was added and heated to 100° C. for 4 h. Then the solvent was removed in vacuo and the crude mixture was purified by preparatory HPLC (20-35% ACN/water, TFA mode) to afford the TFA salt of the titled compound, which was further purified by MeOH and then EtOAc wash and filtered to afford the titled compound (24%) as a white solid. ¹H NMR (400 MHz, DMSO-d₆) δ ppm 1.45 (s, 6 H) 1.70-1.90 (m, 4 H) 2.37 (s, 3 H) 2.39-2.48 (m, 1 H) 2.59 (d, J=4.80 Hz, 3 H) 3.08 (t, J=11.24 Hz, 2 H) 4.46 (d, J=12.38 Hz, 2 H) 6.15 (s, 1 H) 7.33 (s, 1 H) 7.56-7.63 (m, 2 H) 7.83 (q, J=4.46 Hz, 1 H) 7.95-8.03 (m, 2 H) 10.83 (s, 1 H); ESI-MS: m/z 451.2 (M+H)⁺.

Example 275

1-(5-(4-(2-hydroxypropan-2-yl)benzamido)-2-methylpyrazolo[1,5-a]pyrimidin-7-yl)-N,N-dimethylpiperidine-4-carboxamide (261)

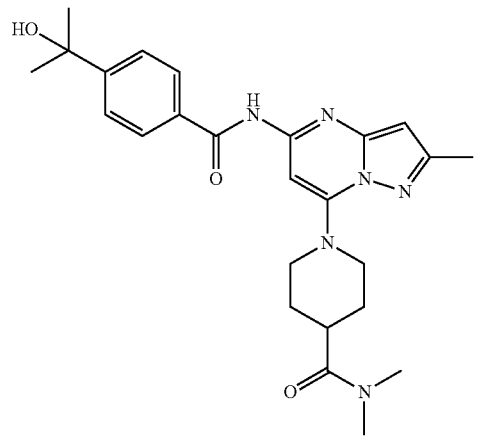

261

N-(7-chloro-2-methylpyrazolo[1,5-a]pyrimidin-5-yl)-4-(2-hydroxypropan-2-yl)benzamide (2F, 0.05 g, 1.0 equivalent) and N,N-dimethylpiperidine-4-carboxamide hydrochloride (2.0 equivalents) in DMF (0.1M) was added Et₃N (6.0 equivalents). The mixture was heated to 80° C. for 2 h. Then the solvent was removed in vacuo and the crude mixture was purified by preparatory HPLC (20-40% ACN/water, TFA mode) to afford the TFA salt of the titled compound (85%) as a white solid. ¹H NMR (400 MHz, DMSO-d₆) δ ppm 1.45 (s, 6 H) 1.69-1.85 (m, 4 H) 2.38 (s, 3 H) 2.83 (s, 3 H) 2.96-3.06 (m, 1 H) 3.08 (s, 3 H) 3.17 (td, J=12.00, 2.78 Hz, 2 H) 4.49 (d, J=12.63 Hz, 2 H) 6.16 (s, 1 H) 7.31 (s, 1 H) 7.60 (m, 2 H) 7.99 (m, 2 H) 10.86 (s, 1 H); ESI-MS: m/z 465.3 (M+H)⁺.

Example 276

N-(7-(2,2-difluorobenzo[d][1,3]dioxol-4-yl)pyrazolo[1,5-a]pyrimidin-5-yl)-4-(2-hydroxypropan-2-yl)benzamide (262)

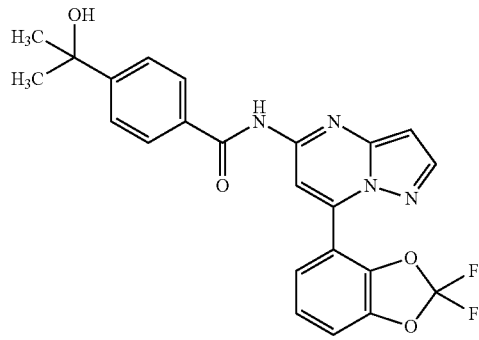

In a 2 mL microwave vial were placed N-(7-chloropyrazolo[1,5-a]pyrimidin-5-yl)-4-(2-hydroxypropan-2-yl)benzamide (2D, 75 mg, 0.23 mmol), 2,2-difluorobenzo[d][1,3]dioxol-4-ylboronic acid (57 mg, 0.28 mmol) and [1,1'-bis(diphenylphosphino)ferrocene]-dichloropalladium(II) (8 mg, 11 μmmol). To the sealed vial were then added 1,4-dioxane (1.5 ml) and saturated aqueous NaHCO$_3$ (0.75 ml) to give a suspension. The mixture was then heated in the microwave at 120° C. for 20 minutes. After cooling to room temperature, the reaction mixture was partitioned between brine and EtOAc. The aqueous layer was extracted once more with EtOAc, and the combined organic layers were dried over MgSO$_4$, filtered and concentrated in vacuo. The residue was purified by preparatory HPLC (50-70% MeCN/H$_2$O gradient+0.01% TFA) to give the titled compound as a white powder (62 mg, 60% yield). $^1$H NMR (400 MHz, DMSO-d$_6$) δ=11.38 (s, 1 H), 8.22 (d, J=2.0 Hz, 1 H), 8.18 (s, 1 H), 8.03 (d, J=8.6 Hz, 2 H), 7.90 (dd, J=1.0, 8.1 Hz, 1 H), 7.71 (dd, J=1.0, 8.1 Hz, 1 H), 7.63 (d, J=8.3 Hz, 2 H), 7.47 (t, J=8.1 Hz, 1 H), 6.64 (d, J=2.3 Hz, 1 H), 1.46 (s, 6 H); ESI-MS: m/z 453.3 (M+H)$^+$.

Example 277

N-(7-(4,4-difluoropiperidin-1-yl)pyrazolo[1,5-a]pyrimidin-5-yl)-4-(2-hydroxypropan-2-yl)benzamide (263)

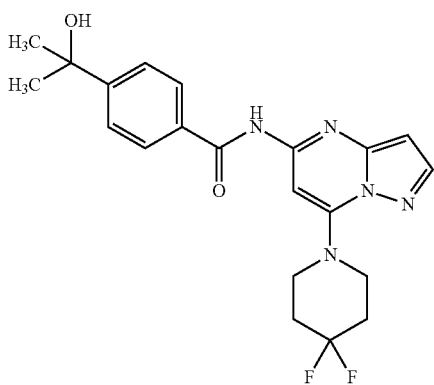

In a 2 mL microwave vial were placed N-(7-chloropyrazolo[1,5-a]pyrimidin-5-yl)-4-(2-hydroxypropan-2-yl)benzamide (2D, 75 mg, 0.23 mmol) and 4,4-difluoropiperidine, HCl salt (71 mg, 0.45 mmol). To the sealed vial were then added NMP (2 ml) and diisopropylethylamine (79 μl, 0.45 mmol), and the mixture was then heated in the microwave at 120° C. for 20 minutes. After cooling to room temperature, the reaction mixture was filtered by syringe filter and was then directly purified by preparatory HPLC (30-70% MeCN/H$_2$O gradient+0.01% TFA). The combined fractions were concentrated in vacuo, and the residue was partitioned between saturated NaHCO$_3$ and EtOAc. The aqueous layer was extracted once more with EtOAc, and the combined organic layers were dried over MgSO$_4$, filtered and concentrated in vacuo to give the titled compound as a white powder (51 mg, 54% yield). $^1$HNMR (400 MHz, DMSO-d$_6$) δ=10.94 (br. s., 1 H), 8.12 (br. s., 1 H), 8.00 (d, J=8.1 Hz, 2 H), 7.60 (d, J=7.8 Hz, 2 H), 7.47 (s, 1 H), 6.38 (br. s., 1 H), 5.19 (s, 1 H), 3.88 (br. s., 4 H), 2.24 (br. s., 4 H), 1.46 (br. s., 6 H); ESI-MS: m/z 416.4 (M+H)$^+$.

Example 278

4-(2-hydroxypropan-2-yl)-N-(7-(4-(trifluoromethyl)piperidin-1-yl)pyrazolo[1,5-a]pyrimidin-5-yl)benzamide (264)

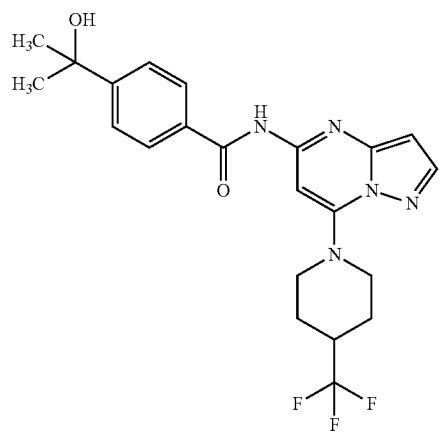

In a 2 mL microwave vial were placed N-(7-chloropyrazolo[1,5-a]pyrimidin-5-yl)-4-(2-hydroxypropan-2-yl)benzamide (2D, 75 mg, 0.23 mmol) and 4-(trifluoromethyl)piperidine, HCl salt (86 mg, 0.45 mmol). To the sealed vial were then added NMP (2 ml) and diisopropylethylamine (79 μl, 0.45 mmol), and the mixture was then heated in the microwave at 120° C. for 20 minutes. After cooling to room temperature, the reaction mixture was filtered by syringe filter and was then directly purified by preparatory HPLC (30-70% MeCN/H$_2$O gradient+0.01% TFA). The combined fractions were concentrated in vacuo, and the residue was partitioned between saturated NaHCO$_3$ and EtOAc. The aqueous layer was extracted once more with EtOAc, and the combined organic layers were dried over MgSO$_4$, filtered and concentrated in vacuo to give the titled compound as a white powder (66 mg, 65% yield). $^1$HNMR (400 MHz, DMSO-d$_6$) δ=10.91 (br. s., 1 H), 8.10 (br. s., 1 H), 8.00 (d, J=7.6 Hz, 2 H), 7.60 (d, J=7.6 Hz, 2 H), 7.45 (br. s., 1 H), 6.36 (br. s., 1 H), 5.19 (br. s., 1 H), 4.55 (br. s., 2 H), 3.19-3.00 (m, 2 H), 2.72 (br. s., 1 H), 2.01 (br. s., 1 H), 1.71 (br. s., 1 H), 1.46 (br. s., 6 H); ESI-MS: m/z 448.4 (M+H)+.

Example 279

4-(2-hydroxypropan-2-yl)-N-(2-methyl-7-(1,2,3,4-tetrahydroisoquinolin-7-yl)pyrazolo[1,5-a]pyrimidin-5-yl)benzamide (265)

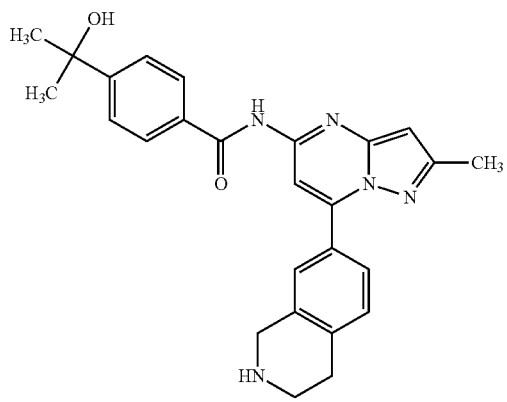

265

Step A: In a 2 mL microwave vial were placed N-(7-chloro-2-methylpyrazolo[1,5-a]pyrimidin-5-yl)-4-(2-hydroxypropan-2-yl)benzamide (2F, 120 mg, 0.348 mmol), 2-(tert-butoxycarbonyl)-1,2,3,4-tetrahydroisoquinolin-7-ylboronic acid (121 mg, 0.44 mmol) and [1,1'-bis(diphenylphosphino)ferrocene]-dichloropalladium(II) (13 mg, 17 μmol). To the sealed vial were then added 1,4-dioxane (2 ml) and saturated aqueous NaHCO$_3$ (1 ml) to give a suspension. The mixture was then heated in the microwave at 120° C. for 30 minutes. After cooling to room temperature, the reaction mixture was partitioned between saturated NaHCO$_3$ and EtOAc. The aqueous layer was extracted once more with EtOAc, and the combined organic layers were dried over MgSO$_4$, filtered and concentrated in vacuo. The crude product tert-butyl 7-(5-(4-(2-hydroxypropan-2-yl)benzamido)-2-methylpyrazolo[1,5-a]pyrimidin-7-yl)-3,4-dihydroisoquinoline-2(1H)-carboxylate was used in the next step without further purification.

Step B: tert-Butyl 7-(5-(4-(2-hydroxypropan-2-yl)benzamido)pyrazolo[1,5-a]pyrimidin-7-yl)-3,4-dihydroisoquinoline-2(1H)-carboxylate from Step A was dissolved in CH$_2$Cl$_2$ (2 ml). Trifluoroacetic acid (1 ml) was then added at 0° C. The mixture was stirred for 30 minutes at that temperature before being concentrated in vacuo. Residual trifluoroacetic acid was removed azeotropically with toluene twice. The residue was then dissolved in acetonitrile before being purified by preparatory HPLC (20-35% MeCN/H$_2$O gradient+0.01% TFA) to give the titled compound as a white powder. $^1$H NMR (400 MHz, DMSO-d$_6$) δ=11.22 (s, 1 H), 9.11 (br. s., 2 H), 8.01 (d, J=8.6 Hz, 2 H), 7.99-7.89 (m, 3 H), 7.62 (d, J=8.6 Hz, 2 H), 7.49 (d, J=8.1 Hz, 1 H), 6.40 (s, 1 H), 4.43 (br. s., 2 H), 3.47 (d, J=7.3 Hz, 2 H), 3.16-3.07 (m, 2 H), 2.40 (s, 3 H), 1.46 (s, 6 H); ESI-MS: m/z 442.2 (M+H)+.

Example 280

1-(5-(4-(2-hydroxypropan-2-yl)benzamido)pyrazolo[1,5-a]pyrimidin-7-yl)-N-methylpiperidine-4-carboxamide (266)

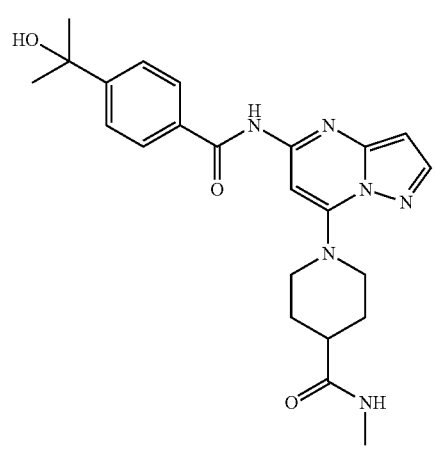

266

A solution of 1-(5-(4-(2-hydroxypropan-2-yl)benzamido)pyrazolo[1,5-a]pyrimidin-7-yl)piperidine-4-carboxylic acid (Compound 244, 80 mg, 0.189 mmol), methylamine (33 μL, 0.378 mmol), EDCI (72 mg, 0.378 mmol), and HOBT (13 mg, 0.094 mmol) in DMF (4 mL) were stirred for 12 hours at room temperature. The reaction was complete as determined by LCMS analysis. The reaction mixture was then partitioned between ethyl acetate and water and the separated organic layer was dried over Mg$_2$SO$_4$, filtered, and concentrated under reduced pressure. Purification by preparatory HPLC, 30-50% (MeCN/H$_2$O gradient+0.01% TFA) provided the titled compound as a yellow oil (45 mg, 55%). $^1$HNMR (DMSO-d$_6$) δ: 10.90 (s, 1H), 8.09 (d, J=2.3 Hz, 1H), 8.00 (d, J=8.8 Hz, 2H), 7.80-7.87 (m, 1H), 7.60 (d, 2H), 7.41 (s, 1H), 6.35 (d, J=2.3 Hz, 1H), 4.46 (d, J=12.1 Hz, 2H), 3.10 (td, J=12.3, 2.8 Hz, 2H), 2.59 (d, J=4.5 Hz, 3H), 1.71-1.90 (m, 4H), 1.44 (s, 6H). ESI-MS: m/z 437.0 (M+H)+.

Example 281

1-(5-(4-(2-hydroxypropan-2-yl)benzamido)pyrazolo[1,5-a]pyrimidin-7-yl)-N-isopropylpiperidine-4-carboxamide (267)

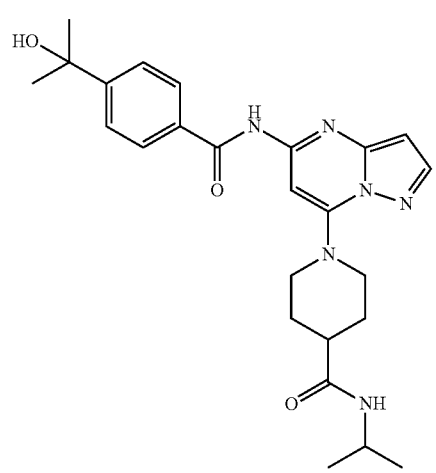

267

A solution of 1-(5-(4-(2-hydroxypropan-2-yl)benzamido)pyrazolo[1,5-a]pyrimidin-7-yl)piperidine-4-carboxylic acid (Compound 244, 80 mg, 0.189 mmol), isopropylamine (22 mg, 0.378 mmol), EDCI (72 mg, 0.378 mmol), and HOBT (13 mg, 0.095 mmol) in DMF (4 mL) were stirred for 12 hours at room temperature. The reaction was complete as determined by LCMS analysis. The reaction mixture was then partitioned between ethyl acetate and water and the separated organic layer was dried over $Mg_2SO_4$, filtered, and concentrated under reduced pressure. Purification by preparatory HPLC, 20-30% (MeCN/$H_2O$ gradient+0.01% TFA) provided the titled compound as a white solid (7.3 mg, 8%). $^1$H NMR (DMSO-$d_6$) δ: 10.88 (s, 1H), 8.08 (d, J=2.3 Hz, 1H), 7.99 (d, J=8.8 Hz, 2H), 7.74 (d, J=7.8 Hz, 1H), 7.59 (d, J=8.8 Hz, 2H), 7.42 (s, 1H), 6.34 (d, J=2.3 Hz, 1H), 4.43-4.50 (m, 3H), 3.84 (dd, J=14.3, 6.4 Hz, 2H), 3.07 (br. s., 2H), 1.73-1.87 (m, 4H), 1.45 (s, 6H), 1.05 (d, J=6.6 Hz, 6H). ESI-MS: m/z 465.0 (M+H)$^+$.

Example 282

(R)-1-(5-(4-(2-hydroxypropan-2-yl)benzamido)pyrazolo[1,5-a]pyrimidin-7-yl)-N-methylpiperidine-3-carboxamide (268)

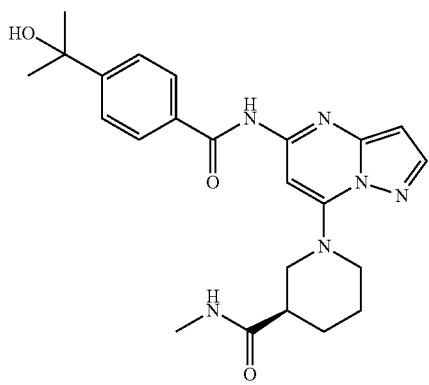

268

A solution of (R)-1-(5-(4-(2-hydroxypropan-2-yl)benzamido)pyrazolo[1,5-a]pyrimidin-7-yl)piperidine-3-carboxylic acid (Compound 84, 100 mg, 0.236 mmol), methylamine (15 mg, 0.472 mmol), EDCI (90 mg, 0.472 mmol), and HOBT (16 mg, 0.118 mmol) in DMF (4.22 mL) were stirred for 12 hours at room temperature. The reaction was complete as determined by LCMS analysis. The reaction mixture was then partitioned between ethyl acetate and water and the separated organic layer was dried over $Mg_2SO_4$, filtered, and concentrated under reduced pressure. Purification by preparatory HPLC, 20-40% (MeCN/$H_2O$ gradient+0.01% TFA) provided the titled compound as a yellow solid (56 mg, 53%). $^1$H NMR (DMSO-$d_6$) δ: 10.90 (s, 1H), 8.10 (d, J=2.3 Hz, 1H), 8.00 (d, J=8.6 Hz, 2H), 7.55-7.65 (m, J=8.6 Hz, 2H), 7.40 (s, 1H), 6.36 (d, J=2.3 Hz, 1H), 4.35 (br. s., 3H), 3.25 (dd, J=12.3, 10.7 Hz, 1H), 3.05 (br. s., 1H), 2.55-2.64 (m, 3H), 1.93 (br. s., 1H), 1.79-1.88 (m, 1H), 1.73 (d, J=10.9 Hz, 2H), 1.45 (s, 6H). ESI-MS: m/z 437.0 (M+H)$^+$.

Example 283

(R)-1-(5-(4-(2-hydroxypropan-2-yl)benzamido)pyrazolo[1,5-a]pyrimidin-7-yl)-N-methylpiperidine-3-carboxamide (269)

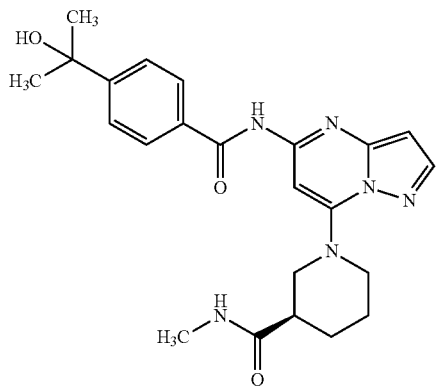

269

In a 2 mL microwave vial were placed N-(7-chloropyrazolo[1,5-a]pyrimidin-5-yl)-4-(2-hydroxypropan-2-yl)benzamide (2D, 437 mg, 1.3 mmol) and (R)-N-methylpiperidine-3-carboxamide, trifluoroacetate salt (585 mg, 2.2 mmol). To the sealed vial were then added NMP (6 ml) and diisopropylethylamine (0.67 ml, 3.85 mmol), and the mixture was then heated in the microwave at 100° C. for 15 minutes. After cooling to room temperature, the reaction mixture was filtered by syringe filter and was then directly purified by preparatory HPLC (25-50% MeCN/$H_2O$ gradient+0.01% TFA). Lyophilization of the combined fractions gave the titled compound as a white powder (510 mg, 88% yield). $^1$H NMR (400 MHz, DMSO-$d_6$) δ=10.96 (br. s., 1H), 8.11 (br. s., 1H), 8.00 (d, J=8.1 Hz, 3H), 7.61 (d, J=8.1 Hz, 2H), 7.35 (s, 1H), 6.39 (br. s., 1H), 4.48-4.25 (m, 2H), 3.29 (t, J=11.1 Hz, 1H), 3.08 (br. s., 1H), 2.61 (s, 3H), 2.60 (m, 1H), 2.08 (s, 1H), 1.94 (br. s., 1H), 1.83 (br. s., 1H), 1.73 (br. s., 2H), 1.46 (s, 6H); ESI-MS: m/z 437.4 (M+H)$^+$.

Example 284

(R)-1-(5-(4-(2-hydroxypropan-2-yl)benzamido)pyrazolo[1,5-a]pyrimidin-7-yl)-N,N-dimethylpiperidine-3-carboxamide (270)

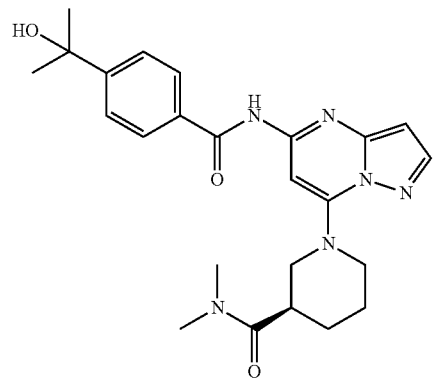

270

A solution of (R)-1-(5-(4-(2-hydroxypropan-2-yl)benzamido)pyrazolo[1,5-a]pyrimidin-7-yl)piperidine-3-carboxylic acid (Compound 84, 100 mg, 0.236 mmol), dimethylamine (236 μL, 0.472 mmol), EDCI (90 mg, 0.472 mmol), and HOBT (16 mg, 0.118 mmol) in DMF (4 mL) were stirred for 12 hours at room temperature. The reaction was complete as determined by LCMS analysis. The reaction mixture was then partitioned between ethyl acetate and water and the separated organic layer was dried over Mg$_2$SO$_4$, filtered, and concentrated under reduced pressure. Purification by preparatory HPLC, 20-40% (MeCN/H$_2$O gradient+0.01% TFA) provided the titled compound as a white solid (71 mg, 69%). $^1$H NMR (DMSO-d$_6$) δ: 10.91 (s, 1H), 8.08 (d, J=2.3 Hz, 1H), 7.95-8.03 (m, J=8.6 Hz, 2H), 7.60 (d, J=8.8 Hz, 2H), 7.37 (s, 1H), 6.36 (d, J=2.0 Hz, 1H), 4.55 (br. s., 1H), 4.35 (br. s., 1H), 2.97-3.18 (m, 6H), 2.83 (s, 3H), 1.57-2.01 (m, 4H), 1.45 (s, 6H). ESI-MS: m/z 451.0 (M+H)$^+$.

Example 285

4-(2-hydroxypropan-2-yl)-N-(7-phenoxypyrazolo[1,5-a]pyrimidin-5-yl)benzamide (271)

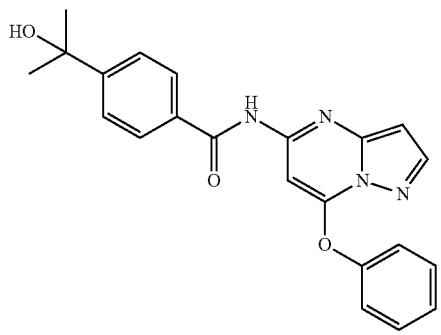

271

A solution of N-(7-chloropyrazolo[1,5-a]pyrimidin-5-yl)-4-(2-hydroxypropan-2-yl)benzamide (2D, 100 mg, 0.302 mmol) and sodium phenoxide (70 mg, 605 mmol) in NMP (3 mL) was stirred at room temperature overnight. After cooling to room temperature, the mixture was diluted with a few drops of DMSO and methanol, and was then purified by preparatory HPLC, 40-50% (MeCN/H$_2$O gradient+0.01% TFA). Lyophilization of the combined fractions gave the titled compound as a white solid (44 mg, 37%). $^1$H NMR (DMSO-d$_6$) δ: 11.11 (s, 1H), 8.21 (d, J=2.3 Hz, 1H), 7.91 (d, J=8.6 Hz, 2H), 7.41-7.68 (m, 7H), 7.17 (s, 1H), 6.51 (d, J=2.3 Hz, 1H), 3.94 (br. s., 1H), 1.43 (s, 6H). ESI-MS: m/z 389.0 (M+H)$^+$.

Example 286

(R)-1-(5-(4-(2-hydroxypropan-2-yl)benzamido)pyrazolo[1,5-a]pyrimidin-7-yl)-N-isopropylpiperidine-3-carboxamide (272)

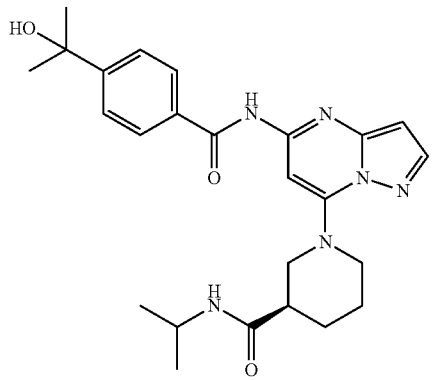

272

A solution of (R)-1-(5-(4-(2-hydroxypropan-2-yl)benzamido)pyrazolo[1,5-a]pyrimidin-7-yl)piperidine-3-carboxylic acid (Compound 84, 100 mg, 0.236 mmol), isopropylamine (14 mg, 0.236 mmol), EDCI (90 mg, 0.472 mmol), and HOBT (16 mg, 0.118 mmol) in DMF (4 mL) were stirred for 12 hours at room temperature. The reaction was complete as determined by LCMS analysis. The reaction mixture was then partitioned between ethyl acetate and water and the separated organic layer was dried over Mg$_2$SO$_4$, filtered, and concentrated under reduced pressure. Purification by preparatory HPLC, 25-35% (MeCN/H$_2$O gradient+0.01% TFA) provided the titled compound as a white solid (43 mg, 39%). $^1$HNMR (DMSO-d$_6$) δ: 10.92 (s, 1H), 8.10 (d, J=2.3 Hz, 1H), 7.97-8.04 (m, 2H), 7.92 (d, J=7.6 Hz, 1H), 7.55-7.66 (m, 2H), 7.39 (s, 1H), 6.37 (d, J=2.3 Hz, 1H), 4.26 (t, J=12.4 Hz, 2H), 3.84 (dq, J=13.8, 6.7 Hz, 1H), 3.36 (dd, J=12.4, 10.4 Hz, 1H), 2.98-3.14 (m, 1H), 2.53-2.58 (m, 1H), 1.67-2.01 (m, 4H), 1.39-1.51 (m, 6H), 1.05 (t, J=6.2 Hz, 6H). ESI-MS: m/z 465.0 (M+H)$^+$.

Example 287

N-(7-(3-fluoropyrrolidin-1-yl)-2-methylpyrazolo[1,5-a]pyrimidin-5-yl)-4-(2-hydroxypropan-2-yl)benzamide (273)

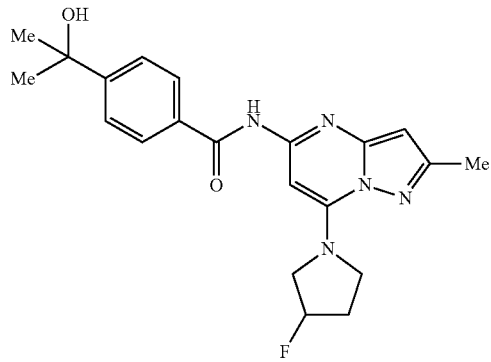

273

A solution of N-(7-chloro-2-methylpyrazolo[1,5-a]pyrimidin-5-yl)-4-(2-hydroxypropan-2-yl)benzamide (2F, 86 mg, 0.25 mmol), 3-fluoropyrrolidine hydrochloride (63 mg, 0.75 mmol), and N,N-diisopropylethylamine (116 mg, 0.90 mmol) in DMF (1.0 mL) was stirred at 100° C. for 2 h. After cooling to room temperature, the mixture was diluted with a few drops of DMSO and methanol, and was then purified by preparatory HPLC (30-30% MeCN/H$_2$O gradient+0.01% TFA). Lyophilization of the combined fractions gave the titled compound as a white solid (73.5 mg, 74%). $^1$H NMR (DMSO-d$_6$) δ: 10.82 (s, 1H), 7.98 (d, J=8.6 Hz, 2H), 7.61 (d, J=8.3 Hz, 2H), 6.89 (s, 1H), 6.11 (s, 1H), 5.50 (d, J=52.0 Hz, 1H), 4.05-4.45 (m, 3H), 3.86-3.96 (m, 1H), 2.35 (s, 3H), 2.24-2.33 (m, 1H), 2.11-2.24 (m, 1H), 1.45 (s, 6H); ESI-MS: m/z 398.3 (M+H)$^+$.

Example 288

N-(7-(4-(2-hydroxyethyl)piperidin-1-yl)-2-methylpyrazolo[1,5-a]pyrimidin-5-yl)-4-(2-hydroxypropan-2-yl)benzamide (274)

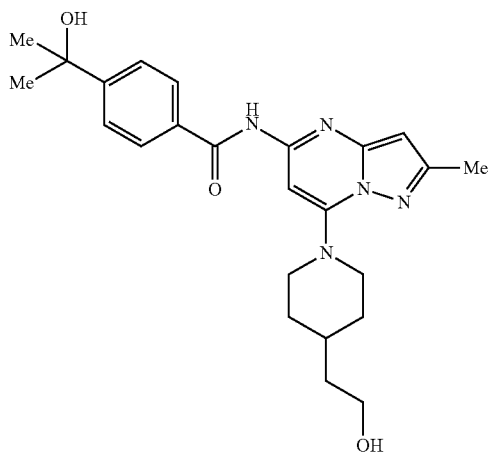

274

A solution of N-(7-chloro-2-methylpyrazolo[1,5-a]pyrimidin-5-yl)-4-(2-hydroxypropan-2-yl)benzamide (2F, 86 mg, 0.25 mmol) and 2-(piperidin-4-yl)ethanol (100 mg, 0.75 mmol) in DMF (1.0 mL) was stirred at 100° C. for 2 h. After cooling to room temperature, the mixture was diluted with a few drops of DMSO and methanol, and was then purified by preparatory HPLC (30-35% MeCN/H$_2$O gradient+0.01% TFA). Lyophilization of the combined fractions gave the titled compound as a white solid (63.9 mg, 58%). Melting point (234.0-234.1° C.). $^1$H NMR (DMSO-d$_6$) δ: 10.93 (s, 1H), 8.00 (d, J=8.6 Hz, 2H), 7.61 (d, J=8.6 Hz, 2H), 7.20 (s, 1H), 6.20 (s, 1H), 4.51 (d, J=12.6 Hz, 2H), 3.50 (t, J=6.4 Hz, 2H), 3.07 (t, J=11.5 Hz, 2H), 2.38 (s, 3H), 1.84 (d, J=12.9 Hz, 2H), 1.68-1.81 (m, 1H), 1.46 (s, 6H), 1.41-1.45 (m, 2H), 1.29-1.41 (m, 2H); ESI-MS: m/z 438.3 (M+H)$^+$.

Example 289

N-(7-(2,3-dihydrobenzo[b][1,4]dioxin-6-yl)-2-methylpyrazolo[1,5-a]pyrimidin-5-yl)-4-(2-hydroxypropan-2-yl)benzamide (275)

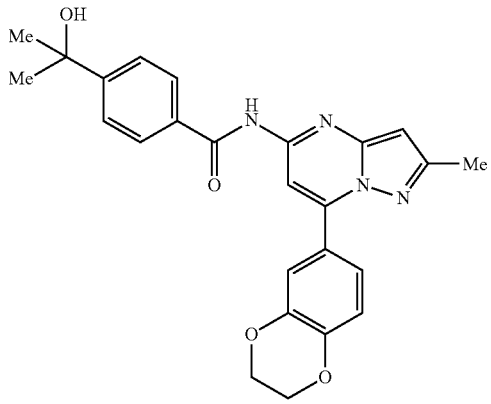

275

A suspension of N-(7-chloro-2-methylpyrazolo[1,5-a]pyrimidin-5-yl)-4-(2-hydroxypropan-2-yl)benzamide (2F, 60 mg, 0.174 mmol), 2,3-dihydrobenzo[b][1,4]dioxin-6-ylboronic acid (41 mg, 0.226 mmol), and 1,1'-bis(diphenylphosphino)ferrocene]dichloropalladium(II) (7 mg, 9.5 μmol) in 2:1 1,4-dioxane/saturated aqueous NaHCO$_3$ (0.58 mL of 1,4-dioxane and 0.29 mL of saturated aqueous NaHCO$_3$) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (55-65% (MeCN/H$_2$O gradient+0.01% TFA). Lyophilization of the combined fractions gave the titled compound as a yellow solid (57.2 mg, 74%). Melting point (99.5-99.6° C.). $^1$H NMR (DMSO-d$_6$) δ: 11.14 (s, 1H), 8.02 (d, J=8.6 Hz, 2H), 7.95 (s, 1H), 7.75 (d, J=2.3 Hz, 1H), 7.61 (d, J=8.3 Hz, 2H), 7.57 (dd, J=8.5, 2.1 Hz, 1H), 7.10 (d, J=8.6 Hz, 1H), 6.36 (s, 1H), 4.31-4.40 (m, 4H), 2.41 (s, 3H), 1.46 (s, 6H); ESI-MS: m/z 445.2 (M+H)$^+$.

Example 290

N-(7-morpholinopyrazolo[1,5-a]pyrimidin-5-yl)-4-(6-oxo-1,6-dihydropyridin-3-yl)benzamide (276)

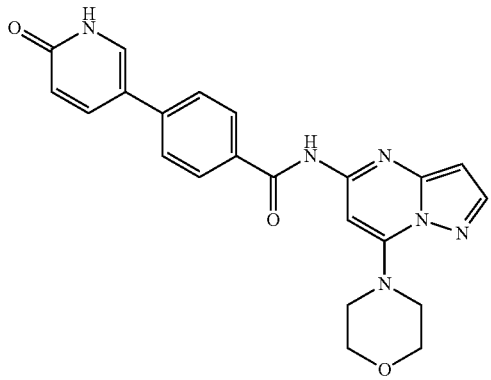

276

In a 2 mL microwave vial were placed 4-bromo-N-(7-morpholinopyrazolo[1,5-c]pyrimidin-5-yl)benzamide (9B, 100 mg, 0.25 mmol), 6-hydroxypyridine-3-boronic acid pinacol ester (63 mg, 0.29 mmol), and [1,1'-bis(diphenylphosphino)ferrocene]-dichloropalladium(II) (9.1 mg, 12 μmmol). To the sealed vial were then added 1,4-dioxane (1.4 ml) and saturated aqueous NaHCO$_3$ (0.7 ml) to give a suspension. The mixture was then heated in the microwave at 120° C. for 30 minutes. After cooling to room temperature, the reaction mixture was filtered with a syringe filter and was then directly purified by preparatory HPLC (20-50% MeCN/H$_2$O gradient+0.01% TFA). Lyophilization of the combined fractions gave the titled compound as a white powder (68 mg, 66% yield). $^1$H NMR (400 MHz, DMSO-d$_6$) δ=11.02 (s, 1 H), 8.20-8.04 (m, 3 H), 7.96 (dd, J=2.8, 9.6 Hz, 1 H), 7.90 (d, J=2.8 Hz, 1 H), 7.77-7.72 (m, 2 H), 7.42 (s, 1 H), 6.46 (d, J=9.6 Hz, 1 H), 6.38 (d, J=2.3 Hz, 1 H), 3.89-3.82 (m, 4 H), 3.77-3.72 (m, 4 H); ESI-MS: m/z 417.4 (M+H)$^+$.

Example (291)

(E)-4-(2-hydroxypropan-2-yl)-N-(2-methyl-7-styrylpyrazolo[1,5-a]pyrimidin-5-yl)benzamide (277)

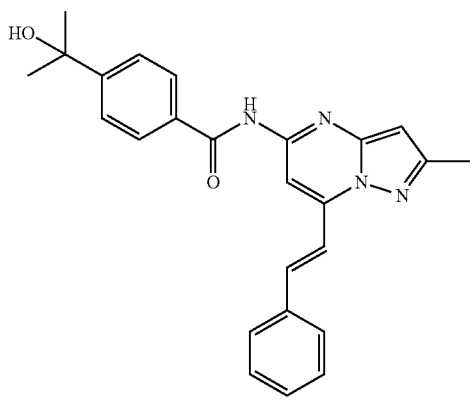

277

N-(7-chloro-2-methylpyrazolo[1,5-a]pyrimidin-5-yl)-4-(2-hydroxypropan-2-yl)benzamide (2F, 0.05 g, 1.0 equivalent) and (E)-styrylboronic acid (2.0 equivalents) and PdCl$_2$(dppf)/DCM (0.10 equivalent) in 2N Na$_2$CO$_3$ (0.2 M), dioxane (0.1M) and DMF (0.5M) was heated at 120° C. for 10 minutes in the microwave. After cooling to room temperature, the mixture was added water and EtOAc; and extracted with EtOAc twice and the combined organic layers were dried over Na$_2$SO$_4$. Then the solvent was removed in vacuo and the crude mixture was purified by preparatory HPLC (50-60% ACN/water, TFA mode) to afford the TFA salt of the titled compound (24%) as a yellow solid. $^1$H NMR (400 MHz, DMSO-d$_6$) δ ppm 1.46 (br. s., 6 H) 2.41 (br. s., 3 H) 5.21 (br. s., 1 H) 6.36 (br. s., 1 H) 7.39-7.56 (m, 3 H) 7.62 (d, J=8.34 Hz, 2 H) 7.73-7.89 (m, 3 H) 8.03 (d, J=7.07 Hz, 2 H) 8.14-8.29 (m, 2 H) 11.11 (br. s., 1 H); ESI-MS: m/z 413.2 (M+H)$^+$.

Example 292

(E)-N-(7-(4-fluorostyryl)-2-methylpyrazolo[1,5-a]pyrimidin-5-yl)-4-(2-hydroxypropan-2-yl)benzamide (278)

278

N-(7-chloro-2-methylpyrazolo[1,5-a]pyrimidin-5-yl)-4-(2-hydroxypropan-2-yl)benzamide (2F, 0.05 g, 1.0 equivalent) and (E)-4-fluorostyrylboronic acid (2.0 equivalents) and PdCl$_2$(dppf)/DCM (0.10 equivalent) in 2N Na$_2$CO$_3$ (0.2 M), dioxane (0.1M) and DMF (0.5M) was heated at 120° C. for 10 minutes in the microwave. After cooling to room temperature, the mixture was added water and EtOAc; and extracted with EtOAc twice and the combined organic layers were dried over Na$_2$SO$_4$. Then the solvent was removed in vacuo and the crude mixture was purified by preparatory HPLC (60-65% ACN/water, TFA mode) to afford the TFA salt of the titled compound (48%) as a yellow solid. $^1$H NMR (400 MHz, DMSO-d$_6$) δ ppm 1.46 (s, 6 H) 2.47 (s, 3 H) 6.36 (d, J=0.51 Hz, 1 H) 7.27-7.35 (m, 2 H) 7.57-7.65 (m, 2 H) 7.75 (d, J=16.42 Hz, 1 H) 7.86-7.93 (m, 2 H) 8.00-8.06 (m, 2 H) 8.16 (s, 1 H) 8.23 (d, J=16.42 Hz, 1 H) 11.11 (s, 1 H); ESI-MS: m/z 431.2 (M+H)$^{30}$.

Example 293

(E)-4-(2-hydroxypropan-2-yl)-N-(7-(3-methoxystyryl)-2-methylpyrazolo[1,5-a]pyrimidin-5-yl)benzamide (279)

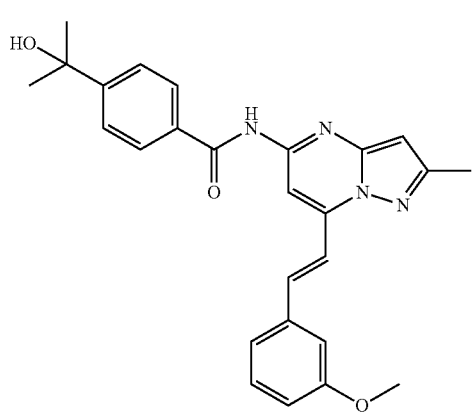

279

N-(7-chloro-2-methylpyrazolo[1,5-a]pyrimidin-5-yl)-4-(2-hydroxypropan-2-yl)benzamide (2F, 0.05 g, 1.0 equivalent) and (E)-3-methoxystyrylboronic acid (2.0 equivalents) and PdCl$_2$(dppf)/DCM (0.10 equivalent) in 2N Na$_2$CO$_3$ (0.2 M), dioxane (0.1M) and DMF (0.5M) was heated at 120° C. for 10 minutes in the microwave. After cooling to room temperature, the mixture was added water and EtOAc; and extracted with EtOAc twice and the combined organic layers were dried over Na$_2$SO$_4$. Then the solvent was removed in vacuo and the crude mixture was purified by preparatory HPLC (60-65% ACN/water, TFA mode) to afford the TFA salt of the titled compound (39%) as a yellow solid. $^1$H NMR (400 MHz, DMSO-d$_6$) δ ppm 1.46 (s, 6 H) 2.48 (s, 3 H) 3.85 (s, 3 H) 5.20 (s, 1 H) 6.37 (s, 1 H) 6.98-7.03 (m, 1 H) 7.39 (d, J=4.80 Hz, 3 H) 7.59-7.64 (m, 2 H) 7.80 (d, J=16.42 Hz, 1 H) 8.01-8.06 (m, 2 H) 8.17 (s, 1H) 8.24 (d, J=16.42 Hz, 1 H) 11.12 (s, 1 H); ESI-MS: m/z 443.2 (M+H)$^{30}$.

Example 294

N-(7-(4-acetamidopiperidin-1-yl)-2-methylpyrazolo[1,5-a]pyrimidin-5-yl)-4-(2-hydroxypropan-2-yl)benzamide (280)

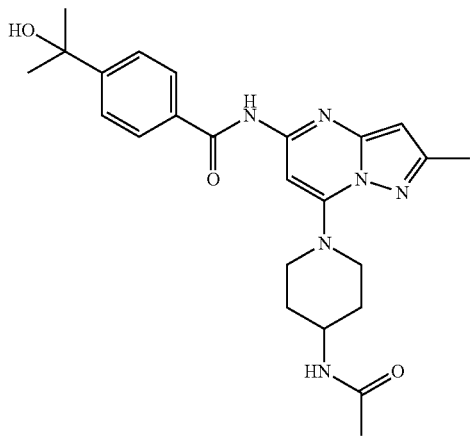

280

N-(7-chloro-2-methylpyrazolo[1,5-a]pyrimidin-5-yl)-4-(2-hydroxypropan-2-yl)benzamide (2F, 0.07 g, 1.0 equivalent) and N-(piperidin-4-yl)acetamide (2.0 equivalents) in DMF (0.1M) was heated to 100° C. for 1 h. Then the solvent was removed in vacuo and the crude mixture was purified by preparatory HPLC (20-30% ACN/water, TFA mode) to afford the TFA salt of the titled compound (65%) as a white solid. Melting point (214.6-214.7° C.). $^1$H NMR (400 MHz, DMSO-d$_6$) δ ppm 1.45 (s, 6 H) 1.51-1.64 (m, 2 H) 1.82 (s, 3 H) 1.91 (d, J=15.92 Hz, 2 H) 2.38 (s, 3 H) 3.23 (t, J=10.99 Hz, 2 H) 3.81-3.98 (m, 1 H) 4.36 (d, J=13.14 Hz, 2 H) 6.16 (s, 1 H) 7.33 (s, 1 H) 7.60 (d, J=8.59 Hz, 2 H) 7.92 (d, J=7.58 Hz, 1 H) 7.99 (d, J=8.84 Hz, 2 H) 10.86 (s, 1 H); ESI-MS: m/z 451.2 (M+H)$^+$.

Example 295

(R)-N-ethyl-1-(5-(4-(2-hydroxypropan-2-yl)benzamido)pyrazolo[1,5-a]pyrimidin-7-yl)piperidine-3-carboxamide (281)

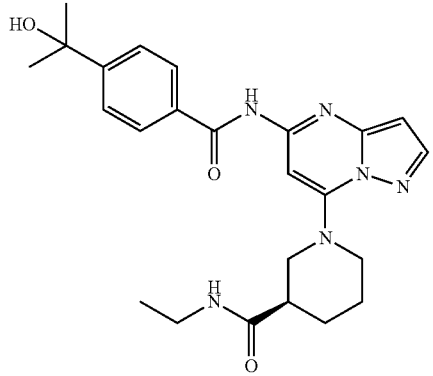

281

A solution of (R)-1-(5-(4-(2-hydroxypropan-2-yl)benzamido)pyrazolo[1,5-a]pyrimidin-7-yl)piperidine-3-carboxylic acid (Compound 84, 100 mg, 0.236 mmol), ethylamine (11 mg, 0.236 mmol), EDCI (90 mg, 0.472 mmol), and HOBT (16 mg, 0.118 mmol) in DMF (4 mL) were stirred for 12 hours at room temperature. The reaction was complete as determined by LCMS analysis. The reaction mixture was then partitioned between ethyl acetate and water and the separated organic layer was dried over Mg$_2$SO$_4$, filtered, and concentrated under reduced pressure. Purification by preparatory HPLC, 25-35% (MeCN/H$_2$O gradient+0.01% TFA) provided the titled compound as a white solid (8.8 mg, 8%). Melting point (227.8-228.7° C.). $^1$H NMR (DMSO-d$_6$) δ: 10.89 (s, 1H), 8.10 (d, J=2.3 Hz, 1H), 8.05 (t, J=5.4 Hz, 1H), 8.00 (d, J=8.6 Hz, 2H), 7.56-7.65 (m, 2H), 7.41 (s, 1H), 6.36 (d, J=2.3 Hz, 1H), 4.31 (br. s., 2H), 3.29 (dd, J=12.0, 10.5 Hz, 2H), 2.93-3.17 (m, 4H), 1.92 (br. s., 1H), 1.77-1.87 (m, 1H), 1.73 (br. s., 2H), 1.45 (s, 6H), 1.02 (t, J=7.3 Hz, 3H). ESI-MS: m/z 451.0 (M+H)$^+$.

Example 296

N-(7-(4-chlorophenyl)pyrazolo[1,5-a]pyrimidin-5-yl)-4-(2-hydroxypropan-2-yl)benzamide (282)

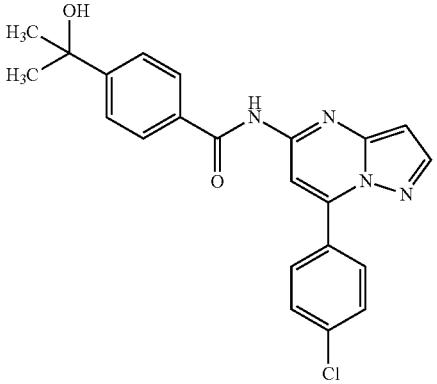

282

In a 2 mL microwave vial were placed N-(7-chloropyrazolo[1,5-a]pyrimidin-5-yl)-4-(2-hydroxypropan-2-yl)benzamide (2D, 75 mg, 0.23 mmol), 4-chlorophenylboronic acid (43 mg, 0.27 mmol), and [1,1'-bis(diphenylphosphino)ferrocene]-dichloropalladium(II) (8 mg, 11 μmmol). To the sealed vial were then added 1,4-dioxane (1 ml) and saturated aqueous NaHCO₃ (0.75 ml) to give a suspension. The mixture was then heated in the microwave at 120° C. for 30 minutes. After cooling to room temperature, the reaction mixture was partitioned between brine and EtOAc. The aqueous layer was extracted once more with EtOAc, and the combined organic layers were dried over MgSO₄, filtered and concentrated in vacuo. The crude product was purified by preparatory HPLC (50-70% MeCN/H₂O gradient+0.01% TFA). Combined fractions were concentrated in vacuo, partitioned between saturated NaHCO₃ and EtOAc, and extracted with EtOAc twice. Combined organic layers were dried over MgSO₄, filtered and concentrated in vacuo. Trituration with Et₂O gave the titled compound as a light yellow solid. ¹H NMR (400 MHz, DMSO-d₆) δ=11.29 (s, 1 H), 8.21 (d, J=2.3 Hz, 1 H), 8.18-8.11 (m, 2H), 8.08 (s, 1 H), 8.03 (d, J=8.6 Hz, 2 H), 7.76-7.67 (m, 2 H), 7.62 (d, J=8.3 Hz, 2 H), 6.60 (d, J=2.3 Hz, 1 H), 5.21 (s, 1 H), 1.46 (s, 6 H); ESI-MS: m/z 407.3 (M+H)⁺.

Example 297

N-(7-(4-fluorophenyl)pyrazolo[1,5-a]pyrimidin-5-yl)-4-(2-hydroxypropan-2-yl)benzamide (283)

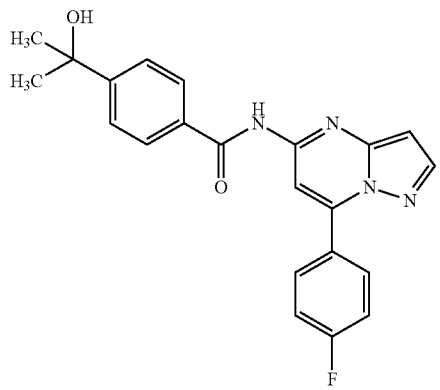

283

In a 2 mL microwave vial were placed N-(7-chloropyrazolo[1,5-a]pyrimidin-5-yl)-4-(2-hydroxypropan-2-yl)benzamide (2D, 75 mg, 0.23 mmol), 4-fluorophenylboronic acid (38 mg, 0.27 mmol), and [1,1'-bis(diphenylphosphino)ferrocene]-dichloropalladium(II) (8 mg, 11 μmmol). To the sealed vial were then added 1,4-dioxane (1 ml) and saturated aqueous NaHCO₃ (0.75 ml) to give a suspension. The mixture was then heated in the microwave at 120° C. for 30 minutes. After cooling to room temperature, the reaction mixture was partitioned between brine and EtOAc. The aqueous layer was extracted once more with EtOAc, and the combined organic layers were dried over MgSO₄, filtered and concentrated in vacuo. The crude product was purified by preparatory HPLC (50-60% MeCN/H₂O gradient+0.01% TFA). Combined fractions were concentrated in vacuo, partitioned between saturated NaHCO₃ and EtOAc, and extracted with EtOAc twice. Combined organic layers were dried over MgSO₄, filtered and concentrated in vacuo. Trituration with Et₂O gave the titled compound as a light yellow solid. ¹H NMR (400 MHz, DMSO-d₆) δ=11.28 (s, 1 H), 8.31-8.13 (m, 3 H), 8.12-7.97 (m, 3 H), 7.62 (d, J=8.6 Hz, 2 H), 7.56-7.42 (m, 2 H), 6.60 (d, J=2.3 Hz, 1 H), 5.20 (s, 1 H), 1.46 (s, 6H); ESI-MS: m/z 407.3 (M+H)⁺.

Example 298

4-(Furan-3-yl)-N-(7-morpholinopyrazolo[1,5-a]pyrimidin-5-yl)benzamide (284)

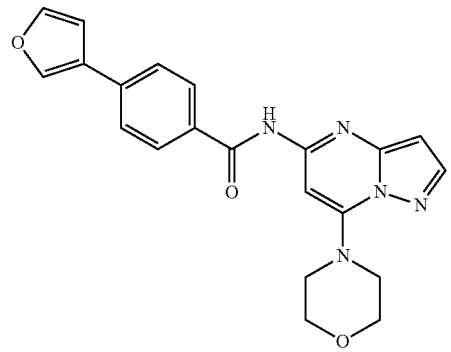

284

In a 2 mL microwave vial were placed 4-bromo-N-(7-morpholinopyrazolo[1,5-a]pyrimidin-5-yl)benzamide (9B, 100 mg, 0.25 mmol), 3-furanboronic acid (31 mg, 0.27 mmol), and [1,1'-bis(diphenylphosphino)ferrocene]-dichloropalladium(II) (4.5 mg, 6.2 μmol). To the sealed vial were then added 1,4-dioxane (1.5 ml) and saturated aqueous NaHCO₃ (0.75 ml) to give a suspension. The mixture was then heated in the microwave at 120° C. for 30 minutes. After cooling to room temperature, the precipitate was collected on a fritted glass funnel and was washed with water and dioxane to give the analytically pure titled compound as a yellow solid (15 mg, 15%). ¹H NMR (400 MHz, DMSO-d₆) δ=11.01 (s, 1 H), 8.37 (s, 1 H), 8.10 (d, J=2.3 Hz, 2 H), 8.08 (s, 1 H), 7.81-7.79 (m, 2 H), 7.78 (s, 1 H), 7.43 (s, 1 H), 7.11-7.08 (m, 1 H), 6.38 (d, J=2.3 Hz, 1 H), 3.88-3.83 (m, 4 H), 3.74 (dd, J=3.3, 5.6 Hz, 4 H); ESI-MS: m/z 390.3 (M+H)⁺.

Example 299

Methyl 1-(4-(7-morpholinopyrazolo[1,5-a]pyrimidin-5-ylcarbamoyl)phenyl)cyclopropanecarboxylate (285)

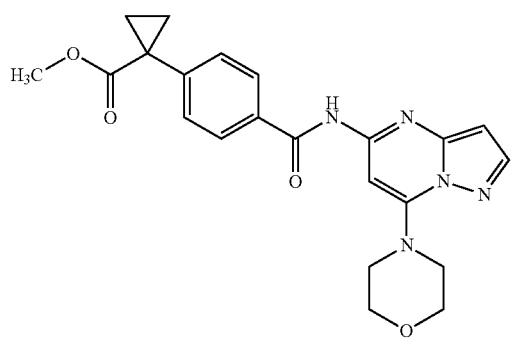

285

7-Morpholinopyrazolo[1,5-a]pyrimidin-5-amine (9A, 110 mg, 0.50 mmol) and 4-(1-(methoxycarbonyl)cyclopropyl)benzoic acid (110 mg, 0.50 mmol) were mixed in pyridine (3 ml). TBTU (160 mg, 0.50 mmol) was then added and the mixture was heated to 80° C. for 15 hours. After cooling to room temperature, additional TBTU (53 mg, 0.17 mmol) was added before the heating continued for another 6 hours. After cooling to room temperature, the reaction mixture was quenched with water and was then concentrated to dryness in vacuo. The crude product was purified by preparatory HPLC (35-55% MeCN/H$_2$O gradient+0.01% TFA). Lyophilization of the combined fractions gave the titled compound as a white powder (72 mg, 35% yield). $^1$H NMR (400 MHz, DMSO-d$_6$) δ=11.00 (s, 1 H), 8.10 (d, J=2.3 Hz, 1 H), 7.99 (d, J=8.3 Hz, 2 H), 7.49 (d, J=8.3 Hz, 2 H), 7.41 (s, 1 H), 6.38 (d, J=2.3 Hz, 1 H), 3.88-3.82 (m, 4 H), 3.78-3.70 (m, 4 H), 3.57 (s, 3 H), 1.56-1.50 (m, 2 H), 1.30-1.24 (m, 2 H); ESI-MS: m/z 422.4 (M+H)$^+$.

Example 300

N-(7-butoxypyrazolo[1,5-a]pyrimidin-5-yl)-4-(2-hydroxypropan-2-yl)benzamide (286)

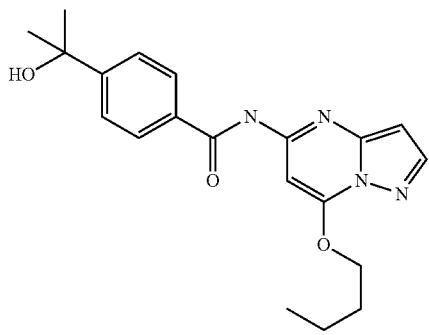

286

Sodium metal was added to dry butanol (5 mL, 54.6 mmol) at 0° C. then the reaction was raised to room temperature. Then, the next day, a solid precipitated. Stir N-(7-chloropyrazolo[1,5-a]pyrimidin-5-yl)-4-(2-hydroxypropan-2-yl)benzamide (100 mg, 0.302 mmol) in dry butanol (5 mL). Add the previously made sodium butoxide (58 mg, 0.605 mmol) at 0° C. then raise to room temperature. After stirring overnight, the majority of the reaction was converted to product. Deamination was observed where the amide bond of the compound was cleaved. The compound was filtered and purified by preparatory HPLC 40-50% (MeCN/H$_2$O gradient+0.01% TFA). Received 29.1 mg of a white solid (26%). $^1$H NMR (DMSO-d$_6$) δ: 11.08 (s, 2H), 8.09 (d, J=2.3 Hz, 2H), 8.01 (d, J=8.6 Hz, 4H), 7.61 (d, J=8.6 Hz, 4H), 7.54 (s, 2H), 6.40 (d, J=2.0 Hz, 2H), 5.19 (s, 2H), 4.46 (t, J=6.4 Hz, 4H), 1.79-1.98 (m, 4H), 1.49-1.62 (m, 4H), 1.46 (s, 12H), 0.99 (t, J=7.5 Hz, 3H). ESI-MS: m/z 369.4 (M+H)$^+$.

Example 301

Methyl 1-(4-(2-methyl-7-phenylpyrazolo[1,5-a]pyrimidin-5-ylcarbamoyl)phenyl)cyclopropanecarboxylate (287)

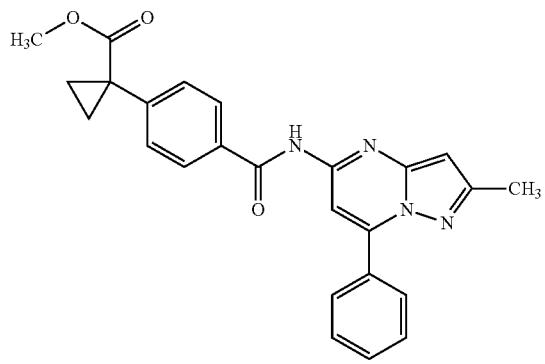

287

4-(1-(Methoxycarbonyl)cyclopropyl)benzoic acid (200 mg, 0.91 mmol) was suspended in CH$_2$Cl$_2$ (5 ml). At 0° C., oxalyl chloride (0.50 ml, 1.0 mmol) was then added, followed by 2 drops of DMF. The mixture was warmed to room temperature. After 2 hours, an additional amount of oxalyl chloride (0.15 ml) was added. After the reaction was completed, 2-methyl-7-phenylpyrazolo[1,5-a]pyrimidin-5-amine (10A, 200 mg, 0.91 mmol) in pyridine (5 ml) was added. After the reaction was complete, water was added and the volatiles were removed in vacuo. The aqueous residue was extracted with EtOAc 3 times. The combined organic layers were dried over MgSO$_4$, filtered and concentrated in vacuo. The crude product was purified by preparatory HPLC (65-80% MeCN/H$_2$O gradient+0.01% TFA). Lyophilization of the combined fractions gave the titled compound as a yellow powder (96 mg, 24% yield). $^1$H NMR (400 MHz, DMSO-d$_6$) δ=11.27 (s, 1 H), 8.08-8.04 (m, 2 H), 8.04-7.99 (m, 2 H), 7.96 (s, 1 H), 7.66-7.60 (m, 3 H), 7.52-7.48 (m, 2 H), 6.40 (s, 1 H), 3.57 (s, 3 H), 2.40 (s, 3 H), 1.56-1.50 (m, 2 H), 1.31-1.25 (m, 2 H); ESI-MS: m/z 427.4 (M+H)$^+$.

Example 302

1-(4-(7-morpholinopyrazolo[1,5-a]pyrimidin-5-ylcarbamoyl)phenyl)cyclopropanecarboxylic acid (288)

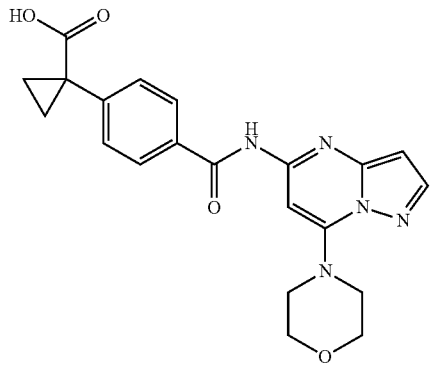

288

Methyl 1-(4-(7-morpholinopyrazolo[1,5-a]pyrimidin-5-ylcarbamoyl)phenyl)cyclopropanecarboxylate (Compound 441, 31 mg, 0.07 mmol) was dissolved in methanol, and 1N NaOH solution (1 ml) was then added. After 8 hours at room temperature, the mixture was acidified with 2N HCl to pH 1. The mixture was concentrated in vacuo. The residue was dissolved in DMSO, and was purified by preparatory HPLC (30-65% MeCN/H$_2$O gradient+0.01% TFA). Lyophilization of the combined fractions gave the titled compound (6.9 mg, 23%) as a white powder. $^1$H NMR (400 MHz, DMSO-d$_6$) δ=12.67-12.24 (m, 1 H), 10.98 (s, 1 H), 8.10 (d, J=2.3 Hz, 1 H), 7.98 (d, J=8.3 Hz, 2 H), 7.47 (d, J=8.3 Hz, 2 H), 7.41 (s, 1 H), 6.37 (d, J=2.3 Hz, 1 H), 3.85 (m, 2 H), 3.74 (m, 2 H), 1.56-1.45 (m, 2 H), 1.26-1.17 (m, 2 H); ESI-MS: m/z 408.4 (M+H)$^+$.

Example 303

4-(2-hydroxypropan-2-yl)-N-(7-methoxypyrazolo[1,5-a]pyrimidin-5-yl)benzamide (289)

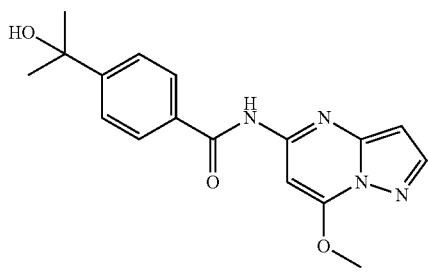

289

A solution of N-(7-chloropyrazolo[1,5-a]pyrimidin-5-yl)-4-(2-hydroxypropan-2-yl)benzamide (2D, 100 mg, 0.302 mmol) and sodium methoxide (1.2 mL from 2M solution in methanol, 0.605 mmol) in DMF (3 mL) was stirred at room temperature overnight. After cooling to room temperature, the mixture was diluted with a few drops of DMSO and methanol, and was then purified by preparatory HPLC, 30-40% (MeCN/H$_2$O gradient+0.01% TFA). Lyophilization of the combined fractions gave the titled compound as a white solid (3.4 mg, 6%). $^1$H NMR (DMSO-d$_6$) δ: 11.10 (s, 1H), 8.10 (d, J=2.0 Hz, 1H), 8.01-8.03 (m, 1H), 7.98-8.01 (m, 1H), 7.61 (d, J=6.6 Hz, 1H), 7.55 (s, 1H), 6.41 (d, J=2.3 Hz, 1H), 5.19 (s, 1H), 4.21 (s, 3H), 1.46 (s, 6H). ESI-MS: m/z 327.3 (M+H)$^+$.

Example 304

N-(7-(5,6-dihydro-[1,2,4]triazolo[4,3-a]pyrazin-7(8H)-yl)-2-methylpyrazolo[1,5-a]pyrimidin-5-yl)-4-(2-hydroxypropan-2-yl)benzamide (290)

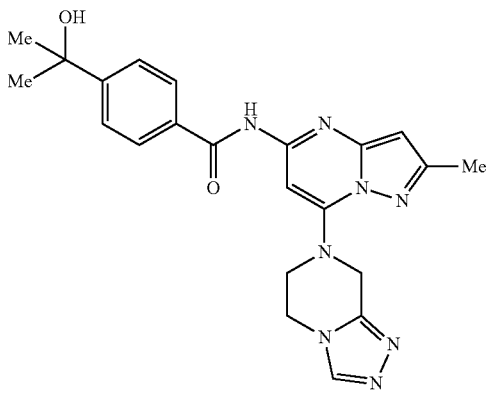

290

A solution of N-(7-chloro-2-methylpyrazolo[1,5-a]pyrimidin-5-yl)-4-(2-hydroxypropan-2-yl)benzamide (2F, 86 mg, 0.25 mmol), 5,6,7,8-tetrahydro-[1,2,4]triazolo[4,3-c]pyrazine hydrochloride (80 mg, 0.50 mmol), and N,N-diisopropylethylamine (116 mg, 0.90 mmol) in DMF (1.0 mL) was stirred at 100° C. for 2 h. After cooling to room temperature, the mixture was diluted with a few drops of DMSO and methanol, and was then purified by preparatory HPLC (20-45% MeCN/H$_2$O gradient+0.01% TFA). Lyophilization of the combined fractions gave the titled compound as a white solid (71.4 mg, 66%). ESI-MS: m/z 433.3 (M+H)$^+$.

Example 305

N-(7-(3,4-dimethoxyphenyl)-2-methylpyrazolo[1,5-a]pyrimidin-5-yl)-4-(2-hydroxypropan-2-yl)benzamide (291)

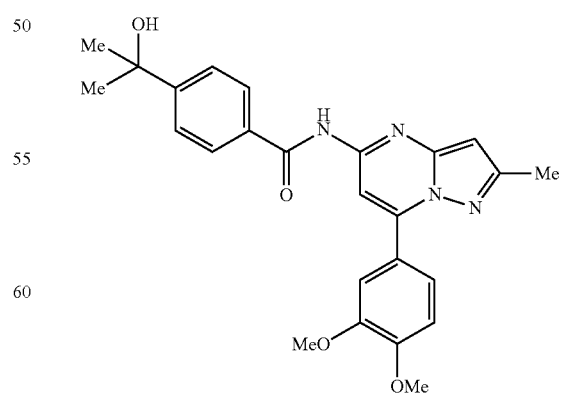

291

A suspension of N-(7-chloro-2-methylpyrazolo[1,5-a]pyrimidin-5-yl)-4-(2-hydroxypropan-2-yl)benzamide (2F, 60 mg, 0.174 mmol), 3,4-dimethoxyphenylboronic acid (41 mg, 0.226 mmol), and 1,1'-bis(diphenylphosphino)ferrocene]dichloropalladium(II) (10 mg, 13.6 µmol) in 2:1 1,4-dioxane/saturated aqueous NaHCO₃ (0.58 mL of 1,4-dioxane and 0.29 mL of saturated aqueous NaHCO₃) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (45-45% MeCN/H₂O gradient+0.01% TFA). Lyophilization of the combined fractions gave the titled compound as a yellow solid (27.8 mg, 36%). ESI-MS: m/z 447.2 (M+H)⁺.

Example 306

N-(7-(3,4-dihydro-2H-benzo[b][1,4]dioxepin-7-yl)-2-methylpyrazolo[1,5-a]pyrimidin-5-yl)-4-(2-hydroxypropan-2-yl)benzamide (292)

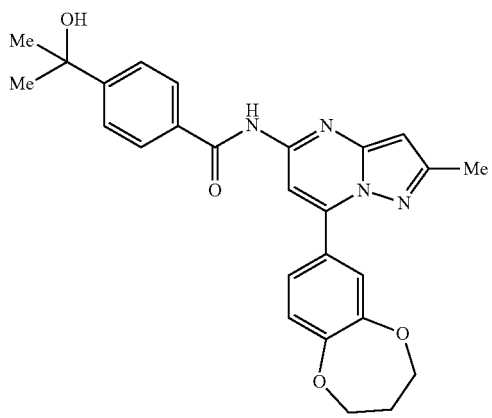

A suspension of N-(7-chloro-2-methylpyrazolo[1,5-a]pyrimidin-5-yl)-4-(2-hydroxypropan-2-yl)benzamide (2F, 60 mg, 0.174 mmol), 3,4-dihydro-2H-benzo[b][1,4]dioxepin-7-ylboronic acid (49 mg, 0.226 mmol), and 1,1'-bis(diphenylphosphino)ferrocene]dichloropalladium(II) (7 mg, 9.5 mmol) in 2:1 1,4-dioxane/saturated aqueous NaHCO₃ (0.58 mL of 1,4-dioxane and 0.29 mL of saturated aqueous NaHCO₃) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (50-55% MeCN/H₂O gradient+0.01% TFA). Lyophilization of the combined fractions gave the titled compound as a yellow solid (20.8 mg, 26%). ESI-MS: m/z 459.2 (M+H)⁺.

Example 307

N-(7-(2,2-difluorobenzo[d][1,3]dioxol-5-yl)-2-methylpyrazolo[1,5-a]pyrimidin-5-yl)-4-(2-hydroxypropan-2-yl)benzamide (293)

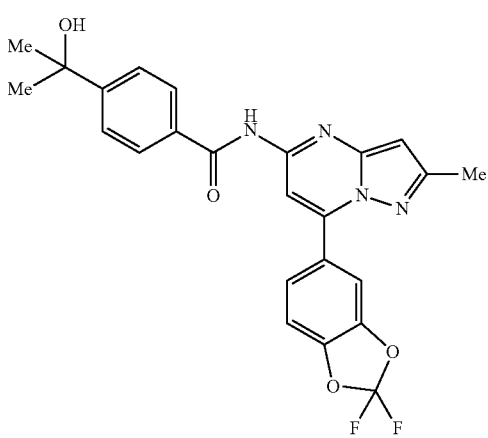

A suspension of N-(7-chloro-2-methylpyrazolo[1,5-a]pyrimidin-5-yl)-4-(2-hydroxypropan-2-yl)benzamide (2F, 60 mg, 0.174 mmol), 2,2-difluorobenzo[d][1,3]dioxol-5-ylboronic acid (46 mg, 0.226 mmol), and 1,1'-bis(diphenylphosphino)ferrocene]dichloropalladium(II) (10 mg, 13.6 µmol) in 2:1 1,4-dioxane/saturated aqueous NaHCO₃ (0.58 mL of 1,4-dioxane and 0.29 mL of saturated aqueous NaHCO₃) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (60-75% MeCN/H₂O gradient+0.01% TFA). Lyophilization of the combined fractions gave the titled compound as a yellow solid (31.4 mg, 39%). ¹H NMR (DMSO-d₆) δ: 11.21 (s, 1H), 8.62 (d, J=1.3 Hz, 1H), 8.26 (d, J=8.6 Hz, 1H), 8.05 (s, 1H), 7.99-8.04 (m, 3H), 7.93 (d, J=5.3 Hz, 1H), 7.67 (d, J=5.6 Hz, 1H), 7.61 (d, J=8.6 Hz, 2H), 6.41 (s, 1H), 5.20 (s, 1H), 2.41 (s, 3H), 1.46 (s, 6H); ESI-MS: m/z 467.2 (M+H)⁺.

Example 308

N-(7-(4-(2-hydroxyethyl)piperidin-1-yl)-2-methylpyrazolo[1,5-a]pyrimidin-5-yl)-2-phenylcyclopropanecarboxamide (294)

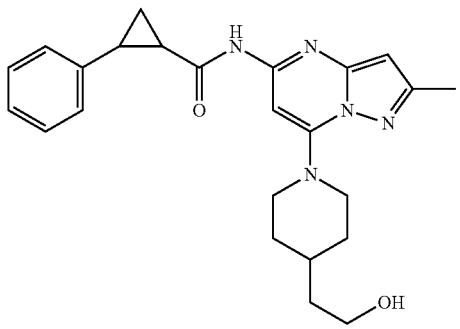

A solution of N-(7-chloro-2-methylpyrazolo[1,5-a]pyrimidin-5-yl)-2-phenylcyclopropanecarboxamide (8C, 200 mg, 0.612 mmol) and 2-(piperidin-4-yl)ethanol (158 mg, 1.2 mmol) in NMP (1.85 mL) was stirred at 100° C. overnight. After cooling to room temperature, the mixture was diluted with a few drops of DMSO and methanol, and was then purified by preparatory HPLC, 40-50% (MeCN/H₂O gradient+0.01% TFA). Lyophilization of the combined fractions gave the titled compound as a white solid (9 mg, 4%). ¹H NMR (METHANOL-d₄) δ: 7.25-7.31 (m, 2H), 7.14-7.23 (m, 4H), 6.07 (s, 1H), 4.41 (d, J=12.1 Hz, 2H), 3.67 (t, J=6.6 Hz, 2H), 2.98 (td, J=12.4, 2.4 Hz, 2H), 2.51 (ddd, J=9.2, 6.4, 4.3 Hz, 1H), 2.40 (s, 3H), 2.15-2.23 (m, 1H), 1.85 (br. s., 2H), 1.29-1.69 (m, 7H). ESI-MS: m/z 420.0 (M+H)⁺.

Example 309

N-(7-(benzo[b]thiophen-5-yl)-2-methylpyrazolo[1,5-a]pyrimidin-5-yl)-4-(2-hydroxypropan-2-yl)benzamide (295)

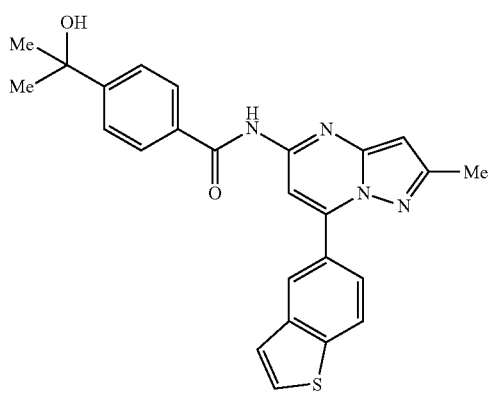

A suspension of N-(7-chloro-2-methylpyrazolo[1,5-a]pyrimidin-5-yl)-4-(2-hydroxypropan-2-yl)benzamide (2F, 60 mg, 0.174 mmol), benzo[b]thiophen-5-ylboronic acid (40 mg, 0.226 mmol), and 1,1'-bis(diphenylphosphino)ferrocene]dichloropalladium(II) (10 mg, 13.6 mmol) in 2:1 1,4-dioxane/saturated aqueous NaHCO₃ (0.58 mL of 1,4-dioxane and 0.29 mL of saturated aqueous NaHCO₃) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (65-65% MeCN/H₂O gradient+0.01% TFA). Lyophilization of the combined fractions gave the titled compound as a yellow solid (28 mg, 36%). ¹HNMR (DMSO-d₆) δ: 11.21 (s, 1H), 8.62 (d, J=1.3 Hz, 1H), 8.26 (d, J=8.6 Hz, 1H), 8.05 (s, 1H), 7.99-8.04 (m, 3H), 7.93 (d, J=5.3 Hz, 1H), 7.67 (d, J=5.6 Hz, 1H), 7.61 (d, J=8.6 Hz, 2H), 6.41 (s, 1H), 5.20 (s, 1H), 2.41 (s, 3H), 1.46 (s, 6H); ESI-MS: m/z 443.2 (M+H)⁺.

Example 310

4-(2-hydroxypropan-2-yl)-N-(2-methyl-7-(4-methyl-3,4-dihydro-2H-benzo[b][1,4]oxazin-7-yl)pyrazolo[1,5-a]pyrimidin-5-yl)benzamide (296)

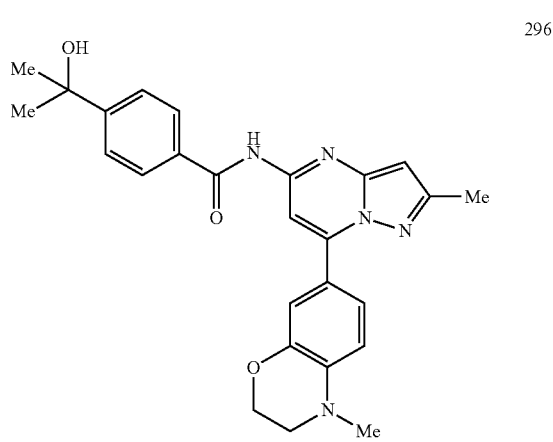 [SMILES: Cc1cc2nc(NC(=O)c3ccc(C(C)(C)O)cc3)cc(-c3ccc4c(c3)OCCN4C)n2n1]

A suspension of N-(7-chloro-2-methylpyrazolo[1,5-a]pyrimidin-5-yl)-4-(2-hydroxypropan-2-yl)benzamide (2F, 60 mg, 0.174 mmol), 4-methyl-3,4-dihydro-2H-benzo[b][1,4]oxazin-7-ylboronic acid (62 mg, 0.226 mmol), and 1,1'-bis(diphenylphosphino)ferrocene]dichloropalladium(II) (10 mg, 13.6 µmol) in 2:1 1,4-dioxane/saturated aqueous NaHCO₃ (0.58 mL of 1,4-dioxane and 0.29 mL of saturated aqueous NaHCO₃) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (50-50% MeCN/H₂O gradient+0.01% TFA). Lyophilization of the combined fractions gave the titled compound as a yellow solid (46.9 mg, 59%). ¹H NMR (DMSO-d₆) δ: 10.99 (s, 1H), 7.95 (d, J=8.6 Hz, 2H), 7.89 (s, 1H), 7.57-7.62 (m, 2H), 7.54 (d, J=8.3 Hz, 2H), 6.81

(d, J=8.8 Hz, 1H), 6.25 (s, 1H), 4.20-4.24 (m, 2H), 3.32-3.35 (m, 2H), 2.91 (s, 3H), 2.35 (s, 3H), 1.39 (s, 6H); ESI-MS: m/z 458.2 (M+H)+.

Example 311

4-(2-hydroxypropan-2-yl)-N-(7-(4-isopropoxyphenyl)-2-methylpyrazolo[1,5-a]pyrimidin-5-yl)benzamide (297)

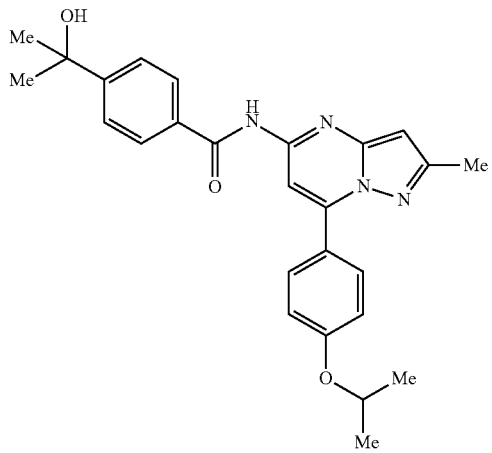

297

A suspension of N-(7-chloro-2-methylpyrazolo[1,5-a]pyrimidin-5-yl)-4-(2-hydroxypropan-2-yl)benzamide (2F, 60 mg, 0.174 mmol), 4-isopropoxyphenylboronic acid (41 mg, 0.226 mmol), and 1,1'-bis(diphenylphosphino)ferrocene]dichloropalladium(II) (10 mg, 13.6 µmol) in 2:1 1,4-dioxane/saturated aqueous NaHCO$_3$ (0.58 mL of 1,4-dioxane and 0.29 mL of saturated aqueous NaHCO$_3$) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (70-70% MeCN/H$_2$O gradient+0.01% TFA). Lyophilization of the combined fractions gave the titled compound as a yellow solid (37.6 mg, 49%). $^1$H NMR (DMSO-d$_6$) δ: 11.07 (s, 1H), 8.03 (d, J=8.8 Hz, 2H), 7.96 (d, J=8.3 Hz, 2H), 7.90 (s, 1H), 7.55 (d, J=8.6 Hz, 2H), 7.08 (d, J=8.8 Hz, 2H), 6.30 (s, 1H), 4.71 (spt, 1H), 2.34 (s, 3H), 1.39 (s, 6H), 1.27 (d, 6H); ESI-MS: m/z 445.3 (M+H)+.

Example 312

(S)-N-(7-(3-acetamidopyrrolidin-1-yl)pyrazolo[1,5-a]pyrimidin-5-yl)-4-(2-hydroxypropan-2-yl)benzamide (298)

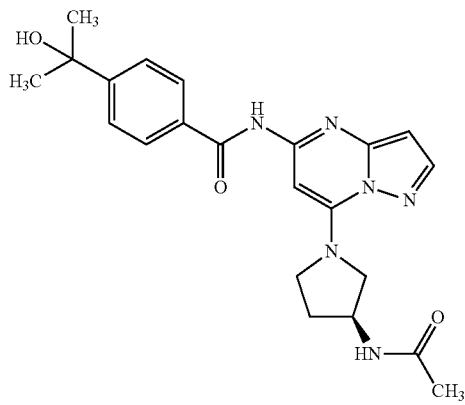

298

In a 2 mL microwave vial were placed N-(7-chloropyrazolo[1,5-a]pyrimidin-5-yl)-4-(2-hydroxypropan-2-yl)benzamide (2D, 80 mg, 0.24 mmol) and (S)-N-(pyrrolidin-3-yl)acetamide (62 mg, 0.48 mmol). To the sealed vial were then added NMP (2 ml), and the mixture was then heated in the microwave at 100° C. for 15 minutes. After cooling to room temperature, the reaction mixture was filtered by syringe filter and was then directly purified by preparatory HPLC (20-40% MeCN/H$_2$O gradient+0.01% TFA). Lyophilization of the combined fractions gave the titled compound as a white powder (110 mg, 99% yield). $^1$H NMR (400 MHz, DMSO-d$_6$) δ=10.88 (s, 1 H), 8.24 (d, J=6.3 Hz, 1 H), 8.02 (d, J=2.3 Hz, 1 H), 8.01-7.96 (m, 2 H), 7.65-7.59 (m, 2 H), 6.87 (s, 1 H), 6.29 (d, J=2.0 Hz, 1 H), 4.41-4.31 (m, 2 H), 2.25-2.13 (m, 1 H), 2.03-1.91 (m, 1 H), 1.83 (s, 3 H), 1.46 (s, 6 H); ESI-MS: m/z 423.4 (M+H)+.

Example 313

(R)-N-(7-(3-acetamidopyrrolidin-1-yl)pyrazolo[1,5-a]pyrimidin-5-yl)-4-(2-hydroxypropan-2-yl)benzamide (299)

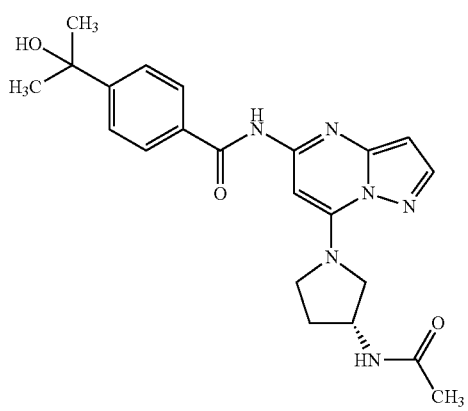

In a 2 mL microwave vial were placed N-(7-chloropyrazolo[1,5-a]pyrimidin-5-yl)-4-(2-hydroxypropan-2-yl)benzamide (2D, 80 mg, 0.24 mmol) and (R)-N-(pyrrolidin-3-yl)acetamide (62 mg, 0.48 mmol). To the sealed vial were then added NMP (2 ml), and the mixture was then heated in the microwave at 100° C. for 15 minutes. After cooling to room temperature, the reaction mixture was filtered by syringe filter and was then directly purified by preparatory HPLC (20-40% MeCN/H₂O gradient+0.01% TFA). Lyophilization of the combined fractions gave the titled compound as a white powder (110 mg, 99% yield). ¹H NMR (400 MHz, DMSO-d₆) δ=10.84 (s, 1 H), 8.24 (d, J=6.3 Hz, 1 H), 8.01 (d, J=2.3 Hz, 1 H), 8.00-7.95 (m, 2 H), 7.65-7.59 (m, 2 H), 6.90 (s, 1 H), 6.28 (d, J=2.3 Hz, 1 H), 4.41-4.31 (m, 1H), 4.19 (br. s., 1 H), 3.96 (br. s., 2 H), 2.19 (dd, J=5.8, 12.6 Hz, 1 H), 2.01-1.91 (m, 1 H), 1.83 (s, 3 H), 1.46 (s, 6 H); ESI-MS: m/z 423.4 (M+H)+.

Example 314

N-(7-((S)-3-fluoropyrrolidin-1-yl)-2-methylpyrazolo[1,5-a]pyrimidin-5-yl)-2-phenylcyclopropanecarboxamide (300)

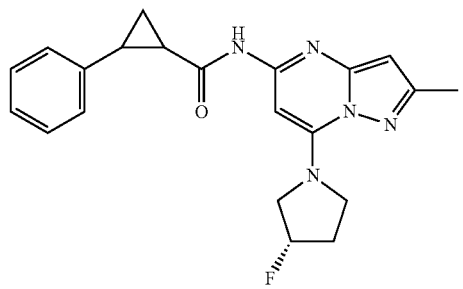

A solution of N-(7-chloro-2-methylpyrazolo[1,5-a]pyrimidin-5-yl)-2-phenylcyclopropanecarboxamide (8C, 200 mg, 1.69 mmol) and (S)-3-fluoropyrrolidine (302 mg, 3.38 mmol) in NMP (5 mL) was stirred at 100° C. overnight. After cooling to room temperature, the mixture was diluted with a few drops of DMSO and methanol, and was then purified by preparatory HPLC (35-40% MeCN/H₂O gradient+0.01% TFA). Lyophilization of the combined fractions gave the titled compound as a white solid (59 mg, 44%). ¹H NMR (DMSO-d₆) δ: 10.87 (s, 1H), 7.26-7.35 (m, 2H), 7.13-7.24 (m, 3H), 6.83 (s, 1H), 5.99 (s, 1H), 5.29-5.58 (m, 1H), 3.72-4.50 (m, 4H), 2.40-2.47 (m, 1H), 2.22-2.36 (m, 5H), 2.15 (br. s., 1H), 1.50 (dt, J=9.2, 4.6 Hz, 1H), 1.35-1.44 (m, 1H). ESI-MS: m/z 380.0 (M+H)+.

Example 315

N-(7-((R)-3-fluoropyrrolidin-1-yl)-2-methylpyrazolo[1,5-a]pyrimidin-5-yl)-2-phenylcyclopropanecarboxamide (301)

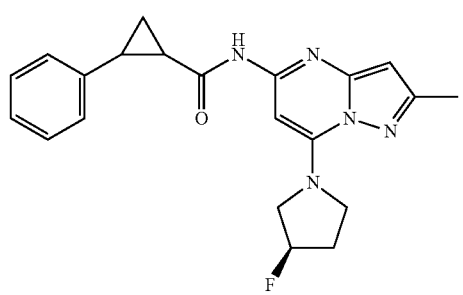

A solution of N-(7-chloro-2-methylpyrazolo[1,5-a]pyrimidin-5-yl)-2-phenylcyclopropanecarboxamide (8C, 200 mg, 0.612 mmol) and (R)-3-fluoropyrrolidine (109 mg, 1.22 mmol) in NMP (1.85 mL) was stirred at 100° C. overnight. After cooling to room temperature, the mixture was diluted with a few drops of DMSO and methanol, and was then purified by preparatory HPLC (35-40% MeCN/H₂O gradient+0.01% TFA). Lyophilization of the combined fractions gave the titled compound as a white solid (60 mg, 26%). $^1$H NMR (DMSO-$d_6$) δ: 10.77 (s, 1H), 7.24-7.35 (m, 2H), 7.11-7.25 (m, 3H), 6.93 (s, 2H), 5.95 (s, 1H), 5.30-5.61 (m, 1H), 3.74-4.41 (m, 4H), 2.01-2.47 (m, 6H), 1.48 (dt, J=9.0, 4.7 Hz, 1H), 1.29-1.42 (m, 1H). ESI-MS: m/z 380.0 (M+H)$^+$.

Example 316

N-(7-(4-methoxyphenyl)-2-methylpyrazolo[1,5-a]pyrimidin-5-yl)-2-phenylcyclopropanecarboxamide (302)

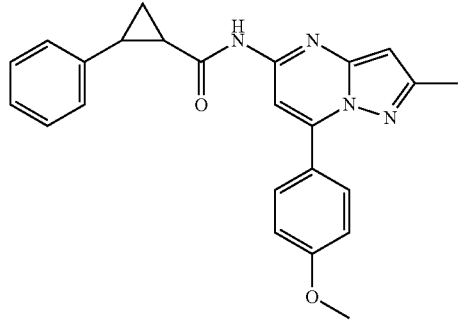

A suspension of N-(7-chloro-2-methylpyrazolo[1,5-a]pyrimidin-5-yl)-2-phenylcyclopropanecarboxamide (8C, 200 mg, 0.612 mmol), 4-methoxyphenylboronic acid (186 mg, 1.22 mmol), and [1,1'-bis(diphenylphosphino)ferrocene]dichloropalladium(II) (35 mg, 49 µmol) in 2:1 1,4-dioxane/saturated aqueous NaHCO$_3$ (660 microliters of 1,4-dioxane and 330 microliters of saturated aqueous NaHCO$_3$) was prepared in a 2 mL microwave reaction vessel and the sealed reaction vessel warmed to 100° C. for 10 minutes. The reaction mixture was cooled to rt, diluted with methanol, filtered, and purified via preparative HPLC (70-75% MeCN/H$_2$O gradient+0.01% TFA). Lyophilization of the combined fractions gave the titled compound as a yellow solid (168 mg, 69%). $^1$H NMR (DMSO-$d_6$) δ: 11.23 (s, 1H), 8.01-8.18 (m, 2H), 7.89 (s, 1H), 7.26-7.37 (m, 2H), 7.08-7.26 (m, 5H), 6.30 (s, 1H), 3.87 (s, 3H), 2.42-2.48 (m, 1H), 2.26-2.43 (m, 4H), 1.49-1.59 (m, 1H), 1.39-1.47 (m, 1H). ESI-MS: m/z 399.0 (M+H)$^+$.

Example 317

(S)-1-(5-(4-(2-hydroxypropan-2-yl)benzamido)pyrazolo[1,5-a]pyrimidin-7-yl)-N-methylpiperidine-3-carboxamide (303)

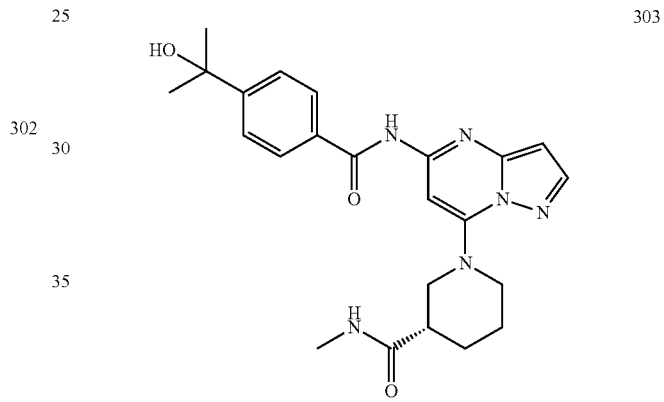

A solution of (S)-1-(5-(4-(2-hydroxypropan-2-yl)benzamido)pyrazolo[1,5-a]pyrimidin-7-yl)piperidine-3-carboxylic acid (Compound 86, 100 mg, 0.236 mmol), methylamine (65 µL, 0.472 mmol), EDCI (90 mg, 0.472 mmol), and HOBT (16 mg, 0.118 mmol) in DMF (4 mL) were stirred for 12 hours at room temperature. The reaction was complete as determined by LCMS analysis. The reaction mixture was then partitioned between ethyl acetate and water and the separated organic layer was dried over Mg$_2$SO$_4$, filtered, and concentrated under reduced pressure. Purification by preparatory HPLC (30-40% MeCN/H$_2$O gradient+0.01% TFA) provided the titled compound as a white solid (65 mg, 63%). $^1$H NMR (DMSO-$d_6$) δ: 10.92 (s, 1H), 8.10 (d, J=2.3 Hz, 1H), 8.00 (d, J=8.8 Hz, 3H), 7.61 (d, J=8.6 Hz, 2H), 7.38 (s, 1H), 6.37 (d, J=2.3 Hz, 1H), 4.37 (d, J=8.8 Hz, 1H), 4.30 (d, J=12.1 Hz, 1H), 3.27 (dd, J=12.4, 10.6 Hz, 1H), 3.05 (d, J=11.4 Hz, 1H), 2.54-2.63 (m, 4H), 1.65-1.99 (m, 4H), 1.46 (s, 6H). ESI-MS: m/z 437.0 (M+H)+.

Example 318

(S)-N-(7-(3-acetamidopiperidin-1-yl)pyrazolo[1,5-a]pyrimidin-5-yl)-4-(2-hydroxypropan-2-yl)benzamide (304)

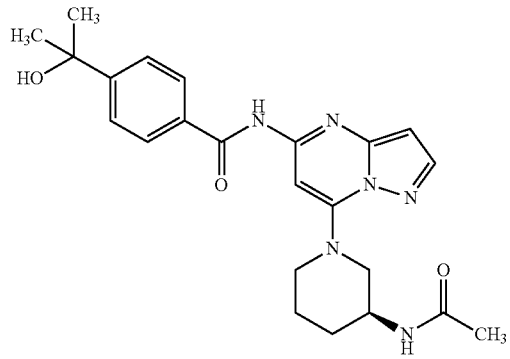

As crude product mixture of (S)-N-(7-(3-aminopiperidin-1-yl)pyrazolo[1,5-c]pyrimidin-5-yl)-4-(2-hydroxypropan-2-yl)benzamide (Compound 305, Example 319), trifluoroacetate salt (50 mg, 0.054 mmol) was dissolved in pyridine (2 ml). At 0° C. acetyl chloride (0.013 ml, 0.18 mmol) was added and the mixture was stirred for 2 hours at room temperature. Afterwards an additional amount of acetyl chloride (0.008 ml) was added to drive the reaction to completion. Water (2 ml) was then added to quench the reaction. The mixture was concentrated in vacuo, and the crude product was purified by preparatory HPLC (25-60% MeCN/H2O gradient+0.01% TFA). Lyophilization of the collected fractions gave the titled compound (50 mg, 33%) as a white powder. 1H NMR (400 MHz, DMSO-d6) δ=10.91 (s, 1 H), 8.09 (d, J=2.3 Hz, 1 H), 8.03-7.95 (m, 3 H), 7.64-7.57 (m, 2 H), 7.38 (s, 1 H), 6.36 (d, J=2.3 Hz, 1 H), 4.13 (br. s., 2 H), 3.87 (br. s., 1 H), 3.22-3.13 (m, 1 H), 3.08 (dd, J=9.5, 11.5 Hz, 1H), 2.00-1.86 (m, 2 H), 1.82 (s, 2 H), 1.76 (br. s., 1 H), 1.52 (br. s., 1 H), 1.46 (s, 5 H); ESI-MS: m/z 437.5 (M+H)+.

Example 319

S)-N-(7-(3-aminopiperidin-1-yl)pyrazolo[1,5-a]pyrimidin-5-yl)-4-(2-hydroxypropan-2-yl)benzamide, trifluoroacetate salt (305)

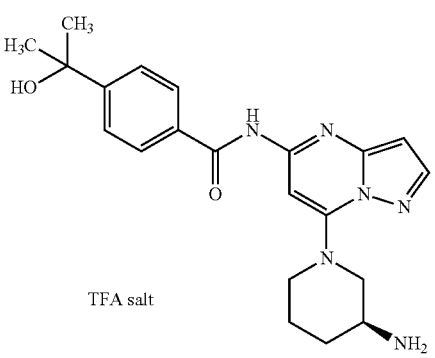

Step A: In a 2 mL microwave vial were placed N-(7-chloropyrazolo[1,5-a]pyrimidin-5-yl)-4-(2-hydroxypropan-2-yl)benzamide (2D, 150 mg, 0.24 mmol) and (S)-3-N-Boc-aminopiperidine (160 mg, 0.68 mmol). To the sealed vial were then added NMP (3 ml) and diisopropylethylamine (0.12 ml, 0.68 mmol), and the mixture was heated in the microwave at 100° C. for 15 minutes. After cooling to room temperature, the reaction mixture was partitioned between saturated NaHCO3 and ethyl acetate, and the aqueous layer was extracted one more time with ethyl acetate. Combined organic layers were dried over MgSO4, filtered and concentrated. The crude product (S)-tert-butyl]-(5-(4-(2-hydroxypropan-2-yl)benzamido)pyrazolo[1,5-c]pyrimidin-7-yl)piperidin-3-ylcarbamate was used in the next step without further purification.

Step B: (S)-tert-butyl 1-(5-(4-(2-hydroxypropan-2-yl)benzamido)pyrazolo[1,5-c]pyrimidin-7-yl)piperidin-3-ylcarbamate was dissolved in CH2Cl2. Trifluoroacetic acid was added and the mixture was let stirred for 6 hours. The reaction mixture was concentrated to dryness in vacuo, and part of the residue was purified by preparatory HPLC (20-50% MeCN/H2O gradient+0.01% TFA). Lyophilization of the combined fractions gave the titled compound as a white powder. 1H NMR (400 MHz, DMSO-d6) δ=10.97 (s, 1 H), 8.12 (d, J=2.3 Hz, 1 H), 8.11-8.03 (m, 2 H), 8.03-7.97 (m, 2 H), 7.64-7.56 (m, 2 H), 7.47 (s, 1 H), 6.40 (d, J=2.3 Hz, 1 H), 4.25 (d, J=8.3 Hz, 1 H), 3.97 (br. s., 2 H), 3.46 (d, J=7.3 Hz, 2 H), 3.35-3.21

(m, 1 H), 2.07 (s, 1 H), 1.95 (br. s., 1 H), 1.85-1.64 (m, 2 H), 1.45 (s, 6 H); ESI-MS: m/z 377.4 (M+H)+.

Example 320

SYR156707B: (R)-N-(7-(3-acetamidopiperidin-1-yl)pyrazolo[1,5-a]pyrimidin-5-yl)-4-(2-hydroxypropan-2-yl)benzamide (306)

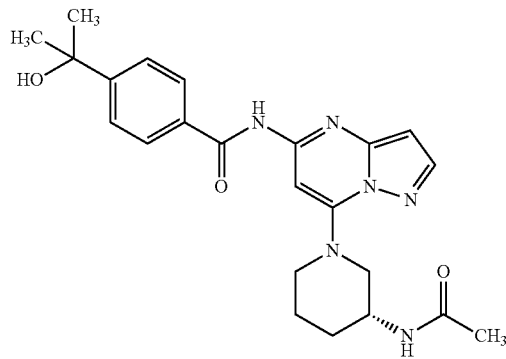

As crude product mixture of (R)-N-(7-(3-aminopiperidin-1-yl)pyrazolo[1,5-c]pyrimidin-5-yl)-4-(2-hydroxypropan-2-yl)benzamide (Compound 309 in Example 323) and trifluoroacetate salt (65 mg, 0.165 mmol) was dissolved in pyridine (2 ml). At 0° C. acetyl chloride (0.025 ml, 0.353 mmol) was added and the mixture was stirred for 2 hours at room temperature. Afterwards an additional amount of acetyl chloride (0.009 ml) was added to drive the reaction to completion. Water (2 ml) was then added to quench the reaction. The mixture was concentrated in vacuo, and the crude product was purified by preparatory HPLC (25-60% MeCN/H$_2$O gradient+0.01% TFA). Lyophilization of the collected fractions gave the titled compound (35 mg, 34% yield). $^1$H NMR (400 MHz, DMSO-d$_6$) δ=10.90 (s, 1 H), 8.08 (d, J=2.3 Hz, 1 H), 8.03-7.94 (m, 4 H), 7.64-7.56 (m, 2 H), 7.36 (s, 1 H), 6.35 (d, J=2.3 Hz, 1 H), 4.26-4.17 (m, 1 H), 4.13 (d, J=11.9 Hz, 1 H), 3.86 (br. s., 1 H), 3.14 (s, 1 H), 3.07 (dd, J=9.5, 11.7 Hz, 1 H), 1.90 (br. s., 2 H), 1.81 (s, 3 H), 1.75 (br. s., 1 H), 1.59-1.47 (m, 1 H), 1.45 (s, 5H); ESI-MS: m/z 437.5 (M+H)+.

Example 321

N-(7-(4-chlorophenyl)-2-methylpyrazolo[1,5-a]pyrimidin-5-yl)-4-(2-hydroxypropan-2-yl)benzamide (307)

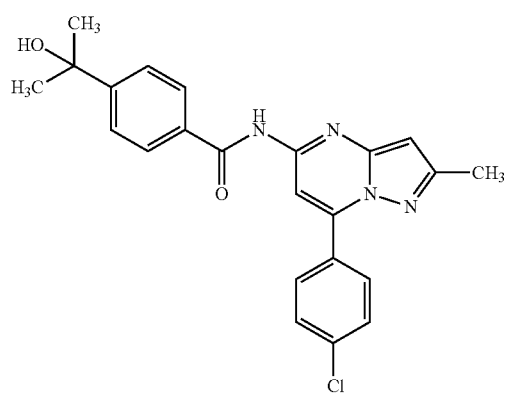

In a 2 ml microwave vial was placed N-(7-chloro-2-methylpyrazolo[1,5-a]pyrimidin-5-yl)-4-(2-hydroxypropan-2-yl)benzamide (2F, 75 mg, 0.22 mmol), [1,1'-bis(diphenylphosphino)ferrocene]-dichloropalladium(II) (9.0 mg, 11 μmmol) and 4-chlorophenylboronic acid (41 mg, 0.26 mmol). To the sealed vial were then added 1,4-dioxane (1 ml) and saturated aqueous NaHCO$_3$ (0.500 ml) to give a suspension. Nitrogen gas is bubbled through the mixture for 15 minutes. The mixture was then heated in the microwave at 120° C. for 20 minutes. DMF (1 mL) was then added. The mixture was then filtered with a syringe filter before being purified by preparatory HPLC (60-85% MeCN/H$_2$O gradient+0.01% TFA). Lyophilization of the collected fractions gave the desired products N-(7-(4-chlorophenyl)-2-methylpyrazolo[1,5-a]pyrimidin-5-yl)-4-(2-hydroxypropan-2-yl)benzamide (36 mg, 39% yield). $^1$H NMR (400 MHz, DMSO-d$_6$) δ=11.22 (s, 1 H), 8.16-8.09 (m, 2 H), 8.05-8.00 (m, 2 H), 7.98 (s, 1 H), 7.74-7.68 (m, 2 H), 7.65-7.58 (m, 2 H), 6.40 (s, 1 H), 5.19 (br. s., 1 H), 2.40 (s, 3H), 1.45 (s, 6 H); ESI-MS: m/z 421.3 (M+H)⁺.

Example 322

N-(7-(4-fluoro-3-methoxyphenyl)-2-methylpyrazolo[1,5-a]pyrimidin-5-yl)-4-(2-hydroxypropan-2-yl)benzamide (308)

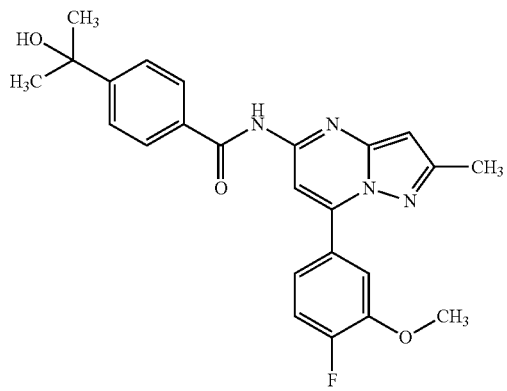

In a 2 ml microwave vial was placed N-(7-chloro-2-methylpyrazolo[1,5-a]pyrimidin-5-yl)-4-(2-hydroxypropan-2-yl)benzamide (2F, 93 mg, 0.27 mmol), 4-fluoro-3-methoxyphenylboronic acid (55 mg, 0.32 mmol), and [1,1'-bis(diphenylphosphino)ferrocene]-dichloropalladium(II) (11 mg, 0.013 mmol) to give a suspension. To the sealed vial were then added 1,4-dioxane (1 ml) and saturated aqueous NaHCO₃ (0.5 ml) to give a suspension. Nitrogen gas is bubbled through the mixture for 15 minutes. The mixture was then heated in the microwave at 120° C. for 20 minutes. The reaction mixture was partitioned between saturated NaHCO₃ and ethyl acetate, and the aqueous layer was extracted one more time with ethyl acetate. Combined organic layers were dried over MgSO₄, filtered and concentrated. The crude product was purified by preparatory HPLC (55-75% MeCN/H₂O gradient+0.01% TFA). Lyophilization of the collected fractions gave the titled product (35 mg, 30% yield). ¹H NMR (400 MHz, DMSO-d₆) δ=11.20 (s, 2 H), 8.05-7.99 (m, 4 H), 7.95 (s, 2 H), 7.88 (dd, J=2.1, 8.5 Hz, 2 H), 7.67-7.58 (m, 6 H), 7.47 (dd, J=8.6, 11.4 Hz, 1 H), 6.40 (s, 1 H), 3.93 (s, 4 H), 2.40 (s, 3 H), 1.45 (s, 6 H); ESI-MS: m/z 435.4 (M+H)⁺.

Example 323

(R)-N-(7-(3-aminopiperidin-1-yl)pyrazolo[1,5-a]pyrimidin-5-yl)-4-(2-hydroxypropan-2-yl)benzamide, trifluoroacetate salt (309)

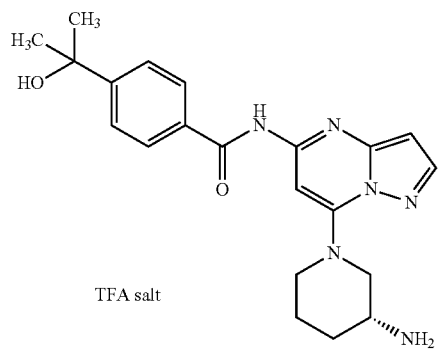

Step A: In a 2 mL microwave vial were placed N-(7-chloropyrazolo[1,5-a]pyrimidin-5-yl)-4-(2-hydroxypropan-2-yl)benzamide (2D, 150 mg, 0.24 mmol) and (R)-3-N-Boc-aminopiperidine (160 mg, 0.68 mmol). To the sealed vial were then added NMP (3 ml) and diisopropylethylamine (0.12 ml, 0.68 mmol), and the mixture was heated in the microwave at 100° C. for 15 minutes. After cooling to room temperature, the reaction mixture was partitioned between saturated NaHCO₃ and ethyl acetate, and the aqueous layer was extracted one more time with ethyl acetate. Combined organic layers were dried over MgSO₄, filtered and concentrated. The crude product (R)-tert-butyl 1-(5-(4-(2-hydroxypropan-2-yl)benzamido)pyrazolo[1,5-c]pyrimidin-7-yl)piperidin-3-ylcarbamate was used in the next step without further purification.

Step B: (R)-tert-butyl 1-(5-(4-(2-hydroxypropan-2-yl)benzamido)pyrazolo[1,5-c]pyrimidin-7-yl)piperidin-3-ylcarbamate was dissolved in CH₂Cl₂. Trifluoroacetic acid was added and the mixture was let stirred for 6 hours. The reaction mixture was concentrated to dryness in vacuo, and part of the residue was purified by preparatory HPLC (20-50% MeCN/H₂O gradient+0.01% TFA). Lyophilization of the combined fractions gave the titled compound as a white powder. ¹HNMR (400 MHz, DMSO-d₆) δ=10.97 (s, 1 H), 8.13 (d, J=2.3 Hz, 1 H), 8.11-8.03 (m, 2 H), 8.03-7.97 (m, 2 H), 7.64-7.57 (m, 2 H), 7.48 (s, 1 H), 6.40 (d, J=2.3 Hz, 1 H), 4.23 (br. s., 1 H), 3.97 (br. s., 2 H), 3.47 (d, J=7.1 Hz, 2 H), 3.28 (br.

s., 1H), 2.08 (br. s., 1 H), 1.96 (br. s., 1 H), 1.85-1.64 (m, 2 H), 1.46 (s, 6 H); ESI-MS: m/z 377.4 (M+H)+.

Example 324

5-(2-hydroxypropan-2-yl)-N-(2-methyl-7-phenylpyrazolo[1,5-a]pyrimidin-5-yl)picolinamide (310)

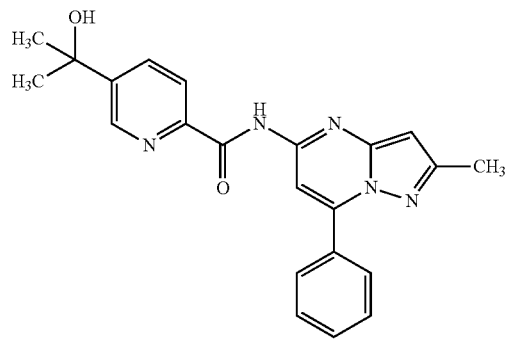

Step A: In a 50 ml round-bottomed flask was added 5-(methoxycarbonyl)pyridine-2-carboxylic acid (500 mg, 2.8 mmol) in toluene (5 ml). To this was then added oxalyl chloride (2.0 M in DCM) (4.1 ml, 8.3 mmol) and a drop of DMF. The resulting suspension was heated to 60° C. for 2 hours, after which the mixture turned into a light brown, clear solution. The mixture was cooled to room temperature for 18 hours, and was then concentrated. To the crude product was added toluene, and the mixture was concentrated once more to remove volatiles. After drying under vacuum for 3 hours, the resulting product methyl 6-(chlorocarbonyl)nicotinate, HCl salt as a beige-colored powder (470 mg, 85%) was used in the next step without further purification. ESI-MS: m/z 196.1 (M+H)+.

Step B: In a 50 ml pear flask was added 2-methyl-7-phenylpyrazolo[1,5-a]pyrimidin-5-amine (10A, 200 mg, 0.89 mmol) in pyridine (5 ml) to give a yellow suspension. At 0° C., methyl 6-(chlorocarbonyl)nicotinate, HCl salt (23 mg, 0.98 mmol) was added as a solid. After 2 hours, HPLC/MS shows complete conversion of starting materials to the desired product. Saturated NaHCO₃ solution (100 ml) was added and the resulting precipitate was collected on a fritted filter funnel. The collected product was washed water and was then dried under a stream of nitrogen gas for 48 h to give methyl 6-(2-methyl-7-phenylpyrazolo[1,5-a]pyrimidin-5-ylcarbamoyl)nicotinate (280 mg, 80% yield) as a yellow solid that is used without further purification. ¹H NMR (400 MHz, DMSO-d₆) δ=10.76 (s, 1 H), 9.22 (d, J=1.5 Hz, 1 H), 8.64-8.52 (m, 2 H), 8.32 (d, J=8.1 Hz, 1 H), 8.14-8.02 (m, 3 H), 7.97 (s, 1 H), 7.71-7.58 (m, 4 H), 6.43 (s, 1 H), 4.02-3.89 (m, 43 H), 2.44-2.33 (m, 3 H); ESI-MS: m/z 383.3 (M+H)+.

Step C: In a 50 ml round-bottomed flask was added methyl 6-(2-methyl-7-phenylpyrazolo[1,5-a]pyrimidin-5-ylcarbamoyl)nicotinate (130 mg, 0.32 mmol) in THF (2 ml) to give a yellow suspension. At 0° C., methylmagnesium bromide (3.0 M in ether) (0.59 ml, 1.8 mmol) was added to give a brown clear solution. After 30 minutes at 0° C., the reaction was quenched with saturated ammonium chloride solution (20 ml). The mixture, which contained more than 50% the hydrolyzed amide product, was then extracted twice with ethyl acetate. Combined organic layers were dried over MgSO₄, filtered and concentrated. The crude product was purified by preparatory HPLC (60-85% MeCN/H₂O gradient+0.01% TFA). The collected fractions were pooled, concentrated in vacuo and partitioned between saturated NaHCO₃ and ethyl acetate. Combined organic layers were dried over MgSO₄, filtered and concentrated in vacuo to give the titled product (21.5 mg, 17% yield) as an off-white solid. ¹H NMR (400 MHz, DMSO-d₆) δ=10.67 (s, 2 H), 8.88 (t, J=1.5 Hz, 1 H), 8.16 (d, J=1.5 Hz, 2 H), 8.09-8.04 (m, 2 H), 8.02 (s, 1 H), 7.67-7.61 (m, 3 H), 6.41 (s, 1 H), 5.48 (s, 1 H), 2.40 (s, 3 H), 1.51 (s, 6 H); ESI-MS: m/z 383.3 (M+H)+.

Example 325

N-(7-(5-chlorothiophen-2-yl)-2-methylpyrazolo[1,5-a]pyrimidin-5-yl)-4-(2-hydroxypropan-2-yl)benzamide (311)

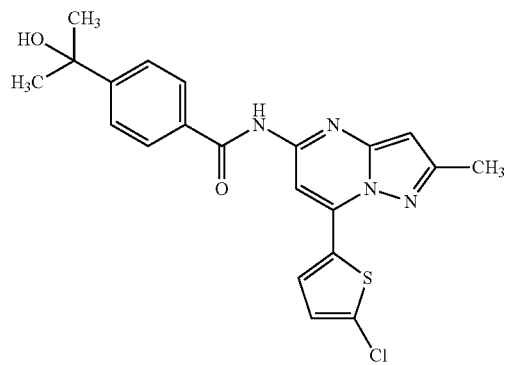

In a 2 ml microwave vial were placed N-(7-chloro-2-methylpyrazolo[1,5-a]pyrimidin-5-yl)-4-(2-hydroxypropan-2-yl)benzamide (2F, 75 mg, 0.22 mmol), 5-chlorothiophen-2-ylboronic acid (42 mg, 0.26 mmol) and [1,1'-bis(diphenylphosphino)ferrocene]-dichloropalladium(II) (9.0 mg, 11 μmmol). To the sealed vial were then added 1,4-dioxane (1 ml) and saturated aqueous NaHCO₃ (0.5 ml) to give a suspension. Nitrogen gas is bubbled through the mixture for 15 minutes. The mixture was then heated in the microwave at 120° C. for 20 minutes. DMF (1 mL) was then added. The crude product was purified by preparatory HPLC (65-90% MeCN/H₂O gradient+0.01% TFA). Lyophilization of the collected fractions gave the titled product (4.2 mg, 4.5% yield). ¹H NMR (400 MHz, DMSO-d₆) δ=11.20 (s, 1 H), 8.42 (s, 1 H), 8.23 (d, J=4.3 Hz, 1 H), 8.03 (d, J=8.6 Hz, 1 H), 7.62 (d, J=8.6 Hz, 1 H), 7.43 (d, J=4.3 Hz, 1 H), 6.43 (s, 1 H), 5.21 (br. s., 1 H), 1.46 (s, 6 H)); ESI-MS: m/z 427.3 (M+H)+.

Example 326

N-(7-(4-acetamidopiperidin-1-yl)-2-methylpyrazolo[1,5-a]pyrimidin-5-yl)-2-phenylcyclopropanecarboxamide (312)

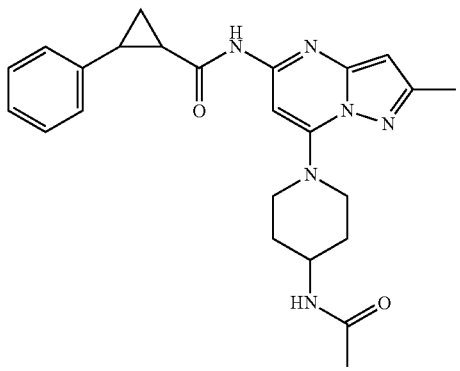

312

A solution of N-(7-chloro-2-methylpyrazolo[1,5-a]pyrimidin-5-yl)-2-phenylcyclopropanecarboxamide (8C, 200 mg, 0.612 mmol) and N-(piperidin-4-yl)acetamide (87 mg, 0.612 mmol) in NMP (2 mL) was stirred at 100° C. overnight. After cooling to room temperature, the mixture was diluted with a few drops of DMSO and methanol, and was then purified by preparatory HPLC (40-50% MeCN/H$_2$O gradient+0.01% TFA). Lyophilization of the combined fractions gave the titled compound as a pink solid (71 mg, 27%). $^1$H NMR (DMSO-d$_6$) δ: 10.94 (s, 1H), 7.91 (d, J=7.8 Hz, 1H), 7.08-7.38 (m, 5H), 6.07 (s, 1H), 4.28 (br. s., 2H), 3.86 (br. s., 1H), 3.08-3.24 (m, 2H), 2.38-2.46 (m, 1H), 2.35 (s, 3H), 1.85-1.95 (m, 2H), 1.82 (s, 3H), 1.45-1.64 (m, 3H), 1.36-1.43 (m, 1H). ESI-MS: m/z 433.0 (M+H)$^+$.

Example 327

N-(7-(3-fluoro-4-methoxyphenyl)-2-methylpyrazolo[1,5-a]pyrimidin-5-yl)-4-(2-hydroxypropan-2-yl)benzamide (313)

313

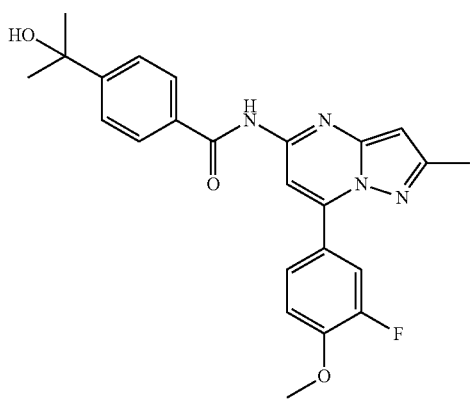

A suspension of N-(7-chloro-2-methylpyrazolo[1,5-a]pyrimidin-5-yl)-4-(2-hydroxypropan-2-yl)benzamide (2F, 90 mg, 0.261 mmol), 3-Fluoro-4-methoxyphenylboronic acid (89 mg, 0.522 mmol), and [1,1'-bis(diphenylphosphino)ferrocene]dichloropalladium(II) (17 mg, 21 μmol) in 2:1 1,4-dioxane/saturated aqueous NaHCO$_3$ (0.5 mL of 1,4-dioxane and 1 mL of saturated aqueous NaHCO$_3$) was prepared in a 2 mL microwave reaction vessel and the sealed reaction vessel warmed to 120° C. for 20 minutes. The reaction mixture was cooled to rt, diluted with methanol, filtered, and purified via preparative HPLC (55-65% MeCN/H$_2$O gradient+0.01% TFA). Lyophilization of the combined fractions gave the titled compound as a yellow solid (29 mg, 26%). $^1$H NMR (DMSO-d$_6$) δ: 11.18 (s, 1H), 7.82-8.28 (m, 5H), 7.61 (d, 2H), 7.43 (t, J=8.8 Hz, 1H), 6.39 (s, 1H), 5.19 (s, 1H), 3.97 (s, 3H), 2.42 (s, 3H), 1.46 (s, 6H). ESI-MS: m/z 435.0 (M+H)$^+$.

Example 328

N-(7-(3-chloro-4-methoxyphenyl)-2-methylpyrazolo[1,5-a]pyrimidin-5-yl)-4-(2-hydroxypropan-2-yl)benzamide (314)

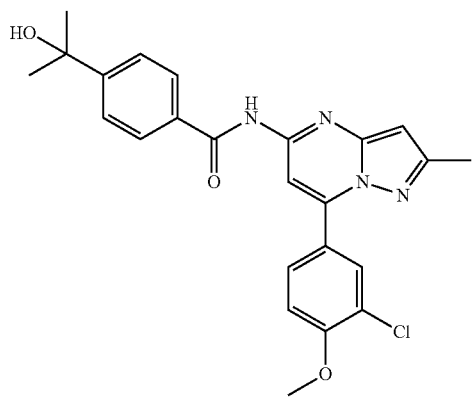

314

A suspension of N-(7-chloro-2-methylpyrazolo[1,5-a]pyrimidin-5-yl)-4-(2-hydroxypropan-2-yl)benzamide (2F, 90 mg, 0.261 mmol), 3-Chloro-4-methoxyphenylboronic acid (97 mg, 0.522 mmol), and [1,1'-bis(diphenylphosphino)ferrocene]dichloropalladium(II) (17 mg, 21 μmol) in 2:1 1,4-dioxane/saturated aqueous NaHCO$_3$ (0.5 mL of 1,4-dioxane and 1 mL of saturated aqueous NaHCO$_3$) was prepared in a 2 mL microwave reaction vessel and the sealed reaction vessel warmed to 120° C. for 20 minutes. The reaction mixture was cooled to rt, diluted with methanol, filtered, and purified via preparative HPLC (60-70% MeCN/H$_2$O gradient+0.01% TFA). Lyophilization of the combined fractions gave the titled compound as a yellow solid (24 mg, 20%). $^1$H NMR (DMSO-d$_6$) δ: 11.19 (s, 1H), 8.25 (d, J=2.3 Hz, 1H), 7.90-

8.17 (m, 4H), 7.54-7.73 (m, 2H), 7.41 (d, J=8.8 Hz, 1H), 6.39 (s, 1H), 5.19 (s, 1H), 3.99 (s, 3H), 2.42 (s, 3H), 1.46 (s, 6H). ESI-MS: m/z 451.0 (M+H)+.

Example 329

6-(2-hydroxypropan-2-yl)-N-(2-methyl-7-phenylpyrazolo[1,5-a]pyrimidin-5-yl)nicotinamide (315)

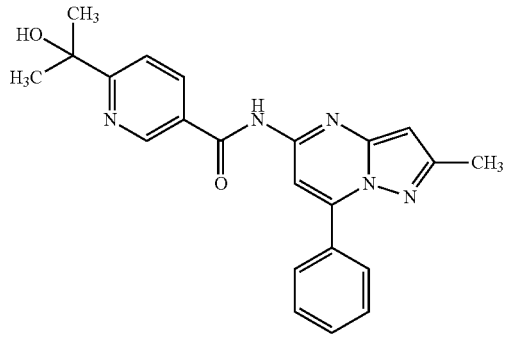

Step A: In a 50 ml pear flask was added 2-methyl-7-phenylpyrazolo[1,5-a]pyrimidin-5-amine (1J, 200 mg, 0.89 mmol) in pyridine (5 ml) to give a suspension. At 0° C., methyl 5-(chlorocarbonyl)picolinate, HCl salt (11A, 23 mg, 0.98 mmol) was added as a solid. The mixture was stirred at room temperature. After 2 hours, HPLC/MS showed incomplete conversion of starting materials. An additional amount of methyl 5-(chlorocarbonyl)picolinate, HCl (11A, 0.25 eq.) was added, and the mixture was stirred overnight at room temperature. Saturated NaHCO$_3$ (40 ml) was added and the mixture was stirred for 15 minutes before the precipitate was collected on a fitted filter and then washed twice with water. The product methyl 5-(2-methyl-7-phenylpyrazolo[1,5-a]pyrimidin-5-ylcarbamoyl)picolinate as a yellow solid (230 mg, 99%) was dried overnight under a stream of nitrogen and was used in the next step without further purification. Melting point (213.4-214° C.). $^1$H NMR (400 MHz, DMSO-d$_6$) δ ppm 2.39 (s, 1 H), 2.40 (s, 3 H), 3.91-3.94 (m, 4 H), 6.39 (s, 1 H), 7.36-7.41 (m, 1 H), 7.61-7.65 (m, 4 H), 7.79 (tt, J=7.61, 1.86 Hz, 1 H), 7.91 (s, 1 H), 8.03-8.08 (m, 2 H), 8.16-8.20 (m, 1 H), 8.52-8.56 (m, 1 H), 8.56-8.59 (m, 1 H), 9.27 (d, J=2.27 Hz, 1 H); ESI-MS: m/z 383.2 (M+H)+.

Step B: In a 50 ml pear flask was added methyl 5-(2-methyl-7-phenylpyrazolo[1,5-a]pyrimidin-5-ylcarbamoyl)picolinate (150 mg, 0.40 mmol) in tetrahydrofuran (2.0 ml). The mixture was cooled to 0° C., and methylmagnesium bromide (3.0 M in ether) (0.53 ml, 1.6 mmol) was added. After 10 minutes, HPLC/MS showed starting material was consumed. Saturated NH$_4$Cl (40 ml) was added to quench the reaction. The mixture was extracted twice with ethyl acetate. Combined organic layers were dried over MgSO$_4$, filtered and concentrated. The crude product was purified by preparatory HPLC (50-60% MeCN/H$_2$O gradient+0.01% TFA). Combined fractions were concentrated and then neutralized with saturated NaHCO$_3$. The aqueous layer was extracted twice with ethyl acetate. Combined organic layers were dried over MgSO$_4$, filtered and concentrated to give the titled product 6-(2-hydroxypropan-2-yl)-N-(2-methyl-7-phenylpyrazolo[1,5-a]pyrimidin-5-yl)nicotinamide (65 mg, 42% yield) as a yellow foam. $^1$H NMR (400 MHz, DMSO-d$_6$) δ ppm 1.48 (s, 6 H), 2.40 (s, 3 H), 5.41 (s, 1 H), 6.40 (s, 1H), 7.63 (d, J=2.02 Hz, 3 H), 7.81 (d, J=8.34 Hz, 1 H), 7.96 (s, 1 H), 8.06 (d, J=3.54 Hz, 2 H), 8.38 (dd, J=8.34, 2.02 Hz, 1 H), 9.10 (s, 1 H), 11.45 (s, 1 H); ESI-MS: m/z 383.3 (M+H)+.

Example 330

6-(2-hydroxypropan-2-yl)-N-(7-morpholinopyrazolo[1,5-a]pyrimidin-5-yl)nicotinamide (316)

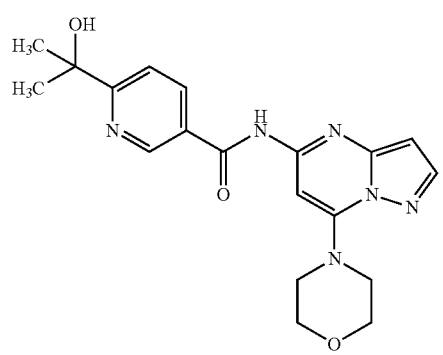

Step A: In a 50 ml pear flask was added 7-morpholinopyrazolo[1,5-a]pyrimidin-5-amine (9A, 200 mg, 0.91 mmol) in pyridine (5 ml) to give a suspension. At 0° C., methyl 5-(chlorocarbonyl)picolinate, HCl salt (11A, 240 mg, 1.0 mmol) was added as a solid. The mixture turned into a thick paste. More pyridine (2 ml) was added, and the mixture was then heated to 40° C. to loosen up the paste. After 2 hours, HPLC/MS showed incomplete conversion of starting materials. An additional amount of methyl 5-(chlorocarbonyl)picolinate, HCl (11A, 0.25 eq.) was added, and the mixture was stirred overnight at room temperature. Saturated NaHCO$_3$ (40 ml) was added and the mixture was stirred for 15 minutes before the precipitate was collected on a fritted filter and then washed twice with water. The crude product methyl 5-(7-morpholinopyrazolo[1,5-a]pyrimidin-5-ylcarbamoyl)picolinate (98 mg, 28% yield) as a light-yellow solid was dried overnight under a stream of nitrogen and was used in the next step without purification. ESI-MS: m/z 383.2 (M+H)+.

Step B: In a 50 ml pear flask was added methyl 5-(7-morpholinopyrazolo[1,5-a]pyrimidin-5-ylcarbamoyl)picolinate (84 mg, 0.22 mmol) in tetrahydrofuran (2.0 ml). The mixture was cooled to 0° C., and methylmagnesium bromide (3.0 M in ether) (0.29 ml, 0.88 mmol) was added. After 10 minutes, HPLC/MS showed starting material was consumed. Saturated NH$_4$Cl (40 ml) was added to quench the reaction. The mixture was extracted twice with ethyl acetate. Combined organic layers were dried over MgSO$_4$, filtered and concentrated. The crude product was purified by preparatory HPLC (35-55% MeCN/H$_2$O gradient+0.01% TFA). Combined fractions were concentrated and then neutralized with saturated NaHCO$_3$. The aqueous mixture was extracted twice with ethyl acetate. Combined organic layers were dried over MgSO$_4$, filtered and concentrated to give the titled product (26 mg, 31% yield) as a off-white foam. $^1$H NMR (400 MHz, DMSO-d$_6$) δ ppm 1.48 (br. s., 6 H) 3.58-4.00 (m, 8 H) 5.40 (s, 1 H) 6.39 (s, 1 H) 7.41 (s, 1 H) 7.80 (br. s., 1 H) 8.11 (s, 1 H) 8.37 (d, J=6.82 Hz, 1 H) 9.08 (s, 1 H) 11.20 (s, 1 H); ESI-MS: m/z 383.3 (M+H)+.

Example 331

(R)-1-(5-(4-(2-hydroxypropan-2-yl)benzamido)-2-methylpyrazolo[1,5-a]pyrimidin-7-yl)-N-methylpiperidine-3-carboxamide (317)

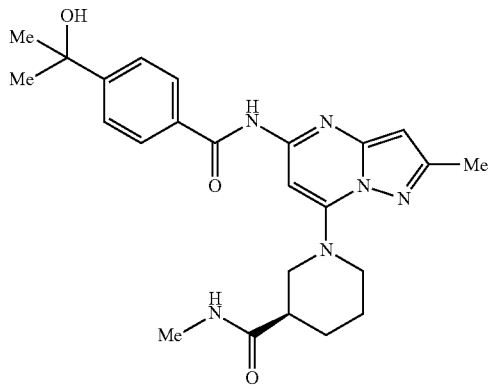

A solution of N-(7-chloro-2-methylpyrazolo[1,5-a]pyrimidin-5-yl)-4-(2-hydroxypropan-2-yl)benzamide (2F, 76 mg, 0.220 mmol) and (R)-N-methylpiperidine-3-carboxamide (62.7 mg, 0.441 mmol) in NMP (1.1 mL) was stirred at 100° C. for 3 h. After cooling to room temperature, the mixture was diluted with a few drops of DMSO and methanol, and was then purified by preparatory HPLC (30-30% MeCN/H2O gradient+0.01% TFA). Lyophilization of the combined fractions gave the titled compound as a white solid (12.5 mg, 13%); ESI-MS: m/z 451.3 (M+H)+.

Example 332

N-(7-(4-chloro-3-methylphenyl)-2-methylpyrazolo[1,5-a]pyrimidin-5-yl)-4-(2-hydroxypropan-2-yl)benzamide (318)

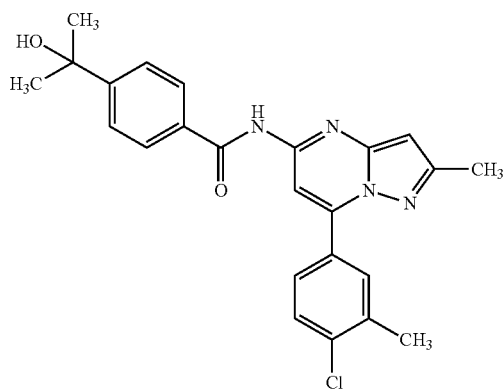

In a 2 ml microwave vial was placed N-(7-chloro-2-methylpyrazolo[1,5-a]pyrimidin-5-yl)-4-(2-hydroxypropan-2-yl)benzamide (2F, 73 mg, 0.21 mmol), (4-chloro-3-methylphenyl)boronic acid (36 mg, 0.21 mmol) and [1,1'-bis(diphenylphosphino)ferrocene]-dichloropalladium(II) (4.4 mg, 5.3 μmol). To the sealed vial were then added 1,4-dioxane (1 ml) and saturated aqueous NaHCO3 (0.5 ml) to give a suspension. The mixture was then heated in the microwave at 120° C. for 20 minutes. After cooling to room temperature, DMF (1 ml) was added and the crude product mixture was filtered by syringe filter and purified by preparatory HPLC (70-85% MeCN/H2O gradient+0.01% TFA). Lyophilization of the collected fractions gave the desired product N-(7-(4-chloro-3-methylphenyl)-2-methylpyrazolo[1,5-a]pyrimidin-5-yl)-4-(2-hydroxypropan-2-yl)benzamide (27 mg, 30% yield) as a yellow powder. 1H NMR (400 MHz, DMSO-d6) δ ppm 1.45 (s, 6 H) 2.40 (s, 4 H) 2.46 (s, 4 H) 6.40 (s, 1 H) 7.61 (d, J=8.59 Hz, 3 H) 7.68 (d, J=8.34 Hz, 1 H) 7.91-7.97 (m, 2 H) 7.99-8.05 (m, 4 H) 11.21 (s, 1 H); ESI-MS: m/z 435.3 (M+H)+.

Example 333

N-(7-(3-chloro-4-hydroxyphenyl)-2-methylpyrazolo[1,5-a]pyrimidin-5-yl)-4-(2-hydroxypropan-2-yl)benzamide (319)

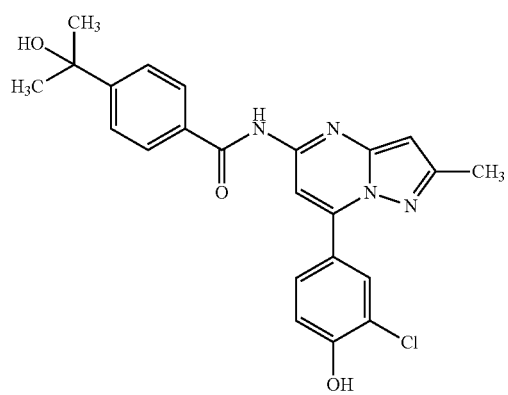

In a 2 ml microwave vial was placed N-(7-chloro-2-methylpyrazolo[1,5-a]pyrimidin-5-yl)-4-(2-hydroxypropan-2-yl)benzamide (2F, 73 mg, 0.21 mmol), 3-chloro-4-hydroxyphenylboronic acid (37 mg, 0.21 mmol) and [1,1'-bis(diphenylphosphino)ferrocene]-dichloropalladium(II) (8.7 mg, 11 μmmol). To the sealed vial was then added 1,4-dioxane (1 ml) and saturated aqueous NaHCO3 (0.5 ml) to give a suspension. The mixture was then heated in the microwave at 120° C. for 20 minutes. After cooling to room temperature, DMF (1 ml) was added and the crude product mixture was filtered by syringe filter and purified by preparatory HPLC (50-60% MeCN/H2O gradient+0.01% TFA). Lyophilization of the collected fractions gave the titled product (39 mg, 42% yield) as a yellow powder. 1H NMR (400 MHz, DMSO-d6) δ ppm 1.45 (s, 6 H) 2.41 (s, 8 H) 6.37 (s, 3 H) 7.19 (d, J=8.59 Hz, 3 H) 7.61 (d, J=8.59 Hz, 5 H) 7.89-7.97 (m, 5 H) 8.02 (d, J=8.59 Hz, 5 H) 8.23 (d, J=2.27 Hz, 3 H) 11.03 (s, 3 H) 11.15 (s, 3H); ESI-MS: m/z 437.2 (M+H)+.

Example 334

N-(7-(4-(2-(dimethylamino)ethoxy)phenyl)-2-methylpyrazolo[1,5-a]pyrimidin-5-yl)-4-(2-hydroxypropan-2-yl)benzamide (320)

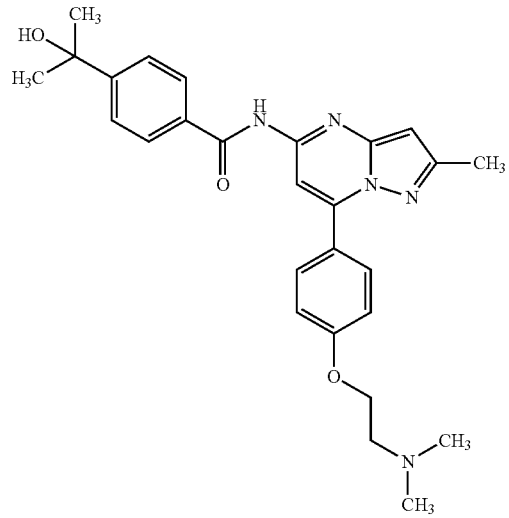

In a 2 ml microwave vial was placed N-(7-chloro-2-methylpyrazolo[1,5-a]pyrimidin-5-yl)-4-(2-hydroxypropan-2-yl)benzamide (2F, 73 mg, 0.21 mmol), 4-(2-(dimethylamino)ethoxy)phenylboronic acid (49 mg, 0.23 mmol) and [1,1'-bis(diphenylphosphino)ferrocene]-dichloropalladium(II) (8.7 mg, 11 μmmol). To the sealed vial was then added 1,4-dioxane (1 ml) and saturated aqueous NaHCO$_3$ (0.5 ml) to give a suspension. The mixture was then heated in the microwave at 120° C. for 20 minutes. After cooling to room temperature, DMF (1 ml) was added and the crude product mixture was filtered by syringe filter and purified by preparatory HPLC (20-45% MeCN/H$_2$O gradient+0.01% TFA). Lyophilization of the collected fractions gave the titled product (44 mg, 43% yield) as a yellow powder. $^1$H NMR (DMSO-d$_6$) δ: 11.18 (s, 1H), 9.72 (br. s., 1H), 8.11-8.18 (m, 3H), 8.02 (d, J=8.8 Hz, 3H), 7.98 (s, 1H), 7.59-7.65 (m, 3H), 7.22-7.30 (m, 2H), 6.38 (s, 1H), 5.20 (br. s., 1H), 4.40-4.49 (m, 2H), 3.59 (br. s., 2H), 2.90 (s, 6H), 2.41 (s, 3H), 1.42-1.51 (m, 6H); ESI-MS: m/z 474.4 (M+H)+.

Example 335

4-(2-hydroxypropan-2-yl)-N-(2-methyl-7-(4-(2-morpholinoethoxy)phenyl)pyrazolo[1,5-a]pyrimidin-5-yl)benzamide (321)

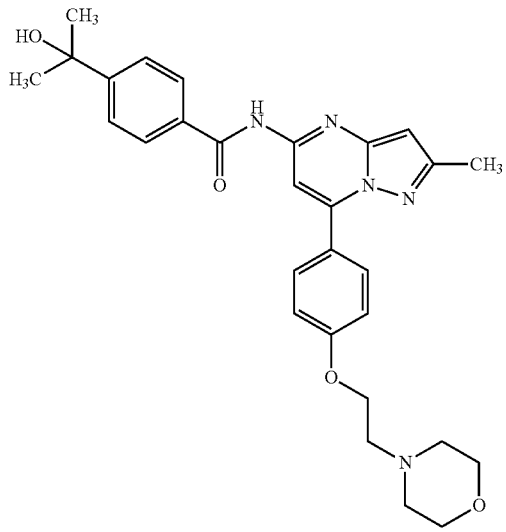

In a 2 ml microwave vial was placed N-(7-chloro-2-methylpyrazolo[1,5-a]pyrimidin-5-yl)-4-(2-hydroxypropan-2-yl)benzamide (2F, 73 mg, 0.212 mmol), 4-{2-[4-(4,4,5,5-tetramethyl-[1,3,2]dioxaborolan-2-yl)-phenoxy]-ethyl}-morpholine (70.6 mg, 0.212 mmol) and [1,1'-bis(diphenylphosphino)ferrocene]-dichloropalladium(II) (8.71 mg, 10.59 μmmol). To the sealed vial was then added 1,4-dioxane (1 ml) and saturated aqueous NaHCO$_3$ (0.5 ml) to give a suspension. The mixture was then heated in the microwave at 120° C. for 20 minutes. After cooling to room temperature, DMF (1 ml) was added and the crude product mixture was filtered by syringe filter and purified by preparatory HPLC (30-45% MeCN/H$_2$O gradient+0.01% TFA). Lyophilization of the collected fractions gave the titled product (18 mg, 16% yield) as a yellow powder. $^1$H NMR (DMSO-d$_6$) δ: 11.19 (s, 2H), 10.08 (br. s., 1H), 8.12-8.20 (m, 3H), 8.02 (d, J=8.6 Hz, 3H), 7.98 (s, 1H), 7.59-7.66 (m, 3H), 7.23-7.30 (m, 3H), 6.39 (s, 1H), 4.47-4.55 (m, 2H), 4.00 (br. s., 3H), 3.66 (br. s., 7H), 3.25 (br. s., 2H), 2.41 (s, 3H), 1.42-1.50 (m, 6H); ESI-MS: m/z 516.4 (M+H)+.

Example 336

4-(2-Hydroxypropan-2-yl)-N-(7-(4-(2-methoxyethoxy)phenyl)-2-methylpyrazolo[1,5-a]pyrimidin-5-yl)benzamide (322)

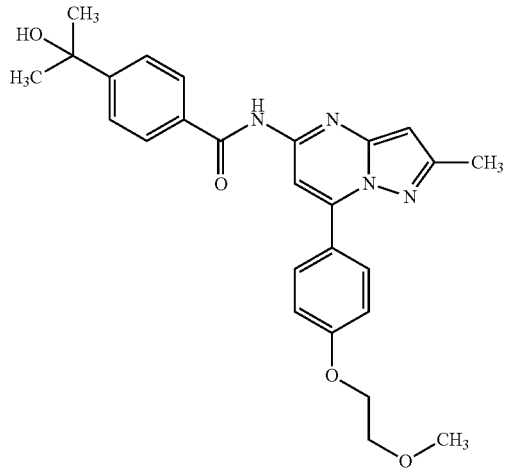

In a 2 ml microwave vial was placed N-(7-chloro-2-methylpyrazolo[1,5-a]pyrimidin-5-yl)-4-(2-hydroxypropan-2-yl)benzamide (2F, 73 mg, 0.212 mmol), 4-(2-methoxyethoxy) phenylboronic acid (42 mg, 0.21 mmol) and [1,1'-bis(diphenylphosphino)ferrocene]-dichloropalladium(II) (8.7 mg, 11 μmmol). To the sealed vial was then added 1,4-dioxane (1 ml) and saturated aqueous NaHCO₃ (0.5 ml) to give a suspension. The mixture was then heated in the microwave at 120° C. for 20 minutes. After cooling to room temperature, DMF (1 ml) was added and the crude product mixture was filtered by syringe filter and purified by preparatory HPLC (55% MeCN/H₂O+0.01% TFA). Lyophilization of the collected fractions gave the titled product (50 mg, 51% yield) as a yellow powder. ¹H NMR (DMSO-d₆) δ: 11.15 (s, 1H), 8.07-8.16 (m, 1H), 7.99-8.05 (m, 1H), 7.97 (s, 0H), 7.57-7.64 (m, 0H), 7.16-7.23 (m, 0H), 6.37 (s, 0H), 4.20-4.26 (m, 0H), 3.68-3.78 (m, 0H), 3.34 (s, 0H), 2.41 (s, 3H), 1.45 (s, 6H); ESI-MS: m/z 461.3 (M+H)+.

Example 337

4-(2-hydroxypropan-2-yl)-N-(2-methyl-7-(4-propionamidopiperidin-1-yl)pyrazolo[1,5-a]pyrimidin-5-yl)benzamide (323)

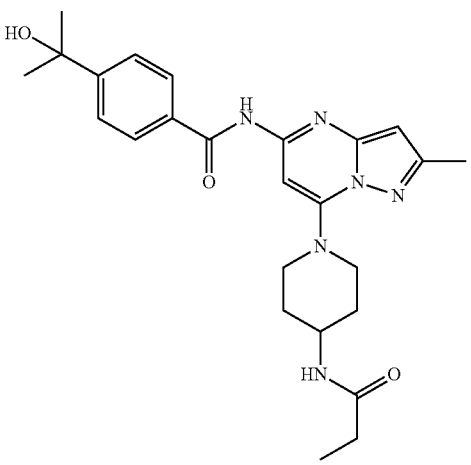

In a 20 mL round-bottomed flask was N-(7-(4-aminopiperidin-1-yl)-2-methylpyrazolo[1,5-a]pyrimidin-5-yl)-4-(2-hydroxypropan-2-yl)benzamide (0.2 g, 0.490 mmol) in Pyridine (Volume: 0.979 ml) at 0° C. to give a brown solution. Propionyl chloride (0.047 ml, 0.539 mmol) was added at 0° C. The solution was raised to room temp. After 1 hr, the reaction was completed and quenched with sat NaHCO₃, and washed with sat NaHCO₃. The organic layers were combined and extracted with ethyl acetate (3×25 mL). The organic was dried MgSO₄, filt and conc. The compound was filtered and purified by preparatory HPLC (30-50% MeCN/H₂O gradient+0.01% TFA). Received 22 mg of a white solid (10%). ¹H NMR (DMSO-d₆) δ: 10.73-10.94 (m, 1H), 7.99 (d, J=8.6 Hz, 2H), 7.77-7.87 (m, 1H), 7.59 (d, J=8.6 Hz, 1H), 7.35 (s, 1H), 6.15 (s, 1H), 4.27-4.45 (m, 2H), 3.11-3.30 (m, 2H), 2.37 (s, 3H), 2.08 (d, J=7.6 Hz, 2H), 1.83-1.97 (m, 1H), 1.50-1.67 (m, 1H), 1.45 (s, 3H), 1.00 (t, J=7.6 Hz, 3H). ESI-MS: m/z 465.4 (M+H)⁺.

Example 338

4-(2-hydroxypropan-2-yl)-N-(2-methyl-7-(4-ureidopiperidin-1-yl)pyrazolo[1,5-a]pyrimidin-5-yl)benzamide (324)

2H), 2.31 (s, 3H), 1.88 (dd, J=13.0, 2.9 Hz, 2H), 1.40-1.53 (m, 2H), 1.39 (s, 6H); ESI-MS: m/z 452.2 (M+H)⁺.

Example 339

N-(7-(4-(2-amino-2-oxoethyl)piperidin-1-yl)-2-methylpyrazolo[1,5-a]pyrimidin-5-yl)-4-(2-hydroxypropan-2-yl)benzamide (325)

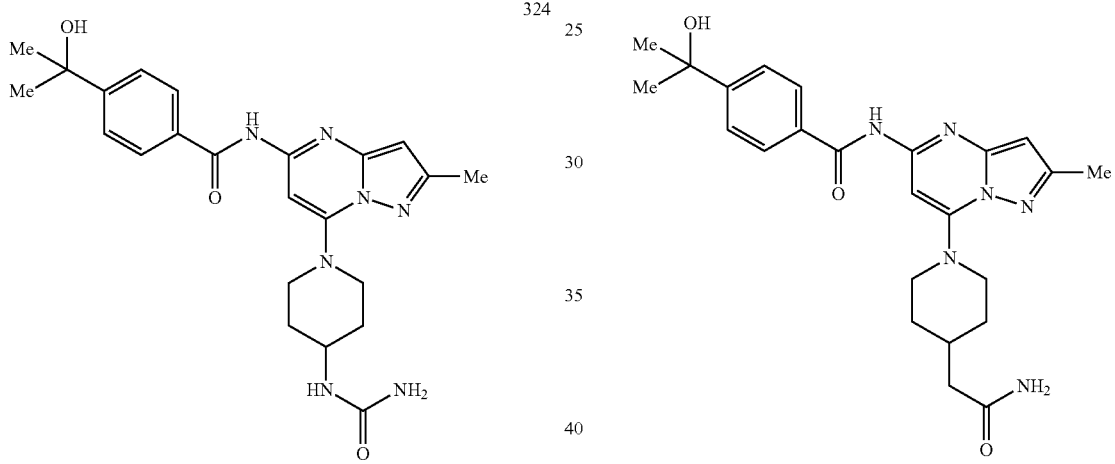

A solution of N-(7-chloro-2-methylpyrazolo[1,5-a]pyrimidin-5-yl)-4-(2-hydroxypropan-2-yl)benzamide (2F, 100 mg, 0.290 mmol), 1-(piperidin-4-yl)urea hydrochloride (83 mg, 0.580 mmol), and N,N-diisopropylethylamine (112 mg, 0.870 mmol) in DMF (2.0 mL) was stirred at 100° C. for 3 h. After cooling to room temperature, the mixture was diluted with a few drops of DMSO and methanol, and was then purified by preparatory HPLC (25-35% MeCN/H₂O gradient+0.01% TFA). Lyophilization of the combined fractions gave the titled compound as a white solid (59.4 mg, 45%). Decomposition was observed at 225.4° C. ¹H NMR (DMSO-d₆) δ: 10.81 (s, 1H), 7.92 (d, J=8.6 Hz, 2H), 7.53 (d, J=8.6 Hz, 2H), 7.23 (s, 1H), 6.11 (s, 1H), 6.06 (br. s., 1H), 4.26 (d, J=12.9 Hz, 2H), 3.63 (t, J=9.6 Hz, 1H), 3.17 (t, J=11.0 Hz, A solution of N-(7-chloro-2-methylpyrazolo[1,5-a]pyrimidin-5-yl)-4-(2-hydroxypropan-2-yl)benzamide (2F, 100 mg, 0.290 mmol), 2-(piperidin-4-yl)acetamide hydrochloride (82 mg, 0.58 mmol), and N,N-diisopropylethylamine (112 mg, 0.870 mmol) in DMF (2.0 mL) was stirred at 100° C. for 3 h. After cooling to room temperature, the mixture was diluted with a few drops of DMSO and methanol, and was then purified by preparatory HPLC (30-35% MeCN/H₂O gradient+0.01% TFA). Lyophilization of the combined fractions gave the titled compound as a white solid (44.4 mg, 34%). ¹H NMR (DMSO-d₆) δ: 10.84 (s, 1H), 7.89-8.10 (m, 2H), 7.53-7.66 (m, 2H), 7.33 (br. s., 1H), 7.28 (s, 1H), 6.81 (br. s., 1H), 6.16 (s, 1H), 4.44 (d, J=12.6 Hz, 2H), 3.00-3.12

(m, 2H), 2.37 (s, 3H), 1.94-2.14 (m, 3H), 1.81 (d, J=13.1 Hz, 2H), 1.41-1.53 (m, 6H), 1.30-1.41 (m, 2H); ESI-MS: m/z 451.2 (M+H)+.

Example 340

N-(7-(benzofuran-5-yl)-2-methylpyrazolo[1,5-a]pyrimidin-5-yl)-4-(2-hydroxypropan-2-yl)benzamide (326)

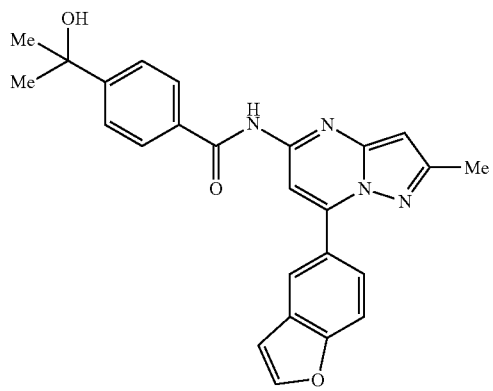

A suspension of N-(7-chloro-2-methylpyrazolo[1,5-a]pyrimidin-5-yl)-4-(2-hydroxypropan-2-yl)benzamide (2F, 80 mg, 0.232 mmol), 5-(4,4,5,5-Tetramethyl-1,3,2-dioxaborolan-2-yl)-1-benzofuran (73.6 mg, 0.302 mmol), and 1,1'-bis(diphenylphosphino)ferrocene]dichloropalladium(II) (16 mg, 22 µmol) in 2:1 1,4-dioxane/saturated aqueous NaHCO₃ (0.774 mL of 1,4-dioxane and 0.387 mL of saturated aqueous NaHCO₃) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (60-70% MeCN/H₂O gradient+0.01% TFA). Lyophilization of the combined fractions gave the titled compound as a yellow solid (34.4 mg, 35%). ¹H NMR (DMSO-d₆) δ: 11.13 (s, 1H), 8.36 (d, J=1.5 Hz, 1H), 8.10 (d, J=2.3 Hz, 1H), 7.89-8.00 (m, 4H), 7.78 (d, J=8.6 Hz, 1H), 7.55 (d, J=8.6 Hz, 2H), 7.10 (dd, 1H), 6.34 (s, 1H), 5.13 (s, 1H), 2.35 (s, 3H), 1.39 (s, 6H); ESI-MS: m/z 452.2 (M+H)+.

Example 341

N-(7-(3-(dimethylamino)phenyl)-2-methylpyrazolo[1,5-a]pyrimidin-5-yl)-4-(2-hydroxypropan-2-yl)benzamide (327)

A suspension of N-(7-chloro-2-methylpyrazolo[1,5-a]pyrimidin-5-yl)-4-(2-hydroxypropan-2-yl)benzamide (2F, 80 mg, 0.232 mmol), 3-(dimethylamino)phenylboronic acid (49.8 mg, 0.302 mmol), and 1,1'-bis(diphenylphosphino)ferrocene]dichloropalladium(II) (17 mg, 23 µmol) in 2:1 1,4-dioxane/saturated aqueous NaHCO₃ (0.774 mL of 1,4-dioxane and 0.387 mL of saturated aqueous NaHCO₃) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (35-40% MeCN/H₂O gradient+0.01% TFA). Lyophilization of the combined fractions gave the titled compound as a yellow solid (25.4 mg, 26%). ¹H NMR (DMSO-d₆) δ: 11.09 (s, 1H), 7.90-7.98 (m, 2H), 7.86 (s, 1H), 7.48-7.60 (m, 2H), 7.31-7.38 (m, 1H), 7.28-7.32 (m, 1H), 7.19 (d, J=8.1 Hz, 1H), 6.92 (dd, J=8.1, 2.3 Hz, 1H), 6.30 (s, 1H), 2.91 (s, 6H), 2.33 (s, 3H), 1.39 (s, 6H); ESI-MS: m/z 430.3 (M+H)+.

Example 342

4-(2-hydroxypropan-2-yl)-N-(7-(6-hydroxypyridin-3-yl)-2-methylpyrazolo[1,5-a]pyrimidin-5-yl)benzamide (328)

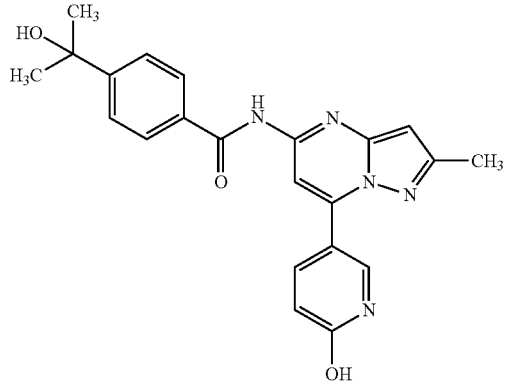

In a 2 ml microwave vial was placed N-(7-chloro-2-methylpyrazolo[1,5-a]pyrimidin-5-yl)-4-(2-hydroxypropan-2-yl) benzamide (2F, 100 mg, 0.29 mmol), 5-(4,4,5,5-tetramethyl-1,3,2-dioxaborolan-2-yl)pyridin-2-ol (64 mg, 0.29 mmol) and [1,1'-bis(diphenylphosphino)ferrocene]-dichloropalladium(II) (7.2 mg, 8.7 μmmol). To the sealed vial was then added 1,4-dioxane (1.3 ml) and saturated aqueous NaHCO₃ (0.6 ml) to give a suspension. The mixture was then heated in the microwave at 120° C. for 20 minutes. After cooling to room temperature, DMF (1 ml) was added and the crude product mixture was filtered by syringe filter and purified by preparatory HPLC (20-40% MeCN/H₂O gradient+0.01% TFA). Lyophilization of the collected fractions gave the desired product 4-(2-hydroxypropan-2-yl)-N-(7-(6-hydroxypyridin-3-yl)-2-methylpyrazolo[1,5-a]pyrimidin-5-yl)benzamide (35 mg, 30% yield) as a yellow powder. ¹H NMR (DMSO-d₆) δ: 12.13-12.32 (m, 1H), 11.14 (s, 1H), 8.85 (d, J=2.8 Hz, 1H), 8.10 (dd, J=9.7, 2.9 Hz, 1H), 8.00-8.05 (m, 2H), 7.58-7.65 (m, 2H), 6.57 (d, J=9.6 Hz, 1H), 6.38 (s, 1H), 2.44 (s, 2H), 1.46 (s, 6H); ESI-MS: m/z 404.3 (M+H)+.

Example 343

4-(2-hydroxypropan-2-yl)-N-(7-(6-methoxypyridin-3-yl)-2-methylpyrazolo[1,5-a]pyrimidin-5-yl)benzamide (329)

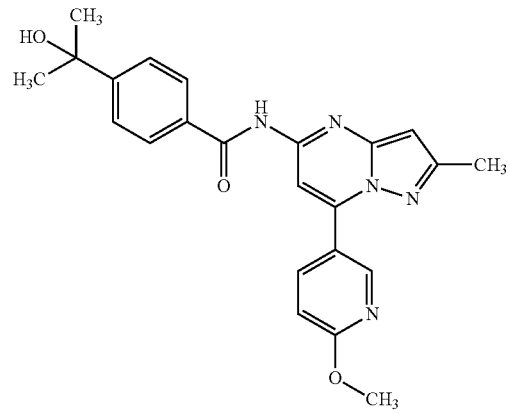

In a 2 ml microwave vial was placed N-(7-chloro-2-methylpyrazolo[1,5-a]pyrimidin-5-yl)-4-(2-hydroxypropan-2-yl) benzamide (2F, 100 mg, 0.29 mmol), 6-methoxypyridin-3-ylboronic acid, HCl (55 mg, 0.29 mmol) and [1,1'-bis (diphenylphosphino)ferrocene]-dichloropalladium(II) (7.2 mg, 8.7 μmol). To the sealed vial was then added 1,4-dioxane (1 ml) and saturated aqueous NaHCO₃ (0.5 ml) to give a suspension. The mixture was then heated in the microwave at 120° C. for 20 minutes. After cooling to room temperature, DMF (1 ml) was added and the crude product mixture was filtered by syringe filter and purified by preparatory HPLC (55-60% MeCN/H₂O gradient+0.01% TFA). Lyophilization of the collected fractions gave the titled product (41 mg, 34% yield) as a pale yellow powder. ¹H NMR (DMSO-d₆) δ: 11.20 (s, 1H), 8.94 (dd, J=2.5, 0.8 Hz, 1H), 8.41 (dd, J=8.6, 2.5 Hz, 1H), 8.00-8.04 (m, 1H), 7.99 (s, 1H), 7.62 (d, J=8.6 Hz, 2H), 7.08 (dd, J=8.8, 0.8 Hz, 1H), 6.39 (d, J=0.5 Hz, 1H), 3.98 (s, 3H), 2.41 (s, 3H), 1.46 (s, 6H); ESI-MS: m/z 418.4 (M+H)+.

Example 344

3,3-dimethyl-N-(2-methyl-7-phenylpyrazolo[1,5-a]pyrimidin-5-yl)-2,3-dihydrobenzofuran-6-carboxamide (330)

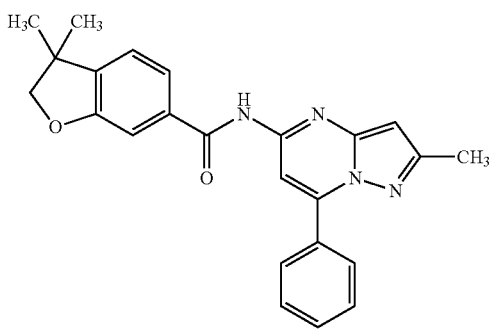

Step A: In a 200 ml pear flask were added methyl 4-bromo-3-hydroxybenzoate (3.5 g, 15 mmol), potassium carbonate (4.2 g, 30 mmol) and tetrabutylammonium iodide (0.084 g, 0.23 mmol) in DMF (35 ml) to give a suspension. At 0° C. was added 3-bromo-2-methylprop-1-ene (1.7 ml, 17 mmol) to this mixture, which was then stirred at room temperature for ~16 h. The reaction mixture was partitioned between brine and ether, and the aqueous layer was extracted one more time with ethyl acetate. Combined organic layers were washed with brine, dried over MgSO$_4$, filtered and concentrated to give the crude product methyl 4-bromo-3-(2-methylallyloxy)benzoate (4.3 g, 99% yield) as a light yellow oil. $^1$H NMR (CHLOROFORM-d) δ: 7.61 (d, J=8.1 Hz, 7H), 7.53 (d, J=1.5 Hz, 7H), 7.50 (dd, J=8.1, 1.8 Hz, 7H), 5.20 (d, J=1.0 Hz, 7H), 5.02-5.07 (m, 7H), 4.56 (s, 2H), 3.92 (s, 3H), 1.87 (s, 3H); ESI-MS: m/z 242.3 (M+H)+.

Step B: In a 20 ml microwave vial were added methyl 4-bromo-3-(2-methylallyloxy)benzoate (1.0 g, 3.5 mmol), sodium formate (0.29 g, 4.2 mmol), sodium acetate (0.72 g, 8.8 mmol) and tetraethylammonium chloride (0.70 g, 4.2 mmol) in DMF (8 ml) to give a yellow suspension. Nitrogen gas was bubbled through the mixture for 15 minutes, before palladium(II) acetate (0.039 g, 0.18 mmol) was added. The mixture was then heated in the microwave for 30 minutes at 110° C., but because conversion was low, additional heating at 120° C. for a total of 2 h in the microwave before being worked up. The reaction mixture was partitioned between brine and ethyl acetate, and the aqueous layer was extracted one more time with ethyl acetate. Combined organic layers were dried over MgSO$_4$, filtered and concentrated. Normal phase column (SiO$_2$, 25% EtOAc/hexanes) failed to separate the closely eluting spots, which include the starting material methyl 4-bromo-3-(2-methylallyloxy)benzoate (1 g, 3.51 mmol) and the desired product. The product-containing fractions were collected and concentrated to be purified by preparatory HPLC (55% MeCN/H$_2$O+0.01% TFA). Collected fractions were concentrated to about 50 mL; saturated NaHCO$_3$ (10 mL) was added to the residue, and the mixture was extracted twice with ethyl acetate. Combined organic layers were dried over MgSO$_4$, filtered and concentrated to give the desired product methyl 3,3-dimethyl-2,3-dihydrobenzofuran-6-carboxylate (32 mg, 4% yield). $^1$H NMR (METHANOL-d$_4$) δ: 7.56 (dd, J=7.7, 1.4 Hz, 8H), 7.31 (s, 1H), 7.20 (d, J=7.8 Hz, 8H), 4.87 (s, 3H), 4.25 (s, 2H), 3.86 (s, 3H), 1.33 (s, 6H); ESI-MS: m/z 207.1 (M+H)+.

Step C: In a 50 ml pear flask containing methyl 3,3-dimethyl-2,3-dihydrobenzofuran-6-carboxylate (32 mg, 0.16 mmol) were added methanol (3 ml) and 1.0 M sodium hydroxide (6 ml, 6 mmol) solution to give a suspension. This was stirred at room temperature for 1 hour. Then 2N hydrochloride solution (3.5 ml) was added to neutralize the excess base. The acidic mixture (pH ~2) was then extracted with EtOAc twice, and the combined organic layers were dried over MgSO$_4$, filtered and concentrated to give the desired 3,3-dimethyl-2,3-dihydrobenzofuran-6-carboxylic acid (23 mg, 77% yield) as a white flakey oily solid that was used in the next step without further purification.

Step D: In a 5 ml pear flask was added 3,3-dimethyl-2,3-dihydrobenzofuran-6-carboxylic acid (23 mg, 0.120 mmol) in anhydrous toluene (Volume: 1 mL) to give a colorless solution. At room temperature, oxalyl dichloride (2.0 M in dichloromethane) (0.24 mL, 0.45 mmol) was added, followed by one small drop of DMF. The mixture was then heated to 65° C. for 2.5 hours, after which HPLC showed all the starting acid had been consumed. The mixture, now yellow, was cooled to room temperature. Toluene (5 ml) was added and the mixture was concentrated to dryness. The process was repeated to remove residual volatiles azeotropically. The crude product 3,3-dimethyl-2,3-dihydrobenzofuran-6-carbonyl chloride as a light brown, oily residue was used in the next step without further purification.

Step E: In a 25 ml pear flask containing crude 3,3-dimethyl-2,3-dihydrobenzofuran-6-carbonyl chloride (25 mg, 0.12 mmol) was added pyridine (1 mL), immediately followed by 2-methyl-7-phenylpyrazolo[1,5-a]pyrimidin-5-amine (10A, 26.9 mg, 0.120 mmol). The mixture was stirred at room temperature for ~16 h. The reaction mixture was partitioned between saturated NaHCO$_3$ and ethyl acetate, and the aqueous layer was extracted one more time with ethyl acetate. Combined organic layers were washed once more with brine, dried over MgSO$_4$, filtered and concentrated. The crude product was purified by SiO$_2$ (20% EtOAc, second spot from the top) to give an off-white solid. To facilitate transfer of the small amount of product, the solid was dissolved in 0.5 mL of acetonitrile, and then suspended in 15 mL of water. Lyophilization of the mixture gave the titled product (5.1 mg, 11% yield). $^1$H NMR (CHLOROFORM-d) δ: 8.58 (s, 1H), 8.08-8.15 (m, 3H), 7.53-7.59 (m, 3H), 7.46 (dd, J=7.7, 1.6 Hz, 1H), 7.34 (d, J=1.3 Hz, 1H), 7.22 (d, J=7.8 Hz, 1H), 6.28 (s, 1H), 4.31-4.34 (m, 2H), 2.50 (s, 3H), 1.36-1.42 (m, 6H); ESI-MS: m/z 399.4 (M+H)+.

Example 345

N-(2-methyl-7-phenylpyrazolo[1,5-a]pyrimidin-5-yl)-2-(pyridin-4-yl)cyclopropanecarboxamide (331)

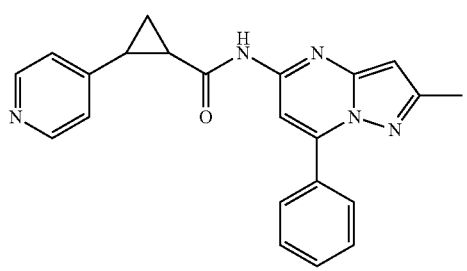

331

In a round-bottomed flask was 2-(pyridin-4-yl)cyclopropanecarbonyl chloride (7D, 190 mg, 1.05 mmol) added in Pyridine (2 mL) to give a yellow suspension. 2-methyl-7-phenylpyrazolo[1,5-a]pyrimidin-5-amine (10A, 213 mg, 0.951 mmol) was added portionwise at 0° C. The temperature was slowly raised to room temperature. The reaction was quenched with saturated sodium bicarbonate and partitioned between ethyl acetate and water. The separated organic layer was dried over Mg$_2$SO$_4$, filtered, and concentrated under reduced pressure (3×100 mL). The reaction mixture was filtered and purified by preparatory, 5-95% (10 mM NH$_4$HCO$_3$ (aq)/10 mM NH$_4$HCO$_3$ in 20/80 (v/v) H$_2$O/MeCN). Received 9 mg (3%) of yellow solid. $^1$H NMR (DMSO-d$_6$) δ: 11.32 (s, 1H), 8.46 (d, J=6.1 Hz, 2H), 7.94-8.06 (m, 2H), 7.88 (s, 1H), 7.53-7.67 (m, 3H), 7.15-7.26 (m, 2H), 6.33 (s, 1H), 2.37 (s, 3H), 1.50-1.66 (m, 2H). ESI-MS: m/z 370.0 (M+H)$^+$.

Example 346

N-(7-(4-(cyclopropanecarboxamido)piperidin-1-yl)-2-methylpyrazolo[1,5-a]pyrimidin-5-yl)-4-(2-hydroxypropan-2-yl)benzamide (332)

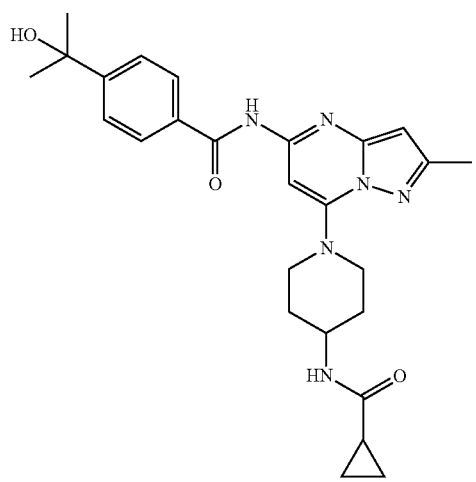

332

N-(7-(4-aminopiperidin-1-yl)-2-methylpyrazolo[1,5-a]pyrimidin-5-yl)-4-(2-hydroxypropan-2-yl)benzamide (6B, 250 mg, 0.612 mmol) was dissolved in anhydrous pyridine (1.2 mL). Cyclopropanecarbonyl chloride (61 µL, 0.673 mmol) was added at 0° C., and the mixture was stirred in an ice bath and warmed to room temperature. The reaction was complete as determined by LCMS analysis. The reaction was then quenched with saturated NaHCO$_3$; pyridine was removed in vacuo and the residue was extracted with EtOAc. Purification by preparatory HPLC (30-50% MeCN/H$_2$O gradient+0.01% TFA) provided the titled compound as a white solid (22 mg, 8%). Melting point (214.0-214.1° C.). $^1$H NMR (DMSO-d$_6$) δ: 10.83 (s, 1H), 8.13 (d, J=7.8 Hz, 1H), 7.99 (d, J=8.8 Hz, 2H), 7.59 (d, J=8.6 Hz, 2H), 7.36 (s, 1H), 6.15 (s, 1H), 4.35 (br. s., 2H), 3.93 (br. s., 2H), 3.15-3.26 (m, 2H), 2.38 (t, 3H), 1.92 (d, J=9.9 Hz, 2H), 1.48-1.71 (m, 3H), 1.45 (s, 6H), 0.55-0.73 (m, 4H). ESI-MS: m/z 477.0 (M+H)$^+$.

Example 347

4-(2-cyanopropan-2-yl)-N-(2-methyl-7-phenylpyrazolo[1,5-a]pyrimidin-5-yl)benzamide (333)

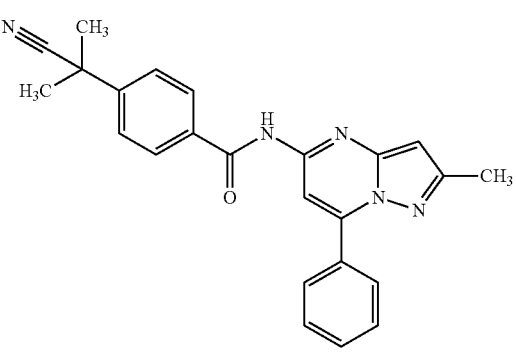

333

Step A: In a 200 ml, nitrogen-flushed pear flask was added indium(III) bromide (0.71 g, 2.0 mmol) in dichloromethane (40 ml) to give a white suspension. To this at room temperature was added trimethylsilyl cyanide (5.3 ml, 40 mmol), followed by drop-wise addition of p,α,α-trimethylbenzyl alcohol (3.1 ml, 20 mmol) to give a moderate exothermic reaction. The mixture slowly turned clear, and HPLC showed mostly the desire product. Saturated NaHCO$_3$ was added and the mixture was concentrated in vacuo to remove the volatiles. The residue was partitioned between saturated NaHCO$_3$ and ethyl acetate, and the aqueous layer was extracted one more time with ethyl acetate. Combined organic layers were dried over MgSO$_4$, filtered and concentrated. The crude product was purified by column chromatography (SiO$_2$, 5% EtOAc/hexanes) to give the desired product 2-methyl-2-p-tolylpropanenitrile (2.3 g, 71% yield) as a colorless oil.

Step B: In a 100 mL round-bottomed flask was added 2-methyl-2-p-tolylpropanenitrile (1.5 g, 9.4 mmol) in pyridine (7.54 m). At room temperature, water (30 ml) was added to give a white suspension, followed by the addition of potassium permanganate (4.5 g, 28 mmol). The mixture was heated to 70° C. for six hours and was then let stand for 9 hours at room temperature. The purplish brown suspension was filtered through a pad of washed Celite, and the flask and pad were rinsed with more water. The filtrate, a hazy pinkish solution, was filtered once more with a syringe filter. The mixture was then acidified with 2N hydrochloric acid to pH 1. The resulting white precipitate was then collected on a medium-pore frit, washed with water and then dried in a stream of nitrogen overnight to give the desired product 4-(2-cyanopropan-2-yl)benzoic acid (1.3 g, 70% yield) as a white powder.

Step C: In a 50 ml pear flask was placed 4-(2-cyanopropan-2-yl)benzoic acid (500 mg, 2.6 mmol) in toluene (13 mL) to give a white suspension. To this at 0° C. was then added oxalyl chloride (2.0 M in dichloromethane) (5.3 mL, 11 mmol), followed by a small drop of DMF. The mixture was then heated to 60° C. for 2 h; after cooling down to room temperature, the mixture was concentrated in vacuo. The residual volatiles were removed azeotropically with toluene twice. The final crude product 4-(2-cyanopropan-2-yl)benzoyl chloride was dried in vacuo overnight, and was used in the next reaction without further purification.

Step D: In a 50 ml pear flask was added 2-methyl-7-phenylpyrazolo[1,5-a]pyrimidin-5-amine (10A, 450 mg, 2.0 mmol) in pyridine (10 ml). To this mixture was added 4-(2-cyanopropan-2-yl)benzoyl chloride (550 mg, 2.6 mmol) and the mixture was stirred at room temperature for 2 h. Saturated NaHCO$_3$ was then added and pyridine was removed in vacuo. The residue was partitioned between saturated NaHCO$_3$ and ethyl acetate, and the aqueous layer was extracted one more time with ethyl acetate. Combined organic layers were dried over MgSO$_4$, filtered and concentrated. The crude product was purified by column chromatography (SiO$_2$, 15-25% EtOAc/hexanes) to give the titled compound (380 mg, 48%). $^1$H NMR (DMSO-d$_6$) δ: 11.35 (s, 1H), 8.10-8.16 (m, 2H), 8.04-8.09 (m, 2H), 7.96 (s, 1H), 7.67-7.73 (m, 2H), 7.60-7.66 (m, 3H), 6.41 (s, 1H), 2.41 (s, 3H), 1.74 (s, 6H); ESI-MS: m/z 396.3 (M+H)$^+$.

Example 348

4-(1-amino-2-methylpropan-2-yl)-N-(2-methyl-7-phenylpyrazolo[1,5-a]pyrimidin-5-yl)benzamide (334)

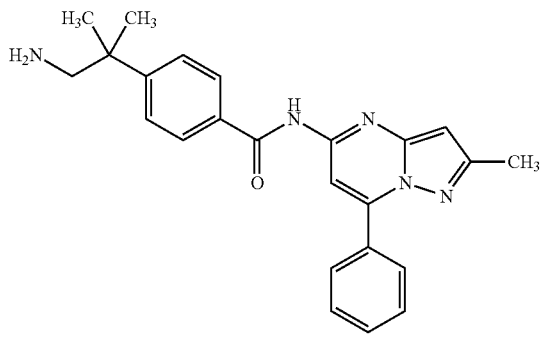

4-(2-Cyanopropan-2-yl)-N-(2-methyl-7-phenylpyrazolo[1,5-a]pyrimidin-5-yl)benzamide (Compound 343 (Example 357), 75 mg, 0.19 mmol) was dissolved in methanol (5 ml). The solution was subjected to hydrogenation conditions in a flow-hydrogenator, using Raney nickel cartridge, with 30 bar of hydrogen pressure, 50° C. temperature and a flow rate of 0.5 ml/min. The reaction mixture was concentrated in vacuo to obtain the titled product 4-(1-amino-2-methylpropan-2-yl)-N-(2-methyl-7-phenylpyrazolo[1,5-a]pyrimidin-5-yl)benzamide (45 mg, 59% yield). $^1$H NMR(CHLOROFORM-d) δ: 8.59 (br. s., 1H), 8.07-8.20 (m, 3H), 7.91 (d, J=8.3 Hz, 2H), 7.46-7.61 (m, 5H), 6.29 (s, 1H), 2.87 (br. s., 2H), 2.50 (s, 5H), 1.36 (s, 8H), 0.87 (br. s., 3H); ESI-MS: m/z 400.4 (M+H)$^+$.

Example 349

2-(2-methyl-2-(4-(2-methyl-7-phenylpyrazolo[1,5-a]pyrimidin-5-ylcarbamoyl)phenyl)propylamino)-2-oxoacetic acid (335)

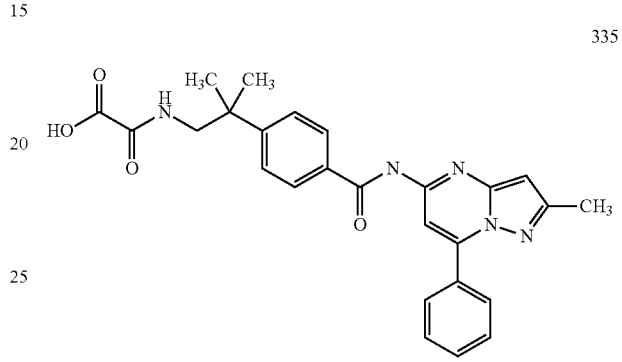

Step A: In a 25 ml pear flask were placed 4-(1-amino-2-methylpropan-2-yl)-N-(2-methyl-7-phenylpyrazolo[1,5-a]pyrimidin-5-yl)benzamide (Compound 334 (Example 348), 36 mg, 0.090 mmol) and N,N-diisopropylethylamine (0.024 ml, 0.14 mmol) in dichloromethane (1 ml). To the mixture at 0° C. was added methyl oxalyl chloride (9.1 μl, 0.099 mmol). In 5 minutes, UPLC showed that most of the starting material has been converted to product. The mixture was stirred for another 30 minutes at 0° C., before being partitioned between brine and ethyl acetate, and the aqueous layer was extracted one more time with ethyl acetate. Combined organic layers were dried over MgSO$_4$, filtered and concentrated to give the crude product methyl 2-(2-methyl-2-(4-(2-methyl-7-phenylpyrazolo[1,5-a]pyrimidin-5-ylcarbamoyl)phenyl)propylamino)-2-oxoacetate.

Step B: Methyl 2-(2-methyl-2-(4-(2-methyl-7-phenylpyrazolo[1,5-a]pyrimidin-5-ylcarbamoyl)phenyl)propylamino)-2-oxoacetate was dissolved in MeOH (1 ml). Lithium hydroxide (2 N aqueous solution, 1 ml) was then added. The mixture was stirred for 30 minutes at room temperature. Hydrochloric acid (2N aqueous solution) was added to acidify the mixture to pH 3. The reaction mixture was partitioned between brine and ethyl acetate, and the aqueous layer was extracted one more time with ethyl acetate. Combined organic layers were dried over MgSO$_4$, filtered and concentrated. The crude product was purified by preparatory HPLC (55-65% MeCN/H$_2$O gradient+0.01% TFA). Combined fractions were concentrated in vacuo to give a suspension. The precipitate was collected on a small fritted funnel, washed with water, and then dried under a stream of nitrogen to give the titled product (16 mg, 38% yield) as a white powder. $^1$H NMR (DMSO-d$_6$) δ: 11.22 (s, 1H), 8.47 (br. s., 1H), 8.00-8.16 (m, 4H), 7.96 (s, 1H), 7.64 (d, J=2.5 Hz, 3H), 7.55 (d, J=8.6 Hz, 2H), 6.40 (s, 1H), 2.40 (s, 3H), 1.30 (s, 6H); ESI-MS: m/z 400.4 (M+H)$^+$.

Example 350

N-(7-(4-acetamidopiperidin-1-yl)-2-methylpyrazolo[1,5-a]pyrimidin-5-yl)-2-(pyridin-4-yl)cyclopropanecarboxamide (336)

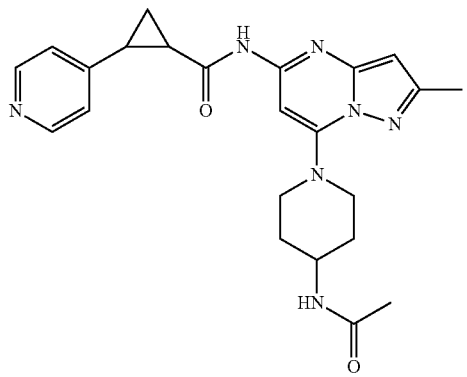

336

A solution of N-(7-chloro-2-methylpyrazolo[1,5-a]pyrimidin-5-yl)-2-(pyridin-4-yl)cyclopropanecarboxamide (7E, 100 mg, 0.305 mmol) and N-(piperidin-4-yl)acetamide (87 mg, 0.610 mmol) in NMP (1 mL) was stirred at room temperature overnight. After cooling to room temperature, the mixture was diluted with a few drops of DMSO and methanol, and was then purified by preparatory HPLC (10-40% MeCN/H$_2$O gradient+0.01% TFA). Lyophilization of the combined fractions gave the titled compound as a white solid (12 mg, 9%). $^1$H NMR (DMSO-d$_6$) δ: 10.98 (s, 1H), 8.45 (d, J=5.8 Hz, 2H), 7.90 (d, J=7.8 Hz, 1H), 7.27 (s, 1H), 7.20 (d, J=6.1 Hz, 2H), 6.08 (s, 1H), 4.28 (br. s., 2H), 3.88 (br. s., 2H), 3.15 (d, J=3.0 Hz, 2H), 2.40-2.47 (m, 2H), 2.30-2.37 (m, 3H), 1.85-1.96 (m, 2H), 1.81 (s, 3H), 1.46-1.62 (m, 3H). ESI-MS: m/z 434.0 (M+H)$^+$.

Example 351

N-(2-methyl-7-(4-ureidopiperidin-1-yl)pyrazolo[1,5-a]pyrimidin-5-yl)-2-(pyridin-4-yl)cyclopropanecarboxamide (337)

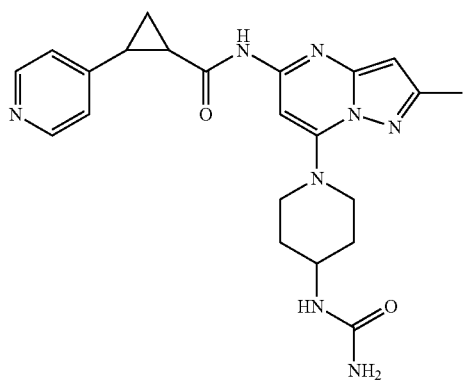

337

A solution of N-(7-chloro-2-methylpyrazolo[1,5-a]pyrimidin-5-yl)-2-(pyridin-4-yl)cyclopropanecarboxamide (7E, 154 mg, 0.469 mmol) and 1-(piperidin-4-yl)urea hydrochloride (169 mg, 0.939 mmol) in NMP (1.5 mL) was stirred at room temperature overnight. After cooling to room temperature, the mixture was diluted with a few drops of DMSO and methanol, and was then purified by preparatory HPLC (10-40% MeCN/H$_2$O gradient+0.01% TFA). Lyophilization of the combined fractions gave the titled compound as a white solid (12 mg, 2%). $^1$H NMR (DMSO-d$_6$) δ: 10.97 (s, 1H), 8.33-8.52 (m, 2H), 7.07-7.37 (m, 4H), 6.08 (s, 2H), 5.41 (s, 2H), 4.24 (br. s., 2H), 3.65 (br. s., 2H), 3.16 (br. s., 2H), 2.35 (s, 3H), 1.89 (br. s., 2H), 1.50 (br. s., 4H). ESI-MS: m/z 435.0 (M+H)$^+$.

Example 352

6-(2-hydroxypropan-2-yl)-N-(7-(4-methoxyphenyl)-2-methylpyrazolo[1,5-a]pyrimidin-5-yl)nicotinamide, trifluoroacetate salt (338)

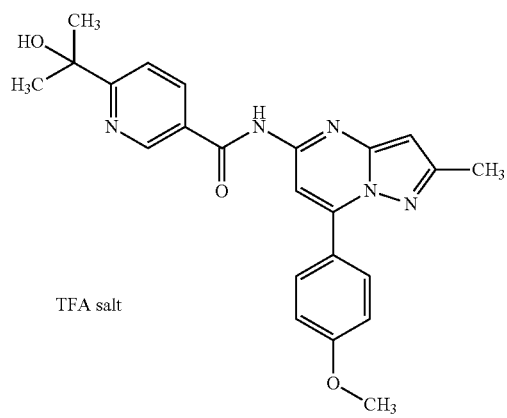

338

TFA salt

In a 2 ml microwave vial were placed N-(7-chloro-2-methylpyrazolo[1,5-a]pyrimidin-5-yl)-6-(2-hydroxypropan-2-yl)nicotinamide (11C, 75 mg, 0.28 mmol), 4-methoxyphenylboronic acid (33 mg, 0.28 mmol) and [1,1'-bis(diphenylphosphino)ferrocene]-dichloropalladium(II) (8.9 mg, 11 μmol). To the sealed vial was then added 1,4-dioxane (1 ml) and saturated aqueous NaHCO$_3$ (0.5 ml) to give a suspension. The mixture was then heated in the microwave at 120° C. for 20 minutes. After cooling to room temperature, DMF (1 ml) was added and the crude product mixture was filtered by syringe filter and purified by preparatory HPLC (40-50% MeCN/H$_2$O gradient+0.01% TFA). Lyophilization of the collected fractions gave the titled product (76 mg, 84% yield) as an off-white powder. $^1$H NMR (DMSO-d$_6$) δ: 11.36 (s, 3H), 9.03 (dd, J=2.3, 0.8 Hz, 3H), 8.34 (dd, J=8.2, 2.1 Hz, 3H), 8.02-8.07 (m, 7H), 7.88 (s, 3H), 7.76 (d, J=8.3 Hz, 3H), 7.10-7.14 (m, 7H), 6.32 (s, 3H), 3.81 (s, 10H), 2.35 (s, 3H), 1.42 (s, 6H); ESI-MS: m/z 418.3 (M+H)$^+$.

Example 353

N-(7-(benzo[d][1,3]dioxol-5-yl)-2-methylpyrazolo[1,5-a]pyrimidin-5-yl)-6-(2-hydroxypropan-2-yl)nicotinamide, trifluoroacetate salt (339)

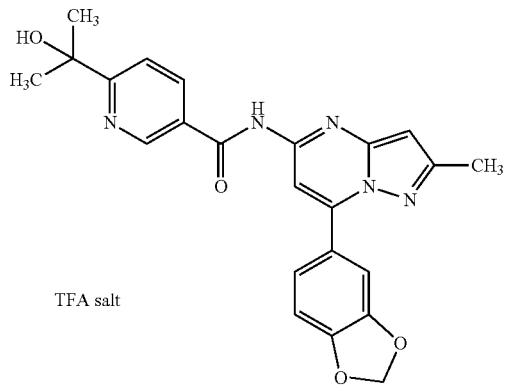

TFA salt

In a 2 ml microwave vial were placed N-(7-chloro-2-methylpyrazolo[1,5-a]pyrimidin-5-yl)-6-(2-hydroxypropan-2-yl)nicotinamide (11C, 75 mg, 0.28 mmol), 3,4-(methylenedioxy)phenylboronic acid (36 .mg, 0.28 mmol) and [1,1'-bis(diphenylphosphino)ferrocene]-dichloropalladium(II) (8.9 mg, 11 µmol). To the sealed vial was then added 1,4-dioxane (1 ml) and saturated aqueous NaHCO$_3$ (0.5 ml) to give a suspension. The mixture was then heated in the microwave at 120° C. for 20 minutes. After cooling to room temperature, DMF (1 ml) was added and the crude product mixture was filtered by syringe filter and purified by preparatory HPLC (40-50% MeCN/H$_2$O gradient+0.01% TFA). Lyophilization of the collected fractions gave the titled product (33 mg, 35% yield) as a light yellow powder. $^1$H NMR (DMSO-d$_6$) δ: 11.41 (s, 2H), 9.09 (dd, J=2.5, 0.8 Hz, 2H), 8.37 (dd, J=8.3, 2.3 Hz, 2H), 7.92 (s, 2H), 7.80 (dd, J=8.2, 0.9 Hz, 2H), 7.70 (d, J=1.8 Hz, 2H), 7.61 (dd, J=8.1, 1.8 Hz, 2H), 7.17 (d, J=8.1 Hz, 2H), 6.39 (s, 2H), 6.18 (s, 4H), 2.41 (s, 5H), 1.48 (s, 6H); ESI-MS: m/z 432.3 (M+H)$^+$.

Example 354

N-(7-(2,3-dihydrobenzofuran-5-yl)-2-methylpyrazolo[1,5-a]pyrimidin-5-yl)-6-(2-hydroxypropan-2-yl)nicotinamide, trifluoroacetate salt (340)

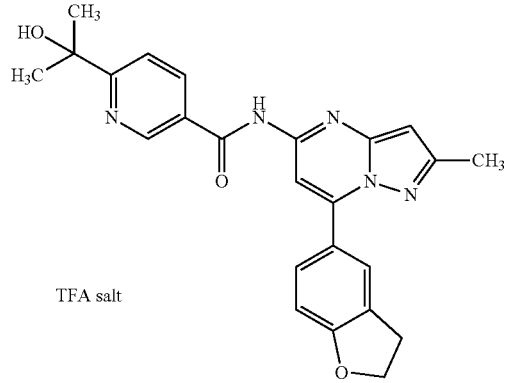

TFA salt

In a 2 m microwave vial was placed N-(7-chloro-2-methylpyrazolo[1,5-a]pyrimidin-5-yl)-6-(2-hydroxypropan-2-yl)nicotinamide (11C, 75 mg, 0.21 mmol), 2,3-dihydrobenzofuran-5-boronic acid (36 mg, 0.21 mmol) and [1,1'-bis(diphenylphosphino)ferrocene]-dichloropalladium(II) (8.9 mg, 11 µmmol). To the sealed vial was then added 1,4-dioxane (1 ml) and saturated aqueous NaHCO$_3$ (0.5 ml) to give a suspension. The mixture was then heated in the microwave at 120° C. for 20 minutes. After cooling to room temperature, DMF (0.5 ml) was added and the crude product mixture was filtered by syringe filter and purified by preparatory HPLC (30-50% MeCN/H$_2$O gradient+0.01% TFA). Lyophilization of the collected fractions gave the titled product (65 mg, 70% yield) as a yellow powder. $^1$H NMR (DMSO-d$_6$) δ: 11.33 (s, 2H), 9.03 (dd, J=2.3, 0.8 Hz, 2H), 8.33 (dd, J=8.3, 2.3 Hz, 2H), 7.95 (d, J=1.8 Hz, 2H), 7.84-7.88 (m, 4H), 7.73-7.76 (m, 2H), 6.94 (d, J=8.3 Hz, 2H), 6.31 (d, J=0.5 Hz, 2H), 4.60 (t, J=8.8 Hz, 4H), 3.23-3.28 (m, 7H), 2.35 (s, 5H), 1.41 (s, 6H); ESI-MS: m/z 430.3 (M+H)+.

Example 355

N-(7-(4-acetamidopiperidin-1-yl)-2-methylpyrazolo[1,5-a]pyrimidin-5-yl)-6-(2-hydroxypropan-2-yl)nicotinamide, trifluoroacetate salt (341)

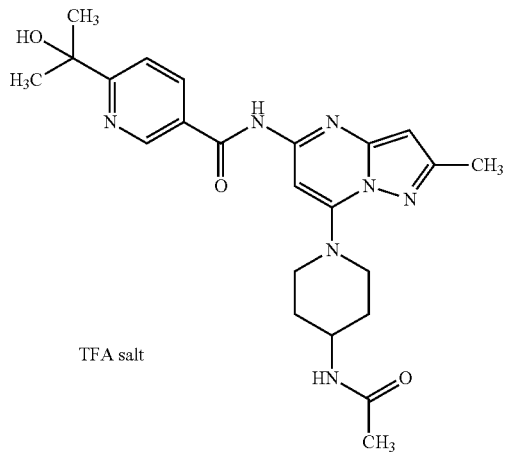

TFA salt

341

In a 2 ml microwave vial was placed N-(7-chloro-2-methylpyrazolo[1,5-a]pyrimidin-5-yl)-6-(2-hydroxypropan-2-yl)nicotinamide (11C, 75 mg, 0.21 mmol) and N-(piperidin-4-yl)acetamide (31 mg, 0.21 mmol). To the sealed vial was then added NMP (1 ml) and then N,N-diisopropylethylamine (0.042 ml, 0.24 mmol) to give a dark yellow solution. The mixture was then heated in the microwave at 100° C. for 10 minutes. After cooling to room temperature, the crude product mixture was purified by preparatory HPLC (20-40% MeCN/H$_2$O gradient+0.01% TFA). Lyophilization of the collected fractions gave the titled product (77 mg, 79% yield) as an off white powder. $^1$H NMR (DMSO-d$_6$) δ: 11.07 (s, 1H), 9.00 (dd, J=2.4, 0.9 Hz, 1H), 8.33 (dd, J=8.3, 2.3 Hz, 1H), 7.89 (d, J=7.8 Hz, 1H), 7.75 (dd, J=8.3, 0.8 Hz, 1H), 7.26 (s, 1H), 6.11 (d, J=0.5 Hz, 1H), 4.28 (br. s., 2H), 3.76-3.90 (m, 2H), 3.11-3.21 (m, 2H), 2.32 (s, 4H), 1.80-1.90 (m, 3H), 1.76 (s, 3H), 1.51 (d, J=8.8 Hz, 3H), 1.41 (s, 6H); ESI-MS: m/z 452.3 (M+H)+.

Example 356

6-(2-hydroxypropan-2-yl)-N-(2-methyl-7-(4-ureidopiperidin-1-yl)pyrazolo[1,5-a]pyrimidin-5-yl)nicotinamide, trifluoroacetate salt (342)

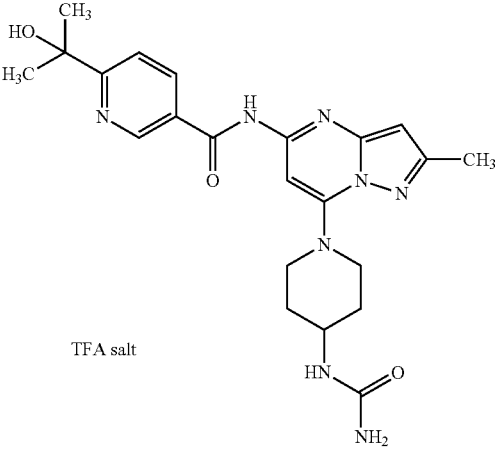

TFA salt

342

In a 2 ml microwave vial was placed N-(7-chloro-2-methylpyrazolo[1,5-a]pyrimidin-5-yl)-6-(2-hydroxypropan-2-yl)nicotinamide (11C, 75 mg, 0.217 mmol) and 1-(piperidin-4-yl)urea, HCl salt (39 mg, 0.22 mmol). To the sealed vial was then added NMP (1 ml) and then N,N-diisopropylethylamine (0.079 ml, 0.46 mmol) to give a deep blue solution. The mixture was then heated in the microwave at 100° C. for 10 minutes. After cooling to room temperature, the crude product mixture was purified by preparatory HPLC (20-40% MeCN/H$_2$O gradient+0.01% TFA). Lyophilization of the collected fractions gave the titled product (47 mg, 48% yield) as an off white powder. $^1$H NMR (DMSO-d$_6$) δ: 11.13 (s, 1H), 9.07 (dd, J=2.4, 0.9 Hz, 1H), 8.38 (dd, J=8.3, 2.3 Hz, 1H), 7.80 (d, J=8.3 Hz, 1H), 7.33 (s, 1H), 6.17 (d, J=0.5 Hz, 1H), 6.06-6.15 (m, 1H), 4.31 (d, J=12.6 Hz, 2H), 3.69 (br. s., 1H), 3.22 (t, J=10.9 Hz, 2H), 2.38 (s, 3H), 1.90-1.99 (m, 2H), 1.51 (br. s., 2H), 1.47 (s, 7H); ESI-MS: m/z 453.3 (M+H)$^+$.

Example 357

N-(7-(4-(2-amino-2-oxoethyl)piperazin-1-yl)-2-methylpyrazolo[1,5-a]pyrimidin-5-yl)-4-(2-hydroxypropan-2-yl)benzamide, trifluoroacetate salt (343)

7.40 (s, 1H), 6.22 (s, 1H), 4.57 (br. s., 2H), 4.04 (s, 2H), 3.49 (br. s., 7H), 2.39 (s, 3H), 1.40-1.54 (m, 6H); ESI-MS: m/z 452.4 (M+H)$^+$.

Example 358

3-methyl-3-(4-(2-methyl-7-phenylpyrazolo[1,5-a]pyrimidin-5-ylcarbamoyl)phenyl)butanoic acid (344)

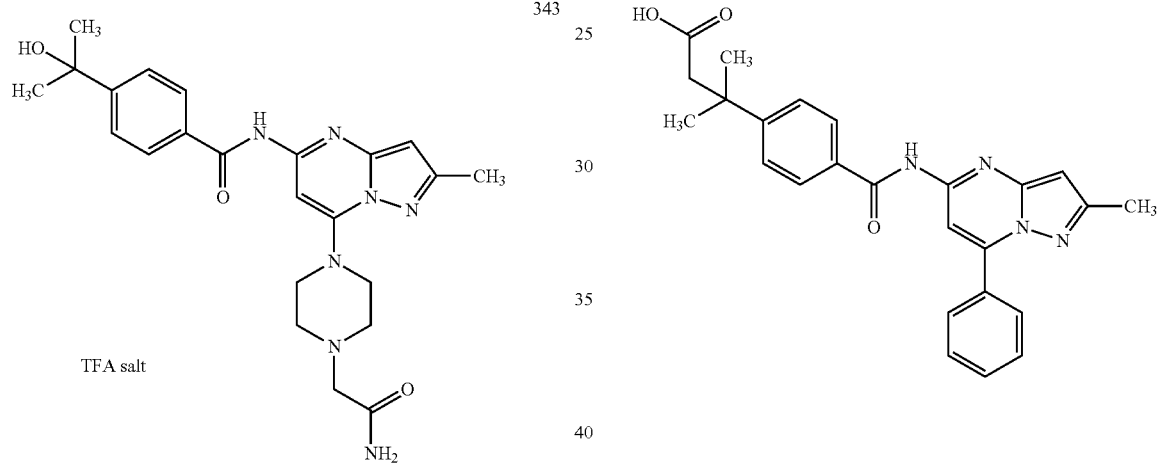

In a 2 ml microwave vial was placed N-(7-chloro-2-methylpyrazolo[1,5-a]pyrimidin-5-yl)-4-(2-hydroxypropan-2-yl)benzamide (2F, 75 mg, 0.22 mmol) and 2-(piperazin-1-yl)acetamide, 2HCl (47.0 mg, 0.22 mmol). To the sealed vial was then added NMP (1 ml) and then N,N-diisopropylethylamine (0.12 ml, 0.70 mmol) to give a deep red solution. The mixture was then heated in the microwave at 100° C. for 10 minutes. After cooling to room temperature, DMF (1 ml) was added. The crude product mixture was filtered by syringe filter and purified by preparatory HPLC (20-30% MeCN/H$_2$O gradient+0.01% TFA). Lyophilization of the collected fractions gave the titled product (42 mg, 43% yield) as a light yellow powder. $^1$H NMR (DMSO-d$_6$) δ: 10.96 (s, 1H), 8.02 (s, 1H), 7.97-8.01 (m, 2H), 7.75 (s, 1H), 7.58-7.63 (m, 2H), In a 50 ml pear flask was added methyl 3-methyl-3-(4-(2-methyl-7-phenylpyrazolo[1,5-a]pyrimidin-5-ylcarbamoyl)phenyl)butanoate (30 mg, 0.068 mmol) in methanol (2 ml) to give a tan solution. To this mixture at room temperature, lithium hydroxide (2N solution) (2 ml, 4.0 mmol) was added. The reaction progress was carefully monitored by HPLC because hydrolysis was a significant competing side reaction. After 2.5 h, most of the starting material has been consumed. The reaction mixture was acidified to pH ~3 with 2N HCl. The resulting suspension was partitioned between brine and ethyl acetate, and the aqueous layer was extracted one more time with ethyl acetate. Combined organic layers were dried over MgSO$_4$, filtered and concentrated. The crude product was purified by preparatory HPLC (55-80% MeCN/H$_2$O gradient+0.01% TFA). Lyophilization of the collected fractions gave the titled product (9.9 mg, 34% yield). $^1$H NMR (DMSO-d$_6$) δ: 11.91 (s, 2H), 11.20 (s, 2H), 8.04-8.08 (m, 3H), 8.02 (d, J=8.8 Hz, 3H), 7.96 (s, 2H), 7.60-7.66 (m, 5H), 7.54 (d, J=8.8 Hz, 2H), 6.40 (s, 1H), 2.66 (s, 2H), 2.40 (s, 3H), 1.41 (s, 6H); ESI-MS: m/z 429.3 (M+H)⁺.

Example 359

Methyl 3-methyl-3-(4-(2-methyl-7-phenylpyrazolo [1,5-a]pyrimidin-5-ylcarbamoyl)phenyl)butanoate (345)

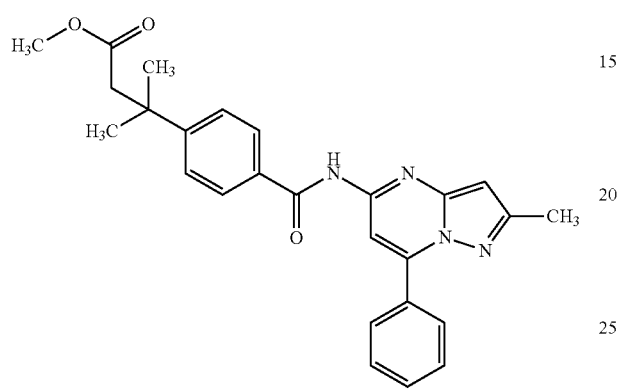

345

Step A: In a 100 ml round-bottomed flask was added methyl 3-methyl-3-p-tolylbutanoate (880 mg, 4.8 mmol) in pyridine (3 mL)). At room temperature, water (12 mL) was added to give a white suspension, followed by the addition of potassium permanganate (2.0 g, 13 mmol). The mixture was heated to 60° C. for 12 hours and was then let stand for 9 hours at room temperature. The purplish brown suspension was filtered through a pad of washed Celite, and the flask and pad were rinsed with more water. The filtrate was then acidified with 2N hydrochloric acid to pH 3. The mixture was partitioned between brine and ethyl acetate, and the aqueous layer was extracted one more time with ethyl acetate. Combined organic layers were dried over MgSO₄, filtered and concentrated to give the crude product 4-(4-methoxy-2-methyl-4-oxobutan-2-yl)benzoic acid (680 mg, 2.88 mmol, 67.5% yield) as an oil. ESI-MS: m/z 237.1 (M+H)⁺.

Step B: In a 25 ml pear flask was added 4-(4-methoxy-2-methyl-4-oxobutan-2-yl)benzoic acid (670 mg, 2.8 mmol) in anhydrous toluene (20 mL). At room temperature, oxalyl dichloride (2.0 M in dichloromethane) (5.7 mL, 11 mmol) was added, followed by two small drops of DMF. The mixture was then heated to 55° C. for 3 hours, after which UPLC showed most of the starting acid had been consumed. The mixture, now yellow, was cooled to room temperature. The mixture was concentrated to dryness. Toluene was added and the mixture was concentrated to dryness again to remove residual volatiles azeotropically. The crude product methyl 3-(4-(chlorocarbonyl)phenyl)-3-methylbutanoate as a light brown, oily residue was used in the next steps without further purification.

Step C: In a 50 ml pear flask was added 2-methyl-7-phenylpyrazolo[1,5-a]pyrimidin-5-amine (10A, 200 mg, 0.89 mmol) in pyridine (5 ml) to give a light yellow solution. A solution of methyl 3-(4-(chlorocarbonyl)phenyl)-3-methylbutanoate (230 mg, 0.89 mmol) in dichloromethane (1 ml) was added to the reaction mixture at room temperature, which was then stirred for 72 h. Saturated NaHCO₃ was added and pyridine was mostly removed in vacuo. The residue was partitioned between saturated NaHCO₃ and ethyl acetate, and the aqueous layer was extracted one more time with ethyl acetate. Combined organic layers were dried over MgSO₄, filtered and concentrated. The crude product was purified by column chromatography (SiO₂, 30-40% ethyl acetate/hexanes) to give the titled product (60 mg, 15% yield) as a yellow foam. ¹H NMR(CHLOROFORM-d) δ: 8.61 (s, 2H), 8.10-8.15 (m, 8H), 7.87-7.92 (m, 5H), 7.54-7.59 (m, 8H), 7.50-7.54 (m, 5H), 6.28 (s, 2H), 3.54 (s, 8H), 2.68-2.71 (m, 5H), 2.50 (s, 8H), 1.49 (s, 6H); ESI-MS: m/z 443.3 (M+H)⁺.

Example 360

(1S,2S)—N-(2-Methyl-7-phenylpyrazolo[1,5-a]pyrimidin-5-yl)-2-phenylcyclopropanecarboxamide (346)

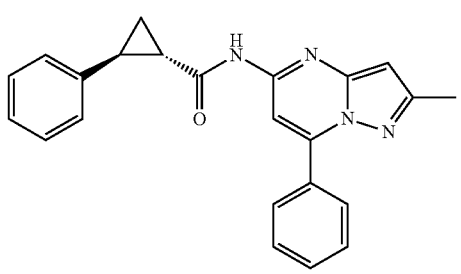

346

In a round-bottomed flask was (1S,2S)-2-phenylcyclopropanecarbonyl chloride (161 mg, 0.892 mmol) added in Pyridine (3 mL) to give a yellow suspension. 2-methyl-7-phenylpyrazolo[1,5-a]pyrimidin-5-amine (10A, 100 mg, 0.446 mmol) was added portionwise at 0° C. The temperature was slowly raised to room temperature. The reaction was quenched with saturated sodium bicarbonate and partitioned between ethyl acetate and water. The separated organic layer was dried over Mg₂SO₄, filtered, and concentrated under reduced pressure (3×100 mL). The reaction mixture was filtered and purified by preparatory HPLC (70-80% MeCN/H₂O gradient+0.01% TFA). Received 46 mg (28%) of yellow solid. ¹H NMR (DMSO-d₆) δ: 11.28 (s, 1H), 7.94-8.06 (m, 2H), 7.90 (s, 1H), 7.52-7.68 (m, 3H), 7.27-7.35 (m, 2H), 7.16-7.26 (m, 3H), 6.33 (s, 1H), 2.42-2.49 (m, 1H), 2.28-2.43

(m, 4H), 1.50-1.57 (m, 1H), 1.44 (ddd, J=8.1, 6.5, 4.0 Hz, 1H); [α]$_D^{20}$=+294° (c=0.6060, MeOH). ESI-MS: m/z 369.0 (M+H)$^+$.

Example 361

(1R,2R)—N-(2-Methyl-7-phenylpyrazolo[1,5-a]pyrimidin-5-yl)-2-phenylcyclopropanecarboxamide (347)

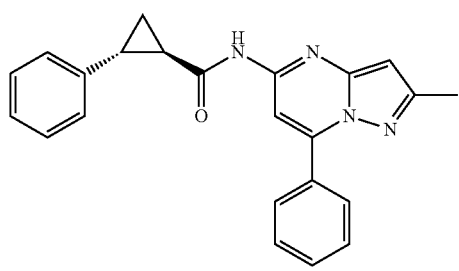

347

In a round-bottomed flask was a mixture of (1R,2R)-2-phenylcyclopropanecarbonyl chloride and cis (+/+, −/−)-2-phenylcyclopropanecarbonyl chloride (200 mg, 1.1 mmol) added in Pyridine (5 mL) to give a yellow suspension. 2-methyl-7-phenylpyrazolo[1,5-a]pyrimidin-5-amine (10A, 124 mg, 0.554 mmol) was added portionwise at 0° C. The temperature was slowly raised to room temperature. The reaction was quenched with saturated sodium bicarbonate and partitioned between ethyl acetate and water. The separated organic layer was dried over Mg$_2$SO$_4$, filtered, and concentrated under reduced pressure (3×100 mL). The reaction mixture was filtered and purified by preparatory HPLC (70-80% MeCN/H$_2$O gradient+0.01% TFA). Received 62 mg (30%) of yellow solid. Melting point (208.2-208.3° C.). $^1$H NMR (DMSO-d$_6$) δ: 11.28 (s, 1H), 7.93-8.10 (m, 2H), 7.90 (s, 1H), 7.55-7.68 (m, 3H), 7.28-7.34 (m, 2H), 7.17-7.25 (m, 3H), 6.33 (s, 1H), 2.42-2.48 (m, 1H), 2.37 (s, 4H), 1.34-1.63 (m, 2H); [α]$_D^{20}$=−238° (c=1.058, MeOH). ESI-MS: m/z 369.0 (M+H)$^+$.

Example 362

(1R,2S)—N-(2-Methyl-7-phenylpyrazolo[1,5-a]pyrimidin-5-yl)-2-phenylcyclopropanecarboxamide (348)

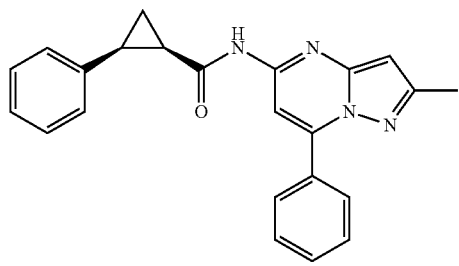

348

Reference protocol for Compound 347 in Example 361. Received 3.8 mg (2%) of yellow solid. $^1$H NMR (DMSO-d$_6$) δ: 11.17 (s, 1H), 7.79-7.94 (m, 2H), 7.49-7.63 (m, 4H), 7.18-7.28 (m, 4H), 7.04-7.16 (m, 1H), 6.29 (s, 1H), 2.58-2.74 (m, 2H), 2.27-2.38 (m, 3H), 1.55-1.71 (m, 1H), 1.26-1.44 (m, 1H). ESI-MS: m/z 369.0 (M+H)$^+$.

Example 363

N-(7-(4-chloro-3-methoxyphenyl)-2-methylpyrazolo[1,5-a]pyrimidin-5-yl)-4-(2-hydroxypropan-2-yl)benzamide (349)

349

A suspension of N-(7-chloro-2-methylpyrazolo[1,5-a]pyrimidin-5-yl)-4-(2-hydroxypropan-2-yl)benzamide (2F, 80 mg, 0.232 mmol), 4-chloro-3-methoxyphenylboronic acid (56.2 mg, 0.302 mmol), and 1,1'-bis(diphenylphosphino)ferrocene]dichloropalladium(II) (16 mg, 22 μmol) in 2:1 1,4-dioxane/saturated aqueous NaHCO$_3$ (0.774 mL of 1,4-dioxane and 0.387 mL of saturated aqueous NaHCO$_3$) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (65-70% MeCN/H$_2$O gradient+0.01% TFA). Lyophilization of the combined fractions gave the titled compound as a yellow solid (42.3 mg, 40%). $^1$H NMR (DMSO-d$_6$) δ: 11.15 (s, 1H), 7.95 (d, J=8.6 Hz, 2H), 7.91 (s, 1H), 7.78 (d, J=1.8 Hz, 1H), 7.59-7.65 (m, 1H), 7.50-7.59 (m, 3H), 6.34 (s, 1H), 3.88 (s, 3H), 2.34 (s, 3H), 1.39 (s, 6H); ESI-MS: m/z 451.1 (M+H)$^+$.

Example 364

N-(2-methyl-7-morpholinopyrazolo[1,5-a]pyrimidin-5-yl)-4-(trifluoromethoxy)benzamide (350)

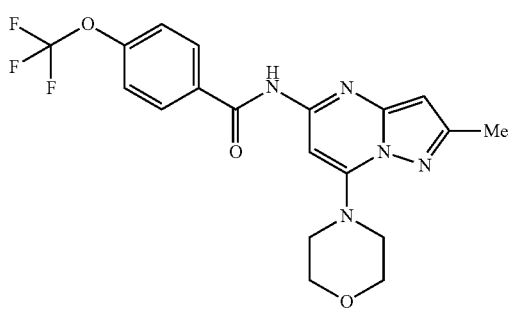

A suspension of 2-methyl-7-morpholinopyrazolo[1,5-a]pyrimidin-5-amine (9B, 52 mg, 0.151 mmol) and pyridine (60 mg, 0.467 mmol) was cooled to 0° C. and treated with 4-trifluoromethoxybenzoyl chloride (78 mg, 0.395 mmol). After stirring for 30 min, the reaction was quenched by the addition of saturated aqueous sodium bicarbonate (5 mL). The aqueous mixture was extracted with ethyl acetate and the combined organics dried over sodium sulfate, filtered, and concentrated in vacuo. The crude material was dissolved in DMF/DMSO, filtered, and purified via preparative HPLC (60-80% MeCN/H$_2$O gradient+0.01% TFA). Lyophilization of the combined fractions gave the titled compound as a yellow solid (44.0 mg, 41%). Melting point (226.2-226.3° C.). $^1$H NMR (DMSO-d$_6$) δ: 11.10 (s, 1H), 8.01-8.27 (m, 2H), 7.51 (dd, J=9.0, 0.9 Hz, 2H), 7.30 (s, 1H), 6.18 (s, 1H), 3.79-3.91 (m, 4H), 3.69-3.75 (m, 4H), 2.38 (s, 3H); ESI-MS: m/z 422.1 (M+H)$^+$. Melting point (226.2-226.3° C.).

Example 365

N-(2-hydroxyethyl)-1-(5-(4-(2-hydroxypropan-2-yl)benzamido)-2-methylpyrazolo[1,5-a]pyrimidin-7-yl)piperidine-3-carboxamide (351)

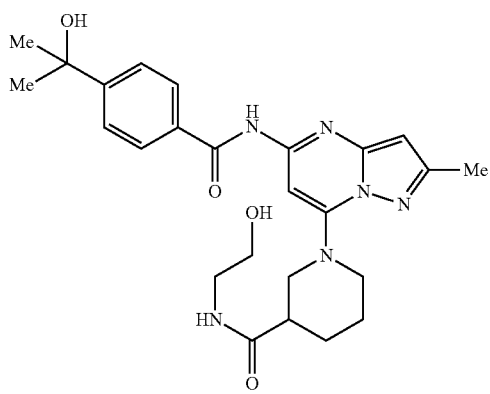

A solution of N-(7-chloro-2-methylpyrazolo[1,5-a]pyrimidin-5-yl)-4-(2-hydroxypropan-2-yl)benzamide (2F, 100 mg, 0.290 mmol), N-(2-hydroxyethyl)piperidine-3-carboxamide (100 mg, 0.580 mmol), and N,N-diisopropylethylamine (112 mg, 0.870 mmol) in DMF (1.0 mL) was stirred at 100° C. for 3 h. After cooling to room temperature, the mixture was diluted with a few drops of DMSO and methanol, and was then purified by preparatory HPLC (20-45% MeCN/H$_2$O gradient+0.01% TFA). Lyophilization of the combined fractions gave the titled compound as a white solid (65.9 mg, 47%). $^1$H NMR (DMSO-d$_6$) δ: 10.95 (s, 1H), 8.12 (t, J=5.6 Hz, 1H), 7.99 (d, J=8.6 Hz, 2H), 7.61 (d, J=8.6 Hz, 2H), 7.22 (s, 1H), 6.21 (s, 1H), 4.16-4.38 (m, 2H), 3.42-3.51 (m, 1H), 3.40 (t, J=6.2 Hz, 2H), 3.04-3.22 (m, 3H), 2.52-2.63 (m, 1H), 2.38 (s, 3H), 1.86-2.00 (m, 1H), 1.61-1.85 (m, 3H), 1.45 (s, 6H); ESI-MS: m/z 481.2 (M+H)$^+$.

Example 366

N-(7-(6-ethoxypyridin-3-yl)-2-methylpyrazolo[1,5-a]pyrimidin-5-yl)-4-(2-hydroxypropan-2-yl)benzamide (352)

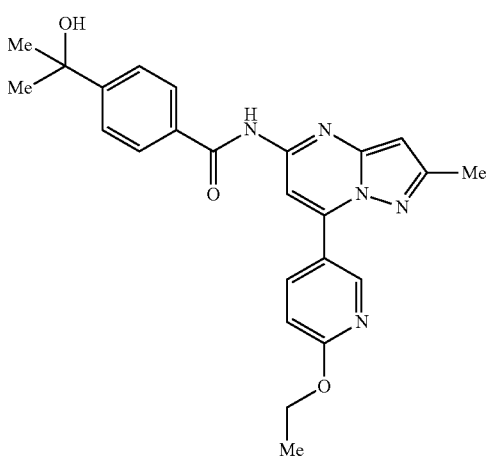

A suspension of N-(7-chloro-2-methylpyrazolo[1,5-a]pyrimidin-5-yl)-4-(2-hydroxypropan-2-yl)benzamide (2F, 100 mg, 0.290 mmol), 6-ethoxypyridin-3-ylboronic acid (63 mg, 0.377 mmol), and 1,1'-bis(diphenylphosphino)ferrocene]dichloropalladium(II) (21 mg, 29 μmol) in 2:1 1,4-dioxane/saturated aqueous NaHCO$_3$ (0.966 mL of 1,4-dioxane and 0.483 mL of saturated aqueous NaHCO$_3$) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (50-60% MeCN/H$_2$O gradient+0.01% TFA). Lyophilization of the combined fractions gave the titled compound as a yellow solid (50.2 mg, 40%). Melting point (183.5-185.5° C.). $^1$H NMR (DMSO-d$_6$) δ: 11.13 (s, 1H), 8.85 (dd, J=2.5, 0.5 Hz, 1H), 8.34 (dd, J=8.6, 2.5 Hz, 1H), 7.95 (d, J=8.8 Hz, 2H), 7.92 (s, 1H), 7.55 (d, J=8.6 Hz, 2H), 6.98 (dd, J=8.8, 0.8 Hz, 1H), 6.32 (s, 1H), 5.11 (br. s., 1H), 4.37 (q, J=6.9 Hz, 2H), 2.34 (s, 3H), 1.39 (s, 6H), 1.31 (t, 3H); ESI-MS: m/z 432.2 (M+H)+. Melting point (183.5-185.5° C.).

Example 367

4-(2-hydroxypropan-2-yl)-N-(7-(6-isopropoxypyridin-3-yl)-2-methylpyrazolo[1,5-a]pyrimidin-5-yl)benzamide (353)

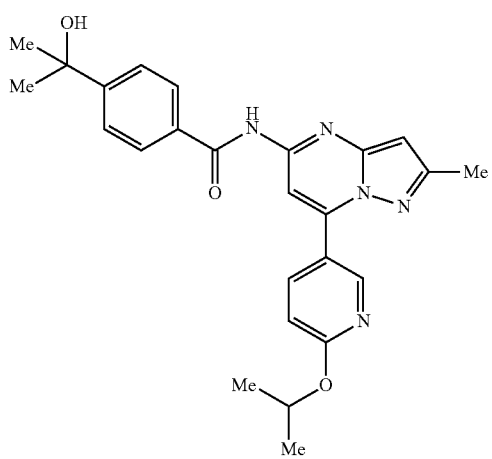

A suspension of N-(7-chloro-2-methylpyrazolo[1,5-a]pyrimidin-5-yl)-4-(2-hydroxypropan-2-yl)benzamide (2F, 100 mg, 0.290 mmol), 2-isopropoxy-5-(4,4,5,5-tetramethyl-1,3,2-dioxaborolan-2-yl)pyridine (78 mg, 0.296 mmol), and 1,1'-bis(diphenylphosphino)ferrocene]dichloropalladium(II) (21 mg, 29 μmol) in 2:1 1,4-dioxane/saturated aqueous NaHCO₃ (0.966 mL of 1,4-dioxane and 0.483 mL of saturated aqueous NaHCO₃) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (50-85% MeCN/H₂O gradient+0.01% TFA). Lyophilization of the combined fractions gave the titled compound as a yellow solid (48.1 mg, 37.2%). ¹H NMR (DMSO-d₆) δ: 11.13 (s, 1H), 8.85 (dd, J=2.5, 0.5 Hz, 1H), 8.30-8.35 (m, 1H), 7.95 (d, J=8.8 Hz, 2H), 7.92 (s, 1H), 7.55 (d, J=8.6 Hz, 2H), 6.92 (dd, J=8.7, 0.6 Hz, 1H), 6.32 (d, J=0.5 Hz, 1H), 5.32 (spt, J=6.2 Hz, 1H), 5.13 (br. s., 1H), 3.50 (s, 1H), 2.34 (s, 3H), 1.39 (s, 6H), 1.29 (d, J=6.1 Hz, 6H); ESI-MS: m/z 446.1 (M+H)+.

Example 368

N-(7-(6-(cyclopropylmethoxy)pyridin-3-yl)-2-methylpyrazolo[1,5-a]pyrimidin-5-yl)-4-(2-hydroxypropan-2-yl)benzamide (354)

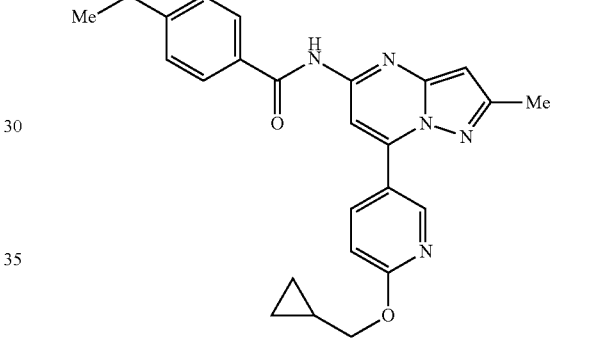

A suspension of N-(7-chloro-2-methylpyrazolo[1,5-a]pyrimidin-5-yl)-4-(2-hydroxypropan-2-yl)benzamide (2F, 100 mg, 0.290 mmol), 2-(cyclopropylmethoxy)-5-(4,4,5,5-tetramethyl-1,3,2-dioxaborolan-2-yl)pyridine (104 mg, 0.377 mmol), and 1,1'-bis(diphenylphosphino)ferrocene]dichloropalladium(II) (21 mg, 29 μmol) in 2:1 1,4-dioxane/saturated aqueous NaHCO₃ (0.966 mL of 1,4-dioxane and 0.483 mL of saturated aqueous NaHCO₃) was prepared in a 10 mL microwave reaction vessel and the sealed reaction vessel warmed to 110° C. for 10 minutes in a CEM microwave reactor. The reaction mixture was cooled to rt, diluted with methanol, filtered, and purified via preparative HPLC (75-75% MeCN/H₂O gradient+0.01% TFA). Lyophilization of the combined fractions gave the titled compound as a yellow solid (53.7 mg, 41%). ¹H NMR (DMSO-d₆) δ: 11.19 (s, 1H), 8.90 (d, J=2.5 Hz, 1H), 8.40 (dd, J=8.8, 2.5 Hz, 1H), 8.01 (d, J=8.6 Hz, 2H), 7.98 (s, 1H), 7.61 (d, J=8.6 Hz, 2H), 7.07 (d, J=8.8 Hz, 1H), 6.38 (s, 1H), 5.19 (br. s., 1H), 4.22 (d, J=7.1 Hz, 2H), 2.40 (s, 3H), 1.45 (s, 6H), 1.25-1.36 (m, 1H), 0.52-0.62 (m, 2H), 0.30-0.42 (m, 2H); ESI-MS: m/z 458.3 (M+H)+.

Example 369

N-(2-methyl-7-phenylpyrazolo[1,5-a]pyrimidin-5-yl)-4-(trifluoromethylthio)benzamide (355)

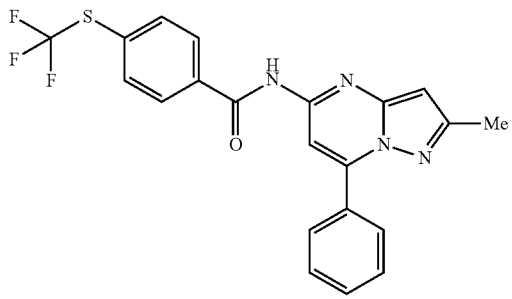

355

A solution of 2-methyl-7-phenylpyrazolo[1,5-a]pyrimidin-5-amine (10A, 62 mg, 0.276 mmol) and pyridine (0.69 mL) in a 20 mL scintillation vial was cooled to 0° C. then treated with 4-(trifluoromethylthio)benzoyl chloride (100 mg, 0.415 mmol). The reaction mixture was stirred for 2 h, partitioned between saturated aqueous sodium bicarbonate and ethyl acetate, and the organic layer subsequently washed with water and then brine. The organic layer was then dried over sodium sulfate, filtered, concentrated under reduced pressure, diluted with methanol, filtered, and purified via preparative HPLC (80-80% MeCN/H$_2$O gradient+0.01% TFA). Lyophilization of the combined fractions gave the titled compound as a yellow solid (58.8 mg, 50%). Melting point (100.9-101.6° C.). $^1$H NMR (DMSO-d$_6$) δ: 11.49 (s, 1H), 8.15 (d, J=8.6 Hz, 2H), 8.06 (dd, J=6.7, 2.9 Hz, 2H), 7.93 (s, 1H), 7.87 (d, J=8.3 Hz, 2H), 7.56-7.66 (m, 3H), 6.41 (s, 1H), 2.40 (s, 3H); ESI-MS: m/z 429.1 (M+H)+. Melting point (100.9-101.6° C.).

Example 370

(1R,2R)—N-(7-(4-acetamidopiperidin-1-yl)-2-methylpyrazolo[1,5-a]pyrimidin-5-yl)-2-phenylcyclopropanecarboxamide (356)

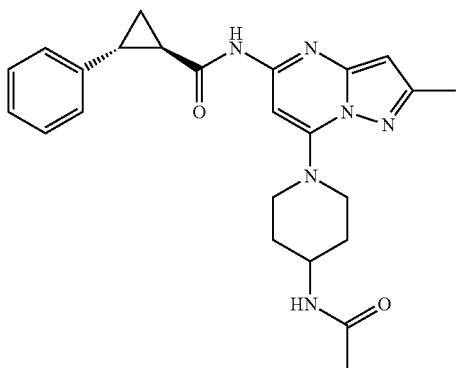

356

The title compound was prepared by combining (1R,2R)—N-(7-chloro-2-methylpyrazolo[1,5-a]pyrimidin-5-yl)-2-phenylcyclopropane carboxamide (8D, 0.1 g, 0.306 mmol) and the N-(piperidin-4-yl)acetamide (0.087 g, 0.612 mmol) in NMP (Volume: 1.020 ml) and heating the mixture at 85° C. overnight. After cooling to room temperature, the mixture was diluted with a few drops of DMSO and methanol, and was then purified by 45-65% preparatory HPLC (MeCN/MeOH)/H$_2$O+0.01% TFA). Lyophilization of the combined fractions gave 87 mg (66%) of the titled compound as a white solid. Melting point (190.2-231.1° C.). $^1$H NMR (DMSO-d$_6$) δ: 10.95 (s, 1H), 7.91 (d, J=7.8 Hz, 1H), 7.23-7.37 (m, 3H), 7.12-7.24 (m, 3H), 6.08 (s, 1H), 4.30 (d, J=12.9 Hz, 2H), 3.88 (br. s., 1H), 3.16 (dd, J=24.3, 11.6 Hz, 2H), 2.39-2.47 (m, 1H), 2.25-2.38 (m, 4H), 1.89 (d, J=13.6 Hz, 2H), 1.82 (s, 3H), 1.46-1.62 (m, 3H), 1.40 (ddd, J=8.2, 6.4, 4.0 Hz, 1H); [α]$_D^{20}$=+218° (C=0.6917, MeOH). ESI-MS: m/z 433.0 (M+H)+. Melting point (190.2-231.1° C.).

Example 371

(1R,2R)—N-(2-methyl-7-(4-ureidopiperidin-1-yl)pyrazolo[1,5-a]pyrimidin-5-yl)-2-phenylcyclopropanecarboxamide (357)

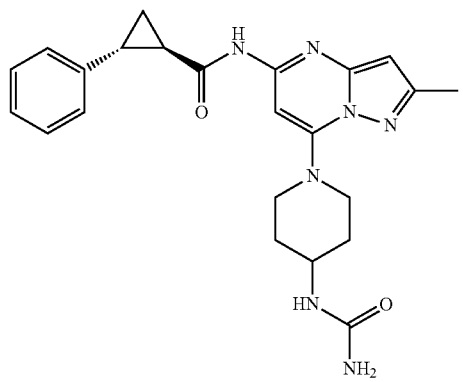

357

The title compound was prepared by combining (1R,2R)—N-(7-chloro-2-methylpyrazolo[1,5-a]pyrimidin-5-yl)-2-phenylcyclopropanecarboxamide (8D, 0.08 g, 0.245 mmol) and the 1-(piperidin-4-yl)urea hydrochloride (0.088 g, 0.490 mmol) in NMP (0.816 ml) and heating the mixture at 85° C. overnight. After cooling to room temperature, the mixture was diluted with a few drops of DMSO and methanol, and was then purified by 40-60% preparatory HPLC (ACN/MeOH)/H$_2$O+0.01% TFA). Lyophilization of the combined fractions gave 63 mg (59%) of the titled compound as a yellow solid. Melting point (160.1-165.7° C.). $^1$H NMR (DMSO-d$_6$) δ: 10.95 (s, 1H), 7.24-7.35 (m, 3H), 7.14-7.24 (m, 3H), 6.08 (s, 3H), 4.24 (d, J=13.1 Hz, 2H), 3.66 (br. s., 2H), 3.17 (dd, J=23.7, 12.1 Hz, 2H), 2.39-2.47 (m, 1H), 2.26-2.38 (m, 4H), 1.90 (d, J=13.1 Hz, 2H), 1.34-1.59 (m, 4H); [α]$_D^{20}$=−202° (c=0.714, MeOH). ESI-MS: m/z 434.0 (M+H)$^+$. Melting point (160.1-165.7° C.).

Example 372

(1S,2S)—N-(7-(4-acetamidopiperidin-1-yl)-2-methylpyrazolo[1,5-a]pyrimidin-5-yl)-2-phenylcyclopropanecarboxamide (358)

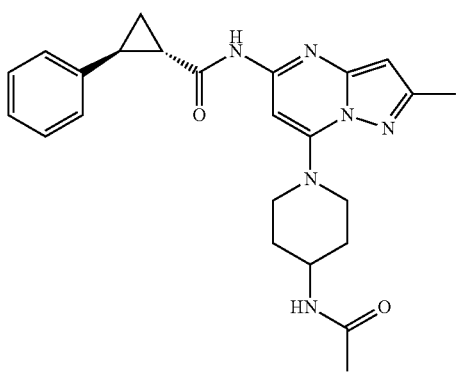

358

The title compound was prepared by combining (1R,2R)—N-(7-chloro-2-methylpyrazolo[1,5-a]pyrimidin-5-yl)-2-phenylcyclopropanecarboxamide (8E, 0.08 g, 0.245 mmol) and the 1-(piperidin-4-yl)urea hydrochloride (0.088 g, 0.490 mmol) in NMP (0.816 ml) and heating the mixture at 85° C. overnight. After cooling to room temperature, the mixture was diluted with a few drops of DMSO and methanol, and was then purified by 40-60% preparatory HPLC (ACN/MeOH)/H$_2$O+0.01% TFA). Lyophilization of the combined fractions gave 63 mg (59%) of the titled compound as a yellow solid. $^1$H NMR (DMSO-d$_6$) δ: 10.95 (s, 1H), 7.24-7.35 (m, 3H), 7.14-7.24 (m, 3H), 6.08 (s, 3H), 4.24 (d, J=13.1 Hz, 2H), 3.66 (br. s., 2H), 3.17 (dd, J=23.7, 12.1 Hz, 2H), 2.39-2.47 (m, 1H), 2.26-2.38 (m, 4H), 1.90 (d, J=13.1 Hz, 2H), 1.34-1.59 (m, 4H); ESI-MS: m/z 433.0 (M+H)$^+$.

Example 373 trans- and cis-2-(4-Fluorophenyl)-N-(2-methyl-7-phenylpyrazolo[1,5-a]pyrimidin-5-yl)cyclopropanecarboxamide (Compounds 359 and 360)

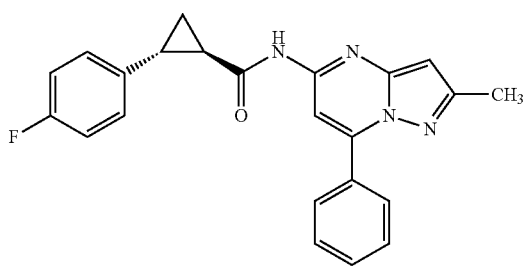

359

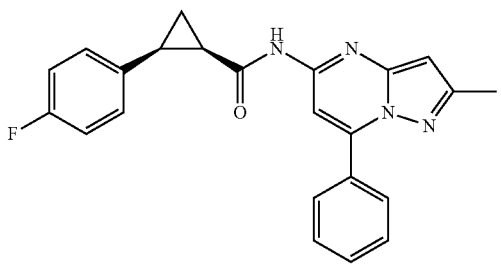

360

In a 2 mL microwave vial were placed N-(7-chloro-2-methylpyrazolo[1,5-c]pyrimidin-5-yl)-2-(4-fluorophenyl)cyclopropanecarboxamide (13B, 0.151 g, 0.437 mmol), phenylboronic acid (0.107 g, 0.875 mmol), and PdCl$_2$(dppf)/DCM (0.029 g, 0.035 mmol). To the sealed vial was then added (2:1) 1,4-Dioxane (1 mL) and saturated sodium bicarbonate (0.5 mL) to give a suspension. The mixture was then heated in the microwave at 120° C. for 20 minutes. After cooling the mixture was filtered and was then purified by preparatory 80-95% HPLC (ACN/MeOH)/H$_2$O HPLC+ 0.01% TFA). Lyophilization of the combined fractions gave both the cis/trans racemic compounds.

The titled trans racemic compound 359 is a yellowish orange solid (103 mg, 61%). $^1$H NMR (DMSO-d$_6$) δ: 11.28 (s, 1H), 7.97-8.06 (m, 2H), 7.89 (s, 1H), 7.56-7.67 (m, 3H), 7.20-7.29 (m, 2H), 7.08-7.18 (m, 2H), 6.33 (s, 1H), 2.44-2.49 (m, 1H), 2.37 (s, 3H), 2.28-2.36 (m, 1H), 1.51 (dt, J=9.5, 4.5 Hz, 1H), 1.43 (ddd, J=8.1, 6.5, 4.3 Hz, 1H); ESI-MS: m/z 387.0 (M+H)$^+$.

The titled cis racemic compound 360 is a yellowish solid (1 mg, 6%). $^1$H NMR (DMSO-d$_6$) δ: 11.28 (s, 1H), 7.98-8.03 (m, 2H), 7.89 (s, 1H), 7.56-7.64 (m, 3H), 7.21-7.30 (m, 2H), 7.08-7.18 (m, 2H), 6.33 (s, 1H), 2.63-2.72 (m, 1H), 2.37 (s, 3H), 2.33 (dd, J=3.7, 1.9 Hz, 1H), 1.48-1.56 (m, 1H), 1.39-1.47 (m, 1H); ESI-MS: m/z 387.3 (M+H)$^+$.

Example 374

N-(7-(4-acetamidopiperidin-1-yl)-2-methylpyrazolo[1,5-a]pyrimidin-5-yl)-2-(4-fluorophenyl)cyclopropanecarboxamide (361)

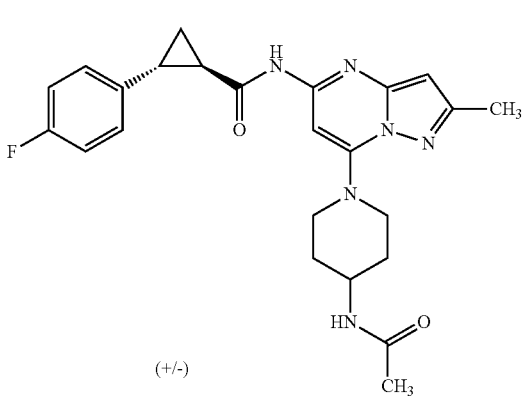

361

The title compound was prepared by combining N-(7-chloro-2-methylpyrazolo[1,5-a]pyrimidin-5-yl)-2-(4-fluorophenyl)cyclopropanecarboxamide (13B, 0.15 g, 0.435 mmol) and the N-(7-chloro-2-methylpyrazolo[1,5-a]pyrimidin-5-yl)-2-(4-fluorophenyl)cyclopropanecarboxamide (0.15 g, 0.435 mmol) in NMP (Volume: 1.450 ml) and heating the mixture at 85° C. overnight. After cooling to room temperature, the mixture was diluted with a few drops of DMSO and methanol, and was then purified by preparatory 60-70% HPLC ([1:1 MeCN/MeOH]/H$_2$O+0.01% TFA). Lyophilization of the combined fractions gave the titled compound as a tan solid (86 mg, 44%). $^1$HNMR (DMSO-d$_6$) δ: 10.95 (s, 1H), 7.91 (d, J=7.8 Hz, 1H), 7.18-7.29 (m, 5H), 7.03-7.17 (m, 4H), 6.08 (s, 1H), 4.30 (d, J=13.1 Hz, 2H), 3.16 (t, J=12.1 Hz, 2H), 2.38-2.48 (m, 2H), 2.35 (s, 3H), 2.24-2.32 (m, 1H), 1.88 (d, J=12.9 Hz, 2H), 1.82 (s, 3H), 1.44-1.62 (m, 4H), 1.35-1.43 (m, 2H), 1.25-1.35 (m, 1H); ESI-MS: m/z 451.3 (M+H)$^+$. It was noted that rotamers were present.

Example 375

2-(4-fluorophenyl)-N-(2-methyl-7-(4-ureidopiperidin-1-yl)pyrazolo[1,5-a]pyrimidin-5-yl)cyclopropanecarboxamide (362)

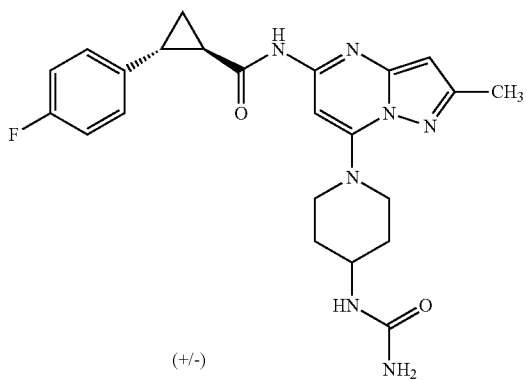

The title compound was prepared by combining N-(7-chloro-2-methylpyrazolo[1,5-a]pyrimidin-5-yl)-2-(4-fluorophenyl)cyclopropanecarboxamide (13B, 0.15 g, 0.435 mmol), Et$_3$NH (0.121 ml, 0.870 mmol), and the 1-(piperidin-4-yl)urea hydrochloride (0.156 g, 0.870 mmol) in NMP (1.450 ml) and heating the mixture at 85° C. overnight. After cooling to room temperature, the mixture was diluted with a few drops of DMSO and methanol, and was then purified by preparatory 45-50% HPLC ([1:1 MeCN/MeOH]/H$_2$O+ 0.01% TFA). Lyophilization of the combined fractions gave the titled compound as a tan solid (85 mg, 43%). $^1$H NMR (DMSO-d$_6$) δ: 10.95 (s, 1H), 7.19-7.31 (m, 3H), 7.07-7.18 (m, 3H), 6.08 (s, 2H), 4.26 (d, J=12.6 Hz, 2H), 3.66 (br. s., 1H), 3.17 (t, J=11.7 Hz, 2H), 2.41-2.49 (m, 1H), 2.35 (s, 3H), 2.24-2.31 (m, 1H), 1.90 (br. s., 2H), 1.74-1.82 (m, 0H), 1.43-1.57 (m, 3H), 1.35-1.43 (m, 1H), 1.32 (ddd, J=8.3, 6.6, 4.3 Hz, 0H); ESI-MS: m/z 452.3 (M+H)$^+$. It was noted that rotamers were present.

Example 376

N-(2-methyl-7-(4-ureidopiperidin-1-yl)pyrazolo[1,5-a]pyrimidin-5-yl)-4-(trifluoromethoxy)benzamide (363)

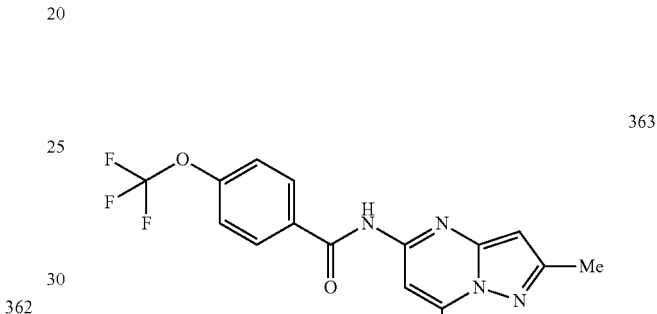

An orange solution of N-(7-chloro-2-methylpyrazolo[1,5-a]pyrimidin-5-yl)-4-(trifluoromethoxy)benzamide (14A, 69 mg, 0.186 mmol), 1-(piperidin-4-yl)urea hydrochloride (40 mg, 0.279 mmol), and N,N-diisopropylethylamine (72 mg, 0.558 mmol) in DMF (1.8 mL) was stirred at 100° C. for 2 h, cooled to 80° C., and stirred overnight. After cooling to room temperature, the mixture was diluted with a few drops of DMSO and methanol, filtered, and then purified by preparatory HPLC (45-60% (1:1 MeOH/MeCN)/H$_2$O gradient+ 0.01% TFA). Lyophilization of the combined fractions gave the titled compound as a yellow solid (26.9 mg, 39%). $^1$H NMR (DMSO-d$_6$) δ: 10.98 (s, 1H), 8.06-8.11 (m, 2H), 7.44 (d, J=7.8 Hz, 2H), 7.25 (s, 1H), 6.09 (s, 1H), 6.02 (d, J=8.1 Hz, 1H), 5.34 (br. s., 2H), 4.23 (d, J=12.1 Hz, 2H), 3.62 (br. s., 1H), 3.15 (t, J=10.7 Hz, 2H), 2.31 (s, 3H), 1.87 (d, J=11.1 Hz, 2H), 1.39-1.51 (m, 2H); ESI-MS: m/z 478.3 (M+H)+.

Example 377

N-(7-(4-(2-amino-2-oxoethyl)piperidin-1-yl)-2-methylpyrazolo[1,5-a]pyrimidin-5-yl)-4-(trifluoromethoxy)benzamide (364)

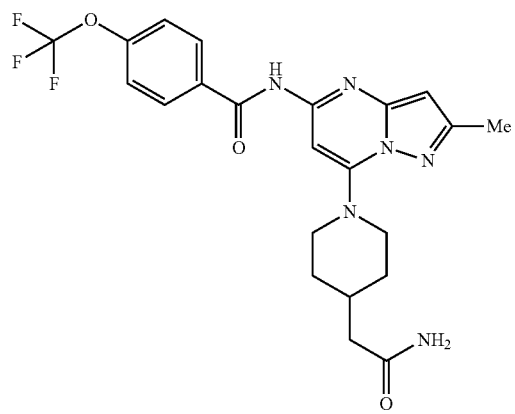

364

An orange solution of N-(7-chloro-2-methylpyrazolo[1,5-a]pyrimidin-5-yl)-4-(trifluoromethoxy)benzamide (14A, 69 mg, 0.186 mmol), 2-(piperidin-4-yl)acetamide hydrochloride (40 mg, 0.279 mmol), and N,N-diisopropylethylamine (96 mg, 0.745 mmol) in DMF (1.8 mL) was stirred at 100° C. for 2 h, cooled to 80° C., and stirred overnight. After cooling to room temperature, the mixture was diluted with a few drops of DMSO and methanol, filtered, and then purified by preparatory HPLC (30-40% MeCN/H₂O gradient+0.01% TFA). Lyophilization of the combined fractions gave the titled compound as a yellow solid (13.1 mg, 15%). ¹H NMR (DMSO-d₆) δ: 10.96 (s, 1H), 8.02-8.14 (m, 2H), 7.44 (d, J=7.8 Hz, 2H), 7.26 (br. s., 1H), 7.23 (s, 1H), 6.74 (br. s., 1H), 6.08 (s, 1H), 4.36 (d, J=12.4 Hz, 2H), 2.90-3.03 (m, 2H), 2.31 (s, 3H), 1.97-2.01 (m, 2H), 1.89-1.97 (m, 1H), 1.74 (d, J=11.6 Hz, 2H), 1.24-1.38 (m, 2H); ESI-MS: m/z 477.4 (M+H)+.

Example 378

N-(7-(4-acetamidopiperidin-1-yl)-2-methylpyrazolo[1,5-a]pyrimidin-5-yl)-4-(trifluoromethoxy)benzamide (365)

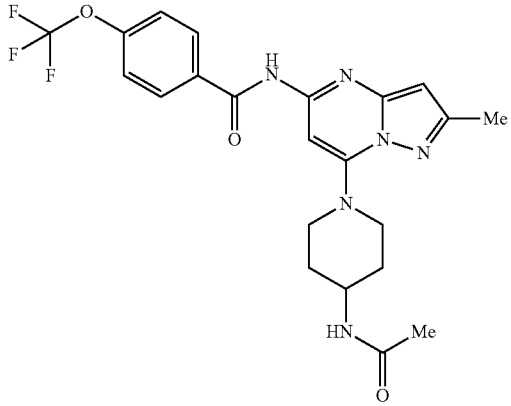

365

An orange solution of N-(7-chloro-2-methylpyrazolo[1,5-a]pyrimidin-5-yl)-4-(trifluoromethoxy)benzamide (14A, 69 mg, 0.186 mmol), N-(piperidin-4-yl)acetamide hydrochloride (40 mg, 0.279 mmol), and N,N-diisopropylethylamine (96 mg, 0.745 mmol) in DMF (1.8 mL) was stirred at 100° C. for 2 h, cooled to 80° C., and stirred overnight. After cooling to room temperature, the mixture was diluted with a few drops of DMSO and methanol, filtered, and then purified by preparatory HPLC (50-70% (1:1 MeOH/MeCN)/H₂O gradient+ 0.01% TFA). Lyophilization of the combined fractions gave the titled compound as a yellow solid (31.3 mg, 35%). ¹HNMR (DMSO-d₆) δ: 10.99 (s, 1H), 8.05-8.12 (m, 2H), 7.85 (d, J=7.6 Hz, 1H), 7.44 (dd, J=9.1, 1.0 Hz, 2H), 7.26 (s, 1H), 6.09 (d, J=0.5 Hz, 1H), 4.28 (d, J=12.4 Hz, 2H), 3.72-

3.94 (m, 1H), 3.14 (t, J=11.0 Hz, 2H), 2.31 (s, 3H), 1.84 (dd, J=13.1, 3.0 Hz, 2H), 1.75 (s, 3H), 1.41-1.58 (m, 2H); ESI-MS: m/z 477.3 (M+H)+.

Example 379

N-(7-(4-acetamidopiperidin-1-yl)-2-methylpyrazolo[1,5-a]pyrimidin-5-yl)-2-(pyridin-4-yl)cyclopropanecarboxamide (366)

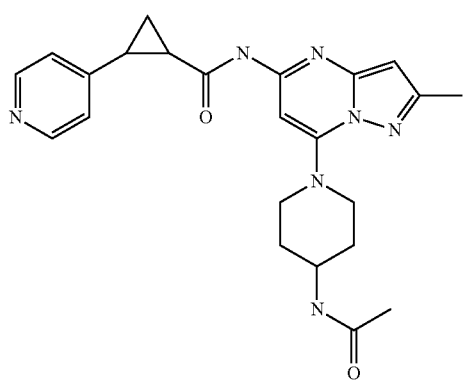

A solution of N-(7-chloro-2-methylpyrazolo[1,5-a]pyrimidin-5-yl)-2-(pyridin-4-yl)cyclopropanecarboxamide (13D, 100 mg, 0.305 mmol) and N-(piperidin-4-yl)acetamide (87 mg, 0.610 mmol) in NMP (1 mL) was stirred at room temperature overnight. The mixture was diluted with a few drops of DMSO and methanol, and was then purified by preparatory HPLC (10-40% MeCN)/H2O gradient+0.01% TFA). Lyophilization of the combined fractions gave the titled compound as a white solid (12 mg, 9%). $^1$H NMR (DMSO-$d_6$) δ: 10.98 (s, 1H), 8.45 (d, J=5.8 Hz, 2H), 7.90 (d, J=7.8 Hz, 1H), 7.27 (s, 1H), 7.20 (d, J=6.1 Hz, 2H), 6.08 (s, 1H), 4.28 (br. s., 2H), 3.88 (br. s., 2H), 3.15 (d, J=3.0 Hz, 2H), 2.40-2.47 (m, 2H), 2.30-2.37 (m, 3H), 1.85-1.96 (m, 2H), 1.81 (s, 3H), 1.46-1.62 (m, 3H). ESI-MS: m/z 434.0 (M+H)+.

Example 380

N-(7-morpholinopyrazolo[1,5-a]pyrimidin-5-yl)cyclopropanecarboxamide (367)

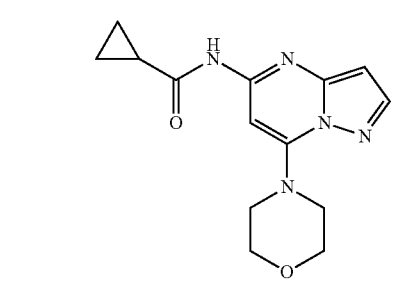

7-Morpholinopyrazolo[1,5-a]pyrimidin-5-amine (9A, 0.10 mmol) in pyridine (0.4 ml), cyclopropanecarboxylic acid (0.15 mmol) in pyridine (0.4 ml), HATU (0.17 mmol) in pyridine (0.4 ml) and DIEA (0.34 mmol) are mixed together before microwave irradiation at 150° C. for 6 minutes. The crude product was then purified by preparatory HPLC to give the titled compound. $^1$H NMR (400 MHz, CHLOROFORM-d) δ ppm 1.00-1.09 (m, 2 H) 1.09-1.16 (m, 2 H) 1.99-2.09 (m, 1 H) 3.91-3.98 (m, 4 H) 4.12-4.21 (m, 4 H) 6.47 (d, J=2.26 Hz, 1 H) 7.27 (s, 1 H) 7.51 (s, 1 H) 7.98 (d, J=2.07 Hz, 1 H) 13.03 (br. s., 1 H); ESI-MS: m/z 288 (M+H)+.

Example 381

Preparation of Compounds 368 to 422

Reaction scheme analogous to that disclosed in Example 381, except for using the correspond boronic acid, ester or trifluoroborate, were used to prepare Compounds 368 to 422.

| Compound | Structure/Name | Physical Characteristics |
| --- | --- | --- |
| 368 | N-(7-morpholinopyrazolo[1,5-a]pyrimidin-5-yl)isobutyramide | $^1$H NMR (400 MHz, CHLOROFORM-d) δ ppm 1.24 (d, J = 6.78 Hz, 6H) 2.81-2.94 (m, 1H) 3.93-3.99 (m, 4H) 4.16-4.25 (m, 4H) 6.47 (d, J = 2.26 Hz, 1H) 7.48 (s, 1H) 7.99 (d, J = 2.26 Hz, 1H) 12.62 (br. s., 1H); ESI-MS: m/z 290 (M + H)+. |

| Compound | Structure/Name | Physical Characteristics |
|---|---|---|
| 369 | 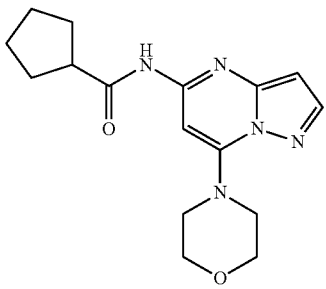<br>N-(7-morpholinopyrazolo[1,5-a]pyrimidin-5-yl)cyclopentanecarboxamide | ESI-MS: m/z 316 (M + H)+. |
| 370 | 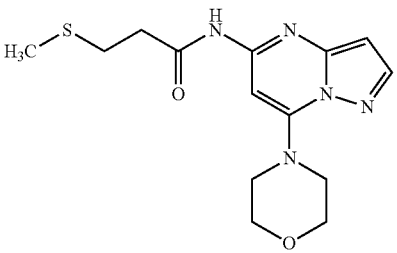<br>3-(methylthio)-N-(7-morpholinopyrazolo[1,5-a]pyrimidin-5-yl)propanamide | ESI-MS: m/z 322 (M + H)+. |
| 371 | 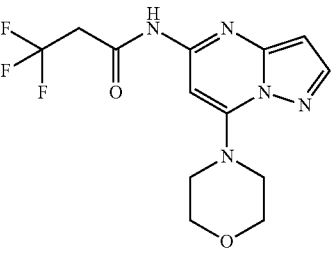<br>3,3,3-trifluoro-N-(7-morpholinopyrazolo[1,5-a]pyrimidin-5-yl)propanamide | ESI-MS: m/z 330 (M + H)+. |
| 372 | 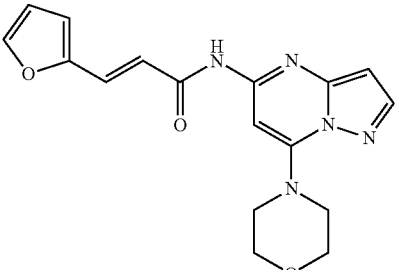<br>(E)-3-(furan-2-yl)-N-(7-morpholinopyrazolo[1,5-a]pyrimidin-5-yl)acrylamide | ESI-MS: m/z 340 (M + H)+. |

| Compound | Structure/Name | Physical Characteristics |
|---|---|---|
| 373 | 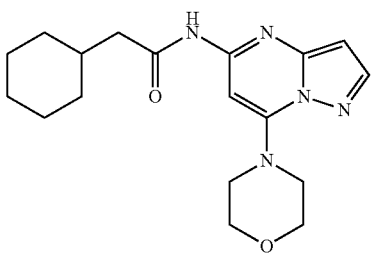<br>2-cyclohexyl-N-(7-morpholinopyrazolo[1,5-a]pyrimidin-5-yl)acetamide | ESI-MS: m/z 344 (M + H)+. |
| 374 | 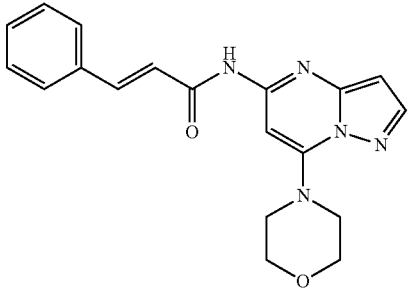<br>N-(7-morpholinopyrazolo[1,5-a]pyrimidin-5-yl)cinnamamide | ESI-MS: m/z 350 (M + H)+. |
| 375 | 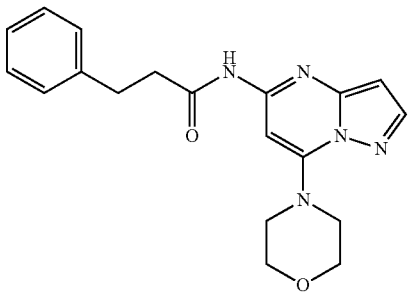<br>N-(7-morpholinopyrazolo[1,5-a]pyrimidin-5-yl)-3-phenylpropanamide | $^1$H NMR (400 MHz, CHLOROFORM-d) δ ppm 2.90-2.97 (m, 2H) 2.99-3.06 (m, 2H) 3.92-3.99 (m, 4H) 4.18-4.26 (m, 4H) 6.44 (d, J = 2.26 Hz, 1H) 7.15-7.34 (m, 6H) 7.99 (d, J = 2.26 Hz, 1H) 12.49 (br. s., 1 H);<br>ESI-MS: m/z 352 (M + H)+. |
| 376 | 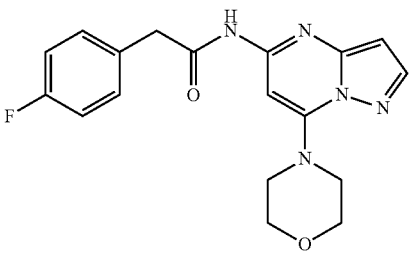<br>2-(4-fluorophenyl)-N-(7-morpholinopyrazolo[1,5-a]pyrimidin-5-yl)acetamide | ESI-MS: m/z 356 (M + H)+. |

| Compound | Structure/Name | Physical Characteristics |
|---|---|---|
| 377 | N-(2-(7-morpholinopyrazolo[1,5-a]pyrimidin-5-ylamino)-2-oxoethyl)benzamide | ESI-MS: m/z 381 (M + H)+. |
| 378 | 3-(1H-indol-3-yl)-N-(7-morpholinopyrazolo[1,5-a]pyrimidin-5-yl)propanamide | ESI-MS: m/z 391 (M + H)+. |
| 379 | N-(3-(7-morpholinopyrazolo[1,5-a]pyrimidin-5-ylamino)-3-oxopropyl)benzamide | ESI-MS: m/z 395 (M + H)+. |
| 380 | 3-(3,4-dimethoxyphenyl)-N-(7-morpholinopyrazolo[1,5-a]pyrimidin-5-yl)propanamide | ESI-MS: m/z 412 (M + H)+. |

| Compound | Structure/Name | Physical Characteristics |
|---|---|---|
| 381 | 2-(biphenyl-4-yl)-N-(7-morpholinopyrazolo[1,5-a]pyrimidin-5-yl)acetamide | ESI-MS: m/z 414 (M + H)+. |
| 382 | N-(7-morpholinopyrazolo[1,5-a]pyrimidin-5-yl)-2,2-diphenylacetamide | ESI-MS: m/z 414 (M + H)+. |
| 383 | tert-butyl 4-(7-morpholinopyrazolo[1,5-a]pyrimidin-5-ylcarbamoyl)piperidine-1-carboxylate | ESI-MS: m/z 431 (M + H)+. |
| 384 | N-(7-morpholinopyrazolo[1,5-a]pyrimidin-5-yl)cyclobutanecarboxamide | ESI-MS: m/z 320 (M + H)+. |

| Compound | Structure/Name | Physical Characteristics |
|---|---|---|
| 385 | 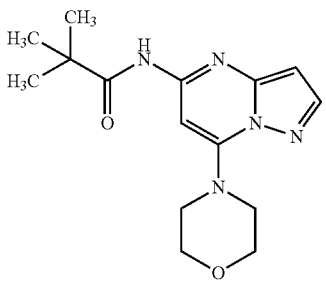<br>N-(7-morpholinopyrazolo[1,5-a]pyrimidin-5-yl)pivalamide | ESI-MS: m/z 304 (M + H)+. |
| 386 | 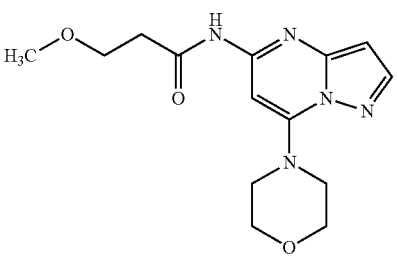<br>3-methoxy-N-(7-morpholinopyrazolo[1,5-a]pyrimidin-5-yl)propanamide | ESI-MS: m/z 306 (M + H)+. |
| 387 | 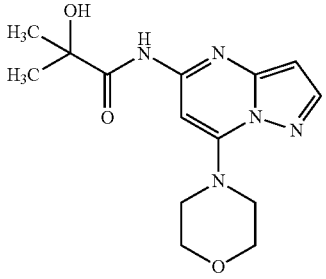<br>2-hydroxy-2-methyl-N-(7-morpholinopyrazolo[1,5-a]pyrimidin-5-yl)propanamide | ESI-MS: m/z 306 (M + H)+. |
| 388 | 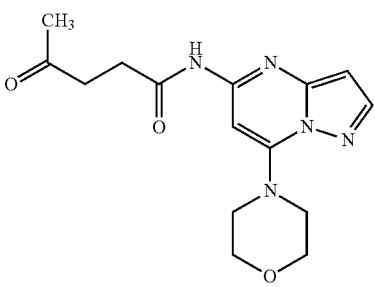<br>N-(7-morpholinopyrazolo[1,5-a]pyrimidin-5-yl)-4-oxopentanamide | ESI-MS: m/z 318 (M + H)+. |

| Compound | Structure/Name | Physical Characteristics |
|---|---|---|
| 389 | 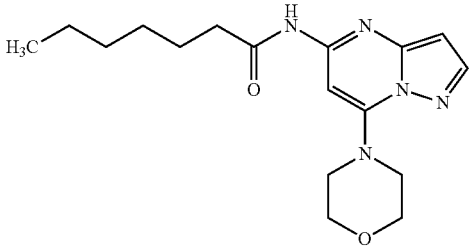<br>N-(7-morpholinopyrazolo[1,5-a]pyrimidin-5-yl)heptanamide | ESI-MS: m/z 332 (M + H)$^+$. |
| 390 | 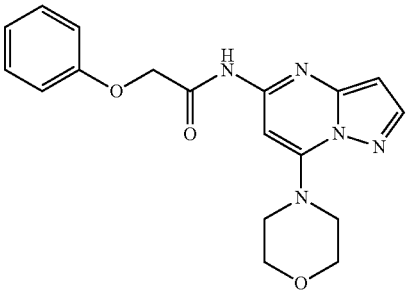<br>N-(7-morpholinopyrazolo[1,5-a]pyrimidin-5-yl)-2-phenoxyacetamide | ESI-MS: m/z 354 (M + H)$^+$. |
| 391 | 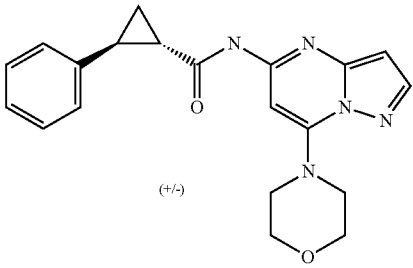<br>(+/-)<br>trans-N-(7-morpholinopyrazolo[1,5-a]pyrimidin-5-yl)-2-phenylcyclopropanecarboxamide | ESI-MS: m/z 364 (M + H)$^+$. |
| 392 | 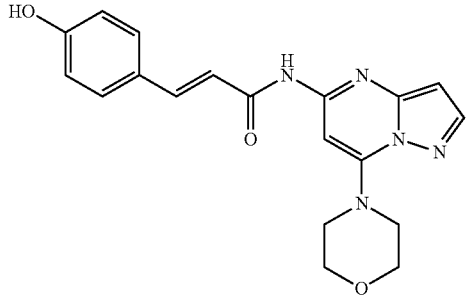<br>(E)-3-(4-hydroxyphenyl)-N-(7-morpholinopyrazolo[1,5-a]pyrimidin-5-yl)acrylamide | ESI-MS: m/z 366 (M + H)$^+$. |

-continued

| Compound | Structure/Name | Physical Characteristics |
|---|---|---|
| 393 | 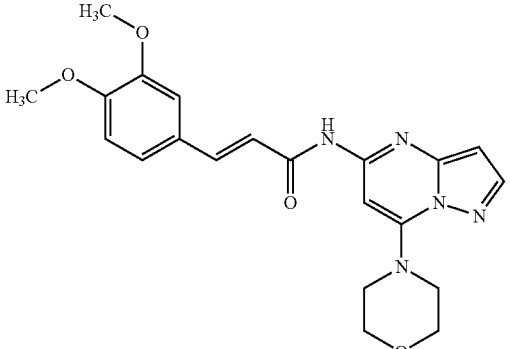<br>(E)-3-(3,4-dimethoxyphenyl)-N-(7-morpholinopyrazolo[1,5-a]pyrimidin-5-yl)acrylamide | ESI-MS: m/z 410 (M + H)$^+$. |
| 394 | 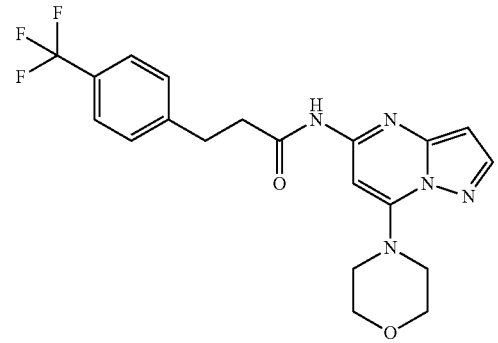<br>N-(7-morpholinopyrazolo[1,5-a]pyrimidin-5-yl)-3-(4-(trifluoromethyl)phenyl)propanamide | ESI-MS: m/z 420 (M + H)$^+$. |
| 395 | 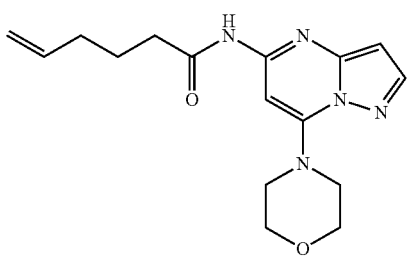<br>N-(7-morpholinopyrazolo[1,5-a]pyrimidin-5-yl)hex-5-enamide | ESI-MS: m/z 316 (M + H)$^+$. |
| 396 | 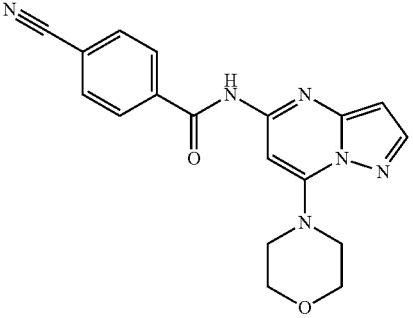<br>4-cyano-N-(7-morpholinopyrazolo[1,5-a]pyrimidin-5-yl)benzamide | ESI-MS: m/z 349 (M + H)$^+$. |

-continued

| Compound | Structure/Name | Physical Characteristics |
|---|---|---|
| 397 | 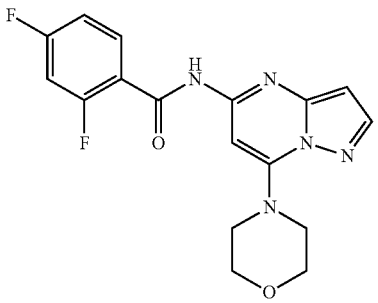<br>2,4-difluoro-N-(7-morpholinopyrazolo[1,5-a]pyrimidin-5-yl)benzamide | ESI-MS: m/z 360 (M + H)+. |
| 398 | 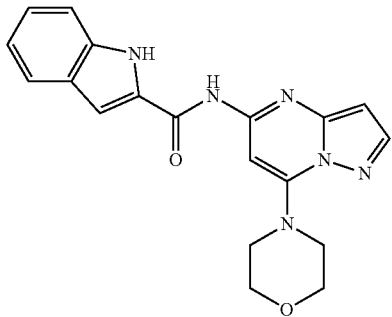<br>N-(7-morpholinopyrazolo[1,5-a]pyrimidin-5-yl)-1H-indole-2-carboxamide | ESI-MS: m/z 363 (M + H)+. |
| 399 | 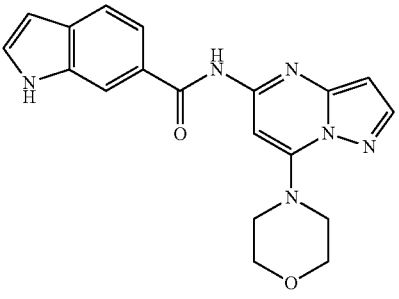<br>N-(7-morpholinopyrazolo[1,5-a]pyrimidin-5-yl)-1H-indole-6-carboxamide | ESI-MS: m/z 363 (M + H)+. |
| 400 | 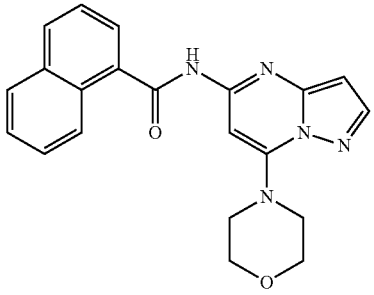<br>N-(7-morpholinopyrazolo[1,5-a]pyrimidin-5-yl)-1-naphthamide | ESI-MS: m/z 374 (M + H)+. |

| Compound | Structure/Name | Physical Characteristics |
|---|---|---|
| 401 | 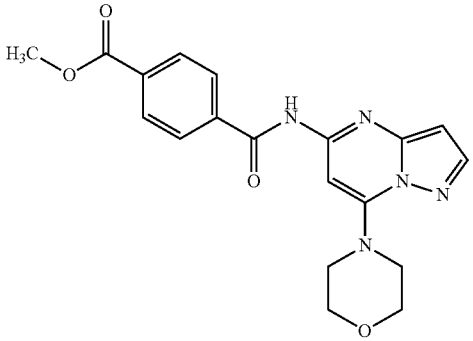<br>methyl 4-(7-morpholinopyrazolo[1,5-a]pyrimidin-5-ylcarbamoyl)benzoate | ESI-MS: m/z 382 (M + H)⁺. |
| 402 | 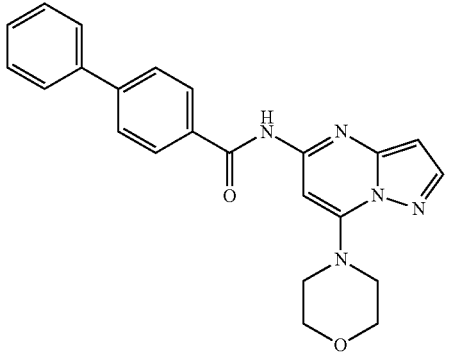<br>N-(7-morpholinopyrazolo[1,5-a]pyrimidin-5-yl)biphenyl-4-carboxamide | ESI-MS: m/z 400 (M + H)⁺. |
| 403 | 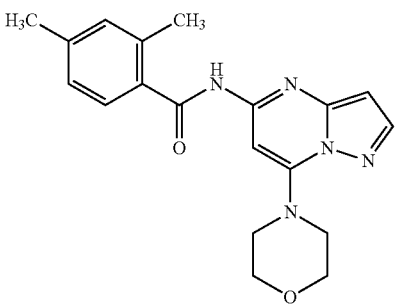<br>2,4-dimethyl-N-(7-morpholinopyrazolo[1,5-a]pyrimidin-5-yl)benzamide | ESI-MS: m/z 352 (M + H)⁺. |

| Compound | Structure/Name | Physical Characteristics |
|---|---|---|
| 404 | 1-hydroxy-N-(7-morpholinopyrazol[1,5-a]pyrimidin-5-yl)-2-naphthamide | ESI-MS: m/z 390 (M + H)+. |
| 405 | 4-methyl-N-(7-morpholinopyrazolo[1,5-a]pyrimidin-5-yl)benzamide | ESI-MS: m/z 338 (M + H)+. |
| 406 | 3-methyl-N-(7-morpholinopyrazolo[1,5-a]pyrimidin-5-yl)benzamide | ESI-MS: m/z 338 (M + H)+. |
| 407 | 2-methoxy-N-(7-morpholinopyrazolo[1,5-a]pyrimidin-5-yl)benzamide | ESI-MS: m/z 354 (M + H)+. |

| Compound | Structure/Name | Physical Characteristics |
| --- | --- | --- |
| 408 | 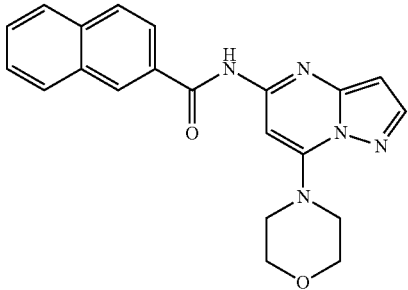<br>N-(7-morpholinopyrazolo[1,5-a]pyrimidin-5-yl)-2-naphthamide | ESI-MS: m/z 374 (M + H)⁺. |
| 409 | 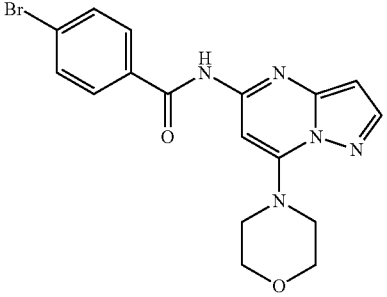<br>4-bromo-N-(7-morpholinopyrazolo[1,5-a]pyrimidin-5-yl)benzamide | ESI-MS: m/z 402 (M + H)⁺. |
| 410 | 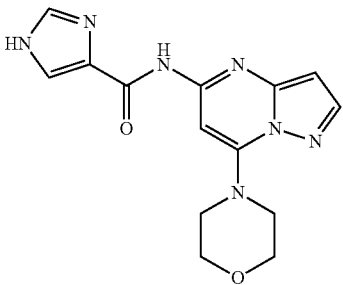<br>N-(7-morpholinopyrazolo[1,5-a]pyrimidin-5-yl)-1H-imidazole-4-carboxamide | ESI-MS: m/z 314 (M + H)⁺. |
| 411 | 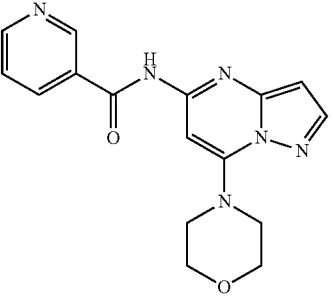<br>N-(7-morpholinopyrazolo[1,5-a]pyrimidin-5-yl)nicotinamide | ESI-MS: m/z 325 (M + H)⁺. |

-continued

| Compound | Structure/Name | Physical Characteristics |
|---|---|---|
| 412 | 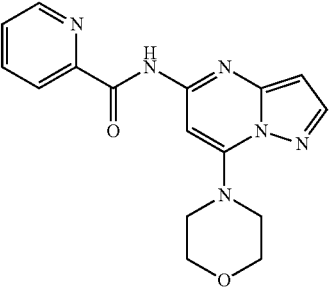<br>N-(7-morpholinopyrazolo[1,5-a]pyrimidin-5-yl)picolinamide | ESI-MS: m/z 325 (M + H)+. |
| 413 | 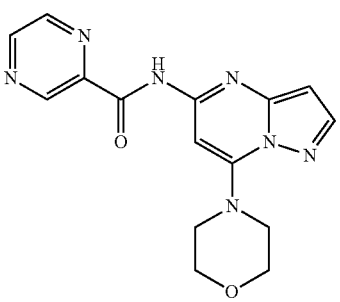<br>N-(7-morpholinopyrazolo[1,5-a]pyrimidin-5-yl)pyrazine-2-carboxamide | ESI-MS: m/z 326 (M + H)+. |
| 414 | 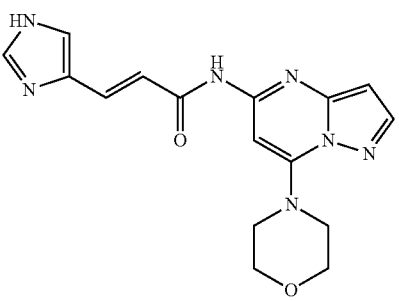<br>(E)-3-(1H-imidazol-4-yl)-N-(7-morpholinopyrazolo[1,5-a]pyrimidin-5-yl)acrylamide | ESI-MS: m/z 340 (M + H)+. |
| 415 | 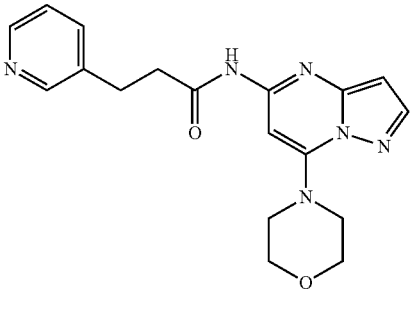<br>N-(7-morpholinopyrazolo[1,5-a]pyrimidin-5-yl)-3-(pyridin-3-yl)propanamide | ESI-MS: m/z 353 (M + H)+. |

| Compound | Structure/Name | Physical Characteristics |
|---|---|---|
| 416 | 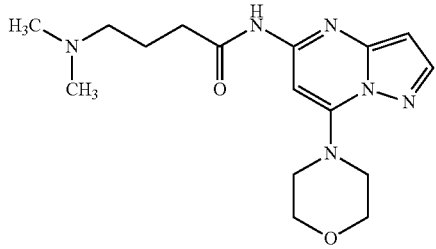<br>4-(dimethylamino)-N-(7-morpholinopyrazolo[1,5-a]pyrimidin-5-yl)butanamide | ESI-MS: m/z 333 (M + H)$^+$. |
| 417 | 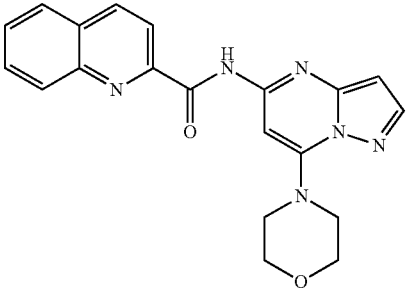<br>N-(7-morpholinopyrazolo[1,5-a]pyrimidin-5-yl)quinoline-2-carboxamide | ESI-MS: m/z 375 (M + H)$^+$. |
| 418 | 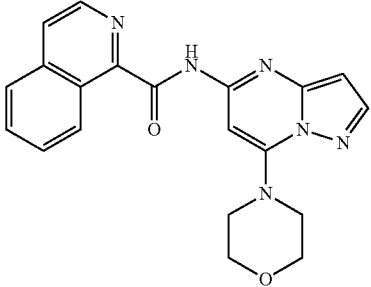<br>N-(7-morpholinopyrazolo[1,5-a]pyrimidin-5-yl)isoquinoline-1-carboxamide | ESI-MS: m/z 375 (M + H)$^+$. |
| 419 | 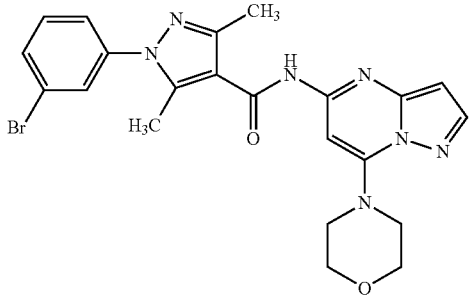<br>1-(3-bromophenyl)-3,5-dimethyl-N-(7-morpholinopyrazolo[1,5-a]pyrimidin-5-yl)-1H-pyrazole-4-carboxamide | ESI-MS: m/z 496 (M + H)$^+$. |

| Compound | Structure/Name | Physical Characteristics |
|---|---|---|
| 420 | 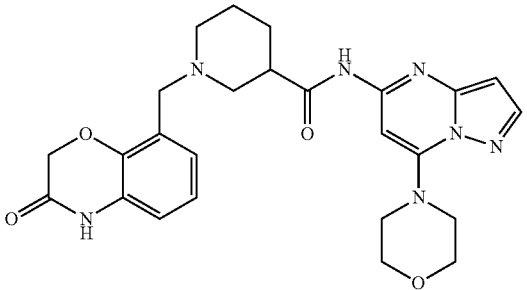<br>N-(7-morpholinopyrazolo[1,5-a]pyrimidin-5-yl)-1-((3-oxo-3,4-dihydro-2H-benzo[b][1,4]oxazin-8-yl)methyl)piperidine-3-carboxamide | ESI-MS: m/z 492 (M + H)+. |
| 421 | 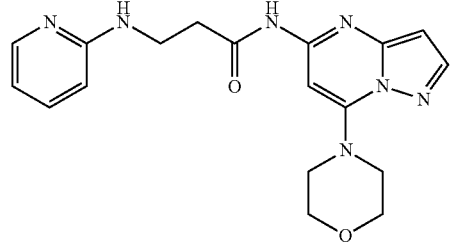<br>N-(7-morpholinopyrazolo[1,5-a]pyrimidin-5-yl)-3-(pyridin-2-ylamino)propanamide | ESI-MS: m/z 368 (M + H)+. |
| 422 | 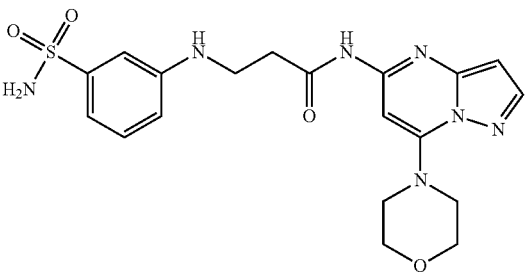<br>N-(7-morpholinopyrazolo[1,5-a]pyrimidin-5-yl)-3-(3-sulfamoylphenylamino)propanamide | ESI-MS: m/z 446 (M + H)+. |

| Compound | Structure/Name | Physical Characteristics |
|---|---|---|
| 423 | 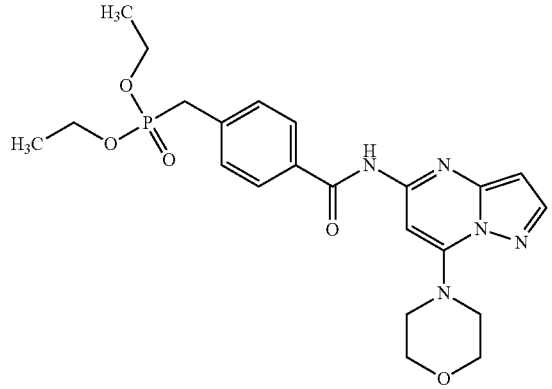<br>diethyl 4-(7-morpholinopyrazolo[1,5-a]pyrimidin-5-ylcarbamoyl)benzylphosphonate | ESI-MS: m/z 474 (M + H)+. |
| 424 | 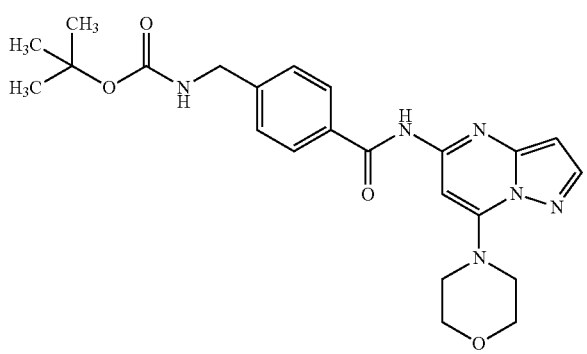<br>tert-butyl 4-(7-morpholinopyrazolo[1,5-a]pyrimidin-5-ylcarbamoyl)benzylcarbamate | ESI-MS: m/z 453 (M + H)+. |
| 425 | 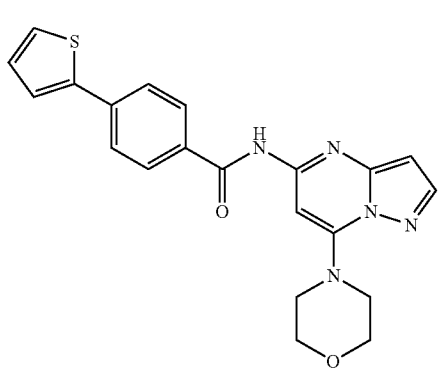<br>N-(7-morpholinopyrazolo[1,5-a]pyrimidin-5-yl)-4-(thiophen-2-yl)benzamide | $^1$H NMR (400 MHz, DMSO-d$_6$) δ ppm 3.72-3.78 (m, 4H) 3.38-3.87 (m, 4H) 6.39 (d, J = 2.26 Hz, 1H) 7.21 (dd, J = 5.09, 3.77 Hz, 1 H) 7.42 (s, 1H) 7.67 (dd, J = 5.09, 1.13 Hz, 1H) 7.72 (dd, J = 3.67, 1.04 Hz, 1H) 7.81 (s, 1H) 7.83 (s, 1H) 8.09 (s, 1H) 8.10-8.12 (m, 2 H) 11.06 (s, 1H);<br>ESI-MS: m/z 406 (M + H)+. |

| Compound | Structure/Name | Physical Characteristics |
|---|---|---|
| 426 | 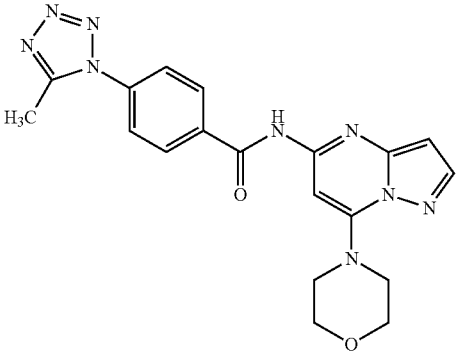<br>4-(5-methyl-1H-tetrazol-1-yl)-N-(7-morpholinopyrazolo[1,5-a]pyrimidin-5-yl)benzamide | $^1$H NMR (400 MHz, DMSO-$d_6$) δ ppm 2.63 (s, 3H) 3.72-3.78 (m, 4H) 3.83-3.88 (m, 4H) 6.40 (d, J = 2.26 Hz, 1H) 7.41 (s, 1H) 7.84-7.86 (m, 1H) 7.87-7.88 (m, 1H) 8.11 (d, J = 2.26 Hz, 1H) 8.25-8.27 (m, 1H) 8.28-8.29 (m, 1H) 11.29 (br. s., 1H); ESI-MS: m/z 406 (M + H)$^+$. |
| 427 | 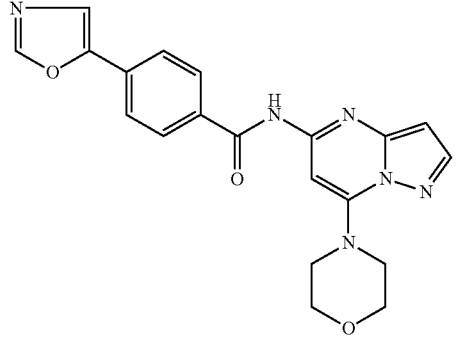<br>N-(7-morpholinopyrazolo[1,5-a]pyrimidin-5-yl)-4-(oxazol-5-yl)benzamide | ESI-MS: m/z 391 (M + H)$^+$. |
| 428 | 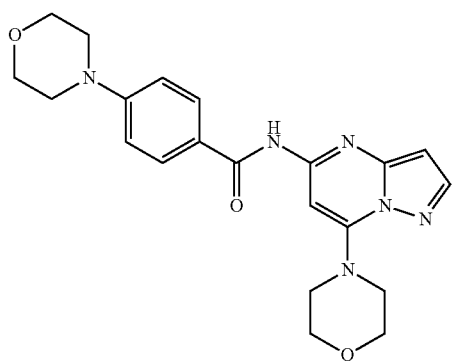<br>4-morpholino-N-(7-morpholinopyrazolo[1,5-a]pyrimidin-5-yl)benzamide | ESI-MS: m/z 409 (M + H)$^+$. |

| Compound | Structure/Name | Physical Characteristics |
|---|---|---|
| 429 | 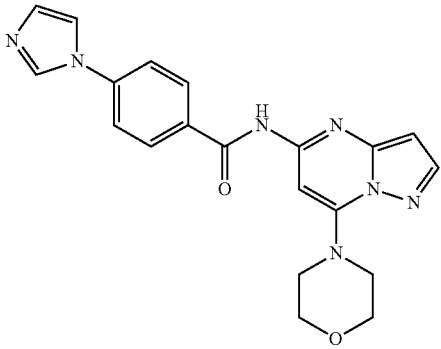<br>4-(1H-imidazol-1-yl)-N-(7-morpholinopyrazolo[1,5-a]pyrimidin-5-yl)benzamide | ESI-MS: m/z 390 (M + H)$^+$. |
| 430 | 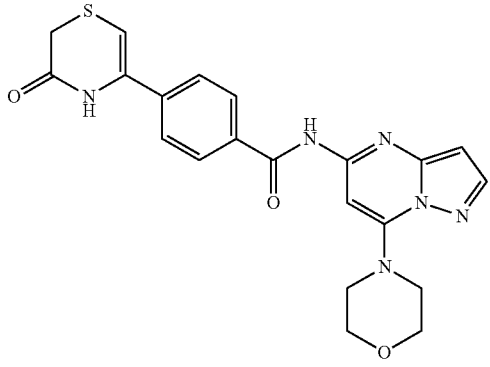<br>N-(7-morpholinopyrazolo[1,5-a]pyrimidin-5-yl)-4-(3-oxo-3,4-dihydro-2H-1,4-thiazin-5-yl)benzamide | ESI-MS: m/z 437 (M + H)$^+$. |
| 431 | 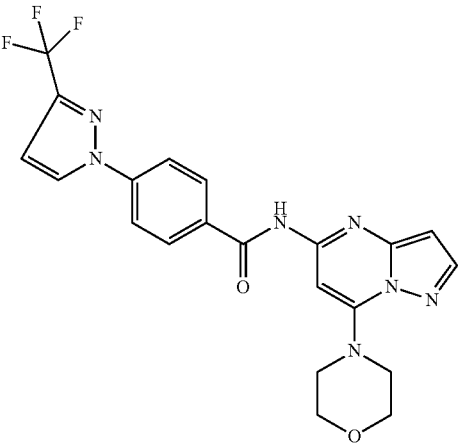<br>N-(7-morpholinopyrazolo[1,5-a]pyrimidin-5-yl)-4-(3-(trifluoromethyl)-1H-pyrazol-1-yl)benzamide | ESI-MS: m/z 458 (M + H)$^+$. |

| Compound | Structure/Name | Physical Characteristics |
|---|---|---|
| 432 | 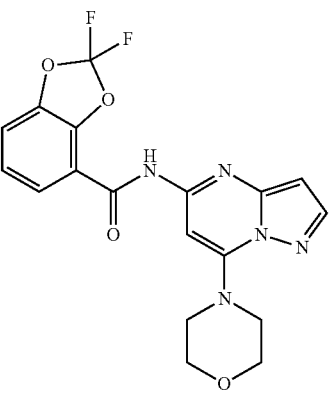<br>2,2-difluoro-N-(7-morpholinopyrazolo[1,5-a]pyrimidin-5-yl)benzo[d][1,3]dioxole-4-carboxamide | ESI-MS: m/z 404 (M + H)$^+$. |
| 433 | 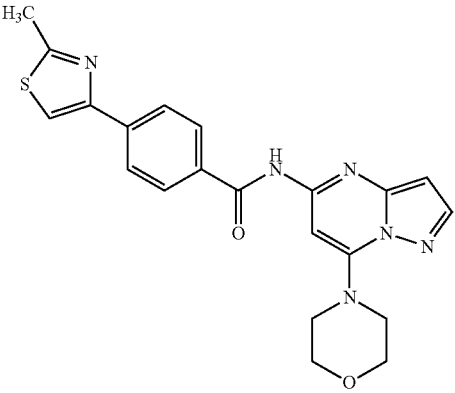<br>4-(2-methylthiazol-4-yl)-N-(7-morpholinopyrazolo[1,5-a]pyrimidin-5-yl)benzamide | ESI-MS: m/z 421 (M + H)$^+$. |
| 434 | 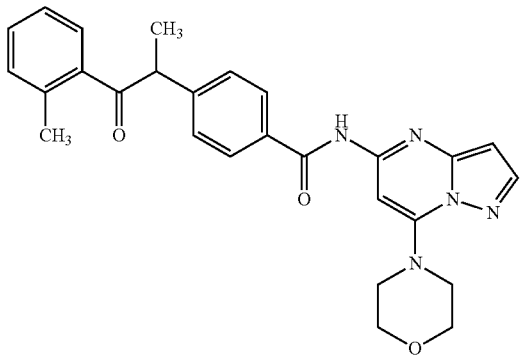<br>N,2-dimethyl-N-(4-(7-morpholinopyrazolo[1,5-a]pyrimidin-5-ylcarbamoyl)phenyl)benzamide | ESI-MS: m/z 471 (M + H)$^+$. |

-continued

| Compound | Structure/Name | Physical Characteristics |
|---|---|---|
| 435 | 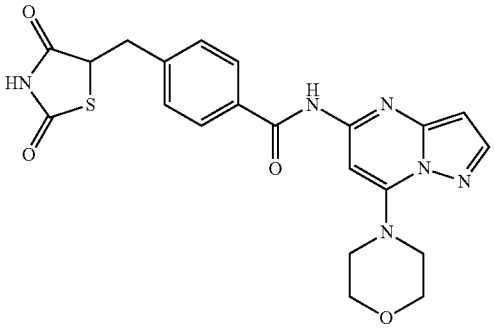<br>4-((2,4-dioxothiazolidin-5-yl)methyl)-N-(7-morpholinopyrazolo[1,5-a]pyrimidin-5-yl)benzamide | ESI-MS: m/z 453 (M + H)$^+$. |
| 436 | 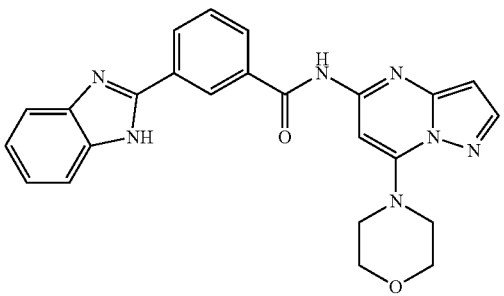<br>3-(1H-benzo[d]imidazol-2-yl)-N-(7-morpholinopyrazolo[1,5-a]pyrimidin-5-yl)benzamide | ESI-MS: m/z 440 (M + H)$^+$. |
| 437 | 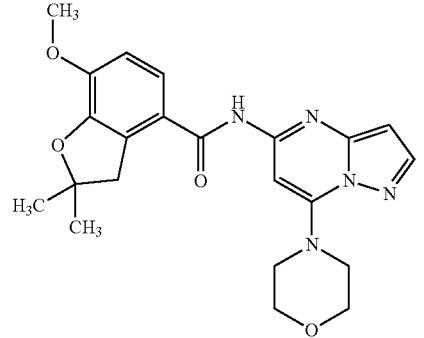<br>7-methoxy-2,2-dimethyl-N-(7-morpholinopyrazolo[1,5-a]pyrimidin-5-yl)-2,3-dihydrobenzofuran-4-carboxamide | ESI-MS: m/z 424 (M + H)$^+$. |

| Compound | Structure/Name | Physical Characteristics |
|---|---|---|
| 438 | 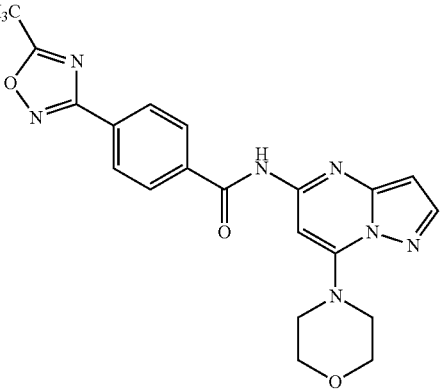<br>4-(5-methyl-1,2,4-oxadiazol-3-yl)-N-(7-morpholinopyrazolo[1,5-a]pyrimidin-5-yl)benzamide | ESI-MS: m/z 406 (M + H)$^+$. |
| 439 | 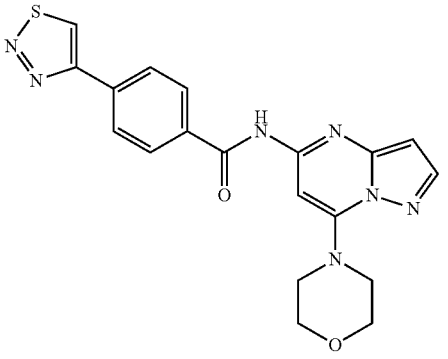<br>N-(7-morpholinopyrazolo[1,5-a]pyrimidin-5-yl)-4-(1,2,3-thiadiazol-4-yl)benzamide | ESI-MS: m/z 408 (M + H)$^+$. |
| 440 | 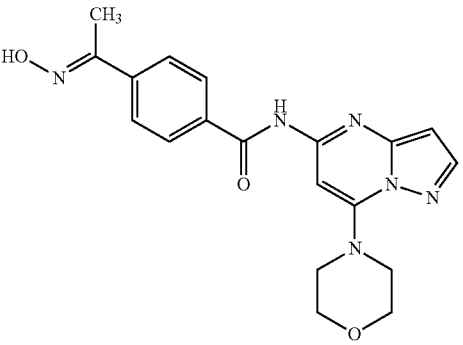<br>(E)-4-(1-(hydroxyimino)ethyl)-N-(7-morpholinopyrazolo[1,5-a]pyrimidin-5-yl)benzamide | ESI-MS: m/z 383 (M + H)$^+$. |

| Compound | Structure/Name | Physical Characteristics |
|---|---|---|
| 441 | 4-(furan-2-yl)-N-(7-morpholinopyrazolo[1,5-a]pyrimidin-5-yl)benzamide | ESI-MS: m/z 390 (M + H)+. |
| 442 | 4-(furan-3-yl)-N-(7-morpholinopyrazolo[1,5-a]pyrimidin-5-yl)benzamide | ESI-MS: m/z 390 (M + H)+. |

In addition, the above reaction schemes and variations thereof can be used to prepare the following compounds. It is understood that recitation of a compound is intended to encompass all of the different possible stereoisomers.

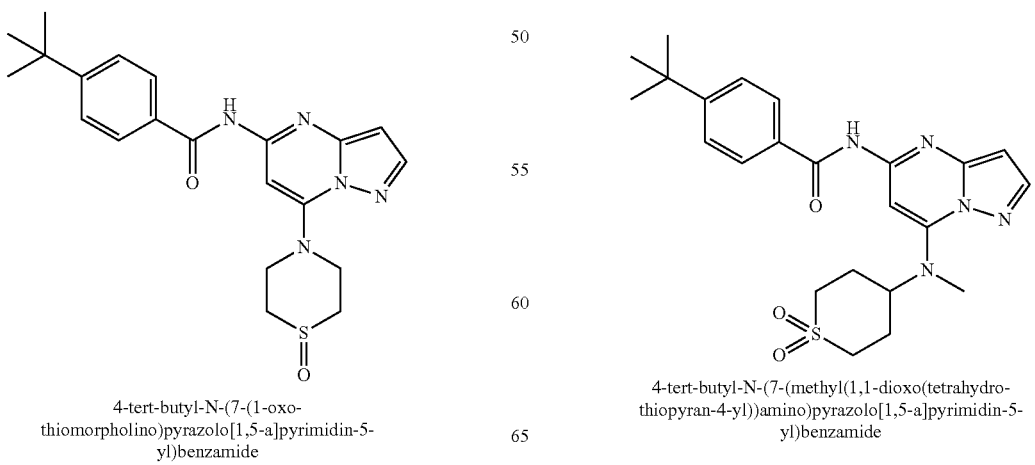

4-tert-butyl-N-(7-(1-oxo-thiomorpholino)pyrazolo[1,5-a]pyrimidin-5-yl)benzamide 4-tert-butyl-N-(7-(methyl(1,1-dioxo(tetrahydro-thiopyran-4-yl))amino)pyrazolo[1,5-a]pyrimidin-5-yl)benzamide

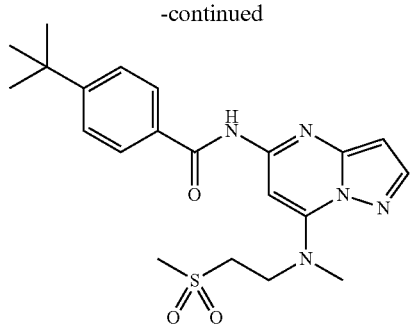

4-tert-butyl-N-(7-(methyl(2-(methylsulfonyl)ethyl)amino)pyrazolo[1,5-a]pyrimidin-5-yl)benzamide

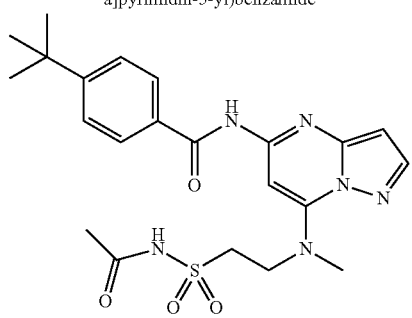

N-(7-((2-(N-acetylsulfamoyl)ethyl)(methyl)amino)pyrazolo[1,5-a]pyrimidin-5-yl)-4-tert-butylbenzamide

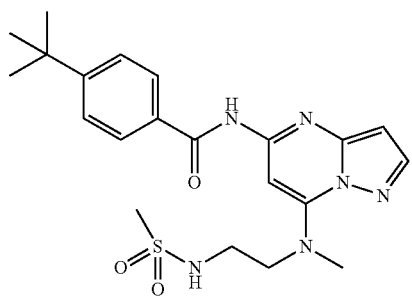

4-tert-butyl-N-(7-(methyl(2-(methylsulfonamido)ethyl)pyrazolo[1,5-a]pyrimidin-5-yl)benzamide

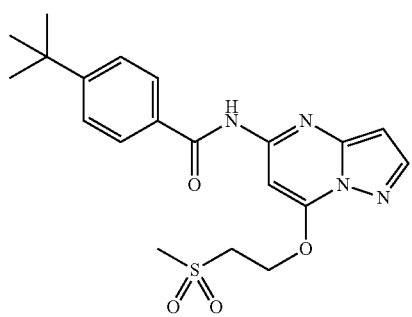

4-tert-butyl-N-(7-(2-(methylsulfonyl)ethoxy)pyrazolo[1,5-a]pyrimidin-5-yl)benzamide Example A Preparation of ASK1 Protein Cloning of cDNA encoding human ASK1 was conducted by PCR using primers, 5'-AAAAGTCGACATGGACTA-CAAGGACGACGATGACAAGGTGAACAC-CATTACCGA AGAGAAGGGGA-3' (SEQ ID NO: 1) and 5'-AAAGCGGCCGCTCAAGTCTGTTTGTTTC-GAAAGTCAATG-3' (SEQ ID NO: 2), from human heart cDNA library (Becton, Dickinson and Company). The PCR product was subjected to agarose gel (1%) electrophoresis, a 2.2 kb DNA fragment containing an ASK1 gene was recovered from the gel, and then digested with restriction enzymes, NotI and SalI, and inserted into a plasmid pFASTBAC1 (Invitrogen) to prepare a plasmid pFB-ASK1. The insert was verified by sequencing. Recombinant baculovirus was prepared according to the procedure of the Bac-to-Bac baculovirus expression system (Invitrogen).

Sf-21 cells were seeded to achieve $1\times10^6$ cells/mL in 100 mL of Sf-900 II SFM medium (Invitrogen) which contains 10% fetal calf serum and then cultured at 27° C. for 24 hrs. To express ASK1 in cells, 0.15 mL of the recombinant baculovirus virus stock was added to cells, and the then cultured for 60 hrs. The cells were separated from the culture solution by centrifugation at 3000 rpm for 10 min and washed once with PBS. The cells were suspended in 10 mL of lysis buffer (25 mM HEPES (pH 7.5), 1% Triton X, 130 mM NaCl, 1 mM EDTA, 1 mM DTT, 25 mM (3-glycerophosphate, Protease inhibitor complete (Roche), 1 mM sodium orthovanadate) and ruptured by four times of treatment with a homogenizer (POLYTRON) at 20000 rpm for 30 seconds. Active ASK1 protein was purified from a supernatant obtained by centrifugal separation at 40000 rpm for 45 min using anti-FLAG M2 Affinity Gel (Sigma).

Example B

Scintillation Assay for Measuring the Inhibitory Effect of Exemplified Compounds of the Invention Against ASK1

The test compounds (2.5 µl) dissolved in DMSO were added to wells containing 37.5 µl of the reaction solution (25 mM HEPES (pH 7.5), 10 mM magnesium acetate, 1 mM DTT) including 30 ng of active ASK1 protein and 1 µg of myelin basic protein (Wako), and incubated at room temperature for 5 min. To start the reaction, 10 µL of ATP solution (2.5 µM ATP, 0.1 µCi [γ-$^{32}$P]ATP) was added to wells. After incubating at room temperature for 30 min, the reaction was terminated by adding 50 µl of 20% TCA solution. The reaction solution was incubated at 4° C. for 30 min and an acid-insoluble fraction was transferred onto a GF/C filter (Packard) with Cell Harvester (Packard), and washed with 250 mM phosphoric acid. After drying at 45° C. for 60 min., 40 µL of Microscint 0 (Packard) was added and the radioactivity was measured with TopCount (Packard). The concentrations ($IC_{50}$ value) of the test compounds necessary for 50% inhibition of kinase activity were calculated by PRISM 3.0 (Graphpad Software).

Example C

Homogeneous Time-Resolved Fluorescence (HTRF) Assay for Measuring the Inhibitory Effect of Exemplified Compounds of the Invention Against ASK1

Recombinant human ASK1 is purchased from Millipore (Cat # 14-606). The enzymatic assay of ASK1 is set up by using HTRF® KinEASE™ STK S3 kit, the Universal Assay for Serine/Threonine Kinases kit from CisBio.

The inhibitory properties of compounds to ASK1 may be determined using a white 384-well-plate format under the following reaction conditions: 25 nM ASK1, 1 µM CisBio STK S3-biotion peptide, 100 µM ATP, and 1%-2% DMSO in kinase assay buffer of 50 mM HEPES, pH 7.3, 10 mM NaCl, 10 mM $MgCl_2$, 0.01% Brij35, 0.2 mM EDTA, and 1 mM DTT. Reaction product is determined quantitatively by HTRF after the addition of detection reagent SA-XL665 and STK-antibody-cryptate.

The assay reaction may be initiated as follows: 2 µl of the mixture of 3 µM CisBio STK S3-biotion peptide and 300 µM ATP with 2 µl of test compound (2 fold serial dilutions for 11 data points for each inhibitor) containing 3%-6% DMSO are added to each well of the plate, followed by the addition of 2 µL of 75 nM ASK1 to initiate the reaction (final enzyme concentration was 25 nM for ASK1). The reaction mixture may then be incubated at room temperature for 1 hour, and quenched and developed by the addition of 6 µL of 100-fold diluted STK-antibody-Cryptate and 250 nM SA-XL665 in Cisbio HTRF detection buffer (50 mM HEPES, pH7.0, 0.1% BSA, 0.8 M KF, and 20 mM EDTA). The fluorescence intensity is measured at 620 nm (Cryptate) and 665 nm (XL665) after a 1-2 hour incubation at room temperature. A ratio is calculated (665/620) for each well and is fitted to the standard $IC_{50}$ curve to determine inhibition constants ($IC_{50}$) which is the molar concentration of the compound that produces 50% inhibition of a test compound.

Alternatively, pIC50 value (negative log of $IC_{50}$) as indicator of the potency of a test compound.

Example D

In Vitro IC50 Values of Compounds of the Invention Against ASK1

The enzyme activities of selected compounds of the present invention against ASK1 were determined using the assay disclosed in Example A and B. The resulted $pIC_{50}$ values are reported in Table 1.

TABLE 1

| pIC$_{50}$ of Exemplified Compounds Against ASK1 | |
| --- | --- |
| Compound No | Enzyme Activity IC$_{50}$ (nM) |
| 1 | <100 |
| 2 | <100 |
| 3 | <100 |
| 4 | <100 |
| 5 | <100 |
| 6 | <100 |
| 7 | <100 |
| 8 | >1,000 |
| 9 | <100 |
| 10 | <100 |
| 11 | <100 |
| 12 | >1,000 |
| 13 | >1,000 |
| 14 | 100-1,000 |
| 15 | <100 |
| 16 | <100 |
| 17 | 100-1,000 |
| 18 | 100-1,000 |
| 19 | <100 |
| 20 | <100 |
| 21 | 100-1,000 |
| 22 | 100-1,000 |
| 23 | <100 |
| 24 | 100-1,000 |
| 29 | <100 |
| 34 | <100 |
| 42 | <100 |
| 64 | <100 |
| 65 | <100 |
| 66 | <100 |
| 67 | 100-1,000 |
| 68 | 100-1,000 |
| 69 | 100-1,000 |
| 70 | 100-1,000 |
| 71 | <100 |
| 72 | <100 |
| 73 | 100-1,000 |
| 74 | 100-1,000 |
| 75 | 100-1,000 |
| 76 | 100-1,000 |
| 77 | <100 |
| 78 | 100-1,000 |
| 79 | 100-1,000 |
| 83 | <100 |
| 84 | 100-1,000 |
| 85 | 100-1,000 |
| 86 | >1,000 |
| 87 | <100 |
| 88 | 100-1,000 |
| 89 | <100 |
| 90 | 100-1,000 |
| 91 | >1,000 |
| 92 | >1,000 |
| 93 | 100-1,000 |
| 95 | 100-1,000 |
| 97 | 100-1,000 |
| 104 | <100 |
| 105 | <100 |
| 112 | <100 |
| 113 | <100 |
| 125 | <100 |
| 127 | >1,000 |
| 128 | <100 |
| 173 | >1,000 |
| 174 | >1,000 |
| 175 | >1,000 |
| 178 | >1,000 |
| 202 | <100 |
| 203 | <100 |
| 315 | 100-1,000 |
| 338 | <100 |
| 347 | <100 |
| 356 | <100 |
| 359 | <100 |
| 361 | <100 |
| 362 | <100 |

What is claimed is:
1. A compound of the formula:

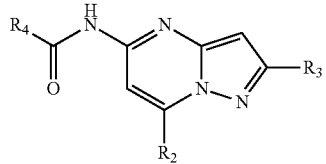

or a pharmaceutically acceptable salt thereof, wherein
$R_2$ is selected from the group consisting of nitro, cyano, thio, carbonyloxy, $(C_{1-10})$alkoxy, $(C_{4-12})$aryloxy, hetero$(C_{1-10})$aryloxy, carbonyl, aminocarbonyl, amino, $(C_{1-10})$alkylamino, sulfonamido, imino, $(C_{1-10})$alkyl, halo$(C_{2-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxoalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted with 1-3 substituents, provided that $R_2$ is not an unsubstituted n-$(C_{1-3})$alkyl;
$R_3$ is selected from the group consisting of hydrogen, halo, nitro, cyano, thio, hydroxy, carbonyloxy, $(C_{1-10})$alkoxy, $(C_{4-12})$aryloxy, hetero$(C_{1-10})$aryloxy, carbonyl, aminocarbonyl, amino, $(C_{1-10})$alkylamino, sulfonamido, imino, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted with 1-2 substituents; and
$R_4$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted with 1-3 substituents,
where
each of said 1-3 substituents of $R_2$ is independently selected from the group consisting of halo, nitro, cyano, oxo, hydroxy, thio, thio$(C_{1-6})$alkyl, arylalkyloxy, carbonyloxy, $(C_{1-10})$alkoxy, $(C_{4-12})$aryloxy, hetero$(C_{1-10})$aryloxy, aminocarbonyloxy, carbonyl, $(C_{1-6})$alkylcarbonyl, amino, amido, carboxamido, $(C_{1-10})$alkylamino, methylcarbonylamino, sulfonamido, imino, $(C_{1-6})$alkylsulfonyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl;

each of said 1-2 substituents of $R_4$ is independently selected from the group consisting of hydroxy, halo, halo($C_{1-6}$)alkyl, ($C_{1-6}$)alkyl, ($C_{3-6}$)cycloalkyl, hetero($C_{1-5}$)cycloalkyl, phenyl, and hetero($C_{1-5}$)aryl;

each of said 1-3 substituents of $R_4$ is independently selected from the group consisting of halo, nitro, cyano, oxo, thio, mercapto, hydroxy, carbonyloxy, ($C_{1-10}$)alkoxy, ($C_{4-12}$)aryloxy, hetero($C_{1-10}$)aryloxy, carbonyl, ($C_{1-10}$)alkoxycarbonyl, ($C_{4-12}$)aryloxycarbonyl, hetero($C_{1-10}$)aryloxycarbonyl, amino, amido, carboxamido, carbamoyl, ($C_{1-10}$)alkylamino,-sulfonamido, sulfamoyl, imino, phosphonyl, ($C_{1-10}$)alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl ($C_{1-10}$)alkyl, sulfinyl($C_{1-10}$)alkyl, phosphonyl ($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl ($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$) alkyl, ($C_{3-12}$)cycloalkyl, hetero($C_{3-12}$) cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$)bicycloaryl, and hetero($C_{4-12}$)bicycloaryl.

2. The compound or pharmaceutically acceptable salt according to claim 1, wherein $R_4$ is selected from the group consisting of cyclopropyl, cyclobutyl, cyclopentyl, cyclohexyl, piperidinyl, piperazinyl, morpholinyl, and admantanyl, each unsubstituted or substituted with said 1-3 substituents.

3. The compound or pharmaceutically acceptable salt according to claim 1, wherein $R_4$ is selected from the group consisting of phenyl, pyridinyl, pyrazinyl, pyrimidinyl, pyridazinyl, and triazinyl, each unsubstituted or substituted with said 1-3 substituents.

4. The compound or pharmaceutically acceptable salt according to claim 3, wherein at least one of said 1-3 substituents is

where $R_{21}$ is selected from the group consisting of hydroxyl, ($C_{1-4}$)alkyl, —$CF_3$, —($CH_2$)OH, —($CH_2$)CN, —($CH_2$)C(O)OH, —($CH_2$)$CONH_2$, —($CH_2$)$NH_2$, —($CH_2$)NHC(O)C(O)OH, —($CH_2$)C(O)$OCH_3$, —O($CH_2$)CH(OH)$CH_2$OH, —($CH_2$)$_n$aryl, —O($CH_2$)$_n$aryl, —($CH_2$)$_n$heteroaryl, —O($CH_2$)$_n$heteroaryl, where n is 0, 1, 2, 3, or 4.

5. The compound or pharmaceutically acceptable salt according to claim 1, wherein $R_4$ is selected from the group consisting of:

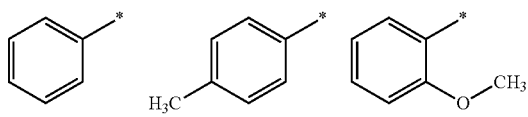

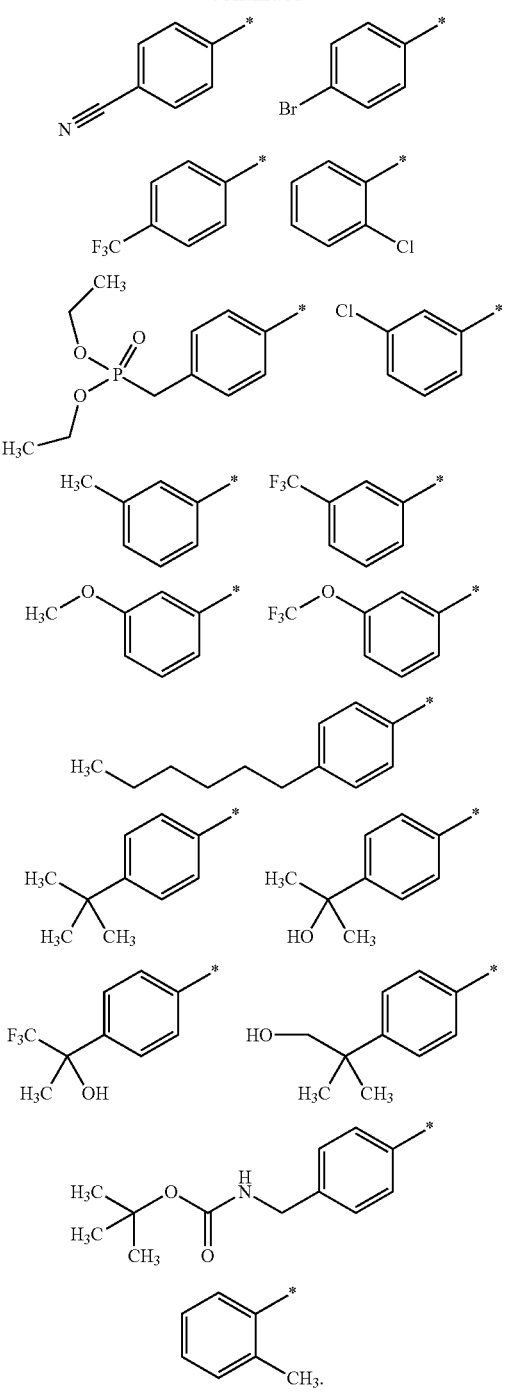

6. The compound or pharmaceutically acceptable salt according to claim 1, wherein $R_4$ is selected from the group consisting of:

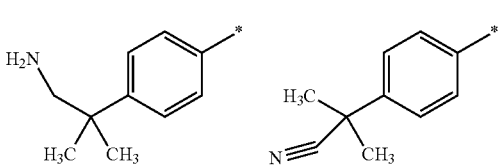

-continued
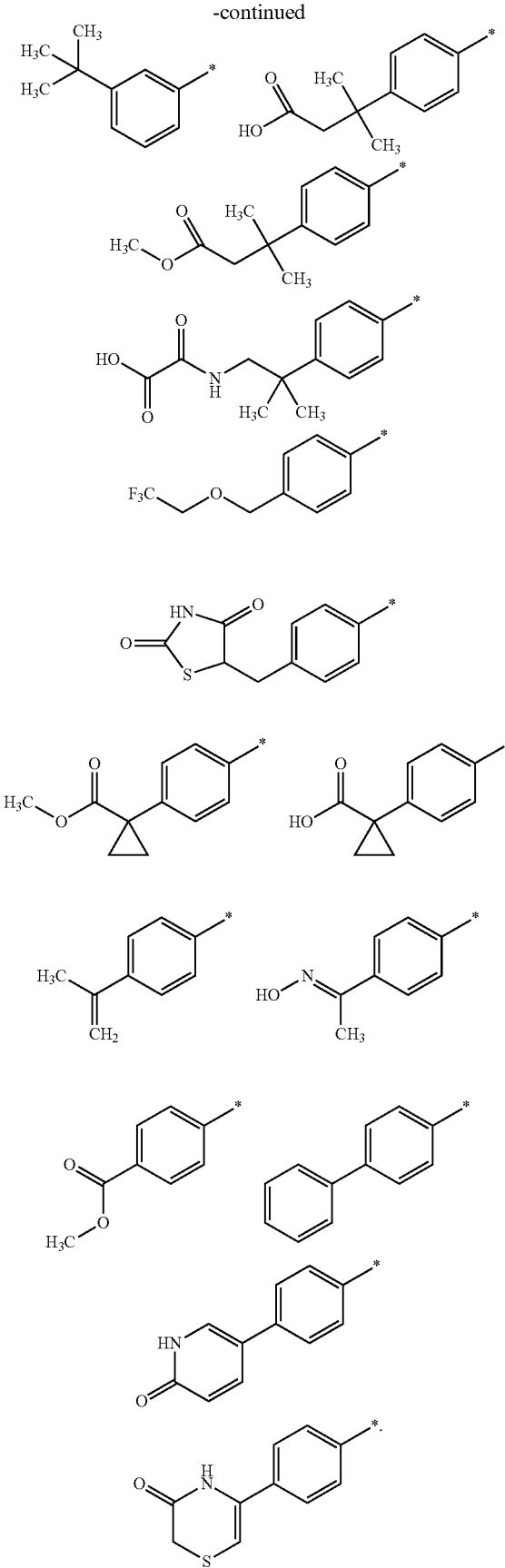
7. The compound or pharmaceutically acceptable salt according to claim 1, wherein $R_4$ is selected from the group consisting of:
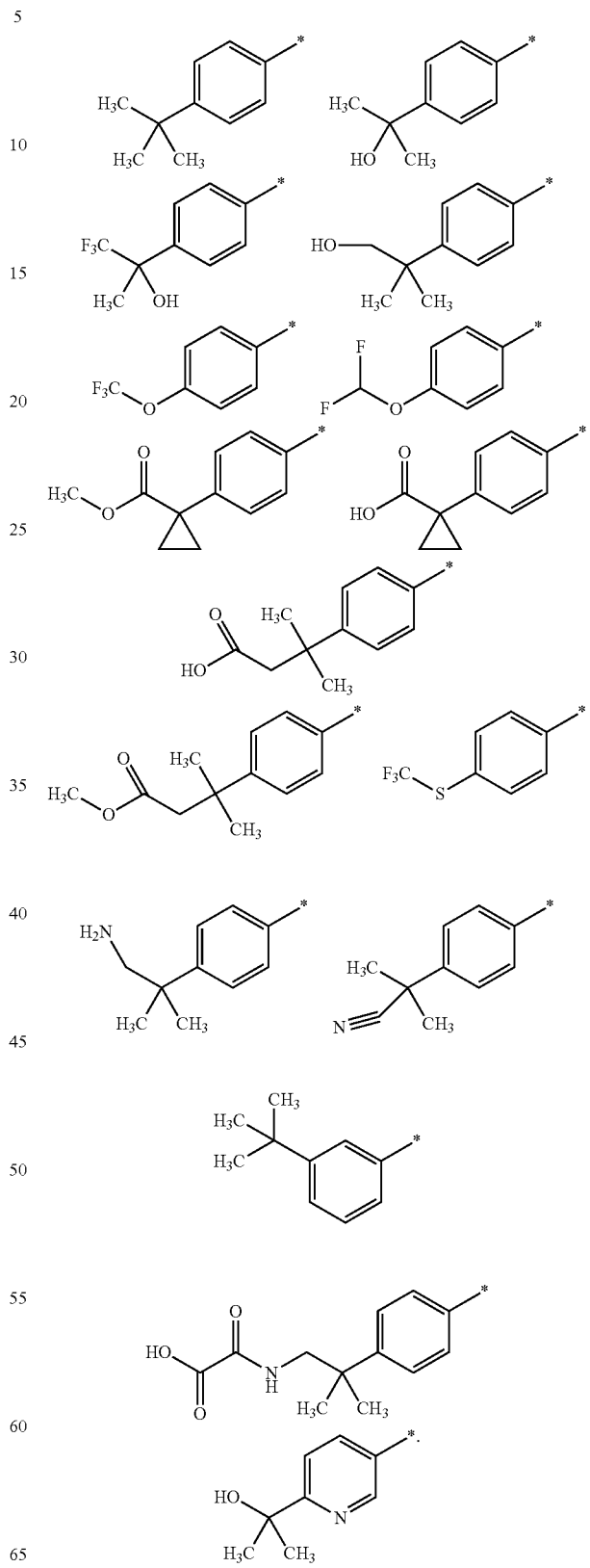

8. The compound or pharmaceutically acceptable salt according to claim 1, wherein $R_4$ is an unsubstituted or substituted phenyl of the formula:

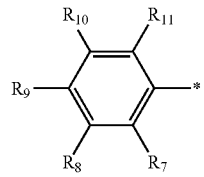

where $R_7$, $R_8$, $R_9$, $R_{10}$, and $R_{11}$ are each independently selected from the group consisting of hydrogen, halo, hydroxyl, nitro, thio, cyano, ($C_{1-6}$)alkyl, ($C_{2-6}$)alkenyl, ($C_{2-6}$)alkynyl, halo($C_{1-6}$)alkyl, ($C_{1-6}$)alkoxy, hydroxyl($C_{1-6}$)alkyl, phosphonylalkyl, mercapto, sulfamoyl, amino, amido, carboxamido, carbamoyl, carbonyl, carbonyloxy, hetero($C_{1-5}$)aryl, and ($C_{4-6}$)aryl, and each unsubstituted or substituted; provided at least two of $R_7$, $R_8$, $R_9$, $R_{10}$, and $R_{11}$ are hydrogen.

9. The compound or pharmaceutically acceptable salt according to claim 8, wherein $R_7$, $R_8$, $R_9$, $R_{10}$, and $R_{11}$ are each independently selected from the group consisting of hydrogen, hydroxyl, nitro, fluoro, chloro, bromo, cyano, ($C_{1-6}$)alkoxy, —OCHF$_2$, —OCF$_3$, furanyloxy, ($C_{1-6}$)alkyl, halo($C_{1-6}$)alkyl, hydroxyl($C_{1-6}$)alkyl, —CH$_2$NHC(O)OC (CH$_3$)$_3$, —C(CH$_3$)(OH)CF$_3$, hetero($C_{1-5}$)aryl($C_{1-6}$)alkyl, —C(CH$_3$)=NOH, —CH$_2$OCH$_2$CF$_3$, —NC(O)CH$_3$, —NHS(O)$_2$CH$_3$, —N(CH$_3$)$_2$, —C(O)OCH$_3$, —OCH(CH$_3$)$_2$, —SCF$_3$, -sulfonylpyrrolidinyl, hetero($C_{1-5}$)aryl, hetero($C_{1-5}$)cycloalkyl,

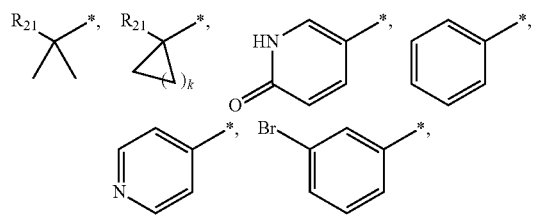

where k is 1, 2, 3, or 4; and $R_{21}$ is selected from the group consisting of —(CH$_2$)$_n$OH, —C(O)OH, —C(O)OCH$_3$, cyano, —(CH$_2$)$_n$NH$_2$, —(CH$_2$)$_n$NHC(O)C(O)OH, —(CH$_2$)$_n$C(O)OH, —(CH$_2$)$_n$C(O)OCH$_3$, (C$_{1-4}$)alkyl, halo(C$_{1-4}$)alkyl, —(CH$_2$)$_n$CN, —(CH$_2$)$_n$CONH$_2$, —(CH$_2$)$_n$aryl, —(CH$_2$)$_n$heteroaryl, —O(CH$_2$)$_n$aryl, —O(CH$_2$)$_n$ heteroaryl, and —O(CH$_2$)$_n$CH(OH)CH$_2$OH, where n is 0, 1, 2, 3, or 4.

10. The compound or pharmaceutically acceptable salt according to claim 9, wherein $R_{21}$ is selected from the group consisting of cyano, hydroxyl, methyl, perfluoromethyl, hydroxylmethyl, —CH$_2$NH$_2$, —(CH$_2$)C(O)OH, —(CH$_2$)C(O)OCH$_3$, —(CH$_2$)NHC(O)C(O)OH, —OCH$_2$CH(OH)CH$_2$OH, and —O(CH$_2$)$_n$heteroaryl where n is 1 or 2.

11. The compound or pharmaceutically acceptable salt according to claim 8, wherein $R_9$ is independently selected from the group consisting of hydrogen, tert-butyl, —CF$_3$, —C(CH$_3$)(OH)CF$_3$, —C(CH$_3$)$_2$CF$_3$, —C(CH$_3$)$_2$OH, —C(CH$_3$)$_2$(CH$_2$OH), —C(O)OCH$_3$,

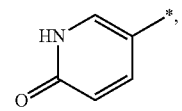

—C(CH$_3$)$_2$(OCH$_2$CH(OH)CH$_2$OH), —C(CH$_3$)$_2$CN, —C(CH$_3$)$_2$CH$_2$CN, —C(CH$_3$)$_2$O(CH$_2$)$_n$heteroaryl where n is 1 or 2, and $R_7$, $R_8$, $R_{10}$, and $R_{11}$ are each hydrogen.

12. The compound or pharmaceutically acceptable salt according to claim 1, wherein $R_4$ is selected from the group consisting of:

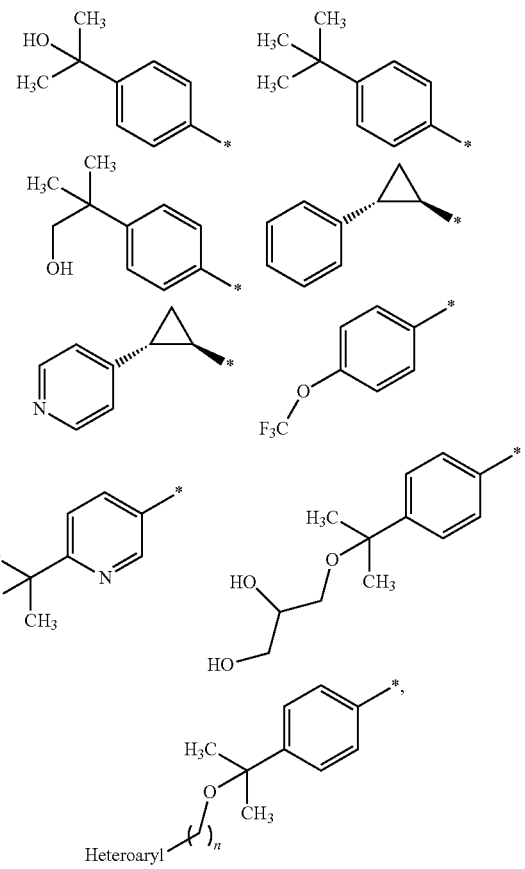

where n is 0, 1, 2 3 or 4.

13. The compound or pharmaceutically acceptable salt according to claim 1, wherein $R_2$ is selected from the group consisting of (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each unsubstituted or substituted with said 1-3 substituents.

14. The compound or pharmaceutically acceptable salt according to claim 13, wherein $R_2$ is selected from the group consisting of furanyl, thienyl, pyrrolyl, pyrrolidinyl, oxazolyl, thiazolyl, imidazolyl, pyrazolyl, triazolyl, isoxazolyl, oxadiazolyl, thiadiazolyl, phenyl, pyridyl, pyrazinyl, pyrimidinyl, pyranyl, thiopyranyl, tetrahydrothiopyranyl, piperidinyl, piperazinyl, pyridazinyl, triazinyl, indolyl, isoindolyl, indolizinyl, benzimidazolyl, purinyl, naphthalenyl, quinolinyl, isoquinolinyl, cinnolinyl, phthalazinlyl, quinazolinyl, quinoxalinyl, naphthyridinyl, pteridinyl, morpholino, thiomorpholinyl, cyclohexyl, cyclopentyl, cyclohexenyl, and cyclopentenyl, each unsubstituted or substituted with said 1-3 substituents.

15. The compound or pharmaceutically acceptable salt according to claim 13, wherein $R_2$ is selected from the group consisting of:

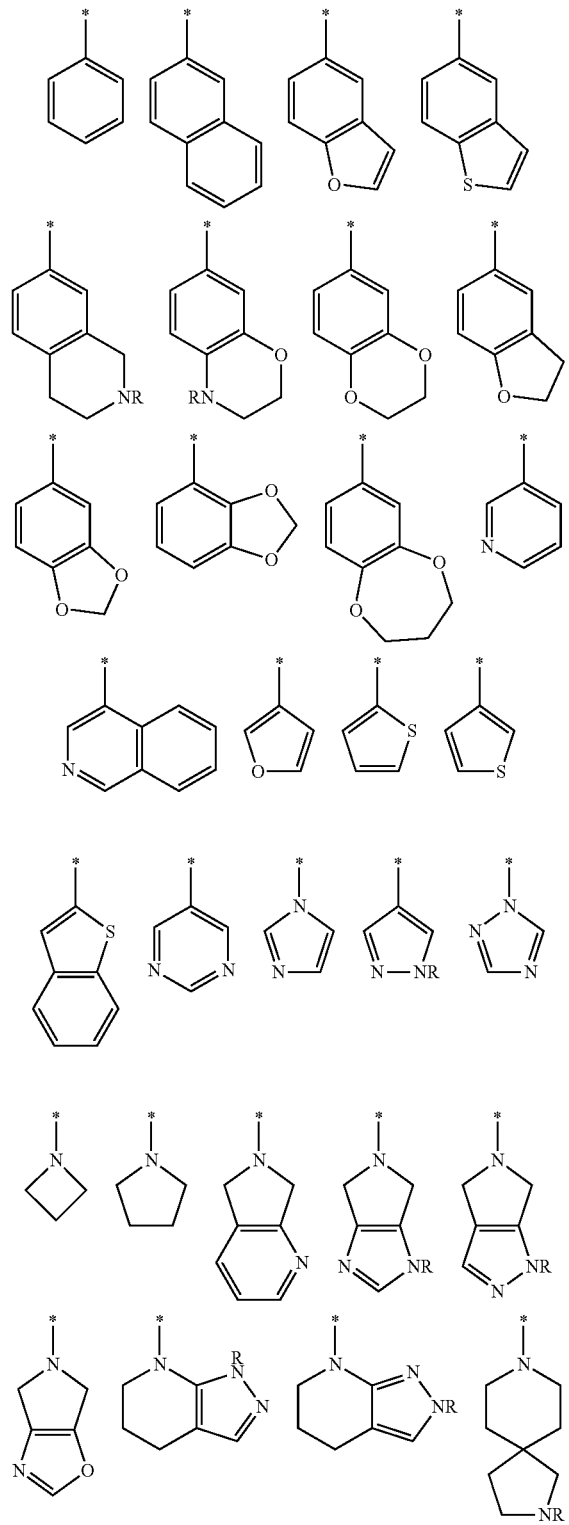

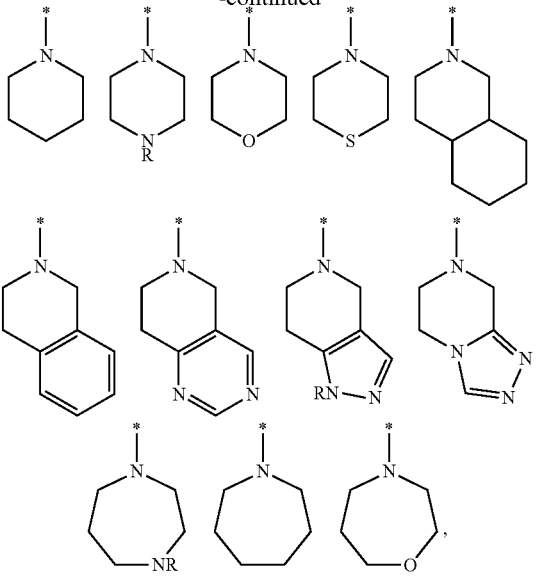

each of which is unsubstituted or substituted with said 1-3 substituents, wherein R is hydrogen or is one of said 1-3 substituents.

16. The compound or pharmaceutically acceptable salt according to claim 13, wherein $R_2$ is a phenyl, unsubstituted or substituted with said 1-3 substituents.

17. The compound or pharmaceutically acceptable salt according to claim 13, wherein $R_2$ is morpholinyl, unsubstituted or substituted with said 1-3 substituents.

18. The compound or pharmaceutically acceptable salt according to claim 1, wherein $R_2$ is unsubstituted phenyl.

19. The compound or pharmaceutically acceptable salt according to claim 1, wherein $R_3$ is selected from the group consisting of hydrogen, $(C_{1-6})$alkyl, $(C_{1-6})$haloalkyl, $(C_{1-6})$cycloalkyl, and $(C_{1-6})$alkoxy, each unsubstituted or substituted with said 1-2 substituents.

20. The compound according to claim 1 having the formula:

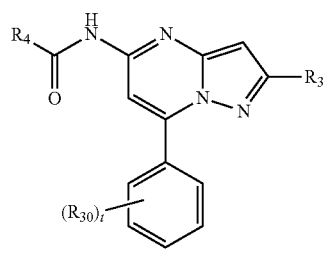

or a pharmaceutically acceptable salt thereof,
wherein
t is 0, 1, 2 or 3; and
each $R_{30}$ is independently selected from the group consisting of hydroxy, nitro, halo, cyano, oxo, $(C_{1-6})$alkoxy, $(C_{4-6})$aryloxy, $(C_{4-6})$aryl$(C_{1-6})$alkoxy, $(C_{1-6})$alkyl, $(C_{1-6})$haloalkyl, hydroxy$(C_{1-6})$alkyl, aminocarbonyl$(C_{1-6})$alkyl, cyanoalkyl, $(C_{1-6})$haloalkoxy, thio, thio$(C_{1-6})$alkyl, amino, sulfonylamino, $(C_{1-6})$alkylamino, $(C_{1-6})$alkylsulfonylamino, amido, aryl, aryl$(C_{1-6})$alkyl, $(C_{1-6})$alkylcarbonyl, $(C_{1-6})$alkoxycarbonyl, carboxamido, hydroxycarbonyl, and $(C_{1-6})$alkylsulfonyl.

21. The compound or pharmaceutically acceptable salt according to claim 20, wherein $R_4$ is selected from the group consisting of:

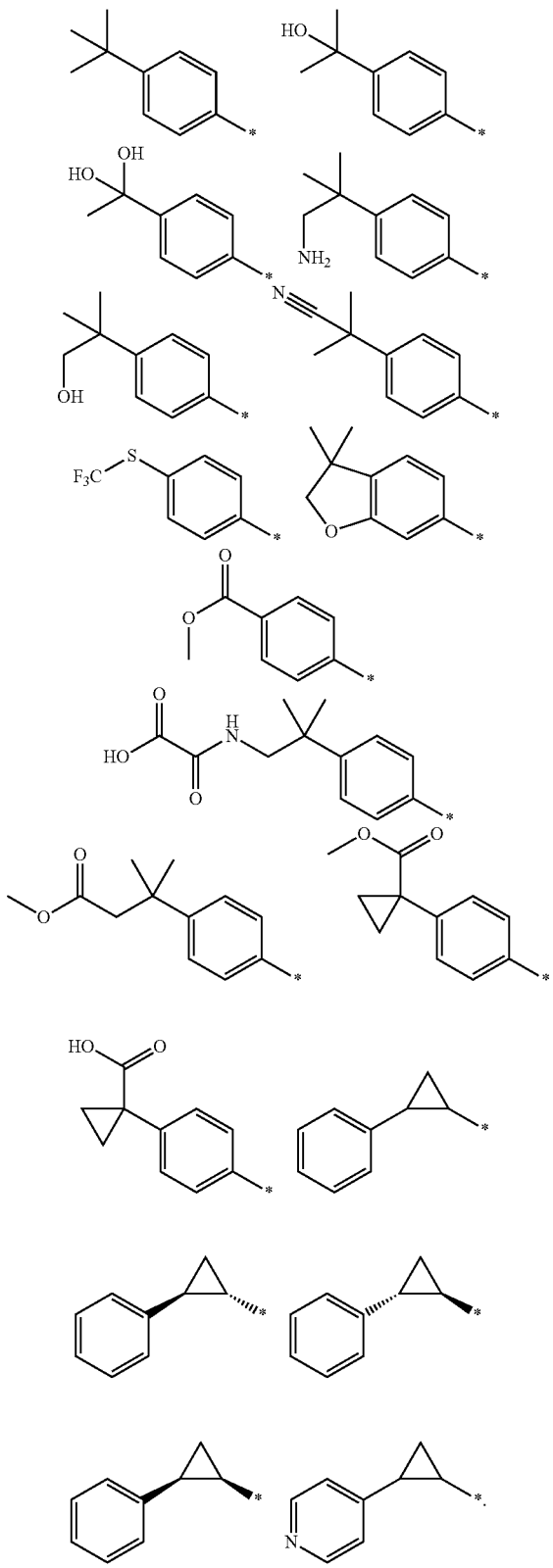

22. The compound or pharmaceutically acceptable salt according to claim 20, wherein $R_4$ is selected from the group consisting of:

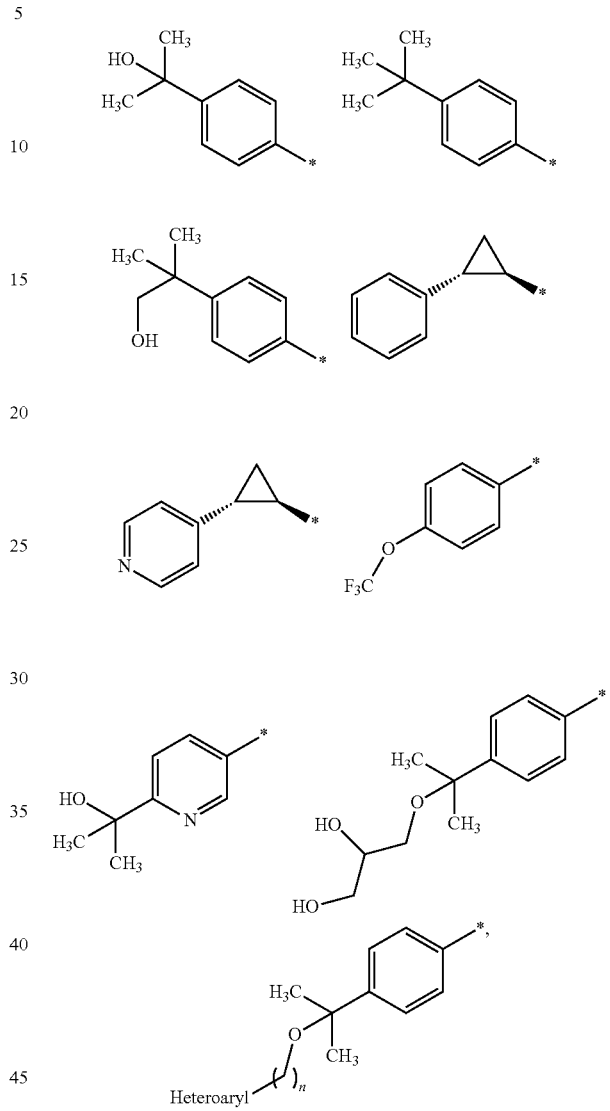

where n is 0, 1, 2, 3 or 4.

23. The compound or pharmaceutically acceptable salt according to claim 20, wherein each $R_{30}$ is independently selected from the group consisting of hydroxyl, nitro, cyano, fluoro, chloro, methyl, cyanomethyl, $-CH_2OCH_3$, isobutyl, $CF_3$, $-CH_2OH$, $-(CH_2)_2OH$, $-(CH_2)_3OH$, $-CH(CH_3)CH_2OH$, $-OCF_3$, isopropyloxy, $-OCH_2C(O)OH$, benzyloxy, $-OCH_2C(O)OCH_2CH_3$, $-OCH_2CH_2N(CH_3)_2$, $-OCH_2CH_2$morpholinyl, $-OCH_2CH_2OCH_3$, $-C(O)CH_3$, $-C(O)NH_2$, $-NHC(O)CH_3$, $-NHS(O)_2CH_3$, $-N(CH_3)_2$, $-SCH_3$, $-S(O)_2CH_3$, and phenyl.

24. The compound or pharmaceutically acceptable salt according to claim 20, wherein t is 0.

25. The compound or pharmaceutically acceptable salt according to claim 20, wherein $R_3$ is selected from the group consisting of hydrogen, $(C_{1-6})$alkyl, $(C_{1-6})$haloalkyl, $(C_{1-6})$cycloalkyl, and $(C_{1-6})$alkoxy, each unsubstituted or substituted with said 1-2 substituents.

26. The compound according to claim 1 having the formula:

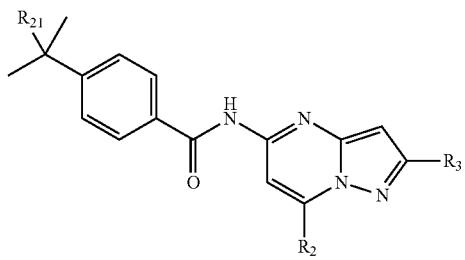

or a pharmaceutically acceptable salt thereof,
wherein
$R_{21}$ is selected from the group consisting of —$(CH_2)_n$OH, —C(O)OH, —C(O)OCH$_3$, cyano, —$(CH_2)_n$NH$_2$, —$(CH_2)_n$NHC(O)C(O)OH, —$(CH_2)_n$C(O)OH, —$(CH_2)_n$C(O)OCH$_3$, (C$_{1-4}$)alkyl, halo(C$_{1-4}$)alkyl, —$(CH_2)_n$CN, —$(CH_2)_n$CONH$_2$, —$(CH_2)_n$aryl, —$(CH_2)_n$heteroaryl, —O$(CH_2)_n$aryl, —O$(CH_2)_n$ heteroaryl, and —O$(CH_2)_n$CH(OH)CH$_2$OH, where n is 0, 1, 2, 3, or 4.

27. The compound or pharmaceutically acceptable salt according to claim 26, wherein $R_{21}$ is selected from the group consisting of cyano, hydroxyl, methyl, perfluoromethyl, hydroxylmethyl, —CH$_2$NH$_2$, —(CH$_2$)NHC(O)C(O)OH, —(CH$_2$)C(O)OH, —(CH$_2$)C(O)OCH$_3$, —O(CH$_2$)$_n$heteroaryl where n is 1 or 2, and —OCH$_2$CH(OH)CH$_2$OH.

28. The compound or pharmaceutically acceptable salt according to claim 26, wherein $R_{21}$ is OH.

29. The compound or pharmaceutically acceptable salt according to claim 26, wherein $R_2$ is selected from the group consisting of:

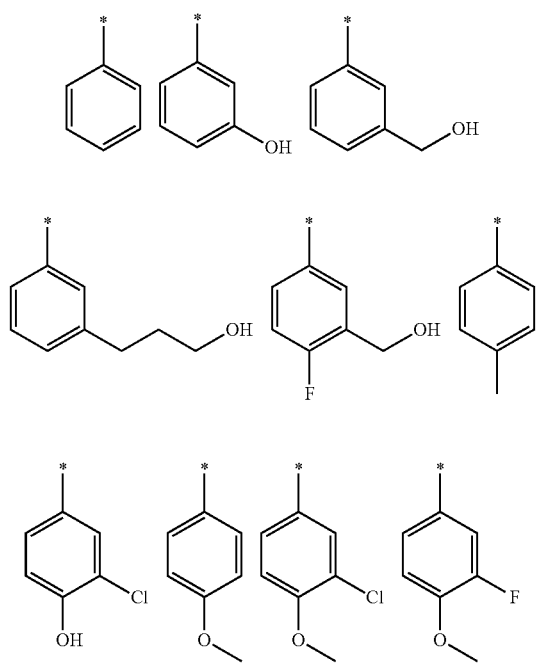

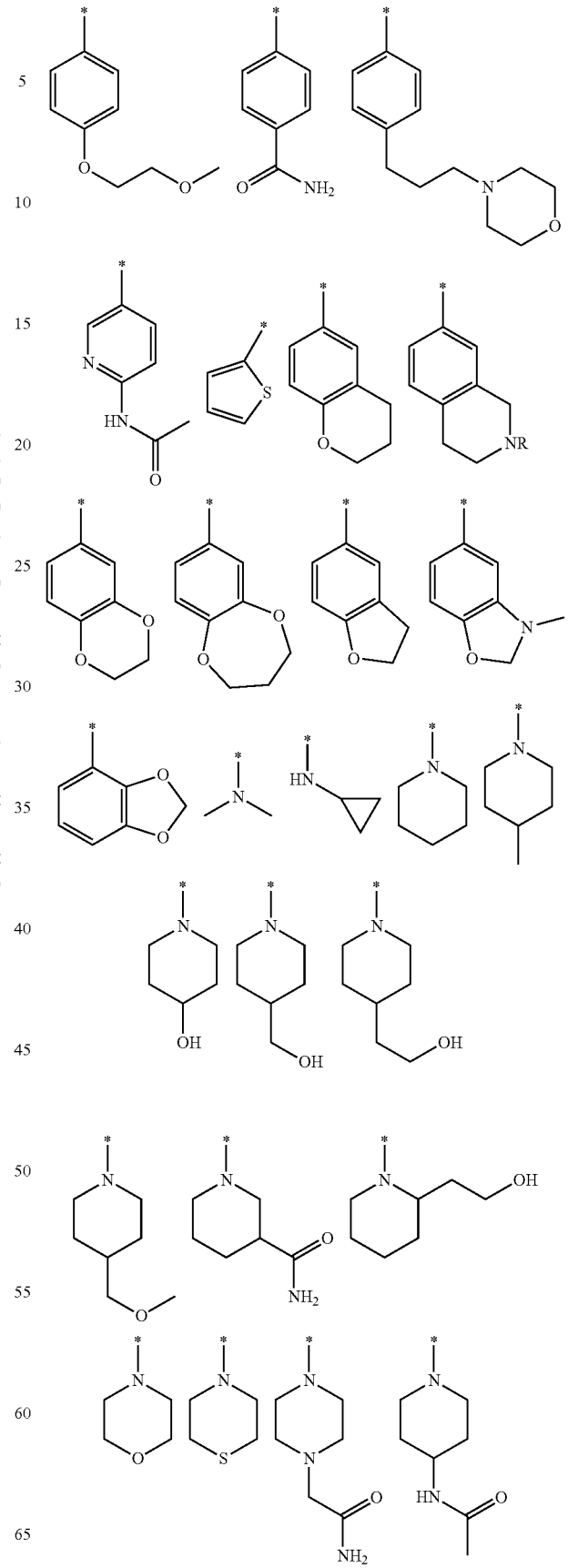

-continued

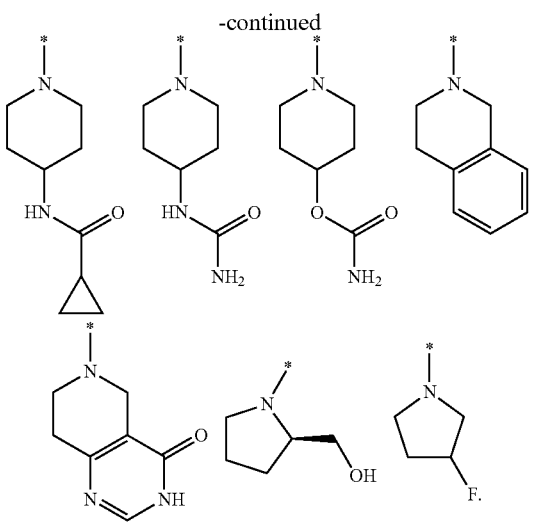

30. The compound or pharmaceutically acceptable salt according to claim 26, wherein $R_2$ is unsubstituted phenyl.

31. The compound or pharmaceutically acceptable salt according to claim 26, wherein $R_3$ is selected from the group consisting of hydrogen, $(C_{1-6})$alkyl, $(C_{1-6})$haloalkyl, $(C_{1-6})$cycloalkyl, and $(C_{1-6})$alkoxy, each unsubstituted or substituted with said 1-2 substituents.

32. A compound according to claim 1, which is selected from the group consisting of:
4-tert-butyl-N-(7-(3-(hydroxymethyl)phenyl)-2-methylpyrazolo[1,5-a]pyrimidin-5-yl)benzamide;
4-tert-butyl-N-(7-(thiophen-2-yl)pyrazolo[1,5-a]pyrimidin-5-yl)benzamide;
4-(tert-butyl)-N-(7-(3-(3-hydroxypropyl)phenyl)-2-methylpyrazolo[1,5-a]pyrimidin-5-yl)benzamide;
4-tert-butyl-N-(7-(4-fluoro-3-(hydroxymethyl)phenyl)-2-methylpyrazolo[1,5-a]pyrimidin-5-yl)benzamide;
4-tert-butyl-N-(7-(3-(hydroxymethyl)phenyl)pyrazolo[1,5-a]pyrimidin-5-yl)benzamide;
N-(7-(3-(hydroxymethyl)phenyl)pyrazolo[1,5-a]pyrimidin-5-yl)-4-(2-hydroxypropan-2-yl)benzamide;
N-(7-(3-(hydroxymethyl)phenyl)pyrazolo[1,5-a]pyrimidin-5-yl)-4-(1,1,1-trifluoro-2-hydroxypropan-2-yl)benzamide;
4-tert-butyl-N-(7-(4-(methylsulfonyl)phenyl)pyrazolo[1,5-a]pyrimidin-5-yl)benzamide;
4-tert-butyl-N-(7-(4-methoxyphenyl)pyrazolo[1,5-a]pyrimidin-5-yl)benzamide;
4-tert-butyl-N-(7-(3-(2-hydroxyethyl)phenyl)pyrazolo[1,5-a]pyrimidin-5-yl)benzamide;
4-tert-butyl-N-(7-(3-(3-hydroxypropyl)phenyl)pyrazolo[1,5-a]pyrimidin-5-yl)benzamide;
N-(7-(3-acetylphenyl)pyrazolo[1,5-a]pyrimidin-5-yl)-4-tert-butylbenzamide;
4-tert-butyl-N-(7-(6-methoxypyridin-3-yl)pyrazolo[1,5-a]pyrimidin-5-yl)benzamide;
N-(7-(6-acetamidopyridin-3-yl)pyrazolo[1,5-a]pyrimidin-5-yl)-4-tert-butylbenzamide;
4-tert-butyl-N-(7-(3-methoxyphenyl)pyrazolo[1,5-a]pyrimidin-5-yl)benzamide;
4-(2-hydroxypropan-2-yl)-N-(7-phenylpyrazolo[1,5-a]pyrimidin-5-yl)benzamide;
4-(2-hydroxypropan-2-yl)-N-(7-(3-(methylsulfonamido)phenyl)pyrazolo[1,5-a]pyrimidin-5-yl)benzamide;
N-(7-(furan-3-yl)pyrazolo[1,5-a]pyrimidin-5-yl)-4-(2-hydroxypropan-2-yl)benzamide;
4-(2-hydroxypropan-2-yl)-N-(7-(4-methoxyphenyl)pyrazolo[1,5-a]pyrimidin-5-yl)benzamide;
4-(2-hydroxypropan-2-yl)-N-(7-p-tolylpyrazolo[1,5-a]pyrimidin-5-yl)benzamide;
N-(7-(3-(cyanomethyl)phenyl)pyrazolo[1,5-a]pyrimidin-5-yl)-4-(2-hydroxypropan-2-yl)benzamide;
N-(7-(4-carbamoylphenyl)pyrazolo[1,5-a]pyrimidin-5-yl)-4-(2-hydroxypropan-2-yl)benzamide;
4-(2-hydroxypropan-2-yl)-N-(7-(4-(methylthio)phenyl)pyrazolo[1,5-a]pyrimidin-5-yl)benzamide;
4-(2-hydroxypropan-2-yl)-N-(7-(4-(trifluoromethyl)phenyl)pyrazolo[1,5-a]pyrimidin-5-yl)benzamide;
N-(7-(3-acetamidophenyl)pyrazolo[1,5-a]pyrimidin-5-yl)-4-(2-hydroxypropan-2-yl)benzamide;
ethyl 2-(3-(5-(4-(2-hydroxypropan-2-yl)benzamido)pyrazolo[1,5-a]pyrimidin-7-yl)phenoxy)acetate;
2-(3-(5-(4-(2-hydroxypropan-2-yl)benzamido)pyrazolo[1,5-a]pyrimidin-7-yl)phenoxy)acetic acid;
4-(2-hydroxypropan-2-yl)-N-(7-(3-(methoxymethyl)phenyl)pyrazolo[1,5-a]pyrimidin-5-yl)benzamide;
4-(1-hydroxy-2-methylpropan-2-yl)-N-(2-methyl-7-phenylpyrazolo[1,5-a]pyrimidin-5-yl)benzamide;
4-(1-hydroxy-2-methylpropan-2-yl)-N-(7-(3-(hydroxymethyl)phenyl)-2-methylpyrazolo[1,5-a]pyrimidin-5-yl)benzamide;
4-(1-hydroxy-2-methylpropan-2-yl)-N-(7-(3-(methoxymethyl)phenyl)-2-methylpyrazolo[1,5-a]pyrimidin-5-yl)benzamide;
4-tert-butyl-N-[7-(4-fluorophenyl)pyrazolo[1,5-a]pyrimidin-5-yl]benzamide;
4-tert-butyl-N-[7-(4-tert-butylphenyl)pyrazolo[1,5-a]pyrimidin-5-yl]benzamide;
4-tert-butyl-N-{7-[3-(cyanomethyl)phenyl]pyrazolo[1,5-a]pyrimidin-5-yl}benzamide;
4-tert-butyl-N-(7-(furan-3-yl)pyrazolo[1,5-a]pyrimidin-5-yl)benzamide;
4-tert-butyl-N-(7-phenylpyrazolo[1,5-a]pyrimidin-5-yl)benzamide;
4-tert-butyl-N-(7-p-tolylpyrazolo[1,5-a]pyrimidin-5-yl)benzamide;
4-tert-butyl-N-(7-(4-cyanophenyl)pyrazolo[1,5-a]pyrimidin-5-yl)benzamide;
4-tert-butyl-N-(7-(3,5-dimethylphenyl)pyrazolo[1,5-a]pyrimidin-5-yl)benzamide;
4-tert-butyl-N-(7-(4-chlorophenyl)pyrazolo[1,5-a]pyrimidin-5-yl)benzamide;
4-tert-butyl-N-(7-(2-chlorophenyl)pyrazolo[1,5-a]pyrimidin-5-yl)benzamide;
4-tert-butyl-N-(7-(4-carbamoylphenyl)pyrazolo[1,5-a]pyrimidin-5-yl)benzamide;
4-tert-butyl-N-(7-(4-(methylthio)phenyl)pyrazolo[1,5-a]pyrimidin-5-yl)benzamide;
N-(7-(benzo[b]thiophen-2-yl)pyrazolo[1,5-a]pyrimidin-5-yl)-4-tert-butylbenzamide;
4-tert-butyl-N-(7-(2,4-dimethoxyphenyl)pyrazolo[1,5-a]pyrimidin-5-yl)benzamide;
4-tert-butyl-N-(7-(3-(trifluoromethyl)phenyl)pyrazolo[1,5-a]pyrimidin-5-yl)benzamide;
4-tert-butyl-N-(7-(4-(trifluoromethoxy)phenyl)pyrazolo[1,5-a]pyrimidin-5-yl)benzamide;
4-tert-butyl-N-(7-o-tolylpyrazolo[1,5-a]pyrimidin-5-yl)benzamide;
4-tert-butyl-N-(7-(2-(hydroxymethyl)phenyl)pyrazolo[1,5-a]pyrimidin-5-yl)benzamide;

N-(7-(2-acetamidophenyl)pyrazolo[1,5-a]pyrimidin-5-yl)-4-tert-butylbenzamide;
N-(7-(biphenyl-2-yl)pyrazolo[1,5-a]pyrimidin-5-yl)-4-tert-butylbenzamide;
4-tert-butyl-N-(7-(2-(methylsulfonamido)phenyl)pyrazolo[1,5-a]pyrimidin-5-yl)benzamide;
4-tert-butyl-N-(7-(2-methoxypyridin-3-yl)pyrazolo[1,5-a]pyrimidin-5-yl)benzamide;
4-tert-butyl-N-(7-(naphthalen-2-yl)pyrazolo[1,5-a]pyrimidin-5-yl)benzamide;
4-tert-butyl-N-(7-(3-nitrophenyl)pyrazolo[1,5-a]pyrimidin-5-yl)benzamide;
4-tert-butyl-N-(7-(4-nitrophenyl)pyrazolo[1,5-a]pyrimidin-5-yl)benzamide;
4-tert-butyl-N-(7-(3,4-difluorophenyl)pyrazolo[1,5-a]pyrimidin-5-yl)benzamide;
4-tert-butyl-N-(7-(4-sec-butylphenyl)pyrazolo[1,5-a]pyrimidin-5-yl)benzamide;
4-tert-butyl-N-(7-(isoquinolin-4-yl)pyrazolo[1,5-a]pyrimidin-5-yl)benzamide;
4-tert-butyl-N-(7-(4-isobutyl-3-nitrophenyl)pyrazolo[1,5-a]pyrimidin-5-yl)benzamide;
4-tert-butyl-N-(7-(2-formylphenyl)pyrazolo[1,5-a]pyrimidin-5-yl)benzamide;
4-tert-butyl-N-(7-(3-(methylsulfonamido)phenyl)pyrazolo[1,5-a]pyrimidin-5-yl)benzamide;
N-(7-(1-benzyl-1H-pyrazol-4-yl)pyrazolo[1,5-a]pyrimidin-5-yl)-4-tert-butylbenzamide;
N-(7-(3,4-dihydroisoquinolin-2(1H)-yl)pyrazolo[1,5-a]pyrimidin-5-yl)-4-(2-hydroxypropan-2-yl)benzamide;
4-tert-butyl-N-(7-morpholinopyrazolo[1,5-a]pyrimidin-5-yl)benzamide;
4-tert-butyl-N-(7-(3,4-dihydroisoquinolin-2(1H)-yl)pyrazolo[1,5-a]pyrimidin-5-yl)benzamide;
(S)-N-(7-(2-(hydroxymethyl)pyrrolidin-1-yl)pyrazolo[1,5-a]pyrimidin-5-yl)-4-(2-hydroxypropan-2-yl)benzamide;
(R)-N-(7-(2-(hydroxymethyl)pyrrolidin-1-yl)pyrazolo[1,5-a]pyrimidin-5-yl)-4-(2-hydroxypropan-2-yl)benzamide;
(R)-4-(2-hydroxypropan-2-yl)-N-(7-(3-hydroxypyrrolidin-1-yl)pyrazolo[1,5-a]pyrimidin-5-yl)benzamide;
(S)-4-(2-hydroxypropan-2-yl)-N-(7-(3-hydroxypyrrolidin-1-yl)pyrazolo[1,5-a]pyrimidin-5-yl)benzamide;
N-(7-(4-hydroxyethyl)piperidin-1-yl)pyrazolo[1,5-a]pyrimidin-5-yl)-4-(2-hydroxypropan-2-yl)benzamide;
4-(2-hydroxypropan-2-yl)-N-(7-morpholinopyrazolo[1,5-a]pyrimidin-5-yl)benzamide;
N-(7-(4-hydroxypiperidin-1-yl)pyrazolo[1,5-a]pyrimidin-5-yl)-4-(2-hydroxypropan-2-yl)benzamide;
N-(7-(2-(2-hydroxyethyl)piperidin-1-yl)pyrazolo[1,5-a]pyrimidin-5-yl)-4-(2-hydroxypropan-2-yl)benzamide;
(S)-4-tert-butyl-N-(7-(3-hydroxypiperidin-1-yl)pyrazolo[1,5-a]pyrimidin-5-yl)benzamide;
(R)-N-(7-(3-hydroxypiperidin-1-yl)pyrazolo[1,5-a]pyrimidin-5-yl)-4-(2-hydroxypropan-2-yl)benzamide;
(R)-4-tert-butyl-N-(7-(3-hydroxypiperidin-1-yl)pyrazolo[1,5-a]pyrimidin-5-yl)benzamide;
(S)-N-(7-(3-hydroxypiperidin-1-yl)pyrazolo[1,5-a]pyrimidin-5-yl)-4-(2-hydroxypropan-2-yl)benzamide;
N-(7-(6,7-dihydro-1H-pyrazolo[4,3-c]pyridin-5(4H)-yl)pyrazolo[1,5-a]pyrimidin-5-yl)-4-(2-hydroxypropan-2-yl)benzamide;
4-(2-hydroxypropan-2-yl)-N-(7-(2-methylpiperidin-1-yl)pyrazolo[1,5-a]pyrimidin-5-yl)benzamide;
4-(2-hydroxypropan-2-yl)-N-(7-(3-methylpiperidin-1-yl)pyrazolo[1,5-a]pyrimidin-5-yl)benzamide;
N-(7-(3,5-dimethylpiperidin-1-yl)pyrazolo[1,5-a]pyrimidin-5-yl)-4-(2-hydroxypropan-2-yl)benzamide;
(R)-1-(5-(4-(2-hydroxypropan-2-yl)benzamido)pyrazolo[1,5-a]pyrimidin-7-yl)piperidine-3-carboxamide;
(R)-1-(5-(4-(2-hydroxypropan-2-yl)benzamido)pyrazolo[1,5-a]pyrimidin-7-yl)piperidine-3-carboxylic acid;
(S)-1-(5-(4-(2-hydroxypropan-2-yl)benzamido)pyrazolo[1,5-a]pyrimidin-7-yl)piperidine-3-carboxamide;
(S)-1-(5-(4-(2-hydroxypropan-2-yl)benzamido)pyrazolo[1,5-a]pyrimidin-7-yl)piperidine-3-carboxylic acid;
4-(2-hydroxypropan-2-yl)-N-(7-(pyrrolidin-1-yl)pyrazolo[1,5-a]pyrimidin-5-yl)benzamide;
N-(7-(cyclopropylamino)pyrazolo[1,5-a]pyrimidin-5-yl)-4-(2-hydroxypropan-2-yl)benzamide;
4-(2-hydroxypropan-2-yl)-N-(7-(4-oxo-3,4,7,8-tetrahydropyrido[4,3-d]pyrimidin-6(5H)-yl)pyrazolo[1,5-a]pyrimidin-5-yl)benzamide;
4-(2-hydroxypropan-2-yl)-N-(7-(4-(methylsulfonyl)piperazin-1-yl)pyrazolo[1,5-a]pyrimidin-5-yl)benzamide;
N-7-(5,6-dihydro-[1,2,4]triazolo[4,3-a]pyrazin-7(8H)-yl)pyrazolo[1,5-a]pyrimidin-5-yl)-4-(2-hydroxypropan-2-yl)benzamide;
(S)-1-(5-(4-(2-hydroxypropan-2-yl)benzamido)pyrazolo[1,5-a]pyrimidin-7-yl)pyrrolidine-2-carboxamide;
4-(2-hydroxypropan-2-yl)-N-(7-(5-oxo-1,4-diazepan-1-yl)pyrazolo[1,5-a]pyrimidin-5-yl)benzamide;
4-(1-hydroxy-2-methylpropan-2-yl)-N-(2-methyl-7-(pyrrolidin-1-yl)pyrazolo[1,5-a]pyrimidin-5-yl)benzamide;
(S)-4-(1-hydroxy-2-methylpropan-2-yl)-N-(7-(2-(hydroxymethyl)pyrrolidin-1-yl)-2-methylpyrazolo[1,5-a]pyrimidin-5-yl)benzamide;
(R)-ethyl 1-(5-(4-(1-hydroxy-2-methylpropan-2-yl)benzamido)-2-methylpyrazolo[1,5-a]pyrimidin-7-yl)piperidine-3-carboxylate;
4-(1-hydroxy-2-methylpropan-2-yl)-N-(7-(3-hydroxyazetidin-1-yl)-2-methylpyrazolo[1,5-a]pyrimidin-5-yl)benzamide;
4-(1-hydroxy-2-methylpropan-2-yl)-N-(2-methyl-7-(4-oxo-3,4,7,8-tetrahydropyrido[4,3-d]pyrimidin-6(5H)-yl)pyrazolo[1,5-a]pyrimidin-5-yl)benzamide;
4-(1-hydroxy-2-methylpropan-2-yl)-N-(2-methyl-7-morpholinopyrazolo[1,5-a]pyrimidin-5-yl)benzamide;
(R)-4-(1-hydroxy-2-methylpropan-2-yl)-N-(7-(3-hydroxypyrrolidin-1-yl)-2-methylpyrazolo[1,5-a]pyrimidin-5-yl)benzamide;
4-(1-hydroxy-2-methylpropan-2-yl)-N-(7-(4-(2-hydroxyethyl)piperidin-1-yl)-2-methylpyrazolo[1,5-a]pyrimidin-5-yl)benzamide;
4-tert-butyl-N-(7-(piperidin-1-yl)pyrazolo[1,5-a]pyrimidin-5-yl)benzamide;
4-tert-butyl-N-(7-morpholinopyrazolo[1,5-a]pyrimidin-5-yl)benzamide;
1-(5-(4-tert-butylbenzamido)pyrazolo[1,5-a]pyrimidin-7-yl)piperidine-3-carboxamide;
4-tert-butyl-N-(7-(2-(2-hydroxyethyl)piperidin-1-yl)pyrazolo[1,5-a]pyrimidin-5-yl)benzamide;
4-tert-butyl-N-(7-(octahydroisoquinolin-2(1H)-yl)pyrazolo[1,5-a]pyrimidin-5-yl)benzamide;
4-tert-butyl-N-(7-(4-hydroxy-4-phenylpiperidin-1-yl)pyrazolo[1,5-a]pyrimidin-5-yl)benzamide;
4-tert-butyl-N-(7-(4-methylpiperazin-1-yl)pyrazolo[1,5-a]pyrimidin-5-yl)benzamide;
4-tert-butyl-N-(7-(4-phenethylpiperazin-1-yl)pyrazolo[1,5-a]pyrimidin-5-yl)benzamide;
4-tert-butyl-N-(7-(6,7-dihydro-2H-pyrazolo[4,3-c]pyridin-5(4H)-yl)pyrazolo[1,5-a]pyrimidin-5-yl)benzamide;

(S)-4-tert-butyl-N-(7-(2-(hydroxymethyl)pyrrolidin-1-yl)pyrazolo[1,5-a]pyrimidin-5-yl)benzamide;
4-tert-butyl-N-(7-(4-hydroxypiperidin-1-yl)pyrazolo[1,5-a]pyrimidin-5-yl)benzamide;
4-tert-butyl-N-(7-(3-hydroxypiperidin-1-yl)pyrazolo[1,5-a]pyrimidin-5-yl)benzamide;
1-(5-(4-tert-butylbenzamido)pyrazolo[1,5-a]pyrimidin-7-yl)piperidine-4-carboxamide;
N-(7-(3-acetamidopyrrolidin-1-yl)pyrazolo[1,5-a]pyrimidin-5-yl)-4-tert-butylbenzamide;
4-tert-butyl-N-(7-(4-(2-hydroxyethyl)piperidin-1-yl)pyrazolo[1,5-a]pyrimidin-5-yl)benzamide;
1-(5-(4-tert-butylbenzamido)pyrazolo[1,5-a]pyrimidin-7-yl)piperidine-3-carboxylic acid;
4-tert-butyl-N-(7-(3-hydroxypyrrolidin-1-yl)pyrazolo[1,5-a]pyrimidin-5-yl)benzamide;
(R)-N-(7-(3-acetamidopyrrolidin-1-yl)pyrazolo[1,5-a]pyrimidin-5-yl)-4-tert-butylbenzamide;
N-(7-(1H-imidazol-1-yl)pyrazolo[1,5-a]pyrimidin-5-yl)-4-tert-butylbenzamide;
N-(7-(1H-1,2,4-triazol-1-yl)pyrazolo[1,5-a]pyrimidin-5-yl)-4-tert-butylbenzamide;
4-tert-butyl-N-(7-(6,7-dihydro-1H-pyrazolo[4,3-b]pyridin-4(5H)-yl)pyrazolo[1,5-a]pyrimidin-5-yl)benzamide;
4-tert-butyl-N-(7-(pyrrolidin-1-yl)pyrazolo[1,5-a]pyrimidin-5-yl)benzamide;
(E)-4-tert-butyl-N-(7-(2-cyclohexylvinyl)pyrazolo[1,5-a]pyrimidin-5-yl)benzamide;
4-tert-butyl-N-(7-(dimethylamino)pyrazolo[1,5-a]pyrimidin-5-yl)benzamide;
N-(7-(benzyl(2-(dimethylamino)ethyl)amino)pyrazolo[1,5-a]pyrimidin-5-yl)-4-tert-butylbenzamide;
4-(1-hydroxy-2-methylpropan-2-yl)-N-(2-methyl-7-(methyl(phenethyl)amino)pyrazolo[1,5-a]pyrimidin-5-yl)benzamide;
4-tert-butyl-N-[7-(cyclopropylamino)pyrazolo[1,5-a]pyrimidin-5-yl]benzamide;
4-tert-butyl-N-{7-[(4-methoxybenzyl)amino]pyrazolo[1,5-a]pyrimidin-5-yl}benzamide;
4-tert-butyl-N-{7-[(1-methyl-1-phenylethyl)amino]pyrazolo[1,5-a]pyrimidin-5-yl}benzamide;
4-tert-butyl-N-[7-(phenylamino)pyrazolo[1,5-a]pyrimidin-5-yl]benzamide;
4-tert-butyl-N-(7-(isobutylamino)pyrazolo[1,5-a]pyrimidin-5-yl)benzamide;
4-tert-butyl-N-(7-(butylamino)pyrazolo[1,5-a]pyrimidin-5-yl)benzamide;
4-tert-butyl-N-(7-(tert-butylamino)pyrazolo[1,5-a]pyrimidin-5-yl)benzamide;
4-tert-butyl-N-(7-(3-hydroxypropylamino)pyrazolo[1,5-a]pyrimidin-5-yl)benzamide;
4-tert-butyl-N-(7-(cyclopentylamino)pyrazolo[1,5-a]pyrimidin-5-yl)benzamide;
4-tert-butyl-N-(7-(furan-2-ylmethylamino)pyrazolo[1,5-a]pyrimidin-5-yl)benzamide;
N-(7-(2-acetamidoethylamino)pyrazolo[1,5-a]pyrimidin-5-yl)-4-tert-butylbenzamide;
4-tert-butyl-N-(7-(2-isopropoxyethylamino)pyrazolo[1,5-a]pyrimidin-5-yl)benzamide;
4-tert-butyl-N-(7-(3-(methylthio)propylamino)pyrazolo[1,5-a]pyrimidin-5-yl)benzamide;
N-(7-(benzylamino)pyrazolo[1,5-a]pyrimidin-5-yl)-4-tert-butylbenzamide;
4-tert-butyl-N-(7-(cyclohexylmethylamino)pyrazolo[1,5-a]pyrimidin-5-yl)benzamide;
4-tert-butyl-N-(7-(phenethylamino)pyrazolo[1,5-a]pyrimidin-5-yl)benzamide;
N-(7-(3-amino-3-oxopropylamino)pyrazolo[1,5-a]pyrimidin-5-yl)-4-tert-butylbenzamide;
4-tert-butyl-N-(7-(3-fluorobenzylamino)pyrazolo[1,5-a]pyrimidin-5-yl)benzamide;
4-tert-butyl-N-(7-(2,3-dihydro-1H-inden-2-ylamino)pyrazolo[1,5-a]pyrimidin-5-yl)benzamide;
4-tert-butyl-N-(7-(4-hydroxyphenethylamino)pyrazolo[1,5-a]pyrimidin-5-yl)benzamide;
4-tert-butyl-N-(7-(2-phenoxyethylamino)pyrazolo[1,5-a]pyrimidin-5-yl)benzamide;
4-tert-butyl-N-(7-(3-(2-oxopyrrolidin-1-yl)propylamino)pyrazolo[1,5-a]pyrimidin-5-yl)benzamide;
N-(7-(benzo[d][1,3]dioxol-5-ylmethylamino)pyrazolo[1,5-a]pyrimidin-5-yl)-4-tert-butylbenzamide;
N-(7-(2-(1H-indol-3-yl)ethylamino)pyrazolo[1,5-a]pyrimidin-5-yl)-4-tert-butylbenzamide;
4-tert-butyl-N-(7-(4-(trifluoromethyl)benzylamino)pyrazolo[1,5-a]pyrimidin-5-yl)benzamide;
4-tert-butyl-N-(7-(3,4-dimethoxyphenethylamino)pyrazolo[1,5-a]pyrimidin-5-yl)benzamide;
4-tert-butyl-N-(7-(4-sulfamoylbenzylamino)pyrazolo[1,5-a]pyrimidin-5-yl)benzamide;
N-(7-(3,5-bis(trifluoromethyl)benzylamino)pyrazolo[1,5-a]pyrimidin-5-yl)-4-tert-butylbenzamide;
4-tert-butyl-N-(7-(2-methoxyethylamino)pyrazolo[1,5-a]pyrimidin-5-yl)benzamide;
4-tert-butyl-N-(7-(pentan-3-ylamino)pyrazolo[1,5-a]pyrimidin-5-yl)benzamide;
N-(7-(2-amino-2-oxoethylamino)pyrazolo[1,5-a]pyrimidin-5-yl)-4-tert-butylbenzamide;
4-tert-butyl-N-(7-(3-methylbenzylamino)pyrazolo[1,5-a]pyrimidin-5-yl)benzamide;
4-tert-butyl-N-(7-(2-(dimethylamino)ethylamino)pyrazolo[1,5-a]pyrimidin-5-yl)benzamide;
4-tert-butyl-N-(7-(pyridin-3-ylmethylamino)pyrazolo[1,5-a]pyrimidin-5-yl)benzamide;
4-tert-butyl-N-(7-(2-(pyridin-2-yl)ethylamino)pyrazolo[1,5-a]pyrimidin-5-yl)benzamide;
4-tert-butyl-N-(7-((5-methylpyrazin-2-yl)methylamino)pyrazolo[1,5-a]pyrimidin-5-yl)benzamide;
N-(7-(3-(1H-imidazol-1-yl)propylamino)pyrazolo[1,5-a]pyrimidin-5-yl)-4-tert-butylbenzamide;
N-(7-(2-(1H-imidazol-5-yl)ethylamino)pyrazolo[1,5-a]pyrimidin-5-yl)-4-tert-butylbenzamide;
(S)-methyl 2-(5-(4-tert-butylbenzamido)pyrazolo[1,5-a]pyrimidin-7-ylamino)-3-(1H-imidazol-5-yl)propanoate;
4-tert-butyl-N-(7-(2-hydroxycyclohexylamino)pyrazolo[1,5-a]pyrimidin-5-yl)benzamide;
4-tert-butyl-N-(7-(pyridin-2-ylamino)pyrazolo[1,5-a]pyrimidin-5-yl)benzamide;
4-tert-butyl-N-(7-(pyridin-3-ylamino)pyrazolo[1,5-a]pyrimidin-5-yl)benzamide;
4-tert-butyl-N-(7-(pyrimidin-2-ylamino)pyrazolo[1,5-a]pyrimidin-5-yl)benzamide;
N-(7-(3-(benzyloxy)phenyl)pyrazolo[1,5-a]pyrimidin-5-yl)-4-(2-hydroxypropan-2-yl)benzamide;
N-(7-(2,3-dihydrobenzofuran-5-yl)pyrazolo[1,5-a]pyrimidin-5-yl)-4-(2-hydroxypropan-2-yl)benzamide;
4-(2-hydroxypropan-2-yl)-N-(7-(3-methoxyphenyl)pyrazolo[1,5-a]pyrimidin-5-yl)benzamide;
(E)-4-(2-hydroxypropan-2-yl)-N-(7-styrylpyrazolo[1,5-a]pyrimidin-5-yl)benzamide;
4-(2-hydroxypropan-2-yl)-N-(7-(thiophen-3-yl)pyrazolo[1,5-a]pyrimidin-5-yl)benzamide;

N-(7-(3-hydroxyazetidin-1-yl)pyrazolo[1,5-a]pyrimidin-5-yl)-4-(2-hydroxypropan-2-yl)benzamide;
4-(2-hydroxypropan-2-yl)-N-(7-(2-methylpyrrolidin-1-yl)pyrazolo[1,5-a]pyrimidin-5-yl)benzamide;
N-(7-(3-fluoropyrrolidin-1-yl)pyrazolo[1,5-a]pyrimidin-5-yl)-4-(2-hydroxypropan-2-yl)benzamide;
4-(2-hydroxypropan-2-yl)-N-(7-(3-oxopiperazin-1-yl)pyrazolo[1,5-a]pyrimidin-5-yl)benzamide;
N-(7-(3-cyanopiperidin-1-yl)pyrazolo[1,5-a]pyrimidin-5-yl)-4-(2-hydroxypropan-2-yl)benzamide;
4-(2-hydroxypropan-2-yl)-N-(7-(3-methyl-4-oxopiperidin-1-yl)pyrazolo[1,5-a]pyrimidin-5-yl)benzamide;
N-(7-(3,3-dimethylpiperidin-1-yl)pyrazolo[1,5-a]pyrimidin-5-yl)-4-(2-hydroxypropan-2-yl)benzamide;
N-(7-(4-formylpiperazin-1-yl)pyrazolo[1,5-a]pyrimidin-5-yl)-4-(2-hydroxypropan-2-yl)benzamide;
(S)-N-(7-(3-(dimethylamino)pyrrolidin-1-yl)pyrazolo[1,5-a]pyrimidin-5-yl)-4-(2-hydroxypropan-2-yl)benzamide;
(R)-4-(2-hydroxypropan-2-yl)-N-(7-(2-(methoxymethyl)pyrrolidin-1-yl)pyrazolo[1,5-a]pyrimidin-5-yl)benzamide;
(R)-N-(7-(3-(dimethylamino)pyrrolidin-1-yl)pyrazolo[1,5-a]pyrimidin-5-yl)-4-(2-hydroxypropan-2-yl)benzamide;
N-(7-(2,5-dimethylpiperazin-1-yl)pyrazolo[1,5-a]pyrimidin-5-yl)-4-(2-hydroxypropan-2-yl)benzamide;
4-(2-hydroxypropan-2-yl)-N-(7-(4-methyl-1,4-diazepan-1-yl)pyrazolo[1,5-a]pyrimidin-5-yl)benzamide;
N-(7-(2,6-dimethylmorpholino)pyrazolo[1,5-a]pyrimidin-5-yl)-4-(2-hydroxypropan-2-yl)benzamide;
N-(7-(3-(hydroxymethyl)piperidin-1-yl)pyrazolo[1,5-a]pyrimidin-5-yl)-4-(2-hydroxypropan-2-yl)benzamide;
N-(7-(4-(hydroxymethyl)piperidin-1-yl)pyrazolo[1,5-a]pyrimidin-5-yl)-4-(2-hydroxypropan-2-yl)benzamide;
4-(2-hydroxypropan-2-yl)-N-(7-(4-methoxypiperidin-1-yl)pyrazolo[1,5-a]pyrimidin-5-yl)benzamide;
4-(2-hydroxypropan-2-yl)-N-(2-methyl-7-morpholinopyrazolo[1,5-a]pyrimidin-5-yl)benzamide;
4-(2-hydroxypropan-2-yl)-N-(2-methyl-7-phenylpyrazolo[1,5-a]pyrimidin-5-yl)benzamide;
(R)-4-(2-hydroxypropan-2-yl)-N-(7-(3-hydroxypyrrolidin-1-yl)-2-methylpyrazolo[1,5-a]pyrimidin-5-yl)benzamide;
4-(2-hydroxypropan-2-yl)-N-(2-methyl-7-(piperidin-1-yl)pyrazolo[1,5-a]pyrimidin-5-yl)benzamide;
N-(7-(benzo[d][1,3]dioxol-4-yl)pyrazolo[1,5-a]pyrimidin-5-yl)-4-(2-hydroxypropan-2-yl)benzamide;
4-(2-hydroxypropan-2-yl)-N-(2-methyl-7-(4-oxo-3,4,7,8-tetrahydropyrido[4,3-d]pyrimidin-6(5H)-yl)pyrazolo[1,5-a]pyrimidin-5-yl)benzamide;
4-(2-hydroxypropan-2-yl)-N-(2-methyl-7-thiomorpholinopyrazolo[1,5-a]pyrimidin-5-yl)benzamide;
4-[5-({[4-(1-hydroxy-1-methylethyl)phenyl]carbonyl}amino)-2-methylpyrazolo[1,5-a]pyrimidin-7-yl]thiomorpholin-1-ium-1-olate;
N-[7-(1,1-dioxidothiomorpholin-4-yl)-2-methylpyrazolo[1,5-a]pyrimidin-5-yl]-4-(1-hydroxy-1-methylethyl)benzamide;
N-(7-(4-(ethylsulfonyl)piperazin-1-yl)-2-methylpyrazolo[1,5-a]pyrimidin-5-yl)-4-(2-hydroxypropan-2-yl)benzamide;
N-(7-(4-(hydroxymethyl)piperidin-1-yl)-2-methylpyrazolo[1,5-a]pyrimidin-5-yl)-4-(2-hydroxypropan-2-yl)benzamide;
N-(2-methyl-7-morpholinopyrazolo[1,5-a]pyrimidin-5-yl)-6-(trifluoromethyl)nicotinamide;
N-(2-methyl-7-(4-oxo-3,4,7,8-tetrahydropyrido[4,3-d]pyrimidin-6(5H)-yl)pyrazolo[1,5-a]pyrimidin-5-yl)-6-(trifluoromethyl)nicotinamide;
N-(2-cyclopropyl-7-phenylpyrazolo[1,5-a]pyrimidin-5-yl)-4-(2-hydroxypropan-2-yl)benzamide;
N-(2-cyclopropyl-7-(3-(hydroxymethyl)phenyl)pyrazolo[1,5-a]pyrimidin-5-yl)-4-(2-hydroxypropan-2-yl)benzamide;
N-(2-cyclopropyl-7-morpholinopyrazolo[1,5-a]pyrimidin-5-yl)-4-(2-hydroxypropan-2-yl)benzamide;
N-(2-cyclopropyl-7-(4-hydroxypiperidin-1-yl)pyrazolo[1,5-a]pyrimidin-5-yl)-4-(2-hydroxypropan-2-yl)benzamide;
methyl 4-(7-chloro-2-(trifluoromethyl)pyrazolo[1,5-a]pyrimidin-5-ylcarbamoyl)benzoate;
4-(2-hydroxypropan-2-yl)-N-(7-(4-(2-hydroxypropan-2-yl)piperidin-1-yl)-2-methylpyrazolo[1,5-a]pyrimidin-5-yl)benzamide;
4-(2-hydroxypropan-2-yl)-N-(7-(4-methoxyphenyl)-2-methylpyrazolo[1,5-a]pyrimidin-5-yl)benzamide;
4-(2-hydroxypropan-2-yl)-N-(7-morpholino-2-(trifluoromethyl)pyrazolo[1,5-a]pyrimidin-5-yl)benzamide;
4-(2-hydroxypropan-2-yl)-N-(7-(4-(methoxymethyl)piperidin-1-yl)pyrazolo[1,5-a]pyrimidin-5-yl)benzamide;
4-(2-hydroxypropan-2-yl)-N-(7-(4-(2-hydroxypropan-2-yl)piperidin-1-yl)pyrazolo[1,5-a]pyrimidin-5-yl)benzamide;
N-(7-(2,3-dihydrobenzofuran-5-yl)-2-methylpyrazolo[1,5-a]pyrimidin-5-yl)-4-(2-hydroxypropan-2-yl)benzamide;
methyl 4-(7-phenyl-2-(trifluoromethyl)pyrazolo[1,5-a]pyrimidin-5-ylcarbamoyl)benzoate;
4-(2-hydroxypropan-2-yl)-N-(7-(4-(methoxymethyl)piperidin-1-yl)-2-methylpyrazolo[1,5-a]pyrimidin-5-yl)benzamide;
1-(5-(4-(2-hydroxypropan-2-yl)benzamido)-2-methylpyrazolo[1,5-a]pyrimidin-7-yl)piperidine-4-carboxylic acid;
N-(2-ethyl-7-(4-methoxyphenyl)pyrazolo[1,5-a]pyrimidin-5-yl)-4-(2-hydroxypropan-2-yl)benzamide;
N-(2-ethyl-7-phenylpyrazolo[1,5-a]pyrimidin-5-yl)-4-(2-hydroxypropan-2-yl)benzamide;
4-(2-hydroxypropan-2-yl)-N-(7-phenyl-2-(trifluoromethyl)pyrazolo[1,5-a]pyrimidin-5-yl)benzamide;
N-(2-ethyl-7-morpholinopyrazolo[1,5-a]pyrimidin-5-yl)-4-(2-hydroxypropan-2-yl)benzamide;
N-(7-(benzo[d][1,3]dioxol-5-yl)-2-methylpyrazolo[1,5-a]pyrimidin-5-yl)-4-(2-hydroxypropan-2-yl)benzamide;
N-(7-(4-(1-hydroxy-2-methylpropyl)piperidin-1-yl)pyrazolo[1,5-a]pyrimidin-5-yl)-4-(2-hydroxypropan-2-yl)benzamide;
N-(7-(4-formyl-1,4-diazepan-1-yl)pyrazolo[1,5-a]pyrimidin-5-yl)-4-(2-hydroxypropan-2-yl)benzamide;
N-(7-(4-acetyl-1,4-diazepan-1-yl)pyrazolo[1,5-a]pyrimidin-5-yl)-4-(2-hydroxypropan-2-yl)benzamide;
4-(2-hydroxypropan-2-yl)-N-(7-(3-hydroxypyrrolidin-1-yl)pyrazolo[1,5-a]pyrimidin-5-yl)benzamide;
N-(7-(4-acetyl-1,4-diazepan-1-yl)-2-ethylpyrazolo[1,5-a]pyrimidin-5-yl)-4-(2-hydroxypropan-2-yl)benzamide;
methyl 1-(5-(4-(2-hydroxypropan-2-yl)benzamido)-2-methylpyrazolo[1,5-a]pyrimidin-7-yl)piperidine-4-carboxylate;
4-(2-hydroxypropan-2-yl)-N-(7-(3-methoxyphenyl)-2-methylpyrazolo[1,5-a]pyrimidin-5-yl)benzamide;
N-(7-(4-(1-hydroxy-2-methylpropyl)piperidin-1-yl)-2-methylpyrazolo[1,5-a]pyrimidin-5-yl)-4-(2-hydroxypropan-2-yl)benzamide;

4-(2-hydroxypropan-2-yl)-N-(2-methyl-7-(1-oxo-2,8-diazaspiro[4.5]decan-8-yl)pyrazolo[1,5-a]pyrimidin-5-yl)benzamide;
4-(2-hydroxypropan-2-yl)-N-(2-methyl-7-(4-(pyrrolidine-1-carbonyl)piperidin-1-yl)pyrazolo[1,5-a]pyrimidin-5-yl)benzamide;
N-(7-(benzo[d][1,3]dioxol-5-yl)pyrazolo[1,5-a]pyrimidin-5-yl)-4-(2-hydroxypropan-2-yl)benzamide;
1-(5-(4-(2-hydroxypropan-2-yl)benzamido)pyrazolo[1,5-a]pyrimidin-7-yl)piperidine-4-carboxylic acid;
Methyl 1-(5-(4-(2-hydroxypropan-2-yl)benzamido)pyrazolo[1,5-a]pyrimidin-7-yl)piperidine-4-carboxylate;
4-(2-hydroxypropan-2-yl)-N-(2-methyl-7-(4-(phenylthio)piperidin-1-yl)pyrazolo[1,5-a]pyrimidin-5-yl)benzamide;
4-(2-hydroxypropan-2-yl)-N-(2-methyl-7-(4-(phenylsulfonyl)piperidin-1-yl)pyrazolo[1,5-a]pyrimidin-5-yl)benzamide;
4-(2-hydroxypropan-2-yl)-N-(2-methyl-7-(4-(phenylsulfonyl)piperazin-1-yl)pyrazolo[1,5-a]pyrimidin-5-yl)benzamide;
N-(7-(4-(N,N-dimethylsulfamoyl)piperazin-1-yl)-2-methylpyrazolo[1,5-a]pyrimidin-5-yl)-4-(2-hydroxypropan-2-yl)benzamide;
4-(2-hydroxypropan-2-yl)-N-(2-methyl-7-(4-(propylsulfonyl)piperazin-1-yl)pyrazolo[1,5-a]pyrimidin-5-yl)benzamide;
4-(2-hydroxypropan-2-yl)-N-(2-methyl-7-(4-(methylsulfonyl)-1,4-diazepan-1-yl)pyrazolo[1,5-a]pyrimidin-5-yl)benzamide;
4-(2-hydroxypropan-2-yl)-N-(7-(1,2,3,4-tetrahydroisoquinolin-7-yl)pyrazolo[1,5-a]pyrimidin-5-yl)benzamide;
1-(5-(4-(2-hydroxypropan-2-yl)benzamido)-2-methylpyrazolo[1,5-a]pyrimidin-7-yl)piperidine-4-carboxamide;
4-(2-hydroxypropan-2-yl)-N-(2-methyl-7-(4-methylpiperidin-1-yl)pyrazolo[1,5-a]pyrimidin-5-yl)benzamide;
4-(2-hydroxypropan-2-yl)-N-(2-methyl-7-(1,4-oxazepan-4-yl)pyrazolo[1,5-a]pyrimidin-5-yl)benzamide;
N-(7-(4-formyl-1,4-diazepan-1-yl)-2-methylpyrazolo[1,5-a]pyrimidin-5-yl)-4-(2-hydroxypropan-2-yl)benzamide;
N-(7-(4-acetyl-1,4-diazepan-1-yl)-2-methylpyrazolo[1,5-a]pyrimidin-5-yl)-4-(2-hydroxypropan-2-yl)benzamide;
(S)-N-(7-(2-(hydroxymethyl)pyrrolidin-1-yl)-2-methylpyrazolo[1,5-a]pyrimidin-5-yl)-4-(2-hydroxypropan-2-yl)benzamide;
N-ethyl-1-(5-(4-(2-hydroxypropan-2-yl)benzamido)-2-methylpyrazolo[1,5-a]pyrimidin-7-yl)piperidine-4-carboxamide;
1-(5-(4-(2-hydroxypropan-2-yl)benzamido)-2-methylpyrazolo[1,5-a]pyrimidin-7-yl)-N-methylpiperidine-4-carboxamide;
1-(5-(4-(2-hydroxypropan-2-yl)benzamido)-2-methylpyrazolo[1,5-a]pyrimidin-7-yl)-N,N-dimethylpiperidine-4-carboxamide;
N-(7-(2,2-difluorobenzo[d][1,3]dioxol-4-yl)pyrazolo[1,5-a]pyrimidin-5-yl)-4-(2-hydroxypropan-2-yl)benzamide;
N-(7-(4,4-difluoropiperidin-1-yl)pyrazolo[1,5-a]pyrimidin-5-yl)-4-(2-hydroxypropan-2-yl)benzamide;
4-(2-hydroxypropan-2-yl)-N-(7-(4-(trifluoromethyl)piperidin-1-yl)pyrazolo[1,5-a]pyrimidin-5-yl)benzamide;
4-(2-hydroxypropan-2-yl)-N-(2-methyl-7-(1,2,3,4-tetrahydroisoquinolin-7-yl)pyrazolo[1,5-a]pyrimidin-5-yl)benzamide;
1-(5-(4-(2-hydroxypropan-2-yl)benzamido)pyrazolo[1,5-a]pyrimidin-7-yl)-N-methylpiperidine-4-carboxamide;
1-(5-(4-(2-hydroxypropan-2-yl)benzamido)pyrazolo[1,5-a]pyrimidin-7-yl)-N-isopropylpiperidine-4-carboxamide;
(R)-1-(5-(4-(2-hydroxypropan-2-yl)benzamido)pyrazolo[1,5-a]pyrimidin-7-yl)-N-methylpiperidine-3-carboxamide;
(R)-1-(5-(4-(2-hydroxypropan-2-yl)benzamido)pyrazolo[1,5-a]pyrimidin-7-yl)-N,N-dimethylpiperidine-3-carboxamide;
4-(2-hydroxypropan-2-yl)-N-(7-phenoxypyrazolo[1,5-a]pyrimidin-5-yl)benzamide;
(R)-1-(5-(4-(2-hydroxypropan-2-yl)benzamido)pyrazolo[1,5-a]pyrimidin-7-yl)-N-isopropylpiperidine-3-carboxamide;
N-(7-(3-fluoropyrrolidin-1-yl)-2-methylpyrazolo[1,5-a]pyrimidin-5-yl)-4-(2-hydroxypropan-2-yl)benzamide;
N-(7-(4-(2-hydroxyethyl)piperidin-1-yl)-2-methylpyrazolo[1,5-a]pyrimidin-5-yl)-4-(2-hydroxypropan-2-yl)benzamide;
N-(7-(2,3-dihydrobenzo[b][1,4]dioxin-6-yl)-2-methylpyrazolo[1,5-a]pyrimidin-5-yl)-4-(2-hydroxypropan-2-yl)benzamide;
N-(7-morpholinopyrazolo[1,5-a]pyrimidin-5-yl)-4-(6-oxo-1,6-dihydropyridin-3-yl)benzamide;
(E)-4-(2-hydroxypropan-2-yl)-N-(2-methyl-7-styrylpyrazolo[1,5-a]pyrimidin-5-yl)benzamide;
(E)-N-(7-(4-fluorostyryl)-2-methylpyrazolo[1,5-a]pyrimidin-5-yl)-4-(2-hydroxypropan-2-yl)benzamide;
(E)-4-(2-hydroxypropan-2-yl)-N-(7-(3-methoxystyryl)-2-methylpyrazolo[1,5-a]pyrimidin-5-yl)benzamide;
N-(7-(4-acetamidopiperidin-1-yl)-2-methylpyrazolo[1,5-a]pyrimidin-5-yl)-4-(2-hydroxypropan-2-yl)benzamide;
(R)-N-ethyl-1-(5-(4-(2-hydroxypropan-2-yl)benzamido)pyrazolo[1,5-a]pyrimidin-7-yl)piperidine-3-carboxamide;
N-(7-(4-chlorophenyl)pyrazolo[1,5-a]pyrimidin-5-yl)-4-(2-hydroxypropan-2-yl)benzamide;
N-(7-(4-fluorophenyl)pyrazolo[1,5-a]pyrimidin-5-yl)-4-(2-hydroxypropan-2-yl)benzamide;
4-(furan-3-yl)-N-(7-morpholinopyrazolo[1,5-a]pyrimidin-5-yl)benzamide;
methyl 1-(4-(7-morpholinopyrazolo[1,5-a]pyrimidin-5-ylcarbamoyl)phenyl)cyclopropanecarboxylate;
N-(7-butoxypyrazolo[1,5-a]pyrimidin-5-yl)-4-(2-hydroxypropan-2-yl)benzamide;
methyl 1-(4-(2-methyl-7-phenylpyrazolo[1,5-a]pyrimidin-5-ylcarbamoyl)phenyl)cyclopropanecarboxylate;
1-(4-(7-morpholinopyrazolo[1,5-a]pyrimidin-5-ylcarbamoyl)phenyl)cyclopropanecarboxylic acid;
4-(2-hydroxypropan-2-yl)-N-(7-methoxypyrazolo[1,5-a]pyrimidin-5-yl)benzamide;
N-(7-(5,6-dihydro-[1,2,4]triazolo[4,3-a]pyrazin-7(8H)-yl)-2-methylpyrazolo[1,5-a]pyrimidin-5-yl)-4-(2-hydroxypropan-2-yl)benzamide;
N-(7-(3,4-dimethoxyphenyl)-2-methylpyrazolo[1,5-a]pyrimidin-5-yl)-4-(2-hydroxypropan-2-yl)benzamide;
N-(7-(3,4-dihydro-2H-benzo[b][1,4]dioxepin-7-yl)-2-methylpyrazolo[1,5-a]pyrimidin-5-yl)-4-(2-hydroxypropan-2-yl)benzamide;

N-(7-(2,2-difluorobenzo[d][1,3]dioxol-5-yl)-2-methylpyrazolo[1,5-a]pyrimidin-5-yl)-4-(2-hydroxypropan-2-yl)benzamide;
N-(7-(4-(2-hydroxyethyl)piperidin-1-yl)-2-methylpyrazolo[1,5-a]pyrimidin-5-yl)-2-phenylcyclopropanecarboxamide;
N-(7-(benzo[b]thiophen-5-yl)-2-methylpyrazolo[1,5-a]pyrimidin-5-yl)-4-(2-hydroxypropan-2-yl)benzamide;
4-(2-hydroxypropan-2-yl)-N-(2-methyl-7-(4-methyl-3,4-dihydro-2H-benzo[b][1,4]oxazin-7-yl)pyrazolo[1,5-a]pyrimidin-5-yl)benzamide;
4-(2-hydroxypropan-2-yl)-N-(7-(4-isopropoxyphenyl)-2-methylpyrazolo[1,5-a]pyrimidin-5-yl)benzamide;
(S)-N-(7-(3-acetamidopyrrolidin-1-yl)pyrazolo[1,5-a]pyrimidin-5-yl)-4-(2-hydroxypropan-2-yl)benzamide;
(R)-N-(7-(3-acetamidopyrrolidin-1-yl)pyrazolo[1,5-a]pyrimidin-5-yl)-4-(2-hydroxypropan-2-yl)benzamide;
N-(7-((S)-3-fluoropyrrolidin-1-yl)-2-methylpyrazolo[1,5-a]pyrimidin-5-yl)-2-phenylcyclopropanecarboxamide;
N-(7-((R)-3-fluoropyrrolidin-1-yl)-2-methylpyrazolo[1,5-a]pyrimidin-5-yl)-2-phenylcyclopropanecarboxamide;
N-(7-(4-methoxyphenyl)-2-methylpyrazolo[1,5-a]pyrimidin-5-yl)-2-phenylcyclopropanecarboxamide;
(S)-1-(5-(4-(2-hydroxypropan-2-yl)benzamido)pyrazolo[1,5-a]pyrimidin-7-yl)-N-methylpiperidine-3-carboxamide;
(S)-N-(7-(3-acetamidopiperidin-1-yl)pyrazolo[1,5-a]pyrimidin-5-yl)-4-(2-hydroxypropan-2-yl)benzamide;
(S)-N-(7-(3-aminopiperidin-1-yl)pyrazolo[1,5-a]pyrimidin-5-yl)-4-(2-hydroxypropan-2-yl)benzamide;
(R)-N-(7-(3-acetamidopiperidin-1-yl)pyrazolo[1,5-a]pyrimidin-5-yl)-4-(2-hydroxypropan-2-yl)benzamide;
N-(7-(4-chlorophenyl)-2-methylpyrazolo[1,5-a]pyrimidin-5-yl)-4-(2-hydroxypropan-2-yl)benzamide;
N-(7-(4-fluoro-3-methoxyphenyl)-2-methylpyrazolo[1,5-a]pyrimidin-5-yl)-4-(2-hydroxypropan-2-yl)benzamide;
(R)-N-(7-(3-aminopiperidin-1-yl)pyrazolo[1,5-a]pyrimidin-5-yl)-4-(2-hydroxypropan-2-yl)benzamide;
5-(2-hydroxypropan-2-yl)-N-(2-methyl-7-phenylpyrazolo[1,5-a]pyrimidin-5-yl)picolinamide;
N-(7-(5-chlorothiophen-2-yl)-2-methylpyrazolo[1,5-a]pyrimidin-5-yl)-4-(2-hydroxypropan-2-yl)benzamide;
N-(7-(4-acetamidopiperidin-1-yl)-2-methylpyrazolo[1,5-a]pyrimidin-5-yl)-2-phenylcyclopropanecarboxamide;
N-(7-(3-fluoro-4-methoxyphenyl)-2-methylpyrazolo[1,5-a]pyrimidin-5-yl)-4-(2-hydroxypropan-2-yl)benzamide;
N-(7-(3-chloro-4-methoxyphenyl)-2-methylpyrazolo[1,5-a]pyrimidin-5-yl)-4-(2-hydroxypropan-2-yl)benzamide;
6-(2-hydroxypropan-2-yl)-N-(2-methyl-7-phenylpyrazolo[1,5-a]pyrimidin-5-yl)nicotinamide;
6-(2-hydroxypropan-2-yl)-N-(7-morpholinopyrazolo[1,5-a]pyrimidin-5-yl)nicotinamide;
(R)-1-(5-(4-(2-hydroxypropan-2-yl)benzamido)-2-methylpyrazolo[1,5-a]pyrimidin-7-yl)-N-methylpiperidine-3-carboxamide;
N-(7-(4-chloro-3-methylphenyl)-2-methylpyrazolo[1,5-a]pyrimidin-5-yl)-4-(2-hydroxypropan-2-yl)benzamide;
N-(7-(3-chloro-4-hydroxyphenyl)-2-methylpyrazolo[1,5-a]pyrimidin-5-yl)-4-(2-hydroxypropan-2-yl)benzamide;
N-(7-(4-(2-(dimethylamino)ethoxy)phenyl)-2-methylpyrazolo[1,5-a]pyrimidin-5-yl)-4-(2-hydroxypropan-2-yl)benzamide;
4-(2-hydroxypropan-2-yl)-N-(2-methyl-7-(4-(2-morpholinoethoxy)phenyl)pyrazolo[1,5-a]pyrimidin-5-yl)benzamide;
4-(2-hydroxypropan-2-yl)-N-(7-(4-(2-methoxyethoxy)phenyl)-2-methylpyrazolo[1,5-a]pyrimidin-5-yl)benzamide;
4-(2-hydroxypropan-2-yl)-N-(2-methyl-7-(4-propionamidopiperidin-1-yl)pyrazolo[1,5-a]pyrimidin-5-yl)benzamide;
4-(2-hydroxypropan-2-yl)-N-(2-methyl-7-(4-ureidopiperidin-1-yl)pyrazolo[1,5-a]pyrimidin-5-yl)benzamide;
N-(7-(4-(2-amino-2-oxoethyl)piperidin-1-yl)-2-methylpyrazolo[1,5-a]pyrimidin-5-yl)-4-(2-hydroxypropan-2-yl)benzamide;
N-(7-(benzofuran-5-yl)-2-methylpyrazolo[1,5-a]pyrimidin-5-yl)-4-(2-hydroxypropan-2-yl)benzamide;
N-(7-(3-(dimethylamino)phenyl)-2-methylpyrazolo[1,5-a]pyrimidin-5-yl)-4-(2-hydroxypropan-2-yl)benzamide;
4-(2-hydroxypropan-2-yl)-N-(7-(6-hydroxypyridin-3-yl)-2-methylpyrazolo[1,5-a]pyrimidin-5-yl)benzamide;
4-(2-hydroxypropan-2-yl)-N-(7-(6-methoxypyridin-3-yl)-2-methylpyrazolo[1,5-a]pyrimidin-5-yl)benzamide;
3,3-dimethyl-N-(2-methyl-7-phenylpyrazolo[1,5-a]pyrimidin-5-yl)-2,3-dihydrobenzofuran-6-carboxamide;
N-(2-methyl-7-phenylpyrazolo[1,5-a]pyrimidin-5-yl)-2-(pyridin-4-yl)cyclopropanecarboxamide;
N-(7-(4-(cyclopropanecarboxamido)piperidin-1-yl)-2-methylpyrazolo[1,5-a]pyrimidin-5-yl)-4-(2-hydroxypropan-2-yl)benzamide;
4-(2-cyanopropan-2-yl)-N-(2-methyl-7-phenylpyrazolo[1,5-a]pyrimidin-5-yl)benzamide;
4-(1-amino-2-methylpropan-2-yl)-N-(2-methyl-7-phenylpyrazolo[1,5-a]pyrimidin-5-yl)benzamide;
2-(2-methyl-2-(4-(2-methyl-7-phenylpyrazolo[1,5-a]pyrimidin-5-ylcarbamoyl)phenyl)propylamino)-2-oxoacetic acid;
N-(7-(4-acetamidopiperidin-1-yl)-2-methylpyrazolo[1,5-a]pyrimidin-5-yl)-2-(pyridin-4-yl)cyclopropanecarboxamide;
N-(2-methyl-7-(4-ureidopiperidin-1-yl)pyrazolo[1,5-a]pyrimidin-5-yl)-2-(pyridin-4-yl)cyclopropanecarboxamide;
6-(2-hydroxypropan-2-yl)-N-(7-(4-methoxyphenyl)-2-methylpyrazolo[1,5-a]pyrimidin-5-yl)nicotinamide;
N-(7-(benzo[d][1,3]dioxol-5-yl)-2-methylpyrazolo[1,5-a]pyrimidin-5-yl)-6-(2-hydroxypropan-2-yl)nicotinamide;
N-(7-(2,3-dihydrobenzofuran-5-yl)-2-methylpyrazolo[1,5-a]pyrimidin-5-yl)-6-(2-hydroxypropan-2-yl)nicotinamide;
N-(7-(4-acetamidopiperidin-1-yl)-2-methylpyrazolo[1,5-a]pyrimidin-5-yl)-6-(2-hydroxypropan-2-yl)nicotinamide;
6-(2-hydroxypropan-2-yl)-N-(2-methyl-7-(4-ureidopiperidin-1-yl)pyrazolo[1,5-a]pyrimidin-5-yl)nicotinamide;
N-(7-(4-(2-amino-2-oxoethyl)piperazin-1-yl)-2-methylpyrazolo[1,5-a]pyrimidin-5-yl)-4-(2-hydroxypropan-2-yl)benzamide;
methyl 3-methyl-3-(4-(2-methyl-7-phenylpyrazolo[1,5-a]pyrimidin-5-ylcarbamoyl)phenyl)butanoate;

(1S,2S)-N-(2-methyl-7-phenylpyrazolo[1,5-a]pyrimidin-5-yl)-2-phenylcyclopropanecarboxamide;
(1R,2R)-N-(2-methyl-7-phenylpyrazolo[1,5-a]pyrimidin-5-yl)-2-phenylcyclopropanecarboxamide;
(1R,2S)-N-(2-methyl-7-phenylpyrazolo[1,5-a]pyrimidin-5-yl)-2-phenylcyclopropanecarboxamide;
N-(7-(4-chloro-3-methoxyphenyl)-2-methylpyrazolo[1,5-a]pyrimidin-5-yl)-4-(2-hydroxypropan-2-yl)benzamide;
N-(2-methyl-7-morpholinopyrazolo[1,5-a]pyrimidin-5-yl)-4-(trifluoromethoxy)benzamide;
N-(2-hydroxyethyl)-1-(5-(4-(2-hydroxypropan-2-yl)benzamido)-2-methylpyrazolo[1,5-a]pyrimidin-7-yl)piperidine-3-carboxamide;
N-(7-(6-ethoxypyridin-3-yl)-2-methylpyrazolo[1,5-a]pyrimidin-5-yl)-4-(2-hydroxypropan-2-yl)benzamide;
4-(2-hydroxypropan-2-yl)-N-(7-(6-isopropoxypyridin-3-yl)-2-methylpyrazolo[1,5-a]pyrimidin-5-yl)benzamide;
N-(7-(6-(cyclopropylmethoxy)pyridin-3-yl)-2-methylpyrazolo[1,5-a]pyrimidin-5-yl)-4-(2-hydroxypropan-2-yl)benzamide;
N-(2-methyl-7-phenylpyrazolo[1,5-a]pyrimidin-5-yl)-4-(trifluoromethylthio)benzamide;
(1R,2R)-N-(7-(4-acetamidopiperidin-1-yl)-2-methylpyrazolo[1,5-a]pyrimidin-5-yl)-2-phenylcyclopropanecarboxamide;
(1R,2R)-N-(2-methyl-7-(4-ureidopiperidin-1-yl)pyrazolo[1,5-a]pyrimidin-5-yl)-2-phenylcyclopropanecarboxamide;
(1S,2S)-N-(7-(4-acetamidopiperidin-1-yl)-2-methylpyrazolo[1,5-a]pyrimidin-5-yl)-2-phenylcyclopropanecarboxamide;
2-(4-fluorophenyl)-N-(2-methyl-7-phenylpyrazolo[1,5-a]pyrimidin-5-yl)cyclopropanecarboxamide;
cis-2-(4-fluorophenyl)-N-(2-methyl-7-phenylpyrazolo[1,5-a]pyrimidin-5-yl)cyclopropanecarboxamide;
N-(7-(4-acetamidopiperidin-1-yl)-2-methylpyrazolo[1,5-a]pyrimidin-5-yl)-2-(4-fluorophenyl)cyclopropanecarboxamide;
2-(4-fluorophenyl)-N-(2-methyl-7-(4-ureidopiperidin-1-yl)pyrazolo[1,5-a]pyrimidin-5-yl)cyclopropanecarboxamide;
N-(2-methyl-7-(4-ureidopiperidin-1-yl)pyrazolo[1,5-a]pyrimidin-5-yl)-4-(trifluoromethoxy)benzamide;
N-(7-(4-(2-amino-2-oxoethyl)piperidin-1-yl)-2-methylpyrazolo[1,5-a]pyrimidin-5-yl)-4-(trifluoromethoxy)benzamide;
N-(7-(4-acetamidopiperidin-1-yl)-2-methylpyrazolo[1,5-a]pyrimidin-5-yl)-4-(trifluoromethoxy)benzamide;
N-(7-(4-acetamidopiperidin-1-yl)-2-methylpyrazolo[1,5-a]pyrimidin-5-yl)-2-(pyridin-4-yl)cyclopropanecarboxamide;
N-(7-morpholinopyrazolo[1,5-a]pyrimidin-5-yl)cyclopropanecarboxamide;
N-(7-morpholinopyrazolo[1,5-a]pyrimidin-5-yl)cyclopentanecarboxamide;
tert-butyl 4-(7-morpholinopyrazolo[1,5-a]pyrimidin-5-ylcarbamoyl)piperidine-1-carboxylate;
N-(7-morpholinopyrazolo[1,5-a]pyrimidin-5-yl)cyclobutanecarboxamide;
trans-N-(7-morpholinopyrazolo[1,5-a]pyrimidin-5-yl)-2-phenylcyclopropanecarboxamide;
4-cyano-N-(7-morpholinopyrazolo[1,5-a]pyrimidin-5-yl)benzamide;
2,4-difluoro-N-(7-morpholinopyrazolo[1,5-a]pyrimidin-5-yl)benzamide;
N-(7-morpholinopyrazolo[1,5-a]pyrimidin-5-yl)-1H-indole-2-carboxamide;
N-(7-morpholinopyrazolo[1,5-a]pyrimidin-5-yl)-1H-indole-6-carboxamide;
N-(7-morpholinopyrazolo[1,5-a]pyrimidin-5-yl)-1-naphthamide;
methyl 4-(7-morpholinopyrazolo[1,5-a]pyrimidin-5-ylcarbamoyl)benzoate;
N-(7-morpholinopyrazolo[1,5-a]pyrimidin-5-yl)biphenyl-4-carboxamide;
2,4-dimethyl-N-(7-morpholinopyrazolo[1,5-a]pyrimidin-5-yl)benzamide;
1-hydroxy-N-(7-morpholinopyrazolo[1,5-a]pyrimidin-5-yl)-2-naphthamide;
4-methyl-N-(7-morpholinopyrazolo[1,5-a]pyrimidin-5-yl)benzamide;
3-methyl-N-(7-morpholinopyrazolo[1,5-a]pyrimidin-5-yl)benzamide;
2-methoxy-N-(7-morpholinopyrazolo[1,5-a]pyrimidin-5-yl)benzamide;
N-(7-morpholinopyrazolo[1,5-a]pyrimidin-5-yl)-2-naphthamide;
4-bromo-N-(7-morpholinopyrazolo[1,5-a]pyrimidin-5-yl)benzamide;
N-(7-morpholinopyrazolo[1,5-a]pyrimidin-5-yl)-1H-imidazole-4-carboxamide;
N-(7-morpholinopyrazolo[1,5-a]pyrimidin-5-yl)nicotinamide;
N-(7-morpholinopyrazolo[1,5-a]pyrimidin-5-yl)picolinamide;
N-(7-morpholinopyrazolo[1,5-a]pyrimidin-5-yl)pyrazine-2-carboxamide;
N-(7-morpholinopyrazolo[1,5-a]pyrimidin-5-yl)quinoline-2-carboxamide;
N-(7-morpholinopyrazolo[1,5-a]pyrimidin-5-yl)isoquinoline-1-carboxamide;
1-(3-bromophenyl)-3,5-dimethyl-N-(7-morpholinopyrazolo[1,5-a]pyrimidin-5-yl)-1H-pyrazole-4-carboxamide;
N-(7-morpholinopyrazolo[1,5-a]pyrimidin-5-yl)-1-((3-oxo-3,4-dihydro-2H-benzo[b][1,4]oxazin-8-yl)methyl)piperidine-3-carboxamide;
diethyl 4-(7-morpholinopyrazolo[1,5-a]pyrimidin-5-ylcarbamoyl)benzylphosphonate;
tert-butyl 4-(7-morpholinopyrazolo[1,5-a]pyrimidin-5-ylcarbamoyl)benzylcarbamate;
N-(7-morpholinopyrazolo[1,5-a]pyrimidin-5-yl)-4-(thiophen-2-yl)benzamide;
4-(5-methyl-1H-tetrazol-1-yl)-N-(7-morpholinopyrazolo[1,5-a]pyrimidin-5-yl)benzamide;
N-(7-morpholinopyrazolo[1,5-a]pyrimidin-5-yl)-4-(oxazol-5-yl)benzamide;
4-morpholino-N-(7-morpholinopyrazolo[1,5-a]pyrimidin-5-yl)benzamide;
4-(1H-imidazol-1-yl)-N-(7-morpholinopyrazolo[1,5-a]pyrimidin-5-yl)benzamide;
N-(7-morpholinopyrazolo[1,5-a]pyrimidin-5-yl)-4-(3-oxo-3,4-dihydro-2H-1,4-thiazin-5-yl)benzamide;
N-(7-morpholinopyrazolo[1,5-a]pyrimidin-5-yl)-4-(3-(trifluoromethyl)-1H-pyrazol-1-yl)benzamide;
2,2-difluoro-N-(7-morpholinopyrazolo[1,5-a]pyrimidin-5-yl)benzo[d][1,3]dioxole-4-carboxamide;
4-(2-methylthiazol-4-yl)-N-(7-morpholinopyrazolo[1,5-a]pyrimidin-5-yl)benzamide;
N,2-dimethyl-N-(4-(7-morpholinopyrazolo[1,5-a]pyrimidin-5-ylcarbamoyl)phenyl)benzamide;

4-((2,4-dioxothiazolidin-5-yl)methyl)-N-(7-morpholinopyrazolo[1,5-a]pyrimidin-5-yl)benzamide;

3-(1H-benzo[d]imidazol-2-yl)-N-(7-morpholinopyrazolo[1,5-a]pyrimidin-5-yl)benzamide;

7-methoxy-2,2-dimethyl-N-(7-morpholinopyrazolo[1,5-a]pyrimidin-5-yl)-2,3-dihydrobenzo furan-4-carboxamide;

4-(5-methyl-1,2,4-oxadiazol-3-yl)-N-(7-morpholinopyrazolo[1,5-a]pyrimidin-5-yl)benzamide;

N-(7-morpholinopyrazolo[1,5-a]pyrimidin-5-yl)-4-(1,2,3-thiadiazol-4-yl)benzamide;

(E)-4-(1-(hydroxyimino)ethyl)-N-(7-morpholinopyrazolo[1,5-a]pyrimidin-5-yl)benzamide;

4-(furan-2-yl)-N-(7-morpholinopyrazolo[1,5-a]pyrimidin-5-yl)benzamide;

4-tert-butyl-N-(7-(1-oxo-thiomorpholino)pyrazolo[1,5-a]pyrimidin-5-yl)benzamide;

4-tert-butyl-N-(7-(methyl(1,1-dioxo(tetrahydro-thiopyran-4-yl))amino)pyrazolo[1,5-a]pyrimidin-5-yl)benzamide;

4-tert-butyl-N-(7-(methyl(2-(methylsulfonyl)ethyl)amino)pyrazolo[1,5-a]pyrimidin-5-yl)benzamide;

N-(7-((2-(N-acetylsulfamoyl)ethyl)(methyl)amino)pyrazolo[1,5-a]pyrimidin-5-yl)-4-tert-butylbenzamide;

4-tert-butyl-N-(7-(methyl(2-(methylsulfonamido)ethyl)amino)pyrazolo[1,5-a]pyrimidin-5-yl)benzamide;

4-tert-butyl-N-(7-(2-(methylsulfonyl)ethoxy)pyrazolo[1,5-a]pyrimidin-5-yl)benzamide; and a pharmaceutically acceptable salt of any one of the aforementioned compounds.

33. The compound according to claim 1, wherein the compound is in the form of a pharmaceutically acceptable salt.

34. The compound or pharmaceutically acceptable salt according to claim 1, which is present in a mixture of stereoisomers.

35. The compound or pharmaceutically acceptable salt according to claim 1, which is present as a single stereoisomer.

36. A pharmaceutical composition comprising a compound or pharmaceutically acceptable salt as defined in claim 1, and a pharmaceutically acceptable excipient.

* * * * *

SEQUENCE LISTING

<160> NUMBER OF SEQ ID NOS: 2

<210> SEQ ID NO 1
<211> LENGTH: 65
<212> TYPE: DNA
<213> ORGANISM: Artificial Sequence
<220> FEATURE:
<223> OTHER INFORMATION: Synthetic Primers

<400> SEQUENCE: 1
aaaagtcgac atggactaca aggacgacga tgacaaggtg aacaccatta ccgaagagaa    60
gggga                                                                65

<210> SEQ ID NO 2
<211> LENGTH: 39
<212> TYPE: DNA
<213> ORGANISM: Artificial Sequence
<220> FEATURE:
<223> OTHER INFORMATION: Synthetic Primers

<400> SEQUENCE: 2
aaagcggccg ctcaagtctg tttgtttcga aagtcaatg                           39